(12) United States Patent
Karow et al.

(10) Patent No.: US 12,570,765 B2
(45) Date of Patent: Mar. 10, 2026

(54) TRISPECIFIC T CELL ENGAGERS

(71) Applicant: GENSUN BIOPHARMA INC.,
Newbury Park, CA (US)

(72) Inventors: Margaret Karow, Newbury Park, CA
(US); Richard Yau, Newbury Park, CA
(US); Jackie Sheng, Newbury Park, CA
(US)

(73) Assignee: SUZHOU ZELGEN
BIOPHARMACEUTICALS CO.
LTD., Kunshan (CN)

( * ) Notice: Subject to any disclaimer, the term of this
patent is extended or adjusted under 35
U.S.C. 154(b) by 0 days.

(21) Appl. No.: 18/758,038

(22) Filed: Jun. 28, 2024

(65) Prior Publication Data

US 2024/0425611 A1     Dec. 26, 2024

Related U.S. Application Data

(63) Continuation of application No. 17/164,696, filed on
Feb. 1, 2021, now Pat. No. 12,060,434.

(60) Provisional application No. 62/991,070, filed on Mar.
17, 2020, provisional application No. 62/981,048,
filed on Feb. 25, 2020, provisional application No.
62/968,999, filed on Jan. 31, 2020.

(51) Int. Cl.
| | |
|---|---|
| *C07K 16/30* | (2006.01) |
| *A61K 39/00* | (2006.01) |
| *A61K 39/395* | (2006.01) |
| *A61K 45/06* | (2006.01) |
| *C07K 16/28* | (2006.01) |
| *C07K 16/46* | (2006.01) |

(52) U.S. Cl.
CPC .... *C07K 16/3092* (2013.01); *A61K 39/39558*
(2013.01); *A61K 45/06* (2013.01); *C07K 16/28*
(2013.01); *C07K 16/2809* (2013.01); *C07K*
*16/2818* (2013.01); *C07K 16/2878* (2013.01);
*C07K 16/30* (2013.01); *C07K 16/468*
(2013.01); *A61K 2039/505* (2013.01); *C07K*
*2317/24* (2013.01); *C07K 2317/31* (2013.01);
*C07K 2317/52* (2013.01); *C07K 2317/55*
(2013.01); *C07K 2317/565* (2013.01); *C07K*
*2317/622* (2013.01); *C07K 2317/732*
(2013.01); *C07K 2317/74* (2013.01); *C07K*
*2317/75* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 4,676,980 A | 6/1987 | Segal et al. | |
| 4,816,567 A | 3/1989 | Cabilly et al. | |
| 4,946,778 A | 8/1990 | Ladner et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 2016/0032006 A1 | 2/2016 | Hudson | |
| 2016/0355600 A1* | 12/2016 | Moore | C07K 16/2887 |
| 2018/0044415 A1 | 2/2018 | Escarpe et al. | |
| 2019/0263907 A1 | 8/2019 | Raum et al. | |

FOREIGN PATENT DOCUMENTS

| | | |
|---|---|---|
| WO | 91/00360 | 1/1991 |
| WO | 93/08829 | 5/1995 |
| WO | 2018191438 | 10/2018 |
| WO | 2019126748 | 6/2019 |
| WO | 2019133961 | 7/2019 |
| WO | 2019140196 | 7/2019 |

OTHER PUBLICATIONS

Ni et al., The Protein Journal, 43, pp. 683-696, Jul. 2024 (Year:
2024).*
Owen et al., Journal of Hematology & Oncology, Publication Date:
Jun. 18, 2019 (Year: 2019).*
Willems et al., Cancer Immunol Immunother, 54: 1059-1071, Pub-
lication Date: May 13, 2005 (Year: 2005).*
McCafferty J, Griffiths AD, Winter G, Chiswell DJ. Phage antibod-
ies: filamentous phage displaying antibody variable domains. Nature.
Dec. 6, 1990;348(6301):552-4.
Sundaresan et al., J Nucl Med 44:1962-9 (2003).
Temple F Smith, Michael S Waterman, Comparison of
biosequences,Advances in Applied Mathematics, vol. 2, Issue 4,
1981, pp. 482-489.
Saul B. Needleman, Christian D. Wunsch, A general method appli-
cable to the search for similarities in the amino acid sequence of two
proteins, Journal of Molecular Biology, vol. 48, Issue 3, 1970, pp.
443-453.
Pearson WR, Lipman DJ. Improved tools for biological sequence
comparison. Proc Natl Acad Sci U S A. Apr. 1988;85(8):2444-8.

(Continued)

*Primary Examiner* — Peter J Reddig
*Assistant Examiner* — Cheng Lu
(74) *Attorney, Agent, or Firm* — Michael Ye; Kalos
Athena Wang PLLC

(57) ABSTRACT

Provided are trispecific T Cell Engagers or TSMAb's, anti-
bodies that can simultaneously engage three different types
of epitopes on the same target or on different targets. More
specifically, the invention is directed to trispecific molecules
that bind to DLL3, MUC17 or CLDN18.2 and activate CD
(cluster of differentiation) molecules (e.g. CD3, CD28 and
CD137). Also provided are methods of treating an ailment
such as cancer using an antibody (or fragment) against
DLL3, MUC17 or CLD18 paired with an antibody (or
fragment) of an agonist antibody that activates CD3, CD28
and/or CD137.

5 Claims, 37 Drawing Sheets

Specification includes a Sequence Listing.

(56)           References Cited

OTHER PUBLICATIONS

Altschul SF, Madden TL, Schäffer AA, Zhang J, Zhang Z, Miller W, Lipman DJ. Gapped BLAST and PSI-BLAST: a new generation of protein database search programs. Nucleic Acids Res. Sep. 1, 1997;25(17):3389-402.

Altschul SF, Gish W, Miller W, Myers EW, Lipman DJ. Basic local alignment search tool. J Mol Biol. Oct. 5, 1990;215(3):403-10.

Mark A. Batzer, James E. Carlton, Prescott L. Deininger, Enhanced evolutionary PCR using oligonucleotides with inosine at the 3'-terminus, Nucleic Acids Research, vol. 19, Issue 18, Sep. 25, 1991, p. 5081.

Ohtsuka E, Matsuki S, Ikehara M, Takahashi Y, Matsubara K. An alternative approach to deoxyoligonucleotides as hybridization probes by insertion of deoxyinosine at ambiguous codon positions. J Biol Chem. Mar. 10, 1985;260(5):2605-8.

Rossolini GM, Cresti S, Ingianni A, Cattani P, Riccio ML, Satta G. Use of deoxyinosine-containing primers vs degenerate primers for polymerase chain reaction based on ambiguous sequence information. Mol Cell Probes. Apr. 1994;8(2):91-8.

Leicher T, Bähring R, Isbrandt D, Pongs O. Coexpression of the KCNA3B gene product with Kv1.5 leads to a novel A-type potassium channel. J Biol Chem. Dec. 25, 1998;273(52):35095-101.

Köhler, G., Milstein, C. Continuous cultures of fused cells secreting antibody of predefined specificity. Nature 256, 495-497 (1975).

Kozbor D, Roder JC. The production of monoclonal antibodies from human lymphocytes. Immunol Today. Mar. 1983;4(3):72-9.

International Search Report and Written Opinion filed in international application PCT/US21/16104 mailed on Jun. 30, 2021.

Marks JD, Griffiths AD, Malmqvist M, Clackson TP, Bye JM, Winter G. By-passing immunization: building high affinity human antibodies by chain shuffling. Biotechnology (N Y). Jul. 1992;10(7):779-83.

Lonberg N, Taylor LD, Harding FA, Trounstine M, Higgins KM, Schramm SR, Kuo CC, Mashayekh R, Wymore K, McCabe JG, et al. Antigen-specific human antibodies from mice comprising four distinct genetic modifications. Nature. Apr. 28, 1994;368(6474):856-9.

Morrison, S. Success in specification. Nature 368, 812-813 (1994).

Fishwild, D., O'Donnell, S., Bengoechea, T. et al. High-avidity human IgGK monoclonal antibodies from a novel strain of minilocus transgenic mice. Nat Biotechnol 14, 845-851 (1996).

Neuberger M. Generating high-avidity human Mabs in mice. Nat Biotechnol. Jul. 1996; 14(7):826.

Lonberg N, Huszar D. Human antibodies from transgenic mice. Int Rev Immunol. 1995; 13(1):65-93.

Traunecker A, Lanzavecchia A, Karjalainen K. Bispecific single chain molecules (Janusins) target cytotoxic lymphocytes on HIV infected cells. Embo J. Dec. 1991;10(12):3655-9.

Suresh MR, Cuello AC, Milstein C. Bispecific monoclonal antibodies from hybrid hybridomas. Methods Enzymol. 1986;121:210-28.

Jones PT, Dear PH, Foote J, Neuberger MS, Winter G. Replacing the complementarity-determining regions in a human antibody with those from a mouse. Nature. May 29-Jun. 4, 1986;321(6069):522-5.

Riechmann L, Clark M, Waldmann H, Winter G. Reshaping human antibodies for therapy. Nature. Mar. 24, 1988;332(6162):323-7.

Verhoeyen M, Milstein C, Winter G. Reshaping human antibodies: grafting an antilysozyme activity. Science. Mar. 25, 1988;239(4847):1534-6.

Leonard G. Presta, Antibody engineering, Current Opinion in Structural Biology, vol. 2, Issue 4, 1992, pp. 593-596.

Wu AM, Senter PD. Arming antibodies: prospects and challenges for immunoconjugates. Nat Biotechnol. Sep. 2005;23(9):1137-46.

Henikoff S, Henikoff JG. Amino acid substitution matrices from protein blocks. Proc Natl Acad Sci U S A. Nov. 15, 1992;89(22):10915-9.

International Search Report and Written Opinion in International Application PCT/US2021/016103 Mailed on Apr. 29, 2021.

* cited by examiner

Scfv-scfv-Fc x Fab-Fc trispecific molecules anti-CD3    anti-CD28    anti-CD137 anti-CD28
anti-DLL3 anti-CD3
anti-DLL3 anti-CD28
anti-DLL3 anti-CD3
anti-CD137
anti-DLL3 anti-CD137
anti-DLL3 anti-CD137
anti-DLL3

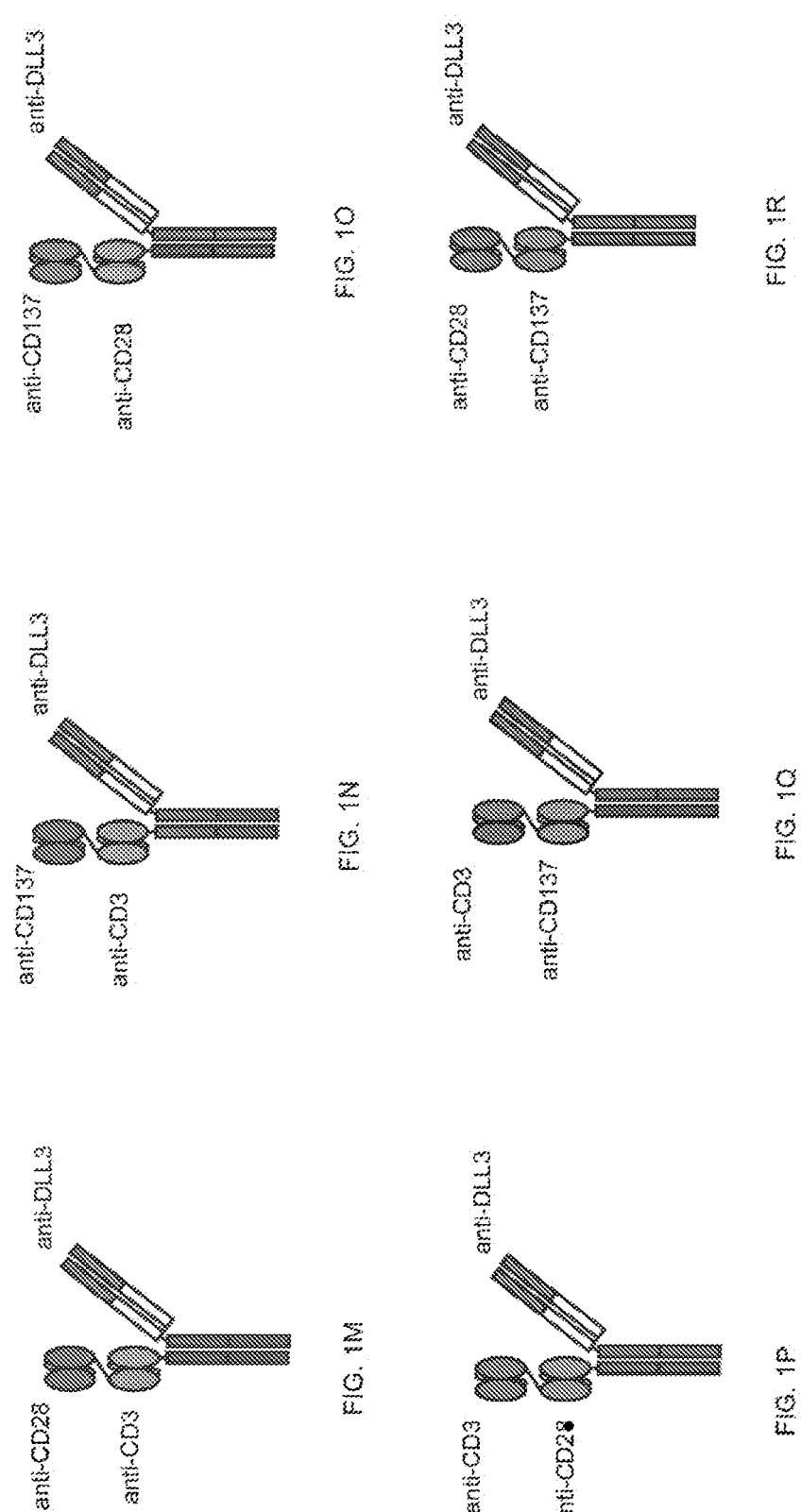

Anti-DLL3 antibodies binding to huDLL3 Expressing CHO cells
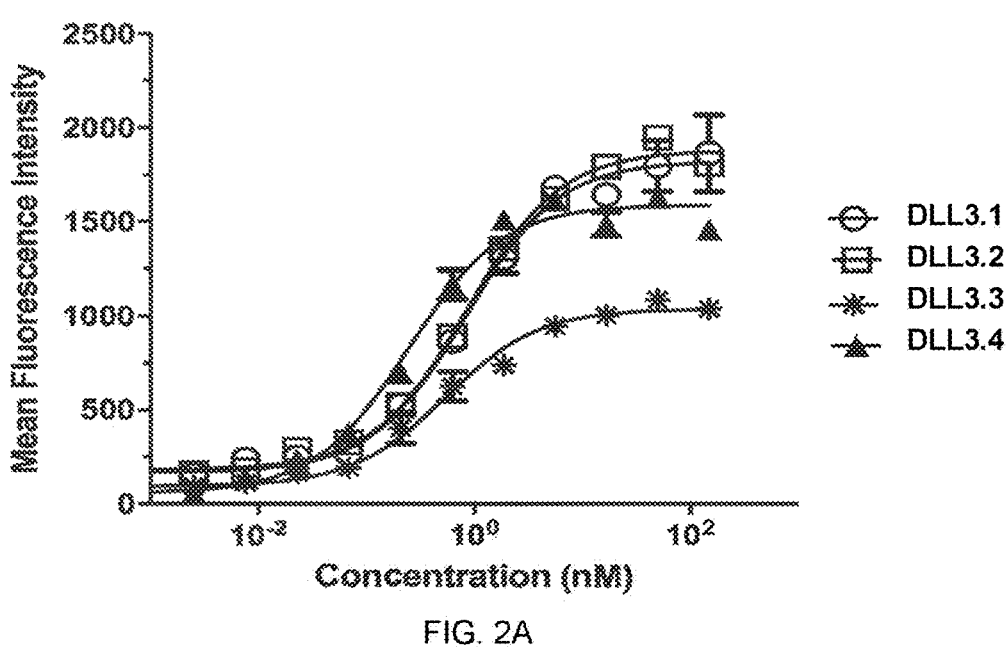
FIG. 2A
Anti-DLL3 binding to Cyno DLL3 CHO
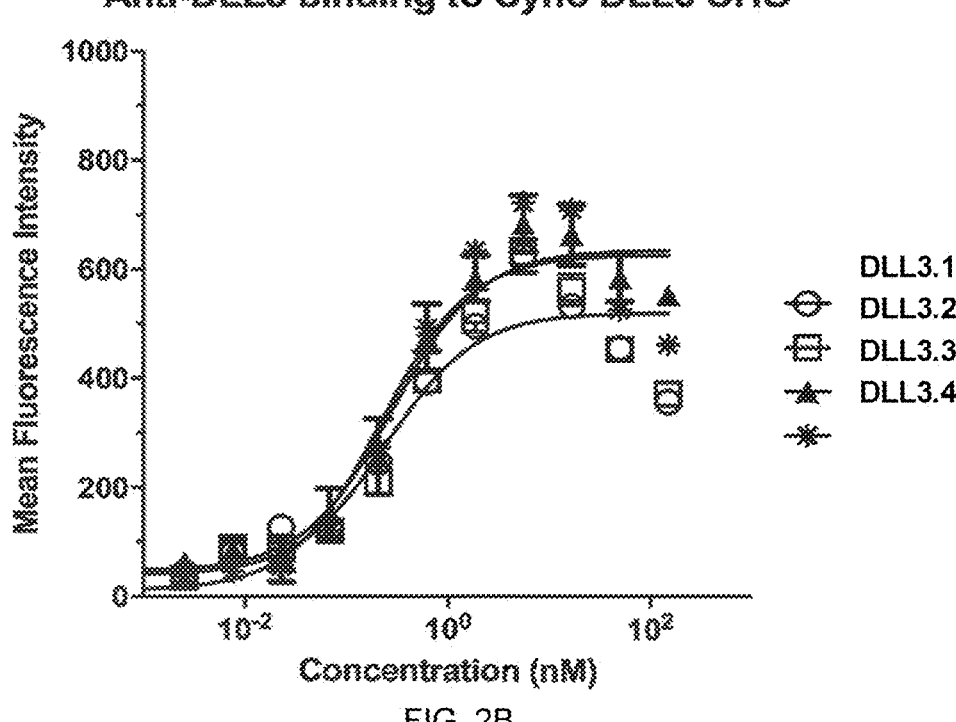
FIG. 2B

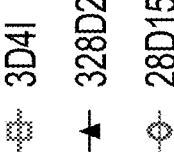
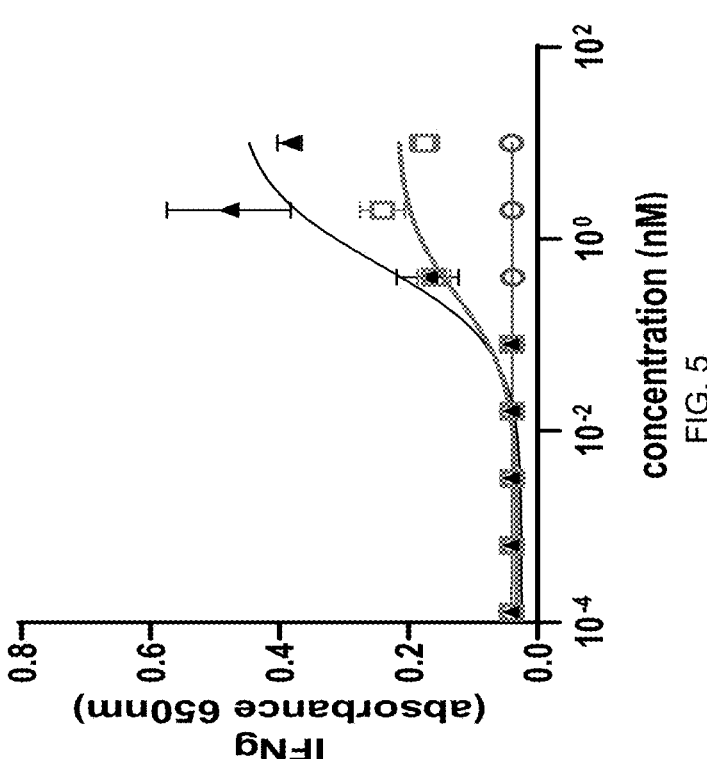
FIG. 5

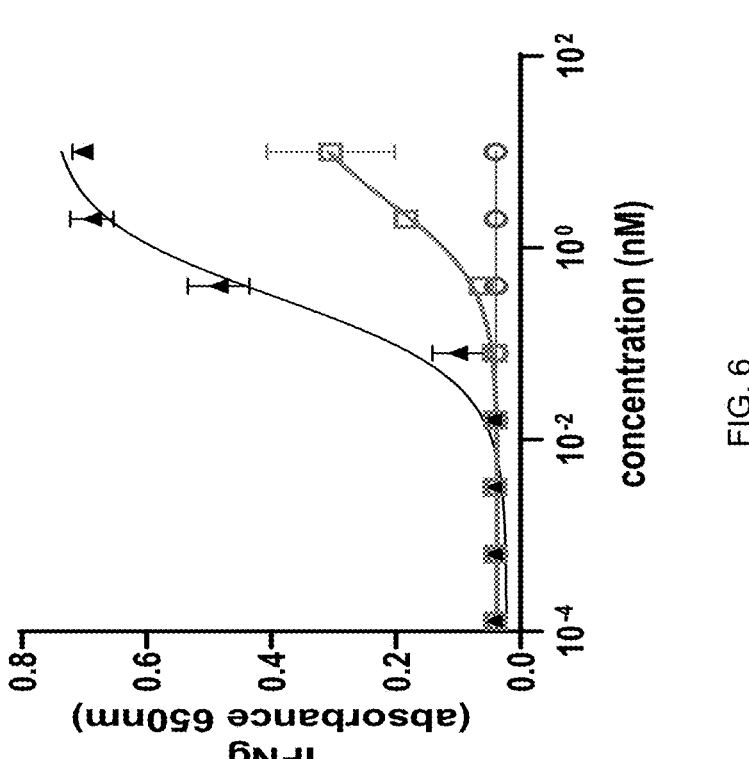
FIG. 6

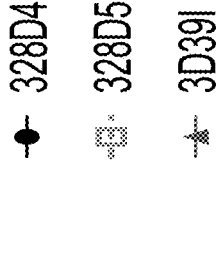
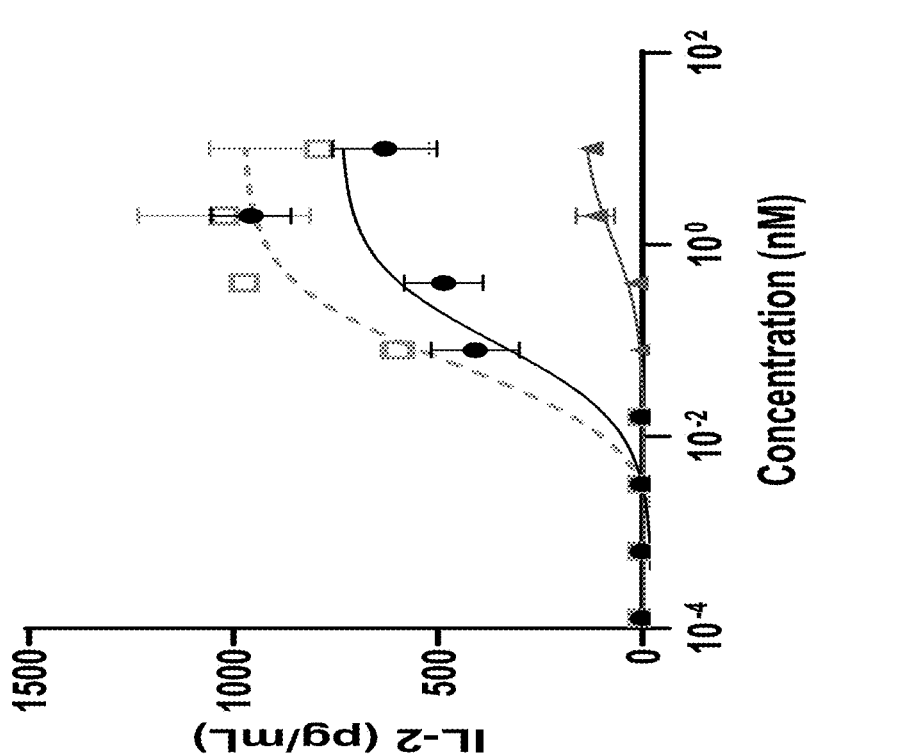
FIG. 7

Bispecific molecules with two CD137 Fab fragments

Bispecific and Trispecific molecules with two Cd137 scfv fragments

Scfv-scfv-Fc x Fab-Fc trispecific molecules anti-CD28 anti-CD3 anti-MUC17

FIG. 10A anti-CD3 anti-CD137 anti-MUC17

FIG. 10B anti-CD28 anti-CD137 anti-MUC17

FIG. 10C anti-CD3 anti-CD28 anti-MUC17

FIG. 10D anti-CD3 anti-CD137 anti-MUC17

FIG. 10E anti-CD137 anti-CD28 anti-MUC17

FIG. 10F anti-CD137
anti-MUC17
anti-CD28 anti-CD28
anti-MUC17
anti-CD137 anti-CD137
anti-MUC17
anti-CD3 anti-CD3
anti-MUC17
anti-CD137 anti-CD28
anti-MUC17
anti-CD3 anti-CD3
anti-MUC17
anti-CD28

MUC17xCD3 Bispecifics bind ASPC1 cells

FIG. 11B

MUC17xCD3 Bispecifics bind CHO Cell Expressing Muc17

FIG. 11A hu1MU11A and hu1MU32A retain Muc17 binding activity in the ScFv format

CD3xCD28xMuc17 trispecific molecules have similar maximum killing of ASPC1 cells by PBMCs as the CD3 bispecific 3M62I Muc17xCD3xcD28 Trispecific molecules 328M2, 328M3, 328M4, and 328M5 activate PBMCs in the presence of ASPC1 cells to secrete IL-2 at levels higher than that of the CD3 bispecific, 3M62I CD3Scfv x CD28SScfvxMUC17-Fab trispecific molecules 328M1 and 328M2 activate T-cells to kill MUC17-CHO cells better than the CD3 bispecific 3M55I, and similar to the combination of CD3 and CD28 bispecifics,3M55I + 28M3

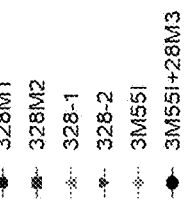
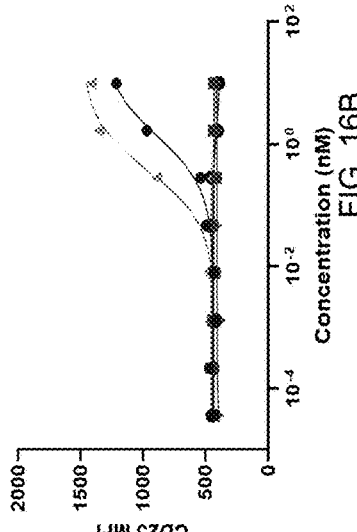
FIG. 16B
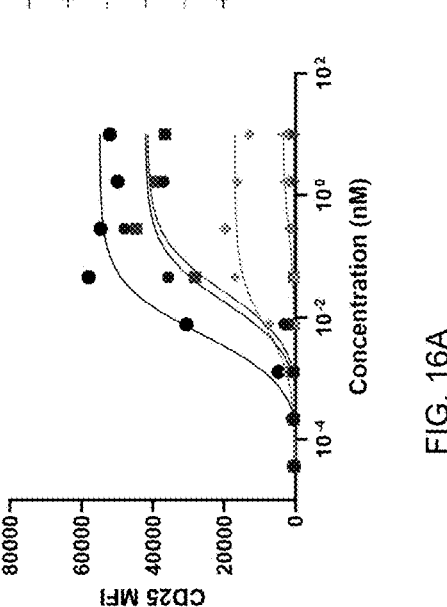
FIG. 16A

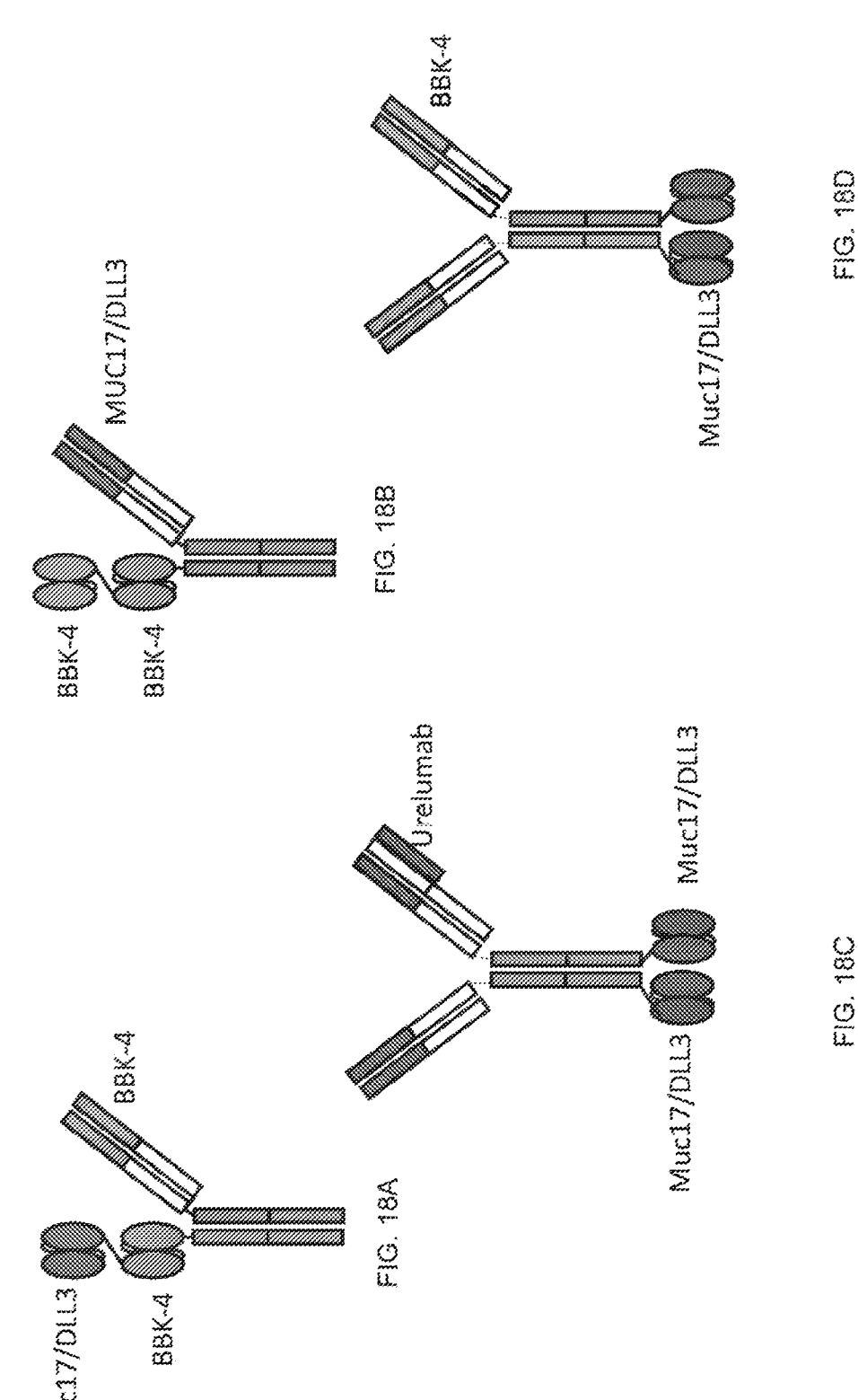

Muc17x CD137 molecules
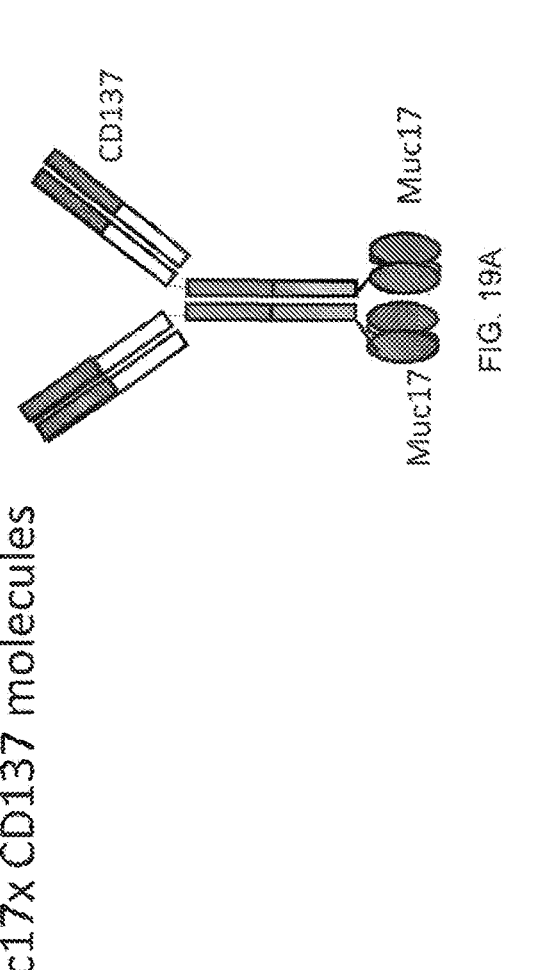
FIG. 19A
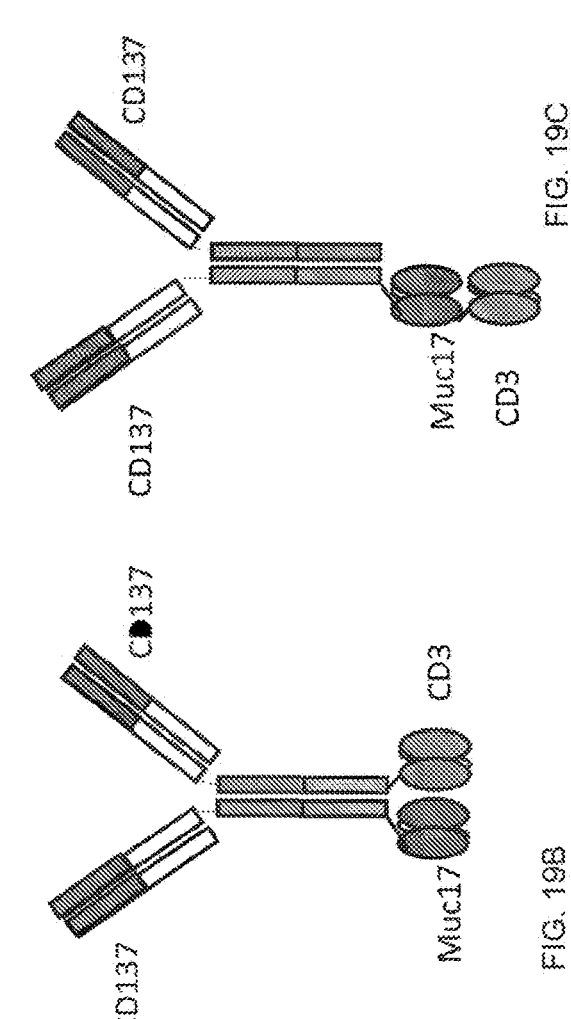
FIG. 19B
FIG. 19C

Scfv-scfv-Fc x Fab-Fc trispecific molecules anti-CD28
anti-CD3
anti-CLDN18.2

FIG. 20A anti-CD137
anti-CD3
anti-CLDN18.2

FIG. 20B anti-CD28
anti-CD137
anti-CLDN18.2

FIG. 20C anti-CD3
anti-CD28
anti-CLDN18.2

FIG. 20D anti-CD3
anti-CD137
anti-CLDN18.2

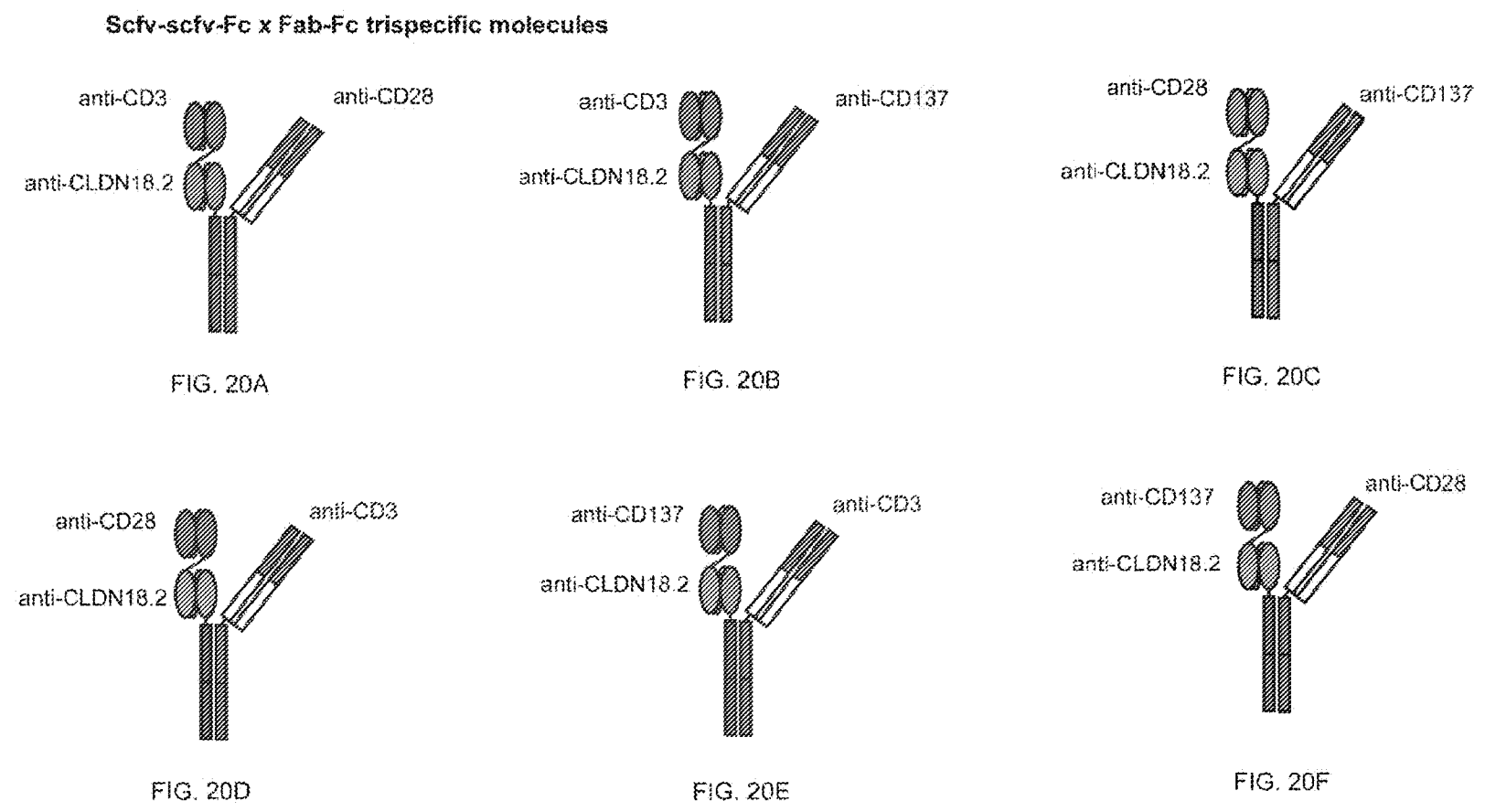

FIG. 20E anti-CD28
anti-CD137
anti-CLDN18.2

FIG. 20F

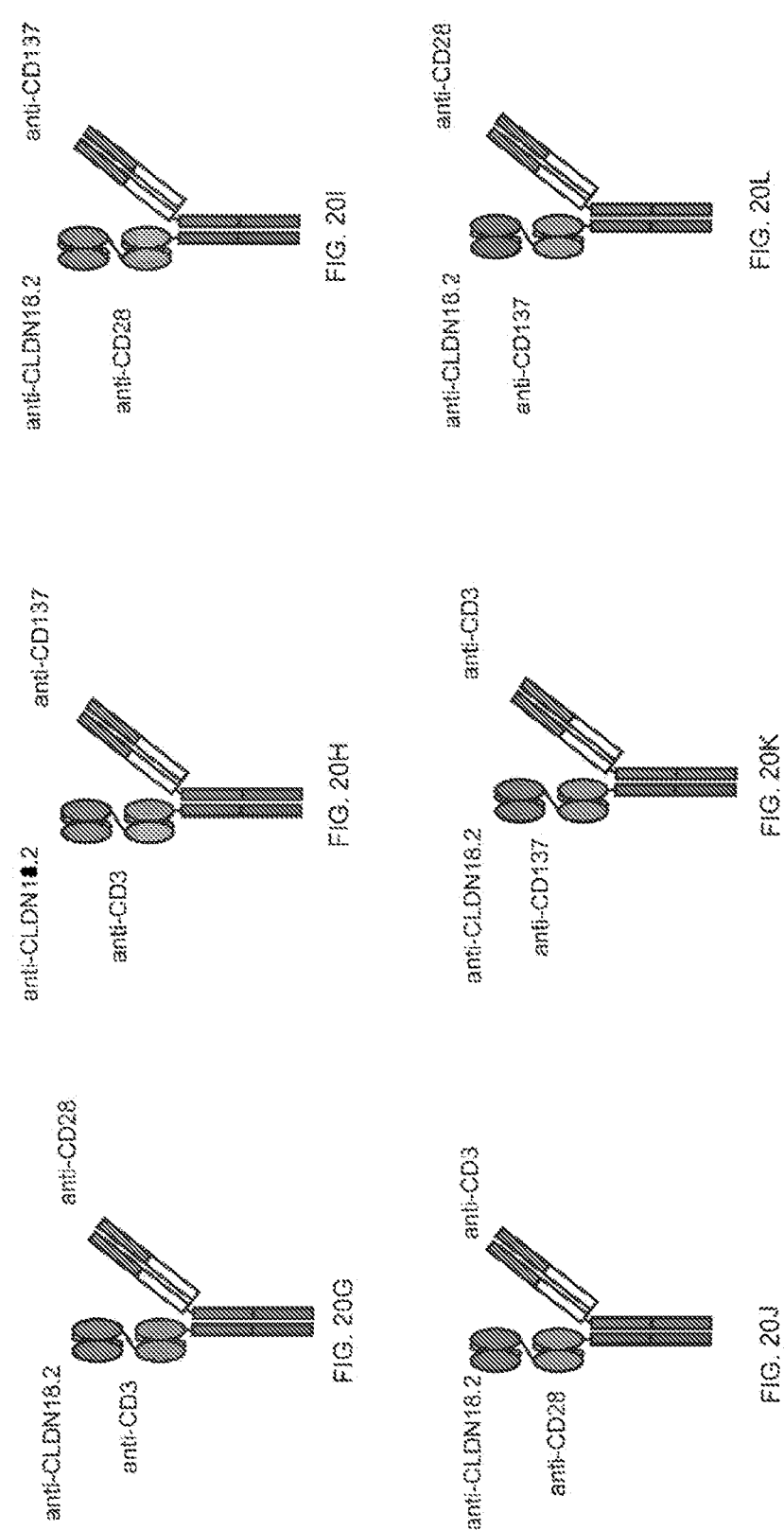

Trispecific molecules 328C1, 328C 2, 328C3, 328C4 activate T-cells to secrete IL-2 better to a greater level than the 3C27l CD3xCldn18.2 bite alone.

CD3xCD137xCldn18.2 trispecific molecules 34C4 and 34C3 activate PBMCs in the presence of SNU-601 cells to express more CD25 than 3C18I CD3xCD137xCldn18.2 trispecific molecules 34C4 and 34C3 activate PBMCs in the presence of SNU-601 cells to secrete more IFNgamma than 3C18I alone CD3xCD137xCLDN18.2 trispecific 34C3 increases CD8 T cell numbers beyond what is stimulated by the CD3 T cell engager 3C27I in the presence of CHO cells expressing CLDN18.2

SEQUENCE LISTING

Sequence total quantity: 509
SEQ ID NO: 1          moltype = AA   length = 10
FEATURE               Location/Qualifiers
REGION                1..10

-continued

```
                          note = Description of Artificial Sequence: Synthetic peptide
source                    1..10
                          mol_type = protein
                          organism = synthetic construct
SEQUENCE: 1
DYIFSNYYIE                                                                           10

SEQ ID NO: 2              moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 2
DYTFSNYYIE                                                                           10

SEQ ID NO: 3              moltype = AA  length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 3
DYYMN                                                                                5

SEQ ID NO: 4              moltype = AA  length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 4
DYYVN                                                                                5

SEQ ID NO: 5              moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 5
GFTFSNYGMH                                                                           10

SEQ ID NO: 6              moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 6
GFTFSSYGMH                                                                           10

SEQ ID NO: 7              moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 7
GFTFSSYGMH                                                                           10

SEQ ID NO: 8              moltype = AA  length = 6
FEATURE                   Location/Qualifiers
REGION                    1..6
                          note = Description of Artificial Sequence: Synthetic peptide
source                    1..6
                          mol_type = protein
                          organism = synthetic construct
SEQUENCE: 8
SAYYWN                                                                               6

SEQ ID NO: 9              moltype = AA  length = 5
FEATURE                   Location/Qualifiers
```

```
REGION                   1..5
                         note = Description of Artificial Sequence: Synthetic peptide
source                   1..5
                         mol_type = protein
                         organism = synthetic construct
SEQUENCE: 9
SYYWS                                                                     5

SEQ ID NO: 10            moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 10
EILPGNGNTV YNEKFKD                                                        17

SEQ ID NO: 11            moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 11
EILPGTGNTV YNEKFKD                                                        17

SEQ ID NO: 12            moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 12
IISPNDGGTN YNQKFKG                                                        17

SEQ ID NO: 13            moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 13
VINPDNGITT YNQKFKG                                                        17

SEQ ID NO: 14            moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 14
VINPYNDITI YNQKFQG                                                        17

SEQ ID NO: 15            moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 15
VISGSGSSKY YADSVKG                                                        17

SEQ ID NO: 16            moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 16
VISHHGSSKY YADSVKG                                                        17

SEQ ID NO: 17            moltype = AA  length = 17
```

-continued

```
FEATURE             Location/Qualifiers
REGION              1..17
                    note = Description of Artificial Sequence: Synthetic peptide
source              1..17
                    mol_type = protein
                    organism = synthetic construct
SEQUENCE: 17
VISHHGSSKY YARSVKG                                                    17

SEQ ID NO: 18       moltype = AA   length = 17
FEATURE             Location/Qualifiers
REGION              1..17
                    note = Description of Artificial Sequence: Synthetic peptide
source              1..17
                    mol_type = protein
                    organism = synthetic construct
SEQUENCE: 18
VISYDGSSKY YADSVKG                                                    17

SEQ ID NO: 19       moltype = AA   length = 16
FEATURE             Location/Qualifiers
REGION              1..16
                    note = Description of Artificial Sequence: Synthetic peptide
source              1..16
                    mol_type = protein
                    organism = synthetic construct
SEQUENCE: 19
YISDVGHNYY NPSLKN                                                     16

SEQ ID NO: 20       moltype = AA   length = 16
FEATURE             Location/Qualifiers
REGION              1..16
                    note = Description of Artificial Sequence: Synthetic peptide
source              1..16
                    mol_type = protein
                    organism = synthetic construct
SEQUENCE: 20
YISDVGSNNY NPSLKN                                                     16

SEQ ID NO: 21       moltype = AA   length = 16
FEATURE             Location/Qualifiers
REGION              1..16
                    note = Description of Artificial Sequence: Synthetic peptide
source              1..16
                    mol_type = protein
                    organism = synthetic construct
SEQUENCE: 21
YVYYSGTTNY NPSLKS                                                     16

SEQ ID NO: 22       moltype = AA   length = 9
FEATURE             Location/Qualifiers
REGION              1..9
                    note = Description of Artificial Sequence: Synthetic peptide
source              1..9
                    mol_type = protein
                    organism = synthetic construct
SEQUENCE: 22
WGDYALFAN                                                             9

SEQ ID NO: 23       moltype = AA   length = 6
FEATURE             Location/Qualifiers
REGION              1..6
                    note = Description of Artificial Sequence: Synthetic peptide
source              1..6
                    mol_type = protein
                    organism = synthetic construct
SEQUENCE: 23
DQVFAY                                                                6

SEQ ID NO: 24       moltype = AA   length = 9
FEATURE             Location/Qualifiers
REGION              1..9
                    note = Description of Artificial Sequence: Synthetic peptide
source              1..9
                    mol_type = protein
                    organism = synthetic construct
SEQUENCE: 24
DWFFYLFDY                                                             9
```

-continued

```
SEQ ID NO: 25          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 25
DWFYFIFDY                                                      9

SEQ ID NO: 26          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 26
DWWELVFDY                                                      9

SEQ ID NO: 27          moltype = AA  length = 13
FEATURE                Location/Qualifiers
REGION                 1..13
                       note = Description of Artificial Sequence: Synthetic peptide
source                 1..13
                       mol_type = protein
                       organism = synthetic construct
SEQUENCE: 27
EGVLYDGYYE GAY                                                 13

SEQ ID NO: 28          moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 28
GVWNYERSFD Y                                                   11

SEQ ID NO: 29          moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 29
SIAVTGFYFD Y                                                   11

SEQ ID NO: 30          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 30
SASSSVSYMH                                                     10

SEQ ID NO: 31          moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 31
KASQNVGIAV A                                                   11

SEQ ID NO: 32          moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 32
KASQNVGTNV A                                                   11
```

```
SEQ ID NO: 33            moltype = AA   length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 33
KSSQSLLHSD AKTFLY                                                    16

SEQ ID NO: 34            moltype = AA   length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 34
KSSQSLLHSD GKTFLY                                                    16

SEQ ID NO: 35            moltype = AA   length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 35
RASESVHSYG NSLIH                                                     15

SEQ ID NO: 36            moltype = AA   length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 36
RSSKSLLHSN GITYLY                                                    16

SEQ ID NO: 37            moltype = AA   length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 37
RSSQSLLHSD AKTFLD                                                    16

SEQ ID NO: 38            moltype = AA   length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 38
RSSQSLLHSD GKTFLD                                                    16

SEQ ID NO: 39            moltype = AA   length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 39
SASYRYS                                                              7

SEQ ID NO: 40            moltype = AA   length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 40
```

```
AASNRYT                                                                 7

SEQ ID NO: 41              moltype = AA  length = 7
FEATURE                    Location/Qualifiers
REGION                     1..7
                           note = Description of Artificial Sequence: Synthetic peptide
source                     1..7
                           mol_type = protein
                           organism = synthetic construct
SEQUENCE: 41
DTSKLAS                                                                  7

SEQ ID NO: 42              moltype = AA  length = 7
FEATURE                    Location/Qualifiers
REGION                     1..7
                           note = Description of Artificial Sequence: Synthetic peptide
source                     1..7
                           mol_type = protein
                           organism = synthetic construct
SEQUENCE: 42
EVSNRAS                                                                  7

SEQ ID NO: 43              moltype = AA  length = 7
FEATURE                    Location/Qualifiers
REGION                     1..7
                           note = Description of Artificial Sequence: Synthetic peptide
source                     1..7
                           mol_type = protein
                           organism = synthetic construct
SEQUENCE: 43
EVSNRFS                                                                  7

SEQ ID NO: 44              moltype = AA  length = 7
FEATURE                    Location/Qualifiers
REGION                     1..7
                           note = Description of Artificial Sequence: Synthetic peptide
source                     1..7
                           mol_type = protein
                           organism = synthetic construct
SEQUENCE: 44
QMSNLAS                                                                  7

SEQ ID NO: 45              moltype = AA  length = 7
FEATURE                    Location/Qualifiers
REGION                     1..7
                           note = Description of Artificial Sequence: Synthetic peptide
source                     1..7
                           mol_type = protein
                           organism = synthetic construct
SEQUENCE: 45
RASNLES                                                                  7

SEQ ID NO: 46              moltype = AA  length = 7
FEATURE                    Location/Qualifiers
REGION                     1..7
                           note = Description of Artificial Sequence: Synthetic peptide
source                     1..7
                           mol_type = protein
                           organism = synthetic construct
SEQUENCE: 46
SASYRYS                                                                  7

SEQ ID NO: 47              moltype = AA  length = 9
FEATURE                    Location/Qualifiers
REGION                     1..9
                           note = Description of Artificial Sequence: Synthetic peptide
source                     1..9
                           mol_type = protein
                           organism = synthetic construct
SEQUENCE: 47
QQYSTYPYT                                                               9

SEQ ID NO: 48              moltype = AA  length = 7
FEATURE                    Location/Qualifiers
REGION                     1..7
                           note = Description of Artificial Sequence: Synthetic peptide
source                     1..7
                           mol_type = protein
                           organism = synthetic construct
```

```
SEQUENCE: 48
AQNLELP                                                                    7

SEQ ID NO: 49          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 49
LQGERLPFT                                                                  9

SEQ ID NO: 50          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 50
LQGIHLPFT                                                                  9

SEQ ID NO: 51          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 51
LQGRELPFT                                                                  9

SEQ ID NO: 52          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 52
QQTNEDP                                                                    7

SEQ ID NO: 53          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 53
QQWSSNPLT                                                                  9

SEQ ID NO: 54          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 54
QQYNNYPLT                                                                  9

SEQ ID NO: 55          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 55
QQYNSYPFT                                                                  9

SEQ ID NO: 56          moltype = AA  length = 118
FEATURE                Location/Qualifiers
REGION                 1..118
                       note = Description of Artificial Sequence: Synthetic
                        polypeptide
source                 1..118
```

```
                                 mol_type = protein
                                 organism = synthetic construct
SEQUENCE: 56
EVQLLESGGG LVQPGGSLRL SCAASGFTFS SYGMHWVRQA PGKGLEWVAV ISGSGSSKYY   60
ADSVKGRFTI SRDNSKNTLY LQMNSLRAED TAVYYCARDW FFYLFDYWGQ GTLVTVSS     118

SEQ ID NO: 57              moltype = AA  length = 118
FEATURE                    Location/Qualifiers
REGION                     1..118
                           note = Description of Artificial Sequence: Synthetic
                            polypeptide
source                     1..118
                           mol_type = protein
                           organism = synthetic construct
SEQUENCE: 57
EVQLLESGGG LVQPGGSLRL SCAASGFTFS SYGMHWVRQA PGKGLEWVAV ISGSGSSKYY   60
ADSVKGRFTI SRDNSKNTLY LQMNSLRAED TAVYYCARDW FYFIFDYWGQ GTLVTVSS     118

SEQ ID NO: 58              moltype = AA  length = 118
FEATURE                    Location/Qualifiers
REGION                     1..118
                           note = Description of Artificial Sequence: Synthetic
                            polypeptide
source                     1..118
                           mol_type = protein
                           organism = synthetic construct
SEQUENCE: 58
EVQLLESGGG LVQPGGSLRL SCAASGFTFS SYGMHWVRQA PGKGLEWVAV ISHHGSSKYY   60
ADSVKGRFTI SRDNSKNTLY LQMNSLRAED TAVYYCARDW FFYLFDYWGQ GTLVTVSS     118

SEQ ID NO: 59              moltype = AA  length = 118
FEATURE                    Location/Qualifiers
REGION                     1..118
                           note = Description of Artificial Sequence: Synthetic
                            polypeptide
source                     1..118
                           mol_type = protein
                           organism = synthetic construct
SEQUENCE: 59
EVQLLESGGG LVQPGGSLRL SCAASGFTFS SYGMHWVRQA PGKGLEWVAV ISHHGSSKYY   60
ADSVKGRFTI SRDNSKNTLY LQMNSLRAED TAVYYCARDW FYFIFDYWGQ GTLVTVSS     118

SEQ ID NO: 60              moltype = AA  length = 118
FEATURE                    Location/Qualifiers
REGION                     1..118
                           note = Description of Artificial Sequence: Synthetic
                            polypeptide
source                     1..118
                           mol_type = protein
                           organism = synthetic construct
SEQUENCE: 60
EVQLLESGGG LVQPGGSLRL SCAASGFTFS SYGMHWVRQA PGKGLEWVAV ISYDGSSKYY   60
ADSVKGRFTI SRDNSKNTLY LQMNSLRAED TAVYYCARDW FFYLFDYWGQ GTLVTVSS     118

SEQ ID NO: 61              moltype = AA  length = 118
FEATURE                    Location/Qualifiers
REGION                     1..118
                           note = Description of Artificial Sequence: Synthetic
                            polypeptide
source                     1..118
                           mol_type = protein
                           organism = synthetic construct
SEQUENCE: 61
EVQLLESGGG LVQPGGSLRL SCAASGFTFS SYGMHWVRQA PGKGLEWVAV ISYDGSSKYY   60
ADSVKGRFTI SRDNSKNTLY LQMNSLRAED TAVYYCARDW FYFIFDYWGQ GTLVTVSS     118

SEQ ID NO: 62              moltype = AA  length = 118
FEATURE                    Location/Qualifiers
REGION                     1..118
                           note = Description of Artificial Sequence: Synthetic
                            polypeptide
source                     1..118
                           mol_type = protein
                           organism = synthetic construct
SEQUENCE: 62
EVQLLESGGG LVQPGGSLRL SCAASGFTFS SYGMHWVRQA PGKGLEWVSV ISHHGSSKYY   60
ADSVKGRFTI SRDNSKNTLY LQMNSLRAED TAVYYCAKDW FFYLFDYWGQ GTLVTVSS     118

SEQ ID NO: 63              moltype = AA  length = 118
```

```
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 63
EVQLLESGGG LVQPGGSLRL SCAASGFTFS SYGMHWVRQA PGKGLEWVSV ISHHGSSKYY   60
ADSVKGRFTI SRDNSKNTLY LQMNSLRAED TAVYYCAKDW FYFIFDYWGQ GTLVTVSS    118

SEQ ID NO: 64           moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 64
EVQLQQSGPV LVKPGASVKM SCKASGFTFT DYYMNWVKQS HGKSLEWIGV INPDNGITTY   60
NQKFKGKATL TVDKSSSTAY MELNGLTSED SAVYYCARGV WNYERSFDYW GQGTTLTVSS  120

SEQ ID NO: 65           moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 65
EVQLVESGGG LVQPGGSLRL SCAASGFTFS NYGMHWVRQA PGKGLEWVAV ISHHGSSKYY   60
ADSVKGRYTI SRDNSKNTLY LQMNSLRAED TAVYYCARDW FFYLFDYWGQ GTLVTVSS    118

SEQ ID NO: 66           moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 66
QVQLQESGPG LVKPSETLSL TCTVSGGSIS SYYWSWIRQP PGKGLEWIGY VYYSGTTNYN   60
PSLKSRVTIS VDTSKNQFSL KLSSVTAADT AVYYCASIAV TGFYFDYWGQ GTLVTVSS    118

SEQ ID NO: 67           moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 67
QVQLQQSGPV LVKPGASVKM SCKASGYSFT DYYVNWVKQS HGKSLEWIGI ISPNDGGTNY   60
NQKFKGKATL TVDKSSSTAY MEVNSLTSED SAVYYCARDD DLGWYFDVWG TGTTVTVSS   119

SEQ ID NO: 68           moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
SEQUENCE: 68
QVQLVESGGG AVQPGRSLRL SCAASGFTFS NYGMHWVRQA PGKGLEWVAV ISHHGSSKYY   60
ARSVKGRFTI SRDNSKNTLY LEMNSLRAED TAVYYCARDW WELVFDYWGQ GTLVTVSS    118

SEQ ID NO: 69           moltype = AA  length = 118
FEATURE                 Location/Qualifiers
REGION                  1..118
                        note = Description of Artificial Sequence: Synthetic
                         polypeptide
source                  1..118
                        mol_type = protein
                        organism = synthetic construct
```

-continued

```
SEQUENCE: 69
QVQLVESGGG VVQPGRSLRL SCAASGFTFS NYGMHWVRQA PGKGLEWVAV ISHHGSSKYY   60
ADSVKGRFTI SRDNSKNTLY LQMNSLRAED TAVYYCARDW FFYLFDYWGQ GTLVTVSS    118

SEQ ID NO: 70          moltype = AA   length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 70
QVQLVESGGG VVQPGRSLRL SCAASGFTFS NYGMHWVRQA PGKGLEWVAV ISHHGSSKYY   60
ADSVKGRFTI SRDNSKNTLY LQMNSLRAED TAVYYCARDW FYFIFDYWGQ GTLVTVSS    118

SEQ ID NO: 71          moltype = AA   length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 71
QVQLVQSGAE VKKPGASVKV SCKASDYTFS NYYIEWVRQA PGQGLEWMGE ILPGNGNTVY   60
NEKFKDRVTM TVDTSTSTAY MELRSLRSDD TAVYYCARWG DYALFANWGQ GTLVTVSS    118

SEQ ID NO: 72          moltype = AA   length = 122
FEATURE                Location/Qualifiers
REGION                 1..122
                       note = Description of Artificial Sequence: Synthetic
                        polypeptide
source                 1..122
                       mol_type = protein
                       organism = synthetic construct
SEQUENCE: 72
QVQLVQSGAE VKKPGASVKV SCKASGYTFT DYFMNWVRQA PGQGLEWMGV INPYNDITIY   60
NQKFQGRVTM TVDRSTSTVY MELSSLRSED TAVYYCAREG VLYDGYYEGA YWGQGTLVTV  120
SS                                                                 122

SEQ ID NO: 73          moltype = AA   length = 118
FEATURE                Location/Qualifiers
REGION                 1..118
                       note = Description of Artificial Sequence: Synthetic
                        polypeptide
source                 1..118
                       mol_type = protein
                       organism = synthetic construct
SEQUENCE: 73
QVQLVQSGAE VKKPGASVKV SCKATDYIFS NYYIEWVRQA PGQGLEWMGE ILPGTGNTVY   60
NEKFKDRVTM TVDTSTSTVY MELSSLRSED TAVYYCARWG DYALFANWGQ GTLVTVSS    118

SEQ ID NO: 74          moltype = AA   length = 116
FEATURE                Location/Qualifiers
REGION                 1..116
                       note = Description of Artificial Sequence: Synthetic
                        polypeptide
source                 1..116
                       mol_type = protein
                       organism = synthetic construct
SEQUENCE: 74
SDVQLQESGP GLVKPSQSLS LTCSVTGYSI TSAYYWNWIR QFPGNKLEWM GYISDVGHNY   60
YNPSLKNRIS ITRDTSKNQF FLKLNSVTPE DTATYYCARD QVFAYWGQGT LVTVSA      116

SEQ ID NO: 75          moltype = AA   length = 115
FEATURE                Location/Qualifiers
REGION                 1..115
                       note = Description of Artificial Sequence: Synthetic
                        polypeptide
source                 1..115
                       mol_type = protein
                       organism = synthetic construct
SEQUENCE: 75
SDVQLQESGP GLVKPSQSLS LTCSVTGYSI TSAYYWNWIR QFPGNKLEWM GYISDVGSNN   60
YNPSLKNRIS ITRDTFKNQF FLKLNSVTTE DTATYFCTRD QVFAYWGQGT LVTVS       115

SEQ ID NO: 76          moltype = AA   length = 107
FEATURE                Location/Qualifiers
```

```
REGION                    1..107
                          note = Description of Artificial Sequence: Synthetic
                           polypeptide
source                    1..107
                          mol_type = protein
                          organism = synthetic construct
SEQUENCE: 76
DIQLTQSPSF LSASVGDRVT ITCKASQNVG IAVAWYQQKP GKAPKLLIYA ASNRYTGVPS  60
RFSGSGSGTE FTLTISSLQP EDFATYYCQQ YSTYPYTFGQ GTKLEIK              107

SEQ ID NO: 77             moltype = AA  length = 107
FEATURE                   Location/Qualifiers
REGION                    1..107
                          note = Description of Artificial Sequence: Synthetic
                           polypeptide
source                    1..107
                          mol_type = protein
                          organism = synthetic construct
SEQUENCE: 77
DIQMTQSPSF LSASVGDRVT ITCKASQNVG TNVAWYQQKP GKAPKPLIYS TSYRYSGVPS  60
RFSGSGSGTE FTLTISSLQP EDFATYYCQQ YNNYPLTFGG GTKVEIK             107

SEQ ID NO: 78             moltype = AA  length = 112
FEATURE                   Location/Qualifiers
REGION                    1..112
                          note = Description of Artificial Sequence: Synthetic
                           polypeptide
source                    1..112
                          mol_type = protein
                          organism = synthetic construct
SEQUENCE: 78
DIQMTQSPSS LSASVGDRVT ITCKSSQSLL HSDAKTFLYW YQQKPGKAPK LLIYEVSNRF  60
SGVPSRFSGS GSGTDFTLTI SSLQPEDFAT YYCLQGERLP FTFGQGTKVE IK        112

SEQ ID NO: 79             moltype = AA  length = 107
FEATURE                   Location/Qualifiers
REGION                    1..107
                          note = Description of Artificial Sequence: Synthetic
                           polypeptide
source                    1..107
                          mol_type = protein
                          organism = synthetic construct
SEQUENCE: 79
DIQMTQSPST LSASVGDRVT ITCKASQNVG TNVAWYQQKP GKAPKALIYS ASYRYSGVPS  60
RFSGSGSGTE FTLTISSLQP DDFATYYCQQ YNSYPFTFGQ GTKLEIK             107

SEQ ID NO: 80             moltype = AA  length = 112
FEATURE                   Location/Qualifiers
REGION                    1..112
                          note = Description of Artificial Sequence: Synthetic
                           polypeptide
source                    1..112
                          mol_type = protein
                          organism = synthetic construct
SEQUENCE: 80
DIVMTQAAFS NPVTVGTSAS ISCRSSKSLL HSNGITYLYW YLQKPGQSPQ LLIYQMSNLA  60
SGVPDRFSSS GSGTDFTLRI SRVEAEDVGV YYCAQNLELP WTFGGGTKLE IK        112

SEQ ID NO: 81             moltype = AA  length = 107
FEATURE                   Location/Qualifiers
REGION                    1..107
                          note = Description of Artificial Sequence: Synthetic
                           polypeptide
source                    1..107
                          mol_type = protein
                          organism = synthetic construct
SEQUENCE: 81
DIVMTQSPKF MSTSVGDRVS VTCKASQNVG TNVAWYQQKP GQSPKALIYS ASYRYSGVPD  60
RFTGSGSGTD FTLTFSSVQS EDLAEYFCQQ YNNYPLTFGG GTKLEIK            107

SEQ ID NO: 82             moltype = AA  length = 112
FEATURE                   Location/Qualifiers
REGION                    1..112
                          note = Description of Artificial Sequence: Synthetic
                           polypeptide
source                    1..112
                          mol_type = protein
                          organism = synthetic construct
SEQUENCE: 82
```

-continued

```
DIVMTQSPLS LPVTPGEPAS ISCKSSQSLL HSDAKTFLYW YLQKPGQSPQ LLIYEVSNRF  60
SGVPDRFSGS GSGTDFTLKI SRVEAEDVGV YYCLQGRELP FTFGQGTKVE IK          112

SEQ ID NO: 83            moltype = AA  length = 112
FEATURE                  Location/Qualifiers
REGION                   1..112
                         note = Description of Artificial Sequence: Synthetic
                          polypeptide
source                   1..112
                         mol_type = protein
                         organism = synthetic construct
SEQUENCE: 83
DIVMTQSPLS LPVTPGEPAS ISCKSSQSLL HSDGKTFLYW YLQKPGQSPQ LLIYEVSNRF  60
SGVPDRFSGS GSGTDFTLKI SRVEAEDVGV YYCLQGERLP FTFGQGTKVE IK          112

SEQ ID NO: 84            moltype = AA  length = 112
FEATURE                  Location/Qualifiers
REGION                   1..112
                         note = Description of Artificial Sequence: Synthetic
                          polypeptide
source                   1..112
                         mol_type = protein
                         organism = synthetic construct
SEQUENCE: 84
DIVMTQSPLS LPVTPGEPAS ISCRSSQSLL HSDAKTFLDW YLQKPGQSPQ LLIYEVSNRA  60
SGVPDRFSGS GSGTDFTLKI SRVEAEDVGV YYCLQGRELP FTFGQGTKVE IK          112

SEQ ID NO: 85            moltype = AA  length = 112
FEATURE                  Location/Qualifiers
REGION                   1..112
                         note = Description of Artificial Sequence: Synthetic
                          polypeptide
source                   1..112
                         mol_type = protein
                         organism = synthetic construct
SEQUENCE: 85
DIVMTQSPLS LPVTPGEPAS ISCRSSQSLL HSDGKTFLDW YLQKPGQSPQ LLIYEVSNRA  60
SGVPDRFSGS GSGTDFTLKI SRVEAEDVGV YYCLQGERLP FTFGQGTKVE IK          112

SEQ ID NO: 86            moltype = AA  length = 112
FEATURE                  Location/Qualifiers
REGION                   1..112
                         note = Description of Artificial Sequence: Synthetic
                          polypeptide
source                   1..112
                         mol_type = protein
                         organism = synthetic construct
SEQUENCE: 86
DIVMTQTPLS LSVTPGQPAS ISCKSSQSLL HSDAKTFLYW YLQKPGQPPQ LLIYEVSNRF  60
SGVPDRFSGS GSGTDFTLKI SRVEAEDVGV YYCLQGRELP FTFGPGTKVE IK          112

SEQ ID NO: 87            moltype = AA  length = 112
FEATURE                  Location/Qualifiers
REGION                   1..112
                         note = Description of Artificial Sequence: Synthetic
                          polypeptide
source                   1..112
                         mol_type = protein
                         organism = synthetic construct
SEQUENCE: 87
DIVMTQTPLS LSVTPGQPAS ISCKSSQSLL HSDGKTFLYW YLQKPGQPPQ LLIYEVSNRF  60
SGVPDRFSGS GSGTDFTLKI SRVEAEDVGV YYCLQGERLP FTFGPGTKVE IK          112

SEQ ID NO: 88            moltype = AA  length = 112
FEATURE                  Location/Qualifiers
REGION                   1..112
                         note = Description of Artificial Sequence: Synthetic
                          polypeptide
source                   1..112
                         mol_type = protein
                         organism = synthetic construct
SEQUENCE: 88
DIVMTQTPLS LSVTPGQPAS ISCKSSQSLL HSDGKTFLYW YLQKPGQPPQ LLIYEVSNRF  60
SGVPDRFSGS GSGTDFTLKI SRVEAEDVGV YYCLQGIHLP FTFGPGTKVE IK          112

SEQ ID NO: 89            moltype = AA  length = 111
FEATURE                  Location/Qualifiers
REGION                   1..111
                         note = Description of Artificial Sequence: Synthetic
```

```
                           polypeptide
source                     1..111
                           mol_type = protein
                           organism = synthetic construct
SEQUENCE: 89
DTVLTQSPAS LAVSLGQRAT ISCRASESVH SYGNSLIHWY QQKPGQPPRL LIYRASNLES  60
GIPARFSGSG SRTDFTLTIN PVEADDVATY YCQQTNEDPL TFGAGTKLEL K            111

SEQ ID NO: 90              moltype = AA  length = 108
FEATURE                    Location/Qualifiers
REGION                     1..108
                           note = Description of Artificial Sequence: Synthetic
                            polypeptide
source                     1..108
                           mol_type = protein
                           organism = synthetic construct
SEQUENCE: 90
EIVLTQSPGT LSLSPGERVT LSCRASQRVN NNYLAWYQQR PGQAPRLLIY GASSRATGIP  60
DRFSGSGSGT DFTLTISRLE PEDFAVYYCQ QYDRSPLTFG GGTKLEIK               108

SEQ ID NO: 91              moltype = AA  length = 106
FEATURE                    Location/Qualifiers
REGION                     1..106
                           note = Description of Artificial Sequence: Synthetic
                            polypeptide
source                     1..106
                           mol_type = protein
                           organism = synthetic construct
SEQUENCE: 91
QIVLTQSPAI MSASPGEKVT MTCSASSSVS YMHWYQQKSG TSPKRWIYDT SKLASGVPAR  60
FSGSGSGTSY SLTISSMEAE DAATYYCQQW SSNPLTFGAG TKLELK                 106

SEQ ID NO: 92              moltype = AA  length = 10
FEATURE                    Location/Qualifiers
REGION                     1..10
                           note = Description of Artificial Sequence: Synthetic peptide
source                     1..10
                           mol_type = protein
                           organism = synthetic construct
SEQUENCE: 92
GFTFSSFGMH                                                         10

SEQ ID NO: 93              moltype = AA  length = 10
FEATURE                    Location/Qualifiers
REGION                     1..10
                           note = Description of Artificial Sequence: Synthetic peptide
source                     1..10
                           mol_type = protein
                           organism = synthetic construct
SEQUENCE: 93
GYAFSDYWIN                                                         10

SEQ ID NO: 94              moltype = AA  length = 10
FEATURE                    Location/Qualifiers
REGION                     1..10
                           note = Description of Artificial Sequence: Synthetic peptide
source                     1..10
                           mol_type = protein
                           organism = synthetic construct
SEQUENCE: 94
GYEFSSHWMN                                                         10

SEQ ID NO: 95              moltype = AA  length = 10
FEATURE                    Location/Qualifiers
REGION                     1..10
                           note = Description of Artificial Sequence: Synthetic peptide
source                     1..10
                           mol_type = protein
                           organism = synthetic construct
SEQUENCE: 95
GYIFSNHWMN                                                         10

SEQ ID NO: 96              moltype = AA  length = 10
FEATURE                    Location/Qualifiers
REGION                     1..10
                           note = Description of Artificial Sequence: Synthetic peptide
source                     1..10
                           mol_type = protein
                           organism = synthetic construct
```

-continued

```
SEQUENCE: 96
GYTFTSYWLN                                                              10

SEQ ID NO: 97          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 97
GYTFTSYWMN                                                              10

SEQ ID NO: 98          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct SEQUENCE: 98
GYTFTSYWMN                                                              10

SEQ ID NO: 99          moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 99
MIHPSDSESR LNQKFKD                                                      17

SEQ ID NO: 100         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct SEQUENCE: 100
MIHPSDSETR LNQEFKD                                                      17

SEQ ID NO: 101         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 101
MIHPSDSETR LNQKFKD                                                      17

SEQ ID NO: 102         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 102
MIHPSDSETR LNQKFTD                                                      17

SEQ ID NO: 103         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 103
QIYPGDGDIN YNEKFRG                                                      17

SEQ ID NO: 104         moltype = AA  length = 17
FEATURE                Location/Qualifiers
REGION                 1..17
                       note = Description of Artificial Sequence: Synthetic peptide
source                 1..17
                       mol_type = protein
```

```
                          organism = synthetic construct
SEQUENCE: 104
QIYPGDGDIN YNGKFRG                                                 17

SEQ ID NO: 105           moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 105
QVYPGDDDIN YNGKFRG                                                 17

SEQ ID NO: 106           moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 106
YISSGSSTIY YADTVKG                                                 17

SEQ ID NO: 107           moltype = AA  length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 107
HGNYVMDY                                                           8

SEQ ID NO: 108           moltype = AA  length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 108
HGNYVMDY                                                           8

SEQ ID NO: 109           moltype = AA  length = 12
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 109
QGIITSVQEF AY                                                      12

SEQ ID NO: 110           moltype = AA  length = 12
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 110
QGVITSVQEF AY                                                      12

SEQ ID NO: 111           moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 111
WGYYGSSYFA Y                                                       11

SEQ ID NO: 112           moltype = AA  length = 8
FEATURE                  Location/Qualifiers
REGION                   1..8
                         note = Description of Artificial Sequence: Synthetic peptide
source                   1..8
```

```
                              mol_type = protein
                              organism = synthetic construct
SEQUENCE: 112
HGNYLMDY                                                              8

SEQ ID NO: 113                moltype = AA   length = 10
FEATURE                       Location/Qualifiers
REGION                        1..10
                              note = Description of Artificial Sequence: Synthetic peptide
source                        1..10
                              mol_type = protein
                              organism = synthetic construct
SEQUENCE: 113
SASSSLNYIY                                                            10

SEQ ID NO: 114                moltype = AA   length = 10
FEATURE                       Location/Qualifiers
REGION                        1..10
                              note = Description of Artificial Sequence: Synthetic peptide
source                        1..10
                              mol_type = protein
                              organism = synthetic construct
SEQUENCE: 114
SASSSVNYIF                                                            10

SEQ ID NO: 115                moltype = AA   length = 10
FEATURE                       Location/Qualifiers
REGION                        1..10
                              note = Description of Artificial Sequence: Synthetic peptide
source                        1..10
                              mol_type = protein
                              organism = synthetic construct
SEQUENCE: 115
SASSSVNYIY                                                            10

SEQ ID NO: 116                moltype = AA   length = 10
FEATURE                       Location/Qualifiers
REGION                        1..10
                              note = Description of Artificial Sequence: Synthetic peptide
source                        1..10
                              mol_type = protein
                              organism = synthetic construct
SEQUENCE: 116
SASSSVSYMF                                                            10

SEQ ID NO: 117                moltype = AA   length = 10
FEATURE                       Location/Qualifiers
REGION                        1..10
                              note = Description of Artificial Sequence: Synthetic peptide
source                        1..10
                              mol_type = protein
                              organism = synthetic construct
SEQUENCE: 117
SVSSNVDYVF                                                            10

SEQ ID NO: 118                moltype = AA   length = 11
FEATURE                       Location/Qualifiers
REGION                        1..11
                              note = Description of Artificial Sequence: Synthetic peptide
source                        1..11
                              mol_type = protein
                              organism = synthetic construct
SEQUENCE: 118
KASEDIYNRL A                                                          11

SEQ ID NO: 119                moltype = AA   length = 7
FEATURE                       Location/Qualifiers
REGION                        1..7
                              note = Description of Artificial Sequence: Synthetic peptide
source                        1..7
                              mol_type = protein
                              organism = synthetic construct
SEQUENCE: 119
RTSNLAS                                                               7

SEQ ID NO: 120                moltype = AA   length = 7
FEATURE                       Location/Qualifiers
REGION                        1..7
                              note = Description of Artificial Sequence: Synthetic peptide
```

```
source                    1..7
                          mol_type = protein
                          organism = synthetic construct
SEQUENCE: 120
RTSNLAT                                                                     7

SEQ ID NO: 121            moltype = AA   length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 121
GATNLET                                                                     7

SEQ ID NO: 122            moltype = AA   length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 122
QQFHDYPRT                                                                   9

SEQ ID NO: 123            moltype = AA   length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 123
QQFHSYPRT                                                                   9

SEQ ID NO: 124            moltype = AA   length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 124
QQFWRTPPT                                                                   9

SEQ ID NO: 125            moltype = AA   length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 125
QQYHSYPLT                                                                   9

SEQ ID NO: 126            moltype = AA   length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 126
CQQFWRTPPT                                                                  10

SEQ ID NO: 127            moltype = AA   length = 117
FEATURE                   Location/Qualifiers
REGION                    1..117
                          note = Description of Artificial Sequence: Synthetic
                           polypeptide
source                    1..117
                          mol_type = protein
                          organism = synthetic construct
SEQUENCE: 127
EVQLVQSGAE VKKPGESLKI SCKGSGYEFS SHWMNWVRQM PGKGLEWMGQ IYPGDGDINY  60
NEKFRGQVTI SADKSISTAY LQWSSLKASD TAMYYCARHG NYVMDYWGQG TLVTVSS     117

SEQ ID NO: 128            moltype = AA   length = 121
```

-continued

```
FEATURE            Location/Qualifiers
REGION             1..121
                   note = Description of Artificial Sequence: Synthetic
                    polypeptide
source             1..121
                   mol_type = protein
                   organism = synthetic construct
SEQUENCE: 128
QVQLVQSGAE VKKPGSSVKV SCKASGYTFT SYWLNWVRQA PGQGLEWMGM IHPSDSESRL   60
NQKFKDRVTI TADKSTSTAY MELSSLRSED TAVYYCARQG IITSVQEFAY WGQGTLVTVS   120
S                                                                   121

SEQ ID NO: 129         moltype = AA  length = 117
FEATURE            Location/Qualifiers
REGION             1..117
                   note = Description of Artificial Sequence: Synthetic
                    polypeptide
source             1..117
                   mol_type = protein
                   organism = synthetic construct
SEQUENCE: 129
QVQLVQSGAE VKKPGASVKV SCKASGYEFS SHWMNWVRQA PGQGLEWMGQ IYPGDGDINY   60
NEKFRGRVTM TRDTSTSTVY MELSSLRSED TAVYYCARHG NYVMDYWGQG TLVTVSS      117

SEQ ID NO: 130         moltype = AA  length = 121
FEATURE            Location/Qualifiers
REGION             1..121
                   note = Description of Artificial Sequence: Synthetic
                    polypeptide
source             1..121
                   mol_type = protein
                   organism = synthetic construct
SEQUENCE: 130
QVQLVQSGAE VKKPGASVKV SCKASGYTFT SYWMNWVRQA PGQGLEWIGM IHPSDSETRL   60
NQKFKDRVTL TVDKSSSTAY MELSSLRSED TAVYYCARQG IITSVQEFAY WGQGTLVTVS   120
S                                                                   121

SEQ ID NO: 131         moltype = AA  length = 121
FEATURE            Location/Qualifiers
REGION             1..121
                   note = Description of Artificial Sequence: Synthetic
                    polypeptide
source             1..121
                   mol_type = protein
                   organism = synthetic construct
SEQUENCE: 131
QVQLVQSGAE VKKPGASVKV SCKASGYTFT SYWMNWVRQA PGQGLEWMGM IHPSDSETRL   60
NQEFKDRVTM TRDTSTSTVY MELSSLRSED TAVYYCARQG VITSVQEFAY WGQGTLVTVS   120
S                                                                   121

SEQ ID NO: 132         moltype = AA  length = 121
FEATURE            Location/Qualifiers
REGION             1..121
                   note = Description of Artificial Sequence: Synthetic
                    polypeptide
source             1..121
                   mol_type = protein
                   organism = synthetic construct
SEQUENCE: 132
QVQLVQSGAE VKKPGASVKV SCKASGYTFT SYWMNWVRQA PGQGLEWMGM IHPSDSETRL   60
NQKFKDRVTL TRDKSISTAY MELSRLRSDD TAVYYCARQG IITSVQEFAY WGQGTLVTVS   120
S                                                                   121

SEQ ID NO: 133         moltype = AA  length = 121
FEATURE            Location/Qualifiers
REGION             1..121
                   note = Description of Artificial Sequence: Synthetic
                    polypeptide
source             1..121
                   mol_type = protein
                   organism = synthetic construct
SEQUENCE: 133
QVQLVQSGAE VKKPGASVKV SCKASGYTFT SYWMNWVRQA PGQGLEWMGM IHPSDSETRL   60
NQKFKDRVTL TVDKSISTAY MELSRLRSDD TAVYYCARQG IITSVQEFAY WGQGTLVTVS   120
S                                                                   121

SEQ ID NO: 134         moltype = AA  length = 121
FEATURE            Location/Qualifiers
REGION             1..121
```

-continued

```
                            note = Description of Artificial Sequence: Synthetic
                             polypeptide
source                      1..121
                            mol_type = protein
                            organism = synthetic construct
SEQUENCE: 134
QVQLVQSGAE VKKPGASVKV SCKASGYTFT SYWMNWVRQA PGQGLEWMGM IHPSDSETRL  60
NQKFKDRVTL TVDTSISTAY MELSRLRSDD TAVYYCARQG IITSVQEFAY WGQGTLVTVS  120
S                                                                   121

SEQ ID NO: 135              moltype = AA  length = 121
FEATURE                     Location/Qualifiers
REGION                      1..121
                            note = Description of Artificial Sequence: Synthetic
                             polypeptide
source                      1..121
                            mol_type = protein
                            organism = synthetic construct
SEQUENCE: 135
QVQLVQSGAE VKKPGASVKV SCKASGYTFT SYWMNWVRQA PGQGLEWMGM IHPSDSETRL  60
NQKFKDRVTM TRDTSISTAY MELSRLRSDD TAVYYCARQG IITSVQEFAY WGQGTLVTVS  120
S                                                                   121

SEQ ID NO: 136              moltype = AA  length = 121
FEATURE                     Location/Qualifiers
REGION                      1..121
                            note = Description of Artificial Sequence: Synthetic
                             polypeptide
source                      1..121
                            mol_type = protein
                            organism = synthetic construct
SEQUENCE: 136
QVQLVQSGAE VKKPGASVKV SCKASGYTFT SYWMNWVRQA PGQGLEWMGM IHPSDSETRL  60
NQKFKDRVTM TRDTSTSTVY MELSSLRSED TAVYYCARQG IITSVQEFAY WGQGTLVTVS  120
S                                                                   121

SEQ ID NO: 137              moltype = AA  length = 121
FEATURE                     Location/Qualifiers
REGION                      1..121
                            note = Description of Artificial Sequence: Synthetic
                             polypeptide
source                      1..121
                            mol_type = protein
                            organism = synthetic construct
SEQUENCE: 137
QVQLVQSGAE VKKPGASVKV SCKASGYTFT SYWMNWVRQA PGQGLEWMGM IHPSDSETRL  60
NQKFKDRVTM TVDKSISTAY MELSRLRSDD TAVYYCARQG IITSVQEFAY WGQGTLVTVS  120
S                                                                   121

SEQ ID NO: 138              moltype = AA  length = 121
FEATURE                     Location/Qualifiers
REGION                      1..121
                            note = Description of Artificial Sequence: Synthetic
                             polypeptide
source                      1..121
                            mol_type = protein
                            organism = synthetic construct
SEQUENCE: 138
QVQLVQSGAE VKKPGASVKV SCKASGYTFT SYWMNWVRQA PGQGLEWMGM IHPSDSETRL  60
NQKFTDRVTM TRDTSTSTVY MELSSLRSED TAVYYCARQG IITSVQEFAY WGQGTLVTVS  120
S                                                                   121

SEQ ID NO: 139              moltype = AA  length = 117
FEATURE                     Location/Qualifiers
REGION                      1..117
                            note = Description of Artificial Sequence: Synthetic
                             polypeptide
source                      1..117
                            mol_type = protein
                            organism = synthetic construct
SEQUENCE: 139
QVQLVQSGAE VKKPGSSVKV SCKASGYAFS DYWINWVRQA PGQGLEWMGQ VYPGDDDINY  60
NGKFRGRVTI TADKSTSTAY MELSSLRSED TAVYYCARHG NYVMDYWGQG TTVTVSS     117

SEQ ID NO: 140              moltype = AA  length = 117
FEATURE                     Location/Qualifiers
REGION                      1..117
                            note = Description of Artificial Sequence: Synthetic
                             polypeptide
```

-continued

```
source                 1..117
                       mol_type = protein
                       organism = synthetic construct
SEQUENCE: 140
QVQLVQSGAE VKKPGSSVKV SCKASGYEFS SHWMNWVRQA PGQGLEWMGQ IYPGDGDINY  60
NEKFRGRVTI TADKSTSTAY MELSSLRSED TAVYYCARHG NYVMDYWGQG TTVTVSS     117

SEQ ID NO: 141         moltype = AA  length = 117
FEATURE                Location/Qualifiers
REGION                 1..117
                       note = Description of Artificial Sequence: Synthetic
                        polypeptide
source                 1..117
                       mol_type = protein
                       organism = synthetic construct
SEQUENCE: 141
QVQLVQSGAE VKKPGSSVKV SCKASGYIFS NHWMNWVRQA PGQGLEWMGQ IYPGDGDINY  60
NGKFRGRVTI TADKSTSTAY MELSSLRSED TAVYYCARHG NYLMDYWGQG TTVTVSS     117

SEQ ID NO: 142         moltype = AA  length = 121
FEATURE                Location/Qualifiers
REGION                 1..121
                       note = Description of Artificial Sequence: Synthetic
                        polypeptide
source                 1..121
                       mol_type = protein
                       organism = synthetic construct
SEQUENCE: 142
QVQLVQSGAE VKKPGSSVKV SCKASGYTFT SYWLNWVRQA PGQGLEWMGM IHPSDSESRL  60
NQKFKDRVTI TADKSTSTAY MELSSLRSED TAVYYCARQG IITSVQEFAY WGQGTLVTVS  120
S                                                                  121

SEQ ID NO: 143         moltype = AA  length = 121
FEATURE                Location/Qualifiers
REGION                 1..121
                       note = Description of Artificial Sequence: Synthetic
                        polypeptide
source                 1..121
                       mol_type = protein
                       organism = synthetic construct
SEQUENCE: 143
QVQLVQSGAE VKKPGSSVKV SCKASGYTFT SYWLNWVRQA PGQGLEWMGM IHPSDSETRL  60
NQKFKDRVTI TADKSTSTAY MELSSLRSED TAVYYCARQG IITSVQEFAY WGQGTLVTVS  120
S                                                                  121

SEQ ID NO: 144         moltype = AA  length = 121
FEATURE                Location/Qualifiers
REGION                 1..121
                       note = Description of Artificial Sequence: Synthetic
                        polypeptide
source                 1..121
                       mol_type = protein
                       organism = synthetic construct
SEQUENCE: 144
QVQLVQSGAE VKKPGSSVKV SCKASGYTFT SYWMNWVRQA PGQGLEWMGM IHPSDSESRL  60
NQKFKDRVTI TADKSTSTAY MELSSLRSED TAVYYCARQG IITSVQEFAY WGQGTLVTVS  120
S                                                                  121

SEQ ID NO: 145         moltype = AA  length = 121
FEATURE                Location/Qualifiers
REGION                 1..121
                       note = Description of Artificial Sequence: Synthetic
                        polypeptide
source                 1..121
                       mol_type = protein
                       organism = synthetic construct
SEQUENCE: 145
QVQLVQSGAE VKKPGSSVKV SCKASGYTFT SYWMNWVRQA PGQGLEWMGM IHPSDSETRL  60
NQKFKDRVTI TADKSTSTAY MELSSLRSED TAVYYCARQG IITSVQEFAY WGQGTLVTVS  120
S                                                                  121

SEQ ID NO: 146         moltype = AA  length = 120
FEATURE                Location/Qualifiers
REGION                 1..120
                       note = Description of Artificial Sequence: Synthetic
                        polypeptide
source                 1..120
                       mol_type = protein
                       organism = synthetic construct
```

```
SEQUENCE: 146
EVQLVESGGG LVQPGGSLRL SCAASGFTFS SFGMHWVRQA PGKGLEWVSY ISSGSSTIYY  60
ADTVKGRFTI SRDNAKNSLY LQMNSLRAED TAVYYCARWG YYGSSYFAYW GQGTLVTVSS  120

SEQ ID NO: 147        moltype = AA  length = 107
FEATURE               Location/Qualifiers
REGION                1..107
                      note = Description of Artificial Sequence: Synthetic
                       polypeptide
source                1..107
                      mol_type = protein
                      organism = synthetic construct
SEQUENCE: 147
DIQMTQSPSS LSASVGDRVT ITCKASEDIY NRLAWYQQKP GKAPKLLIYG ATNLETGVPS  60
RFSGSGSGTD FTFTISSLQP EDIATYYCQQ FWRTPPTFGG GTKVEIK               107

SEQ ID NO: 148        moltype = AA  length = 107
FEATURE               Location/Qualifiers
REGION                1..107
                      note = Description of Artificial Sequence: Synthetic
                       polypeptide
source                1..107
                      mol_type = protein
                      organism = synthetic construct
SEQUENCE: 148
DIQMTQSPSS LSASVGDRVT ITCKASEDIY NRLAWYQQKP GKAPKPLISG ATNLETGVPS  60
RFSGSGSGKD YTLTISSLQP EDIATYYCQQ FWRTPPTFGG GTKVEIK               107

SEQ ID NO: 149        moltype = AA  length = 107
FEATURE               Location/Qualifiers
REGION                1..107
                      note = Description of Artificial Sequence: Synthetic
                       polypeptide
source                1..107
                      mol_type = protein
                      organism = synthetic construct
SEQUENCE: 149
DIQMTQSPSS LSASVGDRVT ITCKASEDIY NRLAWYQQKP GKAPKPLISG ATNLETGVPS  60
RFSGSGSGTD FTFTISSLQP EDIATYYCQQ FWRTPPTFGG GTKVEIK               107

SEQ ID NO: 150        moltype = AA  length = 107
FEATURE               Location/Qualifiers
REGION                1..107
                      note = Description of Artificial Sequence: Synthetic
                       polypeptide
source                1..107
                      mol_type = protein
                      organism = synthetic construct
SEQUENCE: 150
DIQMTQSPSS LSASVGDRVT ITCKASEDIY NRLAWYQQKP GKAPKPLIYG ATNLETGVPS  60
RFSGSGSGTD FTFTISSLQP EDIATYYCQQ FWRTPPTFGG GTKVEIK               107

SEQ ID NO: 151        moltype = AA  length = 106
FEATURE               Location/Qualifiers
REGION                1..106
                      note = Description of Artificial Sequence: Synthetic
                       polypeptide
source                1..106
                      mol_type = protein
                      organism = synthetic construct
SEQUENCE: 151
EIVLTQSPAT LSLSPGERAT LSCSASSSVN YIFWYQQKPG QAPRLLIYRT SNLASGIPAR  60
FSGSGSGTDF TLTISSLEPE DFAVYYCQQY HSYPLTFGGG TKVEIK                106

SEQ ID NO: 152        moltype = AA  length = 106
FEATURE               Location/Qualifiers
REGION                1..106
                      note = Description of Artificial Sequence: Synthetic
                       polypeptide
source                1..106
                      mol_type = protein
                      organism = synthetic construct
SEQUENCE: 152
EIVLTQSPAT LSLSPGERAT LSCSASSSVN YIYWYQQKPG QAPRLLIYRT SNLASGIPAR  60
FSGSGSGTDF TLTISSLEPE DFAVYYCQQY HSYPLTFGGG TKVEIK                106

SEQ ID NO: 153        moltype = AA  length = 106
FEATURE               Location/Qualifiers
REGION                1..106
```

```
                           note = Description of Artificial Sequence: Synthetic
                            polypeptide
source                     1..106
                           mol_type = protein
                           organism = synthetic construct
SEQUENCE: 153
EIVLTQSPAT LSLSPGERAT LSCSASSSVS YMFWYQQKPG QAPRLLIYRT SNLASGIPAR  60
FSGSGSGTDF TLTISSLEPE DFAVYYCQQF HDYPRTFGGG TKVEIK                106

SEQ ID NO: 154            moltype = AA  length = 106
FEATURE                   Location/Qualifiers
REGION                    1..106
                          note = Description of Artificial Sequence: Synthetic
                           polypeptide
source                    1..106
                          mol_type = protein
                          organism = synthetic construct
SEQUENCE: 154
EIVLTQSPAT LSLSPGERAT LSCSASSSVS YMFWYQQKPG QAPRLLIYRT SNLASGIPAR  60
FSGSGSGTDF TLTISSLEPE DFAVYYCQQF HSYPRTFGGG TKVEIK                106

SEQ ID NO: 155            moltype = AA  length = 106
FEATURE                   Location/Qualifiers
REGION                    1..106
                          note = Description of Artificial Sequence: Synthetic
                           polypeptide
source                    1..106
                          mol_type = protein
                          organism = synthetic construct
SEQUENCE: 155
EIVLTQSPAT LSLSPGERAT LSCSASSSVS YMFWYQQKPG QAPRPWIYRT SNLASGIPPR  60
FSGSGSGTDY TLTISSLEPE DFAVYYCQQF HDYPRTFGGG TKVEIK                106

SEQ ID NO: 156            moltype = AA  length = 106
FEATURE                   Location/Qualifiers
REGION                    1..106
                          note = Description of Artificial Sequence: Synthetic
                           polypeptide
source                    1..106
                          mol_type = protein
                          organism = synthetic construct
SEQUENCE: 156
EIVLTQSPAT LSLSPGERAT LSCSVSSNVD YVFWYQQKPG QAPRLLIYRT SNLATGIPAR  60
FSGSGSGTDF TLTISSLEPE DFAVYYCQQF HSYPRTFGGG TKVEIK                106

SEQ ID NO: 157            moltype = AA  length = 106
FEATURE                   Location/Qualifiers
REGION                    1..106
                          note = Description of Artificial Sequence: Synthetic
                           polypeptide
source                    1..106
                          mol_type = protein
                          organism = synthetic construct
SEQUENCE: 157
EIVLTQSPAT LSVSPGERAT LSCSASSSVN YIYWYQQKPG QAPRPWIYRT SNLASGIPAR  60
FSGSGSGTEY TLTISSLQSE DFAVYYCQQY HSYPLTFGGG TKVEIK                106

SEQ ID NO: 158            moltype = AA  length = 106
FEATURE                   Location/Qualifiers
REGION                    1..106
                          note = Description of Artificial Sequence: Synthetic
                           polypeptide
source                    1..106
                          mol_type = protein
                          organism = synthetic construct
SEQUENCE: 158
EIVMTQSPAT LSVSPGERAT LSCSASSSLN YIYWYQQKPG QAPRLLIYRT SNLASGIPAR  60
FSGSGSGTEF TLTISSLQSE DFAVYYCQQY HSYPLTFGGG TKVEIK                106

SEQ ID NO: 159            moltype = AA  length = 106
FEATURE                   Location/Qualifiers
REGION                    1..106
                          note = Description of Artificial Sequence: Synthetic
                           polypeptide
source                    1..106
                          mol_type = protein
                          organism = synthetic construct
SEQUENCE: 159
EIVMTQSPAT LSVSPGERAT LSCSASSSVN YIYWYQQKPG QAPRLLIYRT SNLASGIPAR  60
```

```
FSGSGSGTEF TLTISSLQSE DFAVYYCQQY HSYPLTFGGG TKVEIK                   106

SEQ ID NO: 160          moltype = AA  length = 106
FEATURE                 Location/Qualifiers
REGION                  1..106
                        note = Description of Artificial Sequence: Synthetic
                         polypeptide
source                  1..106
                        mol_type = protein
                        organism = synthetic construct
SEQUENCE: 160
EIVMTQSPAT LSVSPGERAT LSCSASSSVS YMFWYQQKPG QAPRLLIYRT SNLASGIPAR   60
FSGSGSGTEF TLTISSLQSE DFAVYYCQQF HDYPRTFGGG TKVEIK                   106

SEQ ID NO: 161          moltype = AA  length = 105
FEATURE                 Location/Qualifiers
REGION                  1..105
                        note = Description of Artificial Sequence: Synthetic
                         polypeptide
source                  1..105
                        mol_type = protein
                        organism = synthetic construct
SEQUENCE: 161
IQLTQSPSFL SASVGDRVTI TCSASSSVSY MFWYQQKPGK APKLLIYRTS NLASGVPPRF   60
SGSGSGTEFT LTISSLQPED FATYYCQQFH DYPRTFGGGT KVEIK                    105

SEQ ID NO: 162          moltype = AA  length = 106
FEATURE                 Location/Qualifiers
REGION                  1..106
                        note = Description of Artificial Sequence: Synthetic
                         polypeptide
source                  1..106
                        mol_type = protein
                        organism = synthetic construct
SEQUENCE: 162
IQLTQSPSFL SASVGDRVTI TCSASSSVSY MFWYQQKPGK APKLLIYRTS NLASGVPPRF   60
SGSGSGTEYT LTISSLQPED FATYYCQQFH DYPRTFGGGT KVEIKR                   106

SEQ ID NO: 163          moltype = AA  length = 105
FEATURE                 Location/Qualifiers
REGION                  1..105
                        note = Description of Artificial Sequence: Synthetic
                         polypeptide
source                  1..105
                        mol_type = protein
                        organism = synthetic construct
SEQUENCE: 163
IQLTQSPSFL SASVGDRVTI TCSASSSVSY MFWYQQKPGK APKLLIYRTS NLASGVPSRF   60
SGSGSGTEFT LTISSLQPED FATYYCQQFH DYPRTFGGGT KVEIK                    105

SEQ ID NO: 164          moltype = AA  length = 105
FEATURE                 Location/Qualifiers
REGION                  1..105
                        note = Description of Artificial Sequence: Synthetic
                         polypeptide
source                  1..105
                        mol_type = protein
                        organism = synthetic construct
SEQUENCE: 164
IQLTQSPSFL SASVGDRVTI TCSASSSVSY MFWYQQKPGK APKLLIYRTS NLASGVPSRF   60
SGSGSGTEYT LTISSLQPED FATYYCQQFH DYPRTFGGGT KVEIK                    105

SEQ ID NO: 165          moltype = AA  length = 105
FEATURE                 Location/Qualifiers
REGION                  1..105
                        note = Description of Artificial Sequence: Synthetic
                         polypeptide
source                  1..105
                        mol_type = protein
                        organism = synthetic construct
SEQUENCE: 165
IQLTQSPSFL SASVGDRVTI TCSASSSVSY MFWYQQKPGK APKPWIYRTS NLASGVPPRF   60
SGSGSGTEYT LTISSLQPED FATYYCQQFH DYPRTFGGGT KVEIK                    105

SEQ ID NO: 166          moltype = AA  length = 105
FEATURE                 Location/Qualifiers
REGION                  1..105
                        note = Description of Artificial Sequence: Synthetic
                         polypeptide
```

-continued

```
source                   1..105
                         mol_type = protein
                         organism = synthetic construct
SEQUENCE: 166
IQLTQSPSFL SASVGDRVTI TCSASSSVSY MFWYQQKPGK APKPWIYRTS NLASGVPSRF  60
SGSGSGTEFT LTISSLQPED FATYYCQQFH DYPRTFGGGT KVEIK                 105

SEQ ID NO: 167          moltype = AA  length = 105
FEATURE                 Location/Qualifiers
REGION                  1..105
                        note = Description of Artificial Sequence: Synthetic
                         polypeptide
source                  1..105
                        mol_type = protein
                        organism = synthetic construct
SEQUENCE: 167
IQMTQSPSSL SASVGDRVTI TCSASSSVNY IFWYQQKPGK APKLLIYRTS NLASGVPSRF  60
SGSGSGTDFT LTISSLQPED FATYYCQQYH SYPLTFGGGT KVEIK                 105

SEQ ID NO: 168          moltype = AA  length = 105
FEATURE                 Location/Qualifiers
REGION                  1..105
                        note = Description of Artificial Sequence: Synthetic
                         polypeptide
source                  1..105
                        mol_type = protein
                        organism = synthetic construct
SEQUENCE: 168
IQMTQSPSSL SASVGDRVTI TCSASSSVNY IYWYQQKPGK APKLLIYRTS NLASGVPSRF  60
SGSGSGTDFT LTISSLQPED FATYYCQQYH SYPLTFGGGT KVEIK                 105

SEQ ID NO: 169          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 169
DIQMTQSPSS LSASVGDRVT ITCKASEDIY NRLAWYQQKP GKAPKLLIYG ATNLETGVPS  60
RFSGSGSGKD YTLTISSLQP EDIATYYCQQ FWRTPPTFGG GTKVEIK               107

SEQ ID NO: 170          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 170
GFTFSSFGMH                                                        10

SEQ ID NO: 171          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 171
GYAFNNYWMN                                                        10

SEQ ID NO: 172          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 172
GYAFSSYWMN                                                        10

SEQ ID NO: 173          moltype = AA  length = 10
FEATURE                 Location/Qualifiers
REGION                  1..10
                        note = Description of Artificial Sequence: Synthetic peptide
source                  1..10
                        mol_type = protein
```

```
                        organism = synthetic construct
SEQUENCE: 173
GYTFTNFGIT                                                          10

SEQ ID NO: 174          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 174
GYTFTNSGMN                                                          10

SEQ ID NO: 175          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 175
GYTFTNYGMN                                                          10

SEQ ID NO: 176          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 176
EIYPSSGNTF YNEKFKG                                                  17

SEQ ID NO: 177          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 177
QISPGNGNSN FNGKFKG                                                  17

SEQ ID NO: 178          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 178
QIYPGNGNSN FNGKFKA                                                  17

SEQ ID NO: 179          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 179
WINTNTGEPT FAEEFRG                                                  17

SEQ ID NO: 180          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 180
WINTNTGEPT YAEEFKG                                                  17

SEQ ID NO: 181          moltype = AA  length = 17
FEATURE                 Location/Qualifiers
REGION                  1..17
                        note = Description of Artificial Sequence: Synthetic peptide
source                  1..17
```

```
                                mol_type = protein
                                organism = synthetic construct
SEQUENCE: 181
YISSGNSAIY YADTVNG                                                         17

SEQ ID NO: 182          moltype = AA   length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 182
GGGPLRSRYF DY                                                              12

SEQ ID NO: 183          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 183
GGRFGNAMDY                                                                 10

SEQ ID NO: 184          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 184
GGRYGNAMDY                                                                 10

SEQ ID NO: 185          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 185
LRYGNSFDY                                                                  9

SEQ ID NO: 186          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 186
YFYGNSFVY                                                                  9

SEQ ID NO: 187          moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 187
YYYGNSFAY                                                                  9

SEQ ID NO: 188          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 188
KSSQSLLNSG NQKNYLT                                                         17

SEQ ID NO: 189          moltype = AA   length = 17
FEATURE                 Location/Qualifiers
REGION                  1..17
                        note = Description of Artificial Sequence: Synthetic peptide
```

-continued

```
source                      1..17
                            mol_type = protein
                            organism = synthetic construct
SEQUENCE: 189
KSSQSLLNSG NQRNYLT                                                    17

SEQ ID NO: 190              moltype = AA  length = 17
FEATURE                     Location/Qualifiers
REGION                      1..17
                            note = Description of Artificial Sequence: Synthetic peptide
source                      1..17
                            mol_type = protein
                            organism = synthetic construct
SEQUENCE: 190
RSSQSLFSSG NQKNYLT                                                    17

SEQ ID NO: 191              moltype = AA  length = 7
FEATURE                     Location/Qualifiers
REGION                      1..7
                            note = Description of Artificial Sequence: Synthetic peptide
source                      1..7
                            mol_type = protein
                            organism = synthetic construct
SEQUENCE: 191
WASTRES                                                               7

SEQ ID NO: 192              moltype = AA  length = 9
FEATURE                     Location/Qualifiers
REGION                      1..9
                            note = Description of Artificial Sequence: Synthetic peptide
source                      1..9
                            mol_type = protein
                            organism = synthetic construct
SEQUENCE: 192
QNAYFPYT                                                              9

SEQ ID NO: 193              moltype = AA  length = 9
FEATURE                     Location/Qualifiers
REGION                      1..9
                            note = Description of Artificial Sequence: Synthetic peptide
source                      1..9
                            mol_type = protein
                            organism = synthetic construct
SEQUENCE: 193
QNDYYYPLT                                                             9

SEQ ID NO: 194              moltype = AA  length = 9
FEATURE                     Location/Qualifiers
REGION                      1..9
                            note = Description of Artificial Sequence: Synthetic peptide
source                      1..9
                            mol_type = protein
                            organism = synthetic construct
SEQUENCE: 194
QNNYFPLT                                                              9

SEQ ID NO: 195              moltype = AA  length = 9
FEATURE                     Location/Qualifiers
REGION                      1..9
                            note = Description of Artificial Sequence: Synthetic peptide
source                      1..9
                            mol_type = protein
                            organism = synthetic construct
SEQUENCE: 195
QNNYNFPLT                                                             9

SEQ ID NO: 196              moltype = AA  length = 9
FEATURE                     Location/Qualifiers
REGION                      1..9
                            note = Description of Artificial Sequence: Synthetic peptide
source                      1..9
                            mol_type = protein
                            organism = synthetic construct
SEQUENCE: 196
QNNYYYPLT                                                             9

SEQ ID NO: 197              moltype = AA  length = 118
FEATURE                     Location/Qualifiers
REGION                      1..118
```

-continued

```
                            note = Description of Artificial Sequence: Synthetic
                             polypeptide
source                      1..118
                            mol_type = protein
                            organism = synthetic construct
SEQUENCE: 197
EVQLVESGGG LVQPGGSLRL SCAASGFTFS SFGMHWVRQA PGKGLEWVAY ISSGNSAIYY  60
ADTVNGRFTI SRDNPKNTLY LQMNSLRAED TAVYYCARLR YGNSFDYWGQ GTLVTVSS   118

SEQ ID NO: 198             moltype = AA  length = 118
FEATURE                    Location/Qualifiers
REGION                     1..118
                            note = Description of Artificial Sequence: Synthetic
                             polypeptide
source                      1..118
                            mol_type = protein
                            organism = synthetic construct
SEQUENCE: 198
EVQLVESGGG LVQPGGSLRL SCAASGFTFS SFGMHWVRQA PGKGLEWVSY ISSGNSAIYY  60
ADTVNGRFTI SRDNAKNSLY LQMNSLRAED TAVYYCARLR YGNSFDYWGQ GTLVTVSS   118

SEQ ID NO: 199             moltype = AA  length = 118
FEATURE                    Location/Qualifiers
REGION                     1..118
                            note = Description of Artificial Sequence: Synthetic
                             polypeptide
source                      1..118
                            mol_type = protein
                            organism = synthetic construct
SEQUENCE: 199
QIQLVQSGAE VKKPGASVKV SCKASGYTFT NSGMNWVRQA PGQGLEWMGW INTNTGEPTF  60
AEEFRGRVTF TLDTSASTAY MELSRLRSDD TAVYYCARYY YGNSFAYWGQ GTLVTVSS   118

SEQ ID NO: 200             moltype = AA  length = 121
FEATURE                    Location/Qualifiers
REGION                     1..121
                            note = Description of Artificial Sequence: Synthetic
                             polypeptide
source                      1..121
                            mol_type = protein
                            organism = synthetic construct
SEQUENCE: 200
QVQLVQSGAE VKKPGASVKV SCKASGYTFT NFGITWVRQA PGQGLEWIGE IYPSSGNTFY  60
NEKFKGRVTL TADKSSSAAY MELRSLRSDD TAVYYCARGG GPLRSRYFDY WGQGTLVTVS 120
S                                                                  121

SEQ ID NO: 201             moltype = AA  length = 121
FEATURE                    Location/Qualifiers
REGION                     1..121
                            note = Description of Artificial Sequence: Synthetic
                             polypeptide
source                      1..121
                            mol_type = protein
                            organism = synthetic construct
SEQUENCE: 201
QVQLVQSGAE VKKPGASVKV SCKASGYTFT NFGITWVRQA PGQGLEWMGE IYPSSGNTFY  60
NEKFKGRVTM TTDTSTSTAY MELRSLRSDD TAVYYCARGG GPLRSRYFDY WGQGTLVTVS 120
S                                                                  121

SEQ ID NO: 202             moltype = AA  length = 118
FEATURE                    Location/Qualifiers
REGION                     1..118
                            note = Description of Artificial Sequence: Synthetic
                             polypeptide
source                      1..118
                            mol_type = protein
                            organism = synthetic construct
SEQUENCE: 202
QVQLVQSGAE VKKPGASVKV SCKASGYTFT NSGMNWVRQA PGQGLEWMGW INTNTGEPTF  60
AEEFRGRVTM TRDTSISTAY MELSRLRSDD TAVYYCARYY YGNSFAYWGQ GTLVTVSS   118

SEQ ID NO: 203             moltype = AA  length = 118
FEATURE                    Location/Qualifiers
REGION                     1..118
                            note = Description of Artificial Sequence: Synthetic
                             polypeptide
source                      1..118
                            mol_type = protein
                            organism = synthetic construct
```

SEQUENCE: 203
QVQLVQSGAE VKKPGASVKV SCKASGYTFT NYGMNWVRQA PGQGLEWMGW INTNTGEPTY  60
AEEFKGRVTM TRDTSISTAY MELSRLRSDD TAVYYCARYF YGNSFVYWGQ GTLVTVSS  118

SEQ ID NO: 204          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 204
QVQLVQSGAE VKKPGSSVKV SCKASGYAFN NYWMNWVRQA PGQGLEWMGQ ISPGNGNSNF  60
NGKFKGRVTI TADKSTSTAY MELSSLRSED TAVYYCARGG RYGNAMDYWG QGTTVTVSS  119

SEQ ID NO: 205          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 205
QVQLVQSGAE VKKPGSSVKV SCKASGYAFS SYWMNWVRQA PGQGLEWIGQ IYPGNGNSNF  60
NGKFKARVTL TADKSSSTAY MELSSLRSED TAVYYCARGG RFGNAMDYWG QGTTVTVSS  119

SEQ ID NO: 206          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 206
QVQLVQSGAE VKKPGSSVKV SCKASGYAFS SYWMNWVRQA PGQGLEWMGQ IYPGNGNSNF  60
NGKFKARVTI TADKSTSTAY MELSSLRSED TAVYYCARGG RFGNAMDYWG QGTTVTVSS  119

SEQ ID NO: 207          moltype = AA  length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 207
DIVMTQSPDS LAVSLGERAT INCKSSQSLL NSGNQKNYLT WYQQKPGQPP KLLIFWASTR  60
ESGVPDRFSG SGSGTDFTLT ISSLQAEDVA VYYCQNNYYY PLTFGGGTKV EIK  113

SEQ ID NO: 208          moltype = AA  length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 208
DIVMTQSPDS LAVSLGERAT INCKSSQSLL NSGNQKNYLT WYQQKPGQPP KLLIYWASTR  60
ESGVPDRFSG SGSGTDFTLT ISSLQAEDVA VYYCQNNYNF PLTFGGGTKV EIK  113

SEQ ID NO: 209          moltype = AA  length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 209
DIVMTQSPDS LAVSLGERAT INCKSSQSLL NSGNQKNYLT WYQQKPGQPP KLLIYWASTR  60
ESGVPDRFSG SGSGTDFTLT ISSLQAEDVA VYYCQNNYYY PLTFGGGTKV EIK  113

SEQ ID NO: 210          moltype = AA  length = 113
FEATURE                 Location/Qualifiers
REGION                  1..113

```
                        note = Description of Artificial Sequence: Synthetic
                         polypeptide
source                  1..113
                        mol_type = protein
                        organism = synthetic construct
SEQUENCE: 210
DIVMTQSPDS LAVSLGERAT INCKSSQSLL NSGNQRNYLT WYQQKPGQPP KLLIYWASTR  60
ESGVPDRFSG SGSGTDFTLT ISSLQAEDVA VYYCQNAYFY PYTFGGGTKV EIK         113

SEQ ID NO: 211          moltype = AA  length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 211
DIVMTQSPDS LAVSLGERAT INCRSSQSLF SSGNQKNYLT WYQQKPGQPP KLLIYWASTR  60
ESGVPDRFSG SGSGADFTLT ISSLQAEDVA VYYCQNDYYY PLTFGGGTKV EIK         113

SEQ ID NO: 212          moltype = AA  length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 212
DIVMTQSPDS LAVSLGERAT INCRSSQSLF SSGNQKNYLT WYQQKPGQPP KLLIYWASTR  60
ESGVPDRFSG SGSGTDFTLT ISSLQAEDVA VYYCQNDYYY PLTFGGGTKV EIK         113

SEQ ID NO: 213          moltype = AA  length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 213
DIVMTQSPDS LAVSLGERAT MNCKSSQSLL NSGNQKNYLT WYQQKPGQPP KLLIYWASTR  60
ESGVPDRFSG SGSGTDFTLT ISSLQAEDVA VYYCQNAYFY PYTFGGGTKV EIK         113

SEQ ID NO: 214          moltype = AA  length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 214
DIVMTQSPDS LAVSLGERAT INCKSSQSLL NSGNQKNYLT WYQQKPGQPP KLLIYWASTR  60
ESGVPDRFSG SGSGTDFTLT ISSLQAEDVA VYYCQNAYFY PYTFGGGTKV EIK         113

SEQ ID NO: 215          moltype = AA  length = 113
FEATURE                 Location/Qualifiers
REGION                  1..113
                        note = Description of Artificial Sequence: Synthetic
                         polypeptide
source                  1..113
                        mol_type = protein
                        organism = synthetic construct
SEQUENCE: 215
DIVMTQSPDS LAVSLGERAT INCKSSQSLL NSGNQKNYLT WYQQKPGQPP KLLIYWASTR  60
ESGVPDRFSG SGSGTDFTLT ISSLQAEDVA VYYCQNNYFY PLTFGGGTKV EIK         113

SEQ ID NO: 216          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 216
SGGGGS                                                             6
```

-continued

```
SEQ ID NO: 217          moltype = AA   length = 330
FEATURE                 Location/Qualifiers
REGION                  1..330
                        note = Description of Artificial Sequence: Synthetic
                         polypeptide
source                  1..330
                        mol_type = protein
                        organism = synthetic construct
SEQUENCE: 217
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 218          moltype = AA   length = 330
FEATURE                 Location/Qualifiers
REGION                  1..330
                        note = Description of Artificial Sequence: Synthetic
                         polypeptide
source                  1..330
                        mol_type = protein
                        organism = synthetic construct
SEQUENCE: 218
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 219          moltype = AA   length = 330
FEATURE                 Location/Qualifiers
REGION                  1..330
                        note = Description of Artificial Sequence: Synthetic
                         polypeptide
source                  1..330
                        mol_type = protein
                        organism = synthetic construct
SEQUENCE: 219
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPEFEGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPASIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 220          moltype = AA   length = 330
FEATURE                 Location/Qualifiers
REGION                  1..330
                        note = Description of Artificial Sequence: Synthetic
                         polypeptide
source                  1..330
                        mol_type = protein
                        organism = synthetic construct
SEQUENCE: 220
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VCTLPPSRDE  240
LTKNQVSLTC LVEGFYPSDI AVEWESNGQP ENNYKTTPPV LDSDGSFFLY SDLTVDKSRW  300
QQGNVFSCSV MHEALHNHYT QESLSLSPGK                                   330

SEQ ID NO: 221          moltype = AA   length = 330
FEATURE                 Location/Qualifiers
REGION                  1..330
                        note = Description of Artificial Sequence: Synthetic
                         polypeptide
source                  1..330
                        mol_type = protein
                        organism = synthetic construct
SEQUENCE: 221
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPCRKK  240
LTKNQVSLTC LVKGFYPSDI AVEWESNGQP ENNYKTTPPV LKSDGSFFLY SKLTVDKSRW  300
QQGNVFSCSV MHEALHNHYT QKSLSLSPGK                                   330
```

```
SEQ ID NO: 222          moltype = AA  length = 330
FEATURE                 Location/Qualifiers
REGION                  1..330
                        note = Description of Artificial Sequence: Synthetic
                         polypeptide
source                  1..330
                        mol_type = protein
                        organism = synthetic construct
SEQUENCE: 222
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 223          moltype = AA  length = 330
FEATURE                 Location/Qualifiers
REGION                  1..330
                        note = Description of Artificial Sequence: Synthetic
                         polypeptide
source                  1..330
                        mol_type = protein
                        organism = synthetic construct
SEQUENCE: 223
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                   330

SEQ ID NO: 224          moltype = AA  length = 330
FEATURE                 Location/Qualifiers
REGION                  1..330
                        note = Description of Artificial Sequence: Synthetic
                         polypeptide
source                  1..330
                        mol_type = protein
                        organism = synthetic construct
SEQUENCE: 224
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPEFEGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPASIEKTIS KAKGQPREPQ VCTLPPSRDE  240
LTKNQVSLTC LVEGFYPSDI AVEWESNGQP ENNYKTTPPV LDSDGSFFLY SDLTVDKSRW  300
QQGNVFSCSV MHEALHNHYT QESLSLSPGK                                   330

SEQ ID NO: 225          moltype = AA  length = 330
FEATURE                 Location/Qualifiers
REGION                  1..330
                        note = Description of Artificial Sequence: Synthetic
                         polypeptide
source                  1..330
                        mol_type = protein
                        organism = synthetic construct
SEQUENCE: 225
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPEFEGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPASIEKTIS KAKGQPREPQ VYTLPPCRKK  240
LTKNQVSLTC LVKGFYPSDI AVEWESNGQP ENNYKTTPPV LKSDGSFFLY SKLTVDKSRW  300
QQGNVFSCSV MHEALHNHYT QKSLSLSPGK                                   330

SEQ ID NO: 226          moltype = AA  length = 330
FEATURE                 Location/Qualifiers
REGION                  1..330
                        note = Description of Artificial Sequence: Synthetic
                         polypeptide
source                  1..330
                        mol_type = protein
                        organism = synthetic construct
SEQUENCE: 226
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPEFEGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPASIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
```

-continued

```
QQGNVFSCSV MHEALHNHYT QKSLSLSPGK                                        330

SEQ ID NO: 227          moltype = AA   length = 330
FEATURE                 Location/Qualifiers
REGION                  1..330
                        note = Description of Artificial Sequence: Synthetic
                         polypeptide
source                  1..330
                        mol_type = protein
                        organism = synthetic construct
SEQUENCE: 227
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPEFEGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPASIEKTIS KAKGQPREPQ VYTLPPSRDE  240
LTKNQVSLSC AVKGFYPSDI AVEWESNGQP ENNYKTTPPV LDSDGSFFLV SKLTVDKSRW  300
QQGNVFSCSV MHEALHNHYT QKSLSLSPGK                                        330

SEQ ID NO: 228          moltype = AA   length = 330
FEATURE                 Location/Qualifiers
REGION                  1..330
                        note = Description of Artificial Sequence: Synthetic
                         polypeptide
source                  1..330
                        mol_type = protein
                        organism = synthetic construct
SEQUENCE: 228
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VCTLPPSRDE  240
LTKNQVSLTC LVEGFYPSDI AVEWESNGQP ENNYKTTPPV LDSDGSFFLY SDLTVDKSRW  300
QQGNVFSCSV MHEALHNHYT QESLSLSPGK                                        330

SEQ ID NO: 229          moltype = AA   length = 330
FEATURE                 Location/Qualifiers
REGION                  1..330
                        note = Description of Artificial Sequence: Synthetic
                         polypeptide
source                  1..330
                        mol_type = protein
                        organism = synthetic construct
SEQUENCE: 229
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPCRKK  240
LTKNQVSLTC LVKGFYPSDI AVEWESNGQP ENNYKTTPPV LKSDGSFFLY SKLTVDKSRW  300
QQGNVFSCSV MHEALHNHYT QKSLSLSPGK                                        330

SEQ ID NO: 230          moltype = AA   length = 330
FEATURE                 Location/Qualifiers
REGION                  1..330
                        note = Description of Artificial Sequence: Synthetic
                         polypeptide
source                  1..330
                        mol_type = protein
                        organism = synthetic construct
SEQUENCE: 230
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLWC LVKGFYPSDI AVEWESNGQP ENNYKTTPPV LDSDGSFFLY SKLTVDKSRW  300
QQGNVFSCSV MHEALHNHYT QKSLSLSPGK                                        330

SEQ ID NO: 231          moltype = AA   length = 330
FEATURE                 Location/Qualifiers
REGION                  1..330
                        note = Description of Artificial Sequence: Synthetic
                         polypeptide
source                  1..330
                        mol_type = protein
                        organism = synthetic construct
SEQUENCE: 231
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
```

-continued

```
LTKNQVSLSC AVKGFYPSDI AVEWESNGQP ENNYKTTPPV LDSDGSFFLV SKLTVDKSRW    300
QQGNVFSCSV MHEALHNHYT QKSLSLSPGK                                     330

SEQ ID NO: 232          moltype = AA  length = 232
FEATURE                 Location/Qualifiers
REGION                  1..232
                        note = Description of Artificial Sequence: Synthetic
                         polypeptide
source                  1..232
                        mol_type = protein
                        organism = synthetic construct
SEQUENCE: 232
EPKSSDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT    120
ISKAKGQPRE PQVYTLPPSR DELTKNQVSL TCLVKGFYPS DIAVEWESNG QPENNYKTTP    180
PVLDSDGSFF LYSKLTVDKS RWQQGNVFSC SVMHEALHNH YTQKSLSLSP GK            232

SEQ ID NO: 233          moltype = AA  length = 232
FEATURE                 Location/Qualifiers
REGION                  1..232
                        note = Description of Artificial Sequence: Synthetic
                         polypeptide
source                  1..232
                        mol_type = protein
                        organism = synthetic construct
SEQUENCE: 233
EPKSSDKTHT CPPCPAPELL GGPSVFLFPP KPKDTLMISR TPEVTCVVVD VSHEDPEVKF    60
NWYVDGVEVH NAKTKPREEQ YASTYRVVSV LTVLHQDWLN GKEYKCKVSN KALPAPIEKT    120
ISKAKGQPRE PQVYTLPPSR DELTKNQVSL TCLVKGFYPS DIAVEWESNG QPENNYKTTP    180
PVLDSDGSFF LYSKLTVDKS RWQQGNVFSC SVMHEALHNH YTQKSLSLSP GK            232

SEQ ID NO: 234          moltype = AA  length = 232
FEATURE                 Location/Qualifiers
REGION                  1..232
                        note = Description of Artificial Sequence: Synthetic
                         polypeptide
source                  1..232
                        mol_type = protein
                        organism = synthetic construct
SEQUENCE: 234
EPKSSDKTHT CPPCPAPEFE GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPASIEKT    120
ISKAKGQPRE PQVYTLPPSR DELTKNQVSL TCLVKGFYPS DIAVEWESNG QPENNYKTTP    180
PVLDSDGSFF LYSKLTVDKS RWQQGNVFSC SVMHEALHNH YTQKSLSLSP GK            232

SEQ ID NO: 235          moltype = AA  length = 232
FEATURE                 Location/Qualifiers
REGION                  1..232
                        note = Description of Artificial Sequence: Synthetic
                         polypeptide
source                  1..232
                        mol_type = protein
                        organism = synthetic construct
SEQUENCE: 235
EPKSSDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT    120
ISKAKGQPRE PQVCTLPPSR DELTKNQVSL TCLVEGFYPS DIAVEWESNG QPENNYKTTP    180
PVLDSDGSFF LYSDLTVDKS RWQQGNVFSC SVMHEALHNH YTQESLSLSP GK            232

SEQ ID NO: 236          moltype = AA  length = 232
FEATURE                 Location/Qualifiers
REGION                  1..232
                        note = Description of Artificial Sequence: Synthetic
                         polypeptide
source                  1..232
                        mol_type = protein
                        organism = synthetic construct
SEQUENCE: 236
EPKSSDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT    120
ISKAKGQPRE PQVYTLPPCR KKLTKNQVSL TCLVKGFYPS DIAVEWESNG QPENNYKTTP    180
PVLKSDGSFF LYSKLTVDKS RWQQGNVFSC SVMHEALHNH YTQKSLSLSP GK            232

SEQ ID NO: 237          moltype = AA  length = 232
FEATURE                 Location/Qualifiers
REGION                  1..232
                        note = Description of Artificial Sequence: Synthetic
                         polypeptide
source                  1..232
```

```
                            mol_type = protein
                            organism = synthetic construct
SEQUENCE: 237
EPKSSDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR DELTKNQVSL WCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 238             moltype = AA  length = 232
FEATURE                    Location/Qualifiers
REGION                     1..232
                           note = Description of Artificial Sequence: Synthetic
                            polypeptide
source                     1..232
                           mol_type = protein
                           organism = synthetic construct
SEQUENCE: 238
EPKSSDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR DELTKNQVSL SCAVKGFYPS DIAVEWESNG QPENNYKTTP   180
PVLDSDGSFF LVSKLTVDKS RWQQGNVFSC SVMHEALHNH YTQKSLSLSP GK           232

SEQ ID NO: 239             moltype = AA  length = 232
FEATURE                    Location/Qualifiers
REGION                     1..232
                           note = Description of Artificial Sequence: Synthetic
                            polypeptide
source                     1..232
                           mol_type = protein
                           organism = synthetic construct
SEQUENCE: 239
EPKSSDKTHT CPPCPAPEFE GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPASIEKT   120
ISKAKGQPRE PQVCTLPPSR DELTKNQVSL TCLVEGFYPS DIAVEWESNG QPENNYKTTP   180
PVLDSDGSFF LYSDLTVDKS RWQQGNVFSC SVMHEALHNH YTQESLSLSP GK           232

SEQ ID NO: 240             moltype = AA  length = 232
FEATURE                    Location/Qualifiers
REGION                     1..232
                           note = Description of Artificial Sequence: Synthetic
                            polypeptide
source                     1..232
                           mol_type = protein
                           organism = synthetic construct
SEQUENCE: 240
EPKSSDKTHT CPPCPAPEFE GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPASIEKT   120
ISKAKGQPRE PQVYTLPPCR KKLTKNQVSL TCLVKGFYPS DIAVEWESNG QPENNYKTTP   180
PVLKSDGSFF LYSKLTVDKS RWQQGNVFSC SVMHEALHNH YTQKSLSLSP GK           232

SEQ ID NO: 241             moltype = AA  length = 232
FEATURE                    Location/Qualifiers
REGION                     1..232
                           note = Description of Artificial Sequence: Synthetic
                            polypeptide
source                     1..232
                           mol_type = protein
                           organism = synthetic construct
SEQUENCE: 241
EPKSSDKTHT CPPCPAPEFE GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPASIEKT   120
ISKAKGQPRE PQVYTLPPSR DELTKNQVSL WCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 242             moltype = AA  length = 232
FEATURE                    Location/Qualifiers
REGION                     1..232
                           note = Description of Artificial Sequence: Synthetic
                            polypeptide
source                     1..232
                           mol_type = protein
                           organism = synthetic construct
SEQUENCE: 242
EPKSSDKTHT CPPCPAPEFE GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPASIEKT   120
ISKAKGQPRE PQVYTLPPSR DELTKNQVSL SCAVKGFYPS DIAVEWESNG QPENNYKTTP   180
PVLDSDGSFF LVSKLTVDKS RWQQGNVFSC SVMHEALHNH YTQKSLSLSP GK           232

SEQ ID NO: 243             moltype = AA  length = 232
```

```
FEATURE           Location/Qualifiers
REGION            1..232
                  note = Description of Artificial Sequence: Synthetic
                   polypeptide
source            1..232
                  mol_type = protein
                  organism = synthetic construct
SEQUENCE: 243
EPKSSDKTHT CPPCPAPELL GGPSVFLFPP KPKDTLMISR TPEVTCVVVD VSHEDPEVKF   60
NWYVDGVEVH NAKTKPREEQ YASTYRVVSV LTVLHQDWLN GKEYKCKVSN KALPAPIEKT  120
ISKAKGQPRE PQVCTLPPSR DELTKNQVSL TCLVEGFYPS DIAVEWESNG QPENNYKTTP  180
PVLDSDGSFF LYSDLTVDKS RWQQGNVFSC SVMHEALHNH YTQESLSLSP GK          232

SEQ ID NO: 244        moltype = AA  length = 232
FEATURE           Location/Qualifiers
REGION            1..232
                  note = Description of Artificial Sequence: Synthetic
                   polypeptide
source            1..232
                  mol_type = protein
                  organism = synthetic construct
SEQUENCE: 244
EPKSSDKTHT CPPCPAPELL GGPSVFLFPP KPKDTLMISR TPEVTCVVVD VSHEDPEVKF   60
NWYVDGVEVH NAKTKPREEQ YASTYRVVSV LTVLHQDWLN GKEYKCKVSN KALPAPIEKT  120
ISKAKGQPRE PQVYTLPPCR KKLTKNQVSL TCLVKGFYPS DIAVEWESNG QPENNYKTTP  180
PVLKSDGSFF LYSKLTVDKS RWQQGNVFSC SVMHEALHNH YTQKSLSLSP GK          232

SEQ ID NO: 245        moltype = AA  length = 232
FEATURE           Location/Qualifiers
REGION            1..232
                  note = Description of Artificial Sequence: Synthetic
                   polypeptide
source            1..232
                  mol_type = protein
                  organism = synthetic construct
SEQUENCE: 245
EPKSSDKTHT CPPCPAPELL GGPSVFLFPP KPKDTLMISR TPEVTCVVVD VSHEDPEVKF   60
NWYVDGVEVH NAKTKPREEQ YASTYRVVSV LTVLHQDWLN GKEYKCKVSN KALPAPIEKT  120
ISKAKGQPRE PQVYTLPPSR DELTKNQVSL WCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 246        moltype = AA  length = 232
FEATURE           Location/Qualifiers
REGION            1..232
                  note = Description of Artificial Sequence: Synthetic
                   polypeptide
source            1..232
                  mol_type = protein
                  organism = synthetic construct
SEQUENCE: 246
EPKSSDKTHT CPPCPAPELL GGPSVFLFPP KPKDTLMISR TPEVTCVVVD VSHEDPEVKF   60
NWYVDGVEVH NAKTKPREEQ YASTYRVVSV LTVLHQDWLN GKEYKCKVSN KALPAPIEKT  120
ISKAKGQPRE PQVYTLPPSR DELTKNQVSL SCAVKGFYPS DIAVEWESNG QPENNYKTTP  180
PVLDSDGSFF LVSKLTVDKS RWQQGNVFSC SVMHEALHNH YTQKSLSLSP GK          232

SEQ ID NO: 247        moltype = AA  length = 107
FEATURE           Location/Qualifiers
REGION            1..107
                  note = Description of Artificial Sequence: Synthetic
                   polypeptide
source            1..107
                  mol_type = protein
                  organism = synthetic construct
SEQUENCE: 247
RTVAAPSVFI FPPSDEQLKS GTASVVCLLN NFYPREAKVQ WKVDNALQSG NSQESVTEQD   60
SKDSTYSLSS TLTLSKADYE KHKVYACEVT HQGLSSPVTK SFNRGEC               107

SEQ ID NO: 248        moltype = AA  length = 125
FEATURE           Location/Qualifiers
REGION            1..125
                  note = Description of Artificial Sequence: Synthetic
                   polypeptide
source            1..125
                  mol_type = protein
                  organism = synthetic construct
SEQUENCE: 248
EVQLVESGGG LVQPKGSLKL SCAASGFTFN TYAMNWVRQA PGKGLEWVAR IRSKYNNYAT   60
YYADSVKDRF TISRDDSQSI LYLQMNNLKT EDTAMYYCVR HGNFGNSYVS WFAYWGQGTL  120
VTVSS                                                             125
```

-continued

```
SEQ ID NO: 249          moltype = AA  length = 125
FEATURE                 Location/Qualifiers
REGION                  1..125
                        note = Description of Artificial Sequence: Synthetic
                         polypeptide
source                  1..125
                        mol_type = protein
                        organism = synthetic construct
SEQUENCE: 249
EVQLVESGGG LVQPGGSLRL SCAASGFTFS TYAMNWVRQA PGKGLEWVGR IRSKANNYAT  60
YYADSVKGRF TISRDDSKNT LYLQMNSLRA EDTAVYYCVR HGNFGDSYVS WFAYWGQGTL  120
VTVSS                                                              125

SEQ ID NO: 250          moltype = AA  length = 125
FEATURE                 Location/Qualifiers
REGION                  1..125
                        note = Description of Artificial Sequence: Synthetic
                         polypeptide
source                  1..125
                        mol_type = protein
                        organism = synthetic construct
SEQUENCE: 250
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS WFAYWGQGTL  120
VTVSS                                                              125

SEQ ID NO: 251          moltype = AA  length = 125
FEATURE                 Location/Qualifiers
REGION                  1..125
                        note = Description of Artificial Sequence: Synthetic
                         polypeptide
source                  1..125
                        mol_type = protein
                        organism = synthetic construct
SEQUENCE: 251
EVQLVESGGG LVQPGGSLRL SCAASGFTFS TYAMNWVRQA PGKGLEWVGR IRSKINNYAT  60
YYADSVKGRF TISRDDSKNT LYLQMNSLRA EDTAVYYCVR HGNFGDSYVS WFAYWGQGTL  120
VTVSS                                                              125

SEQ ID NO: 252          moltype = AA  length = 125
FEATURE                 Location/Qualifiers
REGION                  1..125
                        note = Description of Artificial Sequence: Synthetic
                         polypeptide
source                  1..125
                        mol_type = protein
                        organism = synthetic construct
SEQUENCE: 252
EVQLVESGGG LVQPGGSLRL SCAASGFTFS TYAMNWVRQA PGKGLEWVGR IRSKLNNYAT  60
YYADSVKGRF TISRDDSKNT LYLQMNSLRA EDTAVYYCVR HGNFGDSYVS WFAYWGQGTL  120
VTVSS                                                              125

SEQ ID NO: 253          moltype = AA  length = 125
FEATURE                 Location/Qualifiers
REGION                  1..125
                        note = Description of Artificial Sequence: Synthetic
                         polypeptide
source                  1..125
                        mol_type = protein
                        organism = synthetic construct
SEQUENCE: 253
EVQLVESGGG LVQPGGSLRL SCAASGFTFS TYAMNWVRQA PGKGLEWVGR IRSKVNNYAT  60
YYADSVKGRF TISRDDSKNT LYLQMNSLRA EDTAVYYCVR HGNFGDSYVS WFAYWGQGTL  120
VTVSS                                                              125

SEQ ID NO: 254          moltype = AA  length = 125
FEATURE                 Location/Qualifiers
REGION                  1..125
                        note = Description of Artificial Sequence: Synthetic
                         polypeptide
source                  1..125
                        mol_type = protein
                        organism = synthetic construct
SEQUENCE: 254
EVQLVESGGG LVQPGGSLRL SCAASGFTFS TYAMNWVRQA PGKGLEWVGR IRSKSNNYAT  60
YYADSVKGRF TISRDDSKNT LYLQMNSLRA EDTAVYYCVR HGNFGDSYVS WFAYWGQGTL  120
VTVSS                                                              125
```

```
SEQ ID NO: 255           moltype = AA  length = 125
FEATURE                  Location/Qualifiers
REGION                   1..125
                         note = Description of Artificial Sequence: Synthetic
                          polypeptide
source                   1..125
                         mol_type = protein
                         organism = synthetic construct
SEQUENCE: 255
EVQLVESGGG LVQPGGSLRL SCAASGFTFS TYAMDWVRQA PGKGLEWVGR IRSKYNNYAT   60
YYADSVKGRF TISRDDSKNT LYLQMNSLRA EDTAVYYCVR HGNFGDSYVS WFAYWGQGTL  120
VTVSS                                                              125

SEQ ID NO: 256           moltype = AA  length = 125
FEATURE                  Location/Qualifiers
REGION                   1..125
                         note = Description of Artificial Sequence: Synthetic
                          polypeptide
source                   1..125
                         mol_type = protein
                         organism = synthetic construct
SEQUENCE: 256
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFEYWGQGTL  120
VTVSS                                                              125

SEQ ID NO: 257           moltype = AA  length = 125
FEATURE                  Location/Qualifiers
REGION                   1..125
                         note = Description of Artificial Sequence: Synthetic
                          polypeptide
source                   1..125
                         mol_type = protein
                         organism = synthetic construct
SEQUENCE: 257
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFDYWGQGTL  120
VTVSS                                                              125

SEQ ID NO: 258           moltype = AA  length = 125
FEATURE                  Location/Qualifiers
REGION                   1..125
                         note = Description of Artificial Sequence: Synthetic
                          polypeptide
source                   1..125
                         mol_type = protein
                         organism = synthetic construct
SEQUENCE: 258
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFNYWGQGTL  120
VTVSS                                                              125

SEQ ID NO: 259           moltype = AA  length = 125
FEATURE                  Location/Qualifiers
REGION                   1..125
                         note = Description of Artificial Sequence: Synthetic
                          polypeptide
source                   1..125
                         mol_type = protein
                         organism = synthetic construct
SEQUENCE: 259
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS YFAYWGQGTL  120
VTVSS                                                              125

SEQ ID NO: 260           moltype = AA  length = 123
FEATURE                  Location/Qualifiers
REGION                   1..123
                         note = Description of Artificial Sequence: Synthetic
                          polypeptide
source                   1..123
                         mol_type = protein
                         organism = synthetic construct
SEQUENCE: 260
QLVESGGGLV QPGGSLRLSC AASGFTFSTY AMNWVRQAPG KGLEWVGRIR SKANNYATYY   60
ADSVKGRFTI SRDDSKNTLY LQMNSLRAED TAVYYCVRHG NFGDSYVSWF AYWGQGTLVT  120
VSS                                                                123

SEQ ID NO: 261           moltype = AA  length = 109
```

```
FEATURE             Location/Qualifiers
REGION              1..109
                    note = Description of Artificial Sequence: Synthetic
                     polypeptide
source              1..109
                    mol_type = protein
                    organism = synthetic construct
SEQUENCE: 261
QAVVTQEPSL TVSPGGTVTL TCGSSTGAVT TSNYANWVQQ KPGKSPRGLI GGTNKRAPGV     60
PARFSGSLLG GKAALTISGA QPEDEADYYC ALWYSNHWVF GGGTKLTVL               109

SEQ ID NO: 262      moltype = AA   length = 486
FEATURE             Location/Qualifiers
REGION              1..486
                    note = Description of Artificial Sequence: Synthetic
                     polypeptide
source              1..486
                    mol_type = protein
                    organism = synthetic construct
SEQUENCE: 262
EVQLVESGGG LVQPGGSLRL SCAASGFTFS TYAMNWVRQA PGKGLEWVGR IRSKANNYAT     60
YYADSVKGRF TISRDDSKNT LYLQMNSLRA EDTAVYYCVR HGNFGDSYVS WFAYWGQGTL    120
VTVSSGKPGS GKPGSGKPGS GKPGSQAVVT QEPSLTVSPG GTVTLTCGSS TGAVTTSNYA    180
NWVQQKPGKS PRGLIGGTNK RAPGVPARFS GSLLGGKAAL TISGAQPEDE ADYYCALWYS    240
NHWVFGGGTK LTVLEPKSSD KTHTCPPCPA PEFEGGPSVF LFPPKPKDTL MISRTPEVTC    300
VVVDVSHEDP EVKFNWYVDG VEVHNAKTKP REEQYNSTYR VVSVLTVLHQ DWLNGKEYKC    360
KVSNKALPAS IEKTISKAKG QPREPQVYTL PPCRKKLTKN QVSLTCLVKG FYPSDIAVEW    420
ESNGQPENNY KTTPPVLKSD GSFFLYSKLT VDKSRWQQGN VFSCSVMHEA LHNHYTQKSL    480
SLSPGK                                                              486

SEQ ID NO: 263      moltype = AA   length = 486
FEATURE             Location/Qualifiers
REGION              1..486
                    note = Description of Artificial Sequence: Synthetic
                     polypeptide
source              1..486
                    mol_type = protein
                    organism = synthetic construct
SEQUENCE: 263
EVQLVESGGG LVQPGGSLRL SCAASGFTFS TYAMNWVRQA PGKGLEWVGR IRSKYNNYAT     60
YYADSVKGRF TISRDDSKNT LYLQMNSLRA EDTAVYYCVR HGNFGDSYVS WFAYWGQGTL    120
VTVSSGKPGS GKPGSGKPGS GKPGSQAVVT QEPSLTVSPG GTVTLTCGSS TGAVTTSNYA    180
NWVQQKPGKS PRGLIGGTNK RAPGVPARFS GSLLGGKAAL TISGAQPEDE ADYYCALWYS    240
NHWVFGGGTK LTVLEPKSSD KTHTCPPCPA PEFEGGPSVF LFPPKPKDTL MISRTPEVTC    300
VVVDVSHEDP EVKFNWYVDG VEVHNAKTKP REEQYNSTYR VVSVLTVLHQ DWLNGKEYKC    360
KVSNKALPAS IEKTISKAKG QPREPQVYTL PPCRKKLTKN QVSLTCLVKG FYPSDIAVEW    420
ESNGQPENNY KTTPPVLKSD GSFFLYSKLT VDKSRWQQGN VFSCSVMHEA LHNHYTQKSL    480
SLSPGK                                                              486

SEQ ID NO: 264      moltype = AA   length = 486
FEATURE             Location/Qualifiers
REGION              1..486
                    note = Description of Artificial Sequence: Synthetic
                     polypeptide
source              1..486
                    mol_type = protein
                    organism = synthetic construct
SEQUENCE: 264
EVQLVESGGG LVQPGGSLRL SCAASGFTFS TYAMNWVRQA PGKGLEWVGR IRSKINNYAT     60
YYADSVKGRF TISRDDSKNT LYLQMNSLRA EDTAVYYCVR HGNFGDSYVS WFAYWGQGTL    120
VTVSSGKPGS GKPGSGKPGS GKPGSQAVVT QEPSLTVSPG GTVTLTCGSS TGAVTTSNYA    180
NWVQQKPGKS PRGLIGGTNK RAPGVPARFS GSLLGGKAAL TISGAQPEDE ADYYCALWYS    240
NHWVFGGGTK LTVLEPKSSD KTHTCPPCPA PEFEGGPSVF LFPPKPKDTL MISRTPEVTC    300
VVVDVSHEDP EVKFNWYVDG VEVHNAKTKP REEQYNSTYR VVSVLTVLHQ DWLNGKEYKC    360
KVSNKALPAS IEKTISKAKG QPREPQVYTL PPCRKKLTKN QVSLTCLVKG FYPSDIAVEW    420
ESNGQPENNY KTTPPVLKSD GSFFLYSKLT VDKSRWQQGN VFSCSVMHEA LHNHYTQKSL    480
SLSPGK                                                              486

SEQ ID NO: 265      moltype = AA   length = 486
FEATURE             Location/Qualifiers
REGION              1..486
                    note = Description of Artificial Sequence: Synthetic
                     polypeptide
source              1..486
                    mol_type = protein
                    organism = synthetic construct
SEQUENCE: 265
EVQLVESGGG LVQPGGSLRL SCAASGFTFS TYAMNWVRQA PGKGLEWVGR IRSKLNNYAT     60
YYADSVKGRF TISRDDSKNT LYLQMNSLRA EDTAVYYCVR HGNFGDSYVS WFAYWGQGTL    120
```

-continued

```
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PEFEGGPSVF LFPPKPKDTL MISRTPEVTC  300
VVVDVSHEDP EVKFNWYVDG VEVHNAKTKP REEQYNSTYR VVSVLTVLHQ DWLNGKEYKC  360
KVSNKALPAS IEKTISKAKG QPREPQVYTL PPCRKKLTKN QVSLTCLVKG FYPSDIAVEW  420
ESNGQPENNY KTTPPVLKSD GSFFLYSKLT VDKSRWQQGN VFSCSVMHEA LHNHYTQKSL  480
SLSPGK                                                            486

SEQ ID NO: 266          moltype = AA  length = 486
FEATURE                 Location/Qualifiers
REGION                  1..486
                        note = Description of Artificial Sequence: Synthetic
                         polypeptide
source                  1..486
                        mol_type = protein
                        organism = synthetic construct
SEQUENCE: 266
EVQLVESGGG LVQPGGSLRL SCAASGFTFS TYAMNWVRQA PGKGLEWVGR IRSKVNNYAT  60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PEFEGGPSVF LFPPKPKDTL MISRTPEVTC  300
VVVDVSHEDP EVKFNWYVDG VEVHNAKTKP REEQYNSTYR VVSVLTVLHQ DWLNGKEYKC  360
KVSNKALPAS IEKTISKAKG QPREPQVYTL PPCRKKLTKN QVSLTCLVKG FYPSDIAVEW  420
ESNGQPENNY KTTPPVLKSD GSFFLYSKLT VDKSRWQQGN VFSCSVMHEA LHNHYTQKSL  480
SLSPGK                                                            486

SEQ ID NO: 267          moltype = AA  length = 486
FEATURE                 Location/Qualifiers
REGION                  1..486
                        note = Description of Artificial Sequence: Synthetic
                         polypeptide
source                  1..486
                        mol_type = protein
                        organism = synthetic construct
SEQUENCE: 267
EVQLVESGGG LVQPGGSLRL SCAASGFTFS TYAMNWVRQA PGKGLEWVGR IRSKSNNYAT  60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PEFEGGPSVF LFPPKPKDTL MISRTPEVTC  300
VVVDVSHEDP EVKFNWYVDG VEVHNAKTKP REEQYNSTYR VVSVLTVLHQ DWLNGKEYKC  360
KVSNKALPAS IEKTISKAKG QPREPQVYTL PPCRKKLTKN QVSLTCLVKG FYPSDIAVEW  420
ESNGQPENNY KTTPPVLKSD GSFFLYSKLT VDKSRWQQGN VFSCSVMHEA LHNHYTQKSL  480
SLSPGK                                                            486

SEQ ID NO: 268          moltype = AA  length = 486
FEATURE                 Location/Qualifiers
REGION                  1..486
                        note = Description of Artificial Sequence: Synthetic
                         polypeptide
source                  1..486
                        mol_type = protein
                        organism = synthetic construct
SEQUENCE: 268
EVQLVESGGG LVQPGGSLRL SCAASGFTFS TYAMDWVRQA PGKGLEWVGR IRSKYNNYAT  60
YYADSVKGRF TISRDDSKNT LYLQMNSLRA EDTAVYYCVR HGNFGDSYVS WFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PEFEGGPSVF LFPPKPKDTL MISRTPEVTC  300
VVVDVSHEDP EVKFNWYVDG VEVHNAKTKP REEQYNSTYR VVSVLTVLHQ DWLNGKEYKC  360
KVSNKALPAS IEKTISKAKG QPREPQVYTL PPCRKKLTKN QVSLTCLVKG FYPSDIAVEW  420
ESNGQPENNY KTTPPVLKSD GSFFLYSKLT VDKSRWQQGN VFSCSVMHEA LHNHYTQKSL  480
SLSPGK                                                            486

SEQ ID NO: 269          moltype = AA  length = 486
FEATURE                 Location/Qualifiers
REGION                  1..486
                        note = Description of Artificial Sequence: Synthetic
                         polypeptide
source                  1..486
                        mol_type = protein
                        organism = synthetic construct
SEQUENCE: 269
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS WFEYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PEFEGGPSVF LFPPKPKDTL MISRTPEVTC  300
```

-continued

```
VVVDVSHEDP EVKFNWYVDG VEVHNAKTKP REEQYNSTYR VVSVLTVLHQ DWLNGKEYKC  360
KVSNKALPAS IEKTISKAKG QPREPQVYTL PPCRKKLTKN QVSLTCLVKG FYPSDIAVEW  420
ESNGQPENNY KTTPPVLKSD GSFFLYSKLT VDKSRWQQGN VFSCSVMHEA LHNHYTQKSL  480
SLSPGK                                                             486

SEQ ID NO: 270          moltype = AA  length = 486
FEATURE                 Location/Qualifiers
REGION                  1..486
                        note = Description of Artificial Sequence: Synthetic
                         polypeptide
source                  1..486
                        mol_type = protein
                        organism = synthetic construct
SEQUENCE: 270
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS WFDYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PEFEGGPSVF LFPPKPKDTL MISRTPEVTC  300
VVVDVSHEDP EVKFNWYVDG VEVHNAKTKP REEQYNSTYR VVSVLTVLHQ DWLNGKEYKC  360
KVSNKALPAS IEKTISKAKG QPREPQVYTL PPCRKKLTKN QVSLTCLVKG FYPSDIAVEW  420
ESNGQPENNY KTTPPVLKSD GSFFLYSKLT VDKSRWQQGN VFSCSVMHEA LHNHYTQKSL  480
SLSPGK                                                             486

SEQ ID NO: 271          moltype = AA  length = 486
FEATURE                 Location/Qualifiers
REGION                  1..486
                        note = Description of Artificial Sequence: Synthetic
                         polypeptide
source                  1..486
                        mol_type = protein
                        organism = synthetic construct
SEQUENCE: 271
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS WFNYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PEFEGGPSVF LFPPKPKDTL MISRTPEVTC  300
VVVDVSHEDP EVKFNWYVDG VEVHNAKTKP REEQYNSTYR VVSVLTVLHQ DWLNGKEYKC  360
KVSNKALPAS IEKTISKAKG QPREPQVYTL PPCRKKLTKN QVSLTCLVKG FYPSDIAVEW  420
ESNGQPENNY KTTPPVLKSD GSFFLYSKLT VDKSRWQQGN VFSCSVMHEA LHNHYTQKSL  480
SLSPGK                                                             486

SEQ ID NO: 272          moltype = AA  length = 486
FEATURE                 Location/Qualifiers
REGION                  1..486
                        note = Description of Artificial Sequence: Synthetic
                         polypeptide
source                  1..486
                        mol_type = protein
                        organism = synthetic construct
SEQUENCE: 272
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS YFAYWGQGTL  120
VTVSSGKPGS GKPGSGKPGS GKPGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLEPKSSD KTHTCPPCPA PEFEGGPSVF LFPPKPKDTL MISRTPEVTC  300
VVVDVSHEDP EVKFNWYVDG VEVHNAKTKP REEQYNSTYR VVSVLTVLHQ DWLNGKEYKC  360
KVSNKALPAS IEKTISKAKG QPREPQVYTL PPCRKKLTKN QVSLTCLVKG FYPSDIAVEW  420
ESNGQPENNY KTTPPVLKSD GSFFLYSKLT VDKSRWQQGN VFSCSVMHEA LHNHYTQKSL  480
SLSPGK                                                             486

SEQ ID NO: 273          moltype = AA  length = 484
FEATURE                 Location/Qualifiers
REGION                  1..484
                        note = Description of Artificial Sequence: Synthetic
                         polypeptide
source                  1..484
                        mol_type = protein
                        organism = synthetic construct
SEQUENCE: 273
QLVESGGGLV QPGGSLRLSC AASGFTFSTY AMNWVRQAPG KGLEWVGRIR SKANNYATYY  60
ADSVKGRFTI SRDDSKNTLY LQMNSLRAED TAVYYCVRHG NFGDSYVSWF AYWGQGTLVT  120
VSSGKPGSGK PGSGKPGSGK PGSQAVVTQE PSLTVSPGGT VTLTCGSSTG AVTTSNYANW  180
VQQKPGKSPR GLIGGTNKRA PGVPARFSGS LLGGKAALTI SGAQPEDEAD YYCALWYSNH  240
WVFGGGTKLT VLEPKSSDKT HTCPPCPAPE FEGGPSVFLF PPKPKDTLMI SRTPEVTCVV  300
VDVSHEDPEV KFNWYVDGVE VHNAKTKPRE EQYNSTYRVV SVLTVLHQDW LNGKEYKCKV  360
SNKALPASIE KTISKAKGQP REPQVYTLPP CRKKLTKNQV SLTCLVKGFY PSDIAVEWES  420
NGQPENNYKT TPPVLKSDGS FFLYSKLTVD KSRWQQGNVF SCSVMHEALH NHYTQKSLSL  480
```

-continued

```
SPGK                                                                        484

SEQ ID NO: 274          moltype = AA  length = 448
FEATURE                 Location/Qualifiers
REGION                  1..448
                        note = Description of Artificial Sequence: Synthetic
                         polypeptide
source                  1..448
                        mol_type = protein
                        organism = synthetic construct
SEQUENCE: 274
EVQLLESGGG LVQPGGSLRL SCAASGFTFS SYGMHWVRQA PGKGLEWVAV ISGSGSSKYY    60
ADSVKGRFTI SRDNSKNTLY LQMNSLRAED TAVYYCARDW FFYLFDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDKTHTCPPC PAPEFEGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP ASIEKTISKA KGQPREPQVC TLPPSRDELT   360
KNQVSLTCLV EGFYPSDIAV EWESNGQPEN NYKTTPPVLD SDGSFFLYSD LTVDKSRWQQ   420
GNVFSCSVMH EALHNHYTQE SLSLSPGK                                      448

SEQ ID NO: 275          moltype = AA  length = 448
FEATURE                 Location/Qualifiers
REGION                  1..448
                        note = Description of Artificial Sequence: Synthetic
                         polypeptide
source                  1..448
                        mol_type = protein
                        organism = synthetic construct
SEQUENCE: 275
EVQLLESGGG LVQPGGSLRL SCAASGFTFS SYGMHWVRQA PGKGLEWVAV ISGSGSSKYY    60
ADSVKGRFTI SRDNSKNTLY LQMNSLRAED TAVYYCARDW FYFIFDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDKTHTCPPC PAPEFEGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP ASIEKTISKA KGQPREPQVC TLPPSRDELT   360
KNQVSLTCLV EGFYPSDIAV EWESNGQPEN NYKTTPPVLD SDGSFFLYSD LTVDKSRWQQ   420
GNVFSCSVMH EALHNHYTQE SLSLSPGK                                      448

SEQ ID NO: 276          moltype = AA  length = 448
FEATURE                 Location/Qualifiers
REGION                  1..448
                        note = Description of Artificial Sequence: Synthetic
                         polypeptide
source                  1..448
                        mol_type = protein
                        organism = synthetic construct
SEQUENCE: 276
EVQLLESGGG LVQPGGSLRL SCAASGFTFS SYGMHWVRQA PGKGLEWVAV ISHHGSSKYY    60
ADSVKGRFTI SRDNSKNTLY LQMNSLRAED TAVYYCARDW FFYLFDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDKTHTCPPC PAPEFEGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP ASIEKTISKA KGQPREPQVC TLPPSRDELT   360
KNQVSLTCLV EGFYPSDIAV EWESNGQPEN NYKTTPPVLD SDGSFFLYSD LTVDKSRWQQ   420
GNVFSCSVMH EALHNHYTQE SLSLSPGK                                      448

SEQ ID NO: 277          moltype = AA  length = 448
FEATURE                 Location/Qualifiers
REGION                  1..448
                        note = Description of Artificial Sequence: Synthetic
                         polypeptide
source                  1..448
                        mol_type = protein
                        organism = synthetic construct
SEQUENCE: 277
EVQLLESGGG LVQPGGSLRL SCAASGFTFS SYGMHWVRQA PGKGLEWVAV ISHHGSSKYY    60
ADSVKGRFTI SRDNSKNTLY LQMNSLRAED TAVYYCARDW FYFIFDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDKTHTCPPC PAPEFEGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP ASIEKTISKA KGQPREPQVC TLPPSRDELT   360
KNQVSLTCLV EGFYPSDIAV EWESNGQPEN NYKTTPPVLD SDGSFFLYSD LTVDKSRWQQ   420
GNVFSCSVMH EALHNHYTQE SLSLSPGK                                      448

SEQ ID NO: 278          moltype = AA  length = 448
FEATURE                 Location/Qualifiers
REGION                  1..448
                        note = Description of Artificial Sequence: Synthetic
                         polypeptide
```

```
source                  1..448
                        mol_type = protein
                        organism = synthetic construct
SEQUENCE: 278
EVQLLESGGG LVQPGGSLRL SCAASGFTFS SYGMHWVRQA PGKGLEWVAV ISYDGSSKYY   60
ADSVKGRFTI SRDNSKNTLY LQMNSLRAED TAVYYCARDW FFYLFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEFEGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP ASIEKTISKA KGQPREPQVC TLPPSRDELT  360
KNQVSLTCLV EGFYPSDIAV EWESNGQPEN NYKTTPPVLD SDGSFFLYSD LTVDKSRWQQ  420
GNVFSCSVMH EALHNHYTQE SLSLSPGK                                     448

SEQ ID NO: 279         moltype = AA  length = 448
FEATURE                Location/Qualifiers
REGION                 1..448
                       note = Description of Artificial Sequence: Synthetic
                       polypeptide
source                 1..448
                       mol_type = protein
                       organism = synthetic construct
SEQUENCE: 279
EVQLLESGGG LVQPGGSLRL SCAASGFTFS SYGMHWVRQA PGKGLEWVAV ISYDGSSKYY   60
ADSVKGRFTI SRDNSKNTLY LQMNSLRAED TAVYYCARDW FYFIFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEFEGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP ASIEKTISKA KGQPREPQVC TLPPSRDELT  360
KNQVSLTCLV EGFYPSDIAV EWESNGQPEN NYKTTPPVLD SDGSFFLYSD LTVDKSRWQQ  420
GNVFSCSVMH EALHNHYTQE SLSLSPGK                                     448

SEQ ID NO: 280         moltype = AA  length = 448
FEATURE                Location/Qualifiers
REGION                 1..448
                       note = Description of Artificial Sequence: Synthetic
                       polypeptide
source                 1..448
                       mol_type = protein
                       organism = synthetic construct
SEQUENCE: 280
EVQLLESGGG LVQPGGSLRL SCAASGFTFS SYGMHWVRQA PGKGLEWVSV ISHHGSSKYY   60
ADSVKGRFTI SRDNSKNTLY LQMNSLRAED TAVYYCAKDW FFYLFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEFEGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP ASIEKTISKA KGQPREPQVC TLPPSRDELT  360
KNQVSLTCLV EGFYPSDIAV EWESNGQPEN NYKTTPPVLD SDGSFFLYSD LTVDKSRWQQ  420
GNVFSCSVMH EALHNHYTQE SLSLSPGK                                     448

SEQ ID NO: 281         moltype = AA  length = 448
FEATURE                Location/Qualifiers
REGION                 1..448
                       note = Description of Artificial Sequence: Synthetic
                       polypeptide
source                 1..448
                       mol_type = protein
                       organism = synthetic construct
SEQUENCE: 281
EVQLLESGGG LVQPGGSLRL SCAASGFTFS SYGMHWVRQA PGKGLEWVSV ISHHGSSKYY   60
ADSVKGRFTI SRDNSKNTLY LQMNSLRAED TAVYYCAKDW FYFIFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEFEGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP ASIEKTISKA KGQPREPQVC TLPPSRDELT  360
KNQVSLTCLV EGFYPSDIAV EWESNGQPEN NYKTTPPVLD SDGSFFLYSD LTVDKSRWQQ  420
GNVFSCSVMH EALHNHYTQE SLSLSPGK                                     448

SEQ ID NO: 282         moltype = AA  length = 450
FEATURE                Location/Qualifiers
REGION                 1..450
                       note = Description of Artificial Sequence: Synthetic
                       polypeptide
source                 1..450
                       mol_type = protein
                       organism = synthetic construct
SEQUENCE: 282
EVQLQQSGPV LVKPGASVKM SCKASGFTFT DYYMNWVKQS HGKSLEWIGV INPDNGITTY   60
NQKFKGKATL TVDKSSSTAY MELNGLTSED SAVYYCARGV WNYERSFDYW GQTTLTVSS   120
ASTKGPSVFP LAPSSKSTSG GTAALGCLVK DYFPEPVTVS WNSGALTSGV HTFPAVLQSS  180
```

-continued

```
GLYSLSSVVT VPSSSLGTQT YICNVNHKPS NTKVDKRVEP KSCDKTHTCP PCPAPEFEGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPASIEKTIS KAKGQPREPQ VCTLPPSRDE   360
LTKNQVSLTC LVEGFYPSDI AVEWESNGQP ENNYKTTPPV LDSDGSFFLY SDLTVDKSRW   420
QQGNVFSCSV MHEALHNHYT QESLSLSPGK                                   450

SEQ ID NO: 283          moltype = AA  length = 448
FEATURE                 Location/Qualifiers
REGION                  1..448
                        note = Description of Artificial Sequence: Synthetic
                         polypeptide
source                  1..448
                        mol_type = protein
                        organism = synthetic construct
SEQUENCE: 283
EVQLVESGGG LVQPGGSLRL SCAASGFTFS NYGMHWVRQA PGKGLEWVAV ISHHGSSKYY   60
ADSVKGRYTI SRDNSKNTLY LQMNSLRAED TAVYYCARDW FFYLFDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDKTHTCPPC PAPEFEGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP ASIEKTISKA KGQPREPQVC TLPPSRDELT   360
KNQVSLTCLV EGFYPSDIAV EWESNGQPEN NYKTTPPVLD SDGSFFLYSD LTVDKSRWQQ   420
GNVFSCSVMH EALHNHYTQE SLSLSPGK                                     448

SEQ ID NO: 284          moltype = AA  length = 448
FEATURE                 Location/Qualifiers
REGION                  1..448
                        note = Description of Artificial Sequence: Synthetic
                         polypeptide
source                  1..448
                        mol_type = protein
                        organism = synthetic construct
SEQUENCE: 284
QVQLQESGPG LVKPSETLSL TCTVSGGSIS SYYWSWIRQP PGKGLEWIGY VYYSGTTNYN   60
PSLKSRVTIS VDTSKNQFSL KLSSVTAADT AVYYCASIAV TGFYFDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDKTHTCPPC PAPEFEGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP ASIEKTISKA KGQPREPQVC TLPPSRDELT   360
KNQVSLTCLV EGFYPSDIAV EWESNGQPEN NYKTTPPVLD SDGSFFLYSD LTVDKSRWQQ   420
GNVFSCSVMH EALHNHYTQE SLSLSPGK                                     448

SEQ ID NO: 285          moltype = AA  length = 449
FEATURE                 Location/Qualifiers
REGION                  1..449
                        note = Description of Artificial Sequence: Synthetic
                         polypeptide
source                  1..449
                        mol_type = protein
                        organism = synthetic construct
SEQUENCE: 285
QVQLQQSGPV LVKPGASVKM SCKASGYSFT DYYVNWVKQS HGKSLEWIGI ISPNDGGTNY   60
NQKFKGKATL TVDKSSSTAY MEVNSLTSED SAVYYCARDD DLGWYFDVWG TGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPEFEGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PASIEKTISK AKGQPREPQV CTLPPSRDEL   360
TKNQVSLTCL VEGFYPSDIA VEWESNGQPE NNYKTTPPVL DSDGSFFLYS DLTVDKSRWQ   420
QGNVFSCSVM HEALHNHYTQ ESLSLSPGK                                    449

SEQ ID NO: 286          moltype = AA  length = 448
FEATURE                 Location/Qualifiers
REGION                  1..448
                        note = Description of Artificial Sequence: Synthetic
                         polypeptide
source                  1..448
                        mol_type = protein
                        organism = synthetic construct
SEQUENCE: 286
QVQLVESGGG AVQPGRSLRL SCAASGFTFS NYGMHWVRQA PGKGLEWVAV ISHHGSSKYY   60
ARSVKGRFTI SRDNSKNTLY LEMNSLRAED TAVYYCARDW WELVFDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDKTHTCPPC PAPEFEGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP ASIEKTISKA KGQPREPQVC TLPPSRDELT   360
KNQVSLTCLV EGFYPSDIAV EWESNGQPEN NYKTTPPVLD SDGSFFLYSD LTVDKSRWQQ   420
GNVFSCSVMH EALHNHYTQE SLSLSPGK                                     448

SEQ ID NO: 287          moltype = AA  length = 448
```

-continued

```
FEATURE              Location/Qualifiers
REGION               1..448
                     note = Description of Artificial Sequence: Synthetic
                      polypeptide
source               1..448
                     mol_type = protein
                     organism = synthetic construct
SEQUENCE: 287
QVQLVESGGG AVQPGRSLRL SCAASGFTFS NYGMHWVRQA PGKGLEWVAV ISHHGSSKYY  60
ARSVKGRFTI SRDNSKNTLY LEMNSLRAED TAVYYCARDW WELVFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEFEGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP ASIEKTISKA KGQPREPQVC TLPPSRDELT  360
KNQVSLTCLV EGFYPSDIAV EWESNGQPEN NYKTTPPVLD SDGSFFLYSD LTVDKSRWQQ  420
GNVFSCSVMH EALHNHYTQE SLSLSPGK                                     448

SEQ ID NO: 288       moltype = AA   length = 448
FEATURE              Location/Qualifiers
REGION               1..448
                     note = Description of Artificial Sequence: Synthetic
                      polypeptide
source               1..448
                     mol_type = protein
                     organism = synthetic construct
SEQUENCE: 288
QVQLVESGGG VVQPGRSLRL SCAASGFTFS NYGMHWVRQA PGKGLEWVAV ISHHGSSKYY  60
ADSVKGRFTI SRDNSKNTLY LQMNSLRAED TAVYYCARDW FFYLFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEFEGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP ASIEKTISKA KGQPREPQVC TLPPSRDELT  360
KNQVSLTCLV EGFYPSDIAV EWESNGQPEN NYKTTPPVLD SDGSFFLYSD LTVDKSRWQQ  420
GNVFSCSVMH EALHNHYTQE SLSLSPGK                                     448

SEQ ID NO: 289       moltype = AA   length = 448
FEATURE              Location/Qualifiers
REGION               1..448
                     note = Description of Artificial Sequence: Synthetic
                      polypeptide
source               1..448
                     mol_type = protein
                     organism = synthetic construct
SEQUENCE: 289
QVQLVESGGG VVQPGRSLRL SCAASGFTFS NYGMHWVRQA PGKGLEWVAV ISHHGSSKYY  60
ADSVKGRFTI SRDNSKNTLY LQMNSLRAED TAVYYCARDW FYFIFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEFEGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP ASIEKTISKA KGQPREPQVC TLPPSRDELT  360
KNQVSLTCLV EGFYPSDIAV EWESNGQPEN NYKTTPPVLD SDGSFFLYSD LTVDKSRWQQ  420
GNVFSCSVMH EALHNHYTQE SLSLSPGK                                     448

SEQ ID NO: 290       moltype = AA   length = 447
FEATURE              Location/Qualifiers
REGION               1..447
                     note = Description of Artificial Sequence: Synthetic
                      polypeptide
source               1..447
                     mol_type = protein
                     organism = synthetic construct
SEQUENCE: 290
QVQLVQSGAE VKKPGASVKV SCKASDYTFS NYYIEWVRQA PGQGLEWMGE ILPGNGNTVY  60
NEKFKDRVTM TVDTSTSTAY MELRSLRSDD TAVYYCARWG DYALFANWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEFEGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP ASIEKTISKA KGQPREPQVC TLPPSRDELK  360
NQVSLTCLVE GFYPSDIAVE WESNGQPENN YKTTPPVLDS DGSFFLYSDL TVDKSRWQQG  420
NVFSCSVMHE ALHNHYTQES LSLSPGK                                      447

SEQ ID NO: 291       moltype = AA   length = 452
FEATURE              Location/Qualifiers
REGION               1..452
                     note = Description of Artificial Sequence: Synthetic
                      polypeptide
source               1..452
                     mol_type = protein
                     organism = synthetic construct
```

-continued

```
SEQUENCE: 291
QVQLVQSGAE VKKPGASVKV SCKASGYTFT DYFMNWVRQA PGQGLEWMGV INPYNDITIY   60
NQKFQGRVTM TVDRSTSTVY MELSSLRSED TAVYYCAREG VLYDGYYEGA YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEFE  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPASIEKT ISKAKGQPRE PQVCTLPPSR  360
DELTKNQVSL TCLVEGFYPS DIAVEWESNG QPENNYKTTP PVLDSDGSFF LYSDLTVDKS  420
RWQQGNVFSC SVMHEALHNH YTQESLSLSP GK                               452

SEQ ID NO: 292          moltype = AA  length = 448
FEATURE                 Location/Qualifiers
REGION                  1..448
                        note = Description of Artificial Sequence: Synthetic
                         polypeptide
source                  1..448
                        mol_type = protein
                        organism = synthetic construct
SEQUENCE: 292
QVQLVQSGAE VKKPGASVKV SCKATDYIFS NYYIEWVRQA PGQGLEWMGE ILPGTGNTVY   60
NEKFKDRVTM TVDTSTSTVY MELSSLRSED TAVYYCARWG DYALFANWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEFEGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP ASIEKTISKA KGQPREPQVC TLPPSRDELT  360
KNQVSLTCLV EGFYPSDIAV EWESNGQPEN NYKTTPPVLD SDGSFFLYSD LTVDKSRWQQ  420
GNVFSCSVMH EALHNHYTQE SLSLSPGK                                    448

SEQ ID NO: 293          moltype = AA  length = 446
FEATURE                 Location/Qualifiers
REGION                  1..446
                        note = Description of Artificial Sequence: Synthetic
                         polypeptide
source                  1..446
                        mol_type = protein
                        organism = synthetic construct
SEQUENCE: 293
SDVQLQESGP GLVKPSQSLS LTCSVTGYSI TSAYYWNWIR QFPGNKLEWM GYISDVGHNY   60
YNPSLKNRIS ITRDTSKNQF FLKLNSVTPE DTATYYCARD QVFAYWGQGT LVTVSAASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEFEGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAS IEKTISKAKG QPREPQVCTL PPSRDELTKN  360
QVSLTCLVEG FYPSDIAVEW ESNGQPENNY KTTPPVLDSD GSFFLYSDLT VDKSRWQQGN  420
VFSCSVMHEA LHNHYTQESL SLSPGK                                      446

SEQ ID NO: 294          moltype = AA  length = 446
FEATURE                 Location/Qualifiers
REGION                  1..446
                        note = Description of Artificial Sequence: Synthetic
                         polypeptide
source                  1..446
                        mol_type = protein
                        organism = synthetic construct
SEQUENCE: 294
SDVQLQESGP GLVKPSQSLS LTCSVTGYSI TSAYYWNWIR QFPGNKLEWM GYISDVGSNN   60
YNPSLKNRIS ITRDTFKNQF FLKLNSVTTE DTATYFCTRD QVFAYWGQGT LVTVSAASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEFEGGPSVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAS IEKTISKAKG QPREPQVCTL PPSRDELTKN  360
QVSLTCLVEG FYPSDIAVEW ESNGQPENNY KTTPPVLDSD GSFFLYSDLT VDKSRWQQGN  420
VFSCSVMHEA LHNHYTQESL SLSPGK                                      446

SEQ ID NO: 295          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 295
DIQLTQSPSF LSASVGDRVT ITCKASQNVG IAVAWYQQKP GKAPKLLIYA ASNRYTGVPS   60
RFSGSGSGTE FTLTISSLQP EDFATYYCQQ YSTYPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 296          moltype = AA  length = 214
```

-continued

```
FEATURE               Location/Qualifiers
REGION                1..214
                      note = Description of Artificial Sequence: Synthetic
                       polypeptide
source                1..214
                      mol_type = protein
                      organism = synthetic construct
SEQUENCE: 296
DIQMTQSPSF LSASVGDRVT ITCKASQNVG TNVAWYQQKP GKAPKPLIYS TSYRYSGVPS   60
RFSGSGSGTE FTLTISSLQP EDFATYYCQQ YNNYPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 297        moltype = AA  length = 219
FEATURE               Location/Qualifiers
REGION                1..219
                      note = Description of Artificial Sequence: Synthetic
                       polypeptide
source                1..219
                      mol_type = protein
                      organism = synthetic construct
SEQUENCE: 297
DIQMTQSPSS LSASVGDRVT ITCKSSQSLL HSDAKTFLYW YQQKPGKAPK LLIYEVSNRF   60
SGVPSRFSGS GSGTDFTLTI SSLQPEDFAT YYCLQGERLP FTFGQGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 298        moltype = AA  length = 214
FEATURE               Location/Qualifiers
REGION                1..214
                      note = Description of Artificial Sequence: Synthetic
                       polypeptide
source                1..214
                      mol_type = protein
                      organism = synthetic construct
SEQUENCE: 298
DIQMTQSPST LSASVGDRVT ITCKASQNVG TNVAWYQQKP GKAPKALIYS ASYRYSGVPS   60
RFSGSGSGTE FTLTISSLQP DDFATYYCQQ YNSYPFTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 299        moltype = AA  length = 219
FEATURE               Location/Qualifiers
REGION                1..219
                      note = Description of Artificial Sequence: Synthetic
                       polypeptide
source                1..219
                      mol_type = protein
                      organism = synthetic construct
SEQUENCE: 299
DIVMTQAAFS NPVTVGTSAS ISCRSSKSLL HSNGITYLYW YLQKPGQSPQ LLIYQMSNLA   60
SGVPDRFSSS GSGTDFTLRI SRVEAEDVGV YYCAQNLELP WTFGGGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 300        moltype = AA  length = 215
FEATURE               Location/Qualifiers
REGION                1..215
                      note = Description of Artificial Sequence: Synthetic
                       polypeptide
source                1..215
                      mol_type = protein
                      organism = synthetic construct
SEQUENCE: 300
DIVMTQSPKF MSTSVGDRVS VTCKASQNVG TNVAWYQQKP GQSPKALIYS ASYRYSGVPD   60
RFTGSGSGTD FTLTFSSVQS EDLAEYFCQQ YNNYPLTFGG GTKLEIKRRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 301        moltype = AA  length = 219
FEATURE               Location/Qualifiers
REGION                1..219
                      note = Description of Artificial Sequence: Synthetic
                       polypeptide
source                1..219
                      mol_type = protein
                      organism = synthetic construct
SEQUENCE: 301
DIVMTQSPLS LPVTPGEPAS ISCKSSQSLL HSDAKTFLYW YLQKPGQSPQ LLIYEVSNRF   60
```

```
SGVPDRFSGS GSGTDFTLKI SRVEAEDVGV YYCLQGRELP FTFGQGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 302            moltype = AA   length = 219
FEATURE                   Location/Qualifiers
REGION                    1..219
                          note = Description of Artificial Sequence: Synthetic
                          polypeptide
source                    1..219
                          mol_type = protein
                          organism = synthetic construct
SEQUENCE: 302
DIVMTQSPLS LPVTPGEPAS ISCKSSQSLL HSDGKTFLYW YLQKPGQSPQ LLIYEVSNRF  60
SGVPDRFSGS GSGTDFTLKI SRVEAEDVGV YYCLQGERLP FTFGQGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 303            moltype = AA   length = 219
FEATURE                   Location/Qualifiers
REGION                    1..219
                          note = Description of Artificial Sequence: Synthetic
                          polypeptide
source                    1..219
                          mol_type = protein
                          organism = synthetic construct
SEQUENCE: 303
DIVMTQSPLS LPVTPGEPAS ISCRSSQSLL HSDAKTFLDW YLQKPGQSPQ LLIYEVSNRA  60
SGVPDRFSGS GSGTDFTLKI SRVEAEDVGV YYCLQGERLP FTFGQGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 304            moltype = AA   length = 219
FEATURE                   Location/Qualifiers
REGION                    1..219
                          note = Description of Artificial Sequence: Synthetic
                          polypeptide
source                    1..219
                          mol_type = protein
                          organism = synthetic construct
SEQUENCE: 304
DIVMTQSPLS LPVTPGEPAS ISCRSSQSLL HSDGKTFLDW YLQKPGQSPQ LLIYEVSNRA  60
SGVPDRFSGS GSGTDFTLKI SRVEAEDVGV YYCLQGERLP FTFGQGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 305            moltype = AA   length = 219
FEATURE                   Location/Qualifiers
REGION                    1..219
                          note = Description of Artificial Sequence: Synthetic
                          polypeptide
source                    1..219
                          mol_type = protein
                          organism = synthetic construct
SEQUENCE: 305
DIVMTQTPLS LSVTPGQPAS ISCKSSQSLL HSDAKTFLYW YLQKPGQPPQ LLIYEVSNRF  60
SGVPDRFSGS GSGTDFTLKI SRVEAEDVGV YYCLQGERLP FTFGPGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 306            moltype = AA   length = 231
FEATURE                   Location/Qualifiers
REGION                    1..231
                          note = Description of Artificial Sequence: Synthetic
                          polypeptide
source                    1..231
                          mol_type = protein
                          organism = synthetic construct
SEQUENCE: 306
DIVMTQTPLS LSVTPGQPAS ISCKSSQSLL HSDAKTFLYW YLQKPGQPPQ LLIYEVSNRF  60
SGVPDRFSGS GSGTDFTLKI SRVEAEDVGV YYCLQGERLP FTFGPGTKVE IKSTFGQGTK  120
VEIKRTVAAP SVFIFPPSDE QLKSGTASVV CLLNNFYPRE AKVQWKVDNA LQSGNSQESV  180
TEQDSKDSTY SLSSTLTLSK ADYEKHKVYA CEVTHQGLSS PVTKSFNRGE C          231

SEQ ID NO: 307            moltype = AA   length = 219
FEATURE                   Location/Qualifiers
REGION                    1..219
                          note = Description of Artificial Sequence: Synthetic
                          polypeptide
```

-continued

```
source                    1..219
                          mol_type = protein
                          organism = synthetic construct
SEQUENCE: 307
DIVMTQTPLS LSVTPGQPAS ISCKSSQSLL HSDGKTFLYW YLQKPGQPPQ LLIYEVSNRF   60
SGVPDRFSGS GSGTDFTLKI SRVEAEDVGV YYCLQGERLP FTFGPGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 308           moltype = AA  length = 231
FEATURE                  Location/Qualifiers
REGION                   1..231
                         note = Description of Artificial Sequence: Synthetic
                          polypeptide
source                   1..231
                         mol_type = protein
                         organism = synthetic construct
SEQUENCE: 308
DIVMTQTPLS LSVTPGQPAS ISCKSSQSLL HSDGKTFLYW YLQKPGQPPQ LLIYEVSNRF   60
SGVPDRFSGS GSGTDFTLKI SRVEAEDVGV YYCLQGERLP FTFGPGTKVE IKSTFGQGTK  120
VEIKRTVAAP SVFIFPPSDE QLKSGTASVV CLLNNFYPRE AKVQWKVDNA LQSGNSQESV  180
TEQDSKDSTY SLSSTLTLSK ADYEKHKVYA CEVTHQGLSS PVTKSFNRGE C           231

SEQ ID NO: 309           moltype = AA  length = 219
FEATURE                  Location/Qualifiers
REGION                   1..219
                         note = Description of Artificial Sequence: Synthetic
                          polypeptide
source                   1..219
                         mol_type = protein
                         organism = synthetic construct
SEQUENCE: 309
DIVMTQTPLS LSVTPGQPAS ISCKSSQSLL HSDGKTFLYW YLQKPGQPPQ LLIYEVSNRF   60
SGVPDRFSGS GSGTDFTLKI SRVEAEDVGV YYCLQGIHLP FTFGPGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 310           moltype = AA  length = 231
FEATURE                  Location/Qualifiers
REGION                   1..231
                         note = Description of Artificial Sequence: Synthetic
                          polypeptide
source                   1..231
                         mol_type = protein
                         organism = synthetic construct
SEQUENCE: 310
DIVMTQTPLS LSVTPGQPAS ISCKSSQSLL HSDGKTFLYW YLQKPGQPPQ LLIYEVSNRF   60
SGVPDRFSGS GSGTDFTLKI SRVEAEDVGV YYCLQGIHLP FTFGPGTKVE IKSTFGQGTK  120
VEIKRTVAAP SVFIFPPSDE QLKSGTASVV CLLNNFYPRE AKVQWKVDNA LQSGNSQESV  180
TEQDSKDSTY SLSSTLTLSK ADYEKHKVYA CEVTHQGLSS PVTKSFNRGE C           231

SEQ ID NO: 311           moltype = AA  length = 218
FEATURE                  Location/Qualifiers
REGION                   1..218
                         note = Description of Artificial Sequence: Synthetic
                          polypeptide
source                   1..218
                         mol_type = protein
                         organism = synthetic construct
SEQUENCE: 311
DTVLTQSPAS LAVSLGQRAT ISCRASESVH SYGNSLIHWY QQKPGQPPRL LIYRASNLES   60
GIPARFSGSG SRTDFTLTIN PVEADDVATY YCQQTNEDPL TFGAGTKLEL KRTVAAPSVF  120
IPPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 312           moltype = AA  length = 215
FEATURE                  Location/Qualifiers
REGION                   1..215
                         note = Description of Artificial Sequence: Synthetic
                          polypeptide
source                   1..215
                         mol_type = protein
                         organism = synthetic construct
SEQUENCE: 312
EIVLTQSPGT LSLSPGERVT LSCRASQRVN NNYLAWYQQR PGQAPRLLIY GASSRATGIP   60
DRFSGSGSGT DFTLTISRLE PEDFAVYYCQ QYDRSPLTFG GGTKLEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215
```

```
SEQ ID NO: 313            moltype = AA  length = 213
FEATURE                   Location/Qualifiers
REGION                    1..213
                          note = Description of Artificial Sequence: Synthetic
                           polypeptide
source                    1..213
                          mol_type = protein
                          organism = synthetic construct
SEQUENCE: 313
QIVLTQSPAI MSASPGEKVT MTCSASSSVS YMHWYQQKSG TSPKRWIYDT SKLASGVPAR   60
FSGSGSGTSY SLTISSMEAE DAATYYCQQW SSNPLTFGAG TKLELKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 314            moltype =   length =
SEQUENCE: 314
000

SEQ ID NO: 315            moltype =   length =
SEQUENCE: 315
000

SEQ ID NO: 316            moltype =   length =
SEQUENCE: 316
000

SEQ ID NO: 317            moltype = AA  length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 317
GSSSG                                                                5

SEQ ID NO: 318            moltype = AA  length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 318
GGGGS                                                                5

SEQ ID NO: 319            moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 319
GGGGSGGGGS                                                          10

SEQ ID NO: 320            moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 320
GGGGSGGGGS GGGGS                                                    15

SEQ ID NO: 321            moltype = AA  length = 20
FEATURE                   Location/Qualifiers
REGION                    1..20
                          note = Description of Artificial Sequence: Synthetic peptide
source                    1..20
                          mol_type = protein
                          organism = synthetic construct
SEQUENCE: 321
GGGGSGGGGS GGGGSGGGGS                                               20

SEQ ID NO: 322            moltype = AA  length = 25
FEATURE                   Location/Qualifiers
REGION                    1..25
```

-continued

```
                      note = Description of Artificial Sequence: Synthetic peptide
source                1..25
                      mol_type = protein
                      organism = synthetic construct
SEQUENCE: 322
GGGGSGGGGS GGGGSGGGGS GGGGS                                            25

SEQ ID NO: 323        moltype = AA  length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 323
PGGGGSP                                                                7

SEQ ID NO: 324        moltype = AA  length = 19
FEATURE               Location/Qualifiers
REGION                1..19
                      note = Description of Artificial Sequence: Synthetic peptide
source                1..19
                      mol_type = protein
                      organism = synthetic construct
SEQUENCE: 324
PGGGGSPGGG GSPGGGGSP                                                   19

SEQ ID NO: 325        moltype = AA  length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 325
GEPGSGE                                                                7

SEQ ID NO: 326        moltype = AA  length = 14
FEATURE               Location/Qualifiers
REGION                1..14
                      note = Description of Artificial Sequence: Synthetic peptide
source                1..14
                      mol_type = protein
                      organism = synthetic construct
SEQUENCE: 326
GEPGSGEGEP GSGE                                                        14

SEQ ID NO: 327        moltype = AA  length = 22
FEATURE               Location/Qualifiers
REGION                1..22
                      note = Description of Artificial Sequence: Synthetic peptide
source                1..22
                      mol_type = protein
                      organism = synthetic construct
SEQUENCE: 327
GEPGSGEGEP GSGEEGEPGS GE                                               22

SEQ ID NO: 328        moltype = AA  length = 32
FEATURE               Location/Qualifiers
REGION                1..32
                      note = Description of Artificial Sequence: Synthetic
                       polypeptide
source                1..32
                      mol_type = protein
                      organism = synthetic construct
SEQUENCE: 328
EGEPGSGEEG EPGSGEEGEP GSGEEGEPGS GE                                    32

SEQ ID NO: 329        moltype = AA  length = 5
FEATURE               Location/Qualifiers
REGION                1..5
                      note = Description of Artificial Sequence: Synthetic peptide
source                1..5
                      mol_type = protein
                      organism = synthetic construct
SEQUENCE: 329
GKPGS                                                                  5

SEQ ID NO: 330        moltype = AA  length = 10
```

-continued

```
FEATURE               Location/Qualifiers
REGION                1..10
                      note = Description of Artificial Sequence: Synthetic peptide
source                1..10
                      mol_type = protein
                      organism = synthetic construct
SEQUENCE: 330
GKPGSGKPGS                                                          10

SEQ ID NO: 331        moltype = AA  length = 15
FEATURE               Location/Qualifiers
REGION                1..15
                      note = Description of Artificial Sequence: Synthetic peptide
source                1..15
                      mol_type = protein
                      organism = synthetic construct
SEQUENCE: 331
GKPGSGKPGS GKPGS                                                    15

SEQ ID NO: 332        moltype = AA  length = 20
FEATURE               Location/Qualifiers
REGION                1..20
                      note = Description of Artificial Sequence: Synthetic peptide
source                1..20
                      mol_type = protein
                      organism = synthetic construct
SEQUENCE: 332
GKPGSGKPGS GKPGSGKPGS                                               20

SEQ ID NO: 333        moltype = AA  length = 25
FEATURE               Location/Qualifiers
REGION                1..25
                      note = Description of Artificial Sequence: Synthetic peptide
source                1..25
                      mol_type = protein
                      organism = synthetic construct
SEQUENCE: 333
GKPGSGKPGS GKPGSGKPGS GKPGS                                         25

SEQ ID NO: 334        moltype = AA  length = 5
FEATURE               Location/Qualifiers
REGION                1..5
                      note = Description of Artificial Sequence: Synthetic peptide
source                1..5
                      mol_type = protein
                      organism = synthetic construct
SEQUENCE: 334
SSSSG                                                                5

SEQ ID NO: 335        moltype = AA  length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 335
SSSSGSSSSG                                                          10

SEQ ID NO: 336        moltype = AA  length = 15
FEATURE               Location/Qualifiers
REGION                1..15
                      note = Description of Artificial Sequence: Synthetic peptide
source                1..15
                      mol_type = protein
                      organism = synthetic construct
SEQUENCE: 336
SSSSGSSSSG SSSSG                                                    15

SEQ ID NO: 337        moltype = AA  length = 20
FEATURE               Location/Qualifiers
REGION                1..20
                      note = Description of Artificial Sequence: Synthetic peptide
source                1..20
                      mol_type = protein
                      organism = synthetic construct
SEQUENCE: 337
SSSSGSSSSG SSSSGSSSSG                                               20
```

-continued

```
SEQ ID NO: 338        moltype = AA   length = 19
FEATURE               Location/Qualifiers
REGION                1..19
                      note = Description of Artificial Sequence: Synthetic peptide
source                1..19
                      mol_type = protein
                      organism = synthetic construct
SEQUENCE: 338
GRPGSGPGSG RPGSGRPGS                                                19

SEQ ID NO: 339        moltype = AA   length = 24
FEATURE               Location/Qualifiers
REGION                1..24
                      note = Description of Artificial Sequence: Synthetic peptide
source                1..24
                      mol_type = protein
                      organism = synthetic construct
SEQUENCE: 339
GRPGSGPGSG RPGSGRPGSG RGPS                                          24

SEQ ID NO: 340        moltype = AA   length = 20
FEATURE               Location/Qualifiers
REGION                1..20
                      note = Description of Artificial Sequence: Synthetic peptide
source                1..20
                      mol_type = protein
                      organism = synthetic construct
SEQUENCE: 340
GKPGSGRPGS GKGPSGRPGS                                               20

SEQ ID NO: 341        moltype = AA   length = 731
FEATURE               Location/Qualifiers
REGION                1..731
                      note = Description of Artificial Sequence: Synthetic
                       polypeptide
source                1..731
                      mol_type = protein
                      organism = synthetic construct
SEQUENCE: 341
QVQLVQSGAE VKKPGASVKV SCKASDYTFS NYYIEWVRQA PGQGLEWMGE ILPGNGNTVY   60
NEKFKDRVTM TVDTSTSTAY MELRSLRSDD TAVYYCARWG DYALFANWGQ GTLVTVSSGG   120
GGSGGGGSGG GGSDIQMTQS PSTLSASVGD RVTITCKASQ NVGTNVAWYQ QKPGKAPKAL   180
IYSASYRYSG VPSRFSGSGS GTEFTLTISS LQPDDFATYY CQQYNSYPFT FGQGTKLEIK   240
SGGGSEVQLV ESGGGLVQPG GSLRLSCAAS GFTFSTYAMN WVRQAPGKGL EWVGRIRSKY   300
NNYATYYADS VKGRFTISRD DSKNTLYLQM NSLRAEDTAV YYCVRHGNFG DSYVSWFAYW   360
GQGTLVTVSS GKPGSGKPGS GKPGSGKPGS QAVVTQEPSL TVSPGGTVTL TCGSSTGAVT   420
TSNYANWVQQ KPGKSPRGLI GGTNKRAPGV PARFSGSLLG GKAALTISGA QPEDEADYYC   480
ALWYSNHWVF GGGTKLTVLE PKSSDKTHTC PPCPAPEFEG GPSVFLFPPK PKDTLMISRT   540
PEVTCVVVDV SHEDPEVKFN WYVDGVEVHN AKTKPREEQY NSTYRVVSVL TVLHQDWLNG   600
KEYKCKVSNK ALPASIEKTI SKAKGQPREP QVYTLPPCRK LTKNQVSLT CLVKGFYPSD    660
IAVEWESNGQ PENNYKTTPP VLKSDGSFFL YSKLTVDKSR WQQGNVFSCS VMHEALHNHY   720
TQKSLSLSPG K                                                        731

SEQ ID NO: 342        moltype = AA   length = 731
FEATURE               Location/Qualifiers
REGION                1..731
                      note = Description of Artificial Sequence: Synthetic
                       polypeptide
source                1..731
                      mol_type = protein
                      organism = synthetic construct
SEQUENCE: 342
QVQLVQSGAE VKKPGASVKV SCKATDYIFS NYYIEWVRQA PGQGLEWMGE ILPGTGNTVY   60
NEKFKDRVTM TVDTSTSTVY MELSSLRSED TAVYYCARWG DYALFANWGQ GTLVTVSSGG   120
GGSGGGGSGG GGSDIQMTQS PSTLSASVGD RVTITCKASQ NVGTNVAWYQ QKPGKAPKAL   180
IYSASYRYSG VPSRFSGSGS GTEFTLTISS LQPDDFATYY CQQYNSYPFT FGQGTKLEIK   240
SGGGSEVQLV ESGGGLVQPG GSLRLSCAAS GFTFSTYAMN WVRQAPGKGL EWVGRIRSKY   300
NNYATYYADS VKGRFTISRD DSKNTLYLQM NSLRAEDTAV YYCVRHGNFG DSYVSWFAYW   360
GQGTLVTVSS GKPGSGKPGS GKPGSGKPGS QAVVTQEPSL TVSPGGTVTL TCGSSTGAVT   420
TSNYANWVQQ KPGKSPRGLI GGTNKRAPGV PARFSGSLLG GKAALTISGA QPEDEADYYC   480
ALWYSNHWVF GGGTKLTVLE PKSSDKTHTC PPCPAPEFEG GPSVFLFPPK PKDTLMISRT   540
PEVTCVVVDV SHEDPEVKFN WYVDGVEVHN AKTKPREEQY NSTYRVVSVL TVLHQDWLNG   600
KEYKCKVSNK ALPASIEKTI SKAKGQPREP QVYTLPPCRK LTKNQVSLT CLVKGFYPSD    660
IAVEWESNGQ PENNYKTTPP VLKSDGSFFL YSKLTVDKSR WQQGNVFSCS VMHEALHNHY   720
TQKSLSLSPG K                                                        731

SEQ ID NO: 343        moltype = AA   length = 735
FEATURE               Location/Qualifiers
REGION                1..735
```

```
                              note = Description of Artificial Sequence: Synthetic
                               polypeptide
source                        1..735
                              mol_type = protein
                              organism = synthetic construct
SEQUENCE: 343
QVQLVQSGAE VKKPGASVKV SCKASGYTFT DYFMNWVRQA PGQGLEWMGV INPYNDITIY   60
NQKFQGRVTM TVDRSTSTVY MELSSLRSED TAVYYCAREG VLYDGYYEGA YWGQGTLVTV  120
SSGGGGSGGG GSGGGGSDIQ LTQSPSFLSA SVGDRVTITC KASQNVGIAV AWYQQKPGKA  180
PKLLIYAASN RYTGVPSRFS GSGSGTEFTL TISSLQPEDF ATYYCQQYST YPYTFGQGTK  240
LEIKSGGGSE VQLVESGGGL VQPGGSLRLS CAASGFTFST YAMNWVRQAP GKGLEWVGRI  300
RSKYNNYATY YADSVKGRFT ISRDDSKNTL YLQMNSLRAE DTAVYYCVRH GNFGDSYVSW  360
FAYWGQGTLV TVSSGKPGSG KPGSGKPGSG KPGSQAVVTQ EPSLTVSPGG TVTLTCGSST  420
GAVTTSNYAN WVQQKPGKSP RGLIGGTNKR APGVPARFSG SLLGGKAALT ISGAQPEDEA  480
DYYCALWYSN HWVFGGGTKL TVLEPKSSDK THTCPPCPAP EFEGGPSVFL FPPKPKDTLM  540
ISRTPEVTCV VVDVSHEDPE VKFNWYVDGV EVHNAKTKPR EEQYNSTYRV VSVLTVLHQD  600
WLNGKEYKCK VSNKALPASI EKTISKAKGQ PREPQVYTLP PCRKKLTKNQ VSLTCLVKGF  660
YPSDIAVEWE SNGQPENNYK TTPPVLKSDG SFFLYSKLTV DKSRWQQGNV FSCSVMHEAL  720
HNHYTQKSLS LSPGK                                                  735

SEQ ID NO: 344             moltype = AA   length = 735
FEATURE                    Location/Qualifiers
REGION                     1..735
                           note = Description of Artificial Sequence: Synthetic
                            polypeptide
source                     1..735
                           mol_type = protein
                           organism = synthetic construct
SEQUENCE: 344
QVQLVQSGAE VKKPGASVKV SCKASGYTFT DYFMNWVRQA PGQCLEWMGV INPYNDITIY   60
NQKFQGRVTM TVDRSTSTVY MELSSLRSED TAVYYCAREG VLYDGYYEGA YWGQGTLVTV  120
SSGGGGSGGG GSGGGGSDIQ LTQSPSFLSA SVGDRVTITC KASQNVGIAV AWYQQKPGKA  180
PKLLIYAASN RYTGVPSRFS GSGSGTEFTL TISSLQPEDF ATYYCQQYST YPYTFGCGTK  240
LEIKSGGGSE VQLVESGGGL VQPGGSLRLS CAASGFTFST YAMNWVRQAP GKGLEWVGRI  300
RSKYNNYATY YADSVKGRFT ISRDDSKNTL YLQMNSLRAE DTAVYYCVRH GNFGDSYVSW  360
FEYWGQGTLV TVSSGKPGSG KPGSGKPGSG KPGSQAVVTQ EPSLTVSPGG TVTLTCGSST  420
GAVTTSNYAN WVQQKPGKSP RGLIGGTNKR APGVPARFSG SLLGGKAALT ISGAQPEDEA  480
DYYCALWYSN HWVFGGGTKL TVLEPKSSDK THTCPPCPAP EFEGGPSVFL FPPKPKDTLM  540
ISRTPEVTCV VVDVSHEDPE VKFNWYVDGV EVHNAKTKPR EEQYNSTYRV VSVLTVLHQD  600
WLNGKEYKCK VSNKALPASI EKTISKAKGQ PREPQVYTLP PCRKKLTKNQ VSLTCLVKGF  660
YPSDIAVEWE SNGQPENNYK TTPPVLKSDG SFFLYSKLTV DKSRWQQGNV FSCSVMHEAL  720
HNHYTQKSLS LSPGK                                                  735

SEQ ID NO: 345             moltype = AA   length = 731
FEATURE                    Location/Qualifiers
REGION                     1..731
                           note = Description of Artificial Sequence: Synthetic
                            polypeptide
source                     1..731
                           mol_type = protein
                           organism = synthetic construct
SEQUENCE: 345
QVQLVQSGAE VKKPGASVKV SCKATDYIFS NYYIEWVRQA PGQGLEWMGE ILPGTGNTVY   60
NEKFKDRVTM TVDTSTSTVY MELSSLRSED TAVYYCARWG DYALFANWGQ GTLVTVSSGG  120
GGSGGGGSGG GGSDIQMTQS PSFLSASVGD RVTITCKASQ NVGTNVAWYQ QKPGKAPKPL  180
IYSTSYRYSG VPSRFSGSGS GTEFTLTISS LQPEDFATYY CQQYNNYPLT FGGGTKVEIK  240
SGGGSEVQLV ESGGGLVQPG GSLRLSCAAS GFTFSTYAMN WVRQAPGKGL EWVGRIRSKY  300
NNYATYYADS VKGRFTISRD DSKNTLYLQM NSLRAEDTAV YYCVRHGNFG DSYVSWFAYW  360
GQGTLVTVSS GKPGSGKPGS GKPGSGKPGS QAVVTQEPSL TVSPGGTVTL TCGSSTGAVT  420
TSNYANWVQQ KPGKSPRGLI GGTNKRAPGV PARFSGSLLG GKAALTISGA QPEDEADYYC  480
ALWYSNHWVF GGGTKLTVLE PKSSDKTHTC PPCPAPEFEG GPSVFLFPPK PKDTLMISRT  540
PEVTCVVVDV SHEDPEVKFN WYVDGVEVHN AKTKPREEQY NSTYRVVSVL TVLHQDWLNG  600
KEYKCKVSNK ALPASIEKTI SKAKGQPREP QVYTLPPCRK KLTKNQVSLT CLVKGFYPSD  660
IAVEWESNGQ PENNYKTTPP VLKSDGSFFL YSKLTVDKSR WQQGNVFSCS VMHEALHNHY  720
TQKSLSLSPG K                                                      731

SEQ ID NO: 346             moltype = AA   length = 735
FEATURE                    Location/Qualifiers
REGION                     1..735
                           note = Description of Artificial Sequence: Synthetic
                            polypeptide
source                     1..735
                           mol_type = protein
                           organism = synthetic construct
SEQUENCE: 346
QVQLVQSGAE VKKPGASVKV SCKASGYTFT DYFMNWVRQA PGQGLEWMGV INPYNDITIY   60
NQKFQGRVTM TVDRSTSTVY MELSSLRSED TAVYYCAREG VLYDGYYEGA YWGQGTLVTV  120
SSGGGGSGGG GSGGGGSDIQ LTQSPSFLSA SVGDRVTITC KASQNVGIAV AWYQQKPGKA  180
PKLLIYAASN RYTGVPSRFS GSGSGTEFTL TISSLQPEDF ATYYCQQYST YPYTFGQGTK  240
```

-continued

```
LEIKSGGGSE VQLVESGGGL VQPGGSLRLS CAASGFTFST YAMNWVRQAP GKGLEWVGRI  300
RSKYNNYATY YADSVKGRFT ISRDDSKNTL YLQMNSLRAE DTAVYYCVRH GNFGDSYVSW  360
FAYWGQGTLV TVSSGKPGSG KPGSGKPGSG KPGSQAVVTQ EPSLTVSPGG TVTLTCGSST  420
GAVTTSNYAN WVQQKPGKSP RGLIGGTNKR APGVPARFSG SLLGGKAALT ISGAQPEDEA  480
DYYCALWYSN HWVFGGGTKL TVLEPKSSDK THTCPPCPAP EFEGGPSVFL FPPKPKDTLM  540
ISRTPEVTCV VVDVSHEDPE VKFNWYVDGV EVHNAKTKPR EEQYNSTYRV VSVLTVLHQD  600
WLNGKEYKCK VSNKALPASI EKTISKAKGQ PREPQVYTLP PCRKKLTKNQ VSLTCLVKGF  660
YPSDIAVEWE SNGQPENNYK TTPPVLKSDG SFFLYSKLTV DKSRWQQGNV FSCSVMHEAL  720
HNHYTQKSLS LSPGK                                                  735
```

```
SEQ ID NO: 347            moltype = AA  length = 735
FEATURE                   Location/Qualifiers
REGION                    1..735
                          note = Description of Artificial Sequence: Synthetic
                           polypeptide
source                    1..735
                          mol_type = protein
                          organism = synthetic construct
SEQUENCE: 347
QVQLVQSGAE VKKPGASVKV SCKASGYTFT DYFMNWVRQA PGQGLEWMGV INPYNDITIY   60
NQKFQGRVTM TVDRSTSTVY MELSSLRSED TAVYYCAREG VLYDGYYEGA YWGQGTLVTV  120
SSGGGGSGGG GSGGGGSDIQ LTQSPSFLSA SVGDRVTITC KASQNVGIAV AWYQQKPGKA  180
PKLLIYAASN RYTGVPSRFS GSGSGTEFTL TISSLQPEDF ATYYCQQYST YPYTFGQGTK  240
LEIKSGGGSE VQLVESGGGL VQPGGSLRLS CAASGFTFST YAMNWVRQAP GKGLEWVGRI  300
RSKYNNYATY YADSVKGRFT ISRDDSKNTL YLQMNSLRAE DTAVYYCVRH GNFGDSYVSW  360
FEYWGQGTLV TVSSGKPGSG KPGSGKPGSG KPGSQAVVTQ EPSLTVSPGG TVTLTCGSST  420
GAVTTSNYAN WVQQKPGKSP RGLIGGTNKR APGVPARFSG SLLGGKAALT ISGAQPEDEA  480
DYYCALWYSN HWVFGGGTKL TVLEPKSSDK THTCPPCPAP EFEGGPSVFL FPPKPKDTLM  540
ISRTPEVTCV VVDVSHEDPE VKFNWYVDGV EVHNAKTKPR EEQYNSTYRV VSVLTVLHQD  600
WLNGKEYKCK VSNKALPASI EKTISKAKGQ PREPQVYTLP PCRKKLTKNQ VSLTCLVKGF  660
YPSDIAVEWE SNGQPENNYK TTPPVLKSDG SFFLYSKLTV DKSRWQQGNV FSCSVMHEAL  720
HNHYTQKSLS LSPGK                                                  735
```

```
SEQ ID NO: 348            moltype = AA  length = 735
FEATURE                   Location/Qualifiers
REGION                    1..735
                          note = Description of Artificial Sequence: Synthetic
                           polypeptide
source                    1..735
                          mol_type = protein
                          organism = synthetic construct
SEQUENCE: 348
QVQLVQSGAE VKKPGASVKV SCKASGYTFT DYFMNWVRQA PGQGLEWMGV INPYNDITIY   60
NQKFQGRVTM TVDRSTSTVY MELSSLRSED TAVYYCAREG VLYDGYYEGA YWGQGTLVTV  120
SSGGGGGSGGG GSGGGGSDIQ LTQSPSFLSA SVGDRVTITC KASQNVGIAV AWYQQKPGKA  180
PKLLIYAASN RYTGVPSRFS GSGSGTEFTL TISSLQPEDF ATYYCQQYST YPYTFGQGTK  240
LEIKSGGGSE VQLVESGGGL VQPGGSLRLS CAASGFTFST YAMNWVRQAP GKGLEWVGRI  300
RSKYNNYATY YADSVKGRFT ISRDDSKNTL YLQMNSLRAE DTAVYYCVRH GNFGDSYVSW  360
FNYWGQGTLV TVSSGKPGSG KPGSGKPGSG KPGSQAVVTQ EPSLTVSPGG TVTLTCGSST  420
GAVTTSNYAN WVQQKPGKSP RGLIGGTNKR APGVPARFSG SLLGGKAALT ISGAQPEDEA  480
DYYCALWYSN HWVFGGGTKL TVLEPKSSDK THTCPPCPAP EFEGGPSVFL FPPKPKDTLM  540
ISRTPEVTCV VVDVSHEDPE VKFNWYVDGV EVHNAKTKPR EEQYNSTYRV VSVLTVLHQD  600
WLNGKEYKCK VSNKALPASI EKTISKAKGQ PREPQVYTLP PCRKKLTKNQ VSLTCLVKGF  660
YPSDIAVEWE SNGQPENNYK TTPPVLKSDG SFFLYSKLTV DKSRWQQGNV FSCSVMHEAL  720
HNHYTQKSLS LSPGK                                                  735
```

```
SEQ ID NO: 349            moltype = AA  length = 733
FEATURE                   Location/Qualifiers
REGION                    1..733
                          note = Description of Artificial Sequence: Synthetic
                           polypeptide
source                    1..733
                          mol_type = protein
                          organism = synthetic construct
SEQUENCE: 349
EVQLVQSGAE VKKPGESLKI SCKGSGYEFS SHWMNWVRQM PGKCLEWMGQ IYPGDGDINY   60
NEKFRGQVTI SADKSISTAY LQWSSLKASD TAMYYCARHG NYVMDYWGQG TLVTVSSGGG  120
GSGGGGSGGG GSGGGGSIQL TQSPSFLSAS VGDRVTITCS ASSSVSYMFW YQQKPGKAPK  180
PWIYRTSNLA SGVPSRFSGS GSGTEFTLTI SSLQPEDFAT YYCQQFHDYP RTFGCGTKVE  240
IKSGGGSEVQ LVESGGGLVQ PGGSLRLSCA ASGFTFSTYA MNWVRQAPGK GLEWVGRIRS  300
KYNNYATYYA DSVKGRFTIS RDDSKNTLYL QMNSLRAEDT AVYYCVRHGN FGDSYVSWFE  360
YWGQGTLVTV SSGKPGSGKP GSGKPGSGKP GSQAVVTQEP SLTVSPGGTV TLTCGSSTGA  420
VTTSNYANWV QQKPGKSPRG LIGGTNKRAP GVPARFSGSL LGGKAALTIS GAQPEDEADY  480
YCALWYSNHW VFGGGTKLTV LEPKSSDKTH TCPPCPAPEF EGGPSVFLFP PKPKDTLMIS  540
RTPEVTCVVV DVSHEDPEVK FNWYVDGVEV HNAKTKPREE QYNSTYRVVS VLTVLHQDWL  600
NGKEYKCKVS NKALPASIEK TISKAKGQPR EPQVYTLPPC RKKLTKNQVS LTCLVKGFYP  660
SDIAVEWESN GQPENNYKTT PPVLKSDGSF FLYSKLTVDK SRWQQGNVFS CSVMHEALHN  720
HYTQKSLSLS PGK                                                    733
```

```
SEQ ID NO: 350         moltype = AA  length = 733
FEATURE                Location/Qualifiers
REGION                 1..733
                       note = Description of Artificial Sequence: Synthetic
                       polypeptide
source                 1..733
                       mol_type = protein
                       organism = synthetic construct
SEQUENCE: 350
EVQLVQSGAE VKKPGESLKI SCKGSGYEFS SHWMNWVRQM PGKGLEWMGQ IYPGDGDINY   60
NEKFRGQVTI SADKSISTAY LQWSSLKASD TAMYYCARHG NYVMDYWGQG TLVTVSSGGG  120
GSGGGGSGGG GSGGGGSIQL TQSPSFLSAS VGDRVTITCS ASSSVSYMFW YQQKPGKAPK  180
PWIYRTSNLA SGVPSRFSGS GSGTEFTLTI SSLQPEDFAT YYCQQFHDYP RTFGGGTKVE  240
IKSGGGSEVQ LVESGGGLVQ PGGSLRLSCA ASGFTFSTYA MNWVRQAPGK GLEWVGRIRS  300
KYNNYATYYA DSVKGRFTIS RDDSKNTLYL QMNSLRAEDT AVYYCVRHGN FGDSYVSWFA  360
YWGQGTLVTV SSGKPGSGKP GSGKPGSGKP GSQAVVTQEP SLTVSPGGTV TLTCGSSTGA  420
VTTSNYANWV QQKPGKSPRG LIGGTNKRAP GVPARFSGSL LGGKAALTIS GAQPEDEADY  480
YCALWYSNHW VFGGGTKLTV LEPKSSDKTH TCPPCPAPEF EGGPSVFLFP PKPKDTLMIS  540
RTPEVTCVVV DVSHEDPEVK FNWYVDGVEV HNAKTKPREE QYNSTYRVVS VLTVLHQDWL  600
NGKEYKCKVS NKALPASIEK TISKAKGQPR EPQVYTLPPC RKKLTKNQVS LTCLVKGFYP  660
SDIAVEWESN GQPENNYKTT PPVLKSDGSF FLYSKLTVDK SRWQQGNVFS CSVMHEALHN  720
HYTQKSLSLS PGK                                                     733

SEQ ID NO: 351         moltype = AA  length = 984
FEATURE                Location/Qualifiers
REGION                 1..984
                       note = Description of Artificial Sequence: Synthetic
                       polypeptide
source                 1..984
                       mol_type = protein
                       organism = synthetic construct
SEQUENCE: 351
QVQLQQWGAG LLKPSETLSL TCAVYGGSFS GYYWSWIRQP PGKCLEWIGD IDASGSTKYN   60
PSLKSRVTIS LDTSKNQFSL KLNSVTAADT AVYFCARKKY STVWSYFDNW GQGTLVTVSS  120
GGGGSGGGGS GGGGSSYELT QPSSVSVPPG QTASITCSGD KLGDKYASWY QQKPGQSPVL  180
VIYQDRKRPS GVPERFSGSN SGNTATLTIS GTQAMDEADY YCQAWGSSTA VFGCGTKLTV  240
LSGGGGSEVQ LVESGGGLVQ PGGSLKLSCA ASGFTFNKYA MNWVRQAPGK GLEWVARIRS  300
KYNNYATYYA DSVKDRFTIS RDDSKNTAYL QMNNLRAEDT AVYYCVRHGN FGNSYISYWA  360
YWGQGTLVTV SSGGGGSGGG GSGGGGSQTV VTQEPSLTVS PGGTVTLTCG SSTGAVTSGN  420
YPNWVQQKPG QAPRGLIGGT KFLAPGTPAR FSGSLLGGKA ALTLSGVQPE DEAEYYCVLW  480
YSNRWVFGGG TKLTVLGGGG DKTHTCPPCP APELLGGPSV FLFPPKPKDT LMISRTPEVT  540
CVVVDVSHED PEVKFNWYVD GVEVHNAKTK PCEEQYGSTY RCVSVLTVLH QDWLNGKEYK  600
CKVSNKALPA PIEKTISKAK GQPREPQVYT LPPSREEMTK NQVSLTCLVK GFYPSDIAVE  660
WESNGQPENN YKTTPPVLDS DGSFFLYSKL TVDKSRWQQG NVFSCSVMHE ALHNHYTQKS  720
LSLSPGKGGG GSGGGGSGGG GSGGGGSGGG GSGGGGSDKT HTCPPCPAPE LLGGPSVFLF  780
PPKPKDTLMI SRTPEVTCVV VDVSHEDPEV KFNWYVDGVE VHNAKTKPCE EQYGSTYRCV  840
SVLTVLHQDW LNGKEYKCKV SNKALPAPIE KTISKAKGQP REPQVYTLPP SREEMTKNQV  900
SLTCLVKGFY PSDIAVEWES NGQPENNYKT TPPVLDSDGS FFLYSKLTVD KSRWQQGNVF  960
SCSVMHEALH NHYTQKSLSL SPGK                                         984

SEQ ID NO: 352         moltype = AA  length = 985
FEATURE                Location/Qualifiers
REGION                 1..985
                       note = Description of Artificial Sequence: Synthetic
                       polypeptide
source                 1..985
                       mol_type = protein
                       organism = synthetic construct
SEQUENCE: 352
QVQLVESGGG VVQPGRSLRL SCAASGFTFS NHGMHWVRQA PGKCLEWVAG IWSEGSNKYY   60
ADAVKGRFTI SRDNSKNTLY LQMNSLRAED TAVYYCARAT YTTGWSYFDY WGQGTLVTVS  120
SGGGGSGGGG SGGGGSSYEL TQPPSVSVSP GQTASITCSG DKLGDKYASW YQQKSGQSPV  180
LVIYQDAKRP SGIPERFSGS NSGNTATLTI SGTQAMDEAD YYCQAFHQST WVFGCGTQLT  240
VLSGGGGSEV QLVESGGGLV QPGGSLKLSC AASGFTFNKY AMNWVRQAPG KGLEWVARIR  300
SKYNNYATYY ADSVKDRFTI SRDDSKNTAY LQMNNLKTED TAVYYCVRHG NFGNSYISYW  360
AYWGQGTLVT VSSGGGGSGG GGSGGGGSQT VVTQEPSLTV SPGGTVTLTC GSSTGAVTSG  420
NYPNWVQQKP GQAPRGLIGG TKFLAPGTPA RFSGSLLGGK AALTLSGVQP EDEAEYYCVL  480
WYSNRWVFGG GTKLTVLGGG GDKTHTCPPC PAPELLGGPS VFLFPPKPKD TLMISRTPEV  540
TCVVVDVSHE DPEVKFNWYV DGVEVHNAKT KPCEEQYGST YRCVSVLTVL HQDWLNGKEY  600
KCKVSNKALP APIEKTISKA KGQPREPQVY TLPPSREEMT KNQVSLTCLV KGFYPSDIAV  660
EWESNGQPEN NYKTTPPVLD SDGSFFLYSK LTVDKSRWQQ GNVFSCSVMH EALHNHYTQK  720
SLSLSPGKGG GGSGGGGSGG GGSGGGGSGG GGSGGGGSDK THTCPPCPAP ELLGGPSVFL  780
FPPKPKDTLM ISRTPEVTCV VVDVSHEDPE VKFNWYVDGV EVHNAKTKPC EEQYGSTYRC  840
VSVLTVLHQD WLNGKEYKCK VSNKALPAPI EKTISKAKGQ PREPQVYTLP PSREEMTKNQ  900
VSLTCLVKGF YPSDIAVEWE SNGQPENNYK TTPPVLDSDG SFFLYSKLTV DKSRWQQGNV  960
FSCSVMHEAL HNHYTQKSLS LSPGK                                        985

SEQ ID NO: 353         moltype = AA  length = 738
FEATURE                Location/Qualifiers
```

-continued

```
REGION                    1..738
                          note = Description of Artificial Sequence: Synthetic
                           polypeptide
source                    1..738
                          mol_type = protein
                          organism = synthetic construct
SEQUENCE: 353
QVQLVQSGAE VKKPGSSVKV SCKASGYTFT SYWLNWVRQA PGQGLEWMGM IHPSDSESRL   60
NQKFKDRVTI TADKSTSTAY MELSSLRSED TAVYYCARQG IITSVQEFAY WGQGTLVTVS  120
SGGGGSGGGG SGGGGSGGGG SIQMTQSPSS LSASVGDRVT ITCSASSSVN YIFWYQQKPG  180
KAPKLLIYRT SNLASGVPSR FSGSGSGTDF TLTISSLQPE DFATYYCQQY HSYPLTFGGG  240
TKVEIKSGGG GSEVQLVESG GGLVQPGGSL RLSCAASGFT FSTYAMNWVR QAPGKGLEWV  300
GRIRSKYNNY ATYYADSVKG RFTISRDDSK NTLYLQMNSL RAEDTAVYYC VRHGNFGDSY  360
VSWFEYWGQG TLVTVSSGKP GSGKPGSGKP GSGKPGSQAV VTQEPSLTVS PGGTVTLTCG  420
SSTGAVTTSN YANWVQQKPG KSPRGLIGGT NKRAPGVPAR FSGSLLGGKA ALTISGAQPE  480
DEADYYCALW YSNHWVFGGG TKLTVLEPKS SDKTHTCPPC PAPEFEGGPS VFLFPPKPKD  540
TLMISRTPEV TCVVVDVSHE DPEVKFNWYV DGVEVHNAKT KPREEQYNST YRVVSVLTVL  600
HQDWLNGKEY KCKVSNKALP ASIEKTISKA KGQPREPQVY TLPPCRKKLT KNQVSLTCLV  660
KGFYPSDIAV EWESNGQPEN NYKTTPPVLK SDGSFFLYSK LTVDKSRWQQ GNVFSCSVMH  720
EALHNHYTQK SLSLSPGK                                                738

SEQ ID NO: 354           moltype = AA  length = 737
FEATURE                  Location/Qualifiers
REGION                   1..737
                         note = Description of Artificial Sequence: Synthetic
                          polypeptide
source                   1..737
                         mol_type = protein
                         organism = synthetic construct
SEQUENCE: 354
QVQLVQSGAE VKKPGSSVKV SCKASGYTFT SYWLNWVRQA PGQGLEWMGM IHPSDSESRL   60
NQKFKDRVTI TADKSTSTAY MELSSLRSED TAVYYCARQG IITSVQEFAY WGQGTLVTVS  120
SGGGGSGGGG SGGGGSGGGG SIQMTQSPSS LSASVGDRVT ITCSASSSVN YIFWYQQKPG  180
KAPKLLIYRT SNLASGVPSR FSGSGSGTDF TLTISSLQPE DFATYYCQQY HSYPLTFGGG  240
TKVEIKSGGG SEVQLVESGG GLVQPGGSLR LSCAASGFTF STYAMNWVRQ APGKGLEWVG  300
RIRSKYNNYA TYYADSVKGR FTISRDDSKN TLYLQMNSLR AEDTAVYYCV RHGNFGDSYV  360
SWFEYWGQG LVTVSSGKPG SGKPGSGKPG SGKPGSQAVV TQEPSLTVSP GGTVTLTCGS  420
STGAVTTSNY ANWVQQKPG SPRGLIGGTN KRAPGVPARF SGSLLGGKAA LTISGAQPED  480
EADYYCALWY SNHWVFGGGT KLTVLEPKSS DKTHTCPPCP APEFEGGPSV FLFPPKPKDT  540
LMISRTPEVT CVVVDVSHED PEVKFNWYVD GVEVHNAKTK PREEQYNSTY RVVSVLTVLH  600
QDWLNGKEYK CKVSNKALPA SIEKTISKAK GQPREPQVYT LPPCRKKLTK NQVSLTCLVK  660
GFYPSDIAVE WESNGQPENN YKTTPPVLKS DGSFFLYSKL TVDKSRWQQG NVFSCSVMHE  720
ALHNHYTQKS LSLSPGK                                                737

SEQ ID NO: 355           moltype = AA  length = 738
FEATURE                  Location/Qualifiers
REGION                   1..738
                         note = Description of Artificial Sequence: Synthetic
                          polypeptide
source                   1..738
                         mol_type = protein
                         organism = synthetic construct
SEQUENCE: 355
QVQLVQSGAE VKKPGSSVKV SCKASGYTFT SYWLNWVRQA PGQGLEWMGM IHPSDSESRL   60
NQKFKDRVTI TADKSTSTAY MELSSLRSED TAVYYCARQG IITSVQEFAY WGQGTLVTVS  120
SGGGGSGGGG SGGGGSGGGG SIQMTQSPSS LSASVGDRVT ITCSASSSVN YIYWYQQKPG  180
KAPKLLIYRT SNLASGVPSR FSGSGSGTDF TLTISSLQPE DFATYYCQQY HSYPLTFGGG  240
TKVEIKSGGG GSEVQLVESG GGLVQPGGSL RLSCAASGFT FSTYAMNWVR QAPGKGLEWV  300
GRIRSKYNNY ATYYADSVKG RFTISRDDSK NTLYLQMNSL RAEDTAVYYC VRHGNFGDSY  360
VSWFEYWGQG TLVTVSSGKP GSGKPGSGKP GSGKPGSQAV VTQEPSLTVS PGGTVTLTCG  420
SSTGAVTTSN YANWVQQKPG KSPRGLIGGT NKRAPGVPAR FSGSLLGGKA ALTISGAQPE  480
DEADYYCALW YSNHWVFGGG TKLTVLEPKS SDKTHTCPPC PAPEFEGGPS VFLFPPKPKD  540
TLMISRTPEV TCVVVDVSHE DPEVKFNWYV DGVEVHNAKT KPREEQYNST YRVVSVLTVL  600
HQDWLNGKEY KCKVSNKALP ASIEKTISKA KGQPREPQVY TLPPCRKKLT KNQVSLTCLV  660
KGFYPSDIAV EWESNGQPEN NYKTTPPVLK SDGSFFLYSK LTVDKSRWQQ GNVFSCSVMH  720
EALHNHYTQK SLSLSPGK                                                738

SEQ ID NO: 356           moltype = AA  length = 738
FEATURE                  Location/Qualifiers
REGION                   1..738
                         note = Description of Artificial Sequence: Synthetic
                          polypeptide
source                   1..738
                         mol_type = protein
                         organism = synthetic construct
SEQUENCE: 356
QVQLVQSGAE VKKPGSSVKV SCKASGYTFT SYWLNWVRQA PGQGLEWMGM IHPSDSETRL   60
NQKFKDRVTI TADKSTSTAY MELSSLRSED TAVYYCARQG IITSVQEFAY WGQGTLVTVS  120
SGGGGSGGGG SGGGGSGGGG SIQMTQSPSS LSASVGDRVT ITCSASSSVN YIFWYQQKPG  180
```

```
KAPKLLIYRT SNLASGVPSR FSGSGSGTDF TLTISSLQPE DFATYYCQQY HSYPLTFGGG  240
TKVEIKSGGG GSEVQLVESG GGLVQPGGSL RLSCAASGFT FSTYAMNWVR QAPGKGLEWV  300
GRIRSKYNNY ATYYADSVKG RFTISRDDSK NTLYLQMNSL RAEDTAVYYC VRHGNFGDSY  360
VSWFEYWGQG TLVTVSSGKP GSGKPGSGKP GSGKPGSQAV VTQEPSLTVS PGGTVTLTCG  420
SSTGAVTTSN YANWVQQKPG KSPRGLIGGT NKRAPGVPAR FSGSLLGGKA ALTISGAQPE  480
DEADYYCALW YSNHWVFGGG TKLTVLEPKS SDKTHTCPPC PAPEFEGGPS VFLFPPKPKD  540
TLMISRTPEV TCVVVDVSHE DPEVKFNWYV DGVEVHNAKT KPREEQYNST YRVVSVLTVL  600
HQDWLNGKEY KCKVSNKALP ASIEKTISKA KGQPREPQVY TLPPCRKKLT KNQVSLTCLV  660
KGFYPSDIAV EWESNGQPEN NYKTTPPVLK SDGSFFLYSK LTVDKSRWQQ GNVFSCSVMH  720
EALHNHYTQK SLSLSPGK                                                 738
```

```
SEQ ID NO: 357              moltype = AA  length = 738
FEATURE                     Location/Qualifiers
REGION                      1..738
                            note = Description of Artificial Sequence: Synthetic
                             polypeptide
source                      1..738
                            mol_type = protein
                            organism = synthetic construct
SEQUENCE: 357
QVQLVQSGAE VKKPGSSVKV SCKASGYTFT SYWLNWVRQA PGQGLEWMGM IHPSDSETRL  60
NQKFKDRVTI TADKSTSTAY MELSSLRSED TAVYYCARQG IITSVQEFAY WGQGTLVTVS  120
SGGGGSGGGG SGGGGSGGGG SIQMTQSPSS LSASVGDRVT ITCSASSSVN YIYWYQQKPG  180
KAPKLLIYRT SNLASGVPSR FSGSGSGTDF TLTISSLQPE DFATYYCQQY HSYPLTFGGG  240
TKVEIKSGGG GSEVQLVESG GGLVQPGGSL RLSCAASGFT FSTYAMNWVR QAPGKGLEWV  300
GRIRSKYNNY ATYYADSVKG RFTISRDDSK NTLYLQMNSL RAEDTAVYYC VRHGNFGDSY  360
VSWFEYWGQG TLVTVSSGKP GSGKPGSGKP GSGKPGSQAV VTQEPSLTVS PGGTVTLTCG  420
SSTGAVTTSN YANWVQQKPG KSPRGLIGGT NKRAPGVPAR FSGSLLGGKA ALTISGAQPE  480
DEADYYCALW YSNHWVFGGG TKLTVLEPKS SDKTHTCPPC PAPEFEGGPS VFLFPPKPKD  540
TLMISRTPEV TCVVVDVSHE DPEVKFNWYV DGVEVHNAKT KPREEQYNST YRVVSVLTVL  600
HQDWLNGKEY KCKVSNKALP ASIEKTISKA KGQPREPQVY TLPPCRKKLT KNQVSLTCLV  660
KGFYPSDIAV EWESNGQPEN NYKTTPPVLK SDGSFFLYSK LTVDKSRWQQ GNVFSCSVMH  720
EALHNHYTQK SLSLSPGK                                                 738
```

```
SEQ ID NO: 358              moltype = AA  length = 737
FEATURE                     Location/Qualifiers
REGION                      1..737
                            note = Description of Artificial Sequence: Synthetic
                             polypeptide
source                      1..737
                            mol_type = protein
                            organism = synthetic construct
SEQUENCE: 358
QVQLVQSGAE VKKPGSSVKV SCKASGYTFT SYWMNWVRQA PGQGLEWMGM IHPSDSESRL  60
NQKFKDRVTI TADKSTSTAY MELSSLRSED TAVYYCARQG IITSVQEFAY WGQGTLVTVS  120
SGGGGSGGGG SGGGGSGGGG SIQMTQSPSS LSASVGDRVT ITCSASSSVN YIFWYQQKPG  180
KAPKLLIYRT SNLASGVPSR FSGSGSGTDF TLTISSLQPE DFATYYCQQY HSYPLTFGGG  240
TKVEIKSGGG GSEVQLVESG GGLVQPGGSL RLSCAASGFT FSTYAMNWVR QAPGKGLEWV  300
GRIRSKYNNY ATYYADSVKG RFTISRDDSK NTLYLQMNSL RAEDTAVYYC VRHGNFGDSY  360
VSWFEYWGQG TLVTVSSGKP GSGKPGSGKP GSGKPGSQAV VTQEPSLTVS PGGTVTLTCG  420
SSTGAVTTSN YANWVQQKPG KSPRGLIGGT NKRAPGVPAR FSGSLLGGKA ALTISGAQPE  480
DEADYYCALW YSNHWVFGGG TKLTVLEPKS SDKTHTCPPC PAPEFEGGPS VFLFPPKPKD  540
TLMISRTPEV TCVVVDVSHE DPEVKFNWYV DGVEVHNAKT KPREEQYNST YRVVSVLTVL  600
HQDWLNGKEY KCKVSNKALP ASIEKTISKA KGQPREPQVY TLPPCRKKLT KNQVSLTCLV  660
KGFYPSDIAV EWESNGQPEN NYKTTPPVLK SDGSFFLYSK LTVDKSRWQQ GNVFSCSVMH  720
EALHNHYTQK SLSLSPG                                                  737
```

```
SEQ ID NO: 359              moltype = AA  length = 738
FEATURE                     Location/Qualifiers
REGION                      1..738
                            note = Description of Artificial Sequence: Synthetic
                             polypeptide
source                      1..738
                            mol_type = protein
                            organism = synthetic construct
SEQUENCE: 359
QVQLVQSGAE VKKPGSSVKV SCKASGYTFT SYWMNWVRQA PGQGLEWMGM IHPSDSESRL  60
NQKFKDRVTI TADKSTSTAY MELSSLRSED TAVYYCARQG IITSVQEFAY WGQGTLVTVS  120
SGGGGSGGGG SGGGGSGGGG SIQMTQSPSS LSASVGDRVT ITCSASSSVN YIYWYQQKPG  180
KAPKLLIYRT SNLASGVPSR FSGSGSGTDF TLTISSLQPE DFATYYCQQY HSYPLTFGGG  240
TKVEIKSGGG GSEVQLVESG GGLVQPGGSL RLSCAASGFT FSTYAMNWVR QAPGKGLEWV  300
GRIRSKYNNY ATYYADSVKG RFTISRDDSK NTLYLQMNSL RAEDTAVYYC VRHGNFGDSY  360
VSWFEYWGQG TLVTVSSGKP GSGKPGSGKP GSGKPGSQAV VTQEPSLTVS PGGTVTLTCG  420
SSTGAVTTSN YANWVQQKPG KSPRGLIGGT NKRAPGVPAR FSGSLLGGKA ALTISGAQPE  480
DEADYYCALW YSNHWVFGGG TKLTVLEPKS SDKTHTCPPC PAPEFEGGPS VFLFPPKPKD  540
TLMISRTPEV TCVVVDVSHE DPEVKFNWYV DGVEVHNAKT KPREEQYNST YRVVSVLTVL  600
HQDWLNGKEY KCKVSNKALP ASIEKTISKA KGQPREPQVY TLPPCRKKLT KNQVSLTCLV  660
KGFYPSDIAV EWESNGQPEN NYKTTPPVLK SDGSFFLYSK LTVDKSRWQQ GNVFSCSVMH  720
EALHNHYTQK SLSLSPGK                                                 738
```

-continued

```
SEQ ID NO: 360          moltype = AA  length = 738
FEATURE                 Location/Qualifiers
REGION                  1..738
                        note = Description of Artificial Sequence: Synthetic
                         polypeptide
source                  1..738
                        mol_type = protein
                        organism = synthetic construct
SEQUENCE: 360
QVQLVQSGAE VKKPGSSVKV SCKASGYTFT SYWMNWVRQA PGQGLEWMGM IHPSDSETRL  60
NQKFKDRVTI TADKSTSTAY MELSSLRSED TAVYYCARQG IITSVQEFAY WGQGTLVTVS  120
SGGGGSGGGG SGGGGSGGGG SIQMTQSPSS LSASVGDRVT ITCSASSSVN YIFWYQQKPG  180
KAPKLLIYRT SNLASGVPSR FSGSGSGTDF TLTISSLQPE DFATYYCQQY HSYPLTFGGG  240
TKVEIKSGGG GSEVQLVESG GGLVQPGGSL RLSCAASGFT FSTYAMNWVR QAPGKGLEWV  300
GRIRSKYNNY ATYYADSVKG RFTISRDDSK NTLYLQMNSL RAEDTAVYYC VRHGNFGDSY  360
VSWFEYWGQG TLVTVSSGKP GSGKPGSGKP GSGKPGSQAV VTQEPSLTVS PGGTVTLTCG  420
SSTGAVTTSN YANWVQQKPG KSPRGLIGGT NKRAPGVPAR FSGSLLGGKA ALTISGAQPE  480
DEADYYCALW YSNHWVFGGG TKLTVLEPKS SDKTHTCPPC PAPEFEGGPS VFLFPPKPKD  540
TLMISRTPEV TCVVVDVSHE DPEVKFNWYV DGVEVHNAKT KPREEQYNST YRVVSVLTVL  600
HQDWLNGKEY KCKVSNKALP ASIEKTISKA KGQPREPQVY TLPPCRKKLT KNQVSLTCLV  660
KGFYPSDIAV EWESNGQPEN NYKTTPPVLK SDGSFFLYSK LTVDKSRWQQ GNVFSCSVMH  720
EALHNHYTQK SLSLSPGK                                                738

SEQ ID NO: 361          moltype = AA  length = 737
FEATURE                 Location/Qualifiers
REGION                  1..737
                        note = Description of Artificial Sequence: Synthetic
                         polypeptide
source                  1..737
                        mol_type = protein
                        organism = synthetic construct
SEQUENCE: 361
QVQLVQSGAE VKKPGSSVKV SCKASGYTFT SYWMNWVRQA PGQGLEWMGM IHPSDSETRL  60
NQKFKDRVTI TADKSTSTAY MELSSLRSED TAVYYCARQG IITSVQEFAY WGQGTLVTVS  120
SGGGGSGGGG SGGGGSGGGG SIQMTQSPSS LSASVGDRVT ITCSASSSVN YIYWYQQKPG  180
KAPKLLIYRT SNLASGVPSR FSGSGSGTDF TLTISSLQPE DFATYYCQQY HSYPLTFGGG  240
TKVEIKSGGG GSEVQLVESG GGLVQPGGSL RLSCAASGFT FSTYAMNWVR QAPGKGLEWV  300
GRIRSKYNNY ATYYADSVKG RFTISRDDSK NTLYLQMNSL RAEDTAVYYC VRHGNFGDSY  360
VSWFEYWGQG TLVTVSSGKP GSGKPGSGKP GSGKPGSQAV VTQEPSLTVS PGGTVTLTCG  420
SSTGAVTTSN YANWVQQKPG KSPRGLIGGT NKRAPGVPAR FSGSLLGGKA ALTISGAQPE  480
DEADYYCALW YSNHWVFGGG TKLTVLEPKS SDKTHTCPPC PAPEFEGGPS VFLFPPKPKD  540
TLMISRTPEV TCVVVDVSHE DPEVKFNWYV DGVEVHNAKT KPREEQYNST YRVVSVLTVL  600
HQDWLNGKEY KCKVSNKALP ASIEKTISKA KGQPREPQVY TLPPCRKKLT KNQVSLTCLV  660
KGFYPSDIAV EWESNGQPEN NYKTTPPVLK SDGSFFLYSK LTVDKSRWQQ GNVFSCSVMH  720
EALHNHYTQK SLSLSPG                                                 737

SEQ ID NO: 362          moltype = AA  length = 737
FEATURE                 Location/Qualifiers
REGION                  1..737
                        note = Description of Artificial Sequence: Synthetic
                         polypeptide
source                  1..737
                        mol_type = protein
                        organism = synthetic construct
SEQUENCE: 362
QVQLVQSGAE VKKPGSSVKV SCKASGYTFT SYWMNWVRQA PGQGLEWMGM IHPSDSETRL  60
NQKFKDRVTI TADKSTSTAY MELSSLRSED TAVYYCARQG IITSVQEFAY WGQGTLVTVS  120
SGGGGSGGGG SGGGGSGGGG SIQMTQSPSS LSASVGDRVT ITCSASSSVN YIYWYQQKPG  180
KAPKLLIYRT SNLASGVPSR FSGSGSGTDF TLTISSLQPE DFATYYCQQY HSYPLTFGGG  240
TKVEIKSGGG SEVQLVESGG GLVQPGGSLR LSCAASGFTF STYAMNWVRQ APGKGLEWVG  300
RIRSKINNYA TYYADSVKGR FTISRDDSKN TLYLQMNSLR AEDTAVYYCV RHGNFGDSYV  360
SWFAYWGQGT LVTVSSGKPG SGKPGSGKPG SGKPGSQAVV TQEPSLTVSP GGTVTLTCGS  420
STGAVTTSNY ANWVQQKPGK SPRGLIGGTN KRAPGVPARF SGSLLGGKAA LTISGAQPED  480
EADYYCALWY SNHWVFGGGT KLTVLEPKSS DKTHTCPPCP APEFEGGPSV FLFPPKPKDT  540
LMISRTPEVT CVVVDVSHED PEVKFNWYVD GVEVHNAKTK PREEQYNSTY RVVSVLTVLH  600
QDWLNGKEYK CKVSNKALPA SIEKTISKAK GQPREPQVYT LPPCRKKLTK NQVSLTCLVK  660
GFYPSDIAVE WESNGQPENN YKTTPPVLKS DGSFFLYSKL TVDKSRWQQG NVFSCSVMHE  720
ALHNHYTQKS LSLSPGK                                                 737

SEQ ID NO: 363          moltype = AA  length = 737
FEATURE                 Location/Qualifiers
REGION                  1..737
                        note = Description of Artificial Sequence: Synthetic
                         polypeptide
source                  1..737
                        mol_type = protein
                        organism = synthetic construct
SEQUENCE: 363
```

```
QVQLVQSGAE VKKPGSSVKV SCKASGYTFT SYWMNWVRQA PGQGLEWMGM IHPSDSETRL   60
NQKFKDRVTI TADKSTSTAY MELSSLRSED TAVYYCARQG IITSVQEFAY WGQGTLVTVS  120
SGGGGSGGGG SGGGGSGGGG SIQMTQSPSS LSASVGDRVT ITCSASSSVN YIYWYQQKPG  180
KAPKLLIYRT SNLASGVPSR FSGSGSGTDF TLTISSLQPE DFATYYCQQY HSYPLTFGGG  240
TKVEIKSGGG SEVQLVESGG GLVQPGGSLR LSCAASGFTF STYAMNWVRQ APGKGLEWVG  300
RIRSKYNNYA TYYADSVKGR FTISRDDSKN TLYLQMNSLR AEDTAVYYCV RHGNFGDSYV  360
SWFAYWQGT LVTVSSGKPG SGKPGSGKPG SGKPGSQAVV TQEPSLTVSP GGTVTLTCGS  420
STGAVTTSNY ANWVQQKPGK SPRGLIGGTN KRAPGVPARF SGSLLGGKAA LTISGAQPED  480
EADYYCALWY SNHWVFGGGT KLTVLEPKSS DKTHTCPPCP APEFEGGPSV FLFPPKPKDT  540
LMISRTPEVT CVVVDVSHED PEVKFNWYVD GVEVHNAKTK PREEQYNSTY RVVSVLTVLH  600
QDWLNGKEYK CKVSNKALPA SIEKTISKAK GQPREPQVYT LPPCRKKLTK NQVSLTCLVK  660
GFYPSDIAVE WESNGQPENN YKTTPPVLKS DGSFFLYSKL TVDKSRWQQG NVFSCSVMHE  720
ALHNHYTQKS LSLSPGK                                                 737

SEQ ID NO: 364          moltype = AA  length = 737
FEATURE                 Location/Qualifiers
REGION                  1..737
                        note = Description of Artificial Sequence: Synthetic
                         polypeptide
source                  1..737
                        mol_type = protein
                        organism = synthetic construct
SEQUENCE: 364
QVQLVQSGAE VKKPGSSVKV SCKASGYTFT SYWMNWVRQA PGQGLEWMGM IHPSDSETRL   60
NQKFKDRVTI TADKSTSTAY MELSSLRSED TAVYYCARQG IITSVQEFAY WGQGTLVTVS  120
SGGGGSGGGG SGGGGSGGGG SIQMTQSPSS LSASVGDRVT ITCSASSSVN YIYWYQQKPG  180
KAPKLLIYRT SNLASGVPSR FSGSGSGTDF TLTISSLQPE DFATYYCQQY HSYPLTFGGG  240
TKVEIKSGGG SEVQLVESGG GLVQPGGSLR LSCAASGFTF STYAMNWVRQ APGKGLEWVG  300
RIRSKYNNYA TYYADSVKGR FTISRDDSKN TLYLQMNSLR AEDTAVYYCV RHGNFGDSYV  360
SWFEYWQGT LVTVSSGKPG SGKPGSGKPG SGKPGSQAVV TQEPSLTVSP GGTVTLTCGS  420
STGAVTTSNY ANWVQQKPGK SPRGLIGGTN KRAPGVPARF SGSLLGGKAA LTISGAQPED  480
EADYYCALWY SNHWVFGGGT KLTVLEPKSS DKTHTCPPCP APEFEGGPSV FLFPPKPKDT  540
LMISRTPEVT CVVVDVSHED PEVKFNWYVD GVEVHNAKTK PREEQYNSTY RVVSVLTVLH  600
QDWLNGKEYK CKVSNKALPA SIEKTISKAK GQPREPQVYT LPPCRKKLTK NQVSLTCLVK  660
GFYPSDIAVE WESNGQPENN YKTTPPVLKS DGSFFLYSKL TVDKSRWQQG NVFSCSVMHE  720
ALHNHYTQKS LSLSPGK                                                 737

SEQ ID NO: 365          moltype = AA  length = 737
FEATURE                 Location/Qualifiers
REGION                  1..737
                        note = Description of Artificial Sequence: Synthetic
                         polypeptide
source                  1..737
                        mol_type = protein
                        organism = synthetic construct
SEQUENCE: 365
QVQLVQSGAE VKKPGSSVKV SCKASGYTFT SYWMNWVRQA PGQGLEWMGM IHPSDSETRL   60
NQKFKDRVTI TADKSTSTAY MELSSLRSED TAVYYCARQG IITSVQEFNY WGQGTLVTVS  120
SGGGGSGGGG SGGGGSGGGG SIQMTQSPSS LSASVGDRVT ITCSASSSVN YIYWYQQKPG  180
KAPKLLIYRT SNLASGVPSR FSGSGSGTDF TLTISSLQPE DFATYYCQQY HSYPLTFGGG  240
TKVEIKSGGG SEVQLVESGG GLVQPGGSLR LSCAASGFTF STYAMNWVRQ APGKGLEWVG  300
RIRSKYNNYA TYYADSVKGR FTISRDDSKN TLYLQMNSLR AEDTAVYYCV RHGNFGDSYV  360
SWFAYWQGT LVTVSSGKPG SGKPGSGKPG SGKPGSQAVV TQEPSLTVSP GGTVTLTCGS  420
STGAVTTSNY ANWVQQKPGK SPRGLIGGTN KRAPGVPARF SGSLLGGKAA LTISGAQPED  480
EADYYCALWY SNHWVFGGGT KLTVLEPKSS DKTHTCPPCP APEFEGGPSV FLFPPKPKDT  540
LMISRTPEVT CVVVDVSHED PEVKFNWYVD GVEVHNAKTK PREEQYNSTY RVVSVLTVLH  600
QDWLNGKEYK CKVSNKALPA SIEKTISKAK GQPREPQVYT LPPCRKKLTK NQVSLTCLVK  660
GFYPSDIAVE WESNGQPENN YKTTPPVLKS DGSFFLYSKL TVDKSRWQQG NVFSCSVMHE  720
ALHNHYTQKS LSLSPGK                                                 737

SEQ ID NO: 366          moltype = AA  length = 474
FEATURE                 Location/Qualifiers
REGION                  1..474
                        note = Description of Artificial Sequence: Synthetic
                         polypeptide
source                  1..474
                        mol_type = protein
                        organism = synthetic construct
SEQUENCE: 366
EVQLVQSGAE VKKPGESLKI SCKGSGYEFS SHWMNWVRQM PGKGLEWMGQ IYPGDGDINY   60
NEKFRGQVTI SADKSISTAY LQWSSLKASD TAMYYCARHG NYVMDYWGQG TLVTVSSGKP  120
GSGKPGSGKP GSGKPGSIQL TQSPSFLSAS VGDRVTITCS ASSSVSYMFW YQQKPGKAPK  180
PWIYRTSNLA SGVPSRFSGS GSGTEFTLTI SSLQPEDFAT YYCQQFHDYP RTFGGGTKVE  240
IKEPKSSDKT HTCPPCPAPE FEGGPSVFLF PPKPKDTLMI SRTPEVTCVV VDVSHEDPEV  300
KFNWYVDGVE VHNAKTKPRE EQYNSTYRVV SVLTVLHQDW LNGKEYKCKV SNKALPASIE  360
KTISKAKGQP REPQVYTLPP CRKKLTKNQV SLTCLVKGFY PSDIAVEWES NGQPENNYKT  420
TPPVLKSDGS FFLYSKLTVD KSRWQQGNVF SCSVMHEALH NHYTQKSLSL SPGK        474

SEQ ID NO: 367          moltype = AA  length = 478
```

```
FEATURE            Location/Qualifiers
REGION             1..478
                   note = Description of Artificial Sequence: Synthetic
                    polypeptide
source             1..478
                   mol_type = protein
                   organism = synthetic construct
SEQUENCE: 367
QVQLVQSGAE VKKPGSSVKV SCKASGYTFT SYWMNWVRQA PGQGLEWMGM IHPSDSETRL   60
NQKFKDRVTI TADKSTSTAY MELSSLRSED TAVYYCARQG IITSVQEFAY WGQGTLVTVS  120
SGKPGSGKPG SGKPGSGKPG SIQMTQSPSS LSASVGDRVT ITCSASSSVN YIYWYQQKPG  180
KAPKLLIYRT SNLASGVPSR FSGSGSGTDF TLTISSLQPE DFATYYCQQY HSYPLTFGGG  240
TKVEIKEPKS SDKTHTCPPC PAPEFEGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
ASIEKTISKA KGQPREPQVY TLPPCRKKLT KNQVSLTCLV KGFYPSDIAV EWESNGQPEN  420
NYKTTPPVLK SDGSFFLYSK LTVDKSRWQQ GNVFSCSVMH EALHNHYTQK SLSLSPGK    478

SEQ ID NO: 368       moltype = AA   length = 450
FEATURE            Location/Qualifiers
REGION             1..450
                   note = Description of Artificial Sequence: Synthetic
                    polypeptide
source             1..450
                   mol_type = protein
                   organism = synthetic construct
SEQUENCE: 368
EVQLVESGGG LVQPGGSLRL SCAASGFTFS SFGMHWVRQA PGKGLEWVSY ISSGSSTIYY   60
ADTVKGRFTI SRDNAKNSLY LQMNSLRAED TAVYYCARWG YYGSSYFAYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPEFEGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPASIEKTIS KAKGQPREPQ VCTLPPSRDE  360
LTKNQVSLTC LVEGFYPSDI AVEWESNGQP ENNYKTTPPV LDSDGSFFLY SDLTVDKSRW  420
QQGNVFSCSV MHEALHNHYT QESLSLSPGK                                  450

SEQ ID NO: 369       moltype = AA   length = 447
FEATURE            Location/Qualifiers
REGION             1..447
                   note = Description of Artificial Sequence: Synthetic
                    polypeptide
source             1..447
                   mol_type = protein
                   organism = synthetic construct
SEQUENCE: 369
EVQLVQSGAE VKKPGESLKI SCKGSGYEFS SHWMNWVRQM PGKGLEWMGQ IYPGDGDINY   60
NEKFRGQVTI SADKSISTAY LQWSSLKASD TAMYYCARHG NYVMDYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKRVEPKSC DKTHTCPPCP APEFEGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA SIEKTISKAK GQPREPQVCT LPPSRDELTK  360
NQVSLTCLVE GFYPSDIAVE WESNGQPENN YKTTPPVLDS DGSFFLYSDL TVDKSRWQQG  420
NVFSCSVMHE ALHNHYTQES LSLSPGK                                     447

SEQ ID NO: 370       moltype = AA   length = 447
FEATURE            Location/Qualifiers
REGION             1..447
                   note = Description of Artificial Sequence: Synthetic
                    polypeptide
source             1..447
                   mol_type = protein
                   organism = synthetic construct
SEQUENCE: 370
QVQLVQSGAE VKKPGASVKV SCKASGYEFS SHWMNWVRQA PGQGLEWMGQ IYPGDGDINY   60
NEKFRGRVTM TRDTSTSTVY MELSSLRSED TAVYYCARHG NYVMDYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKRVEPKSC DKTHTCPPCP APEFEGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA SIEKTISKAK GQPREPQVCT LPPSRDELTK  360
NQVSLTCLVE GFYPSDIAVE WESNGQPENN YKTTPPVLDS DGSFFLYSDL TVDKSRWQQG  420
NVFSCSVMHE ALHNHYTQES LSLSPGK                                     447

SEQ ID NO: 371       moltype = AA   length = 451
FEATURE            Location/Qualifiers
REGION             1..451
                   note = Description of Artificial Sequence: Synthetic
                    polypeptide
source             1..451
                   mol_type = protein
                   organism = synthetic construct
```

```
SEQUENCE: 371
QVQLVQSGAE VKKPGASVKV SCKASGYTFT SYWMNWVRQA PGQGLEWIGM IHPSDSETRL   60
NQKFKDRVTL TVDKSSSTAY MELSSLRSED TAVYYCARQG IITSVQEFAY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVCTLPPSRD  360
ELTKNQVSLT CLVEGFYPSD IAVEWESNGQ PENNYKTTPP VLDSDGSFFL YSDLTVDKSR  420
WQQGNVFSCS VMHEALHNHY TQESLSLSPG K                                 451

SEQ ID NO: 372          moltype = AA  length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 372
QVQLVQSGAE VKKPGASVKV SCKASGYTFT SYWMNWVRQA PGQGLEWMGM IHPSDSETRL   60
NQEFKDRVTM TRDTSTSTVY MELSSLRSED TAVYYCARQG VITSVQEFAY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVCTLPPSRD  360
ELTKNQVSLT CLVEGFYPSD IAVEWESNGQ PENNYKTTPP VLDSDGSFFL YSDLTVDKSR  420
WQQGNVFSCS VMHEALHNHY TQESLSLSPG K                                 451

SEQ ID NO: 373          moltype = AA  length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 373
QVQLVQSGAE VKKPGASVKV SCKASGYTFT SYWMNWVRQA PGQGLEWMGM IHPSDSETRL   60
NQKFKDRVTL TRDKSISTAY MELSRLRSDD TAVYYCARQG IITSVQEFAY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVCTLPPSRD  360
ELTKNQVSLT CLVEGFYPSD IAVEWESNGQ PENNYKTTPP VLDSDGSFFL YSDLTVDKSR  420
WQQGNVFSCS VMHEALHNHY TQESLSLSPG K                                 451

SEQ ID NO: 374          moltype = AA  length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 374
QVQLVQSGAE VKKPGASVKV SCKASGYTFT SYWMNWVRQA PGQGLEWMGM IHPSDSETRL   60
NQKFKDRVTL TVDKSISTAY MELSRLRSDD TAVYYCARQG IITSVQEFAY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVCTLPPSRD  360
ELTKNQVSLT CLVEGFYPSD IAVEWESNGQ PENNYKTTPP VLDSDGSFFL YSDLTVDKSR  420
WQQGNVFSCS VMHEALHNHY TQESLSLSPG K                                 451

SEQ ID NO: 375          moltype = AA  length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 375
QVQLVQSGAE VKKPGASVKV SCKASGYTFT SYWMNWVRQA PGQGLEWMGM IHPSDSETRL   60
NQKFKDRVTL TVDTSISTAY MELSRLRSDD TAVYYCARQG IITSVQEFAY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVCTLPPSRD  360
```

-continued

```
ELTKNQVSLT CLVEGFYPSD IAVEWESNGQ PENNYKTTPP VLDSDGSFFL YSDLTVDKSR   420
WQQGNVFSCS VMHEALHNHY TQESLSLSPG K                                  451

SEQ ID NO: 376             moltype = AA  length = 451
FEATURE                    Location/Qualifiers
REGION                     1..451
                           note = Description of Artificial Sequence: Synthetic
                            polypeptide
source                     1..451
                           mol_type = protein
                           organism = synthetic construct
SEQUENCE: 376
QVQLVQSGAE VKKPGASVKV SCKASGYTFT SYWMNWVRQA PGQGLEWMGM IHPSDSETRL   60
NQKFKDRVTM TRDTSISTAY MELSRLRSDD TAVYYCARQG IITSVQEFAY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPEFEG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPASIEKTI SKAKGQPREP QVCTLPPSRD   360
ELTKNQVSLT CLVEGFYPSD IAVEWESNGQ PENNYKTTPP VLDSDGSFFL YSDLTVDKSR   420
WQQGNVFSCS VMHEALHNHY TQESLSLSPG K                                  451

SEQ ID NO: 377             moltype = AA  length = 451
FEATURE                    Location/Qualifiers
REGION                     1..451
                           note = Description of Artificial Sequence: Synthetic
                            polypeptide
source                     1..451
                           mol_type = protein
                           organism = synthetic construct
SEQUENCE: 377
QVQLVQSGAE VKKPGASVKV SCKASGYTFT SYWMNWVRQA PGQGLEWMGM IHPSDSETRL   60
NQKFKDRVTM TRDTSTSTVY MELSSLRSED TAVYYCARQG IITSVQEFAY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPEFEG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPASIEKTI SKAKGQPREP QVCTLPPSRD   360
ELTKNQVSLT CLVEGFYPSD IAVEWESNGQ PENNYKTTPP VLDSDGSFFL YSDLTVDKSR   420
WQQGNVFSCS VMHEALHNHY TQESLSLSPG K                                  451

SEQ ID NO: 378             moltype = AA  length = 451
FEATURE                    Location/Qualifiers
REGION                     1..451
                           note = Description of Artificial Sequence: Synthetic
                            polypeptide
source                     1..451
                           mol_type = protein
                           organism = synthetic construct
SEQUENCE: 378
QVQLVQSGAE VKKPGASVKV SCKASGYTFT SYWMNWVRQA PGQGLEWMGM IHPSDSETRL   60
NQKFKDRVTM TVDKSISTAY MELSRLRSDD TAVYYCARQG IITSVQEFAY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPEFEG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPASIEKTI SKAKGQPREP QVCTLPPSRD   360
ELTKNQVSLT CLVEGFYPSD IAVEWESNGQ PENNYKTTPP VLDSDGSFFL YSDLTVDKSR   420
WQQGNVFSCS VMHEALHNHY TQESLSLSPG K                                  451

SEQ ID NO: 379             moltype = AA  length = 447
FEATURE                    Location/Qualifiers
REGION                     1..447
                           note = Description of Artificial Sequence: Synthetic
                            polypeptide
source                     1..447
                           mol_type = protein
                           organism = synthetic construct
SEQUENCE: 379
QVQLVQSGAE VKKPGSSVKV SCKASGYEFS SHWMNWVRQA PGQGLEWMGQ IYPGDGDINY   60
NEKFRGRVTI TADKSTSTAY MELSSLRSED TAVYYCARHG NYVMDYWGQG TTVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC DKTHTCPPCP APEFEGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA SIEKTISKAK GQPREPQVCT LPPSRDELTK   360
NQVSLTCLVE GFYPSDIAVE WESNGQPENN YKTTPPVLDS DGSFFLYSDL TVDKSRWQQG   420
NVFSCSVMHE ALHNHYTQES LSLSPGK                                       447

SEQ ID NO: 380             moltype = AA  length = 451
FEATURE                    Location/Qualifiers
REGION                     1..451
                           note = Description of Artificial Sequence: Synthetic
```

-continued

```
                        polypeptide
source                  1..451
                        mol_type = protein
                        organism = synthetic construct
SEQUENCE: 380
QVQLVQSGAE VKKPGSSVKV SCKASGYTFT SYWMNWVRQA PGQGLEWMGM IHPSDSETRL  60
NQKFKDRVTI TADKSTSTAY MELSSLRSED TAVYYCARQG IITSVQEFAY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVCTLPPSRD  360
ELTKNQVSLT CLVEGFYPSD IAVEWESNGQ PENNYKTTPP VLDSDGSFFL YSDLTVDKSR  420
WQQGNVFSCS VMHEALHNHY TQESLSLSPG K                                 451

SEQ ID NO: 381        moltype = AA  length = 214
FEATURE               Location/Qualifiers
REGION                1..214
                      note = Description of Artificial Sequence: Synthetic
                       polypeptide
source                1..214
                      mol_type = protein
                      organism = synthetic construct
SEQUENCE: 381
DIQMTQSPSS LSASVGDRVT ITCKASEDIY NRLAWYQQKP GKAPKLLIYG ATNLETGVPS  60
RFSGSGSGKD YTLTISSLQP EDIATYYCQQ FWRTPPTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 382        moltype = AA  length = 214
FEATURE               Location/Qualifiers
REGION                1..214
                      note = Description of Artificial Sequence: Synthetic
                       polypeptide
source                1..214
                      mol_type = protein
                      organism = synthetic construct
SEQUENCE: 382
DIQMTQSPSS LSASVGDRVT ITCKASEDIY NRLAWYQQKP GKAPKLLIYG ATNLETGVPS  60
RFSGSGSGTD FTFTISSLQP EDIATYYCQQ FWRTPPTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 383        moltype = AA  length = 214
FEATURE               Location/Qualifiers
REGION                1..214
                      note = Description of Artificial Sequence: Synthetic
                       polypeptide
source                1..214
                      mol_type = protein
                      organism = synthetic construct
SEQUENCE: 383
DIQMTQSPSS LSASVGDRVT ITCKASEDIY NRLAWYQQKP GKAPKPLISG ATNLETGVPS  60
RFSGSGSGKD YTLTISSLQP EDIATYYCQQ FWRTPPTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 384        moltype = AA  length = 214
FEATURE               Location/Qualifiers
REGION                1..214
                      note = Description of Artificial Sequence: Synthetic
                       polypeptide
source                1..214
                      mol_type = protein
                      organism = synthetic construct
SEQUENCE: 384
DIQMTQSPSS LSASVGDRVT ITCKASEDIY NRLAWYQQKP GKAPKPLISG ATNLETGVPS  60
RFSGSGSGTD FTFTISSLQP EDIATYYCQQ FWRTPPTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 385        moltype = AA  length = 214
FEATURE               Location/Qualifiers
REGION                1..214
                      note = Description of Artificial Sequence: Synthetic
                       polypeptide
source                1..214
                      mol_type = protein
                      organism = synthetic construct
SEQUENCE: 385
```

```
DIQMTQSPSS LSASVGDRVT ITCKASEDIY NRLAWYQQKP GKAPKPLIYG ATNLETGVPS  60
RFSGSGSGTD FTFTISSLQP EDIATYYCQQ FWRTPPTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 386          moltype = AA  length = 213
FEATURE                 Location/Qualifiers
REGION                  1..213
                        note = Description of Artificial Sequence: Synthetic
                         polypeptide
source                  1..213
                        mol_type = protein
                        organism = synthetic construct
SEQUENCE: 386
EIVLTQSPAT LSLSPGERAT LSCSASSSVN YIYWYQQKPG QAPRLLIYRT SNLASGIPAR  60
FSGSGSGTDF TLTISSLEPE DFAVYYCQQY HSYPLTFGGG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                             213

SEQ ID NO: 387          moltype = AA  length = 213
FEATURE                 Location/Qualifiers
REGION                  1..213
                        note = Description of Artificial Sequence: Synthetic
                         polypeptide
source                  1..213
                        mol_type = protein
                        organism = synthetic construct
SEQUENCE: 387
EIVLTQSPAT LSLSPGERAT LSCSASSSVS YMFWYQQKPG QAPRLLIYRT SNLASGIPAR  60
FSGSGSGTDF TLTISSLEPE DFAVYYCQQF HDYPRTFGGG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                             213

SEQ ID NO: 388          moltype = AA  length = 213
FEATURE                 Location/Qualifiers
REGION                  1..213
                        note = Description of Artificial Sequence: Synthetic
                         polypeptide
source                  1..213
                        mol_type = protein
                        organism = synthetic construct
SEQUENCE: 388
EIVLTQSPAT LSLSPGERAT LSCSASSSVS YMFWYQQKPG QAPRPWIYRT SNLASGIPPR  60
FSGSGSGTDY TLTISSLEPE DFAVYYCQQF HDYPRTFGGG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                             213

SEQ ID NO: 389          moltype = AA  length = 213
FEATURE                 Location/Qualifiers
REGION                  1..213
                        note = Description of Artificial Sequence: Synthetic
                         polypeptide
source                  1..213
                        mol_type = protein
                        organism = synthetic construct
SEQUENCE: 389
EIVLTQSPAT LSVSPGERAT LSCSASSSVN YIYWYQQKPG QAPRPWIYRT SNLASGIPAR  60
FSGSGSGTEY TLTISSLQSE DFAVYYCQQY HSYPLTFGGG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                             213

SEQ ID NO: 390          moltype = AA  length = 213
FEATURE                 Location/Qualifiers
REGION                  1..213
                        note = Description of Artificial Sequence: Synthetic
                         polypeptide
source                  1..213
                        mol_type = protein
                        organism = synthetic construct
SEQUENCE: 390
EIVMTQSPAT LSVSPGERAT LSCSASSSVN YIYWYQQKPG QAPRLLIYRT SNLASGIPAR  60
FSGSGSGTEF TLTISSLQSE DFAVYYCQQY HSYPLTFGGG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                             213

SEQ ID NO: 391          moltype = AA  length = 213
FEATURE                 Location/Qualifiers
REGION                  1..213
                        note = Description of Artificial Sequence: Synthetic
```

-continued

```
                               polypeptide
source                         1..213
                               mol_type = protein
                               organism = synthetic construct
SEQUENCE: 391
EIVMTQSPAT LSVSPGERAT LSCSASSSVS YMFWYQQKPG QAPRLLIYRT SNLASGIPAR   60
FSGSGSGTEF TLTISSLQSE DFAVYYCQQF HDYPRTFGGG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                               213

SEQ ID NO: 392                 moltype = AA   length = 212
FEATURE                        Location/Qualifiers
REGION                         1..212
                               note = Description of Artificial Sequence: Synthetic
                                polypeptide
source                         1..212
                               mol_type = protein
                               organism = synthetic construct
SEQUENCE: 392
IQLTQSPSFL SASVGDRVTI TCSASSSVSY MFWYQQKPGK APKLLIYRTS NLASGVPPRF   60
SGSGSGTEFT LTISSLQPED FATYYCQQFH DYPRTFGGGT KVEIKRTVAA PSVFIFPPSD  120
EQLKSGTASV VCLLNNFYPR EAKVQWKVDN ALQSGNSQES VTEQDSKDST YSLSSTLTLS  180
KADYEKHKVY ACEVTHQGLS SPVTKSFNRG EC                                212

SEQ ID NO: 393                 moltype = AA   length = 212
FEATURE                        Location/Qualifiers
REGION                         1..212
                               note = Description of Artificial Sequence: Synthetic
                                polypeptide
source                         1..212
                               mol_type = protein
                               organism = synthetic construct
SEQUENCE: 393
IQLTQSPSFL SASVGDRVTI TCSASSSVSY MFWYQQKPGK APKLLIYRTS NLASGVPPRF   60
SGSGSGTEYT LTISSLQPED FATYYCQQFH DYPRTFGGGT KVEIKRTVAA PSVFIFPPSD  120
EQLKSGTASV VCLLNNFYPR EAKVQWKVDN ALQSGNSQES VTEQDSKDST YSLSSTLTLS  180
KADYEKHKVY ACEVTHQGLS SPVTKSFNRG EC                                212

SEQ ID NO: 394                 moltype = AA   length = 212
FEATURE                        Location/Qualifiers
REGION                         1..212
                               note = Description of Artificial Sequence: Synthetic
                                polypeptide
source                         1..212
                               mol_type = protein
                               organism = synthetic construct
SEQUENCE: 394
IQLTQSPSFL SASVGDRVTI TCSASSSVSY MFWYQQKPGK APKLLIYRTS NLASGVPSRF   60
SGSGSGTEFT LTISSLQPED FATYYCQQFH DYPRTFGGGT KVEIKRTVAA PSVFIFPPSD  120
EQLKSGTASV VCLLNNFYPR EAKVQWKVDN ALQSGNSQES VTEQDSKDST YSLSSTLTLS  180
KADYEKHKVY ACEVTHQGLS SPVTKSFNRG EC                                212

SEQ ID NO: 395                 moltype = AA   length = 212
FEATURE                        Location/Qualifiers
REGION                         1..212
                               note = Description of Artificial Sequence: Synthetic
                                polypeptide
source                         1..212
                               mol_type = protein
                               organism = synthetic construct
SEQUENCE: 395
IQLTQSPSFL SASVGDRVTI TCSASSSVSY MFWYQQKPGK APKLLIYRTS NLASGVPSRF   60
SGSGSGTEFT LTISSLQPED FATYYCQQFH QYPRTFGGGT KVEIKRTVAA PSVFIFPPSD  120
EQLKSGTASV VCLLNNFYPR EAKVQWKVDN ALQSGNSQES VTEQDSKDST YSLSSTLTLS  180
KADYEKHKVY ACEVTHQGLS SPVTKSFNRG EC                                212

SEQ ID NO: 396                 moltype = AA   length = 212
FEATURE                        Location/Qualifiers
REGION                         1..212
                               note = Description of Artificial Sequence: Synthetic
                                polypeptide
source                         1..212
                               mol_type = protein
                               organism = synthetic construct
SEQUENCE: 396
IQLTQSPSFL SASVGDRVTI TCSASSSVSY MFWYQQKPGK APKLLIYRTS NLASGVPSRF   60
SGSGSGTEYT LTISSLQPED FATYYCQQFH DYPRTFGGGT KVEIKRTVAA PSVFIFPPSD  120
EQLKSGTASV VCLLNNFYPR EAKVQWKVDN ALQSGNSQES VTEQDSKDST YSLSSTLTLS  180
KADYEKHKVY ACEVTHQGLS SPVTKSFNRG EC                                212
```

SEQ ID NO: 397          moltype = AA  length = 212
FEATURE                 Location/Qualifiers
REGION                  1..212
                        note = Description of Artificial Sequence: Synthetic
                         polypeptide
source                  1..212
                        mol_type = protein
                        organism = synthetic construct
SEQUENCE: 397
IQLTQSPSFL SASVGDRVTI TCSASSSVSY MFWYQQKPGK APKPWIYRTS NLASGVPPRF  60
SGSGSGTEYT LTISSLQPED FATYYCQQFH DYPRTFGGGT KVEIKRTVAA PSVFIFPPSD  120
EQLKSGTASV VCLLNNFYPR EAKVQWKVDN ALQSGNSQES VTEQDSKDST YSLSSTLTLS  180
KADYEKHKVY ACEVTHQGLS SPVTKSFNRG EC                                212

SEQ ID NO: 398          moltype = AA  length = 212
FEATURE                 Location/Qualifiers
REGION                  1..212
                        note = Description of Artificial Sequence: Synthetic
                         polypeptide
source                  1..212
                        mol_type = protein
                        organism = synthetic construct
SEQUENCE: 398
IQLTQSPSFL SASVGDRVTI TCSASSSVSY MFWYQQKPGK APKPWIYRTS NLASGVPSRF  60
SGSGSGTEFT LTISSLQPED FATYYCQQFH DYPRTFGGGT KVEIKRTVAA PSVFIFPPSD  120
EQLKSGTASV VCLLNNFYPR EAKVQWKVDN ALQSGNSQES VTEQDSKDST YSLSSTLTLS  180
KADYEKHKVY ACEVTHQGLS SPVTKSFNRG EC                                212

SEQ ID NO: 399          moltype = AA  length = 212
FEATURE                 Location/Qualifiers
REGION                  1..212
                        note = Description of Artificial Sequence: Synthetic
                         polypeptide
source                  1..212
                        mol_type = protein
                        organism = synthetic construct
SEQUENCE: 399
IQMTQSPSSL SASVGDRVTI TCSASSSVNY IYWYQQKPGK APKLLIYRTS NLASGVPSRF  60
SGSGSGTDFT LTISSLQPED FATYYCQQYH SYPLTFGGGT KVEIKRTVAA PSVFIFPPSD  120
EQLKSGTASV VCLLNNFYPR EAKVQWKVDN ALQSGNSQES VTEQDSKDST YSLSSTLTLS  180
KADYEKHKVY ACEVTHQGLS SPVTKSFNRG EC                                212

SEQ ID NO: 400          moltype = AA  length = 216
FEATURE                 Location/Qualifiers
REGION                  1..216
                        note = Description of Artificial Sequence: Synthetic
                         polypeptide
source                  1..216
                        mol_type = protein
                        organism = synthetic construct
SEQUENCE: 400
QAVVTQEPSL TVSPGGTVTL TCGSSTGAVT TSNYANWVQQ KPGKSPRGLI GGTNKRAPGV  60
PARFSGSLLG GKAALTISGA QPEDEADYYC ALWYSNHWVF GGGTKLTVLR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                            216

SEQ ID NO: 401          moltype = AA  length = 448
FEATURE                 Location/Qualifiers
REGION                  1..448
                        note = Description of Artificial Sequence: Synthetic
                         polypeptide
source                  1..448
                        mol_type = protein
                        organism = synthetic construct
SEQUENCE: 401
EVQLVESGGG LVQPGGSLRL SCAASGFTFS SFGMHWVRQA PGKGLEWVAY ISSGNSAIYY  60
ADTVNGRFTI SRDNPKNTLY LQMNSLRAED TAVYYCARLR YGNSFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEFEGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP ASIEKTISKA KGQPREPQVC TLPPSRDELT  360
KNQVSLTCLV EGFYPSDIAV EWESNGQPEN NYKTTPPVLD SDGSFFLYSD LTVDKSRWQQ  420
GNVFSCSVMH EALHNHYTQE SLSLSPGK                                     448

SEQ ID NO: 402          moltype = AA  length = 448
FEATURE                 Location/Qualifiers
REGION                  1..448
                        note = Description of Artificial Sequence: Synthetic

```
                         polypeptide
source                   1..448
                         mol_type = protein
                         organism = synthetic construct
SEQUENCE: 402
EVQLVESGGG LVQPGGSLRL SCAASGFTFS SFGMHWVRQA PGKGLEWVSY ISSGNSAIYY   60
ADTVNGRFTI SRDNAKNSLY LQMNSLRAED TAVYYCARLR YGNSFDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDKTHTCPPC PAPEFEGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP ASIEKTISKA KGQPREPQVC TLPPSRDELT   360
KNQVSLTCLV EGFYPSDIAV EWESNGQPEN NYKTTPPVLD SDGSFFLYSD LTVDKSRWQQ   420
GNVFSCSVMH EALHNHYTQE SLSLSPGK                                      448

SEQ ID NO: 403           moltype = AA   length = 448
FEATURE                  Location/Qualifiers
REGION                   1..448
                         note = Description of Artificial Sequence: Synthetic
                         polypeptide
source                   1..448
                         mol_type = protein
                         organism = synthetic construct
SEQUENCE: 403
QIQLVQSGAE VKKPGASVKV SCKASGYTFT NSGMNWVRQA PGQGLEWMGW INTNTGEPTF   60
AEEFRGRVTF TLDTSASTAY MELSRLRSDD TAVYYCARYY YGNSFAYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDKTHTCPPC PAPEFEGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP ASIEKTISKA KGQPREPQVC TLPPSRDELT   360
KNQVSLTCLV EGFYPSDIAV EWESNGQPEN NYKTTPPVLD SDGSFFLYSD LTVDKSRWQQ   420
GNVFSCSVMH EALHNHYTQE SLSLSPGK                                      448

SEQ ID NO: 404           moltype = AA   length = 451
FEATURE                  Location/Qualifiers
REGION                   1..451
                         note = Description of Artificial Sequence: Synthetic
                         polypeptide
source                   1..451
                         mol_type = protein
                         organism = synthetic construct
SEQUENCE: 404
QVQLVQSGAE VKKPGASVKV SCKASGYTFT NFGITWVRQA PGQGLEWIGE IYPSSGNTFY   60
NEKFKGRVTL TADKSSSAAY MELRSLRSDD TAVYYCARGG GPLRSRYFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPEFEG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPASIEKTI SKAKGQPREP QVCTLPPSRD   360
ELTKNQVSLT CLVEGFYPSD IAVEWESNGQ PENNYKTTPP VLDSDGSFFL YSDLTVDKSR   420
WQQGNVFSCS VMHEALHNHY TQESLSLSPG K                                  451

SEQ ID NO: 405           moltype = AA   length = 451
FEATURE                  Location/Qualifiers
REGION                   1..451
                         note = Description of Artificial Sequence: Synthetic
                         polypeptide
source                   1..451
                         mol_type = protein
                         organism = synthetic construct
SEQUENCE: 405
QVQLVQSGAE VKKPGASVKV SCKASGYTFT NFGITWVRQA PGQGLEWMGE IYPSSGNTFY   60
NEKFKGRVTM TTDTSTSTAY MELRSLRSDD TAVYYCARGG GPLRSRYFDY WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPEFEG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPASIEKTI SKAKGQPREP QVCTLPPSRD   360
ELTKNQVSLT CLVEGFYPSD IAVEWESNGQ PENNYKTTPP VLDSDGSFFL YSDLTVDKSR   420
WQQGNVFSCS VMHEALHNHY TQESLSLSPG K                                  451

SEQ ID NO: 406           moltype = AA   length = 448
FEATURE                  Location/Qualifiers
REGION                   1..448
                         note = Description of Artificial Sequence: Synthetic
                         polypeptide
source                   1..448
                         mol_type = protein
                         organism = synthetic construct
SEQUENCE: 406
QVQLVQSGAE VKKPGASVKV SCKASGYTFT NSGMNWVRQA PGQGLEWMGW INTNTGEPTF   60
AEEFRGRVTM TRDTSISTAY MELSRLRSDD TAVYYCARYY YGNSFAYWGQ GTLVTVSSAS   120
```

```
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDKTHTCPPC PAPEFEGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP ASIEKTISKA KGQPREPQVC TLPPSRDELT   360
KNQVSLTCLV EGFYPSDIAV EWESNGQPEN NYKTTPPVLD SDGSFFLYSD LTVDKSRWQQ   420
GNVFSCSVMH EALHNHYTQE SLSLSPGK                                     448

SEQ ID NO: 407              moltype = AA  length = 448
FEATURE                     Location/Qualifiers
REGION                      1..448
                            note = Description of Artificial Sequence: Synthetic
                             polypeptide
source                      1..448
                            mol_type = protein
                            organism = synthetic construct
SEQUENCE: 407
QVQLVQSGAE VKKPGASVKV SCKASGYTFT NYGMNWVRQA PGQGLEWMGW INTNTGEPTY   60
AEEFKGRVTM TRDTSISTAY MELSRLRSDD TAVYYCARYF YGNSFVYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDKTHTCPPC PAPEFEGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP ASIEKTISKA KGQPREPQVC TLPPSRDELT   360
KNQVSLTCLV EGFYPSDIAV EWESNGQPEN NYKTTPPVLD SDGSFFLYSD LTVDKSRWQQ   420
GNVFSCSVMH EALHNHYTQE SLSLSPGK                                     448

SEQ ID NO: 408              moltype = AA  length = 449
FEATURE                     Location/Qualifiers
REGION                      1..449
                            note = Description of Artificial Sequence: Synthetic
                             polypeptide
source                      1..449
                            mol_type = protein
                            organism = synthetic construct
SEQUENCE: 408
QVQLVQSGAE VKKPGSSVKV SCKASGYAFN NYWMNWVRQA PGQGLEWMGQ ISPGNGNSNF   60
NGKFKGRVTI TADKSTSTAY MELSSLRSED TAVYYCARGG RYGNAMDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPEFEGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PASIEKTISK AKGQPREPQV CTLPPSRDEL   360
TKNQVSLTCL VEGFYPSDIA VEWESNGQPE NNYKTTPPVL DSDGSFFLYS DLTVDKSRWQ   420
QGNVFSCSVM HEALHNHYTQ ESLSLSPGK                                    449

SEQ ID NO: 409              moltype = AA  length = 449
FEATURE                     Location/Qualifiers
REGION                      1..449
                            note = Description of Artificial Sequence: Synthetic
                             polypeptide
source                      1..449
                            mol_type = protein
                            organism = synthetic construct
SEQUENCE: 409
QVQLVQSGAE VKKPGSSVKV SCKASGYAFS SYWMNWVRQA PGQGLEWIGQ IYPGNGNSNF   60
NGKFKARVTL TADKSSSTAY MELSSLRSED TAVYYCARGG RFGNAMDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPEFEGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PASIEKTISK AKGQPREPQV CTLPPSRDEL   360
TKNQVSLTCL VEGFYPSDIA VEWESNGQPE NNYKTTPPVL DSDGSFFLYS DLTVDKSRWQ   420
QGNVFSCSVM HEALHNHYTQ ESLSLSPGK                                    449

SEQ ID NO: 410              moltype = AA  length = 449
FEATURE                     Location/Qualifiers
REGION                      1..449
                            note = Description of Artificial Sequence: Synthetic
                             polypeptide
source                      1..449
                            mol_type = protein
                            organism = synthetic construct
SEQUENCE: 410
QVQLVQSGAE VKKPGSSVKV SCKASGYAFS SYWMNWVRQA PGQGLEWMGQ IYPGNGNSNF   60
NGKFKARVTI TADKSTSTAY MELSSLRSED TAVYYCARGG RFGNAMDYWG QGTTVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPEFEGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PASIEKTISK AKGQPREPQV CTLPPSRDEL   360
TKNQVSLTCL VEGFYPSDIA VEWESNGQPE NNYKTTPPVL DSDGSFFLYS DLTVDKSRWQ   420
QGNVFSCSVM HEALHNHYTQ ESLSLSPGK                                    449
```

-continued

```
SEQ ID NO: 411            moltype = AA   length = 220
FEATURE                   Location/Qualifiers
REGION                    1..220
                          note = Description of Artificial Sequence: Synthetic
                          polypeptide
source                    1..220
                          mol_type = protein
                          organism = synthetic construct
SEQUENCE: 411
DIVMTQSPDS LAVSLGERAT INCKSSQSLL NSGNQKNYLT WYQQKPGQPP KLLIFWASTR    60
ESGVPDRFSG SGSGTDFTLT ISSLQAEDVA VYYCQNNYYY PLTFGGGTKV EIKRTVAAPS   120
VFIFPPSDEQ LKSGTASVVC LLNNFYPREA KVQWKVDNAL QSGNSQESVT EQDSKDSTYS   180
LSSTLTLSKA DYEKHKVYAC EVTHQGLSSP VTKSFNRGEC                         220

SEQ ID NO: 412            moltype = AA   length = 220
FEATURE                   Location/Qualifiers
REGION                    1..220
                          note = Description of Artificial Sequence: Synthetic
                          polypeptide
source                    1..220
                          mol_type = protein
                          organism = synthetic construct
SEQUENCE: 412
DIVMTQSPDS LAVSLGERAT INCKSSQSLL NSGNQKNYLT WYQQKPGQPP KLLIYWASTR    60
ESGVPDRFSG SGSGTDFTLT ISSLQAEDVA VYYCQNAYFY PYTFGGGTKV EIKRTVAAPS   120
VFIFPPSDEQ LKSGTASVVC LLNNFYPREA KVQWKVDNAL QSGNSQESVT EQDSKDSTYS   180
LSSTLTLSKA DYEKHKVYAC EVTHQGLSSP VTKSFNRGEC                         220

SEQ ID NO: 413            moltype = AA   length = 220
FEATURE                   Location/Qualifiers
REGION                    1..220
                          note = Description of Artificial Sequence: Synthetic
                          polypeptide
source                    1..220
                          mol_type = protein
                          organism = synthetic construct
SEQUENCE: 413
DIVMTQSPDS LAVSLGERAT INCKSSQSLL NSGNQKNYLT WYQQKPGQPP KLLIYWASTR    60
ESGVPDRFSG SGSGTDFTLT ISSLQAEDVA VYYCQNNYFY PLTFGGGTKV EIKRTVAAPS   120
VFIFPPSDEQ LKSGTASVVC LLNNFYPREA KVQWKVDNAL QSGNSQESVT EQDSKDSTYS   180
LSSTLTLSKA DYEKHKVYAC EVTHQGLSSP VTKSFNRGEC                         220

SEQ ID NO: 414            moltype = AA   length = 220
FEATURE                   Location/Qualifiers
REGION                    1..220
                          note = Description of Artificial Sequence: Synthetic
                          polypeptide
source                    1..220
                          mol_type = protein
                          organism = synthetic construct
SEQUENCE: 414
DIVMTQSPDS LAVSLGERAT INCKSSQSLL NSGNQKNYLT WYQQKPGQPP KLLIYWASTR    60
ESGVPDRFSG SGSGTDFTLT ISSLQAEDVA VYYCQNNYNF PLTFGGGTKV EIKRTVAAPS   120
VFIFPPSDEQ LKSGTASVVC LLNNFYPREA KVQWKVDNAL QSGNSQESVT EQDSKDSTYS   180
LSSTLTLSKA DYEKHKVYAC EVTHQGLSSP VTKSFNRGEC                         220

SEQ ID NO: 415            moltype = AA   length = 220
FEATURE                   Location/Qualifiers
REGION                    1..220
                          note = Description of Artificial Sequence: Synthetic
                          polypeptide
source                    1..220
                          mol_type = protein
                          organism = synthetic construct
SEQUENCE: 415
DIVMTQSPDS LAVSLGERAT INCKSSQSLL NSGNQKNYLT WYQQKPGQPP KLLIYWASTR    60
ESGVPDRFSG SGSGTDFTLT ISSLQAEDVA VYYCQNNYYY PLTFGGGTKV EIKRTVAAPS   120
VFIFPPSDEQ LKSGTASVVC LLNNFYPREA KVQWKVDNAL QSGNSQESVT EQDSKDSTYS   180
LSSTLTLSKA DYEKHKVYAC EVTHQGLSSP VTKSFNRGEC                         220

SEQ ID NO: 416            moltype = AA   length = 220
FEATURE                   Location/Qualifiers
REGION                    1..220
                          note = Description of Artificial Sequence: Synthetic
                          polypeptide
source                    1..220
                          mol_type = protein
                          organism = synthetic construct
SEQUENCE: 416
```

```
DIVMTQSPDS LAVSLGERAT INCKSSQSLL NSGNQRNYLT WYQQKPGQPP KLLIYWASTR  60
ESGVPDRFSG SGSGTDFTLT ISSLQAEDVA VYYCQNAYFY PYTFGGGTKV EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 417          moltype = AA  length = 220
FEATURE                 Location/Qualifiers
REGION                  1..220
                        note = Description of Artificial Sequence: Synthetic
                         polypeptide
source                  1..220
                        mol_type = protein
                        organism = synthetic construct
SEQUENCE: 417
DIVMTQSPDS LAVSLGERAT INCRSSQSLF SSGNQKNYLT WYQQKPGQPP KLLIYWASTR  60
ESGVPDRFSG SGSGADFTLT ISSLQAEDVA VYYCQNDYYY PLTFGGGTKV EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 418          moltype = AA  length = 220
FEATURE                 Location/Qualifiers
REGION                  1..220
                        note = Description of Artificial Sequence: Synthetic
                         polypeptide
source                  1..220
                        mol_type = protein
                        organism = synthetic construct
SEQUENCE: 418
DIVMTQSPDS LAVSLGERAT INCRSSQSLF SSGNQKNYLT WYQQKPGQPP KLLIYWASTR  60
ESGVPDRFSG SGSGTDFTLT ISSLQAEDVA VYYCQNDYYY PLTFGGGTKV EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 419          moltype = AA  length = 220
FEATURE                 Location/Qualifiers
REGION                  1..220
                        note = Description of Artificial Sequence: Synthetic
                         polypeptide
source                  1..220
                        mol_type = protein
                        organism = synthetic construct
SEQUENCE: 419
DIVMTQSPDS LAVSLGERAT MNCKSSQSLL NSGNQKNYLT WYQQKPGQPP KLLIYWASTR  60
ESGVPDRFSG SGSGTDFTLT ISSLQAEDVA VYYCQNAYFY PYTFGGGTKV EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 420          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 420
QVQLVQSGAE VKKPGASVKV SCKASGYTFT SYYIHWVRQA PGQGLEWIGC IYPGNVNTNY  60
NEKFKDRATL TVDTSISTAY MELSRLRSDD TAVYFCTRSH YGLDWNFDVW GQGTTVTVSS  120

SEQ ID NO: 421          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
SEQUENCE: 421
QVQLVQSGAE VKKPGASVKV SCKASGYTFT SYYIHWVRQA PGQGLEWIGS IYPGNVNTNY  60
NEKFKDRATL TVDTSISTAY MELSRLRSDD TAVYFCTRSH YGLDWNFDVW GQGTTVTVSS  120

SEQ ID NO: 422          moltype = AA  length = 120
FEATURE                 Location/Qualifiers
REGION                  1..120
                        note = Description of Artificial Sequence: Synthetic
                         polypeptide
source                  1..120
                        mol_type = protein
                        organism = synthetic construct
```

-continued

```
SEQUENCE: 422
QVQLVQSGAE VKKPGASVKV SCKASGYTFT SYYIHWVRQA PGQGLEWIGA IYPGNVNTNY    60
NEKFKDRATL TVDTSISTAY MELSRLRSDD TAVYFCTRSH YGLDWNFDVW GQGTTVTVSS   120

SEQ ID NO: 423           moltype = AA  length = 120
FEATURE                  Location/Qualifiers
REGION                   1..120
                         note = Description of Artificial Sequence: Synthetic
                          polypeptide
source                   1..120
                         mol_type = protein
                         organism = synthetic construct
SEQUENCE: 423
QVQLVQSGAE VKKPGASVKV SCKASGYTFT SYYIHWVRQA PGQGLEWIGG IYPGNVNTNY    60
NEKFKDRATL TVDTSISTAY MELSRLRSDD TAVYFCTRSH YGLDWNFDVW GQGTTVTVSS   120

SEQ ID NO: 424           moltype = AA  length = 107
FEATURE                  Location/Qualifiers
REGION                   1..107
                         note = Description of Artificial Sequence: Synthetic
                          polypeptide
source                   1..107
                         mol_type = protein
                         organism = synthetic construct
SEQUENCE: 424
DIQMTQSPSS LSASVGDRVT ITCHASQNIY VWLNWYQQKP GKAPKLLIYK ASNLHTGVPS    60
RFSGSGSGTD FTLTISSLQP EDFATYYCQQ GQTYPYTFGG GTKVEIK              107

SEQ ID NO: 425           moltype = AA  length = 450
FEATURE                  Location/Qualifiers
REGION                   1..450
                         note = Description of Artificial Sequence: Synthetic
                          polypeptide
source                   1..450
                         mol_type = protein
                         organism = synthetic construct
SEQUENCE: 425
QVQLVQSGAE VKKPGASVKV SCKASGYTFT SYYIHWVRQA PGQGLEWIGC IYPGNVNTNY    60
NEKFKDRATL TVDTSISTAY MELSRLRSDD TAVYFCTRSH YGLDWNFDVW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKRVEP KSCDKTHTCP PCPAPEFEGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPASIEKTIS KAKGQPREPQ VCTLPPSRDE   360
LTKNQVSLTC LVEGFYPSDI AVEWESNGQP ENNYKTTPPV LDSDGSFFLY SDLTVDKSRW   420
QQGNVFSCSV MHEALHNHYT QESLSLSPGK                                  450

SEQ ID NO: 426           moltype = AA  length = 214
FEATURE                  Location/Qualifiers
REGION                   1..214
                         note = Description of Artificial Sequence: Synthetic
                          polypeptide
source                   1..214
                         mol_type = protein
                         organism = synthetic construct
SEQUENCE: 426
DIQMTQSPSS LSASVGDRVT ITCHASQNIY VWLNWYQQKP GKAPKLLIYK ASNLHTGVPS    60
RFSGSGSGTD FTLTISSLQP EDFATYYCQQ GQTYPYTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                             214

SEQ ID NO: 427           moltype = AA  length = 479
FEATURE                  Location/Qualifiers
REGION                   1..479
                         note = Description of Artificial Sequence: Synthetic
                          polypeptide
source                   1..479
                         mol_type = protein
                         organism = synthetic construct
SEQUENCE: 427
QVQLVQSGAE VKKPGASVKV SCKASGYTFT SYYIHWVRQA PGQGLEWIGC IYPGNVNTNY    60
NEKFKDRATL TVDTSISTAY MELSRLRSDD TAVYFCTRSH YGLDWNFDVW GQGTTVTVSS   120
GKPGSGKPGS GKPGSGKPGS DIQMTQSPSS LSASVGDRVT ITCHASQNIY VWLNWYQQKP   180
GKAPKLLIYK ASNLHTGVPS RFSGSGSGTD FTLTISSLQP EDFATYYCQQ GQTYPYTFGG   240
GTKVEIKEPK SSDKTHTCPP CPAPEFEGGP SVFLFPPKPK DTLMISRTPE VTCVVVDVSH   300
EDPEVKFNWY VDGVEVHNAK TKPREEQYNS TYRVVSVLTV LHQDWLNGKE YKCKVSNKAL   360
PASIEKTISK AKGQPREPQV YTLPPCRKKL TKNQVSLTCL VKGFYPSDIA VEWESNGQPE   420
NNYKTTPPVL KSDGSFFLYS KLTVDKSRWQ QGNVFSCSVM HEALHNHYTQ KSLSLSPGK    479

SEQ ID NO: 428           moltype = AA  length = 479
```

```
FEATURE          Location/Qualifiers
REGION           1..479
                 note = Description of Artificial Sequence: Synthetic
                  polypeptide
source           1..479
                 mol_type = protein
                 organism = synthetic construct
SEQUENCE: 428
QVQLVQSGAE VKKPGASVKV SCKASGYTFT SYYIHWVRQA PGQGLEWIGG IYPGNVNTNY  60
NEKFKDRATL TVDTSISTAY MELSRLRSDD TAVYFCTRSH YGLDWNFDVW GQGTTVTVSS  120
GKPGSGKPGS GKPGSGKPGS DIQMTQSPSS LSASVGDRVT ITCHASQNIY VWLNWYQQKP  180
GKAPKLLIYK ASNLHTGVPS RFSGSGSGTD FTLTISSLQP EDFATYYCQQ GQTYPYTFGG  240
GTKVEIKEPK SSDKTHTCPP CPAPEFEGGP SVFLFPPKPK DTLMISRTPE VTCVVVDVSH  300
EDPEVKFNWY VDGVEVHNAK TKPREEQYNS TYRVVSVLTV LHQDWLNGKE YKCKVSNKAL  360
PASIEKTISK AKGQPREPQV YTLPPCRKKL TKNQVSLTCL VKGFYPSDIA VEWESNGQPE  420
NNYKTTPPVL KSDGSFFLYS KLTVDKSRWQ QGNVFSCSVM HEALHNHYTQ KSLSLSPGK   479

SEQ ID NO: 429      moltype = AA  length = 479
FEATURE          Location/Qualifiers
REGION           1..479
                 note = Description of Artificial Sequence: Synthetic
                  polypeptide
source           1..479
                 mol_type = protein
                 organism = synthetic construct
SEQUENCE: 429
QVQLVQSGAE VKKPGASVKV SCKASGYTFT SYYIHWVRQA PGQGLEWIGA IYPGNVNTNY  60
NEKFKDRATL TVDTSISTAY MELSRLRSDD TAVYFCTRSH YGLDWNFDVW GQGTTVTVSS  120
GKPGSGKPGS GKPGSGKPGS DIQMTQSPSS LSASVGDRVT ITCHASQNIY VWLNWYQQKP  180
GKAPKLLIYK ASNLHTGVPS RFSGSGSGTD FTLTISSLQP EDFATYYCQQ GQTYPYTFGG  240
GTKVEIKEPK SSDKTHTCPP CPAPEFEGGP SVFLFPPKPK DTLMISRTPE VTCVVVDVSH  300
EDPEVKFNWY VDGVEVHNAK TKPREEQYNS TYRVVSVLTV LHQDWLNGKE YKCKVSNKAL  360
PASIEKTISK AKGQPREPQV YTLPPCRKKL TKNQVSLTCL VKGFYPSDIA VEWESNGQPE  420
NNYKTTPPVL KSDGSFFLYS KLTVDKSRWQ QGNVFSCSVM HEALHNHYTQ KSLSLSPGK   479

SEQ ID NO: 430      moltype = AA  length = 479
FEATURE          Location/Qualifiers
REGION           1..479
                 note = Description of Artificial Sequence: Synthetic
                  polypeptide
source           1..479
                 mol_type = protein
                 organism = synthetic construct
SEQUENCE: 430
QVQLVQSGAE VKKPGASVKV SCKASGYTFT SYYIHWVRQA PGQGLEWIGS IYPGNVNTNY  60
NEKFKDRATL TVDTSISTAY MELSRLRSDD TAVYFCTRSH YGLDWNFDVW GQGTTVTVSS  120
GKPGSGKPGS GKPGSGKPGS DIQMTQSPSS LSASVGDRVT ITCHASQNIY VWLNWYQQKP  180
GKAPKLLIYK ASNLHTGVPS RFSGSGSGTD FTLTISSLQP EDFATYYCQQ GQTYPYTFGG  240
GTKVEIKEPK SSDKTHTCPP CPAPEFEGGP SVFLFPPKPK DTLMISRTPE VTCVVVDVSH  300
EDPEVKFNWY VDGVEVHNAK TKPREEQYNS TYRVVSVLTV LHQDWLNGKE YKCKVSNKAL  360
PASIEKTISK AKGQPREPQV YTLPPCRKKL TKNQVSLTCL VKGFYPSDIA VEWESNGQPE  420
NNYKTTPPVL KSDGSFFLYS KLTVDKSRWQ QGNVFSCSVM HEALHNHYTQ KSLSLSPGK   479

SEQ ID NO: 431      moltype = AA  length = 472
FEATURE          Location/Qualifiers
REGION           1..472
                 note = Description of Artificial Sequence: Synthetic
                  polypeptide
source           1..472
                 mol_type = protein
                 organism = synthetic construct
SEQUENCE: 431
QVQLVQSGAE VKKPGASVKV SCKASDYTFS NYYIEWVRQA PGQGLEWMGE ILPGNGNTVY  60
NEKFKDRVTM TVDTSTSTAY MELRSLRSDD TAVYYCARWG DYALFANWGQ GTLVTVSSGG  120
GGSGGGGSGG GGSDIQMTQS PSTLSASVGD RVTITCKASQ NVGTNVAWYQ QKPGKAPKAL  180
IYSASYRYSG VPSRFSGSGS GTEFTLTISS LQPDDFATYY CQQYNSYPFT FGQGTKLEIK  240
EPKSSDKTHT CPPCPAPEFE GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALPASIEKT  360
ISKAKGQPRE PQVYTLPPCR KKLTKNQVSL TCLVKGFYPS DIAVEWESNG QPENNYKTTP  420
PVLKSDGSFF LYSKLTVDKS RWQQGNVFSC SVMHEALHNH YTQKSLSLSP GK          472

SEQ ID NO: 432      moltype = AA  length = 476
FEATURE          Location/Qualifiers
REGION           1..476
                 note = Description of Artificial Sequence: Synthetic
                  polypeptide
source           1..476
                 mol_type = protein
                 organism = synthetic construct
```

```
SEQUENCE: 432
QVQLVQSGAE VKKPGASVKV SCKASGYTFT DYFMNWVRQA PGQGLEWMGV INPYNDITIY  60
NQKFQGRVTM TVDRSTSTVY MELSSLRSED TAVYYCAREG VLYDGYYEGA YWGQGTLVTV  120
SSGGGGSGGG GSGGGGSDIQ LTQSPSFLSA SVGDRVTITC KASQNVGIAV AWYQQKPGKA  180
PKLLIYAASN RYTGVPSRFS GSGSGTEFTL TISSLQPEDF ATYYCQQYST YPYTFGQGTK  240
LEIKEPKSSD KTHTCPPCPA PEFEGGPSVF LFPPKPKDTL MISRTPEVTC VVVDVSHEDP  300
EVKFNWYVDG VEVHNAKTKP REEQYNSTYR VVSVLTVLHQ DWLNGKEYKC KVSNKALPAS  360
IEKTISKAKG QPREPQVYTL PPCRKKLTKN QVSLTCLVKG FYPSDIAVEW ESNGQPENNY  420
KTTPPVLKSD GSFFLYSKLT VDKSRWQQGN VFSCSVMHEA LHNHYTQKSL SLSPGK      476

SEQ ID NO: 433              moltype = AA  length = 472
FEATURE                     Location/Qualifiers
REGION                      1..472
                            note = Description of Artificial Sequence: Synthetic
                             polypeptide
source                      1..472
                            mol_type = protein
                            organism = synthetic construct
SEQUENCE: 433
QVQLVQSGAE VKKPGASVKV SCKATDYIFS NYYIEWVRQA PGQGLEWMGE ILPGTGNTVY  60
NEKFKDRVTM TVDTSTSTVY MELSSLRSED TAVYYCARWG DYALFANWGQ GTLVTVSSGG  120
GGSGGGGSGG GGSDIQMTQS PSFLSASVGD RVTITCKASQ NVGTNVAWYQ QKPGKAPKPL  180
IYSTSYRYSG VPSRFSGSGS GTEFTLTISS LQPEDFATYY CQQYNNYPLT FGGGTKVEIK  240
EPKSSDKTHT CPPCPAPEFE GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALPASIEKT  360
ISKAKGQPRE PQVYTLPPCR KKLTKNQVSL TCLVKGFYPS DIAVEWESNG QPENNYKTTP  420
PVLKSDGSFF LYSKLTVDKS RWQQGNVFSC SVMHEALHNH YTQKSLSLSP GK          472

SEQ ID NO: 434              moltype = AA  length = 472
FEATURE                     Location/Qualifiers
REGION                      1..472
                            note = Description of Artificial Sequence: Synthetic
                             polypeptide
source                      1..472
                            mol_type = protein
                            organism = synthetic construct
SEQUENCE: 434
QVQLVQSGAE VKKPGASVKV SCKATDYIFS NYYIEWVRQA PGQGLEWMGE ILPGTGNTVY  60
NEKFKDRVTM TVDTSTSTVY MELSSLRSED TAVYYCARWG DYALFANWGQ GTLVTVSSGG  120
GGSGGGGSGG GGSDIQMTQS PSTLSASVGD RVTITCKASQ NVGTNVAWYQ QKPGKAPKAL  180
IYSASYRYSG VPSRFSGSGS GTEFTLTISS LQPDDFATYY CQQYNSYPFT FGQGTKLEIK  240
EPKSSDKTHT CPPCPAPEFE GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALPASIEKT  360
ISKAKGQPRE PQVYTLPPCR KKLTKNQVSL TCLVKGFYPS DIAVEWESNG QPENNYKTTP  420
PVLKSDGSFF LYSKLTVDKS RWQQGNVFSC SVMHEALHNH YTQKSLSLSP GK          472

SEQ ID NO: 435              moltype = AA  length = 479
FEATURE                     Location/Qualifiers
REGION                      1..479
                            note = Description of Artificial Sequence: Synthetic
                             polypeptide
source                      1..479
                            mol_type = protein
                            organism = synthetic construct
SEQUENCE: 435
QVQLVQSGAE VKKPGASVKV SCKASGYTFT SYYIHWVRQA PGQCLEWIGS IYPGNVNTNY  60
NEKFKDRATL TVDTSISTAY MELSRLRSDD TAVYFCTRSH YGLDWNFDVW GQGTTVTVSS  120
GKPGSGKPGS GKPGSGKPGS DIQMTQSPSS LSASVGDRVT ITCHASQNIY VWLNWYQQKP  180
GKAPKLLIYK ASNLHTGVPS RFSGSGSGTD FTLTISSLQP EDFATYYCQQ GQTYPYTFGC  240
GTKVEIKEPK SSDKTHTCPP CPAPEFEGGP SVFLFPPKPK DTLMISRTPE VTCVVVDVSH  300
EDPEVKFNWY VDGVEVHNAK TKPREEQYNS TYRVVSVLTV LHQDWLNGKE YKCKVSNKAL  360
PASIEKTISK AKGQPREPQV YTLPPCRKKL TKNQVSLTCL VKGFYPSDIA VEWESNGQPE  420
NNYKTTPPVL KSDGSFFLYS KLTVDKSRWQ QGNVFSCSVM HEALHNHYTQ KSLSLSPGK   479

SEQ ID NO: 436              moltype = AA  length = 479
FEATURE                     Location/Qualifiers
REGION                      1..479
                            note = Description of Artificial Sequence: Synthetic
                             polypeptide
source                      1..479
                            mol_type = protein
                            organism = synthetic construct
SEQUENCE: 436
QVQLVQSGAE VKKPGASVKV SCKASGYTFT SYYIHWVRQA PGQGLEWIGS IYPGNVNTNY  60
NEKFKDRATL TVDTSISTAY MELSRLRSDD TAVYFCTRSH YGLDWNFDVW GQGTTVTVSS  120
GGGGSGGGGS GGGGSGGGGS DIQMTQSPSS LSASVGDRVT ITCHASQNIY VWLNWYQQKP  180
GKAPKLLIYK ASNLHTGVPS RFSGSGSGTD FTLTISSLQP EDFATYYCQQ GQTYPYTFGG  240
GTKVEIKEPK SSDKTHTCPP CPAPEFEGGP SVFLFPPKPK DTLMISRTPE VTCVVVDVSH  300
EDPEVKFNWY VDGVEVHNAK TKPREEQYNS TYRVVSVLTV LHQDWLNGKE YKCKVSNKAL  360
```

```
PASIEKTISK AKGQPREPQV YTLPPCRKKL TKNQVSLTCL VKGFYPSDIA VEWESNGQPE  420
NNYKTTPPVL KSDGSFFLYS KLTVDKSRWQ QGNVFSCSVM HEALHNHYTQ KSLSLSPGK   479

SEQ ID NO: 437          moltype = AA  length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 437
QVQLQQWGAG LLKPSETLSL TCAVYGGSFS GYYWSWIRQS PEKGLEWIGE INHGGYVTYN  60
PSLESRVTIS VDTSKNQFSL KLSSVTAADT AVYYCARDYG PGNYDWYFDL WGRGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVCTLPPSRD  360
ELTKNQVSLT CLVEGFYPSD IAVEWESNGQ PENNYKTTPP VLDSDGSFFL YSDLTVDKSR  420
WQQGNVFSCS VMHEALHNHY TQESLSLSPG K                                 451

SEQ ID NO: 438          moltype = AA  length = 216
FEATURE                 Location/Qualifiers
REGION                  1..216
                        note = Description of Artificial Sequence: Synthetic
                         polypeptide
source                  1..216
                        mol_type = protein
                        organism = synthetic construct
SEQUENCE: 438
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPPALTF GGGTKVEIKR TVAAPSVFIF  120
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                            216

SEQ ID NO: 439          moltype = AA  length = 449
FEATURE                 Location/Qualifiers
REGION                  1..449
                        note = Description of Artificial Sequence: Synthetic
                         polypeptide
source                  1..449
                        mol_type = protein
                        organism = synthetic construct
SEQUENCE: 439
QVQLVQSGAE VKKPGASVKV SCKASGYTFS SYWMHWVRQA PGQRLEWMGE INPGNGHTNY  60
SQKFQGRVTI TVDKSASTAY MELSSLRSED TAVYYCARSF TTARAFAYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPEFEGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PASIEKTISK AKGQPREPQV CTLPPSRDEL  360
TKNQVSLTCL VEGFYPSDIA VEWESNGQPE NNYKTTPPVL DSDGSFFLYS DLTVDKSRWQ  420
QGNVFSCSVM HEALHNHYTQ ESLSLSPGK                                    449

SEQ ID NO: 440          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 440
DIVMTQSPPT LSLSPGERVT LSCRASQSIS DYLHWYQQKP GQSPRLLIKY ASQSISGIPA  60
RFSGSGSGTD FTLTISSLEP EDFAVYYCQD GHSFPPTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 441          moltype = AA  length = 482
FEATURE                 Location/Qualifiers
REGION                  1..482
                        note = Description of Artificial Sequence: Synthetic
                         polypeptide
source                  1..482
                        mol_type = protein
                        organism = synthetic construct
SEQUENCE: 441
QVQLQQWGAG LLKPSETLSL TCAVYGGSFS GYYWSWIRQS PEKGLEWIGE INHGGYVTYN  60
PSLESRVTIS VDTSKNQFSL KLSSVTAADT AVYYCARDYG PGNYDWYFDL WGRGTLVTVS  120
SGKPGSGKPG SGKPGSGKPG SEIVLTQSPA TLSLSPGERA TLSCRASQSV SSYLAWYQQK  180
```

```
PGQAPRLLIY DASNRATGIP ARFSGSGSGT DFTLTISSLE PEDFAVYYCQ QRSNWPPALT 240
FGGGTKVEIK EPKSSDKTHT CPPCPAPEFE GGPSVFLFPP KPKDTLMISR TPEVTCVVVD 300
VSHEDPEVKF NWYVDGVEVH NAKTKPREEQ YNSTYRVVSV LTVLHQDWLN GKEYKCKVSN 360
KALPASIEKT ISKAKGQPRE PQVYTLPPCR KKLTKNQVSL TCLVKGFYPS DIAVEWESNG 420
QPENNYKTTP PVLKSDGSFF LYSKLTVDKS RWQQGNVFSC SVMHEALHNH YTQKSLSLSP 480
GK                                                                 482

SEQ ID NO: 442          moltype = AA  length = 478
FEATURE                 Location/Qualifiers
REGION                  1..478
                        note = Description of Artificial Sequence: Synthetic
                         polypeptide
source                  1..478
                        mol_type = protein
                        organism = synthetic construct
SEQUENCE: 442
QVQLQQWGAG LLKPSETLSL TCAVYGGSFS GYYWSWIRQS PEKGLEWIGE INHGGYVTYN 60
PSLESRVTIS VDTSKNQFSL KLSSVTAADT AVYYCARDYG PGNYDWYFDL WGRGTLVTVS 120
SGGGGSGGGG SGGGGSEIVL TQSPATLSLS PGERATLSCR ASQSVSSYLA WYQQKPGQAP 180
RLLIYDASNR ATGIPARFSG SGSGTDFTLT ISSLEPEDFA VYYCQQRSNW PPALTFGGGT 240
KVEIKREPKS SDKTHTCPPC PAPEFEGGPS VFLFPPKPKD TLMISRTPEV TCVVVDVSHE 300
DPEVKFNWYV DGVEVHNAKT KPREEQYNST YRVVSVLTVL HQDWLNGKEY KCKVSNKALP 360
ASIEKTISKA KGQPREPQVY TLPPCRKKLT KNQVSLTCLV KGFYPSDIAV EWESNGQPEN 420
NYKTTPPVLK SDGSFFLYSK LTVDKSRWQQ GNVFSCSVMH EALHNHYTQK SLSLSPGK   478

SEQ ID NO: 443          moltype = AA  length = 492
FEATURE                 Location/Qualifiers
REGION                  1..492
                        note = Description of Artificial Sequence: Synthetic
                         polypeptide
source                  1..492
                        mol_type = protein
                        organism = synthetic construct
SEQUENCE: 443
QVQLQQWGAG LLKPSETLSL TCAVYGGSFS GYYWSWIRQS PEKGLEWIGE INHGGYVTYN 60
PSLESRVTIS VDTSKNQFSL KLSSVTAADT AVYYCARDYG PGNYDWYFDL WGRGTLVTVS 120
SGGGGSGGGG SGGGGSGGGG SGGGGSGGGG SEIVLTQSPA TLSLSPGERA TLSCRASQSV 180
SSYLAWYQQK PGQAPRLLIY DASNRATGIP ARFSGSGSGT DFTLTISSLE PEDFAVYYCQ 240
QRSNWPPALT FGGGTKVEIK EPKSSDKTHT CPPCPAPEFE GGPSVFLFPP KPKDTLMISR 300
TPEVTCVVVD VSHEDPEVKF NWYVDGVEVH NAKTKPREEQ YNSTYRVVSV LTVLHQDWLN 360
GKEYKCKVSN KALPASIEKT ISKAKGQPRE PQVYTLPPCR KKLTKNQVSL TCLVKGFYPS 420
DIAVEWESNG QPENNYKTTP PVLKSDGSFF LYSKLTVDKS RWQQGNVFSC SVMHEALHNH 480
YTQKSLSLSP GK                                                       492

SEQ ID NO: 444          moltype = AA  length = 482
FEATURE                 Location/Qualifiers
REGION                  1..482
                        note = Description of Artificial Sequence: Synthetic
                         polypeptide
source                  1..482
                        mol_type = protein
                        organism = synthetic construct
SEQUENCE: 444
EIVLTQSPAT LSLSPGERAT LSCRASQSVS SYLAWYQQKP GQAPRLLIYD ASNRATGIPA 60
RFSGSGSGTD FTLTISSLEP EDFAVYYCQQ RSNWPPALTF GGGTKVEIKG KPGSGKPGSG 120
KPGSGKPGSQ VQLQQWGAGL LKPSETLSLT CAVYGGSFSG YYWSWIRQSP EKGLEWIGEI 180
NHGGYVTYNP SLESRVTISV DTSKNQFSLK LSSVTAADTA VYYCARDYGP GNYDWYFDLW 240
GRGTLVTVSS EPKSSDKTHT CPPCPAPEFE GGPSVFLFPP KPKDTLMISR TPEVTCVVVD 300
VSHEDPEVKF NWYVDGVEVH NAKTKPREEQ YNSTYRVVSV LTVLHQDWLN GKEYKCKVSN 360
KALPASIEKT ISKAKGQPRE PQVYTLPPCR KKLTKNQVSL TCLVKGFYPS DIAVEWESNG 420
QPENNYKTTP PVLKSDGSFF LYSKLTVDKS RWQQGNVFSC SVMHEALHNH YTQKSLSLSP 480
GK                                                                 482

SEQ ID NO: 445          moltype = AA  length = 478
FEATURE                 Location/Qualifiers
REGION                  1..478
                        note = Description of Artificial Sequence: Synthetic
                         polypeptide
source                  1..478
                        mol_type = protein
                        organism = synthetic construct
SEQUENCE: 445
QVQLQQWGAG LLKPSETLSL TCAVYGGSFS GYYWSWIRQS PEKGLEWIGE INHGGYVTYN 60
PSLESRVTIS VDTSKNQFSL KLSSVTAADT AVYYCARDYG PGNYDWYFDL WGRGTLVTVS 120
SGGGGSGGGG SGGGGSEIVL TQSPATLSLS PGERATLSCR ASQSVSSYLA WYQQKPGQAP 180
RLLIYDASNR ATGIPARFSG SGSGTDFTLT ISSLEPEDFA VYYCQQRSNW PPALTFGGGT 240
KVEIKREPKS SDKTHTCPPC PAPEFEGGPS VFLFPPKPKD TLMISRTPEV TCVVVDVSHE 300
DPEVKFNWYV DGVEVHNAKT KPREEQYNST YRVVSVLTVL HQDWLNGKEY KCKVSNKALP 360
ASIEKTISKA KGQPREPQVY TLPPCRKKLT KNQVSLTCLV KGFYPSDIAV EWESNGQPEN 420
```

```
NYKTTPPVLK SDGSFFLYSK LTVDKSRWQQ GNVFSCSVMH EALHNHYTQK SLSLSPGK     478

SEQ ID NO: 446           moltype = AA   length = 483
FEATURE                  Location/Qualifiers
REGION                   1..483
                         note = Description of Artificial Sequence: Synthetic
                          polypeptide
source                   1..483
                         mol_type = protein
                         organism = synthetic construct
SEQUENCE: 446
QVQLQESGPG LVKPSETLSL TCTVSGGSFS GYYWSWIRQP PGKGLEWIGE INHGGYVTYN   60
PSLESRVTIS VDTSKNQFSL KLSSVTAADT AVYYCARDYG PGNYDWYFDL WGRGTLVTVS   120
SGKPGSGKPG SGKPGSGKPG SEIVLTQSPG TLSLSPGERA TLSCRASQSV SSSYLAWYQQ   180
KPGQAPRLLI YDASNRATGI PDRFSGSGSG TDFTLTISRL EPEDFAVYYC QQRSNWPPAL   240
TFGGGTKVEI KEPKSSDKTH TCPPCPAPEF EGGPSVFLFP PKPKDTLMIS RTPEVTCVVV   300
DVSHEDPEVK FNWYVDGVEV HNAKTKPREE QYNSTYRVVS VLTVLHQDWL NGKEYKCKVS   360
NKALPASIEK TISKAKGQPR EPQVYTLPPC RKKLTKNQVS LTCLVKGFYP SDIAVEWESN   420
GQPENNYKTT PPVLKSDGSF FLYSKLTVDK SRWQQGNVFS CSVMHEALHN HYTQKSLSLS   480
PGK                                                                483

SEQ ID NO: 447           moltype = AA   length = 483
FEATURE                  Location/Qualifiers
REGION                   1..483
                         note = Description of Artificial Sequence: Synthetic
                          polypeptide
source                   1..483
                         mol_type = protein
                         organism = synthetic construct
SEQUENCE: 447
EVQLLESGGG LVQPGGSLRL SCAASGGSFS GYYWSWVRQA PGKGLEWVSE INHGGYVTYN   60
PSLESRFTIS RDNSKNTLYL QMNSLRAEDT AVYYCAKDYG PGNYDWYFDL WGRGTLVTVS   120
SGKPGSGKPG SGKPGSGKPG SEIVLTQSPG TLSLSPGERA TLSCRASQSV SSSYLAWYQQ   180
KPGQAPRLLI YDASNRATGI PDRFSGSGSG TDFTLTISRL EPEDFAVYYC QQRSNWPPAL   240
TFGGGTKVEI KEPKSSDKTH TCPPCPAPEF EGGPSVFLFP PKPKDTLMIS RTPEVTCVVV   300
DVSHEDPEVK FNWYVDGVEV HNAKTKPREE QYNSTYRVVS VLTVLHQDWL NGKEYKCKVS   360
NKALPASIEK TISKAKGQPR EPQVYTLPPC RKKLTKNQVS LTCLVKGFYP SDIAVEWESN   420
GQPENNYKTT PPVLKSDGSF FLYSKLTVDK SRWQQGNVFS CSVMHEALHN HYTQKSLSLS   480
PGK                                                                483

SEQ ID NO: 448           moltype = AA   length = 483
FEATURE                  Location/Qualifiers
REGION                   1..483
                         note = Description of Artificial Sequence: Synthetic
                          polypeptide
source                   1..483
                         mol_type = protein
                         organism = synthetic construct
SEQUENCE: 448
QVQLVQSGAE VKKPGSSVKV SCKASGGSFS GYYWSWVRQA PGQGLEWMGE INHGGYVTYN   60
PSLESRVTIT ADESTSTAYM ELSSLRSEDT AVYYCARDYG PGNYDWYFDL WGRGTLVTVS   120
SGKPGSGKPG SGKPGSGKPG SEIVLTQSPG TLSLSPGERA TLSCRASQSV SSSYLAWYQQ   180
KPGQAPRLLI YDASNRATGI PDRFSGSGSG TDFTLTISRL EPEDFAVYYC QQRSNWPPAL   240
TFGGGTKVEI KEPKSSDKTH TCPPCPAPEF EGGPSVFLFP PKPKDTLMIS RTPEVTCVVV   300
DVSHEDPEVK FNWYVDGVEV HNAKTKPREE QYNSTYRVVS VLTVLHQDWL NGKEYKCKVS   360
NKALPASIEK TISKAKGQPR EPQVYTLPPC RKKLTKNQVS LTCLVKGFYP SDIAVEWESN   420
GQPENNYKTT PPVLKSDGSF FLYSKLTVDK SRWQQGNVFS CSVMHEALHN HYTQKSLSLS   480
PGK                                                                483

SEQ ID NO: 449           moltype = AA   length = 482
FEATURE                  Location/Qualifiers
REGION                   1..482
                         note = Description of Artificial Sequence: Synthetic
                          polypeptide
source                   1..482
                         mol_type = protein
                         organism = synthetic construct
SEQUENCE: 449
QVQLQQWGAG LLKPSETLSL TCAVYGGSFS GYYWSWIRQS PEKCLEWIGE INHGGYVTYN   60
PSLESRVTIS VDTSKNQFSL KLSSVTAADT AVYYCARDYG PGNYDWYFDL WGRGTLVTVS   120
SGKPGSGKPG SGKPGSGKPG SEIVLTQSPA TLSLSPGERA TLSCRASQSV SSYLAWYQQK   180
PGQAPRLLIY DASNRATGIP ARFSGSGSGT DFTLTISSLE PEDFAVYYCQ QRSNWPPALT   240
FGCGTKVEIK EPKSSDKTHT CPPCPAPEFE GGPSVFLFPP KPKDTLMISR TPEVTCVVVD   300
VSHEDPEVKF NWYVDGVEVH NAKTKPREEQ YNSTYRVVSV LTVLHQDWLN GKEYKCKVSN   360
KALPASIEKT ISKAKGQPRE PQVYTLPPCK KLTKNQVSLT CLVKGFYPSD IAVEWESNG   420
QPENNYKTTP PVLKSDGSFF LYSKLTVDKS RWQQGNVFSC SVMHEALHNH YTQKSLSLSP   480
GK                                                                 482

SEQ ID NO: 450           moltype = AA   length = 482
```

```
FEATURE             Location/Qualifiers
REGION              1..482
                    note = Description of Artificial Sequence: Synthetic
                     polypeptide
source              1..482
                    mol_type = protein
                    organism = synthetic construct
SEQUENCE: 450
QVQLQQWGAG LLKPSETLSL TCAVYGGSFS GYYWSWIRQS PEKCLEWIGE INHGGYVTYN    60
PSLESRVTIS VDTSKNQFSL KLSSVTAADT AVYYCARDYG PGNYDWYFDL WGRGTLVTVS   120
SGKPGSGKPG SGKPGSGKPG SEIVLTQSPA TLSLSPGERA TLSCRASQSV SSYLAWYQQK   180
PGQAPRLLIY DASNRATGIP ARFSGSGSGT DFTLTISSLE PEDFAVYYCQ QRSNWPPALT   240
FGCGTKVEIK EPKSSDKTHT CPPCPAPEFE GGPSVFLFPP KPKDTLMISR TPEVTCVVVD   300
VSHEDPEVKF NWYVDGVEVH NAKTKPREEQ YNSTYRVVSV LTVLHQDWLN GKEYKCKVSN   360
KALPASIEKT ISKAKGQPRE PQVYTLPPCR KKLTKNQVSL TCLVKGFYPS DIAVEWESNG   420
QPENNYKTTP PVLKSDGSFF LYSKLTVDKS RWQQGNVFSC SVMHEALHNH YTQKSLSLSP   480
GK                                                                 482

SEQ ID NO: 451          moltype = AA  length = 478
FEATURE                 Location/Qualifiers
REGION                  1..478
                        note = Description of Artificial Sequence: Synthetic
                         polypeptide
source                  1..478
                        mol_type = protein
                        organism = synthetic construct
SEQUENCE: 451
QVQLVQSGAE VKKPGASVKV SCKASGYTFS SYWMHWVRQA PGQRLEWMGE INPGNGHTNY    60
SQKFQGRVTI TVDKSASTAY MELSSLRSED TAVYYCARSF TTARAFAYWG QGTLVTVSSG   120
KPGSGKPGSG KPGSGKPGSD IVMTQSPPTL SLSPGERVTL SCRASQSISD YLHWYQQKPG   180
QSPRLLIKYA SQSISGIPAR FSGSGSGTDF TLTISSLEPE DFAVYYCQDG HSFPPTFGGG   240
TKVEIKEPKS SDKTHTCPPC PAPEFEGGPS VFLFPPKPKD TLMISRTPEV TCVVVDVSHE   300
DPEVKFNWYV DGVEVHNAKT KPREEQYNST YRVVSVLTVL HQDWLNGKEY KCKVSNKALP   360
ASIEKTISKA KGQPREPQVY TLPPCRKKLT KNQVSLTCLV KGFYPSDIAV EWESNGQPEN   420
NYKTTPPVLK SDGSFFLYSK LTVDKSRWQQ GNVFSCSVMH EALHNHYTQK SLSLSPGK    478

SEQ ID NO: 452          moltype = AA  length = 478
FEATURE                 Location/Qualifiers
REGION                  1..478
                        note = Description of Artificial Sequence: Synthetic
                         polypeptide
source                  1..478
                        mol_type = protein
                        organism = synthetic construct
SEQUENCE: 452
QVQLVQSGAE VKKPGASVKV SCKASGYTFS SYWMHWVRQA PGQRLEWMGE INPGNGHTNY    60
AQKFQGRVTI TVDKSASTAY MELSSLRSED TAVYYCARSF TTARAFAYWG QGTLVTVSSG   120
KPGSGKPGSG KPGSGKPGSD IVMTQSPPTL SLSPGERVTL SCRASQSISD YLHWYQQKPG   180
QSPRLLIKYA SQSISGIPAR FSGSGSGTDF TLTISSLEPE DFAVYYCQDG HSFPPTFGGG   240
TKVEIKEPKS SDKTHTCPPC PAPEFEGGPS VFLFPPKPKD TLMISRTPEV TCVVVDVSHE   300
DPEVKFNWYV DGVEVHNAKT KPREEQYNST YRVVSVLTVL HQDWLNGKEY KCKVSNKALP   360
ASIEKTISKA KGQPREPQVY TLPPCRKKLT KNQVSLTCLV KGFYPSDIAV EWESNGQPEN   420
NYKTTPPVLK SDGSFFLYSK LTVDKSRWQQ GNVFSCSVMH EALHNHYTQK SLSLSPGK    478

SEQ ID NO: 453          moltype = AA  length = 478
FEATURE                 Location/Qualifiers
REGION                  1..478
                        note = Description of Artificial Sequence: Synthetic
                         polypeptide
source                  1..478
                        mol_type = protein
                        organism = synthetic construct
SEQUENCE: 453
QVQLVQSGAE VKKPGASVKV SCKASGYTFS SYWMHWVRQA PGQRLEWMGE INPGNGHTNY    60
NQKFQGRVTI TVDKSASTAY MELSSLRSED TAVYYCARSF TTARAFAYWG QGTLVTVSSG   120
KPGSGKPGSG KPGSGKPGSD IVMTQSPPTL SLSPGERVTL SCRASQSISD YLHWYQQKPG   180
QSPRLLIKYA SQSISGIPAR FSGSGSGTDF TLTISSLEPE DFAVYYCQDG HSFPPTFGGG   240
TKVEIKEPKS SDKTHTCPPC PAPEFEGGPS VFLFPPKPKD TLMISRTPEV TCVVVDVSHE   300
DPEVKFNWYV DGVEVHNAKT KPREEQYNST YRVVSVLTVL HQDWLNGKEY KCKVSNKALP   360
ASIEKTISKA KGQPREPQVY TLPPCRKKLT KNQVSLTCLV KGFYPSDIAV EWESNGQPEN   420
NYKTTPPVLK SDGSFFLYSK LTVDKSRWQQ GNVFSCSVMH EALHNHYTQK SLSLSPGK    478

SEQ ID NO: 454          moltype = AA  length = 479
FEATURE                 Location/Qualifiers
REGION                  1..479
                        note = Description of Artificial Sequence: Synthetic
                         polypeptide
source                  1..479
                        mol_type = protein
```

```
                          organism = synthetic construct
SEQUENCE: 454
EVQLVESGGG LVQPGGSLRL SCAASGFTFS DYWMSWVRQA PGKGLEWVAD IKNDGSYTNY    60
APSLTNRFTI SRDNAKNSLY LQMNSLRAED TAVYYCAREL TGTWGQGTMV TVSSGKPGSG   120
KPGSGKPGSG KPGSDIVMTQ SPDSLAVSLG ERATINCKSS QSLLSSGNQK NYLAWYQQKP   180
GQPPKLLIYY ASTRQSGVPD RFSGSGSGTD FTLTISSLQA EDVAVYYCLQ YDRYPFTFGQ   240
GTKLEIKEPK SSDKTHTCPP CPAPEFEGGP SVFLFPPKPK DTLMISRTPE VTCVVVDVSH   300
EDPEVKFNWY VDGVEVHNAK TKPREEQYNS TYRVVSVLTV LHQDWLNGKE YKCKVSNKAL   360
PASIEKTISK AKGQPREPQV YTLPPCRKKL TKNQVSLTCL VKGFYPSDIA VEWESNGQPE   420
NNYKTTPPVL KSDGSFFLYS KLTVDKSRWQ QGNVFSCSVM HEALHNHYTQ KSLSLSPGK    479

SEQ ID NO: 455           moltype = AA  length = 479
FEATURE                  Location/Qualifiers
REGION                   1..479
                         note = Description of Artificial Sequence: Synthetic
                          polypeptide
source                   1..479
                         mol_type = protein
                         organism = synthetic construct
SEQUENCE: 455
EVQLVESGGG LVQPGGSLRL SCAASGFTFS DYWMSWVRQA PGKGLEWVAD IKNDGSYTNY    60
VDSVKGRFTI SRDNAKNSLY LQMNSLRAED TAVYYCAREL TGTWGQGTLV TVSSGKPGSG   120
KPGSGKPGSG KPGSDIIMTQ SPDSLAVSLG ERATINCKSS QSLLSSGNQK NYLAWYQQKP   180
GQPPELLIYY ASTRQSGVPD RFSGSGSGTD FTLTISSLQA EDVAVYYCLQ YDRYPFTFGQ   240
GTKLEIKEPK SSDKTHTCPP CPAPEFEGGP SVFLFPPKPK DTLMISRTPE VTCVVVDVSH   300
EDPEVKFNWY VDGVEVHNAK TKPREEQYNS TYRVVSVLTV LHQDWLNGKE YKCKVSNKAL   360
PASIEKTISK AKGQPREPQV YTLPPCRKKL TKNQVSLTCL VKGFYPSDIA VEWESNGQPE   420
NNYKTTPPVL KSDGSFFLYS KLTVDKSRWQ QGNVFSCSVM HEALHNHYTQ KSLSLSPGK    479

SEQ ID NO: 456           moltype = AA  length = 479
FEATURE                  Location/Qualifiers
REGION                   1..479
                         note = Description of Artificial Sequence: Synthetic
                          polypeptide
source                   1..479
                         mol_type = protein
                         organism = synthetic construct
SEQUENCE: 456
EVQLVESGGG LVQPGGSLRL SCAASGFTFS DYWMSWVRQA PGKGLEWVAD IKNDGSYTNY    60
VDSVKGRFTI SRDNAKNSLY LQMNSLRAED TAVYYCAREL TGTWGQGTLV TVSSGKPGSG   120
KPGSGKPGSG KPGSDIVMTQ SPDSLAVSLG ERATINCKSS QSLLSSGNQK NYLAWYQQKP   180
GQPPKLLIYY ASTRQSGVPD RFSGSGSGTD FTLTISSLQA EDVAVYYCLQ YDRYPFTFGQ   240
GTKLEIKEPK SSDKTHTCPP CPAPEFEGGP SVFLFPPKPK DTLMISRTPE VTCVVVDVSH   300
EDPEVKFNWY VDGVEVHNAK TKPREEQYNS TYRVVSVLTV LHQDWLNGKE YKCKVSNKAL   360
PASIEKTISK AKGQPREPQV YTLPPCRKKL TKNQVSLTCL VKGFYPSDIA VEWESNGQPE   420
NNYKTTPPVL KSDGSFFLYS KLTVDKSRWQ QGNVFSCSVM HEALHNHYTQ KSLSLSPGK    479

SEQ ID NO: 457           moltype = AA  length = 479
FEATURE                  Location/Qualifiers
REGION                   1..479
                         note = Description of Artificial Sequence: Synthetic
                          polypeptide
source                   1..479
                         mol_type = protein
                         organism = synthetic construct
SEQUENCE: 457
EVQLVESGGG LVQPGGSLRL SCAASGFTFS DYWMSWVRQA PGKGMEWVGD IKNDGSYTNY    60
APSLTNRFTI SRDNARNSLY LQMNSLRAED TAVYYCTREL TGTWGQGTLV TVSSGKPGSG   120
KPGSGKPGSG KPGSDIIMTQ SPDSLAVSLG ERATINCKSS QSLLSSGNQK NYLAWYQQKP   180
GQPPELLIYY ASTRQSGVPD RFSGSGSGTD FTLTISSLQA EDVAVYYCLQ YDRYPFTFGQ   240
GTKLEIKEPK SSDKTHTCPP CPAPEFEGGP SVFLFPPKPK DTLMISRTPE VTCVVVDVSH   300
EDPEVKFNWY VDGVEVHNAK TKPREEQYNS TYRVVSVLTV LHQDWLNGKE YKCKVSNKAL   360
PASIEKTISK AKGQPREPQV YTLPPCRKKL TKNQVSLTCL VKGFYPSDIA VEWESNGQPE   420
NNYKTTPPVL KSDGSFFLYS KLTVDKSRWQ QGNVFSCSVM HEALHNHYTQ KSLSLSPGK    479

SEQ ID NO: 458           moltype = AA  length = 479
FEATURE                  Location/Qualifiers
REGION                   1..479
                         note = Description of Artificial Sequence: Synthetic
                          polypeptide
source                   1..479
                         mol_type = protein
                         organism = synthetic construct
SEQUENCE: 458
EVQLVESGGG LVQPGGSLRL SCAASGFTFS DYWMSWVRQA PGKGMEWVGD IKNDGSYTNY    60
APSLTNRFTI SRDNARNSLY LQMNSLRAED TAVYYCTREL TGTWGQGTLV TVSSGKPGSG   120
KPGSGKPGSG KPGSDIVMTQ SPDSLAVSLG ERATINCKSS QSLLSSGNQK NYLAWYQQKP   180
GQPPKLLIYY ASTRQSGVPD RFSGSGSGTD FTLTISSLQA EDVAVYYCLQ YDRYPFTFGQ   240
GTKLEIKEPK SSDKTHTCPP CPAPEFEGGP SVFLFPPKPK DTLMISRTPE VTCVVVDVSH   300
```

-continued

```
EDPEVKFNWY VDGVEVHNAK TKPREEQYNS TYRVVSVLTV LHQDWLNGKE YKCKVSNKAL   360
PASIEKTISK AKGQPREPQV YTLPPCRKKL TKNQVSLTCL VKGFYPSDIA VEWESNGQPE   420
NNYKTTPPVL KSDGSFFLYS KLTVDKSRWQ QGNVFSCSVM HEALHNHYTQ KSLSLSPGK    479

SEQ ID NO: 459            moltype = AA  length = 478
FEATURE                   Location/Qualifiers
REGION                    1..478
                          note = Description of Artificial Sequence: Synthetic
                           polypeptide
source                    1..478
                          mol_type = protein
                          organism = synthetic construct
SEQUENCE: 459
QVKLVESGAE VKKPGASVKV SCKASGYTFT SYWMHWVRQA PGQVLEWMGE INPGNGHTSY   60
AQKFQGRVTL TVDKSTSTAY MELSSLRSED TAVYYCARSF TTARAFAYWG QGTTVTVSSG   120
KPGSGKPGSG KPGSGKPGSD IQMTQSPSSL SASVGDRVTI TCRASQSISD YLHWYQQKPG   180
KAPKLLIKYA SQSISGVPSR FSGSGSGTDF TLTISSLQPE DFATYYCQDS HSFPPTFGGG   240
TKVEIKEPKS SDKTHTCPPC PAPEFEGGPS VFLFPPKPKD TLMISRTPEV TCVVVDVSHE   300
DPEVKFNWYV DGVEVHNAKT KPREEQYNST YRVVSVLTVL HQDWLNGKEY KCKVSNKALP   360
ASIEKTISKA KGQPREPQVY TLPPCRKKLT KNQVSLTCLV KGFYPSDIAV EWESNGQPEN   420
NYKTTPPVLK SDGSFFLYSK LTVDKSRWQQ GNVFSCSVMH EALHNHYTQK SLSLSPGK     478

SEQ ID NO: 460            moltype = AA  length = 478
FEATURE                   Location/Qualifiers
REGION                    1..478
                          note = Description of Artificial Sequence: Synthetic
                           polypeptide
source                    1..478
                          mol_type = protein
                          organism = synthetic construct
SEQUENCE: 460
QVKLVESGAE VKKPGASVKV SCKASGYTFT SYWMHWVRQA PGQVLEWMGE INPGNGHTSY   60
AQKFQGRVTL TVDKSTSTAY MELSSLRSED TAVYYCARSF TTARAFAYWG QGTTVTVSSG   120
KPGSGKPGSG KPGSGKPGSD IVMTQSPPTL SLSPGERVTL SCRASQSISD YLHWYQQKPG   180
QSPRLLIKYA SQSISGIPAR FSGSGSGTDF TLTISSLEPE DFAVYYCQDG HSFPPTFGGG   240
TKVEIKEPKS SDKTHTCPPC PAPEFEGGPS VFLFPPKPKD TLMISRTPEV TCVVVDVSHE   300
DPEVKFNWYV DGVEVHNAKT KPREEQYNST YRVVSVLTVL HQDWLNGKEY KCKVSNKALP   360
ASIEKTISKA KGQPREPQVY TLPPCRKKLT KNQVSLTCLV KGFYPSDIAV EWESNGQPEN   420
NYKTTPPVLK SDGSFFLYSK LTVDKSRWQQ GNVFSCSVMH EALHNHYTQK SLSLSPGK     478

SEQ ID NO: 461            moltype = AA  length = 479
FEATURE                   Location/Qualifiers
REGION                    1..479
                          note = Description of Artificial Sequence: Synthetic
                           polypeptide
source                    1..479
                          mol_type = protein
                          organism = synthetic construct
SEQUENCE: 461
QVQLVQSGAE VKKPGASVKL SCKASGYTFS SYWMEIWVRQ APGQGLEWIG EINPGNGHTN   60
YNEKFKSRVT MTRDTSTSTA YMELSSLRSE DTAVYYCARS FKTARAFAYW GQGTLVTVSS   120
GKPGSGKPGS GKPGSGKPGS DIVMTQSPAF LSVTPGEKVT ITCRASQTIS DYLHWYQQKP   180
DQAPKLLIKY ASQSISGIPS RFSGSGSGTD FTFTISSLEA EDAATYYCQD GHSWPPTFGQ   240
GTKLEIKEPK SSDKTHTCPP CPAPEFEGGP SVFLFPPKPK DTLMISRTPE VTCVVVDVSH   300
EDPEVKFNWY VDGVEVHNAK TKPREEQYNS TYRVVSVLTV LHQDWLNGKE YKCKVSNKAL   360
PASIEKTISK AKGQPREPQV YTLPPCRKKL TKNQVSLTCL VKGFYPSDIA VEWESNGQPE   420
NNYKTTPPVL KSDGSFFLYS KLTVDKSRWQ QGNVFSCSVM HEALHNHYTQ KSLSLSPGK    479

SEQ ID NO: 462            moltype = AA  length = 478
FEATURE                   Location/Qualifiers
REGION                    1..478
                          note = Description of Artificial Sequence: Synthetic
                           polypeptide
source                    1..478
                          mol_type = protein
                          organism = synthetic construct
SEQUENCE: 462
QVQLVQSGAE VKKPGASVKV SCKASGYTFT SYWMHWVRQA PGQGLEWMGI INPGNGHTSY   60
AQKFQGRVTM TRDTSTSTVY MELSSLRSED TAVYYCARSF TTARAFAYWG QGTTVTVSSG   120
KPGSGKPGSG KPGSGKPGSD IQMTQSPSSL SASVGDRVTI TCRASQSISD YLHWYQQKPG   180
KAPKLLIKYA SQSISGVPSR FSGSGSGTDF TLTISSLQPE DFATYYCQDS HSFPPTFGGG   240
TKVEIKEPKS SDKTHTCPPC PAPEFEGGPS VFLFPPKPKD TLMISRTPEV TCVVVDVSHE   300
DPEVKFNWYV DGVEVHNAKT KPREEQYNST YRVVSVLTVL HQDWLNGKEY KCKVSNKALP   360
ASIEKTISKA KGQPREPQVY TLPPCRKKLT KNQVSLTCLV KGFYPSDIAV EWESNGQPEN   420
NYKTTPPVLK SDGSFFLYSK LTVDKSRWQQ GNVFSCSVMH EALHNHYTQK SLSLSPGK     478

SEQ ID NO: 463            moltype = AA  length = 478
FEATURE                   Location/Qualifiers
REGION                    1..478
```

```
                            note = Description of Artificial Sequence: Synthetic
                             polypeptide
source                      1..478
                            mol_type = protein
                            organism = synthetic construct
SEQUENCE: 463
QVQLVQSGAE VKKPGASVKV SCKASGYTFT SYWMHWVRQA PGQGLEWMGI INPGNGHTSY  60
AQKFQGRVTM TRDTSTSTVY MELSSLRSED TAVYYCARSF TTARAFAYWG QGTTVTVSSG  120
KPGSGKPGSG KPGSGKPGSD IVMTQSPPTL SLSPGERVTL SCRASQSISD YLHWYQQKPG  180
QSPRLLIKYA SQSISGIPAR FSGSGSGTDF TLTISSLEPE DFAVYYCQDG HSFPPTFGGG  240
TKVEIKEPKS SDKTHTCPPC PAPEFEGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
ASIEKTISKA KGQPREPQVY TLPPCRKKLT KNQVSLTCLV KGFYPSDIAV EWESNGQPEN  420
NYKTTPPVLK SDGSFFLYSK LTVDKSRWQQ GNVFSCSVMH EALHNHYTQK SLSLSPGK    478

SEQ ID NO: 464           moltype = AA   length = 478
FEATURE                  Location/Qualifiers
REGION                   1..478
                            note = Description of Artificial Sequence: Synthetic
                             polypeptide
source                      1..478
                            mol_type = protein
                            organism = synthetic construct
SEQUENCE: 464
QVQLVQSGAE VKKPGASVKV SCKASGYTFT SYWMHWVRQA PGQRLEWMGE INPSNGHTKY  60
SQKFQGRVTI TVDKSASTAY MELSSLRSED TAVYYCARSF TTARAFAYWG QGTLVTVSSG  120
KPGSGKPGSG KPGSGKPGSD IQMTQSPSSL SASVGDRVTI TCRASQSISD YLHWYQQKPG  180
KAPKLLIKYA SQSISGVPSR FSGSGSGTDF TLTISSLQPE DFATYYCQDS HSFPPTFGGG  240
TKVEIKEPKS SDKTHTCPPC PAPEFEGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
ASIEKTISKA KGQPREPQVY TLPPCRKKLT KNQVSLTCLV KGFYPSDIAV EWESNGQPEN  420
NYKTTPPVLK SDGSFFLYSK LTVDKSRWQQ GNVFSCSVMH EALHNHYTQK SLSLSPGK    478

SEQ ID NO: 465           moltype = AA   length = 478
FEATURE                  Location/Qualifiers
REGION                   1..478
                            note = Description of Artificial Sequence: Synthetic
                             polypeptide
source                      1..478
                            mol_type = protein
                            organism = synthetic construct
SEQUENCE: 465
QVQLVQSGAE VKKPGASVKV SCKASGYTFT SYWMHWVRQA PGQRLEWMGE INPSNGHTKY  60
SQKFQGRVTI TVDKSASTAY MELSSLRSED TAVYYCARSF TTARAFAYWG QGTLVTVSSG  120
KPGSGKPGSG KPGSGKPGSD IVMTQSPPTL SLSPGERVTL SCRASQSISD YLHWYQQKPG  180
QSPRLLIKYA SQSISGIPAR FSGSGSGTDF TLTISSLEPE DFAVYYCQDG HSFPPTFGGG  240
TKVEIKEPKS SDKTHTCPPC PAPEFEGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
ASIEKTISKA KGQPREPQVY TLPPCRKKLT KNQVSLTCLV KGFYPSDIAV EWESNGQPEN  420
NYKTTPPVLK SDGSFFLYSK LTVDKSRWQQ GNVFSCSVMH EALHNHYTQK SLSLSPGK    478

SEQ ID NO: 466           moltype = AA   length = 481
FEATURE                  Location/Qualifiers
REGION                   1..481
                            note = Description of Artificial Sequence: Synthetic
                             polypeptide
source                      1..481
                            mol_type = protein
                            organism = synthetic construct
SEQUENCE: 466
QVQLVQSGAE VKKPGASVKV SCKASGYTFT DYFMNWVRQA PGQCLEWMGV INPYNDITIY  60
NQKFQGRVTM TVDRSTSTVY MELSSLRSED TAVYYCAREG VLYDGYYEGA YWGQGTLVTV  120
SSGKPGSGKP GSGKPGSGKP GSDIQLTQSP SFLSASVGDR VTITCKASQN VGIAVAWYQQ  180
KPGKAPKLLI YAASNRYTGV PSRFSGSGSG TEFTLTISSL QPEDFATYYC QQYSTYPYTF  240
GCGTKLEIKE PKSSDKTHTC PPCPAPEFEG GPSVFLFPPK PKDTLMISRT PEVTCVVVDV  300
SHEDPEVKFN WYVDGVEVHN AKTKPREEQY NSTYRVVSVL TVLHQDWLNG KEYKCKVSNK  360
ALPASIEKTI SKAKGQPREP QVYTLPPCRK KLTKNQVSLT CLVKGFYPSD IAVEWESNGQ  420
PENNYKTTPP VLKSDGSFFL YSKLTVDKSR WQQGNVFSCS VMHEALHNHY TQKSLSLSPG  480
K                                                                 481

SEQ ID NO: 467           moltype = AA   length = 482
FEATURE                  Location/Qualifiers
REGION                   1..482
                            note = Description of Artificial Sequence: Synthetic
                             polypeptide
source                      1..482
                            mol_type = protein
                            organism = synthetic construct
SEQUENCE: 467
```

```
EVQLLESGGG LVQPGGSLRL SCAASGFTFS SYGMHWVRQA PGKGLEWVAV ISHHGSSKYY   60
ADSVKGRFTI SRDNSKNTLY LQMNSLRAED TAVYYCARDW FFYLFDYWGQ GTLVTVSSGK  120
PGSGKPGSGK PGSGKPGSDI VMTQSPLSLP VTPGEPASIS CKSSQSLLHS DGKTFLYWYL  180
QKPGQSPQLL IYEVSNRFSG VPDRFSGSGS GTDFTLKISR VEAEDVGVYY CLQGERLPFT  240
FGQGTKVEIK EPKSSDKTHT CPPCPAPEFE GGPSVFLFPP KPKDTLMISR TPEVTCVVVD  300
VSHEDPEVKF NWYVDGVEVH NAKTKPREEQ YNSTYRVVSV LTVLHQDWLN GKEYKCKVSN  360
KALPASIEKT ISKAKGQPRE PQVYTLPPCR KKLTKNQVSL TCLVKGFYPS DIAVEWESNG  420
QPENNYKTTP PVLKSDGSFF LYSKLTVDKS RWQQGNVFSC SVMHEALHNH YTQKSLSLSP  480
GK                                                                 482

SEQ ID NO: 468            moltype = AA  length = 728
FEATURE                   Location/Qualifiers
REGION                    1..728
                          note = Description of Artificial Sequence: Synthetic
                           polypeptide
source                    1..728
                          mol_type = protein
                          organism = synthetic construct
SEQUENCE: 468
QVQLVQSGAE VKKPGASVKV SCKASGYTFT DYFMNWVRQA PGQGLEWMGV INPYNDITIY   60
NQKFQGRVTM TVDRSTSTVY MELSSLRSED TAVYYCAREG VLYDGYYEGA YWGQGTLVTV  120
SSGGGGSGGG GSGGGGSDIQ LTQSPSFLSA SVGDRVTITC KASQNVGIAV AWYQQKPGKA  180
PKLLIYAASN RYTGVPSRFS GSGSGTEFTL TISSLQPEDF ATYYCQQYST YPYTFGQGTK  240
LEIKSGGGGS QVQLVQSGAE VKKPGASVKV SCKASGYTFS SYWMHWVRQA PGQRLEWMGE  300
INPGNGHTNY SQKFQGRVTI TVDKSASTAY MELSSLRSED TAVYYCARSF TTARAFAYWG  360
QGTLVTVSSG KPGSGKPGSG KPGSGKPGSD IVMTQSPPTL SLSPGERVTL SCRASQSISD  420
YLHWYQQKPG QSPRLLIKYA SQSISGIPAR FSGSGSGTDF TLTISSLEPE DFAVYYCQDG  480
HSFPPTFGGG TKVEIKEPKS SDKTHTCPPC PAPEFEGGPS VFLFPPKPKD TLMISRTPEV  540
TCVVVDVSHE DPEVKFNWYV DGVEVHNAKT KPREEQYNST YRVVSVLTVL HQDWLNGKEY  600
KCKVSNKALP ASIEKTISKA KGQPREPQVY TLPPCRKKLT KNQVSLTCLV KGFYPSDIAV  660
EWESNGQPEN NYKTTPPVLK SDGSFFLYSK LTVDKSRWQQ GNVFSCSVMH EALHNHYTQK  720
SLSLSPGK                                                           728

SEQ ID NO: 469            moltype = AA  length = 730
FEATURE                   Location/Qualifiers
REGION                    1..730
                          note = Description of Artificial Sequence: Synthetic
                           polypeptide
source                    1..730
                          mol_type = protein
                          organism = synthetic construct
SEQUENCE: 469
QVQLVQSGAE VKKPGASVKV SCKASGYTFS SYWMHWVRQA PGQRLEWMGE INPGNGHTNY   60
SQKFQGRVTI TVDKSASTAY MELSSLRSED TAVYYCARSF TTARAFAYWG QGTLVTVSSG  120
GGGSGGGGSG GGGSGGGGSD IVMTQSPPTL SLSPGERVTL SCRASQSISD YLHWYQQKPG  180
QSPRLLIKYA SQSISGIPAR FSGSGSGTDF TLTISSLEPE DFAVYYCQDG HSFPPTFGGG  240
TKVEIKSGGG GSQVQLVQSG AEVKKPGASV KVSCKASGYT FSSYWMHWVR QAPGQRLEWM  300
GEINPGNGHT NYSQKFQGRV TITVDKSAST AYMELSSLRS EDTAVYYCAR SFTTARAFAY  360
WGQGTLVTVS SGKPGSGKPG SGKPGSGKPG SDIVMTQSPP TLSLSPGERV TLSCRASQSI  420
SDYLHWYQQK PGQSPRLLIK YASQSISGIP ARFSGSGSGT DFTLTISSLE PEDFAVYYCQ  480
DGHSFPPTFG GGTKVEIKEP KSSDKTHTCP PCPAPEFEGG PSVFLFPPKP KDTLMISRTP  540
EVTCVVVDVS HEDPEVKFNW YVDGVEVHNA KTKPREEQYN STYRVVSVLT VLHQDWLNGK  600
EYKCKVSNKA LPASIEKTIS KAKGQPREPQ VYTLPPCRKK LTKNQVSLTC LVKGFYPSDI  660
AVEWESNGQP ENNYKTTPPV LKSDGSFFLY SKLTVDKSRW QQGNVFSCSV MHEALHNHYT  720
QKSLSLSPGK                                                         730

SEQ ID NO: 470            moltype = AA  length = 699
FEATURE                   Location/Qualifiers
REGION                    1..699
                          note = Description of Artificial Sequence: Synthetic
                           polypeptide
source                    1..699
                          mol_type = protein
                          organism = synthetic construct
SEQUENCE: 470
QVQLVQSGAE VKKPGASVKV SCKASGYTFS SYWMHWVRQA PGQRLEWMGE INPGNGHTNY   60
SQKFQGRVTI TVDKSASTAY MELSSLRSED TAVYYCARSF TTARAFAYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPEFEGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PASIEKTISK AKGQPREPQV CTLPPSRDEL  360
TKNQVSLTCL VEGFYPSDIA VEWESNGQPE NNYKTTPPVL DSDGSFFLYS DLTVDKSRWQ  420
QGNVFSCSVM HEALHNHYTQ ESLSLSPGKS GGGGSQVQLV QSGAEVKKPG ASVKVSCKAS  480
GYTFTDYFMN WVRQAPGQGL EWMGVINPYN DITIYNQKFQ GRVTMTVDRS TSTVYMELSS  540
LRSEDTAVYY CAREGVLYDG YYEGAYWGQG TLVTVSSGGG GSGGGGSGGG GSDIQLTQSP  600
SFLSASVGDR VTITCKASQN VGIAVAWYQQ KPGKAPKLLI YAASNRYTGV PSRFSGSGSG  660
TEFTLTISSL QPEDFATYYC QQYSTYPYTF GQGTKLEIK                          699

SEQ ID NO: 471            moltype = AA  length = 701
```

-continued

```
FEATURE           Location/Qualifiers
REGION            1..701
                  note = Description of Artificial Sequence: Synthetic
                   polypeptide
source            1..701
                  mol_type = protein
                  organism = synthetic construct
SEQUENCE: 471
QVQLQQWGAG LLKPSETLSL TCAVYGGSFS GYYWSWIRQS PEKGLEWIGE INHGGYVTYN   60
PSLESRVTIS VDTSKNQFSL KLSSVTAADT AVYYCARDYG PGNYDWYFDL WGRGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVYTLPPCRK  360
KLTKNQVSLT CLVKGFYPSD IAVEWESNGQ PENNYKTTPP VLKSDGSFFL YSKLTVDKSR  420
WQQGNVFSCS VMHEALHNHY TQKSLSLSPG KSGGGGSQVQ LVQSGAEVKK PGASVKVSCK  480
ASGYTFTDYF MNWVRQAPGQ GLEWMGVINP YNDITIYNQK FQGRVTMTVD RSTSTVYMEL  540
SSLRSEDTAV YYCAREGVLY DGYYEGAYWG QGTLVTVSSG GGGSGGGGSG GGGSDIQLTQ  600
SPSFLSASVG DRVTITCKAS QNVGIAVAWY QQKPGKAPKL LIYAASNRYT GVPSRFSGSG  660
SGTEFTLTIS SLQPEDFATY YCQQYSTYPY TFGQGTKLEI K                      701

SEQ ID NO: 472          moltype = AA  length = 699
FEATURE           Location/Qualifiers
REGION            1..699
                  note = Description of Artificial Sequence: Synthetic
                   polypeptide
source            1..699
                  mol_type = protein
                  organism = synthetic construct
SEQUENCE: 472
QVQLVQSGAE VKKPGASVKV SCKASGYTFS SYWMHWVRQA PGQRLEWMGE INPGNGHTNY   60
SQKFQGRVTI TVDKSASTAY MELSSLRSED TAVYYCARSF TTARAFAYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPEFEGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PASIEKTISK AKGQPREPQV YTLPPCRKKL  360
TKNQVSLTCL VKGFYPSDIA VEWESNGQPE NNYKTTPPVL KSDGSFFLYS KLTVDKSRWQ  420
QGNVFSCSVM HEALHNHYTQ KSLSLSPGKS GGGGSQVQL VQSGAEVKKG ASVKVSCKAS  480
GYTFTDYFMN WVRQAPGQGL EWMGVINPYN DITIYNQKFQ GRVTMTVDRS TSTVYMELSS  540
LRSEDTAVYY CAREGVLYDG YYEGAYWGQG TLVTVSSGGG GSGGGGSGGG GSDIQLTQSP  600
SFLSASVGDR VTITCKASQN VGIAVAWYQQ KPGKAPKLLI YAASNRYTGV PSRFSGSGSG  660
TEFTLTISSL QPEDFATYYC QQYSTYPYTF GQGTKLEIK                          699

SEQ ID NO: 473          moltype = AA  length = 701
FEATURE           Location/Qualifiers
REGION            1..701
                  note = Description of Artificial Sequence: Synthetic
                   polypeptide
source            1..701
                  mol_type = protein
                  organism = synthetic construct
SEQUENCE: 473
QVQLQQWGAG LLKPSETLSL TCAVYGGSFS GYYWSWIRQS PEKGLEWIGE INHGGYVTYN   60
PSLESRVTIS VDTSKNQFSL KLSSVTAADT AVYYCARDYG PGNYDWYFDL WGRGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVCTLPPSRD  360
ELTKNQVSLT CLVEGFYPSD IAVEWESNGQ PENNYKTTPP VLDSDGSFFL YSDLTVDKSR  420
WQQGNVFSCS VMHEALHNHY TQESLSLSPG KSGGGGSQVQ LVQSGAEVKK PGASVKVSCK  480
ASGYTFTDYF MNWVRQAPGQ GLEWMGVINP YNDITIYNQK FQGRVTMTVD RSTSTVYMEL  540
SSLRSEDTAV YYCAREGVLY DGYYEGAYWG QGTLVTVSSG GGGSGGGGSG GGGSDIQLTQ  600
SPSFLSASVG DRVTITCKAS QNVGIAVAWY QQKPGKAPKL LIYAASNRYT GVPSRFSGSG  660
SGTEFTLTIS SLQPEDFATY YCQQYSTYPY TFGQGTKLEI K                      701

SEQ ID NO: 474          moltype = AA  length = 474
FEATURE           Location/Qualifiers
REGION            1..474
                  note = Description of Artificial Sequence: Synthetic
                   polypeptide
source            1..474
                  mol_type = protein
                  organism = synthetic construct
SEQUENCE: 474
EVQLVQSGAE VKKPGESLKI SCKGSGYEFS SHWMNWVRQM PGKCLEWMGQ IYPGDGDINY   60
NEKFRGQVTI SADKSISTAY LQWSSLKASD TAMYYCARHG NYVMDYWGQG TLVTVSSGKP  120
GSGKPGSGKP GSGKPGSIQL TQSPSFLSAS VGDRVTITCS ASSVSYMFW YQQKPGKAPK  180
PWIYRTSNLA SGVPSRFSGS GSGTEFTLTI SSLQPEDFAT YYCQQFHDYP RTFGCGTKVE  240
IKEPKSSDKT HTCPPCPAPE FEGGPSVFLF PPKPKDTLMI SRTPEVTCVV VDVSHEDPEV  300
```

```
KFNWYVDGVE VHNAKTKPRE EQYNSTYRVV SVLTVLHQDW LNGKEYKCKV SNKALPASIE   360
KTISKAKGQP REPQVYTLPP CRKKLTKNQV SLTCLVKGFY PSDIAVEWES NGQPENNYKT   420
TPPVLKSDGS FFLYSKLTVD KSRWQQGNVF SCSVMHEALH NHYTQKSLSL SPGK         474

SEQ ID NO: 475          moltype = AA  length = 486
FEATURE                 Location/Qualifiers
REGION                  1..486
                        note = Description of Artificial Sequence: Synthetic
                         polypeptide
source                  1..486
                        mol_type = protein
                        organism = synthetic construct
SEQUENCE: 475
QVQLVQSGAE VKKPGASVKV SCKASGYTFT NFGITWVRQA PGQGLEWMGE IYPSSGNTFY   60
NEKFKGRVTM TTDTSTSTAY MELRSLRSDD TAVYYCARGG GPLRSRYFDY WGQGTLVTVS   120
SGKPGSGKPG SGKPGSGKPG SDIVMTQSPD SLAVSLGERA TINCRSSQSL FSSGNQKNYL   180
TWYQQKPGQP PKLLIYWAST RESGVPDRFS GSGSGTDFTL TISSLQAEDV AVYYCQNDYY   240
YPLTFGGGTK VEIKEPKSSD KTHTCPPCPA PEFEGGPSVF LFPPKPKDTL MISRTPEVTC   300
VVVDVSHEDP EVKFNWYVDG VEVHNAKTKP REEQYNSTYR VVSVLTVLHQ DWLNGKEYKC   360
KVSNKALPAS IEKTISKAKG QPREPQVYTL PPCRKKLTKN QVSLTCLVKG FYPSDIAVEW   420
ESNGQPENNY KTTPPVLKSD GSFFLYSKLT VDKSRWQQGN VFSCSVMHEA LHNHYTQKSL   480
SLSPGK                                                             486

SEQ ID NO: 476          moltype = AA  length = 483
FEATURE                 Location/Qualifiers
REGION                  1..483
                        note = Description of Artificial Sequence: Synthetic
                         polypeptide
source                  1..483
                        mol_type = protein
                        organism = synthetic construct
SEQUENCE: 476
EVQLVESGGG LVQPGGSLRL SCAASGFTFS SFGMHWVRQA PGKGLEWVSY ISSGNSAIYY   60
ADTVNGRFTI SRDNAKNSLY LQMNSLRAED TAVYYCARLR YGNSFDYWGQ GTLVTVSSGK   120
PGSGKPGSGK PGSGKPGSDI VMTQSPDSLA VSLGERATIN CKSSQSLLNS GNQKNYLTWY   180
QQKPGQPPKL LIYWASTRES GVPDRFSGSG SGTDFTLTIS SLQAEDVAVY YCQNNYYYPL   240
TFGGGTKVEI KEPKSSDKTH TCPPCPAPEF EGGPSVFLFP PKPKDTLMIS RTPEVTCVVV   300
DVSHEDPEVK FNWYVDGVEV HNAKTKPREE QYNSTYRVVS VLTVLHQDWL NGKEYKCKVS   360
NKALPASIEK TISKAKGQPR EPQVYTLPPC RKKLTKNQVS LTCLVKGFYP SDIAVEWESN   420
GQPENNYKTT PPVLKSDGSF FLYSKLTVDK SRWQQGNVFS CSVMHEALHN HYTQKSLSLS   480
PGK                                                                483

SEQ ID NO: 477          moltype = AA  length = 484
FEATURE                 Location/Qualifiers
REGION                  1..484
                        note = Description of Artificial Sequence: Synthetic
                         polypeptide
source                  1..484
                        mol_type = protein
                        organism = synthetic construct
SEQUENCE: 477
QVQLVQSGAE VKKPGSSVKV SCKASGYAFN NYWMNWVRQA PGQGLEWMGQ ISPGNGNSNF   60
NGKFKGRVTI TADKSTSTAY MELSSLRSED TAVYYCARGG RYGNAMDYWG QGTTVTVSSG   120
KPGSGKPGSG KPGSGKPGSD IVMTQSPDSL AVSLGERATI NCKSSQSLLN SGNQRNYLTW   180
YQQKPGQPPK LLIYWASTRE SGVPDRFSGS GSGTDFTLTI SSLQAEDVAV YYCQNAYFYP   240
YTFGGGTKVE IKEPKSSDKT HTCPPCPAPE FEGGPSVFLF PPKPKDTLMI SRTPEVTCVV   300
VDVSHEDPEV KFNWYVDGVE VHNAKTKPRE EQYNSTYRVV SVLTVLHQDW LNGKEYKCKV   360
SNKALPASIE KTISKAKGQP REPQVYTLPP CRKKLTKNQV SLTCLVKGFY PSDIAVEWES   420
NGQPENNYKT TPPVLKSDGS FFLYSKLTVD KSRWQQGNVF SCSVMHEALH NHYTQKSLSL   480
SPGK                                                               484

SEQ ID NO: 478          moltype = AA  length = 483
FEATURE                 Location/Qualifiers
REGION                  1..483
                        note = Description of Artificial Sequence: Synthetic
                         polypeptide
source                  1..483
                        mol_type = protein
                        organism = synthetic construct
SEQUENCE: 478
QVQLVQSGAE VKKPGASVKV SCKASGYTFT NSGMNWVRQA PGQGLEWMGW INTNTGEPTF   60
AEEFRGRVTM TRDTSISTAY MELSRLRSDD TAVYYCARYY YGNSFAYWGQ GTLVTVSSGK   120
PGSGKPGSGK PGSGKPGSDI VMTQSPDSLA VSLGERATIN CKSSQSLLNS GNQKNYLTWY   180
QQKPGQPPKL LIYWASTRES GVPDRFSGSG SGTDFTLTIS SLQAEDVAVY YCQNNYFYPL   240
TFGGGTKVEI KEPKSSDKTH TCPPCPAPEF EGGPSVFLFP PKPKDTLMIS RTPEVTCVVV   300
DVSHEDPEVK FNWYVDGVEV HNAKTKPREE QYNSTYRVVS VLTVLHQDWL NGKEYKCKVS   360
NKALPASIEK TISKAKGQPR EPQVYTLPPC RKKLTKNQVS LTCLVKGFYP SDIAVEWESN   420
GQPENNYKTT PPVLKSDGSF FLYSKLTVDK SRWQQGNVFS CSVMHEALHN HYTQKSLSLS   480
PGK                                                                483
```

-continued

```
SEQ ID NO: 479          moltype = AA  length = 478
FEATURE                 Location/Qualifiers
REGION                  1..478
                        note = Description of Artificial Sequence: Synthetic
                         polypeptide
source                  1..478
                        mol_type = protein
                        organism = synthetic construct
SEQUENCE: 479
QVQLVQSGAE VKKPGASVKV SCKASGYTFT SYWMHWVRQA PGQGLEWMGI INPGNGHTSY  60
AQKFQGRVTM TRDTSTSTVY MELSSLRSED TAVYYCARSF TTARAFAYWG QGTTVTVSSG  120
KPGSGKPGSG KPGSGKPGSD IQMTQSPSSL SASVGDRVTI TCRASQSISD YLHWYQQKPG  180
KAPKLLIKYA SQSISGVPSR FSGSGSGTDF TLTISSLQPE DFATYYCQDS HSFPPTFGGG  240
TKVEIKEPKS SDKTHTCPPC PAPEFEGGPS VFLFPPKPKD TLMISRTPEV TCVVVDVSHE  300
DPEVKFNWYV DGVEVHNAKT KPREEQYNST YRVVSVLTVL HQDWLNGKEY KCKVSNKALP  360
ASIEKTISKA KGQPREPQVY TLPPCRKKLT KNQVSLTCLV KGFYPSDIAV EWESNGQPEN  420
NYKTTPPVLK SDGSFFLYSK LTVDKSRWQQ GNVFSCSVMH EALHNHYTQK SLSLSPGK    478

SEQ ID NO: 480          moltype = AA  length = 739
FEATURE                 Location/Qualifiers
REGION                  1..739
                        note = Description of Artificial Sequence: Synthetic
                         polypeptide
source                  1..739
                        mol_type = protein
                        organism = synthetic construct
SEQUENCE: 480
EVQLVESGGG LVQPGGSLRL SCAASGFTFS TYAMNWVRQA PGKGLEWVGR IRSKYNNYAT  60
YYADSVKGRF TISRDDSKNT LYLQMNSLRA EDTAVYYCVR HGNFGDSYVS WFEYWGQGTL  120
VTVSSGGGGS GGGGSGGGGS GGGGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLSGGGGS QVQLVQSGAE VKKPGASVKV SCKASGYTFT SYYIHWVRQA  300
PGQGLEWIGS IYPGNVTNYN EKFKDRATL  TVDTSISTAY MELSRLRSDD TAVYFCTRSH  360
YGLDWNFDVW GQGTTVTVSS GKPGSGKPGS GKPGSGKPGS DIQMTQSPSS LSASVGDRVT  420
ITCHASQNIY VWLNWYQQKP GKAPKLLIYK ASNLHTGVPS RFSGSGSGTD FTLTISSLQP  480
EDFATYYCQQ GQTYPYTFGG GTKVEIKEPK SSDKTHTCPP CPAPEFEGGP SVFLFPPKPK  540
DTLMISRTPE VTCVVVDVSH EDPEVKFNWY VDGVEVHNAK TKPREEQYNS TYRVVSVLTV  600
LHQDWLNGKE YKCKVSNKAL PASIEKTISK AKGQPREPQV YTLPPCRKKL TKNQVSLTCL  660
VKGFYPSDIA VEWESNGQPE NNYKTTPPVL KSDGSFFLYS KLTVDKSRWQ QGNVFSCSVM  720
HEALHNHYTQ KSLSLSPGK                                              739

SEQ ID NO: 481          moltype = AA  length = 739
FEATURE                 Location/Qualifiers
REGION                  1..739
                        note = Description of Artificial Sequence: Synthetic
                         polypeptide
source                  1..739
                        mol_type = protein
                        organism = synthetic construct
SEQUENCE: 481
QVQLVQSGAE VKKPGASVKV SCKASGYTFT SYYIHWVRQA PGQGLEWIGS IYPGNVNTNY  60
NEKFKDRATL TVDTSISTAY MELSRLRSDD TAVYFCTRSH YGLDWNFDVW GQGTTVTVSS  120
GKPGSGKPGS GKPGSGKPGS DIQMTQSPSS LSASVGDRVT ITCHASQNIY VWLNWYQQKP  180
GKAPKLLIYK ASNLHTGVPS RFSGSGSGTD FTLTISSLQP EDFATYYCQQ GQTYPYTFGG  240
GTKVEIKSGG GGSEVQLVES GGGLVQPGGS LRLSCAASGF TFSTYAMNWV RQAPGKGLEW  300
VGRIRSKYNN YATYYADSVK GRFTISRDDS KNTLYLQMNS LRAEDTAVYY CVRHGNFGDS  360
YVSWFEYWGQ GTLVTVSSGG GGSGGGGSGG GGSGGGGSQA VVTQEPSLTV SPGGTVTLTC  420
GSSTGAVTTS NYANWVQQKP GKSPRGLIGG TNKRAPGVPA RFSGSLLGGK AALTISGAQP  480
EDEADYYCAL WYSNHWVFGG GTKLTVLEPK SSDKTHTCPP CPAPEFEGGP SVFLFPPKPK  540
DTLMISRTPE VTCVVVDVSH EDPEVKFNWY VDGVEVHNAK TKPREEQYNS TYRVVSVLTV  600
LHQDWLNGKE YKCKVSNKAL PASIEKTISK AKGQPREPQV YTLPPCRKKL TKNQVSLTCL  660
VKGFYPSDIA VEWESNGQPE NNYKTTPPVL KSDGSFFLYS KLTVDKSRWQ QGNVFSCSVM  720
HEALHNHYTQ KSLSLSPGK                                              739

SEQ ID NO: 482          moltype = AA  length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 482
DVQLQESGPG LVKPSQSLSL TCTVTGYSIT SDYAWNWIRQ FPGNKLEWMG YIRYSGSTSY  60
NPSLKSRISI TRDTSKNQFF LQLNSVTTED TATYYCARDW PRPSYWYFDV WGAGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
GPSVFLFPPK PKDTLMISRT PEVTCVVVDV SHEDPEVKFN WYVDGVEVHN AKTKPREEQY  300
```

-continued

```
NSTYRVVSVL TVLHQDWLNG KEYKCKVSNK ALPASIEKTI SKAKGQPREP QVCTLPPSRD   360
ELTKNQVSLT CLVEGFYPSD IAVEWESNGQ PENNYKTTPP VLDSDGSFFL YSDLTVDKSR   420
WQQGNVFSCS VMHEALHNHY TQESLSLSPG K                                  451

SEQ ID NO: 483           moltype = AA   length = 214
FEATURE                  Location/Qualifiers
REGION                   1..214
                         note = Description of Artificial Sequence: Synthetic
                          polypeptide
source                   1..214
                         mol_type = protein
                         organism = synthetic construct
SEQUENCE: 483
DIQTTQTTSS LSASLGDRVT ISCRAGQDIS NYLNWYQQKP DGTVKLLIYY TSRLHSGVPS   60
RFSGSGSGTD YSLTISNLEQ EDIATYFCQQ GHTLPWTFGG GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 484           moltype = AA   length = 739
FEATURE                  Location/Qualifiers
REGION                   1..739
                         note = Description of Artificial Sequence: Synthetic
                          polypeptide
source                   1..739
                         mol_type = protein
                         organism = synthetic construct
SEQUENCE: 484
EVQLVESGGG LVQPGGSLRL SCAASGFTFS DYWMSWVRQA PGKGLEWVAD IKNDGSYTNY   60
APSLTNRFTI SRDNAKNSLY LQMNSLRAED TAVYYCAREL TGTWGQGTMV TVSSGGGGSG   120
GGGSGGGGSG GGGSDIVMTQ SPDSLAVSLG ERATINCKSS QSLLSSGNQK NYLAWYQQKP   180
GQPPKLLIYY ASTRQSGVPD RFSGSGSGTD FTLTISSLQA EDVAVYYCLQ YDRYPFTFGQ   240
GTKLEIKSGG GGSEVQLVES GGGLVQPGGS LRLSCAASGF TFSTYAMNWV RQAPGKGLEW   300
VGRIRSKYNN YATYYADSVK GRFTISRDDS KNTLYLQMNS LRAEDTAVYY CVRHGNFGDS   360
YVSWFEYWGQ GTLVTVSSGK PGSGKPGSGK PGSGKPGSGA VVTQEPSLTV SPGGTVTLTC   420
GSSTGAVTTS NYANWVQQKP GKSPRGLIGG TNKRAPGVPA RFSGSLLGGK AALTISGAQP   480
EDEADYYCAL WYSNHWVFGG GTKLTVLEPK SSDKTHTCPP CPAPEFEGGP SVFLFPPKPK   540
DTLMISRTPE VTCVVVDVSH EDPEVKFNWY VDGVEVHNAK TKPREEQYNS TYRVVSVLTV   600
LHQDWLNGKE YKCKVSNKAL PASIEKTISK AKGQPREPQV YTLPPCRKKL TKNQVSLTCL   660
VKGFYPSDIA VEWESNGQPE NNYKTTPPVL KSDGSFFLYS KLTVDKSRWQ QGNVFSCSVM   720
HEALHNHYTQ KSLSLSPGK                                               739

SEQ ID NO: 485           moltype = AA   length = 711
FEATURE                  Location/Qualifiers
REGION                   1..711
                         note = Description of Artificial Sequence: Synthetic
                          polypeptide
source                   1..711
                         mol_type = protein
                         organism = synthetic construct
SEQUENCE: 485
QVQLQQWGAG LLKPSETLSL TCAVYGGSFS GYYWSWIRQS PEKGLEWIGE INHGGYVTYN   60
PSLESRVTIS VDTSKNQFSL KLSSVTAADT AVYYCARNYG PGNYDWYFDL WGRGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPEFEG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPASIEKTI SKAKGQPREP QVYTLPPCRK   360
KLTKNQVSLT CLVKGFYPSD IAVEWESNGQ PENNYKTTPP VLKSDGSFFL YSKLTVDKSR   420
WQQGNVFSCS VMHEALHNHY TQKSLSLSPG KSGGGGSEVQ LVESGGGLVQ PGGSLRLSCA   480
ASGFTFSTYA MNWVRQAPGK GLEWVGRIRS KYNNYATYYA DSVKGRFTIS RDDSKNTLYL   540
QMNSLRAEDT AVYYCVRHGN FGDSYVSWFE YWGQGTLVTV SSGGGGSGGG GSGGGGSGGG   600
GSQAVVTQEP SLTVSPGGTV TLTCGSSTGA VTTSNYANWV QQKPGKSPRG LIGGTNKRAP   660
GVPARFSGSL LGGKAALTIS GAQPEDEADY YCALWYSNHW VFGGGTKLTV L           711

SEQ ID NO: 486           moltype = AA   length = 738
FEATURE                  Location/Qualifiers
REGION                   1..738
                         note = Description of Artificial Sequence: Synthetic
                          polypeptide
source                   1..738
                         mol_type = protein
                         organism = synthetic construct
SEQUENCE: 486
QVQLVQSGAE VKKPGASVKV SCKASGYTFS SYWMHWVRQA PGQRLEWMGE INPGNGHTNY   60
SQKFQGRVTI TVDKSASTAY MELSSLRSED TAVYYCARSF TTARAFAYWG QGTLVTVSSG   120
GGGSGGGGSG GGGSGGGGSD IVMTQSPPTL SLSPGERVTL SCRASQSISD YLHWYQQKPG   180
QSPRLLIKYA SQSISGIPAR FSGSGSGTDF TLTISSLEPE DFAVYYCQDG HSFPPTFGGG   240
TKVEIKSGGG GSEVQLVESG GGLVQPGGSL RLSCAASGFT FSTYAMNWVR QAPGKGLEWV   300
GRIRSKYNNY ATYYADSVKG RFTISRDDSK NTLYLQMNSL RAEDTAVYYC VRHGNFGDSY   360
VSWFEYWGQG TLVTVSSGKP GSGKPGSGKP GSGKPGSQAV VTQEPSLTVS PGGTVTLTCG   420
```

```
SSTGAVTTSN YANWVQQKPG KSPRGLIGGT NKRAPGVPAR FSGSLLGGKA ALTISGAQPE   480
DEADYYCALW YSNHWVFGGG TKLTVLEPKS SDKTHTCPPC PAPEFEGGPS VFLFPPKPKD   540
TLMISRTPEV TCVVVDVSHE DPEVKFNWYV DGVEVHNAKT KPREEQYNST YRVVSVLTVL   600
HQDWLNGKEY KCKVSNKALP ASIEKTISKA KGQPREPQVY TLPPCRKKLT KNQVSLTCLV   660
KGFYPSDIAV EWESNGQPEN NYKTTPPVLK SDGSFFLYSK LTVDKSRWQQ GNVFSCSVMH   720
EALHNHYTQK SLSLSPGK                                                 738

SEQ ID NO: 487        moltype = AA  length = 711
FEATURE               Location/Qualifiers
REGION                1..711
                      note = Description of Artificial Sequence: Synthetic
                       polypeptide
source                1..711
                      mol_type = protein
                      organism = synthetic construct
SEQUENCE: 487
QVQLQQWGAG LLKPSETLSL TCAVYGGSFS GYYWSWIRQS PEKGLEWIGE INHGGYVTYN    60
PSLESRVTIS VDTSKNQFSL KLSSVTAADT AVYYCARDYG PGNYDWYFDL WGRGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPEFEG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPASIEKTI SKAKGQPREP QVYTLPPCRK   360
KLTKNQVSLT CLVKGFYPSD IAVEWESNGQ PENNYKTTPP VLKSDGSFFL YSKLTVDKSR   420
WQQGNVFSCS VMHEALHNHY TQKSLSLSPG KSGGGGSEVQ LVESGGGLVQ PGGSLRLSCA   480
ASGFTFSTYA MNWVRQAPGK GLEWVGRIRS KYNNYATYYA DSVKGRFTIS RDDSKNTLYL   540
QMNSLRAEDT AVYYCVRHGN FGDSYVSWFE YWGQGTLVTV SSGGGGSGGG GSGGGGSGGG   600
GSQAVVTQEP SLTVSPGGTV TLTCGSSTGA VTTSNYANWV QQKPGKSPRG LIGGTNKRAP   660
GVPARFSGSL LGGKAALTIS GAQPEDEADY CALWYSNHW VFGGGTKLTV L             711

SEQ ID NO: 488        moltype = AA  length = 483
FEATURE               Location/Qualifiers
REGION                1..483
                      note = Description of Artificial Sequence: Synthetic
                       polypeptide
source                1..483
                      mol_type = protein
                      organism = synthetic construct
SEQUENCE: 488
EPKSSDKTHT CPPCPAPEFE GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPASIEKT   120
ISKAKGQPRE PQVCTLPPSR DELTKNQVSL TCLVEGFYPS DIAVEWESNG QPENNYKTTP   180
PVLDSDGSFF LYSDLTVDKS RWQQGNVFSC SVMHEALHNH YTQESLSLSP GKSGGGSQVQ   240
LVQSGAEVKK PGASVKVSCK ASGYTFSSYW MHWVRQAPGQ RLEWMGEINP GNGHTNYSQK   300
FQGRVTITVD KSASTAYMEL SSLRSEDTAV YYCARSFTTA RAFAYWGQGT LVTVSSGKPG   360
SGKPGSGKPG SGKPGSDIVM TQSPPTLSLS PGERVTLSCR ASQSISDYLH WYQQKPGQSP   420
RLLIKYASQS ISGIPARFSG SGSGTDFTLT ISSLEPEDFA VYYCQDGHSF PPTFGGGTKV   480
EIK                                                                 483

SEQ ID NO: 489        moltype = AA  length = 734
FEATURE               Location/Qualifiers
REGION                1..734
                      note = Description of Artificial Sequence: Synthetic
                       polypeptide
source                1..734
                      mol_type = protein
                      organism = synthetic construct
SEQUENCE: 489
EPKSSDKTHT CPPCPAPEFE GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPASIEKT   120
ISKAKGQPRE PQVCTLPPSR DELTKNQVSL TCLVEGFYPS DIAVEWESNG QPENNYKTTP   180
PVLDSDGSFF LYSDLTVDKS RWQQGNVFSC SVMHEALHNH YTQESLSLSP GKSGGGSQVQ   240
LVQSGAEVKK PGASVKVSCK ASGYTFSSYW MHWVRQAPGQ RLEWMGEINP GNGHTNYSQK   300
FQGRVTITVD KSASTAYMEL SSLRSEDTAV YYCARSFTTA RAFAYWGQGT LVTVSSGKPG   360
SGKPGSGKPG SGKPGSDIVM TQSPPTLSLS PGERVTLSCR ASQSISDYLH WYQQKPGQSP   420
RLLIKYASQS ISGIPARFSG SGSGTDFTLT ISSLEPEDFA VYYCQDGHSF PPTFGGGTKV   480
EIKSGGGSQV QLVQSGAEVK KPGASVKVSC KASGYTFSSY WMHWVRQAPG QRLEWMGEIN   540
PGNGHTNYSQ KFQGRVTITV DKSASTAYME LSSLRSEDTA VYYCARSFTT ARAFAYWGQG   600
TLVTVSSGKP GSGKPGSGKP GSGKPGSDIV MTQSPPTLSL SPGERVTLSC RASQSISDYL   660
HWYQQKPGQS PRLLIKYASQ SISGIPARFS GSGSGTDFTL TISSLEPEDF AVYYCQDGHS   720
FPPTFGGGTK VEIK                                                     734

SEQ ID NO: 490        moltype = AA  length = 739
FEATURE               Location/Qualifiers
REGION                1..739
                      note = Description of Artificial Sequence: Synthetic
                       polypeptide
source                1..739
                      mol_type = protein
                      organism = synthetic construct
```

```
SEQUENCE: 490
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFEYWGQGTL  120
VTVSSGGGGS GGGGSGGGGS GGGGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLSGGGGS EVQLVESGGG LVQPGGSLRL SCAASGFTFS DYWMSWVRQA  300
PGKGLEWVAD IKNDGSYTNY APSLTNRFTI SRDNAKNSLY LQMNSLRAED TAVYYCAREL  360
TGTWGQGTMV TVSSGKPGSG KPGSGKPGSG KPGSDIVMTQ SPDSLAVSLG ERATINCKSS  420
QSLLSSGNQK NYLAWYQQKP GQPPKLLIYY ASTRQSGVPD RFSGSGSGTD FTLTISSLQA  480
EDVAVYYCLQ YDRYPFTFGQ GTKLEIKEPK SSDKTHTCPP CPAPEFEGGP SVFLFPPKPK  540
DTLMISRTPE VTCVVVDVSH EDPEVKFNWY VDGVEVHNAK TKPREEQYNS TYRVVSVLTV  600
LHQDWLNGKE YKCKVSNKAL PASIEKTISK AKGQPREPQV YTLPPCRKKL TKNQVSLTCL  660
VKGFYPSDIA VEWESNGQPE NNYKTTPPVL KSDGSFFLYS KLTVDKSRWQ QGNVFSCSVM  720
HEALHNHYTQ KSLSLSPGK                                              739

SEQ ID NO: 491          moltype = AA  length = 738
FEATURE                 Location/Qualifiers
REGION                  1..738
                        note = Description of Artificial Sequence: Synthetic
                         polypeptide
source                  1..738
                        mol_type = protein
                        organism = synthetic construct
SEQUENCE: 491
EVQLVESGGG LVQPGGSLRL SCAASGFTFS TYAMNWVRQA PGKGLEWVGR IRSKYNNYAT   60
YYADSVKGRF TISRDDSKNT LYLQMNSLRA EDTAVYYCVR HGNFGDSYVS WFEYWGQGTL  120
VTVSSGGGGS GGGGSGGGGS GGGGSQAVVT QEPSLTVSPG GTVTLTCGSS TGAVTTSNYA  180
NWVQQKPGKS PRGLIGGTNK RAPGVPARFS GSLLGGKAAL TISGAQPEDE ADYYCALWYS  240
NHWVFGGGTK LTVLSGGGGS QVQLVQSGAE VKKPGASVKV SCKASGYTFS SYWMHWVRQA  300
PGQRLEWMGE INPGNGHTNY SQKFQGRVTI TVDKSASTAY MELSSLRSED TAVYYCARSF  360
TTARAFAYWG QGTLVTVSSG KPGSGKPGSG KPGSGKPGSD IVMTQSPPTL SLSPGERVTL  420
SCRASQSISD YLHWYQQKPG QSPRLLIKYA SQSISGIPAR FSGSGSGTDF TLTISSLEPE  480
DFAVYYCQDG HSFPPTFGGG TKVEIKEPKS SDKTHTCPPC PAPEFEGGPS VFLFPPKPKD  540
TLMISRTPEV TCVVVDVSHE DPEVKFNWYV DGVEVHNAKT KPREEQYNST YRVVSVLTVL  600
HQDWLNGKEY KCKVSNKALP ASIEKTISKA KGQPREPQVY TLPPCRKKLT KNQVSLTCLV  660
KGFYPSDIAV EWESNGQPEN NYKTTPPVLK SDGSFFLYSK LTVDKSRWQQ GNVFSCSVMH  720
EALHNHYTQK SLSLSPGK                                               738

SEQ ID NO: 492          moltype = AA  length = 746
FEATURE                 Location/Qualifiers
REGION                  1..746
                        note = Description of Artificial Sequence: Synthetic
                         polypeptide
source                  1..746
                        mol_type = protein
                        organism = synthetic construct
SEQUENCE: 492
QVQLVQSGAE VKKPGASVKV SCKASGYTFT NFGITWVRQA PGQGLEWMGE IYPSSGNTFY   60
NEKFKGRVTM TTDTSTSTAY MELRSLRSDD TAVYYCARGG GPLRSRYFDY WGQGTLVTVS  120
SGGGGSGGGG SGGGGSGGGG SDIVMTQSPD SLAVSLGERA TINCRSSQSL FSSGNQKNYL  180
TWYQQKPGQP PKLLIYWAST RESGVPDRFS GSGSGTDFTL TISSLQAEDV AVYYCQNDYS  240
YPLTFGGGTK VEIKSGGGGS EVQLVESGGG LVQPGGSLRL SCAASGFTFS TYAMNWVRQA  300
PGKGLEWVGR IRSKYNNYAT YYADSVKGRF TISRDDSKNT LYLQMNSLRA EDTAVYYCVR  360
HGNFGDSYVS WFEYWGQGTL VTVSSGKPGS GKPGSGKPGS GKPGSQAVVT QEPSLTVSPG  420
GTVTLTCGSS TGAVTTSNYA NWVQQKPGKS PRGLIGGTNK RAPGVPARFS GSLLGGKAAL  480
TISGAQPEDE ADYYCALWYS NHWVFGGGTK LTVLEPKSSD KTHTCPPCPA PEFEGGPSVF  540
LFPPKPKDTL MISRTPEVTC VVVDVSHEDP EVKFNWYVDG VEVHNAKTKP REEQYNSTYR  600
VVSVLTVLHQ DWLNGKEYKC KVSNKALPAS IEKTISKAKG QPREPQVYTL PPCRKKLTKN  660
QVSLTCLVKG FYPSDIAVEW ESNGQPENNY KTTPPVLKSD GSFFLYSKLT VDKSRWQQGN  720
VFSCSVMHEA LHNHYTQKSL SLSPGK                                      746

SEQ ID NO: 493          moltype = AA  length = 743
FEATURE                 Location/Qualifiers
REGION                  1..743
                        note = Description of Artificial Sequence: Synthetic
                         polypeptide
source                  1..743
                        mol_type = protein
                        organism = synthetic construct
SEQUENCE: 493
QVQLVQSGAE VKKPGASVKV SCKASGYTFT NSGMNWVRQA PGQGLEWMGW INTNTGEPTF   60
AEEFRGRVTM TRDTSISTAY MELSRLRSDD TAVYYCARYY YGNSFAYWGQ GTLVTVSSGG  120
GGSGGGGSGG GGSGGGGSDI VMTQSPDSLA VSLGERATIN CKSSQSLLNS GNQKNYLTWY  180
QQKPGQPPKL LIYWASTRES GVPDRFSGSG SGTDFTLTIS SLQAEDVAVY YCQNNYFYPL  240
TFGGGTKVEI KSGGGGSEVQ LVESGGGLVQ PGGSLRLSCA ASGFTFSTYA MNWVRQAPGK  300
GLEWVGRIRS KYNNYATYYA DSVKGRFTIS RDDSKNTLYL QMNSLRAEDT AVYYCVRHGN  360
FGDSYVSWFE YWGQGTLVTV SSGKPGSGKP GSGKPGSGKP GSQAVVTQEP SLTVSPGGTV  420
TLTCGSSTGA VTTSNYANWV QQKPGKSPRG LIGGTNKRAP GVPARFSGSL LGGKAALTIS  480
GAQPEDEADY YCALWYSNHW VFGGGTKLTV LEPKSSDKTH TCPPCPAPEF EGGPSVFLFP  540
```

```
PKPKDTLMIS RTPEVTCVVV DVSHEDPEVK FNWYVDGVEV HNAKTKPREE QYNSTYRVVS  600
VLTVLHQDWL NGKEYKCKVS NKALPASIEK TISKAKGQPR EPQVYTLPPC RKKLTKNQVS  660
LTCLVKGFYP SDIAVEWESN GQPENNYKTT PPVLKSDGSF FLYSKLTVDK SRWQQGNVFS  720
CSVMHEALHN HYTQKSLSLS PGK                                         743

SEQ ID NO: 494              moltype = AA  length = 961
FEATURE                     Location/Qualifiers
REGION                      1..961
                            note = Description of Artificial Sequence: Synthetic
                             polypeptide
source                      1..961
                            mol_type = protein
                            organism = synthetic construct
SEQUENCE: 494
QVQLQQWGAG LLKPSETLSL TCAVYGGSFS GYYWSWIRQS PEKGLEWIGE INHGGYVTYN  60
PSLESRVTIS VDTSKNQFSL KLSSVTAADT AVYYCARDYG PGNYDWYFDL WGRGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVYTLPPCRK  360
KLTKNQVSLT CLVKGFYPSD IAVEWESNGQ PENNYKTTPP VLKSDGSFFL YSKLTVDKSR  420
WQQGNVFSCS VMHEALHNHY TQKSLSLSPG KSGGGGSEVQ LVESGGGLVQ PGGSLRLSCA  480
ASGFTFSTYA MNWVRQAPGK GLEWVGRIRS KYNNYATYYA DSVKGRFTIS RDDSKNTLYL  540
QMNSLRAEDT AVYYCVRHGN FGDSYVSWFE YWGQGTLVTV SSGGGGSGGG GSGGGGSGGG  600
GSQAVVTQEP SLTVSPGGTV TLTCGSSTGA VTTSNYANWV QQKPGKSPRG LIGGTNKRAP  660
GVPARFSGSL LGGKAALTIS GAQPEDEADY YCALWYSNHW VFGGGTKLTV LSGGGGSQVQ  720
LVQSGAEVKK PGASVKVSCK ASGYTFTDYF MNWVRQAPGQ GLEWMGVINP YNDITIYNQK  780
FQGRVTMTVD RSTSTVYMEL SSLRSEDTAV YYCAREGVLY DGYYEGAYWG QGTLVTVSSG  840
GGGSGGGGSG GGGSDIQLTQ SPSFLSASVG DRVTITCKAS QNVGIAVAWY QQKPGKAPKL  900
LIYAASNRYT GVPSRFSGSG SGTEFTLTIS SLQPEDFATY YCQQYSTYPY TFGQGTKLEI  960
K                                                                961

SEQ ID NO: 495              moltype = AA  length = 709
FEATURE                     Location/Qualifiers
REGION                      1..709
                            note = Description of Artificial Sequence: Synthetic
                             polypeptide
source                      1..709
                            mol_type = protein
                            organism = synthetic construct
SEQUENCE: 495
QVQLVQSGAE VKKPGASVKV SCKASGYTFS SYWMHWVRQA PGQRLEWMGE INPGNGHTNY  60
SQKFQGRVTI TVDKSASTAY MELSSLRSED TAVYYCARSF TTARAFAYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPEFEGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PASIEKTISK AKGQPREPQV CTLPPSRDEL  360
TKNQVSLTCL VEGFYPSDIA VEWESNGQPE NNYKTTPPVL DSDGSFFLYS DLTVDKSRWQ  420
QGNVFSCSVM HEALHNHYTQ ESLSLSPGKS GGGGSEVQLV ESGGGLVQPG GSLRLSCAAS  480
GFTFSTYAMN WVRQAPGKGL EWVGRIRSKY NNYATYYADS VKGRFTISRD DSKNTLYLQM  540
NSLRAEDTAV YYCVRHGNFG DSYVSWFEYW GQGTLVTVSS GGGGSGGGGS GGGGSGGGGS  600
QAVVTQEPSL TVSPGGTVTL TCGSSTGAVT TSNYANWVQQ KPGKSPRGLI GGTNKRAPGV  660
PARFSGSLLG GKAALTISGA QPEDEADYYC ALWYSNHWVF GGGTKLTVL               709

SEQ ID NO: 496              moltype = AA  length = 959
FEATURE                     Location/Qualifiers
REGION                      1..959
                            note = Description of Artificial Sequence: Synthetic
                             polypeptide
source                      1..959
                            mol_type = protein
                            organism = synthetic construct
SEQUENCE: 496
QVQLVQSGAE VKKPGASVKV SCKASGYTFS SYWMHWVRQA PGQRLEWMGE INPGNGHTNY  60
SQKFQGRVTI TVDKSASTAY MELSSLRSED TAVYYCARSF TTARAFAYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPEFEGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PASIEKTISK AKGQPREPQV CTLPPSRDEL  360
TKNQVSLTCL VEGFYPSDIA VEWESNGQPE NNYKTTPPVL DSDGSFFLYS DLTVDKSRWQ  420
QGNVFSCSVM HEALHNHYTQ ESLSLSPGKS GGGGSEVQLV ESGGGLVQPG GSLRLSCAAS  480
GFTFSTYAMN WVRQAPGKGL EWVGRIRSKY NNYATYYADS VKGRFTISRD DSKNTLYLQM  540
NSLRAEDTAV YYCVRHGNFG DSYVSWFEYW GQGTLVTVSS GGGGSGGGGS GGGGSGGGGS  600
QAVVTQEPSL TVSPGGTVTL TCGSSTGAVT TSNYANWVQQ KPGKSPRGLI GGTNKRAPGV  660
PARFSGSLLG GKAALTISGA QPEDEADYYC ALWYSNHWVF GGGTKLTVLS GGGGSQVQLV  720
QSGAEVKKPG ASVKVSCKAS GYTFTDYFMN WVRQAPGQGL EWMGVINPYN DITIYNQKFQ  780
GRVTMTVDRS TSTVYMELSS LRSEDTAVYY CAREGVLYDG YYEGAYWGQG TLVTVSSGGG  840
GSGGGGSGGG GSDIQLTQSP SFLSASVGDR VTITCKASQN VGIAVAWYQQ KPGKAPKLLI  900
YAASNRYTGV PSRFSGSGSG TEFTLTISSL QPEDFATYYC QQYSTYPYTF GQGTKLEIK   959
```

```
SEQ ID NO: 497          moltype = AA  length = 986
FEATURE                 Location/Qualifiers
REGION                  1..986
                        note = Description of Artificial Sequence: Synthetic
                         polypeptide
source                  1..986
                        mol_type = protein
                        organism = synthetic construct
SEQUENCE: 497
QVQLVQSGAE VKKPGASVKV SCKASGYTFT DYFMNWVRQA PGQGLEWMGV INPYNDITIY   60
NQKFQGRVTM TVDRSTSTVY MELSSLRSED TAVYYCAREG VLYDGYYEGA YWGQGTLVTV  120
SSGGGGSGGG GSGGGGSDIQ LTQSPSFLSA SVGDRVTITC KASQNVGIAV AWYQQKPGKA  180
PKLLIYAASN RYTGVPSRFS GSGSGTEFTL TISSLQPEDF ATYYCQQYST YPYTFGQGTK  240
LEIKSGGGSE VQLVESGGGL VQPGGSLRLS CAASGFTFST YAMNWVRQAP GKGLEWVGRI  300
RSKYNNYATY YADSVKGRFT ISRDDSKNTL YLQMNSLRAE DTAVYYCVRH GNFGDSYVSW  360
FEYWGQGTLV TVSSGKPGSG KPGSGKPGSG KPGSQAVVTQ EPSLTVSPGG TVTLTCGSST  420
GAVTTSNYAN WVQQKPGKSP RGLIGGTNKR APGVPARFSG SLLGGKAALT ISGAQPEDEA  480
DYYCALWYSN HWVFGGGTKL TVLEPKSSDK THTCPPCPAP EFEGGPSVFL FPPKPKDTLM  540
ISRTPEVTCV VVDVSHEDPE VKFNWYVDGV EVHNAKTKPR EEQYNSTYRV VSVLTVLHQD  600
WLNGKEYKCK VSNKALPASI EKTISKAKGQ PREPQVYTLP PCRKKLTKNQ VSLTCLVKGF  660
YPSDIAVEWE SNGQPENNYK TTPPVLKSDG SFFLYSKLTV DKSRWQQGNV FSCSVMHEAL  720
HNHYTQKSLS LSPGKSGGGS QVQLVQSGAE VKKPGASVKV SCKASGYTFS SYWMHWVRQA  780
PGQRLEWMGE INPGNGHTNY SQKFQGRVTI TVDKSASTAY MELSSLRSED TAVYYCARSF  840
TTARAFAYWG QGTLVTVSSG KPGSGKPGSG KPGSGKPGSD IVMTQSPPTL SLSPGERVTL  900
SCRASQSISD YLHWYQQKPG QSPRLLIKYA SQSISGIPAR FSGSGSGTDF TLTISSLEPE  960
DFAVYYCQDG HSFPPTFGGG TKVEIK                                      986

SEQ ID NO: 498          moltype = AA  length = 703
FEATURE                 Location/Qualifiers
REGION                  1..703
                        note = Description of Artificial Sequence: Synthetic
                         polypeptide
source                  1..703
                        mol_type = protein
                        organism = synthetic construct
SEQUENCE: 498
QVQLVQSGAE VKKPGASVKV SCKASGYTFT DYFMNWVRQA PGQGLEWMGV INPYNDITIY   60
NQKFQGRVTM TVDRSTSTVY MELSSLRSED TAVYYCAREG VLYDGYYEGA YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEFE  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPASIEKT ISKAKGQPRE PQVCTLPPSR  360
DELTKNQVSL TCLVEGFYPS DIAVEWESNG QPENNYKTTP PVLDSDGSFF LYSDLTVDKS  420
RWQQGNVFSC SVMHEALHNH YTQESLSLSP GKSGGGSQVQ LVQSGAEVKK PGASVKVSCK  480
ASGYTFSSYW MHWVRQAPGQ RLEWMGEINP GNGHTNYSQK FQGRVTITVD KSASTAYMEL  540
SSLRSEDTAV YYCARSFTTA RAFAYWGQGT LVTVSSGKPG SGKPGSGKPG SGKPGSDIVM  600
TQSPPTLSLS PGERVTLSCR ASQSISDYLH WYQQKPGQSP RLLIKYASQS ISGIPARFSG  660
SGSGTDFTLT ISSLEPEDFA VYYCQDGHSF PPTFGGGTKV EIK                   703

SEQ ID NO: 499          moltype = AA  length = 954
FEATURE                 Location/Qualifiers
REGION                  1..954
                        note = Description of Artificial Sequence: Synthetic
                         polypeptide
source                  1..954
                        mol_type = protein
                        organism = synthetic construct
SEQUENCE: 499
QVQLVQSGAE VKKPGASVKV SCKASGYTFT DYFMNWVRQA PGQGLEWMGV INPYNDITIY   60
NQKFQGRVTM TVDRSTSTVY MELSSLRSED TAVYYCAREG VLYDGYYEGA YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEFE  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPASIEKT ISKAKGQPRE PQVCTLPPSR  360
DELTKNQVSL TCLVEGFYPS DIAVEWESNG QPENNYKTTP PVLDSDGSFF LYSDLTVDKS  420
RWQQGNVFSC SVMHEALHNH YTQESLSLSP GKSGGGSQVQ LVQSGAEVKK PGASVKVSCK  480
ASGYTFSSYW MHWVRQAPGQ RLEWMGEINP GNGHTNYSQK FQGRVTITVD KSASTAYMEL  540
SSLRSEDTAV YYCARSFTTA RAFAYWGQGT LVTVSSGKPG SGKPGSGKPG SGKPGSDIVM  600
TQSPPTLSLS PGERVTLSCR ASQSISDYLH WYQQKPGQSP RLLIKYASQS ISGIPARFSG  660
SGSGTDFTLT ISSLEPEDFA VYYCQDGHSF PPTFGGGTKV EIKSGGGSQV QLVQSGAEVK  720
KPGASVKVSC KASGYTFSSY WMHWVRQAPG QRLEWMGEIN PGNGHTNYSQ KFQGRVTITV  780
DKSASTAYME LSSLRSEDTA VYYCARSFTT ARAFAYWGQG TLVTVSSGKP GSGKPGSGKP  840
GSGKPGSDIV MTQSPPTLSL SPGERVTLSC RASQSISDYL HWYQQKPGQS PRLLIKYASQ  900
SISGIPARFS GSGSGTDFTL TISSLEPEDF AVYYCQDGHS FPPTFGGGTK VEIK        954

SEQ ID NO: 500          moltype = AA  length = 731
FEATURE                 Location/Qualifiers
REGION                  1..731
```

```
                           note = Description of Artificial Sequence: Synthetic
                            polypeptide
source                     1..731
                           mol_type = protein
                           organism = synthetic construct
SEQUENCE: 500
QVQLVQSGAE VKKPGASVKV SCKASGYTFT SYYIHWVRQA PGQGLEWIGS IYPGNVNTNY  60
NEKFKDRATL TVDTSISTAY MELSRLRSDD TAVYFCTRSH YGLDWNFDVW GQGTTVTVSS  120
GGGGSGGGGS GGGGSGGGGS DIQMTQSPSS LSASVGDRVT ITCHASQNIY VWLNWYQQKP  180
GKAPKLLIYK ASNLHTGVPS RFSGSGSGTD FTLTISSLQP EDFATYYCQQ GQTYPYTFGG  240
GTKVEIKSGG GGSQVQLVQS GAEVKKPGAS VKVSCKASGY TFSSYWMHWV RQAPGQRLEW  300
MGEINPGNGH TNYSQKFQGR VTITVDKSAS TAYMELSSLR SEDTAVYYCA RSFTTARAFA  360
YWGQGTLVTV SSGKPGSGKP GSGKPGSGKP GSDIVMTQSP PTLSLSPGER VTLSCRASQS  420
ISDYLHWYQQ KPGQSPRLLI KYASQSISGI PARFSGSGSG TDFTLTISSL EPEDFAVYYC  480
QDGHSFPPTF GGGTKVEIKE PKSSDKTHTC PPCPAPEFEG GPSVFLFPPK PKDTLMISRT  540
PEVTCVVVDV SHEDPEVKFN WYVDGVEVHN AKTKPREEQY NSTYRVVSVL TVLHQDWLNG  600
KEYKCKVSNK ALPASIEKTI SKAKGQPREP QVYTLPPCRK KLTKNQVSLT CLVKGFYPSD  660
IAVEWESNGQ PENNYKTTPP VLKSDGSFFL YSKLTVDKSR WQQGNVFSCS VMHEALHNHY  720
TQKSLSLSPG K                                                       731

SEQ ID NO: 501           moltype = AA  length = 732
FEATURE                  Location/Qualifiers
REGION                   1..732
                         note = Description of Artificial Sequence: Synthetic
                          polypeptide
source                   1..732
                         mol_type = protein
                         organism = synthetic construct
SEQUENCE: 501
QVQLVQSGAE VKKPGASVKV SCKASGYTFT SYYIHWVRQA PGQGLEWIGS IYPGNVNTNY  60
NEKFKDRATL TVDTSISTAY MELSRLRSDD TAVYFCTRSH YGLDWNFDVW GQGTTVTVSS  120
GGGGSGGGGS GGGGSGGGGS DIQMTQSPSS LSASVGDRVT ITCHASQNIY VWLNWYQQKP  180
GKAPKLLIYK ASNLHTGVPS RFSGSGSGTD FTLTISSLQP EDFATYYCQQ GQTYPYTFGG  240
GTKVEIKSGG GGSEVQLVES GGGLVQPGGS LRLSCAASGF TFSDYWMSWV RQAPGKGLEW  300
VADIKNDGSY TNYAPSLTNR FTISRDNAKN SLYLQMNSLR AEDTAVYYCA RELTGTWGQG  360
TMVTVSSGKP GSGKPGSGKP GSGKPGSDIV MTQSPDSLAV SLGERATINC KSSQSLLSSG  420
NQKNYLAWYQ QKPGQPPKLL IYYASTRQSG VPDRFSGSGS GTDFTLTISS LQAEDVAVYY  480
CLQYDRYPFT FGQGTKLEIK EPKSSDKTHT CPPCPAPEFE GGPSVFLFPP KPKDTLMISR  540
TPEVTCVVVD VSHEDPEVKF NWYVDGVEVH NAKTKPREEQ YNSTYRVVSV LTVLHQDWLN  600
GKEYKCKVSN KALPASIEKT ISKAKGQPRE PQVYTLPPCR KKLTKNQVSL TCLVKGFYPS  660
DIAVEWESNG QPENNYKTTP PVLKSDGSFF LYSKLTVDKS RWQQGNVFSC SVMHEALHNH  720
YTQKSLSLSP GK                                                     732

SEQ ID NO: 502           moltype = AA  length = 731
FEATURE                  Location/Qualifiers
REGION                   1..731
                         note = Description of Artificial Sequence: Synthetic
                          polypeptide
source                   1..731
                         mol_type = protein
                         organism = synthetic construct
SEQUENCE: 502
QVQLVQSGAE VKKPGASVKV SCKASGYTFS SYWMHWVRQA PGQRLEWMGE INPGNGHTNY  60
SQKFQGRVTI TVDKSASTAY MELSSLRSED TAVYYCARSF TTARAFAYWG QGTLVTVSSG  120
GGGSGGGGSD IVMTQSPPTL SLSPGERVTL SCRASQSISD YLHWYQQKP  180
QSPRLLIKYA SQSISGIPAR FSGSGSGTDF TLTISSLEPE DFAVYYCQDG HSFPPTFGGG  240
TKVEIKSGGG GSQVQLVQSG AEVKKPGASV KVSCKASGYT FTSYYIHWVR QAPGQGLEWI  300
GSIYPGNVNT NYNEKFKDRA TLTVDTSIST AYMELSRLRS DDTAVYFCTR SHYGLDWNFD  360
VWGQGTTVTV SSGKPGSGKP GSGKPGSGKP GSDIQMTQSP SSLSASVGDR VTITCHASQN  420
IYVWLNWYQQ KPGKAPKLLI YKASNLHTGV PSRFSGSGSG TDFTLTISSL QPEDFATYYC  480
QQGQTYPYTF GGGTKVEIKE PKSSDKTHTC PPCPAPEFEG GPSVFLFPPK PKDTLMISRT  540
PEVTCVVVDV SHEDPEVKFN WYVDGVEVHN AKTKPREEQY NSTYRVVSVL TVLHQDWLNG  600
KEYKCKVSNK ALPASIEKTI SKAKGQPREP QVYTLPPCRK KLTKNQVSLT CLVKGFYPSD  660
IAVEWESNGQ PENNYKTTPP VLKSDGSFFL YSKLTVDKSR WQQGNVFSCS VMHEALHNHY  720
TQKSLSLSPG K                                                       731

SEQ ID NO: 503           moltype = AA  length = 732
FEATURE                  Location/Qualifiers
REGION                   1..732
                         note = Description of Artificial Sequence: Synthetic
                          polypeptide
source                   1..732
                         mol_type = protein
                         organism = synthetic construct
SEQUENCE: 503
EVQLVESGGG LVQPGGSLRL SCAASGFTFS DYWMSWVRQA PGKGLEWVAD IKNDGSYTNY  60
APSLTNRFTI SRDNAKNSLY LQMNSLRAED TAVYYCAREL TGTWGQGTMV TVSSGGGGSG  120
GGGSGGGGSG GGGDIVMTQ SPDSLAVSLG ERATINCKSS QSLLSSGNQK NYLAWYQQKP  180
GQPPKLLIYY ASTRQSGVPD RFSGSGSGTD FTLTISSLQA EDVAVYYCLQ YDRYPFTFGQ  240
```

-continued

```
GTKLEIKSGG GGSQVQLVQS GAEVKKPGAS VKVSCKASGY TFTSYYIHWV RQAPGQGLEW  300
IGSIYPGNVN TNYNEKFKDR ATLTVDTSIS TAYMELSRLR SDDTAVYFCT RSHYGLDWNF  360
DVWGQGTTVT VSSGKPGSGK PGSGKPGSGK PGSDIQMTQS PSSLSASVGD RVTITCHASQ  420
NIYVWLNWYQ QKPGKAPKLL IYKASNLHTG VPSRFSGSGS GTDFTLTISS LQPEDFATYY  480
CQQGQTYPYT FGGGTKVEIK EPKSSDKTHT CPPCPAPEFE GGPSVFLFPP KPKDTLMISR  540
TPEVTCVVVD VSHEDPEVKF NWYVDGVEVH NAKTKPREEQ YNSTYRVVSV LTVLHQDWLN  600
GKEYKCKVSN KALPASIEKT ISKAKGQPRE PQVYTLPPCR KKLTKNQVSL TCLVKGFYPS  660
DIAVEWESNG QPENNYKTTP PVLKSDGSFF LYSKLTVDKS RWQQGNVFSC SVMHEALHNH  720
YTQKSLSLSP GK                                                     732

SEQ ID NO: 504          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 504
GGGGS                                                             5

SEQ ID NO: 505          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 505
GKPGS                                                             5

SEQ ID NO: 506          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 506
GEPGS                                                             5

SEQ ID NO: 507          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 507
GGPGS                                                             5

SEQ ID NO: 508          moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 508
GKPGSGKPGS GKPGSGKPGS                                             20

SEQ ID NO: 509          moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 509
GGGGSGGGGS GGGGSGGGGS                                             20
```

TRISPECIFIC T CELL ENGAGERS

RELATED APPLICATIONS

This application is a continuation application of U.S. patent application Ser. No. 17/164,696, filed on Feb. 1, 2021, which claims priority to U.S. provisional patent application Ser. No. 62/968,999 filed on Jan. 31, 2020, U.S. provisional patent application Ser. No. 62/981,048 filed on Feb. 25, 2020 and U.S. provisional patent application Ser. No. 62/991,070 filed on Mar. 17, 2020. The contents of the aforementioned applications are incorporated herein by reference.

REFERENCE TO SEQUENCE LISTING

The application contains a Sequence Listing which has been submitted electronically in .XML format and is hereby incorporated by reference in its entirety. Said .XML copy, created on Nov. 26, 2024, is named "2022-007 CONT.xml" and is 770,597 bytes in size. The sequence listing contained in this .XML file is part of the specification and is hereby incorporated by reference herein in its entirety.

FIELD OF INVENTION

This invention relates generally to cancer therapies, and more specifically, to novel compounds comprising anti-DLL3, CLDN18.2 and Muc17 antibodies or immunoreactive fragments thereof for the treatment of cancer.

BACKGROUND

Cancer is generally defined as a group of diseases involving abnormal cell growth with the potential to invade or spread to other parts of the body. In 2019, roughly 1.8 million people were diagnosed with cancer in the United States. Each year, an estimated 606,880 people will die from cancer in the United States. Lung and bronchus cancer is responsible for the most deaths. Colorectal cancer and pancreatic cancer are the second and third most common causes of cancer death respectively.

Cancer has been linked to several factors including smoking, obesity, poor diet, lack of physical activity and excessive consumption of alcohol. Other factors include certain infections, exposure to ionizing radiation and environmental pollutants. Certain cancers have been linked to infections such as *Helicobacter pylori*, hepatitis B, hepatitis C, human papillomavirus infection, Epstein-Barr virus and human immunodeficiency virus (HIV).

Conventional cancer treatments are directed at removing cancerous tissue and preventing it from spreading. Such treatment options include surgery, chemotherapy, radiation therapy, hormonal therapy, targeted therapy and palliative care. Treatments are usually pursued based on the type, location and grade of the cancer as well as the patient's health and preferences. These options have limitations. They can be ineffective, particularly when cancer has metastasized. Moreover, chemotherapy and radiation therapy have a range of side-effects related to cell toxicity.

Because cancer cells divide faster than most normal cells, they can be sensitive to chemotherapy drugs. However, chemotherapy drugs will also attack other cells in the body, especially fast-dividing cells such as blood cells and the cells lining the mouth, stomach, and intestines. Accordingly, there is a need for improved medications and methods of treating cancer that are more targeted and have less deleterious side effects.

A promising area for the development of treatments includes targeted therapies using antibodies. For example, the use of antibody drug conjugates can be used to target a drug toward a tumor. Immunoconjugates are antibodies conjugated joined) to a second molecule, usually a toxin, radioisotope or label. Immunoconjugates can provide for relatively high concentrations of drug within the tumor whereas systemic administration of unconjugated (i.e., untargeted) drug to achieve the same tumor concentration can lead to levels that are toxic to normal cells.

Another promising area is development of treatments that harness the immune system to attack and kill tumor cells. Checkpoint inhibitors, such as anti-CTLA4, anti-PD1 and anti-POL1 therapies have changed the way cancer is treated. Similarly, the direct activation of cytotoxic T cells by bispecific T cell engagers or CAR-T engineered T cells, has led to previously unseen cures in many types of cancers.

Delta-like ligand 3 (DLL3) is an inhibitory notch ligand that is expressed at relatively low levels in normal tissues. It is expressed at high levels in small cell lung cancer (SCLC) and other neuroendocrine tumors, thus presenting potential therapeutic target in cancer diagnosis and treatment.

Mucin 17, also referred to as MUC17, is a member of the mucin family that is composed of more than 20 members. Mucins are large, highly glycosylated membrane bound proteins. They generally function in mucosal areas to protect epithelial cells from their environment, as well as to regulate proliferation and survival of cells. MUC17 is expressed in pancreatic, appendiceal, and some colon cancers and thus is a target antigen for these cancers. Thus, MUC17 is a candidate for targeting of therapies such as antibody drug conjugates, T cell engagers, and CAR-T cells.

Claudin-18 (CLDN18) is a protein in humans that is encoded by the CLDN18 gene. It belongs to the group of claudins, a family of proteins that form components of tight cell junction strands in epithelial cells. Studies have demonstrated that Isoform 2 (Claudin 18.2 or CLDN18.2) is abundant in gastric tumors. It has exposed extracellular loops and is available for monoclonal antibody binding. These biological characteristics have led to the development of monoclonal antibodies against claudin 18.2, such as claudiximab (IMAB362).

CD3, CD28 and CD137 are receptors present on T-cells. T cells can be activated though CD3, CD28 and CD137, by antigen-presenting cells that utilize the activation signals MHC Class I and II, CD80 and CD86, and 4-1BBL, respectively. CD3 is part of the T cell receptor (TCR) and is the signaling component for the receptor. There are three CD3 subunits, epsilon, delta and gamma. Epsilon associates with both delta and zeta and together they are responsible for signaling. CD3 signaling is considered signal 1 that is required to activate T cells. The co-receptors, CD28 and CD137, are considered signal 2. Both signal 1 and signal 2 are required for full activation, proliferation and survival of T cells.

The present invention discloses trispecific T Cell Engagers. The trispecific and trispecific molecules can bind to DLL3, MUC17 and/or CLDN18.2 and activate CD (cluster of differentiation) molecules (e.g. CD3, CD28 and CD137). Also provided are methods of treating an ailment such as cancer using antibodies and antibody conjugates, pharmaceutical compositions thereof, and articles of manufacture.

SUMMARY

The inventions described and claimed herein have many attributes and embodiments including, but not limited to, those set forth or described or referenced in this brief summary. The inventions described and claimed herein are not limited to, or by, the features or embodiments identified in this summary, which is included for purposes of illustration only and not restriction.

An aspect of the invention is an antibody against DLL3. The antibody can be a fragment such as an antigen binding fragment (Fab) or a single chain variable fragment (Scfvs).

An aspect of the invention is an agonist antibody that activates CD3, CD28 and/or CD137.

An aspect of the invention is a bispecific or trispecific molecule that includes an antibody (or fragment) against DLL3 paired with an antibody (or fragment) of an agonist antibody that activates CD3, CD28 or CD137.

An aspect of the invention is a method of treating an ailment such as cancer using an antibody (or fragment) against DLL3 paired with an antibody (or fragment) of an agonist antibody that activates CD3, CD28 or CD137.

An aspect of the invention is a method of treating an ailment that uses two or more of the trispecific molecules described herein in combination with one another.

An aspect of the invention is a method of treating an ailment that uses one bispecific and one trispecific molecule described herein in combination with one another.

An aspect of the invention is a method of treating an ailment that uses two or more trispecific molecules described herein in combination with one another.

An aspect on the invention is a method of activating T-cell cytotoxicity against DLL3 expressing cells.

An aspect of the invention is a method of activating T-cell cytotoxicity using a bispecific molecule the includes an antibody (or fragment) against DLL3 paired with an antibody (or fragment) of an agonist antibody that activates CD3, CD28 or CD137.

An aspect of the invention is a humanized antibody which binds to human DLL3 protein comprising a heavy chain variable domain having at least 95%, at least 96%, at least 97%, at least 98%, at least 99%, or at least 100% sequence identity to SEQ ID NO: 56-74 or 75.

The disclosed methods can utilize any DLL3 antibody, including for example, an anti-DLL3 antibody comprising three CDRs of a heavy chain variable region amino acid sequence of SEQ ID NO: 1-27 or 29.

An aspect of the invention is a humanized antibody which binds to human DLL3 protein comprising a light chain variable domain having at least 95%, at least 96%, at least 97%, at least 98%, at least 99%, or at least 100% sequence identity to SEQ ID NO: 76-90 or 91.

The disclosed methods can utilize any DLL3 antibody, including for example, an anti-DLL3 antibody comprising three CDRs of a light chain variable region amino acid sequence of SEQ ID NO: 32-54 or 55.

An aspect of the invention is an antibody against MUC17. The antibody can be a fragment such as an antigen binding fragment (Fab) or a single chain variable fragment (Scfv).

An aspect of the invention is an agonist antibody that activates CD3, CD28 and/or CD137.

An aspect of the invention is a bispecific or trispecific molecule that includes an antibody (or fragment) against MUC17 paired with an antibody (or fragment) of an agonist antibody that activates CD3, CD28 or CD137.

An aspect of the invention is a method of treating an ailment such as cancer using an antibody (or fragment) against MUC17 paired with an antibody (or fragment) of an agonist antibody that activates CD3, CD28 or CD137.

An aspect of the invention is a method of treating an ailment that uses two or more of the bispecific or trispecific molecules described herein in combination with one another.

An aspect on the invention is a method of activating T-cell cytotoxicity against MUC17 expressing cells.

An aspect of the invention is a method of activating T-cell cytotoxicity using a bispecific or trispecific molecule the includes an antibody (or fragment) against MUC17 paired with an antibody (or fragment) of an agonist antibody that activates CD3, CD28 or CD137.

An aspect of the invention is a humanized antibody which binds to human MUC17 protein comprising a heavy chain variable domain having at least 95%, at least 96%, at least 97%, at least 98%, at least 99%, or at least 100% sequence identity to SEQ ID NO: 127-245 or 246.

The disclosed methods can utilize any MUC17 antibody, including for example, an anti-MUC17 antibody comprising three CDRs of a heavy chain variable region amino acid sequence of SEQ ID NO: 92-111 or 112.

The disclosed methods can utilize any MUC17 antibody, including for example, an anti-MUC17 antibody comprising three CDRs of a light chain variable region amino acid sequence of SEQ ID NO: 113-125 or 126.

An aspect of the invention is a humanized antibody which binds to human MUC17 protein comprising a light chain variable domain having at least 95%, at least 96%, at least 97%, at least 98%, at least 99%, or at least 100% sequence identity to SEQ ID NO: 147-168 or 169.

The disclosed methods can utilize any MUC17 antibody, including for example, an anti-MUC17 antibody comprising three CDRs of a heavy chain variable region amino acid sequence of SEQ ID NO: 92-111 or 112.

The disclosed methods can utilize any MUC17 antibody, including for example, an anti-MUC17 antibody comprising three CDRs of a light chain variable region amino acid sequence of SEQ ID NO: 113-125 or 126.

An aspect of the invention is a method of treating an ailment such as cancer using an antibody (or fragment) against CLDN18.2 paired with an antibody (or fragment) of an agonist antibody that activates CD3, CD28 or CD137.

An aspect on the invention is a method of activating T-cell cytotoxicity against CLDN18.2 expressing cells.

An aspect of the invention is a method of activating T-cell cytotoxicity using a bispecific or trispecific molecule the includes an antibody (or fragment) against CLDN18.2 paired with an antibody (or fragment) of an agonist antibody that activates CD3, CD28 or CD137.

An aspect of the invention is a method of activating T-cell cytotoxicity using a trispecific molecule the includes an antibody (or fragment) against CLDN18.2 paired with an antibody (or fragment) of an agonist antibody that activates CD3, CD28 and/or CD137.

The disclosed methods can utilize any CLDN18.2 antibody, including for example, an anti-CLDN18.2 antibody comprising three CDRs of a heavy chain variable region amino acid sequence of SEQ ID NO: 170-186 or 187.

An aspect of the invention is a humanized antibody which binds to human CLDN18.2 protein comprising a heavy chain variable domain having at least 95%, at least 96%, at least 97%, at least 98%, at least 99%, or at least 100% sequence identity to SEQ ID NO: 197-205 or 206.

The disclosed methods can utilize any CLDN18.2 antibody, including for example, an anti-CLDN18.2 antibody comprising three CDRs of a light chain variable region amino acid sequence of SEQ ID NO: 188-195 or 196.

An aspect of the invention is a humanized antibody which binds to human CLDN18.2 protein comprising a light chain variable domain having at least 95%, at least 96%, at least 97%, at least 98%, at least 99%, or at least 100% sequence identity to SEQ ID NO: 207-212 or 213.

The disclosed methods can utilize any CLDN18.2 antibody, including for example, an anti-CLDN18.2 antibody comprising three CDRs of a heavy chain variable region amino acid sequence of SEQ ID NO: 170-186 or 187.

The disclosed methods can utilize any CLDN18.2 antibody, including for example, an anti-CLDN18.2 antibody comprising three CDRs of a light chain variable region amino acid sequence of SEQ ID NO: 188-195 or 196.

Another aspect of the invention is a method of activating T-cell cytotoxicity using a trispecific molecule the includes more than one antibodies (or fragments) against DLL3, MUC17 and/or CLDN18.2 paired with one or more antibodies (or fragments) of an agonist antibodies that activate one or more of CD3, CD28 or CD137.

Another aspect of the invention is a trispecific molecule that includes (a) an anti-DLL3 antibody, an anti-Muc17 antibody or an anti-Cldn18.2 antibody, (b) a first antigen binding entity and (c) a second antigen binding entity. In one embodiment, the first antigen binding entity is comprised of an anti-CD28 scFv domain and the second antigen binding entity is comprised of an anti-CD3 Scfv-Fc domain. The first antigen binding entity and the second antigen binding entity form a heterodimer configuration. In one embodiment, the trispecific molecule includes a first chain of SEQ. ID NO: 347, a second chain of SEQ. ID NO: 276 and a third chain of SEQ. ID NO: 297. In another embodiment, the trispecific molecule includes a first chain of SEQ. ID NO: 430, a second chain of SEQ. ID NO: 276 and a third chain of SEQ. ID NO: 297. Alternatively, the trispecific molecule can include a first chain of SEQ. ID NO: 481, a second chain of SEQ. ID NO: 406 and a third chain of SEQ. ID NO: 413.

In some embodiments, the targeting domains are linked to one another by peptide bonds via peptide linkers or through covalent conjugates using appropriate crosslinking technologies known in the art.

In some embodiments, the targeting domains comprise antibody variable regions. In some embodiments, the targeting domains are in the form of a single domain antibody (sdAb), a fragment variable (Fv) heterodimer, a single chain Fv (scFv), a Fab fragment, a TriFab, or a combination thereof.

In some embodiments, the trispecific molecules are administered with a checkpoint inhibitor.

In some embodiments, the trispecific molecules are administered with an anti-PD1 and/or anti-POL1 antagonists.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings:

FIG. 1A to 1R depict Scfv-scfv-FcxFab-Fc formats for the trispecific molecules of the invention.

FIG. 1A depicts an anti-CD3, anti-DLL3, anti-CD28 (scfv-scfv-FcxFab-Fc) molecule.

FIG. 1B depicts an anti-CD3, anti-DLL3, anti-CD137 (scfv-scfv-FcxFab-Fc) molecule.

FIG. 1C depicts an anti-CD28, anti-DLL3, anti-CD137 (scfv-scfv-FcxFab-Fc) molecule.

FIG. 1D depicts an anti-CD28, anti-DLL3, anti-CD3 (scfv-scfv-FcxFab-Fc) molecule.

FIG. 1E depicts an anti-CD137, anti-DLL3, anti-CD3 (scfv-scfv-FcxFab-Fc) molecule.

FIG. 1F depicts an anti-CD137, anti-DLL3, anti-CD28 (scfv-scfv-FcxFab-Fc) molecule.

FIG. 1 K depicts an anti-DLL3, anti-CD137, anti-CD3 (scfv-scfv-FcxFab-Fc) molecule.

FIG. 1 L depicts an anti-DLL3, anti-CD 137, anti-CD28 (scfv-scfv-FcxFab-Fc) molecule.

FIG. 1 M depicts an anti-CD28, anti-CD3, anti-DLL3 (scfv-scfv-FcxFab-Fc) molecule.

FIG. 1 N depicts an anti-CD137, anti-CD3, anti-DLL3 (scfv-scfv-FcxFab-Fc) molecule.

FIG. 1O depicts an anti-CD 137, anti-CD28, anti-DLL3 (scfv-scfv-FcxFab-Fc) molecule.

FIG. 1 P depicts an anti-CD3, anti-CD28, anti-DLL3 (scfv-scfv-FcxFab-Fc) molecule.

FIG. 1Q depicts an anti-CD3, anti-CD137, anti-DLL3 (scfv-scfv-FcxFab-Fc) molecule.

FIG. 1 R depicts an anti-CD28, anti-CD137, anti-DLL3 (scfv-scfv-FcxFab-Fc)

FIG. 2A is a graph that demonstrates the binding of anti-DLL3 antibodies to human DLL3 expressing CHO cells.

FIG. 2B is a graph that demonstrates the binding of anti-DLL3 antibodies to CHO cells expressing cynomolgus DLL3.

FIG. 5 is a graph that demonstrates CD28scfv-CD3scFv-FcxDLL3-Fab-Fc trispecific molecule 328D2 activates PBMCs to secrete IFNgamma in the presence of CHO-DLL3 cells to higher levels than the CD3scfv-FcxDLL3Fab-Fc bispecific molecule 3D41 or CD28scfv-FcxDLL3Fab-Fc bispecific molecule 28D15.

FIG. 6 is a graph that demonstrates CD28scfv-CD3scFv-FcxDLL3-Fab-Fc trispecific molecule 328D1 activates PBMCs to secrete IFNgamma in the presence of CHO-DLL3 cells to higher levels than the CD3scfv-Fcx DLL3Fab-Fc bispecific molecule 3D221 or CD28scfv-Fcx DLL3Fab-Fc bispecific molecule 28D17

FIG. 7 is a graph that demonstrates CD28scfv-CD3scFv-Fcx DLL3-Fab-Fc trispecific molecules 328D4 and 328D5 activate PBMCs to secrete more IL-2 in the presence of NCI-H82 cells greater than the CD3scfv-Fcx DLL3Fab-Fc bispecific, 3D391.

FIG. 8A depicts a bispecific molecule of anti-CD137, anti-DLL3, anti-DLL3 (scfv-scfv-Fcx Fab-Fc) molecule.

FIG. 8B depicts an anti-CD137, anti-DLL3, anti-CD3 (scfv-scfv-Fcx Fab-Fc) molecule.

FIG. 8C depicts an anti-CD137, anti-DLL3, anti-CD3 (scfv-scfv-Fcx Fab-Fc) molecule.

FIG. 9A depicts an anti-DLL3, anti-CD3, anti-CD137, anti-CD137 (scfv-scfv-Fcx Fe-Scfv) molecule.

FIG. 9B depicts an anti-DLL3, anti-CD3, anti-CD137, anti-CD137 (scfv-scfv-Fcx Scfv-Fc-Scfv) molecule.

FIG. 9C depicts an anti-CD137, anti-CD137, anti-DLL3 (scfv-scfv-Fcx Fab-Fc) molecule.

FIG. 9D depicts an anti-DLL3, anti-CD137, anti-CD137 (scfv-scfv-Fcx Fab-Fc) molecule.

FIG. 9E depicts an anti-DLL3, anti-CD3, anti-CD137 (Fab-Fc-ScfvxScfv-Fc-Scfv) molecule.

FIG. 9F depicts an anti-DLL3, anti-CD3, anti-CD137, anti-CD137 (Fab-Fc-Scfv-ScfvxScfv-Fc) molecule.

FIG. 10A to 10R depict Scfv-scfv-FcxFab-Fc formats for the trispecific molecules of the invention.

FIG. 10A depicts an anti-CD3, anti-MUC17, anti-CD28 (scfv-scfv-FcxFab-Fc) molecule.

FIG. 10B depicts an anti-CD3, anti-MUC17, anti-CD137 (scfv-scfv-FcxFab-Fc) molecule.

FIG. 10C depicts an anti-CD28, anti-MUC17, anti-CD137 (scfv-scfv-FcxFab-Fc) molecule.

FIG. 10D depicts an anti-CD28, anti-MUC17, anti-CD3 (scfv-scfv-FcxFab-Fc) molecule.

FIG. 10E depicts an anti-CD137, anti-MUC17, anti-CD3 (scfv-scfv-FcxFab-Fc) molecule.

FIG. 10F depicts an anti-CD137, anti-MUC17, anti-CD28 (scfv-scfv-FcxFab-Fc) molecule.

FIG. 10 M depicts an anti-CD28, anti-CD3, anti-MUC17 (scfv-scfv-Fcx Fab-Fc) molecule.

FIG. 10N depicts an anti-CD137, anti-CD3, anti-MUC17 (scfv-scfv-Fcx Fab-Fc) molecule.

FIG. 10O depicts an anti-CD137, anti-CD28, anti-MUC17 (scfv-scfv-Fcx Fab-Fc) molecule.

FIG. 10P depicts an anti-CD3, anti-CD28, anti-MUC17 (scfv-scfv-Fcx Fab-Fc) molecule.

FIG. 10Q depicts an anti-CD3, anti-CD137, anti-MUC17 (scfv-scfv-Fcx Fab-Fc) molecule.

FIG. 10R depicts an anti-CD28, anti-CD137, anti-MUC17 (scfv-scfv-Fcx Fab-Fc) molecule.

FIG. 11A is a graph that demonstrates MUC17xCD3 Bispecifics bind CHOK1 cells expressing MUC17.

FIG. 11B is a graph that demonstrates MUC17xCD3 Bispecifics bind to ASPC1 tumor cells.

FIG. 16A-16B are graphs that demonstrate CD28scfvx CD3scfvxMuc17Fab trispecific 328M2 activates PBMCs to express CD25 only when in the presence of Muc17 express-ing CHO cells and cannot activate without Muc17 target cells. In contrast the CD3scFvxCD28scFvxMuc17-Fab trispecific 328M1 is able to non-specifically activate cells in the absence of Muc17, similarly to the bispecific lacking Muc17 binding, 328-1.

FIG. 16A shows the expression of CD25(MFI) stimulated by increasing concentrations of the bispecific and trispecific molecules T cells when PBMCs are in the presence of MUCI 7 expressing CHO cells. FIG. 16B shows the expression of CD25(MFI) stimulated by increasing concentrations of the bispecific and trispecific molecules T cells when PBMCs are in the presence of parental CHO cells

FIG. 18A-18D depict Muc17xCD137 and DLL3xCD137 bispecific molecules.

FIG. 19A-19C depict MUC17 bispecific and trispecific molecules with two CD137 Fab fragments.

FIG. 19A depicts an anti-CD137, anti-MUC17, anti-MUC17 (Fab-Fc-Scfv) molecule.

FIG. 19B depicts an anti-CD137, anti-MUC17, anti-CD3 (Fab-Fc-ScfvxFab-Fc-Scfv) molecule.

FIG. 19C depicts an anti-CD137, anti-MUC17, anti-CD3 (Fab-FcxFc-Scfv-Scfv) molecule.

FIG. 19D depicts an anti-CD137, anti-CD137, anti-MUC17, (scfv-scfv-FcxFab-Fc) molecule.

FIG. 19E depicts an anti-MUC17, anti-CD137, anti-CD137 (scfv-scfv-FcxFab-Fc) molecule.

FIG. 19F depicts an anti-MUC17, anti-CD137, anti-CD3, anti-CD137 (Fab-Fc-ScfvxScfv-Fc-Scfv) molecule.

FIG. 19G depicts an anti-MUC17, anti-CD137, anti-CD137, anti-CD3 (Fab-Fc-Scfv-ScfvxScfv-Fc) molecule.

FIG. 19H depicts an anti-MUC17, anti-CD3, anti-CD137, anti-CD137 (scfv-scfv-Fc-ScfvxFc-Scfv) molecule.

FIG. 19I depicts an anti-DLL3, anti-CD3, anti-CD137, anti-MUC17, anti-CD137 (scfv-scfv-FcxScfv-Fc-Scfv) molecule.

FIG. 20A to 20R depict Scfv-scfv-FcxFab-Fc formats for the trispecific molecules of the invention.

FIG. 20A depicts an anti-CD3, anti-CLDN18.2, anti-CD28 (scfv-scfv-FcxFab-Fc) molecule.

FIG. 20B depicts an anti-CD3, anti-CLDN18.2, anti-CD137 (scfv-scfv-FcxFab-Fc) molecule.

FIG. 20C depicts an anti-CD28, anti-CLDN18.2, anti-CD137 (scfv-scfv-FcxFab-Fc) molecule.

FIG. 20D depicts an anti-CD28, anti-CLDN18.2, anti-CD3 (scfv-scfv-FcxFab-Fc) molecule.

FIG. 20E depicts an anti-CD137, anti-CLDN18.2, anti-CD3 (scfv-scfv-FcxFab-Fc) molecule.

FIG. 20F depicts an anti-CD137, anti-CLDN18.2, anti-CD28 (scfv-scfv-FcxFab-Fc) molecule.

FIG. 20G depicts an anti-CLDN18.2, anti-CD3, anti-CD28 (scfv-scfv-FcxFab-Fc) molecule.

FIG. 20H depicts an anti-CLDN18.2, anti-CD3, anti-CD137 (scfv-scfv-FcxFab-Fc) molecule.

FIG. 20I depicts an anti-CLDN18.2, anti-CD28, anti-CD137 (scfv-scfv-FcxFab-Fc) molecule.

FIG. 20J depicts an anti-CLDN18.2, anti-CD28, anti-CD3 (scfv-scfv-FcxFab-Fc) molecule.

FIG. 20K depicts an anti-CLDN18.2, anti-CD137, anti-CD3 (scfv-scfv-FcxFab-Fc) molecule.

FIG. 20L depicts an anti-CLDN18.2, anti-CD137, anti-CD28 (scfv-scfv-FcxFab-Fc) molecule.

FIG. 20M depicts an anti-CD28, anti-CD3, anti-CLDN18.2 (scfv-scfv-FcxFab-Fc) molecule.

FIG. 20N depicts an anti-CD137, anti-CD3, anti-CLDN18.2 (scfv-scfv-FcxFab-Fc) molecule.

FIG. 20O depicts an anti-CD137, anti-CD28, anti-CLDN18.2 (scfv-scfv-FcxFab-Fc) molecule.

FIG. 20P depicts an anti-CD3, anti-CD28, anti-CLDN18.2 (scfv-scfv-FcxFab-Fc) molecule.

FIG. 20Q depicts an anti-CD3, anti-CD137, anti-CLDN18.2 (scfv-scfv-FcxFab-Fc) molecule.

FIG. 20R depicts an anti-CD28, anti-CD137, anti-CLDN18.2 (scfv-scfv-FcxFab-Fc) molecule.

FIG. 25A depicts an anti-CD137, anti-CLDN18.2, anti-CLDN (scfv-scfv-FcxFab-Fc) molecule.

FIG. 25B depicts an anti-CD137, anti-CLDN18.2, anti-CD3 trispecific molecule (Fab-Fc-ScfvxFab-Fc-Scfv) molecule.

FIG. 25C depicts an anti-CD137, anti-CLDN18.2, anti-CD3 trispecific molecule (Fab-Fc-Scfv-ScfvxFab-Fc)

DEFINITIONS

Figures 1A, 1B, 1C, 1D, 1E, 1F:
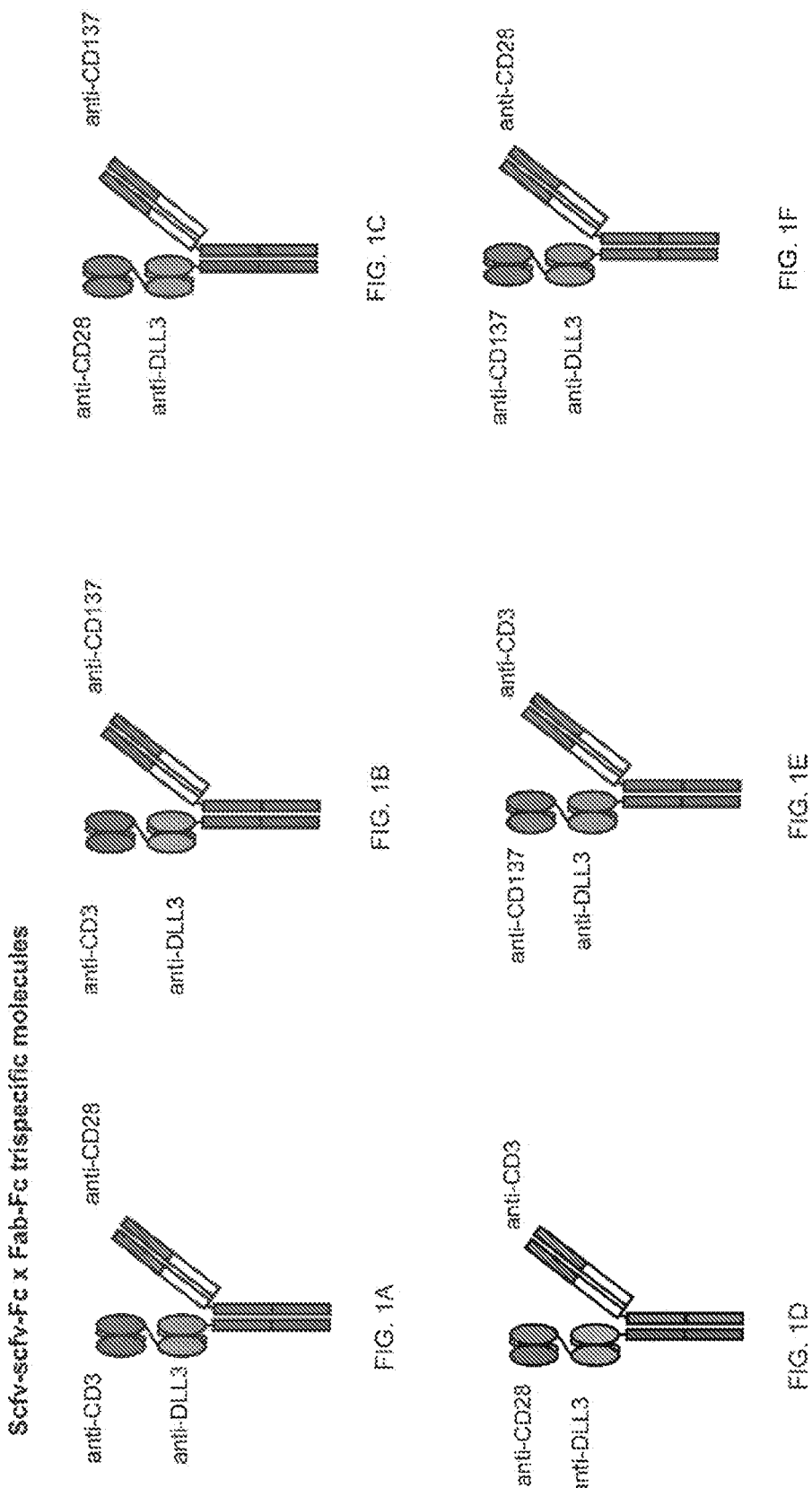
Figures 1G, 1H, 1I, 1J, 1K, 1L:
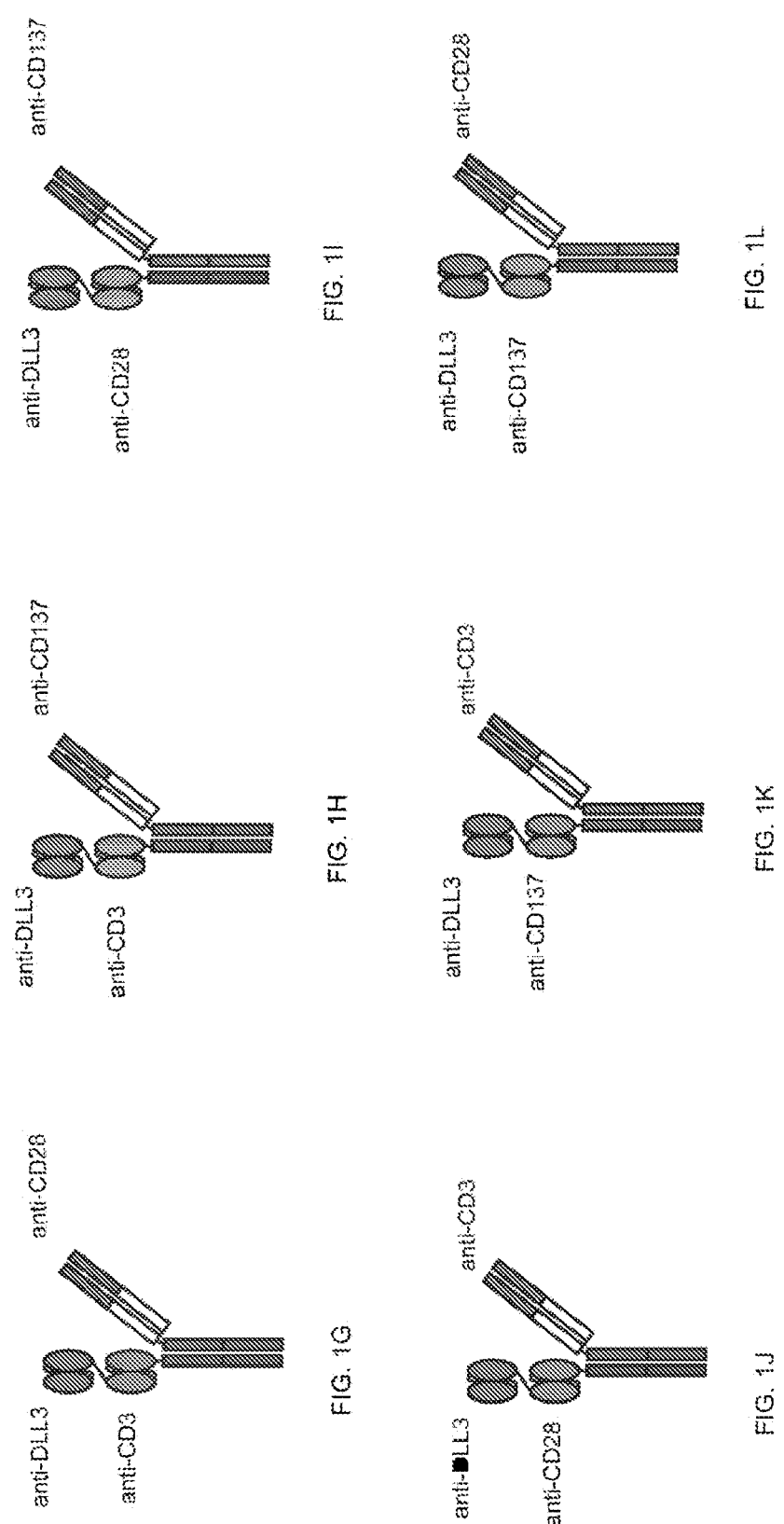
FIG. 1G depicts an anti-DLL3, anti-CD3, anti-CD28 (scfv-scfv-FcxFab-Fc) molecule.
FIG. 1H depicts an anti-DLL3, anti-CD3, anti-CD137 (scfv-scfv-FcxFab-Fc) molecule.
FIG. 1I depicts an anti-DLL3, anti-CD28, anti-CD137 (scfv-scfv-FcxFab-Fc) molecule.
FIG. 1J depicts an anti-DLL3, anti-CD28, anti-CD3 (scfv-scfv-FcxFab-Fc) molecule.

Reference in this specification to "one embodiment/aspect" or "an embodiment/aspect" means that a particular feature, structure, or characteristic described in connection with the embodiment/aspect is included in at least one embodiment/aspect of the disclosure. The use of the phrase "in one embodiment/aspect" or "in another embodiment/aspect" in various places in the specification are not necessarily all referring to the same embodiment/aspect, nor are separate or alternative embodiments/aspects mutually exclusive of other embodiments/aspects. Moreover, various features are described which may be exhibited by some embodiments/aspects and not by others. Similarly, various requirements are described which may be requirements for some embodiments/aspects but not other embodiments/aspects. Embodiment and aspect can in certain instances be used interchangeably.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

As applicable, the terms "about" or "generally", as used herein in the specification and appended claims, and unless otherwise indicated, means a margin of +/−20%. Also, as applicable, the term "substantially" as used herein in the specification and appended claims, unless otherwise indicated, means a margin of +/−10%. It is to be appreciated that not all uses of the above terms are quantifiable such that the referenced ranges can be applied.

The term "subject" or "patient" refers to any single animal, more preferably a mammal (including such non-human animals as, for example, dogs, cats, horses, rabbits, zoo animals, cows, pigs, sheep, and non-human primates) for which treatment is desired. Most preferably, the patient herein is a human. In an embodiment, a "subject" of diagnosis or treatment is a prokaryotic or a eukaryotic cell, a tissue culture, a tissue or an animal, e.g. a mammal, including a human.

As used herein, the term "comprising" is intended to mean that the compositions and methods include the listed elements, but do not exclude other unlisted elements. "Consisting essentially of" when used to define compositions and methods, excludes other elements that alters the basic nature of the composition and/or method, but does not exclude other unlisted elements. Thus, a composition consisting essentially of the elements as defined herein would not exclude trace amounts of elements, such as contaminants from any isolation and purification methods or pharmaceutically acceptable carriers, such as phosphate buffered saline, preservatives, and the like, but would exclude additional unspecified amino acids. "Consisting of" excludes more than trace elements of other ingredients and substantial method steps for administering the compositions described herein. Embodiments defined by each of these transition terms are within the scope of this disclosure and the inventions embodied therein.

The term "tri-specific monoclonal antibody" or "TSMAb" refers to an antibody that can simultaneously engage three different types of epitopes.

The term "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed. An active agent can be a primary active agent, or in other words, the component(s) of a composition to which the whole or part of the effect of the composition is attributed. An active agent can be a secondary agent, or in other words, the component(s) of a composition to which an additional part and/or other effect of the composition is attributed.

In an embodiment, a "pharmaceutical composition" is intended to include the combination of an active agent, such as an anti-DLL3, anti-MUC17 or anti-CLDN18.2 antibody and antibody conjugates, with a carrier, inert or active, in a sterile composition suitable for diagnostic or therapeutic use in vitro, in vivo or ex vivo. In one aspect, the pharmaceutical composition is substantially free of endotoxins or is nontoxic to recipients at the dosage or concentration employed.

In an embodiment, "an effective amount" refers, without limitation, to the amount of the defined component sufficient to achieve the desired therapeutic result. In an embodiment, that result can be effective cancer treatment.

In an embodiment, as used herein, the terms "treating," "treatment" and the like are used herein, without limitation, to mean obtaining a desired pharmacologic and/or physiologic effect. The effect may be prophylactic in terms of completely or partially preventing a disorder or sign or symptom thereof, and/or may be therapeutic in terms of amelioration of the symptoms of the disease or infection, or a partial or complete cure for a disorder and/or adverse effect attributable to the disorder.

As used herein, the term "recombinant" refers to polypeptides or polynucleotides that do not exist naturally and which may be created by combining polynucleotides or polypeptides in arrangements that would not normally occur together. The term can refer to a polypeptide produced through a biological host, selected from a mammalian expression system, an insect cell expression system, a yeast expression system, and a bacterial expression system.

The term "Delta-like 3" or "DLL3" refers to a protein which in humans is encoded by the DLL3 gene. Mutations in the gene cause the autosomal recessive genetic disorder Jarcho-Levin syndrome. DLL3 is expressed normally on the inside of cells and at low levels on normal tissues. However, lung tumor cells overexpress the gene and cell surface DLL3 levels are increased.

The term "Mucin 17" or "MUC17" refers to a member of the mucin family that includes more than 20 members. Mucins are large, highly glycosylated membrane bound proteins. They are expressed almost exclusively in the intestine. Their general function is to protect epithelial cells from their environment, as well as to regulate proliferation and survival of cells. MUC17 is highly expressed in pancreatic adenocarcinoma tissue (at protein level). MUC17 is expressed in pancreatic, appendiceal, and some colon cancers. Its expression is not detectable in normal pancreas, in pancreatitis or in cell lines derived from other cancers.

The term "Claudin-18" or "CLD 18" refers to a protein that in humans is encoded by the CLDN18 gene. CLDN18 belongs to the large claudin family of proteins, which form tight junction strands in epithelial cells. "Claudin 18.2" or "CLDN18.2" denotes isoform 2 which is abundant in tumors, particularly those of the gastric system.

The term "CD" or "cluster of differentiation molecules" refers to cell surface markers that are useful for the identification and characterization of leukocytes such as CD3, CD28 and CD137. CD3 is the signaling component of the T cell receptor (TCR) complex. Because CD3 is required for T cell activation, drugs (often monoclonal antibodies) that target it are being investigated as immunostimulants for the treatment of cancer.

CD28 is the major costimulatory molecule required in the generation of T cell-mediated immune responses. Upon interaction with its ligands CD80 and CD86, CD28 transduces activation signals that lead to the expression of anti-apoptotic proteins and enhance the synthesis of several cytokines including IL-2. CD28 costimulatory receptor is present on all T-cells. Agonist antibodies directed against CD28 have led to severe adverse events in the clinic, in contrast to antibodies directed against the other CD28 family members CTLA-4, PD-1, or their B7 ligands, which function as checkpoint inhibitors to overcome tumor immune tolerance and can be used in cancer immunotherapy.

CD137 is a member of the tumor necrosis factor (TNF) receptor family. Its alternative names are tumor necrosis factor receptor superfamily member 9 (TNFRSF9), 4-1BB and induced lymphocyte activation. Agonistic anti-CD137 antibody acts as an activating costimulatory molecule especially important for effector/memory T cells and promotes the survival and proliferation of T lymphocytes. For example, BBK-4, Urelumab and Utomilumab (PF-05082566) targets this receptor to stimulate a more intense immune system attack on cancers.

PD-1 (Programmed cell death protein 1 or CD279) is a protein on the surface of cells that has a role in regulating the immune system's response to the cells of the human body by down-regulating the immune system and promoting self-tolerance by suppressing T cell inflammatory activity. Engagement of PD-1 by either of its ligands, PD-L1 or PD-L2, on an adjacent cell inhibits TCR signaling and TCR-mediated proliferation, transcriptional activation and cytokine production. This prevents autoimmune diseases, but it can also prevent the immune system from killing cancer cells. Therapeutic antibodies designed to block the PD-1/PD-L1 interaction have potential for the treatment of cancer.

Programmed death-ligand 1 (PD-L1) also known as cluster of differentiation 274 (CD274) or B7 homolog 1 (B7-H1) is a protein that in humans is encoded by the CD274 gene. PD-L1 binds to its receptor, PD-1, found on activated T cells, B cells, and myeloid cells, to modulate activation or inhibition.

As used herein, the term "antibody" refers to a polypeptide or a polypeptide complex that specifically recognizes and binds to an antigen through one or more immunoglobulin variable regions. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding and is encoded by the variable domain. An antibody can be a whole antibody, an antigen binding fragment or a single chain thereof.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to variable domains of the light and heavy chain respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain VL-CL joined to VH-CH1 by a disulfide bond. While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

Accordingly, in either aspect of the invention, the term antibody also embraces minibodies, scFvs, diabodies, triabodies and the like. ScFvs and Diabodies are small bivalent biospecific antibody fragments with high avidity and specificity. Their high signal to noise ratio is typically better due to a better specificity and fast blood clearance increasing their potential for diagnostic and therapeutic targeting of specific antigen (Sundaresan et al., *J Nucl Med* 44:1962-9 (2003). In addition, these antibodies are advantageous because they can be engineered if necessary as different types of antibody fragments ranging from a small single chain Fv (scFv) to an intact IgG with varying isoforms (Wu & Senter, *Nat. Biotechnol.* 23:1137-1146 (2005)). In some embodiments, the antibody fragment is part of a scFv-scFv or diabody. In some embodiments, in either aspect, the invention provides high avidity antibodies for use according to the invention.

The term "agonist antibody" refers to an antibody that stimulates or activates an organ. An antibody can act as an agonist of a receptor, essentially replacing the activity of the normal ligand. The agonist activity can occur when the antibody binds the receptor in a manner that mimics the binding of the physiological ligand resulting in antibody-mediated agonism. For example, agonistic antibodies against the thyrotropin receptor in Grave's disease stimulate the thyroid gland to release thyroid hormones that produce hyperthyroidism. Agonistic antibodies may also stimulate when clustered, either via the Fe portion of the antibody engaging an Fc receptor in trans or cis, or through antigen mediated clustering. The latter clustering mechanism requires antigen engagement by one half of a bispecific or trispecific molecule and engagement of the stimulatory receptor by the second half of a bispecific or trispecific molecule. Exemplary stimulatory receptors are CD3, CD28 and 4-1BB, which stimulate T cells.

The terms "antibody fragment" or "antigen-binding fragment" are used with reference to a portion of an antibody, such as Fab', Fab, Fv, scFv and the like. Regardless of structure, an antibody fragment binds with the same antigen that is recognized by the intact antibody. The term "antibody fragment" also includes diabodies and any synthetic or genetically engineered proteins comprising immunoglobulin variable regions that act like an antibody by binding to a specific antigen to form a complex.

The term "antigen-binding fragment" or "Fab" refers to a region on an antibody that binds to antigens. It includes one constant and one variable domain of each of the heavy and the light chain (i.e. four domains: VH, CH1, VL and CL1). The variable domain contains the paratope (the antigen-binding site), that includes a set of complementary determining regions at the amino terminal end of the monomer. Each arm of the Y thus binds an epitope on the antigen.

The term "Fc region" or "fragment crystallizable region" refers to the tail region of an antibody CH2-CH3 that interacts with cell surface receptors called Fc receptors and some proteins of the complement system. This "effector function" allows antibodies to activate the immune system leading to cellular cytotoxicity (ADCC), antibody-dependent cellular phagocytosis (ADCP), and/or complement dependent cytotoxicity (CDC). ADCC and ADCP are mediated through the binding of the Fc to Fc receptors on the surface of cells of the immune system. CDC is mediated through the binding of the Fe with proteins of the complement system, (e.g. C1q).

In IgG, IgA and IgD antibody isotypes, the Fe region has two identical protein fragments, derived from the second and third constant domains of the antibody's two heavy chains. IgM and IgE Fc regions have three heavy chain constant domains (CH domains 2-4) in each polypeptide chain whereas IgG is composed of 2 CH domains, 2 and 3. The Fc regions of IgGs bear a highly conserved N-glycosylation site. Glycosylation of the $F_c$ fragment is essential for $F_c$ receptor-mediated activity. The N-glycans attached to this site are predominantly core-fucosylated diantennary structures of the complex type. In addition, small amounts of these N-glycans also bear bisecting GlcNAc and a-2,6 linked sialic acid residues.

A particular IgG subclass can be preferred for a particular use. For example, IgG1 is more effective than IgG2 and IgG4 at mediating ADCC and CDC. Thus, IgG2 $F_c$ can be preferred when effector function is undesirable. However, IgG2 Fe-containing molecules are generally more difficult to manufacture and can be less stable than IgG1 $F_c$-containing molecules. Further, the effector function of an antibody can be increased, or decreased, by introducing one or more mutations into the $F_c$ (see, for example, Strohl, Curr. Opin. Biotech., 20:685-691, 2009). Exemplary IgG1 $F_c$ molecules having increased effector function include those having the following substitutions:

S239D/I332E, S239D/A330St1332E, S2390/A330L/1332E, S298A/0333A/K334A, P2471/A339D, P2471/A339Q, 0280H/K290D, 0280H/K290S/S298D, 0280H/K290S/S298V, F243L/R292P/Y300L, F243L/R292P/Y300L/P396L, F243L/R292P/Y300L/V3051/P396L, G236A/S239D/I332E, K326A/E333A, K326W/E333S, K290E/S298G/T299A, K290N/S298G/T299A, K290E/S298G/T299A/K326E, K290N/S298G/T299A/K326E

Fucosylation is another method of increasing effector function of IgG Fe-containing proteins. Removal of the core fucose from the biantennary complex-type oligosaccharides attached to the $F_c$ greatly increases ADCC effector function without altering antigen binding or CDC effector function. There are different ways to reduce or abolish fucosylation of Fe-containing molecules. These include recombinant expression in certain mammalian cell lines including a FUT8 knockout cell line, variant CHO line Lec13, rat hybridoma cell line YB2/0, a cell line comprising a small interfering RNA specifically against the FUT8 gene, and a cell line co-expressing β-1,4-N-acetylglucosaminyltransferase Ill and Golgi a-mannosidase II. Alternatively, the $F_c$-containing molecule can be expressed in a non-mammalian cell such as a plant cell, yeast, or prokaryotic cell, e.g., *E. coli*.

It may be desirable to decrease effector function. Exemplary $F_c$ molecules having decreased effector function include those having the following substitutions:

N297A or N297Q (IgG1), L234A/L235A (IgG1), V234A/ G237A (IgG2), L235A/G237A/E318A (IgG4), H268Q/ V309L/A330S/A331S (IgG2), C220S/C226S/C229S/ P238S (IgG1), C226S/C229S/E233P/L234V/L235A (IgG1), L234F/L235E/P331S (IgG1), S267E/L328F (IgG1)

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CHI, CH2 and CH3) confer important biological properties such as secretion, transplacental mobility, Fe receptor binding, complement binding, and the like. By convention, the numbering of the constant region domains in conventional antibodies increases as they become more distal from the antigen-binding site or amino-terminus of the antibody. In conventional antibodies, the N-terminal portion is a variable region and at the C-terminal portion is a constant region; the CH3 and CL domains comprise the carboxyterminus of the heavy and light chain, respectively.

As used herein, the term "heavy chain constant region" includes amino acid sequences derived from an immunoglobulin heavy chain. A polypeptide comprising a heavy chain constant region comprises at least one of: a CHI domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CHI domain; a polypeptide chain comprising a CHI domain, at least a portion of a hinge domain, and a CH2 domain; a polypeptide chain comprising a CHI domain and a CH3 domain; a polypeptide chain comprising a CHI domain, at least a portion of a hinge domain, and a CH3 domain, or a polypeptide chain comprising a CHI domain, at least a portion of a hinge domain, a CH2 domain, and a CH3 domain. In some embodiments, a polypeptide of the disclosure comprises a polypeptide chain comprising a CH3 domain. Further, an antibody for use in the disclosure may lack at least a portion of a CH2 domain (e.g., all or part of a CH2 domain). It should be understood that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CHI domain derived from an IgG1 molecule and a hinge region derived from an IgG3 molecule. In another example, a heavy chain constant region can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain constant region" includes amino acid sequences derived from antibody light chain. Preferably, the light chain constant region comprises at least one of a constant kappa domain or constant lambda domain. A "light chain heavy chain pair" refers to the collection of a light chain and heavy chain that can form a dimer through a disulfide bond between the CL domain of the light chain and the CHI domain of the heavy chain.

The subunit structures and three-dimensional configurations of the constant regions of the various immunoglobulin classes are well known. As used herein, the term "VH domain" includes the amino terminal variable domain of an immunoglobulin heavy chain and the term "CHI domain" includes the first (most amino terminal) constant region domain of an immunoglobulin heavy chain. The CHI domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system). The CH2 domain is unique in that it is not closely paired with another domain. Rather, two N-linked branched carbohydrate chains are interposed between the two CH2 domains of an intact native IgG molecule. The CH3 domain extends from the CH2 domain to the C-terminal of the IgG molecule and comprises approximately 108 residues.

As used herein, the term "hinge region" includes the portion of a heavy chain molecule that joins the CHI domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains.

The term "bi-specific monoclonal antibody" or "BSMAb" refers to an antibody that can simultaneously engage two different types of epitopes on the same target or on different targets. An advantage is their ability to redirect specific polyclonal immune cells (e.g. T cells and NK cells) to tumor cells to enhance tumor killing. These antibodies can be divided into two types: IgG like bispecific antibodies which carry an $F_c$ region and therefore retain Fe-mediated effector functions and the non-IgG like formats which rely on their antigen binding capacity to exert their effects. Recombinant techniques have also led to the creation of small fragment molecules. Single chain variable fragments from two different monoclonal antibodies can be combined to form bivalent bispecific antibodies. Examples include bispecific T cell engagers (BiTEs), tandem single chain variable fragments (taFvs), diabodies (Dbs), single chain diabodies (scDbs), and triple bodies. These scFv based antibody fragments have high tumor specificity and tumor penetration due to their small size (ranging from 50 to 60 kDa).

The term "tri-specific monoclonal antibody" or "TSMAb" refers to an antibody that can simultaneously engage three different types of epitopes on the same target or on different targets.

The term "scFv" or "scFv fragment antibody" refers to a small molecular antibody, consisting of VH and VL domains, either in the configuration of VL-VH or VH-VL, with a linker region between them. The scFv fragment antibody can more easily penetrate blood vessel wall and the solid tumor, which makes it a preferred carrier of targeting drugs.

The term "scFvs" or "single-chain variable fragment" refers to divalent (or bivalent) single-chain variable fragments (di-scFvs, bi-scFvs) that can be engineered by linking two scFvs. This can be done by producing a single peptide chain with two VH and two VL regions, yielding tandem scFvs, also known as scFv-scFv molecules. Another possibility is the creation of scFvs with linker peptides that are too short for the two variable regions to fold together (about five amino acids), forcing scFvs to dimerize. This type is known as diabodies.

The term "humanized antibody" refers to an antibody from non-human species whose protein sequences have been modified to increase its similarity to antibody variants produced naturally in humans. The process of "humanization" is usually applied to monoclonal antibodies developed for administration to humans (e.g. antibodies developed as anti-cancer drugs). Humanization can be necessary when the process of developing a specific antibody involves generation in a non-human immune system (such as that in mice).

Bispecific or trispecific antibodies can be generated by chemical cross-linking or by the hybrid hybridoma technology. Alternatively, bispecific or trispecific antibody molecules can be produced by recombinant techniques, for example by linking 2 scFv molecules together with a short linker. For example, VH1-Linker1-VL1-Linker2-VH2-Linker3-VL2. With Linker1 and Linker3 having lengths between 15-30 amino acids and Linker2 being 5-10 amino acids in length. Linkers may be composed of a variety of amino acids, for example repeating units of GGGGS (SEQ ID NO: 504, GKPGS (SEQ ID NO: 505, GEPGS (SEQ ID NO: 506, and/or GGPGS (SEQ ID NO: 507. Dimerization across 2 scFv molecules can be promoted by reducing the length of the linker joining the VH and the VL domain from about 15 amino acids, routinely used to produce scFv fragments, to about 5 amino acids. These linkers favor intrachain assembly of the VH and VL domains, with the configuration VH1-linker1-VL2-Linker2-VH2-Linker3VL1 and linkers 1 and 3 being 5 amino acids in length. Any suitable short linker can be used. Thus, two fragments assemble into a dimeric molecule. Further reduction of the linker length to 0-2 amino acids can generate trimeric (triabodies) or tetrameric (tetrabodies) molecules.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

One of the challenges for efficiently producing bispecific antibody preparations concerns reducing the formation of homodimeric molecules in favor of heterodimeric molecules, when co-expressing chains of different binding specificities. A "heterodimeric antibody" can utilize the "knobs-into-holes" or "charge-pair" formats to preferentially promote correct association of the 2 molecules to form a heterodimer with 2 specificities. These formats are specific to the heavy chain $F_c$ part of the constant region in antibodies. For the knob-into-holes format, the "knobs" part is engineered by replacing a small amino acid with a larger one. It fits into the "hole," which is engineered by replacing a large amino acid with a smaller one. Introduction of T366W mutations in the first $F_c$ creates the "knob" and introduction of T366S, L368A, and Y407V mutations in the second $F_c$ creates the "hole" (numbering of the residues according to the Kabat EU numbering system). For the charge pair format, heterodimerization is favored through stabilizing ionic interactions by introducing interfacing charge residues in the opposing $F_c$ domains. For example, D356K, E357K, and D399K in a first $F_c$ domain, and the mutations K370E, K409D, and K439E into a second $F_c$ domain, or combination thereof. For example, K392D and K409D mutations in a first $F_c$ chain, and D399K and D356K mutations in a second $F_c$ chain, K409E in the first $F_c$ and D399K in the $F_c$, K409E in the first $F_c$ and D399R in the second $F_c$, K409D in the first $F_c$ and D0399K in the second $F_c$, K409D in the first $F_c$ and D399R in the second $F_c$, K392E in the first Fe and D399R in the second Fe, K392E in the first Fe and 0399K in the second Fe, K392D in the first $F_c$ and D399R in the second $F_c$, K392D in the first $F_c$ and 0399K in the second $F_c$, K409D and K360D in the first $F_c$ and D399K and D356K in the second $F_c$, K409D and K370D in the first $F_c$ and D399K and E357K in the second $F_c$, K409D and K392D in the first $F_c$ and D399K, D356K, and E357K in the second $F_c$, K409D and K392D in the first $F_c$ and D399K in the second $F_c$, K409D and K392D in the first $F_c$ and D399K and D356K in the second $F_c$, K409D and K392D in the first $F_c$ and D399K and E357K in the second $F_c$, K409D and K370D in the first $F_c$ and D399K and D357K in the second $F_c$, D399K in the first $F_c$ and K409D and K360D in the second $F_c$, and/or K409D and K439D in the first $F_c$ and D399K and D356K in the second $F_c$, numbered according to the Kabat EU numbering system. Additionally, cysteines may be introduced to stabilize the pairing of heterodimers, for example S234C in the first $F_c$ and Y349C in the second $F_c$ or Y349C in the first $F_c$ and S344C in the second $F_c$.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Using Antibodies, A*

*Laboratory Manual*(1998) for a description of immunoassay formats and conditions that can be used to determine specific immunoreactivity).

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity, neurodegeneration or pathological inflammation, normal human cells or tissues.

An "immunoregulator" refers to a substance, an agent, a signaling pathway or a component thereof that regulates an immune response. "Regulating," "modifying" or "modulating" an immune response refers to any alteration in a cell of the immune system or in the activity of such cell. Such regulation includes stimulation or suppression of the immune system which may be manifested by an increase or decrease in the number of various cell types, an increase or decrease in the activity of these cells, or any other changes which can occur within the immune system. Both inhibitory and stimulatory immunoregulators have been identified, some of which may have enhanced function in the cancer, infectious disease or neurodegenerative microenvironment.

A cytotoxic T cell (also known as TC, cytotoxic T lymphocyte, CTL, T-killer cell, cytolytic T cell, CD8+ T-cell or killer T cell) is a T lymphocyte (a type of white blood cell) that kills cancer cells, cells that are infected (particularly with viruses), or cells that are damaged in other ways.

The term "immunotherapy" refers to the treatment of a subject afflicted with, or at risk of contracting or suffering a recurrence of, a disease by a method comprising inducing, enhancing, suppressing or otherwise modifying an immune response. "Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication, condition or biochemical indicia associated with a disease.

"Potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

Nucleic acid is "operably linked" when it is placed into a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to the full length of the reference sequence, usually about 25 to 100, or 50 to about 150, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher et al., *J. Biol. Chem.* 273(52):35095-35101 (1998).

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

As used herein, the term "prevention" means all of the actions by which the occurrence of the disease is restrained or retarded.

As used herein, the term "treatment" means all of the actions by which the symptoms of the disease have been alleviated, improved or ameliorated. In the present specification, "treatment" means that the symptoms of cancer, neurodegeneration, or infectious disease are alleviated, improved or ameliorated by administration of the antibodies disclosed herein.

The term "administration" refers to the introduction of an amount of a predetermined substance into a patient by a certain suitable method. The composition disclosed herein may be administered via any of the common routes, as long as it is able to reach a desired tissue, for example, but is not limited to, intraperitoneal, intravenous, intramuscular, subcutaneous, intradermal, oral, topical, intranasal, intrapulmonary, or intrarectal administration. However, since peptides are digested upon oral administration, active ingredients of a composition for oral administration should be coated or formulated for protection against degradation in the stomach.

The term "subject" refers to those suspected of having or diagnosed with cancer, a neurodegenerative or an infectious disease. However, any subject to be treated with the pharmaceutical composition disclosed herein is included without limitation. The pharmaceutical composition including an anti-DLL3 antibody disclosed herein is administered to a subject suspected of having cancer, a neurodegenerative or an infectious disease.

Construction of suitable vectors containing the desired sequences and control sequences employs standard ligation and restriction techniques, which are well understood in the art (see Maniatis et al., in *Molecular Cloning: A Laboratory Manual*, Cold Spring Harbor Laboratory, New York (1982)). Isolated plasmids, DNA sequences, or synthesized oligonucleotides are cleaved, tailored, and re-ligated in the form desired.

For preparation of antibodies, e.g., recombinant, monoclonal, or polyclonal antibodies, many techniques known in the art can be used (see, e.g., Kohler & Milstein, *Nature* 256:495-497 (1975); Kozbor et al., *Immunology Today* 4:72 (1983); Cole et al., in *Monoclonal Antibodies and Cancer Therapy*, Alan R. Liss, Inc., pp. 77-96 (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121-210 (1986)). Antibodies can also be heteroconjugates, e.g., two covalently joined antibodies, or immunotoxins (see, e.g., U.S. Pat. No. 4,676,980, WO 91/00360; and WO 92/200373).

Methods for humanizing antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The term "cancer" refers to human cancers and carcinomas, sarcomas, adenocarcinomas, etc., including solid tumors, kidney, breast, lung, kidney, bladder, urinary tract, urethra, penis, vulva, vagina, cervical, colon, ovarian, prostate, pancreas, stomach, brain, head and neck, skin, uterine, testicular, esophagus, and liver cancer. Additional cancers include, for example, Hodgkin's Disease, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, thyroid cancer, neuroblastoma, esophageal cancer, genitourinary tract cancer, malignant hypercalcemia, cervical cancer, endometrial cancer, and adrenal cortical cancer.

The term "checkpoint inhibitor" or "immune checkpoint inhibitor" refers to an agent such as a drug that inhibits/blocks the inhibitory checkpoint molecules. Some cancers can protect themselves from attack by stimulating immune checkpoint targets. Checkpoint therapy can block inhibitory checkpoints, restoring immune system function.

The term "immune checkpoint regulator" refers to receptors and their associated ligands, which together provide a means for inhibiting or stimulating signaling pathways that otherwise lead to T-cell activation. Immune checkpoint regulators include TIGIT and its CD155 ligand, PVR; PD-1 and its ligands, PD-L1 and PD-L2; CTLA-4 and its ligands, B7-1 and B7-2; TIM-3 and its ligand, Galectin-9; LAG-3 and its ligands, including liver sinusoidal endothelial cell lectin (LSECtin) and Galectin-3; CD122 and its CD122R ligands; CD70, B7H3, B and T lymphocyte attenuator (BTLA), and VISTA.

The term "checkpoint regulator antagonist," "immune checkpoint binding antagonist" and "immune checkpoint antagonist" refer to a class of agents that interfere with (or inhibit) the activity of an immune checkpoint regulator so that, as a result of the binding to the checkpoint regulator or its ligand, signaling through the checkpoint regulator receptor is blocked or inhibited. By inhibiting this signaling, immune-suppression can be reversed so that T cell immunity against cancer cells can be re-established or enhanced. Immune checkpoint regulator antagonists include antibody fragments, peptide inhibitors, dominant negative peptides and small molecule drugs, either in isolated forms or as part of a fusion protein or conjugate. Example targets of checkpoint regulator antagonists include PD1, POL1, CTLA4, LAG3, TIM-3, TIGIT, VISTA.

The term "immune checkpoint binding agonist" and "immune checkpoint agonist" refer to a class of agents that stimulate the activity of an immune checkpoint regulator so that, as a result of the binding to the checkpoint regulator or its ligand, signaling through the checkpoint regulator receptor is stimulated. By stimulating this signaling, T cell immunity against cancer cells can be re-established or enhanced. The targets of checkpoint regulator agonists include members of the tumor necrosis factor (TNF) receptor superfamily, such as CD27, CD40, OX40 (CD 134), glucocorticoid-induced TNFR family-related protein (GITR), and 4-1BB (CD137) and their ligands. Additional targets of checkpoint regulator agonists belong to the B7-CD28 superfamily, including CD28 and ICOS.

In any of the embodiments above, one or more cancer therapies, e.g., chemotherapy, radiation therapy, immunotherapy, surgery, or hormone therapy can be co-administered further with an antibody of the invention.

In one embodiment, the chemotherapeutic reagent is an alkylating agent: nitrogen mustards, nitrosoureas, tetrazines, aziridines, cisplatins and derivatives, and non-classical alkylating agents. Nitrogen mustards include mechlorethamine, cyclophosphamide, melphalan, chlorambucil, ifosfamide and busulfan. Nitrosoureas include N-Nitroso-N-methylurea (MNU), carmustine (BCNU), lomustine (CCNU) and semustine (MeCCNU), fotemustine and streptozotocin. Tetrazines include dacarbazine, mitozolomide and temozolomide. Aziridines include thiotepa, mytomycin and diazi-quone (AZQ). Cisplatin and derivatives include cisplatin, carboplatin and oxaliplatin. In one embodiment the chemotherapeutic reagent is an anti-metabolites: the anti-folates (e.g., methotrexate), fluoropyrimidines (e.g., fluorouracil and capecitabine), deoxynucleoside analogues and thiopurines. In another embodiment the chemoptheraputic reagent is an anti-microtubule agent such as *vinca* alkaloids (e.g., vincristine and vinblastine) and taxanes (e.g., paclitaxel and docetaxel). In another embodiment the chemotherapeutic reagent is a topoisomerase inhibitor or a cytotoxic antibiotic such as doxorubicin, mitoxantrone, bleomycin, actinomycin, and mitomycin.

The contacting of the patient with the antibody or antibody fragment, can be by administering the antibody to the patient intravenously, intraperitoneally, intramuscularly, intratumorally, or intradermally. In some embodiments the antibody is co-administered with a cancer therapy agent.

The term "formulation" as used herein refers to the antibodies disclosed herein and excipients combined together which can be administered and has the ability to bind to the corresponding receptors and initiate a signal transduction pathway resulting in the desired activity. The formulation can optionally comprise other agents.

All numerical designations, e.g., pH, temperature, time, concentration, and molecular weight, including ranges, are to be understood as approximations in accordance with common practice in the art. When used herein, the term "about" may connote variation (+) or (−) 1%, 5% or 10% of the stated amount, as appropriate given the context. It is to be understood, although not always explicitly stated, that the reagents described herein are merely exemplary and that equivalents of such are known in the art.

Many known and useful compounds and the like can be found in Remington's Pharmaceutical Sciences (13th Ed), Mack Publishing Company, Easton, PA—a standard reference for various types of administration. As used herein, the term "formulation(s)" means a combination of at least one active ingredient with one or more other ingredient, also commonly referred to as excipients, which may be independently active or inactive. The term "formulation" may or may not refer to a pharmaceutically acceptable composition for administration to humans or animals and may include compositions that are useful intermediates for storage or research purposes.

As the patients and subjects of the invention method are, in addition to humans, veterinary subjects, formulations suitable for these subjects are also appropriate. Such subjects include livestock and pets as well as sports animals such as horses, greyhounds, and the like.

DETAILED DESCRIPTION

The DLL3 gene provides instructions for making a protein that helps control the Notch pathway, an important pathway in embryonic development. DLL3 is usually an intracellular protein but it is also expressed on the surface of cancer cells. DLL3 is expressed normally on the inside of cells and at low levels on normal tissues. However, lung tumor cells overexpress the gene and cell surface DLL3 levels are increased. Recent studies have reported that DLL3 is also expressed in other tumor types of neuroendocrine origin, including melanoma, glioblastoma multiforme, small cell bladder cancer, metastatic castration-resistant prostate cancer, and neuroendocrine lung tumors.

CD (cluster of differentiation) molecules (e.g. CD3, CD28 and CD137) CD3, CD28 and CD137 are receptors present on T cells. T cells can be activated by antigen-presenting cells via CD3, CD28 and CD137. Two parallel therapeutic strategies are pursued for activating or engaging T cells to kill tumor cells.

Embodiments of the invention include methods of diagnosing, prognosing, treating, monitoring and preventing cancer, including refractory cancer, using anti-DLL3 antibodies and antibody conjugates, pharmaceutical compositions thereof, and articles of manufacture. More specifically, the invention is directed to bispecific or trispecific molecules that bind to DLL3 and activate CD (cluster of differentiation) molecules (e.g. CD3, CD28 and CD137).

Embodiments of the invention also include methods of diagnosing, prognosing, treating, monitoring and preventing cancer, including refractory cancer, using anti-MUC17 antibodies and antibody conjugates, pharmaceutical compositions thereof, and articles of manufacture. More specifically, the invention is directed to bispecific or trispecific molecules that bind to MUC17 and activate CD (cluster of differentiation) molecules (e.g. CD3, CD28 and CD137).

Embodiments of the invention also include methods of diagnosing, prognosing, treating, monitoring and preventing cancer, including refractory cancer, using anti-CLDN18.2 antibodies and antibody conjugates, pharmaceutical compositions thereof, and articles of manufacture. More specifically, the invention is directed to trispecific molecules that bind to CLDN18.2 and activate CD (cluster of differentiation) molecules (e.g. CD3, CD28 and CD137).

DLL3 T-Cell Engagers

Embodiments of the invention include bispecific and trispecific monoclonal antibodies (BSMAbs and TSMAbs, respectively). The single chain variable fragment (scFv) of a first antibody can be joined with the antigen binding fragment (Fab) of a second antibody. For example, the scFv portion of an antibody against CD3 can be linked to a Fab portion of an antibody against DLL3. They can be joined with 4×GKPGS (SEQ ID NO: 508) or 4×G4S (SEQ ID NO: 509) linkers. The IgG1 Fc can be heterodimerized with charge pair or "knob into hole" mutations or charge pair mutations. The Fc effector function can be minimized through the introduction of N297A/G mutations or LLP mutations. The combination can bring an effector cell (T-cell or NK cell) into the proximity of the tumor cell to enhance antitumor effect.

FIGS. 1A-1R, 8A-8C and 9A-9F depict several formats for trispecific molecules of the invention. The DLL3×CD3 trispecific molecules can activate T cell cytotoxicity against DLL3 expressing CHO cells or NCI-H82 tumor cells. This is exemplified by the release of LDH upon cell death, as well as the upregulation of CD25 on the T cells. When combined with DLL3×CD28 or DLL3×CD137 trispecific molecules, the T cells are further activated, proliferate, and release IFN gamma and IL-2.

CD28 signaling is essential for the activity of anti-PD1 and anti-PDL1 antibodies, thus co-dosing the DLL3×CD28 trispecific molecules with anti-PD1 and anti-PDL1 can improve the responses to the inhibition of the PD1/PDL1 pathway. CD137 is highly expressed on exhausted T cells, which cannot be stimulated by PD1/PDL1 stimulation alone. However, DLL3×CD137 or DLL3×CD28×CD137 stimulation combined with PD-1 blockade results in robust antitumor immunity.

FIG. 1A-1R depict trispecific molecules with combinations of an anti-DLL3 with anti-CD3, anti-CD28 and anti-CD137 in the Scfv-Scfv-Fc×Fab-Fc configuration. FIG. 1A-1F depict trispecific with the configuration scfv-DLL3scfv-Fc×Fab-Fc. FIG. 1G-1L depict trispecific molecules with the configuration DLL3scfv-scfv-Fc×Fab-Fc. FIG. 1M-1R depict depict trispecific molecules with the configuration scfv-scfv-Fc×DLL3Fab-Fc.

Figure 8A:
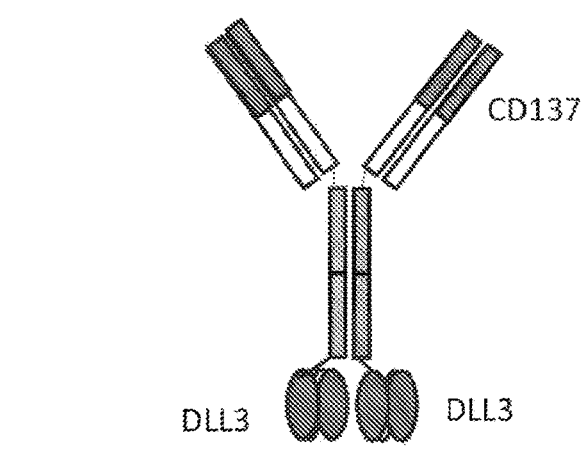
FIG. 8A-8C depict bispecific and trispecific molecules with two CD137 Fab fragments.
Figure 8B:
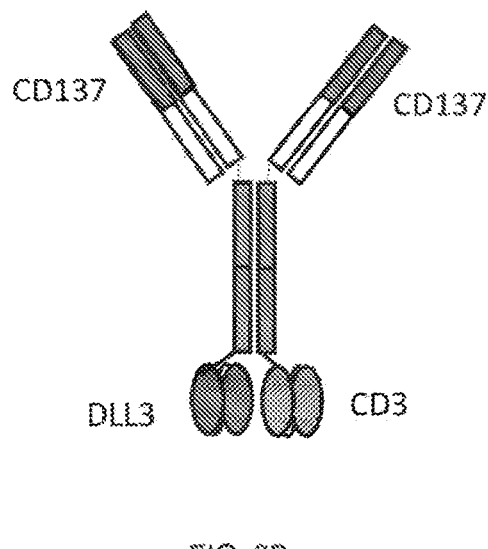
Figure 8C:
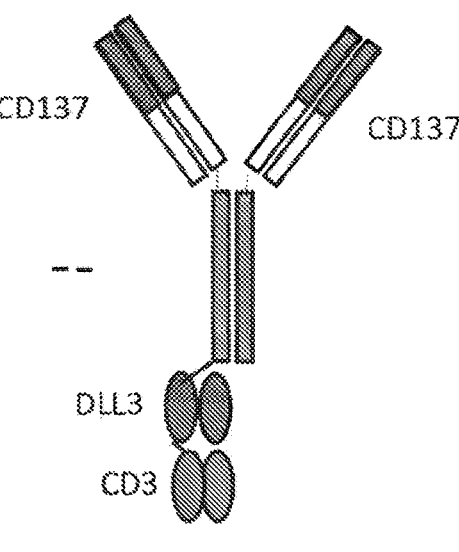

FIG. 8A-8C depict bispecific and trispecific molecules with two CD137 Fab fragments. FIG. 8A depicts an anti-CD137, anti-DLL3, anti-DLL3 (Fab-Fc-Scfv) molecule. FIG. 8B depicts an anti-CD137, anti-DLL3, anti-CD3 (Fab-Fc-Scfv×Fab-Fc-Scfv) molecule. FIG. 8C depicts an anti-CD137, anti-DLL3, anti-CD3 (Fab-Fc-Scfv-Scfv×Fab-Fc) molecule.

Figure 9A:
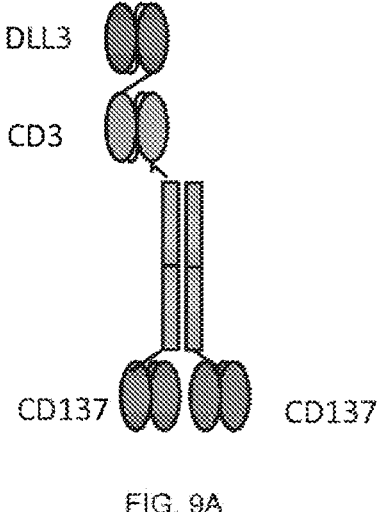
FIG. 9A-9F depict bispecific molecules and trispecific molecules with two CD137 scfv fragments.
Figure 9B:
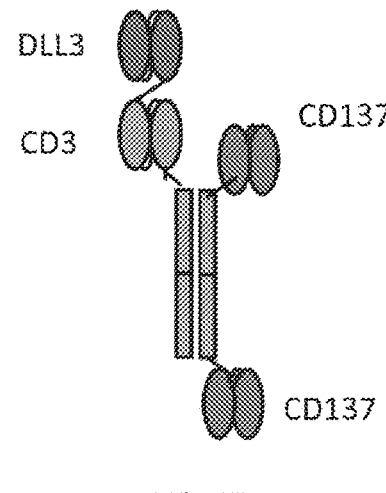
Figures 9C, 9D, 9E, 9F:
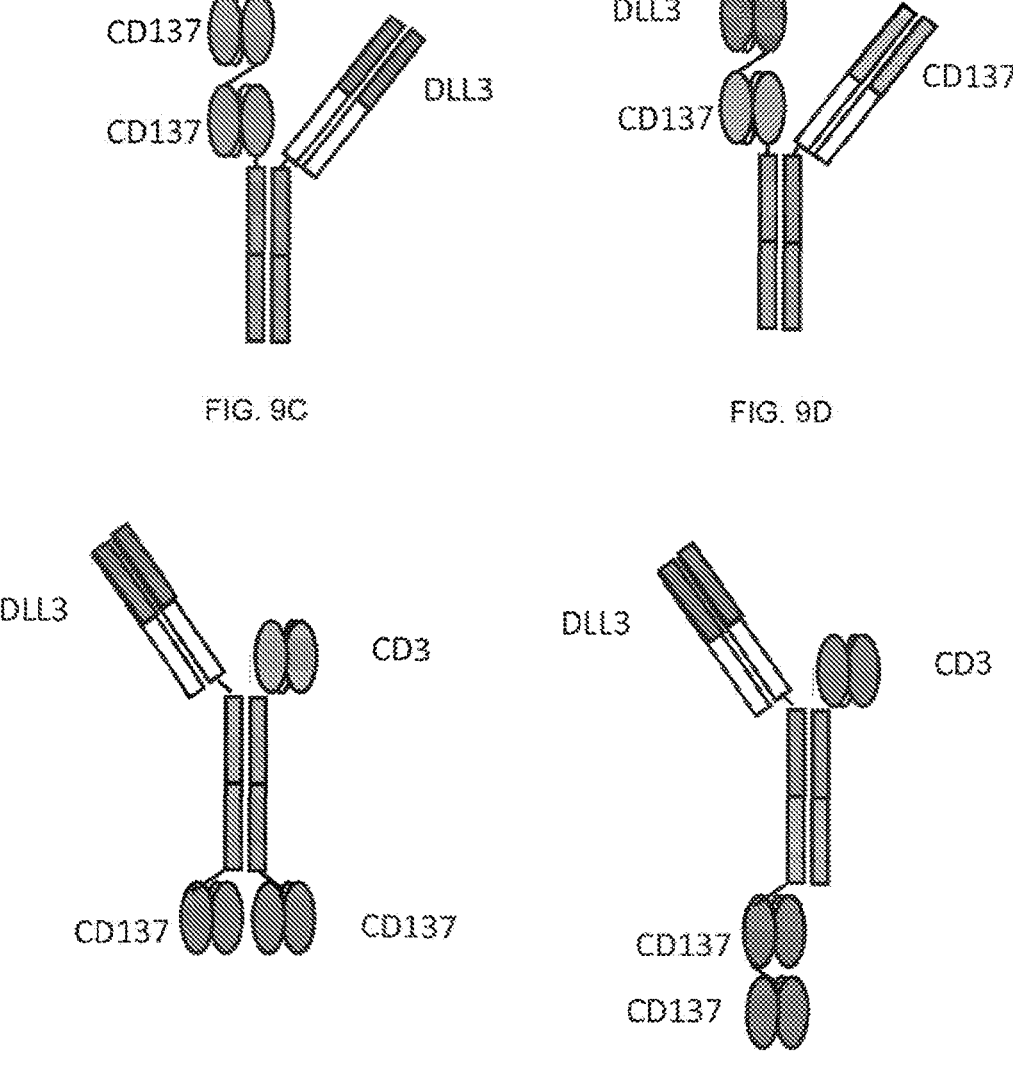

FIG. 9A-9F depict trispecific molecules with two CD137 fragments. FIG. 9A depicts an anti-DLL3, anti-CD3, anti-CD137, anti-CD137 (scfv-scfv-Fc-Scfv×Fc-Scfv) molecule. FIG. 9B depicts an anti-DLL3, anti-CD3, anti-CD137, anti-CD137 (scfv-scfv-Fc×Scfv-Fc-Scfv) molecule. FIG. 9C depicts an anti-CD137, anti-CD137, anti-DLL3 (scfv-scfv-Fc×Fab-Fc) molecule. FIG. 9D depicts an anti-DLL3, anti-CD137, anti-CD137 (scfv-scfv-Fc×Fab-Fc) molecule. FIG. 9E depicts an anti-DLL3, anti-CD3, anti-DLL3, anti-CD137 (Fab-Fc-Scfv×Scfv-Fc-Scfv) molecule. FIG. 9F depicts an anti-DLL3, anti-CD3, anti-CD137, anti-CD137 (Fab-Fc-Scfv-Scfv×Scfv-Fc) molecule.

MUC17 T-Cell Engagers

FIGS. 10A-10R, 18A-18D and 19A-19I depict several formats for trispecific molecules of the invention.

Figures 10A, 10B, 10C, 10D, 10E, 10F:
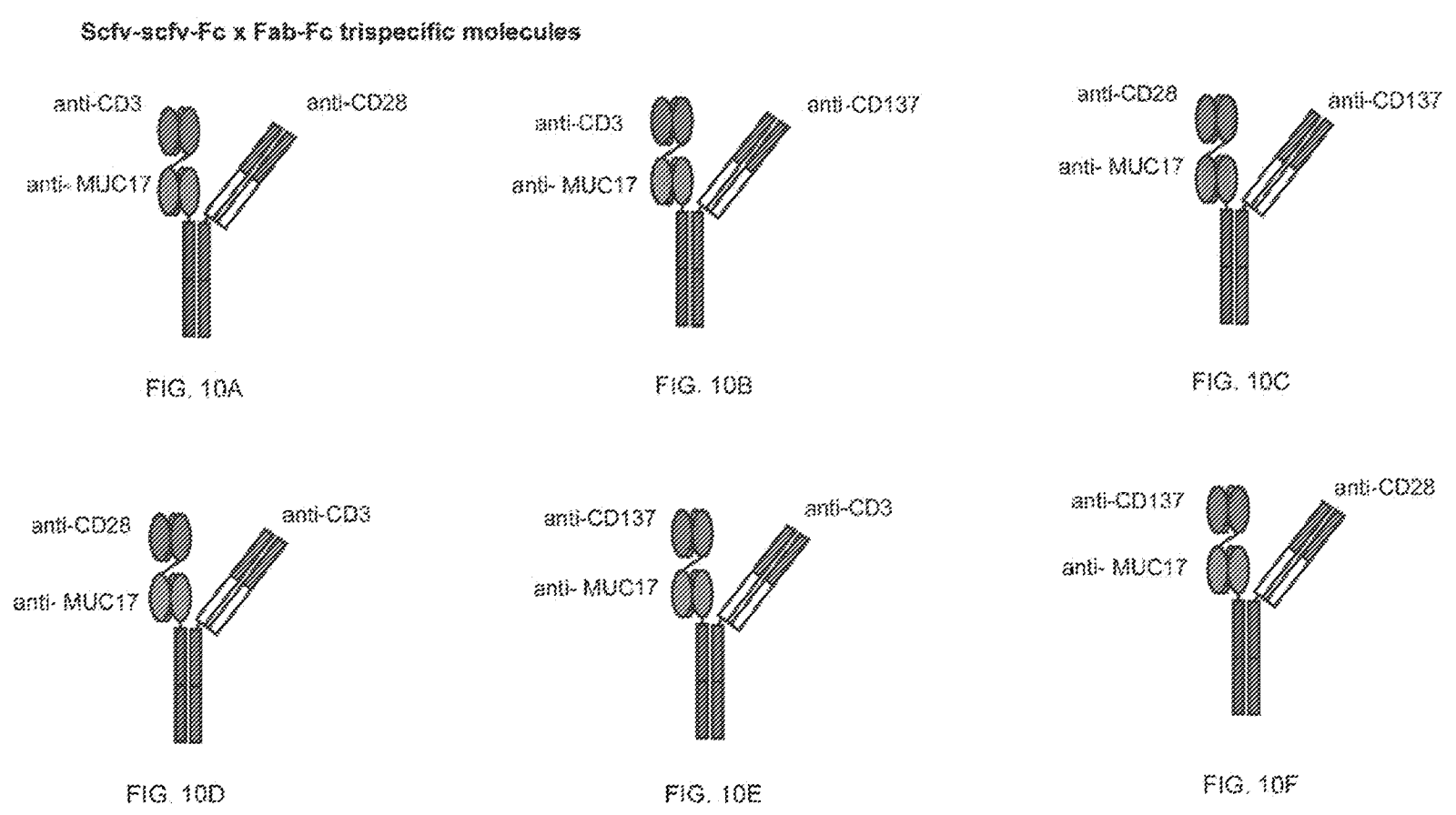
Figures 10G, 10H, 10I, 10J, 10K, 10L:
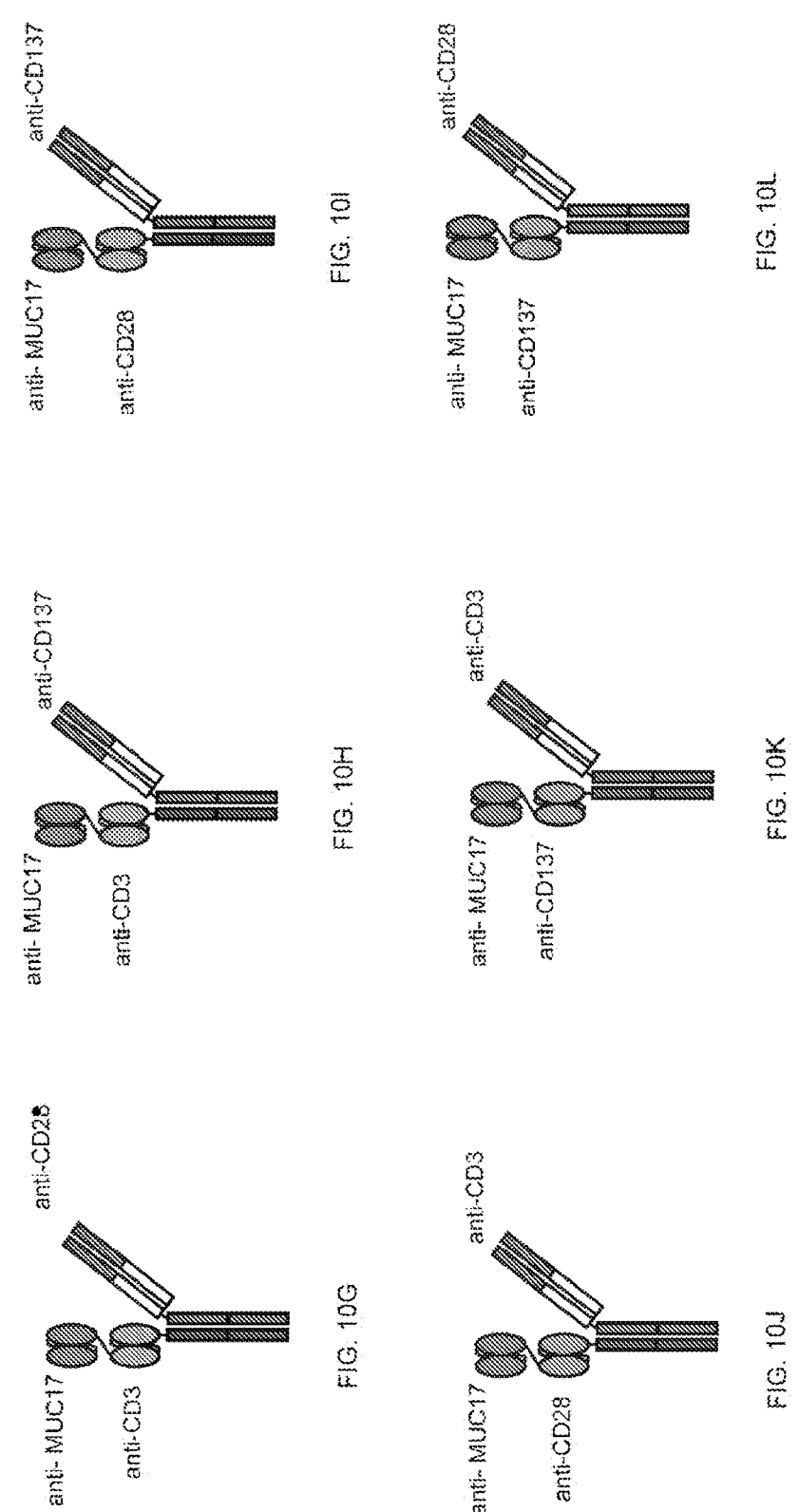
FIG. 10G depicts an anti-MUC17, anti-CD3, anti-CD28 (scfv-scfv-FcxFab-Fc) molecule.
FIG. 10H depicts an anti-MUC17, anti-CD3, anti-CD137 (scfv-scfv-FcxFab-Fc) molecule.
FIG. 10I depicts an anti-MUC17, anti-CD28, anti-CD137 (scfv-scfv-Fcx Fab-Fc) molecule.
FIG. 10J depicts an anti-MUC17, anti-CD28, anti-CD3 (scfv-scfv-Fcx Fab-Fc) molecule.
FIG. 10K depicts an anti-MUC17, anti-CD137, anti-CD3 (scfv-scfv-Fcx Fab-Fc) molecule.
FIG. 10L depicts an anti-MUC17, anti-CD137, anti-CD28 (scfv-scfv-Fcx Fab-Fc) molecule.
Figures 10M, 10N, 10O, 10P, 10Q, 10R:
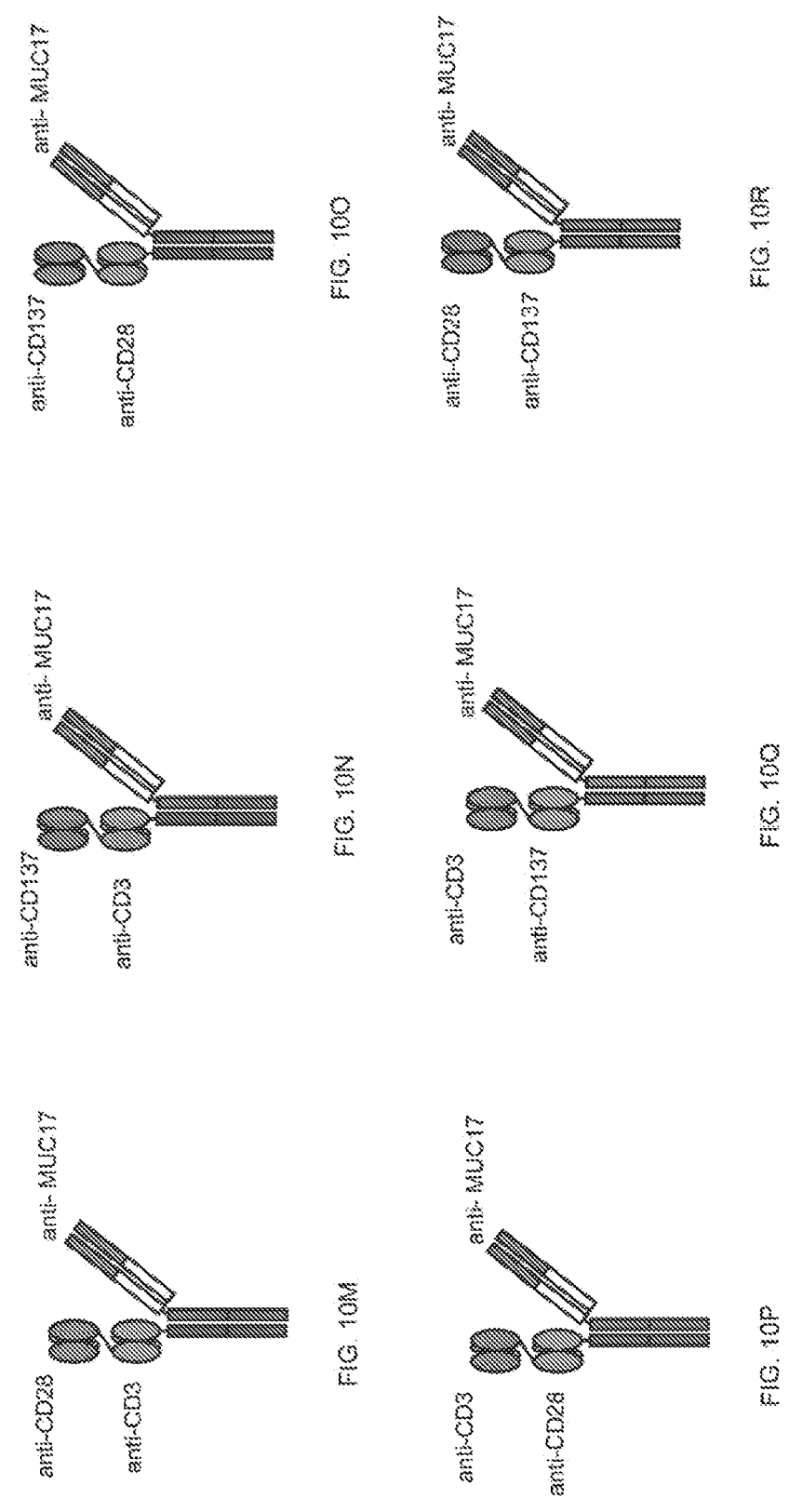

FIG. 10A-10R depict trispecific molecules with combinations of an anti-MUC17 with anti-CD3, anti-CD28 and anti-CD137 in the Scfv-scfv-Fc×Fab-Fc configuration. FIG. 10A-10F depict trispecific with the configuration scfv-MUC17scfv-Fc×Fab-Fc. FIG. 1G-1L depict trispecific molecules with the configuration MUC17scfv-scfv-Fc×Fab-Fc. FIG. 1M-1R depict depict trispecific molecules with the configuration scfv-scfv-Fc×MUC17Fab-Fc.

FIG. 18A-18D depict Muc17×CD137 and DLL3×CD137 bispecific molecules

Figures 19D, 19E, 19F, 19G:
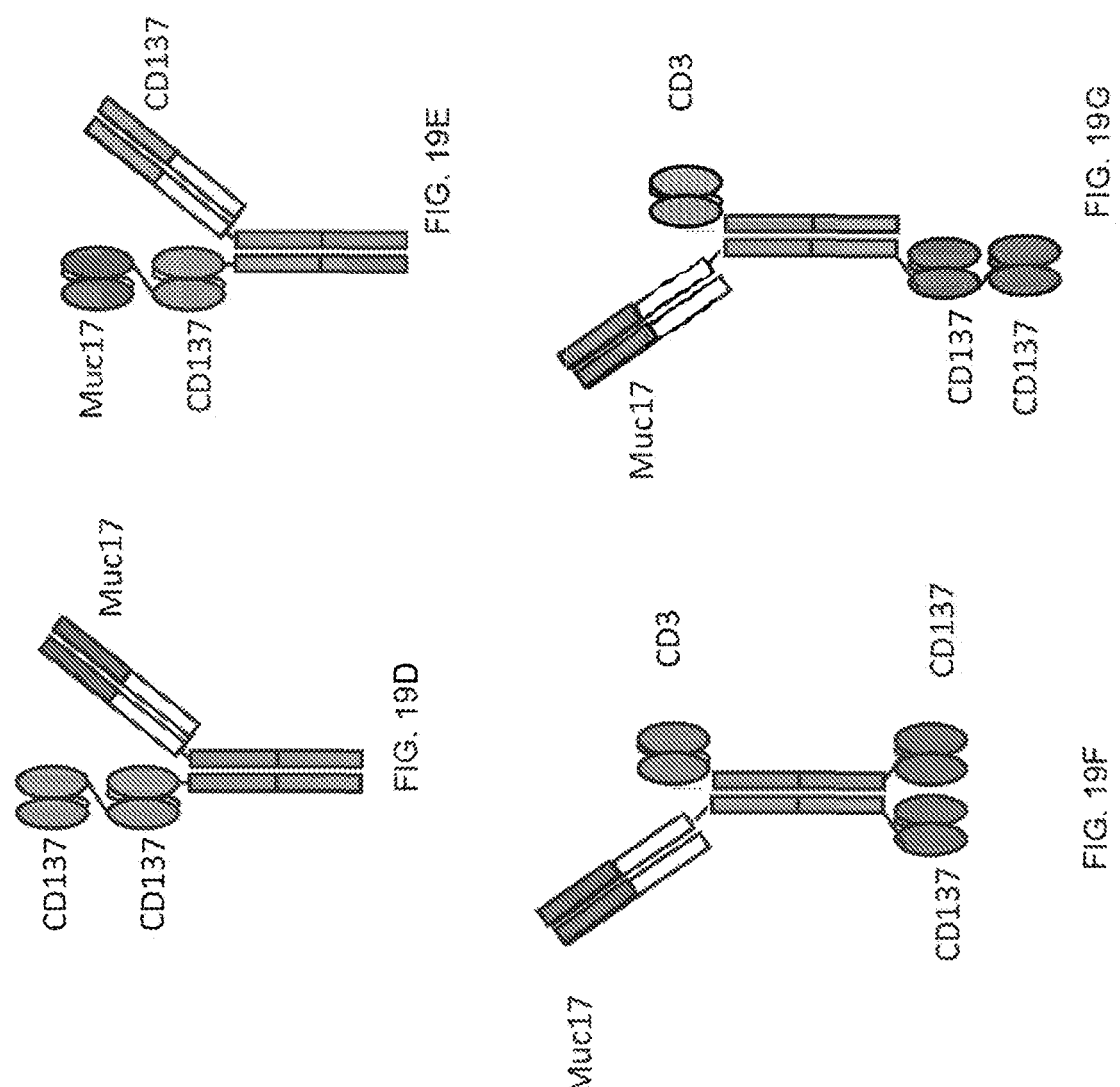
FIG. 19D-19I depict bispecific molecules and trispecific molecules with two anti-CD137 fragments.
Figure 19I:
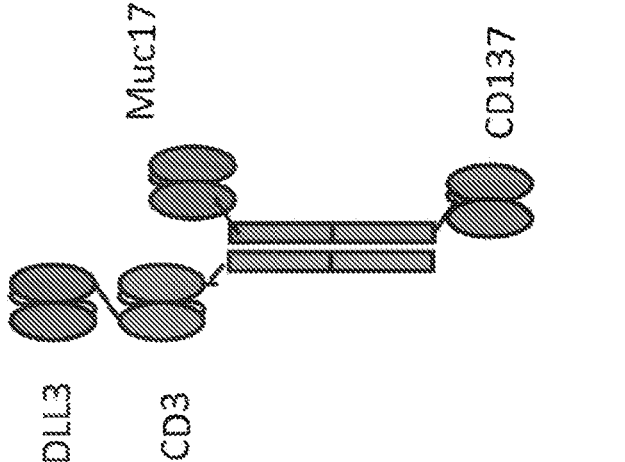
Figure 19H:
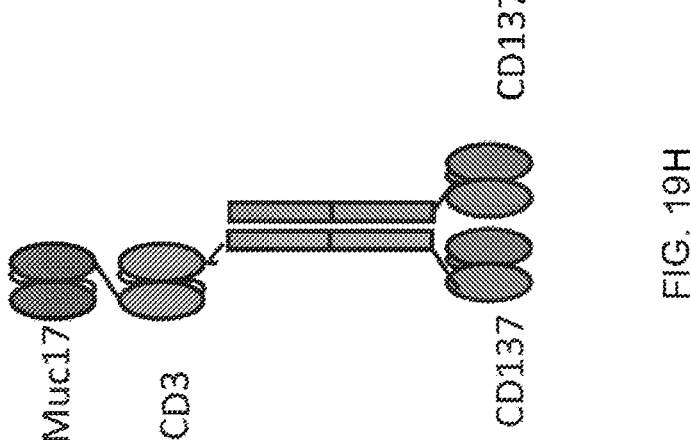

FIG. 19A-19C depict trispecific molecules with two CD137 Fab fragments. FIG. 19A depicts an anti-CD137, anti-MUC17, anti-MUC17 (Fab-Fc-Scfv-Scfv) molecule. FIG. 19B depicts an anti-CD137, anti-MUC17, anti-CD3 (Fab-Fc-Scfv×Fab-Fc-Scfv) molecule. FIG. 19C depicts an anti-CD137, anti-MUC17, anti-CD3 (Fab-Fc-Scfv-Scfv× Fab-Fc) molecule. FIG. 19D-19I depict bispecific molecules and trispecific molecules with two CD137 scfv fragments. FIG. 19D depicts an, anti-anti-CD137, anti-CD137, anti-MUC17 (scfv-scfv-Fc×Fab-Fc) molecule. FIG. 19E depicts an anti-MUC17, anti-CD137, anti-CD137 (scfv-scfv-Fc× Fab-Fc) molecule. FIG. 19F depicts an anti-MUC17, anti-CD137, CD3, CD137 (Fab-Fc-Scfv×Scfv-Fc-Scfv) molecule. FIG. 19G depicts an anti-MUC17, anti-CD137, anti-CD137, CD3 (Fab-Fc-Scfv-Scfv×Scfv-Fc) molecule. FIG. 19H depicts an anti-MUC17, anti-CD3, anti-CD137, anti-CD137 (scfv-scfv-FScfv×Fc-Scfv) molecule. FIG. 19I depicts an anti-DLL3, anti-CD3, anti-CD137, anti-MUC17 (scfv-scfv-Fc×Scfv-Fc-Scfv) molecule.

In an embodiment, the trispecific molecule can be co-administered or combined with an antagonist such as PD1, PDL1, TIGIT, LAG3, TIM3, VISTA or CTLA4. Alternatively, the trispecific molecule can be co-administered or combined with a bispecific antagonist such as PD1×TIGIT, LAG3×TIGIT, PD1×LAG3, PD1×TIM3 or VEGF× TGFBR2. The trispecific molecule can also be co-administered or combined with an agonist such as CD40, GITR, CD27, OX40 or 4-1BB.

CLDN18.2 T-Cell Engagers

Embodiments of the invention include bispecific and trispecific monoclonal antibodies (BSMAbs and TSMAbs, respectively). The single chain variable fragment (scFv) of a first antibody can be joined with the antigen binding fragment (Fab) of a second antibody. For example, the scFv portion of an antibody against CD3 can be linked to a Fab portion of an antibody against CLDN8.2. They can be joined with 4×GKPGS or 4×G4S linkers. The IgG1 Fc can be heterodimerized with charge pair or "knob into hole" mutations or charge pair mutations. The Fc effector function can be minimized through the introduction of N297A/G mutations or LLP mutations. The combination can bring an effector cell (T-cell or NK cell) into the proximity of the tumor cell to enhance antitumor effect.

CD28 signaling is essential for the activity of anti-PD1 and anti-PDL1 antibodies, thus co-dosing the CLDN18.2× CD28 trispecific molecules with anti-PD1 and anti-PDL1 can improve the responses to the inhibition of the PD1/ PDL1 pathway. CD137 is highly expressed on exhausted T cells, which cannot be stimulated by PD1/PDL1 stimulation alone. However, CLDN18.2×CD137 or CLDN18.2×CD28× CD137 stimulation combined with PD-1 blockade results in robust antitumor immunity.

FIGS. 20A-20R and 25A-25I depict several formats for trispecific molecules of the invention. The CLDN18.2×CD3 trispecific molecules can activate T cell cytotoxicity against CLDN18.2 expressing CHO cells or NCI-H82 tumor cells. This is exemplified by the release of LDH upon cell death, as well as the upregulation of CD25 on the T cells. When combined with CLDN18.2×CD28 or CLDN18.2×CD137 trispecific molecules, the T cells are further activated, proliferate, and release IFN gamma and IL-2.

Figures 20M, 20N, 20O, 20P, 20Q, 20R:
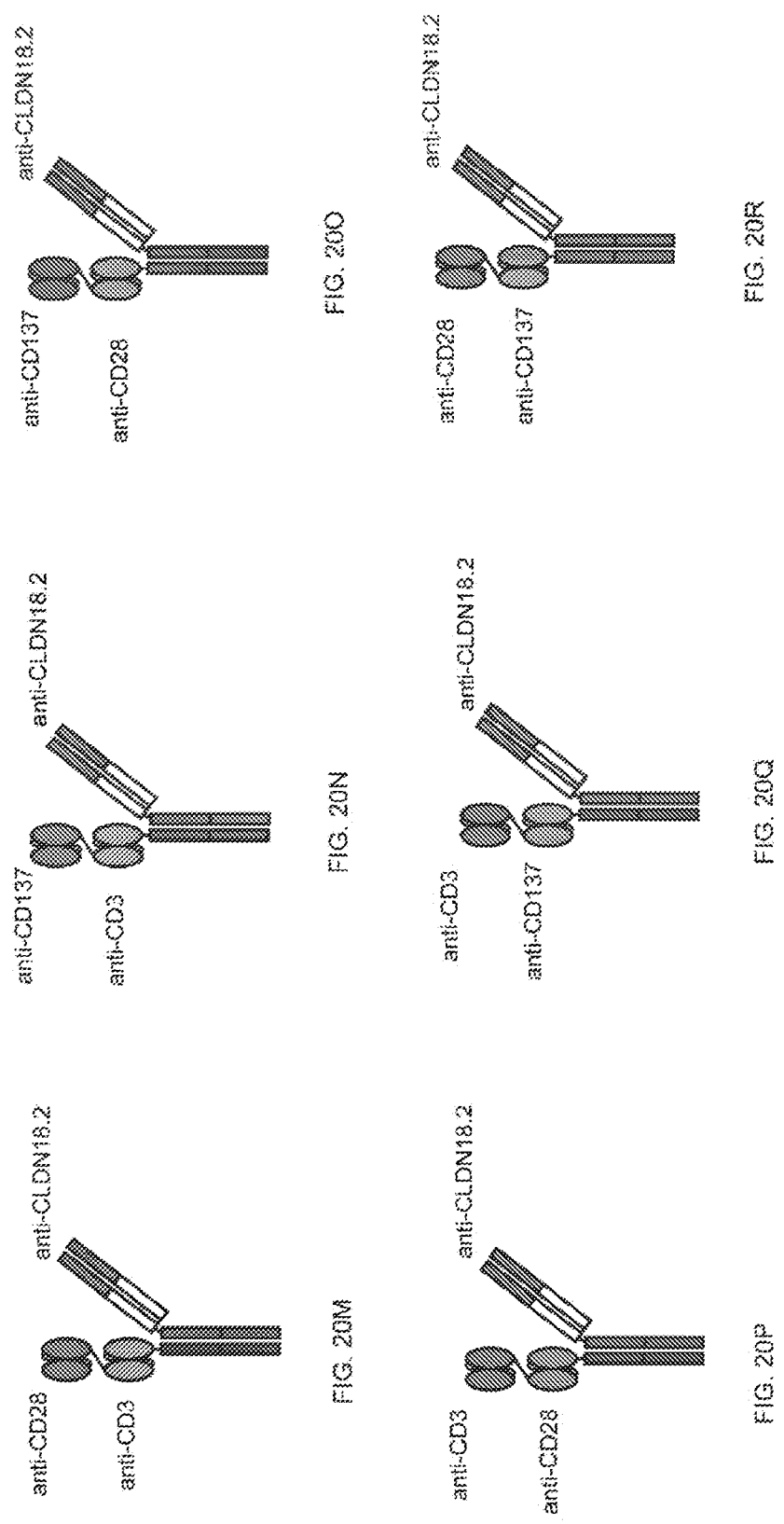

FIG. 20A-20R depict trispecific molecules with combinations of an anti-CLDN18.2 with anti-CD3, anti-CD28 and anti-CD137 in the Scfv-scfv-Fc×Fab-Fc configuration. FIG. 20A-20F depict trispecific with the configuration scfv-CLDn18.1scfv-Fc×Fab-Fc. FIG. 20G-20L depict trispecific molecules with the configuration CLDN18.2scfv-scfv-Fc× Fab-Fc. FIG. 20M-20R depict depict trispecific molecules with the configuration scfv-scfv-Fc×CLDN18.2Fab-Fc.

Figures 25A, 25B, 25C:
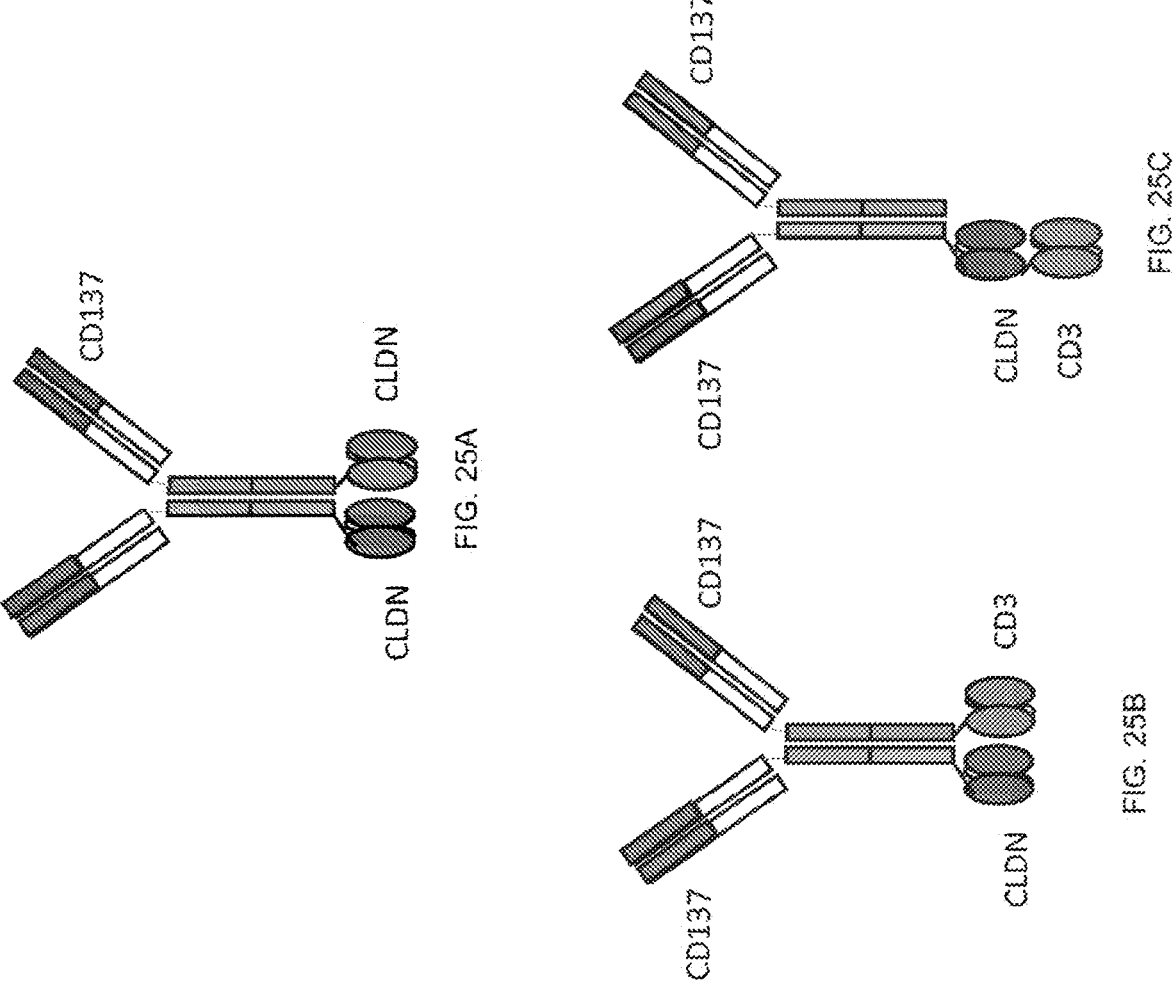
FIG. 25A-25C depict CLDN18.2 bispecific and trispecific molecules with two CD137 Fab or Scfv fragments.

FIG. 25A-25C depict CLDN18.2 bispecific and trispecific molecules with two CD137 Fab fragments.

Figures 25D, 25E:
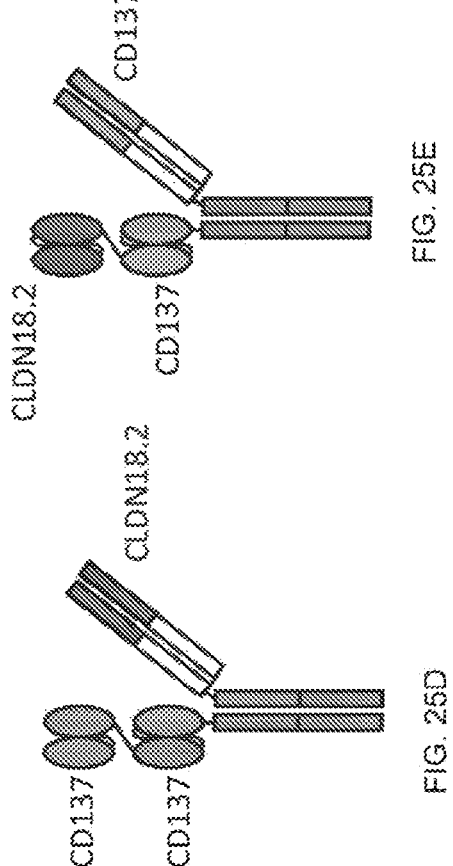
FIG. 25D depicts an anti-CD137, anti-CD137, anti-CLDN18.2 bispecific molecule (Scfv-Scfv-FcxFab-Fc)
FIG. 25E depicts an anti-CLDN18.2, anti-CD137, anti-CD137, trispecific molecule (Scfv-Scfv-FcxFab-Fc)

FIG. 25A depicts an anti-CD137, anti-CLDN18.2, anti-CLDN (Fab-Fc-Scfv) molecule. FIG. 25B depicts an anti-CD137, anti-CLDN18.2, anti-CD3 (Fab-Fc-Scfv×Fab-Fc-Scfv) molecule. FIGS. 25D and 25E depict trispecific molecules with two CD137 fragments.

FIG. 25D depicts an anti-CD137, anti-CD137, anti-CLDN18.2 bispecific molecule (Scfv-Scfv-Fc×Fab-Fc). Similarly, FIG. 25E depicts an anti-CLDN18.2, anti-CD137, anti-CD137, trispecific molecule (Scfv-Scfv-Fc×Fab-Fc)

Figures 25F, 25G:
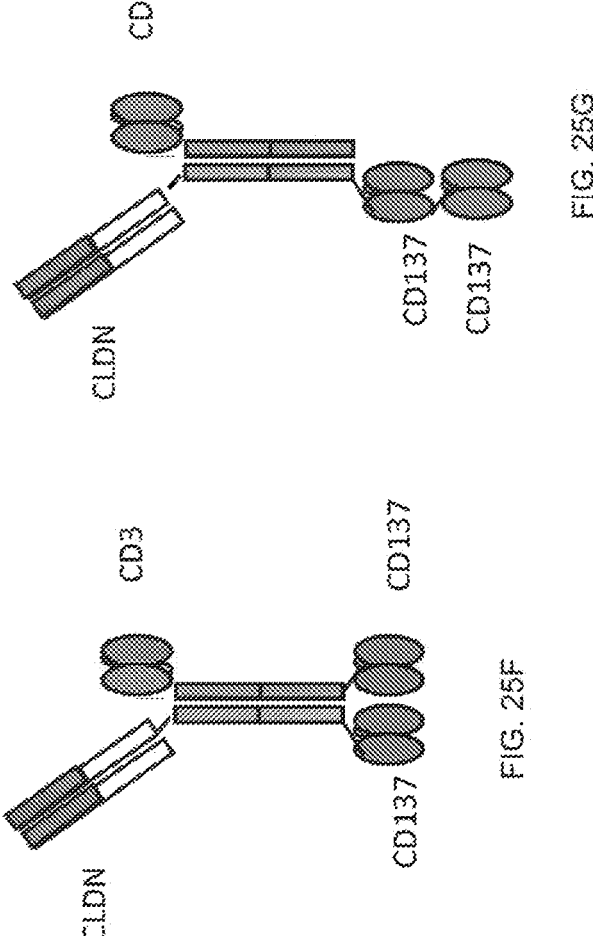
FIG. 25F depicts an anti-CLDN18.2, anti-CD137, anti-CD3, anti-CD137 18.2 (Fab-Fc-ScfvxScfv-Fc-Scfv) molecule.
FIG. 25G depicts an anti-CLDN18.2, anti-CD3, anti-CD137, anti-CD137 (Fab-Fc-Scfv-ScfvxScfv-Fc) molecule.
Figure 25H:
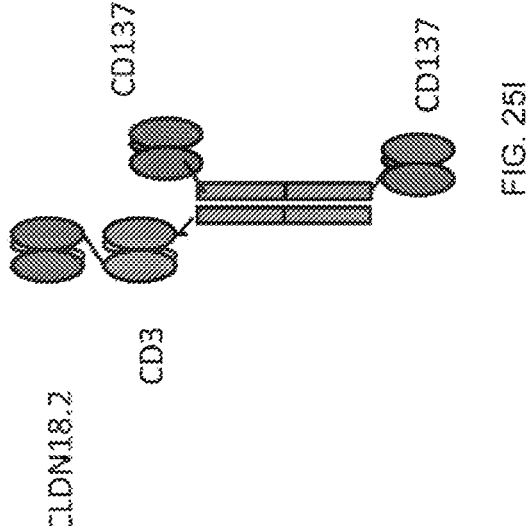
FIG. 25H depicts an anti-CLDN18.2, anti-CD3, anti-CD137, anti-CD137 (scfv-scfv-Fc-ScfvxFc-Scfv) molecule.
Figure 25I:
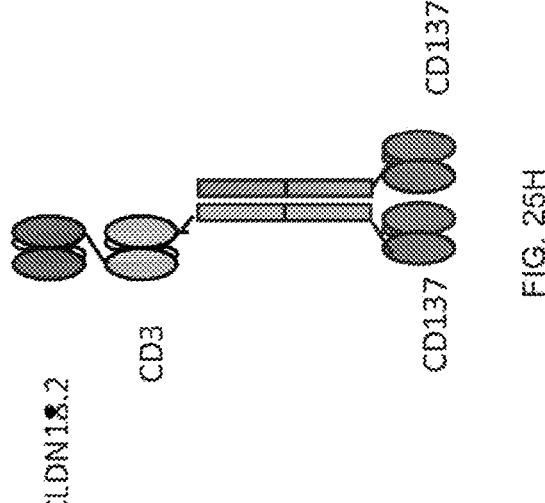
FIG. 25I depicts an anti-CLDN18.2, anti-CD3, anti-CD137, anti-CD137 (scfv-scfv-FcxScfv-Fc-Scfv) molecule.

FIG. 25F-25I depict trispecific molecules with two CD137 scfv fragments. FIG. 25F depicts an anti-CLDN18.2, anti-CD3, anti-CD137, anti-CD137 (Fab-Fc-ScfvxScfvFc-Scfv) molecule. FIG. 25G depicts an anti-CLDN18.2, anti-CD3, anti-CD137, anti-CD137 (Fab-Fc-Scfv-ScfvxScfv-Fc) molecule. FIG. 25H depicts an anti-CLDN18.2, anti-CD3, anti-CD137, anti-CD137 (scfv-scfv-Fc-ScfvxFc-Scfv) molecule. FIG. 25I depicts an anti-CLDN18.2, anti-CD3, anti-CD137, anti-CD137 (scfv-scfv-FcxScfv-Fc-Scfv) molecule.

In an embodiment, the trispecific molecule can be co-administered or combined with an antagonist such as PD1, PDL1, TIGIT, LAG3, TIM3, VISTA or CTLA4. Alternatively, the trispecific molecule can be co-administered or combined with a bispecific antagonist such as PD1xTIGIT, LAG3xTIGIT, PD1xLAG3, PD1xTIM3 or VEGFx TGFBR2. The trispecific molecule can also be co-administered or combined with an agonist such as CD40, GITR, CD27, OX40 or 4-1BB.

Methods from Producing Trispecific T-Cell Engagers

Another aspect relates to a method for producing a trispecific antibody comprising culturing a cell transiently or stably expressing one or more constructs encoding one or more polypeptide chains in the trispecific antibody; and purifying the trispecific antibody from the cultured cells. Any cell capable of producing a functional trispecific antibody can be used. In preferred embodiments, the trispecific antibody-expressing cell is of eukaryotic or mammalian origin, preferably a human cell or Chinese hamster cell. Cells from various tissue cell types may be used to express the trispecific antibodies. In other embodiments, the cell is a yeast cell, an insect cell or a bacterial cell. Preferably, the trispecific antibody-producing cell is stably transformed with a vector expressing the trispecific antibody.

One or more expression vectors encoding the antibody heavy or light chains can be introduced into a cell by any conventional method, such as by naked DNA technique, cationic lipid-mediated transfection, polymer-mediated transfection, peptide-mediated transfection, virus-mediated infection, physical or chemical agents or treatments, electroporation, etc. In addition, cells may be transfected with one or more expression vectors for expressing the trispecific antibody along with a selectable marker facilitating selection of stably transformed clones expressing the trispecific antibody. The antibodies produced by such cells may be collected and/or purified according to techniques known in the art, such as by centrifugation, chromatography, etc.

Examples of suitable selectable markers for mammalian cells include dihydrofolate reductase (DHFR), thymidine kinase, neomycin, neomycin analog G418, hydromycin, zeocin, blasticidin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are CHO DHFR cells and mouse LTK cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, mycophenolic acid, or hygromycin. The three examples employ bacterial genes under eukaryotic control to convey resistance to the appropriate drug G418 or neomycin (geneticin), xgpt (mycophenolic acid) or hygromycin, respectively. Others include the neomycin analog G418 and puromycin.

Exemplary trispecific antibody-expressing cells include human Jurkat, human embryonic kidney (HEK) 293, Chinese hamster ovary (CHO) cells, mouse WEHI fibrosarcoma cells, as well as unicellular protozoan species, such as *Leishmania tarentolae*. In addition, stably transformed, antibody producing cell lines may be produced using primary cells immortalized with c-myc or other immortalizing agents.

In some embodiments, the cell lines express at least 1 mg, at least 2 mg, at least 5 mg, at least 10 mg, at least 20 mg, at least 50 mg, at least 100 mg, at least 500 mg, at least 1 gram, at least 2 grams, at least 4 grams, or at least 10 grams of the trispecific antibody/liter of culture. Trispecific antibodies can be isolated from trispecific antibody expressing cells following culture and maintenance in any appropriate culture medium, such as RPMI, DMEM, and AIM VO. The trispecific antibodies can be purified using conventional protein purification methodologies (e.g., affinity purification, chromatography, etc.), including the use of Protein-A or Protein-G immunoaffinity purification. In some embodiments, trispecific antibodies are engineered for secretion into culture supernatants for isolation therefrom.

Methods of Treatment

Another aspect of the present application relates to a method for treating a cell proliferative disorder. The method comprises administering to a subject in need thereof an effective amount of a trispecific antibody according to the present disclosure. In another aspect, a method for treating a cell proliferative disorder comprises administering to a subject in need thereof an effective amount of one or more expression vectors expressing a trispecific antibody according to the present disclosure.

Any suitable route or mode of administration can be employed for providing the patient with a therapeutically or prophylactically effective dose of the trispecific antibody. Exemplary routes or modes of administration include parenteral {e.g., intravenous, intraarterial, intramuscular, subcutaneous, intratumoral), oral, topical (nasal, transdermal, intradermal or intraocular), mucosal {e.g., nasal, sublingual, buccal, rectal, vaginal), inhalation, intralymphatic, intraspinal, intracranial, intraperitoneal, intratracheal, intravesical, intrathecal, enteral, intrapulmonary, intralymphatic, intracavital, intraorbital, intracapsular and transurethral, as well as local delivery by catheter or stent.

A pharmaceutical composition comprising a trispecific antibody in accordance with the present disclosure can be formulated in any pharmaceutically acceptable carrier(s) or excipient(s). As used herein, the term "pharmaceutically acceptable carrier" includes any and all solvents, dispersion media, coatings, antibacterial and antifungal agents, isotonic and absorption delaying agents, and the like that are physiologically compatible. Pharmaceutical compositions can include suitable solid or gel phase carriers or excipients. Exemplary carriers or excipients include calcium carbonate, calcium phosphate, various sugars, starches, cellulose derivatives, gelatin, and polymers such as polyethylene glycols. Exemplary pharmaceutically acceptable carriers include one or more of water, saline, phosphate buffered saline, dextrose, glycerol, ethanol and the like, as well as combinations thereof. In many cases it will be preferable to include isotonic agents, for example, sugars, polyalcohols such as mannitol, sorbitol, or sodium chloride in the composition. Pharmaceutically acceptable carriers can further comprise minor amounts of auxiliary substances such as wetting or emulsifying agents, preservatives or buffers, which enhance the shelf life or effectiveness of the therapeutic agents.

The trispecific antibody can be incorporated into a pharmaceutical composition suitable for parenteral administration. Suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05%>polysorbate-80 (optimally 0.005-0.01%). Additional surfactants include but are not limited to polysorbate 20 and BRIJ surfactants.

Therapeutic trispecific antibody preparations can be lyophilized and stored as sterile powders, preferably under vacuum, and then reconstituted in bacteriostatic water (containing, for example, benzyl alcohol preservative) or in sterile water prior to injection. Pharmaceutical compositions can be formulated for parenteral administration by injection e.g., by bolus injection or continuous infusion.

The therapeutic agents in the pharmaceutical compositions may be formulated in a "therapeutically effective amount" or a "prophylactically effective amount". A "therapeutically effective amount" refers to an amount effective, at dosages and for periods of time necessary, to achieve the desired therapeutic result. A therapeutically effective amount of the recombinant vector may vary depending on the condition to be treated, the severity and course of the condition, the mode of administration, whether the antibody or agent is administered for preventive or therapeutic purposes, the bioavailability of the particular agent(s), the ability of the trispecific antibody to elicit a desired response in the individual, previous therapy, the age, weight and sex of the patient, the patient's clinical history and response to the antibody, the type of the trispecific antibody used, discretion of the attending physician, etc. A therapeutically effective amount is also one in which any toxic or detrimental effects of the recombinant vector is outweighed by the therapeutically beneficial effects. A "prophylactically effective amount" refers to an amount effective, at dosages and for periods of time necessary, to achieve the desired prophylactic result.

Preferably, the polypeptide domains in the trispecific antibody are derived from the same host in which they are to be administered in order to reduce inflammatory responses against the administered therapeutic agents.

The trispecific antibody is suitably administered to the patent at one time or over a series of treatments and may be administered to the patient at any time from diagnosis onwards. The trispecific antibody may be administered as the sole treatment or in conjunction with other drugs or therapies useful in treating the condition in question.

As a general proposition, a therapeutically effective amount or prophylactically effective amount of the trispecific antibody will be administered in a range from about 1 ng/kg body weight/day to about 100 mg/kg body weight/day whether by one or more administrations. In a particular embodiment, each trispecific antibody is administered in the range of from about 1 ng/kg body weight/day to about 10 mg/kg body weight/day, about 1 ng/kg body weight/day to about 1 mg/kg body weight/day, about 1 ng/kg body weight/day to about 100 g/kg body weight/day, about 1 ng/kg body weight/day to about 10 g/kg body weight/day, about 1 ng/kg body weight/day to about 1 g/kg body weight/day, about 1 ng/kg body weight/day to about 100 ng/kg body weight/day, about 1 ng/kg body weight/day to about 10 ng/kg body weight/day, about 10 ng/kg body weight/day to about 100 mg/kg body weight/day, about 10 ng/kg body weight/day to about 10 mg/kg body weight/day, about 10 ng/kg body weight/day to about 1 mg/kg body weight/day, about 10 ng/kg body weight/day to about 100 g/kg body weight/day, about 10 ng/kg body weight/day to about 10 mg/kg body weight/day, about 10 ng/kg body weight/day to about 1 mg/kg body weight/day, 10 ng/kg body weight/day to about 100 ng/kg body weight/day, about 100 ng/kg body weight/day to about 100 mg/kg body weight/day, about 100 ng/kg body weight/day to about 10 mg/kg body weight/day, about 100 ng/kg body weight/day to about 1 mg/kg body weight/day, about 100 ng/kg body weight/day to about 100 mg/kg body weight/day, about 100 ng/kg body weight/day to about 10 mg/kg body weight/day, about 100 ng/kg body weight/day to about 1 mg/kg body weight/day, about 1 mg/kg body weight/day to about 100 mg/kg body weight/day, about 1 mg/kg body weight/day to about 10 mg/kg body weight/day, about 1 mg/kg body weight/day to about 1 mg/kg body weight/day, about 1 mg/kg body weight/day to about 100 mg/kg body weight/day, about 1 mg/kg body weight/day to about 10 mg/kg body weight/day, about 10 mg/kg body weight/day to about 100 mg/kg body weight/day, about 10 mg/kg body weight/day to about 10 mg/kg body weight/day, about 10 mg/kg body weight/day to about 1 mg/kg body weight/day, about 10 mg/kg body weight/day to about 100 mg/kg body weight/day, about 100 mg/kg body weight/day to about 100 mg/kg body weight/day, about 100 mg/kg body weight/day to about 10 mg/kg body weight/day, about 100 mg/kg body weight/day to about 1 mg/kg body weight/day, about 1 mg/kg body weight/day to about 100 mg/kg body weight/day, about 1 mg/kg body weight/day to about 10 mg/kg body weight/day, about 10 mg/kg body weight/day to about 100 mg/kg body weight/day.

In other embodiments, the trispecific antibody is administered at a dose of 500 g to 20 g every three days, or 25 mg/kg body weight every three days.

In other embodiments, each trispecific antibody is administered in the range of about 10 ng to about 100 ng per individual administration, about 10 ng to about 1 g per individual administration, about 10 ng to about 10 g per individual administration, about 10 ng to about 100 mg per individual administration, about 10 ng to about 1 mg per individual administration, about 10 ng to about 10 mg per individual administration, about 10 ng to about 100 mg per individual administration, about 10 ng to about 1000 mg per injection, about 10 ng to about 10,000 mg per individual administration, about 100 ng to about 1 mg per individual administration, about 100 ng to about 10 mg per individual administration, about 100 ng to about 100 mg per individual administration, about 100 ng to about 1 mg per individual administration, about 100 ng to about 10 mg per individual administration, about 100 ng to about 100 mg per individual administration, about 100 ng to about 1000 mg per injection, about 100 ng to about 10,000 mg per individual administration, about 1 mg to about 10 mg per individual administration, about 1 mg to about 100 mg per individual administration, about 1 mg to about 1 mg per individual administration, about 1 mg to about 10 mg per individual administration, about 1 mg to about 100 mg per individual administration, about 1 mg to about 1000 mg per injection, about 1 mg to about 10,000 mg per individual administration, about 10 mg to about 100 mg per individual administration, about 10 mg to about 1 mg per individual administration, about 10 mg to about 10 mg per individual administration, about 10 mg to about 100 mg per individual administration, about 10 mg to about 1000 mg per injection, about 10 mg to about 10,000 mg per individual administration, about 100 mg to about 1 mg per individual administration, about 100 mg to about 10 mg per individual administration, about 100 mg to about 100 mg per individual administration, about 100 mg to about 1000 mg per injection, about 100 mg to about 10,000 mg per individual administration, about 1 mg to about 10 mg per individual administration, about 1 mg to about 100 mg per individual administration, about 1 mg to about 1000 mg per injection, about 1 mg to about 10,000 mg per individual administration, about 10 mg to about 100 mg per individual administration, about 10 mg to about 1000 mg per injection, about 10 mg to about 10,000 mg per individual administration, about 100 mg to about 1000 mg per injection, about 100 mg to about 10,000 mg per individual administration and about 1000 mg to about 10,000 mg per individual administration. The trispecific antibody may be administered daily, every 2, 3, 4, 5, 6 or 7 days, or every 1, 2, 3 or 4 weeks.

In other particular embodiments, the amount of the trispecific antibody may be administered at a dose of about 0.0006 mg/day, 0.001 mg/day, 0.003 mg/day, 0.006 mg/day, 0.01 mg/day, 0.03 mg/day, 0.06 mg/day, 0.1 mg/day, 0.3 mg/day, 0.6 mg/day, 1 mg/day, 3 mg/day, 6 mg/day, 10 mg/day, 30 mg/day, 60 mg/day, 100 mg/day, 300 mg/day, 600 mg/day, 1000 mg/day, 2000 mg/day, 5000 mg/day or 10,000 mg/day. As expected, the dosage will be dependent on the condition, size, age and condition of the patient.

In certain embodiments, the coding sequences for a trispecific antibody are incorporated into a suitable expression vector (e.g., viral or non-viral vector) for expressing an effective amount of the trispecific antibody in patient with a cell proliferative disorder. In certain embodiments comprising administration of e.g., one or more recombinant AAV (rAAV) viruses, the pharmaceutical composition may comprise the rAAVs in an amount comprising at least $10^{10}$, at least $10^{11}$, at least $10^{12}$, at least $10^{13}$, or at least $10^{14}$ genome copies (GC) or recombinant viral particles per kg, or any range thereof. In certain embodiments, the pharmaceutical composition comprises an effective amount of the recombinant virus, such as rAAV, in an amount comprising at least $10^{10}$, at least $10^{11}$, at least $10^{12}$, at least $10^{13}$, at least $10^{14}$, at least $10^{15}$ genome copies or recombinant viral particles genome copies per subject, or any range thereof.

Dosages can be tested in several art-accepted animal models suitable for any particular cell proliferative disorder.

Delivery methodologies may also include the use of polycationic condensed DNA linked or unlinked to killed viruses, ligand linked DNA, liposomes, eukaryotic cell delivery vehicles cells, deposition of photopolymerized hydrogel materials, use of a handheld gene transfer particle gun, ionizing radiation, nucleic charge neutralization or fusion with cell membranes, particle mediated gene transfer and the like.

In other aspects of this embodiment, a pharmaceutical composition compound disclosed herein reduces the size of a tumor by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a pharmaceutical composition disclosed herein reduces the size of a tumor from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A pharmaceutical composition disclosed herein is in an amount sufficient to allow customary administration to an individual. In aspects of this embodiment, a pharmaceutical composition disclosed herein may be, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg of a pharmaceutical composition. In other aspects of this embodiment, a pharmaceutical composition disclosed herein may be, e.g., at least 5 mg, at least 10 mg, at least 20 mg, at least 25 mg, at least 50 mg, at least 75 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg of a pharmaceutical composition. In yet other aspects of this embodiment, a pharmaceutical composition disclosed herein may be in the range of, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In still other aspects of this embodiment, a pharmaceutical composition disclosed herein may be in the range of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg.

A pharmaceutical composition disclosed herein may comprise a solvent, emulsion or other diluent in an amount sufficient to dissolve a pharmaceutical composition disclosed herein. In other aspects of this embodiment, a pharmaceutical composition disclosed herein may comprise a solvent, emulsion or a diluent in an amount of, e.g., less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v). In other aspects of this embodiment, a pharmaceutical composition disclosed herein may comprise a solvent, emulsion or other diluent in an amount in a range of, e.g., about 1% (v/v) to 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2% (v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20% (v/v), about 6% (v/v) to 10% (v/v), about 8% (v/v) to 50% (v/v), about 8% (v/v) to 40% (v/v), about 8% (v/v) to 30% (v/v), about 8% (v/v) to 20% (v/v), about 8% (v/v) to 15% (v/v), or about 8% (v/v) to 12% (v/v).

The final concentration of a pharmaceutical composition disclosed herein in a pharmaceutical composition disclosed herein may be of any concentration desired. In an aspect of this embodiment, the final concentration of a pharmaceutical composition in a pharmaceutical composition may be a therapeutically effective amount. In other aspects of this embodiment, the final concentration of a pharmaceutical composition in a pharmaceutical composition may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL or at least 500 mg/mL. In other aspects of this embodiment, the final concentration of a pharmaceutical composition in a pharmaceutical composition may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

Aspects of the present specification disclose, in part, treating an individual suffering from cancer. As used herein, the term "treating," refers to reducing or eliminating in an individual a clinical symptom of cancer; or delaying or preventing in an individual the onset of a clinical symptom of cancer. For example, the term "treating" can mean reducing a symptom of a condition characterized by a cancer, including, but not limited to, tumor size, by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with cancer are well known and can be determined by a person of ordinary skill in the art by taking into account factors, including, without limitation, the location of the cancer, the cause of the cancer, the severity of the cancer, and/or the tissue or organ affected by the cancer. Those of skill in the art will know the appropriate symptoms or indicators associated with a specific type of cancer and will know how to determine if an individual is a candidate for treatment as disclosed herein.

In another aspect, a pharmaceutical composition disclosed herein reduces the severity of a symptom of a disorder associated with a cancer. In aspects of this embodiment, a pharmaceutical composition disclosed herein reduces the severity of a symptom of a disorder associated with a cancer by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a pharmaceutical composition disclosed herein reduces the severity of a symptom of a disorder associated with a cancer by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In aspects of this embodiment, a therapeutically effective amount of a pharmaceutical composition disclosed herein reduces a symptom associated with cancer by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a pharmaceutical composition disclosed herein reduces a symptom associated with cancer by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a pharmaceutical composition disclosed herein reduces a symptom associated with cancer by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In yet other aspects of this embodiment, a therapeutically effective amount of a pharmaceutical composition disclosed herein generally is in the range of about 0.001 mg/kg to about 100 mg/kg and administered, for example, every 3, 5, 7, 10 or 14 days. In aspects of this embodiment, an effective amount of a pharmaceutical composition disclosed herein may be, e.g., at least 0.001 mg/kg, at least 0.01 mg/kg, at least 0.1 mg/kg, at least 1.0 mg/kg, at least 5.0 mg/kg, at least 10 mg/kg, at least 15 mg/kg, at least 20 mg/kg, at least 25 mg/kg, at least 30 mg/kg, at least 35 mg/kg, at least 40 mg/kg, at least 45 mg/kg, or at least 50 mg/kg and administered, for example, every 3, 5, 7, 10 or 14 days. In other aspects of this embodiment, an effective amount of a pharmaceutical composition disclosed herein may be in the range of, e.g., about 0.001 mg/kg to about 10 mg/kg, about 0.001 mg/kg/day to about 15 mg/kg, about 0.001 mg/kg to about 20 mg/kg, about 0.001 mg/kg to about 25 mg/kg, about 0.001 mg/kg to about 30 mg/kg, about 0.001 mg/kg to about 35 mg/kg, about 0.001 mg/kg to about 40 mg/kg, about 0.001 mg/kg to about 45 mg/kg, about 0.001 mg/kg to about 50 mg/kg, about 0.001 mg/kg to about 75 mg/kg, or about 0.001 mg/kg to about 100 mg/kg and administered, for example, every 3, 5, 7, 10 or 14 days. In yet other aspects of this embodiment, an effective amount of a pharmaceutical composition disclosed herein may be in the range of, e.g., about 0.01 mg/kg to about 10 mg/kg, about 0.01 mg/kg to about 15 mg/kg, about 0.01 mg/kg to about 20 mg/kg, about 0.01 mg/kg to about 25 mg/kg, about 0.01 mg/kg to about 30 mg/kg, about 0.01 mg/kg to about 35 mg/kg, about 0.01 mg/kg to about 40 mg/kg, about 0.01 mg/kg to about 45 mg/kg, about 0.01 mg/kg to about 50 mg/kg, about 0.01 mg/kg to about 75 mg/kg, or about 0.01 mg/kg to about 100 mg/kg and administered, for example, every 3, 5, 7, 10 or 14 days. In still other aspects of this embodiment, an effective amount of a pharmaceutical composition disclosed herein may be in the range of, e.g., about 0.1 mg/kg to about 10 mg/kg, about 0.1 mg/kg to about 15 mg/kg, about 0.1 mg/kg to about 20 mg/kg, about 0.1 mg/kg to about 25 mg/kg, about 0.1 mg/kg to about 30 mg/kg, about 0.1 mg/kg to about 35 mg/kg, about 0.1 mg/kg to about 40 mg/kg, about 0.1 mg/kg to about 45 mg/kg, about 0.1 mg/kg to about 50 mg/kg, about 0.1 mg/kg to about 75 mg/kg, or about 0.1 mg/kg to about 100 mg/kg and administered, for example, every 3, 5, 7, 10 or 14 days.

Dosing can be single dosage or cumulative (serial dosing), and can be readily determined by one skilled in the art. For instance, treatment of a cancer may comprise a one-time administration of an effective dose of a pharmaceutical composition disclosed herein. Alternatively, treatment of a cancer may comprise multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

In one embodiment, a cancer therapeutic disclosed herein is capable of reducing the number of cancer cells or tumor size in an individual suffering from a cancer by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment. In other aspects of this embodiment, a cancer therapeutic is capable of reducing the number of cancer cells or tumor size in an individual suffering from a cancer by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% as compared to a patient not receiving the same treatment.

In a further embodiment, a cancer therapeutic and its derivatives have half-lives of 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 1 week, 2 weeks, 3 weeks, 4 weeks, one month, two months, three months, four months or more.

In an embodiment, the period of administration of a cancer therapeutic is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In aspects of this embodiment, a therapeutically effective amount of a cancer therapeutic disclosed herein reduces or maintains a cancer cell population and/or tumor cell size in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a cancer therapeutic disclosed herein reduces or maintains a cancer cell population and/or tumor cell size in an individual by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a cancer therapeutic disclosed herein reduces or maintains a cancer cell population and/or tumor cell size in an individual by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

A pharmaceutical composition or cancer therapeutic is administered to an individual. An individual is typically a human being, but can be an animal, including, but not limited to, dogs, cats, birds, cattle, horses, sheep, goats, reptiles and other animals, whether domesticated or not. Typically, any individual who is a candidate for treatment is a candidate with some form of cancer, whether the cancer is benign or malignant, a tumor, solid or otherwise, a cancer call not located in a tumor or some other form of cancer. Among the most common types of cancer include, but are not limited to, bladder cancer, breast cancer, colon and rectal cancer, endometrial cancer, kidney cancer, renal cancer, leukemia, lung cancer, melanoma, non-Hodgkins lymphoma, pancreatic cancer, prostate cancer, stomach cancer and thyroid cancer. Pre-operative evaluation typically includes routine history and physical examination in addition to thorough informed consent disclosing all relevant risks and benefits of the procedure.

In one aspect, a pharmaceutical composition disclosed herein reduces a symptom of a disorder associated with a cancer. In aspects of this embodiment, a pharmaceutical composition disclosed herein reduces a symptom of a disorder associated with a cancer by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a pharmaceutical composition disclosed herein reduces a symptom of a disorder associated with a cancer by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another aspect, a pharmaceutical composition disclosed herein reduces the frequency of a symptom of a disorder associated with a cancer incurred over a given time period. In aspects of this embodiment, a pharmaceutical composition disclosed herein reduces the frequency of a symptom of a disorder associated with a cancer incurred over a given time period by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a pharmaceutical composition disclosed herein reduces the frequency of a symptom of a disorder associated with a cancer incurred over a given time period by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

TABLE 1

| | | | | | | | | |
|---|---|---|---|---|---|---|---|---|
| DLL3 HC and LC Pairs | | | | | | | | |
| Full ab name | VH Seq ID | VL seq ID | HCDR1 Seq ID | HCDR2 Seq ID | HDCR3 Seq ID | LCDR1 Seq ID | LCDR2 Seq ID | LCDR3 Seq ID |
| DLL3.3 | 72 | 76 | 7 | 14 | 27 | 31 | 40 | 47 |
| DLL3.4 | 73 | 77 | 1 | 11 | 22 | 32 | 39 | 54 |
| DLL3.26 | 58 | 78 | 6 | 16 | 24 | 33 | 43 | 49 |
| DLL3.27 | 65 | 78 | 5 | 16 | 24 | 33 | 43 | 49 |
| DLL3.1 | 71 | 79 | 2 | 10 | 22 | 32 | 46 | 55 |
| DLL3.2 | 73 | 79 | 1 | 11 | 22 | 32 | 46 | 55 |
| DLL3.8 | 67 | 80 | 4 | 12 | 23 | 36 | 44 | 48 |
| DLL3.9 | 64 | 81 | 3 | 13 | 28 | 32 | 46 | 54 |
| DLL3.22 | 57 | 82 | 6 | 15 | 25 | 33 | 43 | 51 |
| DLL3.23 | 59 | 82 | 6 | 16 | 25 | 33 | 43 | 51 |
| DLL3.24 | 61 | 82 | 6 | 18 | 25 | 33 | 43 | 51 |
| DLL3.25 | 63 | 82 | 6 | 16 | 25 | 33 | 43 | 51 |
| DLL3.15 | 56 | 83 | 6 | 15 | 24 | 34 | 43 | 49 |
| DLL3.5 | 58 | 83 | 6 | 16 | 24 | 34 | 43 | 49 |
| DLL3.16 | 60 | 83 | 6 | 18 | 24 | 34 | 43 | 49 |
| DLL3.17 | 62 | 83 | 6 | 16 | 24 | 34 | 43 | 49 |
| DLL3.18 | 57 | 84 | 6 | 15 | 25 | 37 | 42 | 51 |
| DLL3.19 | 59 | 84 | 6 | 16 | 25 | 37 | 42 | 51 |
| DLL3.20 | 61 | 84 | 6 | 18 | 25 | 37 | 42 | 51 |

TABLE 1-continued

| | | DLL3 HC and LC Pairs | | | | | |
|---|---|---|---|---|---|---|---|
| Full ab name | VH Seq ID | VL seq ID | HCDR1 Seq ID | HCDR2 Seq ID | HDCR3 Seq ID | LCDR1 Seq ID | LCDR2 Seq ID | LCDR3 Seq ID |

| Full ab name | VH Seq ID | VL seq ID | HCDR1 Seq ID | HCDR2 Seq ID | HDCR3 Seq ID | LCDR1 Seq ID | LCDR2 Seq ID | LCDR3 Seq ID |
|---|---|---|---|---|---|---|---|---|
| DLL3.21 | 63 | 84 | 6 | 16 | 25 | 37 | 42 | 51 |
| DLL3.11 | 56 | 85 | 7 | 15 | 24 | 38 | 42 | 49 |
| DLL3.12 | 58 | 85 | 6 | 16 | 24 | 38 | 42 | 49 |
| DLL3.13 | 60 | 85 | 6 | 18 | 24 | 38 | 42 | 49 |
| DLL3.14 | 62 | 85 | 6 | 16 | 24 | 38 | 42 | 49 |
| DLL3.32 | 70 | 86 | 5 | 16 | 25 | 33 | 43 | 51 |
| DLL3.33 | 70 | 86 | 5 | 16 | 25 | 33 | 43 | 51 |
| DLL3.10 | 69 | 87 | 5 | 16 | 24 | 34 | 43 | 49 |
| DLL3.31 | 69 | 87 | 5 | 16 | 24 | 34 | 43 | 49 |
| DLL3.29 | 68 | 88 | 5 | 17 | 26 | 34 | 43 | 50 |
| DLL3.30 | 68 | 88 | 5 | 17 | 26 | 34 | 43 | 50 |
| DLL3.36 | 68 | 88 | 5 | 17 | 26 | 34 | 43 | 50 |
| DLL3.34 | 74 | 89 | 8 | 19 | 23 | 35 | 45 | 52 |
| DLL3.28 | 66 | 90 | 9 | 21 | 29 | 32 | 39 | 54 |

TABLE 2

| | | DLL3-CD3 | | |
|---|---|---|---|---|
| format | Molecule Name | Seq ID chain1 | seq ID chain2 | seq ID chain3 |
| DLL3-scFvxCD3-scFv | 3D34C | 341 | 239 | — |
| DLL3-scFvxCD3-scFv | 3D35C | 342 | 239 | — |
| DLL3-scFvxCD3-scFv | 3D36C | 346 | 239 | — |
| DLL3-scFvxCD3-scFv | 3D36D | 343 | 239 | — |
| DLL3-scFvxCD3-scFv | 3D36I | 347 | 239 | — |
| DLL3-scFvxCD3-scFv | 3D36K | 348 | 239 | — |
| DLL3-scFvxCD3-scFv | 3D37C | 345 | 239 | — |
| DLL3-scFvxCD3-scFv | 3D44I | 344 | 239 | — |
| DLL3-Fab/CD3-scFv | 3D1 | 273 | 290 | 298 |
| DLL3-Fab/CD3-scFv | 3D10 | 273 | 292 | 296 |
| DLL3-Fab/CD3-scFv | 3D10B | 262 | 292 | 296 |
| DLL3-Fab/CD3-scFv | 3D10C | 263 | 292 | 296 |
| DLL3-Fab/CD3-scFv | 3D11B | 262 | 286 | 310 |
| DLL3-Fab/CD3-scFv | 3D11C | 263 | 286 | 310 |
| DLL3-Fab/CD3-scFv | 3D12B | 262 | 288 | 308 |
| DLL3-Fab/CD3-scFv | 3D12C | 263 | 288 | 308 |
| DLL3-Fab/CD3-scFv | 3D13B | 262 | 289 | 306 |
| DLL3-scFvxCD3-scFv/DLL3-Fab | 3D34-22C | 341 | 276 | 302 |
| DLL3-scFvxCD3-scFv/DLL3-Fab | 3D35-22C | 342 | 276 | 302 |

TABLE 2-continued

| | | DLL3-CD3 | | |
|---|---|---|---|---|
| format | Molecule Name | Seq ID chain1 | seq ID chain2 | seq ID chain3 |
| DLL3-scFvxCD3-scFv/DLL3-Fab | 3D36-22C | 346 | 276 | 302 |
| DLL3-scFvxCD3-scFv/DLL3-Fab | 3D37-22C | 345 | 276 | 302 |
| DLL3-Fab/CD3-scFv | 3D13C | 263 | 289 | 306 |
| DLL3-scFvxCD3-scFv/DLL3-Fab | 3D45I | 347 | 276 | 297 |
| DLL3-Fab/CD3-scFv | 3D14B | 262 | 284 | 312 |
| DLL3-Fab/CD3-scFv | 3D14C | 263 | 284 | 312 |
| DLL3-Fab/CD3-scFv | 3D15C | 263 | 287 | 309 |
| DLL3-Fab/CD3-scFv | 3D16C | 263 | 288 | 307 |
| DLL3-Fab/CD3-scFv | 3D17C | 263 | 289 | 305 |
| DLL3-Fab/CD3-scFv | 3D18C | 263 | 276 | 304 |
| DLL3-Fab/CD3-scFv | 3D19C | 263 | 274 | 304 |
| DLL3-Fab/CD3-scFv | 3D1B | 262 | 290 | 298 |
| DLL3-Fab/CD3-scFv | 3D1C | 263 | 290 | 298 |
| DLL3-Fab/CD3-scFv | 3D1I | 269 | 290 | 298 |
| DLL3-Fab/CD3-scFv | 3D20C | 263 | 278 | 304 |
| DLL3-Fab/CD3-scFv | 3D21C | 263 | 280 | 304 |
| DLL3-scFvxCD3-scFv-Fc-Fc | 3DBM | Benchmark CD3xDLL3 | | |
| DLL3-Fab/CD3-scFv | 3D22C | 263 | 276 | 302 |
| DLL3-Fab/CD3-scFv | 3D22D | 264 | 276 | 302 |
| DLL3-Fab/CD3-scFv | 3D22I | 269 | 276 | 302 |
| DLL3-Fab/CD3-scFv | 3D22K | 271 | 276 | 302 |
| DLL3-Fab/CD3-scFv | 3D23C | 263 | 274 | 302 |

TABLE 2-continued

| | DLL3-CD3 | | | |
|---|---|---|---|---|
| format | Molecule Name | Seq ID chain1 | seq ID chain2 | seq ID chain3 |
| DLL3-Fab/CD3-scFv | 3D24C | 263 | 278 | 302 |
| DLL3-Fab/CD3-scFv | 3D25C | 263 | 280 | 302 |
| DLL3-Fab/CD3-scFv | 3D26C | 263 | 277 | 303 |
| DLL3-Fab/CD3-scFv | 3D27C | 263 | 275 | 303 |
| DLL3-scFvxCD3-scFv/DLL3-Fab | 3D34-16C | 341 | 288 | 307 |
| DLL3-scFvxCD3-scFv/DLL3-Fab | 3D35-16C | 342 | 288 | 307 |
| DLL3-scFvxCD3-scFv/DLL3-Fab | 3D36-16C | 346 | 288 | 307 |
| DLL3-scFvxCD3-scFv/DLL3-Fab | 3D37-16C | 345 | 288 | 307 |
| DLL3-Fab/CD3-scFv | 3D28C | 263 | 279 | 303 |
| DLL3-Fab/CD3-scFv | 3D29C | 263 | 281 | 303 |
| DLL3-Fab/CD3-scFv | 3D30C | 263 | 277 | 301 |
| DLL3-Fab/CD3-scFv | 3D31C | 263 | 275 | 301 |
| DLL3-Fab/CD3-scFv | 3D32C | 263 | 279 | 301 |
| DLL3-Fab/CD3-scFv | 3D33C | 263 | 281 | 301 |
| DLL3-Fab/CD3-scFv | 3D38I | 269 | 283 | 297 |
| DLL3-scFvxCD3-scFv/DLL3-Fab | 3D34-1C | 341 | 290 | 298 |
| DLL3-scFvxCD3-scFv/DLL3-Fab | 3D35-1C | 342 | 290 | 298 |
| DLL3-scFvxCD3-scFv/DLL3-Fab | 3D36-1C | 346 | 290 | 298 |
| DLL3-scFvxCD3-scFv/DLL3-Fab | 3D37-1C | 345 | 290 | 298 |
| DLL3-Fab/CD3-scFv | 3D39I | 269 | 276 | 297 |
| DLL3-Fab/CD3-scFv | 3D4 | 273 | 291 | 295 |
| DLL3-Fab/CD3-scFv | 3D40I | 269 | 285 | 299 |
| DLL3-Fab/CD3-scFv | 3D41I | 269 | 282 | 300 |
| DLL3-Fab/CD3-scFv | 3D42I | 269 | 294 | 313 |
| DLL3-Fab/CD3-scFv | 3D43I | 269 | 293 | 311 |
| DLL3-Fab/CD3-scFv | 3D4B | 262 | 291 | 295 |
| DLL3-Fab/CD3-scFv | 3D4C | 263 | 291 | 295 |
| DLL3-Fab/CD3-scFv | 3D4D | 264 | 291 | 295 |
| DLL3-Fab/CD3-scFv | 3D4E | 265 | 291 | 295 |
| DLL3-Fab/CD3-scFv | 3D4F | 266 | 291 | 295 |
| DLL3-Fab/CD3-scFv | 3D4G | 267 | 291 | 295 |
| DLL3-scFvxCD3-scFv/DLL3-Fab | 3D34-4C | 341 | 291 | 295 |
| DLL3-scFvxCD3-scFv/DLL3-Fab | 3D35-4C | 342 | 291 | 295 |
| DLL3-scFvxCD3-scFv/DLL3-Fab | 3D36-4C | 346 | 291 | 295 |
| DLL3-scFvxCD3-scFv/DLL3-Fab | 3D37-4C | 345 | 291 | 295 |
| DLL3-Fab/CD3-scFv | 3D4H | 268 | 291 | 295 |
| DLL3-Fab/CD3-scFv | 3D4I | 269 | 291 | 295 |
| DLL3-Fab/CD3-scFv | 3D4J | 270 | 291 | 295 |
| DLL3-Fab/CD3-scFv | 3D4K | 271 | 291 | 295 |
| DLL3-Fab/CD3-scFv | 3D4L | 272 | 291 | 295 |
| DLL3-Fab/CD3-scFv | 3D7 | 273 | 292 | 298 |
| DLL3-scFvxCD3-scFv/DLL3-Fab | 3D34-7C | 341 | 292 | 298 |

TABLE 3

| | DLL3-CD28 | | | |
|---|---|---|---|---|
| format | Molecule Name | Seq ID chain 1 | Seq Id chain 2 | seq id chain 3 |
| CD28-Fab/DLL3-scFv | 28D1 | 425 | 426 | 431 |
| CD28-Fab/DLL3-scFv | 28D2 | 425 | 426 | 434 |
| CD28-Fab/DLL3-scFv | 28D3 | 425 | 426 | 432 |
| CD28-Fab/DLL3-scFv | 28D4 | 425 | 426 | 433 |
| CD28-scFv/DLL3-Fab | 28D9 | 427 | 290 | 298 |
| CD28-scFv/DLL3-Fab | 28D10 | 427 | 291 | 295 |
| CD28-scFv/DLL3-Fab | 28D11 | 427 | 292 | 298 |
| CD28-scFv/DLL3-Fab | 28D12 | 427 | 292 | 296 |
| CD28-scFv/DLL3-Fab | 28D13 | 428 | 291 | 295 |
| CD28-scFv/DLL3-Fab | 28D14 | 429 | 291 | 295 |

TABLE 3-continued

| | | DLL3-CD28 | | |
|---|---|---|---|---|
| format | Molecule Name | Seq ID chain 1 | Seq Id chain 2 | seq id chain 3 |
| CD28-scFv/DLL3-Fab | 28D15 | 430 | 291 | 295 |
| CD28-scFv/DLL3-Fab | 28D16 | 430 | 292 | 296 |
| CD28-scFv/DLL3-Fab | 28D17 | 430 | 276 | 302 |
| CD28-scFv/DLL3-Fab | 28D18 | 430 | 290 | 298 |
| CD28-scFv/DLL3-Fab | 28D19 | 430 | 276 | 297 |

TABLE 4

| | | DLL4-41 BB | | |
|---|---|---|---|---|
| format | Molecule Name | Seq ID chain1 | seq ID chain2 | seq Id chain3 |
| 4-1BB-Fab/DLL3-scFv | 4D1 | 437 | 438 | 431 |
| 4-1BB-Fab/DLL3-scFv | 4D2 | 437 | 438 | 434 |
| 4-1BB-Fab/DLL3-scFv | 4D3 | 437 | 438 | 432 |
| 4-1BB-Fab/DLL3-scFv | 4D4 | 437 | 438 | 433 |
| 4-1BB-scFv/DLL3-Fab | 4D5 | 441 | 291 | 295 |
| 4-1BB-scFv/DLL3-Fab | 4D6 | 442 | 291 | 295 |
| 4-1BB-scFv/DLL3-Fab | 4D7 | 445 | 291 | 295 |
| 4-1BB-Fab/DLL3-scFv | 4D8 | 437 | 438 | 466 |
| 4-1BB-Fab/DLL3-scFv | 4D9 | 437 | 438 | 467 |
| 4-1BB-scFv/DLL3-Fab | 4D10 | 446 | 291 | 295 |
| 4-1BB-scFv/DLL3-Fab | 4D11 | 447 | 291 | 295 |
| 4-1BB-scFv/DLL3-Fab | 4D12 | 448 | 291 | 295 |
| 4-1BB-scFv/DLL3-Fab | 4D13 | 444 | 291 | 295 |
| 4-1BB-scFv/DLL3-Fab | 4D14 | 443 | 290 | 298 |
| DLL3-scFv/4-1BB-Fab | 4D15 | 432 | 439 | 440 |
| DLL3scFv-41BBscFv-fc X 41BBfab-fc | 4D16 | 468 | 439 | 440 |
| 4-1BBscFv-41BBscFv-Fc x DLL3Fab-Fe | 4D17 | 469 | 291 | 295 |
| 41BBFab-Fe-DLL3scFv | 4D18 | 470 | 472 | 440 |
| 41BBFab-Fe-DLL3scFv | 4D19 | 471 | 473 | 298 |

TABLE 5

| | | DLL3 × CD3 × CD28 | | |
|---|---|---|---|---|
| format | Molecule Name | Seq Id chain 1 | seq ID Chain 2 | Seq ID chain 3 |
| CD28scFvxCD3scFv/DLL3-Fab | 328D1 | 481 | 276 | 302 |
| CD28scFvxCD3scFv/DLL3-Fab | 328D2 | 481 | 291 | 295 |
| CD28scFvxCD3scFv/DLL3-Fab | 328D3 | 481 | 290 | 298 |
| CD28scFvxCD3scFv/DLL3-Fab | 328D4 | 481 | 276 | 297 |
| DLL3scFvxCD3scFv/CD28-Fab | 328D5 | 343 | 425 | 426 |

TABLE 6

| | | DLL3 × CD3 × CD137 | | |
|---|---|---|---|---|
| format | Molecule Name | Seq ID chain 1 | Seq ID Chain2 | Seq Id chain 3 |
| DLL3-scFvxCD3scFv/4-1BB-Fab | 34D1 | 343 | 437 | 438 |
| DLL3-scFvxCD3scFv/4-1BB-Fab | 34D2 | 341 | 437 | 438 |
| DLL3-scFvxCD3scFv/4-1BB-Fab | 34D3 | 342 | 437 | 438 |
| DLL3-scFvxCD3scFv/4-1BB-Fab | 34D4 | 343 | 437 | 438 |
| DLL3-scFvxCD3scFv/4-1BB-Fab | 34D5 | 346 | 439 | 440 |
| DLL3-scFvxCD3scFv/4-1BB-Fab | 34D6 | 341 | 439 | 440 |
| DLL3-scFvxCD3scFv/4-1BB-Fab | 34D7 | 342 | 439 | 440 |
| DLL3-scFvxCD3scFv/4-1BB-Fab | 34D8 | 343 | 439 | 440 |
| 4-1BBfab-Fc-CD3scFv x 4-1BBFab-Fc-DLL3scFv | 34D9 | 487 | 471 | 438 |
| 4-1BB-FabxFcxCD3scFvxDLL3-scFv/4-1BB-Fab | 34D10 | 494 | 437 | 438 |
| 4-1BB-FabxFcxCD3scFv/4-1BB-FabxFcxDLL3-scFv | 34D11 | 495 | 472 | 440 |
| 4-1BB-FabxFcxCD3scFvxDLL3-scFv/4-1BB-Fab | 34D12 | 496 | 496 | 440 |
| CD3-scFvxFcx4-1BB-scFv/DLL3-Fab-Fc-4-1BBscFv | 34D13 | 486 | 498 | 295 |
| CD3-scFv x DLL3Fab-Fc-4-1BBscFv-4-1BB-scFv | 34D14 | 269 | 499 | 295 |
| DLL3scFv-CD3scFv-Fc-4-1BBscFv x Fc-4-1BBscFv | 34D15 | 497 | 488 | — |
| DLL3-scFvxCD3scFv/Fcx4-1BB-scFvx4-1BB-scFv | 34D16 | 346 | 489 | — |

TABLE 7

| | | | MUC17 VH and VL pairs | | | | | |
|---|---|---|---|---|---|---|---|---|
| AB Name | VH Seq ID | VL Seq ID | HCDR1 Seq ID | HCDR2 Seq ID | HDCR3 Seq ID | LCDR1 Seq ID | LCDR2 Seq ID | LCDR3 SeqID |
| Muc17.7 | 146 | 149 | 92 | 106 | 111 | 118 | 121 | 124 |
| Muc17.21 | 146 | 148 | 92 | 106 | 111 | 118 | 121 | 124 |
| Muc17.22 | 146 | 150 | 92 | 106 | 111 | 118 | 121 | 124 |
| Muc17.23 | 146 | 169 | 92 | 106 | 111 | 118 | 121 | 124 |
| Muc17.24 | 146 | 147 | 92 | 106 | 111 | 118 | 121 | 126 |

TABLE 7-continued

| | | | | | | | | |
|---|---|---|---|---|---|---|---|---|
| | | | | MUC17 VH and VL pairs | | | | |
| AB Name | VH Seq ID | VL Seq ID | HCDR1 Seq ID | HCDR2 Seq ID | HDCR3 Seq ID | LCDR1 Seq ID | LCDR2 Seq ID | LCDR3 SeqID |
| Muc17.2 | 139 | 154 | 93 | 105 | 108 | 116 | 119 | 123 |
| Muc17.1 | 127 | 166 | 94 | 103 | 108 | 116 | 119 | 122 |
| Muc17.10 | 127 | 164 | 94 | 103 | 108 | 116 | 119 | 122 |
| Muc17.11 | 127 | 162 | 94 | 103 | 108 | 116 | 119 | 122 |
| muc17.12 | 127 | 165 | 94 | 103 | 108 | 116 | 119 | 122 |
| Muc17.13 | 127 | 161 | 94 | 103 | 108 | 116 | 119 | 122 |
| Muc17.14 | 127 | 160 | 94 | 103 | 108 | 116 | 119 | 122 |
| Muc17.25 | 140 | 163 | 94 | 103 | 108 | 116 | 119 | 122 |
| Muc17.26 | 140 | 160 | 94 | 103 | 108 | 116 | 119 | 122 |
| Muc17.27 | 140 | 153 | 94 | 103 | 108 | 116 | 119 | 122 |
| Muc17.28 | 140 | 155 | 94 | 103 | 108 | 116 | 119 | 122 |
| Muc17.29 | 129 | 163 | 94 | 103 | 108 | 116 | 119 | 122 |
| Muc17.30 | 129 | 160 | 94 | 103 | 108 | 116 | 119 | 127 |
| Muc17.31 | 129 | 153 | 94 | 103 | 108 | 116 | 119 | 122 |
| Muc17.8 | 127 | 153 | 94 | 107 | 108 | 116 | 119 | 122 |
| Muc17.9 | 127 | 163 | 94 | 103 | 108 | 116 | 119 | 122 |
| Muc17.3 | 141 | 156 | 95 | 104 | 112 | 117 | 120 | 123 |
| Muc17.15 | 145 | 159 | 97 | 101 | 109 | 115| | 119 | 125 |
| Muc17.16 | 145 | 152 | 97 | 101 | 109 | 115 | 119 | 125 |
| Muc17.17 | 128 | 152 | 96 | 99 | 109 | 115 | 119 | 125 |
| Muc17.18 | 145 | 151 | 97 | 101 | 109 | 114 | 119 | 125 |
| Muc17.19 | 145 | 167 | 97 | 101 | 109 | 114 | 119 | 125 |
| Muc17.31 | 136 | 168 | 98 | 101 | 109 | 115 | 119 | 125 |
| Muc17.32 | 135 | 168 | 97 | 101 | 109 | 115 | 119 | 125 |
| Muc17.33 | 135 | 159 | 97 | 101 | 109 | 115 | 119 | 125 |
| Muc17.34 | 135 | 152 | 97 | 101 | 109 | 115 | 119 | 125 |
| Muc17.35 | 133 | 168 | 97 | 101 | 109 | 115 | 119 | 125 |
| Muc17.20 | 131 | 157 | 97 | 100 | 110 | 115 | 119 | 125 |
| Muc17.36 | 134 | 168 | 97 | 101 | 109 | 115 | 119 | 125 |
| Muc17.37 | 132 | 168 | 97 | 101 | 109 | 115 | 119 | 125 |
| Muc17.38 | 137 | 168 | 97 | 101 | 109 | 115 | 119 | 125 |
| Muc17.39 | 144 | 152 | 97 | 99 | 109 | 115 | 119 | 125 |
| Muc17.4 | 145 | 168 | 97 | 101 | 109 | 115 | 119 | 125 |
| Muc17.40 | 144 | 168 | 97 | 99 | 109 | 115 | 119 | 125 |
| Muc17.41 | 144 | 167 | 97 | 99 | 109 | 114 | 119 | 125 |
| Muc17.42 | 143 | 152 | 96 | 101 | 109 | 115 | 119 | 125 |
| Muc17.43 | 143 | 168 | 96 | 101 | 109 | 115 | 119 | 125 |
| Muc17.44 | 143 | 167 | 96 | 101 | 109 | 114 | 119 | 125 |
| Muc17.45 | 130 | 159 | 97 | 101 | 109 | 115 | 119 | 125 |
| Muc17.46 | 142 | 167 | 96 | 99 | 109 | 114 | 119 | 125 |
| Muc17.47 | 142 | 168 | 96 | 99 | 109 | 115 | 119 | 125 |
| Muc17.48 | 136 | 159 | 97 | 101 | 109 | 115 | 119 | 125 |
| Muc17.5 | 131 | 159 | 97 | 100 | 110 | 115 | 119 | 125 |
| Muc17.49 | 136 | 152 | 97 | 101 | 109 | 115 | 119 | 125 |

TABLE 8

TABLE 8-continued

| | MUC17 VH × CD3 | | | |
|---|---|---|---|---|
| format | Molecule Name | SEQID Chain1 | SEQID Chain2 | SEQ ID Chain3 |
| Muc17-Fab/CD3-scFv | 3M23C | 263 | 379 | 387 |
| Muc17-Fab/CD3-scFv | 3M24C | 263 | 379 | 388 |
| Muc17-Fab/CD3-scFv | 3M25C | 263 | 372 | 390 |
| Muc17-Fab/CD3-scFv | 3M26C | 263 | 372 | 389 |
| Muc17-Fab/CD3-scFv | 3M27C | 263 | 377 | 390 |
| Muc17-Fab/CD3-scFv | 3M28C | 263 | 371 | 390 |
| Muc17-Fab/CD3-scFv | 3M29C | 263 | 368 | 382 |
| Muc17-scFvxCD3-scFv-scfc | 3M2C2 | 352 | | |
| Muc17-Fab/CD3-scFv | 3M30C | 263 | 368 | 383 |

| | MUC17 VH × CD3 | | | |
|---|---|---|---|---|
| format | Molecule Name | SEQID Chain1 | SEQID Chain2 | SEQ ID Chain3 |
| Muc17-Fab/CD3-scFv | 3M31C | 263 | 368 | 385 |
| Muc17-Fab/CD3-scFv | 3M32C | 263 | 368 | 384 |
| Muc17-Fab/CD3-scFv | 3M33C | 263 | 368 | 381 |
| Muc17-Fab/CD3-scFv | 3M34C | 263 | 370 | 394 |
| Muc17-Fab/CD3-scFv | 3M35C | 263 | 370 | 391 |
| Muc17-Fab/CD3-scFv | 3M36C | 263 | 370 | 387 |
| Muc17-Fab/CD3-scFv | 3M37C | 263 | 369 | 394 |
| Muc17-Fab/CD3-scFv | 3M38C | 263 | 369 | 391 |
| Muc17-Fab/CD3-scFv | 3M39C | 263 | 369 | 387 |

TABLE 8-continued

| | | | | SEQ |
|---|---|---|---|---|
| | Molecule | SEQID | SEQID | ID |
| format | Name | Chain1 | Chain2 | Chain3 |
| Muc17-Fab/CD3-scFv | 3M40C | 263 | 379 | 394 |
| Muc17-Fab/CD3-scFv | 3M41C | 263 | 379 | 391 |
| Muc17-Fab/CD3-scFv | 3M42C | 263 | 379 | 387 |
| Muc17-Fab/CD3-scFv | 3M43C | 263 | 376 | 399 |
| Muc17-Fab/CD3-scFv | 3M44C | 263 | 376 | 386 |
| Muc17-Fab/CD3-scFv | 3M45C | 263 | 376 | 390 |
| Muc17-Fab/CD3-scFv | 3M46C | 263 | 380 | 399 |
| Muc17-Fab/CD3-scFv | 3M47C | 263 | 380 | 386 |
| Muc17-Fab/CD3-scFv | 3M48C | 263 | 380 | 390 |
| Muc17-Fab/CD3-scFv | 3M49C | 263 | 377 | 399 |
| Muc17-Fab/CD3-scFv | 3M50C | 263 | 377 | 386 |
| Muc17-Fab/CD3-scFv | 3M51C | 263 | 377 | 390 |
| Muc17-Fab/CD3-scFv | 3M52C | 263 | 369 | 397 |
| Muc17-Fab/CD3-scFv | 3M53C | 263 | 369 | 392 |
| Muc17-Fab/CD3-scFv | 3M54C | 263 | 369 | 396 |
| Muc17-Fab/CD3-scFv | 3M55C | 263 | 369 | 398 |
| Muc17-scFv/CD3-Fab | 3M55D | 264 | 369 | 400 |
| Muc17-scFv/CD3-Fab | 3M55I | 269 | 369 | 400 |
| Muc17-scFv/CD3-Fab | 3M55K | 271 | 369 | 400 |
| Muc17-Fab/CD3-scFv | 3M56C | 263 | 374 | 399 |
| Muc17-Fab/CD3-scFv | 3M57C | 263 | 375 | 399 |
| Muc17-Fab/CD3-scFv | 3M58C | 263 | 373 | 399 |
| Muc17-Fab/CD3-scFv | 3M59C | 263 | 378 | 399 |
| Muc17-Fab/CD3-scFv | 3M60C | 263 | 369 | 393 |
| Muc17-scFvxCD3-scFv | 3M61C | 350 | 239 | |
| Muc17-scFvxCD3-scFv | 3M62C | 363 | 239 | |
| Muc17-scFvxCD3-scFv | 3M62D | 362 | 239 | |
| Muc17-scFvxCD3-scFv | 3M62I | 364 | 239 | |
| Muc17-scFvxCD3-scFv | 3M62K | 365 | 239 | |
| Muc17-scFvxCD3-scFv/Muc17-Fab | 3M63C | 350 | 380 | 399 |
| Muc17-scFvxCD3-scFv/Muc17-Fab | 3M64C | 363 | 369 | 398 |
| Muc17-scFv/CD3-Fab | 3M65C | 366 | 263 | 400 |
| Muc17-scFv/CD3-Fab | 3M66C | 367 | 263 | 400 |
| Muc17-scFvxCD3-scFv | 3M67I | 349 | 239 | |
| Muc17-scFvxCD3-scFv | 3M68I | 354 | 239 | |
| Muc17-scFvxCD3-scFv-scfc | 3M8B7 | 351 | | |
| 1MU32scFv-CD3scFv-Fe | | 361 | 239 | |

TABLE 8-continued

| | | | | SEQ |
|---|---|---|---|---|
| | Molecule | SEQID | SEQID | ID |
| format | Name | Chain1 | Chain2 | Chain3 |
| 1MU8AscFv-CD3scFv-Fe | | | 353 | 239 |
| 1MU32scFv(Y32F)-CD3scFv-Fe | | | 360 | 239 |
| 1MU32scFv(M34L)-CD3scFv-Fe | | | 357 | 239 |
| 1 MU32scFv(T58S)-CD3scFv-Fe | | | 359 | 239 |

TABLE 9

MUC17 × CD28

| format | Molecule Name | SeqID Chain1 | SeqID Chain2 | SeqID Chain3 |
|---|---|---|---|---|
| Muc17-Fab/CD28-scFv | 28M1 | 427 | 368 | 384 |
| Muc17-Fab/CD28-scFv | 28M2 | 427 | 380 | 399 |
| Muc17-Fab/CD28-scFv | 28M3 | 427 | 369 | 398 |
| Muc17-Fab/CD28-scFv | 28M4 | 430 | 368 | 384 |
| Muc17-Fab/CD28-scFv | 28M5 | 430 | 380 | 399 |
| Muc17-Fab/CD28-scFv | 28M6 | 430 | 369 | 398 |

TABLE 10

MUC17 × 4188

| format | Molecule Name | Seq ID chain1 | seq ID chain2 | seq Id chain3 |
|---|---|---|---|---|
| Muc17-scfv/4-1BB-Fab | 4M1 | 366 | 437 | 438 |
| Muc17-scfv/4-1BB-Fab | 4M2 | 367 | 437 | 438 |
| Muc17-scfv/4-1BB-Fab | 4M3 | 474 | 437 | 438 |
| 4-1BB-scFv/Muc17-Fab | 4M4 | 451 | 369 | 398 |
| 4-1BB-scFv/Muc17-Fab | 4M5 | 545 | 369 | 398 |
| 4-1BB-scFv/Muc17-Fab | 4M6 | 450 | 369 | 398 |
| 4-1BB-scFv/Muc17-Fab | 4M7 | 451 | 380 | 399 |
| 4-1BB-scFv/Muc17-Fab | 4M8 | 452 | 380 | 399 |

TABLE 10-continued

| | MUC17 × 4188 | | | |
|---|---|---|---|---|
| format | Molecule Name | Seq ID chain1 | seq ID chain2 | seq Id chain3 |
| 4-1BB-scFv/Muc17-Fab | 4M9 | 453 | 369 | 398 |
| 4-1BB-scFv/Muc17-Fab | 4M10 | 447 | 369 | 398 |
| 4-1BB-scFv/Muc17-Fab | 4M11 | 448 | 369 | 398 |
| 4-1BB-scFv/Muc17-Fab | 4M12 | 444 | 369 | 398 |
| 4-1BB-scFv/Muc17-Fab | 4M13 | 443 | 369 | 398 |
| 4-1BB-scFv/Muc17-Fab | 4M14 | 452 | 380 | 399 |
| 4-1BB-scFv/Muc17-Fab | 4M15 | 453 | 380 | 399 |

TABLE 11

| | MUC17 × CD3 × CD28 | | | |
|---|---|---|---|---|
| format | Molecule Name | Seq Id chain 1 | seq ID Chain 2 | Seq ID chain 3 |
| CD3-scFvxCD28-scFv/Muc17-Fab | 328M1 | 480 | 369 | 398 |

TABLE 11-continued

| | MUC17 × CD3 × CD28 | | | |
|---|---|---|---|---|
| format | Molecule Name | Seq Id chain 1 | seq ID Chain 2 | Seq ID chain 3 |
| CD28-scFvxCD3-scFv/Muc17-Fab | 328M2 | 481 | 369 | 398 |
| CD28-scFvxCD3-scFv/Muc17-Fab | 328M3 | 481 | 380 | 399 |
| CD28-scFvxCD3-scFv/Muc17-Fab | 328M4 | 481 | 368 | 384 |
| Muc17-scFvxCD3-scFv/CD28-Fab | 328M5 | 362 | 482 | 483 |

TABLE 12

| | MUC17 × CD3 × CD137 | | | |
|---|---|---|---|---|
| format | Molecule Name | Seq Id chain 1 | seq ID Chain 2 | Seq ID chain 3 |
| Muc17-scFvxCD3-scFv/4-1BB-Fab | 34M1 | 362 | 437 | 438 |
| 4-1BB-scFvxCD3-scFv/Muc17-Fab | 34M2 | 486 | 380 | 399 |
| 4-1BB-scFvxCD3-scFv/Muc17-Fab | 34M3 | 484 | 380 | 399 |
| Muc17-scFvxCD3-scFv/4-1BB-Fab | 34M4 | 362 | 439 | 440 |

TABLE 13

| | CLDN18.2 VH and HL pairs | | | | | | | |
|---|---|---|---|---|---|---|---|---|
| AB Name | VH Seq ID | VL Seq ID | HCDR1 Seq ID | HCDR2 Seq ID | HDCR3 Seq ID | LCDR1 Seq ID | LCDR2 Seq ID | LCDR3 Seq ID |
| CLDN182.1 | 203 | 208 | 175 | 180 | 186 | 188 | 191 | 195 |
| CLDN182.2 | 202 | 207 | 174 | 179 | 187 | 188 | 191 | 194 |
| CLDN182.3 | 198 | 209 | 170 | 181 | 185 | 188 | 191 | 196 |
| CLDN182.7 | 198 | 207 | 170 | 181 | 185 | 188 | 191 | 196 |
| cldn18.2.4 | 201 | 212 | 173 | 176 | 182 | 190 | 191 | 193 |
| CLDN18.8 | 201 | 211 | 173 | 176 | 182 | 190 | 191 | 193 |
| CLDN182.5 | 204 | 210 | 171 | 177 | 184 | 189 | 191 | 192 |
| CLDN182.6 | 206 | 206 | 172 | 178 | 183 | 188 | 191 | 192 |
| CLDN182.9 | 206 | 213 | 172 | 178 | 183 | 188 | 191 | 192 |
| CLDN182.10 | 200 | 212 | 173 | 176 | 182 | 190 | 191 | 193 |
| CLDN182.11 | 200 | 211 | 173 | 176 | 182 | 190 | 191 | 193 |
| CLDN182.12 | 197 | 209 | 170 | 181 | 185 | 188 | 191 | 196 |
| CLDN182.13 | 197 | 207 | 170 | 181 | 185 | 188 | 191 | 196 |
| CLDN182.14 | 199 | 207 | 174 | 179 | 187 | 188 | 191 | 194 |
| CLDN182.15 | 205 | 206 | 172 | 178 | 183 | 188 | 191 | 192 |
| CLDN182.16 | 205 | 213 | 172 | 178 | 183 | 188 | 191 | 192 |

TABLE 14

| | | | | |
|---|---|---|---|---|
| CLDN18.2 × CD3 | | | | |
| format | Molecule Name | SEQID Chain 1 | SEQID Chain 2 | SEQID Chain 3 |
| Cldn-Fab/CD3-scFv | 3C17C | 263 | 407 | 414 |
| Cldn-Fab/CD3-scFv | 3C18C | 263 | 405 | 418 |
| Cldn-Fab/CD3-scFv | 3C19C | 263 | 405 | 417 |
| Cldn-Fab/CD3-scFv | 3C20C | 263 | 404 | 418 |
| Cldn-Fab/CD3-scFv | 3C21C | 263 | 404 | 417 |
| Cldn-Fab/CD3-scFv | 3C22C | 263 | 402 | 415 |
| Cldn-Fab/CD3-scFv | 3C23C | 263 | 402 | 411 |
| Cldn-Fab/CD3-scFv | 3C24C | 263 | 401 | 415 |
| Cldn-Fab/CD3-scFv | 3C25C | 263 | 401 | 411 |
| Cldn-Fab/CD3-scFv | 3C26C | 263 | 408 | 416 |
| Cldn-F&W/CD3-scFv | 3C27C | 263 | 406 | 413 |
| Cldn-F&W/CD3-scFv | 3C28C | 263 | 403 | 413 |
| Cldn-F&W/CD3-scFv | 3C29C | 263 | 410 | 412 |
| Cldn-F&W/CD3-scFv | 3C30C | 263 | 410 | 419 |
| Cldn-F&W/CD3-scFv | 3C31C | 263 | 409 | 412 |
| Cldn-F&W/CD3-scFv | 3C32C | 263 | 409 | 419 |
| Cldn-F&W/CD3-scFv | 3C18D | 264 | 405 | 418 |
| Cldn-F&W/CD3-scFv | 3C18I | 269 | 405 | 418 |
| Cldn-F&W/CD3-scFv | 3C18K | 271 | 405 | 418 |
| Cldn-F&W/CD3-scFv | 3C22D | 264 | 402 | 415 |
| Cldn-F&W/CD3-scFv | 3C22I | 269 | 402 | 415 |
| Cldn-F&W/CD3-scFv | 3C22K | 271 | 402 | 415 |
| Cldn-F&W/CD3-scFv | 3C26D | 264 | 408 | 416 |
| Cldn-F&W/CD3-scFv | 3C26I | 269 | 408 | 416 |
| Cldn-F&W/CD3-scFv | 3C26K | 271 | 408 | 416 |

TABLE 14-continued

| | | | | |
|---|---|---|---|---|
| CLDN18.2 × CD3 | | | | |
| format | Molecule Name | SEQID Chain 1 | SEQID Chain 2 | SEQID Chain 3 |
| Cldn-F&W/CD3-scFv | 3C27D | 264 | 406 | 413 |
| Cldn-F&W/CD3-scFv | 3C27I | 269 | 406 | 413 |
| Cldn-Fab/CD3-scFv | 3C27K | 271 | 406 | 413 |
| CLDN-scFvxCD3-scFv-scfc | 3CBM | | | |

TABLE 15

| | | | | |
|---|---|---|---|---|
| CLDN18.2 × CD28 | | | | |
| format | Molecule Name | SeqID Chain1 | SeqID Chain2 | SeqID Chain3 |
| Cldn-Fab/CD28-scFv | 28C1 | 427 | 405 | 418 |
| Cldn-Fab/CD28-scFv | 28C2 | 427 | 402 | 415 |
| Cldn-Fab/CD28-scFv | 28C3 | 427 | 408 | 416 |
| Cldn-Fab/CD28-scFv | 28C4 | 427 | 406 | 413 |
| Cldn-Fab/CD28-scFv | 28C5 | 430 | 405 | 418 |
| Cldn-Fab/CD28-scFv | 28C6 | 430 | 402 | 415 |
| Cldn-Fab/CD28-scFv | 28C7 | 430 | 408 | 416 |
| Cldn-Fab/CD28-scFv | 28C8 | 430 | 406 | 413 |
| Cldn-Fab/CD28-scFv | 28C9 | 435 | 408 | 416 |
| Cldn-Fab/CD28-scFv | 28C10 | 436 | 408 | 416 |

TABLE 16

| | | | | |
|---|---|---|---|---|
| CLDN18.2 × 4188 | | | | |
| format | Molecule Name | SeqID chain 1 | SeqID chain 2 | SeqID chain 3 |
| Cldn-scfv/4-1BB-Fab | 4C1 | 475 | 437 | 438 |
| Cldn-scfv/4-1BB-Fab | 4C2 | 476 | 437 | 438 |
| Cldn-scfv/4-1BB-Fab | 4C3 | 477 | 437 | 438 |
| Cldn-scfv/4-1BB-Fab | 4C4 | 478 | 437 | 438 |

TABLE 16-continued

| | | | | |
|---|---|---|---|---|
| | | CLDN18.2 × 4188 | | |
| format | Molecule Name | SeqID chain 1 | SeqID chain 2 | SeqID chain 3 |
| Cldn-Fab/4-1BB-scFv | 4C5 | 451 | 405 | 418 |
| Cldn-Fab/4-1BB-scFv | 4C6 | 454 | 405 | 418 |
| Cldn-Fab/4-1BB-scFv | 4C7 | 451 | 408 | 416 |
| Cldn-Fab/4-1BB-scFv | 4C8 | 459 | 408 | 416 |
| Cldn-Fab/4-1BB-scFv | 4C9 | 479 | 408 | 416 |
| Cldn-Fab/4-1BB-scFv | 4C10 | 464 | 408 | 416 |
| Cldn-Fab/4-1BB-scFv | 4C11 | 460 | 408 | 416 |
| Cldn-Fab/4-1BB-scFv | 4C12 | 463 | 408 | 416 |
| Cldn-Fab/4-1BB-scFv | 4C13 | 465 | 408 | 416 |
| Cldn-Fab/4-1BB-scFv | 4C14 | 461 | 408 | 416 |
| Cldn-Fab/4-1BB-scFv | 4C15 | 454 | 408 | 416 |
| Cldn-Fab/4-1BB-scFv | 4C16 | 457 | 408 | 416 |
| Cldn-Fab/4-1BB-scFv | 4C17 | 455 | 408 | 416 |
| Cldn-Fab/4-1BB-scFv | 4C18 | 458 | 408 | 416 |
| Cldn-Fab/4-1BB-scFv | 4C19 | 456 | 408 | 416 |

TABLE 17

| | | | | |
|---|---|---|---|---|
| | | CLDN18.2 × CD3 × CD28 | | |
| format | Molecule Name | Seq ID chain1 | seq ID chain2 | seq Id chain3 |
| CD3-scFvxCD28-scFv/Cldn-Fab | 328C1 | 481 | 405 | 418 |
| CD3-scFvxCD28-scFv/Cldn-Fab | 328C2 | 481 | 402 | 415 |
| CD3-scFvxCD28-scFv/Cldn-Fab | 328C3 | 481 | 408 | 416 |
| CD3-scFvxCD28-scFv/Cldn-Fab | 328C4 | 481 | 406 | 413 |

TABLE 18

| | | | | |
|---|---|---|---|---|
| | | CLDN18.2 × CD3 × CD137 | | |
| format | Molecule Name | Seq ID chain1 | seq ID chain2 | seq Id chain3 |
| CD3-scFvx4-1BB-scFv/Cldn-Fab | 34C1 | 491 | 405 | 418 |
| CD3-scFvx4-1BB-scFv/Cldn-Fab | 34C2 | 490 | 405 | 418 |
| 4-1BB-scFvxCD3-scFv/Cldn-Fab | 34C3 | 486 | 405 | 418 |
| 4-1BB-scFvxCD3-scFv/Cldn-Fab | 34C4 | 484 | 405 | 418 |
| Cldn-scFvxCD3-scFv/4-1BB-Fab | 34C5 | 492 | 437 | 438 |
| Cldn-scFvxCD3-scFv/4-1BB-Fab | 34C6 | 493 | 437 | 438 |
| Cldn-scFvxCD3-scFv/4-1BB-Fab | 34C7 | 492 | 439 | 440 |
| Cldn-scFvxCD3-scFv/4-1BB-Fab | 34C8 | 493 | 439 | 440 |

TABLE 19

| | | | | |
|---|---|---|---|---|
| | | CLDN18.2 × CD28 × CD137 | | |
| format | Molecule Name | Seq ID chain1 | seq ID chain2 | seq Id chain3 |
| CD28-scFvx4-1BB-scFv/Cldn-Fab | 284C1 | 500 | 405 | 418 |
| CD28-scFvx4-1BB-scFv/Cldn-Fab | 284C2 | 501 | 405 | 418 |
| 4-1BB-scFvxCD28-scFv/Cldn-Fab | 284C3 | 502 | 405 | 418 |
| 4-1BB-scFvxCD28-scFv/Cldn-Fab | 284C4 | 503 | 405 | 418 |

EXAMPLES

The compositions and methods described herein will be further understood by reference to the following examples, which are intended to be purely exemplary. The compositions and methods described herein are not limited in scope by the exemplified embodiments, which are intended as illustrations of single aspects only. Any methods that are functionally equivalent are within the scope of the invention. Various modifications of the compositions and methods described herein in addition to those expressly described herein will become apparent to those skilled in the art from the foregoing description and accompanying figures. Such modifications fall within the scope of the invention.

Example 1

Humanized Anti-DLL3 Antibodies Binding to Human and Cynomolgus DLL3 Expressing CHO Cells To evaluate the ability of anti-DLL3 antibodies to bind, human serial dilutions of the anti-DLL3 antibodies were added to CHO-K1 cells (20,000 cells/well) over-expressing human or cyno DLL3. The mixtures were incubated at 4° C. for 20 minutes, washed 3 times, and stained with the secondary antibody, PE labeled F(ab')2-Goat anti-human IgG Fc (Thermo H10104) at 4° C. for 20 minutes. Cells were washed and resuspended in 7-Amino-Actinomycin D (7-AAD) solution and fixed in 10% neutral buffered formalin solution for 15 minutes before analysis with the iQue Intellicyt system. FIG. 2A is a graph of the concentration (nM) versus the mean fluorescence intensity.

Four humanized antibodies were used in this example (DLL3.1, DLL3.2, DLL3.3, DLL3.4). The experiment was repeated with cynomolgus monkey DLL3 expressing CHO cells. FIG. 2B is a graph of the concentration (nM) of the antibodies versus the mean fluorescence intensity for binding to the cells.

Example 2

Anti-DLL3Scfv-Fc Binding to huDLL3 Expressing CHO Cells

Figure 3:
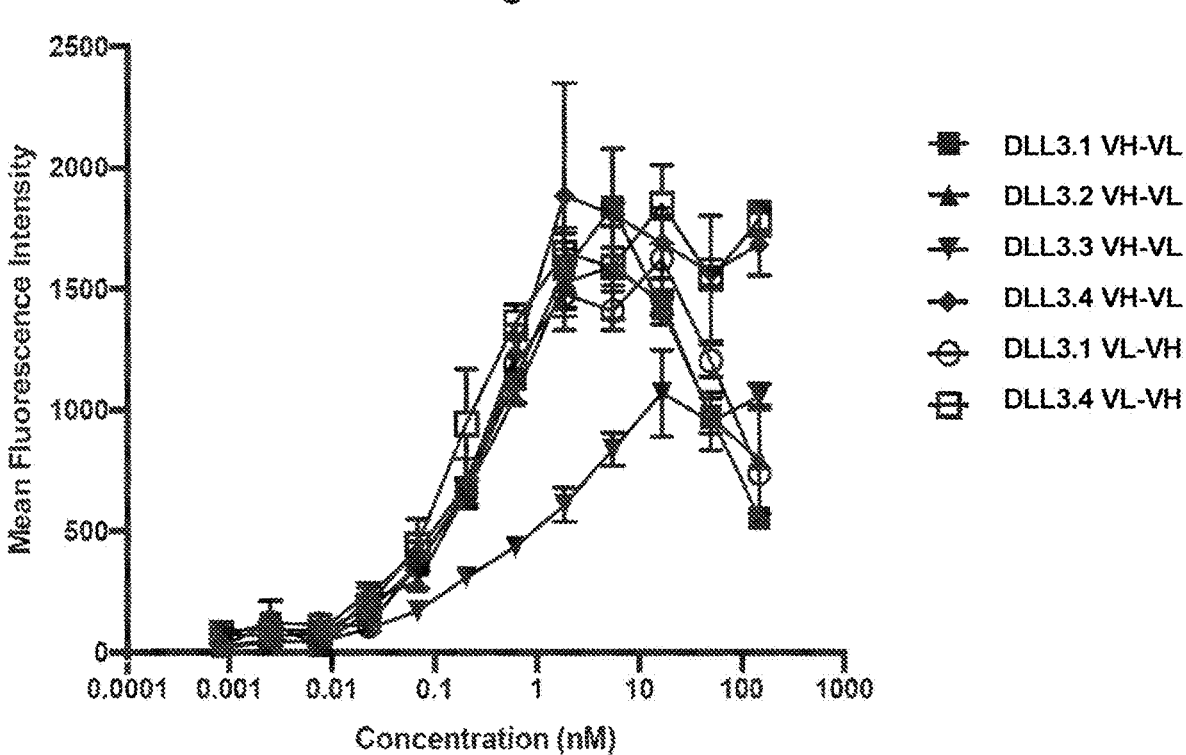
FIG. 3 is a graph that demonstrates the binding of anti-DLL3 scfv-Fc to human DLL3 expressing CHO cells.

The experiment was repeated to evaluate the ability of anti-DLL3scfv-Fc antibody fragment to bind human DLL3. FIG. 3 is a graph of the concentration (nM) of the DLL3 molecules versus the mean fluorescence intensity for binding to the cells. Six antibody fragments were used in this example (DLL3.1 VH-VL, DLL3.2 VH-VL, DLL3.3 VH-VL, DLL3.4 VH-VL, DLL3.1 VL-VH and DLL3.4 VL-VH).

Example 3

CD28Scfv-CD3scFv-Fc×DLL3-Fab-Fc Trispecific Molecule 328D3 Activates PBMCs to Secrete IFN Gamma in the Presence of CHO-DLL3 Cells to Higher Levels than the CD3Scfv-Fc×DLL3Fab-Fc Bispecific Molecule 3D11 or CD28Scfv-Fc×DLL3Fab-Fc Bispecific Molecule 28D18

Figure 4:
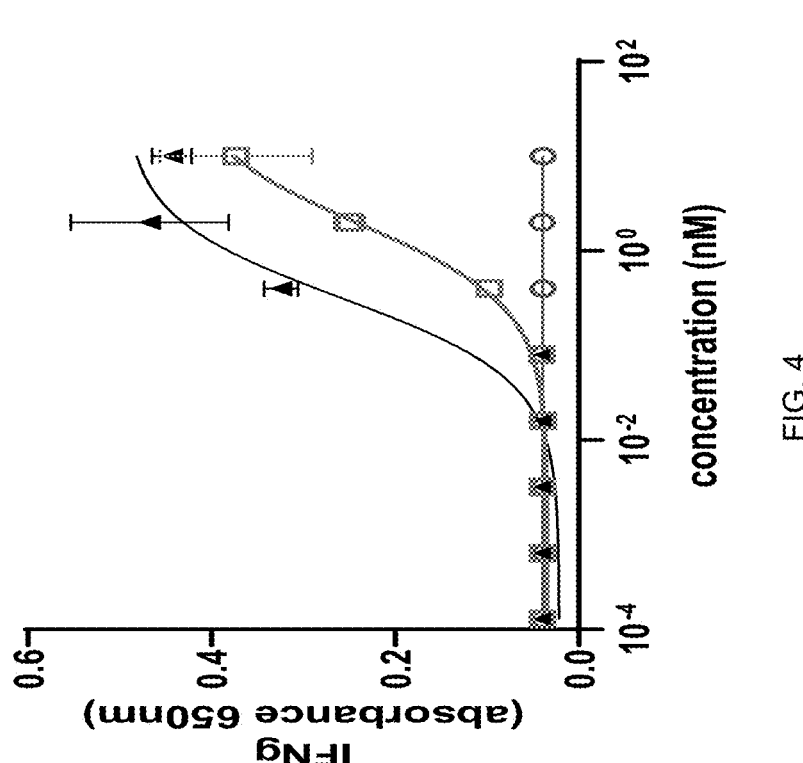
FIG. 4 is a graph that demonstrates CD28scfv-CD3scFv-FcxDLL3-Fab-Fc trispecific molecule 328D3 activates PBMCs to secrete IFN gamma in the presence of CHO-DLL3 cells to higher levels than the CD3scfv-FcxDLL3Fab-Fc bispecific molecule 3D1I or CD28scfv-FcxDLL3Fab-Fc bispecific molecule 28D18.

FIG. 4 is a graph of concentration (nM) of the molecules versus the IFNgamma as detected by ELISA (absorbance at 650 nm). The ELISA utilized high protein-binding 96-well plates that were coated overnight with 50 uL of mouse anti-human IFNgamma capture antibody at a concentration of 2 µg/ml. Plates were washed with PBS+0.05% Tween-20 (PBST) and blocked with 200 ul PBS with 1% BSA. After washing, the coated plates were incubated for 120 minutes with 50 uL of the supernatant from the PBMC:Target cell cultures stimulated with the molecules. Plates were washed, and then incubated for 60 minutes with 50 µL of biotinylated mouse anti-human IFNgamma detection antibody at a concentration of 0.5 µg/ml. Plates were washed and incubated with streptavidin-HRP for 20 minutes. After washing, captured IFNgamma was quantified using 3,3',5,5'-tetramethyl-benzidine (TMB)

Example 4

CD28Scfv-CD3scFv-Fc×DLL3-Fab-Fc Trispecific Molecule 328D2 Activates PBMCs to Secrete IFNgamma in the Presence of CHO-DLL3 Cells to Higher Levels than the CD3Scfv-Fc×DLL3Fab-Fc Bispecific Molecule 3D41 or CD28Scfv-Fc×DLL3Fab-Fc Bispecific Molecule 28D15

FIG. 5 is a graph of concentration (nM) of the molecules versus the IFNg (absorbance at 650 nm) as detected by ELISA as described in Example 3.

Example 5

CD28Scfv-CD3scFv-Fc×DLL3-Fab-Fc Trispecific Molecule 328D1 Activates PBMCs to Secrete IFNgamma in the Presence of CHO-DLL3 Cells to Higher Levels than the CD3Scfv-FcxDLL3Fab-Fc Bispecific Molecule 3D221 or CD28Scfv-FcxDLL3Fab-Fc Bispecific Molecule 28D17.

FIG. 6 is a graph of concentration (nM) of the molecules versus the IFNg (absorbance at 650 nm) as detected by ELISA as described in Example 3.

Example 6

CD28Scfv-CD3scFv-Fc×DLL3-Fab-Fc Trispecific Molecules 328D4 and 328D5 Activate PBMCs to Secrete More IL-2 in the Presence of NCI-H82 Cells Greater than the CD3Scfv-Fc×DLL3Fab-Fc Bispecific, 3D39I FIG. 7 is a graph of concentration (nM) versus the IFNg (absorbance at 650 nm). After 48 hours of culture, T cell activation was measured as an increase in IL-2 secreted into the medium. IL-2 secretion was measured using an IL-2 ELISA. The ELISA utilized high protein-binding 96-well plates that were coated overnight with 50 µL of mouse anti-human IL-2 capture antibody at a concentration of 2 µg/ml. Plates were washed with PBS+0.05% Tween-20 (PBST) and blocked with 200 µL PBS with 1% BSA. After washing, the coated plates were incubated for 120 minutes with 50 µL of the supernatant from the PBMC:Target cell cultures stimulated with bispecific molecules. Plates were washed, and then incubated for 60 minutes with 50 µL of biotinylated mouse anti-human IL-2 detection antibody at a concentration of 0.5 µg/ml. Plates were washed and incubated with streptavidin-HRP for 20 minutes. After washing, captured IL-2 was quantified using 3,3',5,5'-tetramethylben-zidine (TMB).

Example 7

MUC17×CD3 Bispecifics Bind Muc17-CHOK1 and ASPC1 Cells

Seven humanized antibodies, 1MU11A, 1MU32A, 1MU36A, 1MU16A, 1MU37A, 1MU43A, and 1MU47A, were assessed for the ability to bind to CHO-K1 cells expressing the membrane proximal fragment of MUC17.

Figures 11A, 11B:
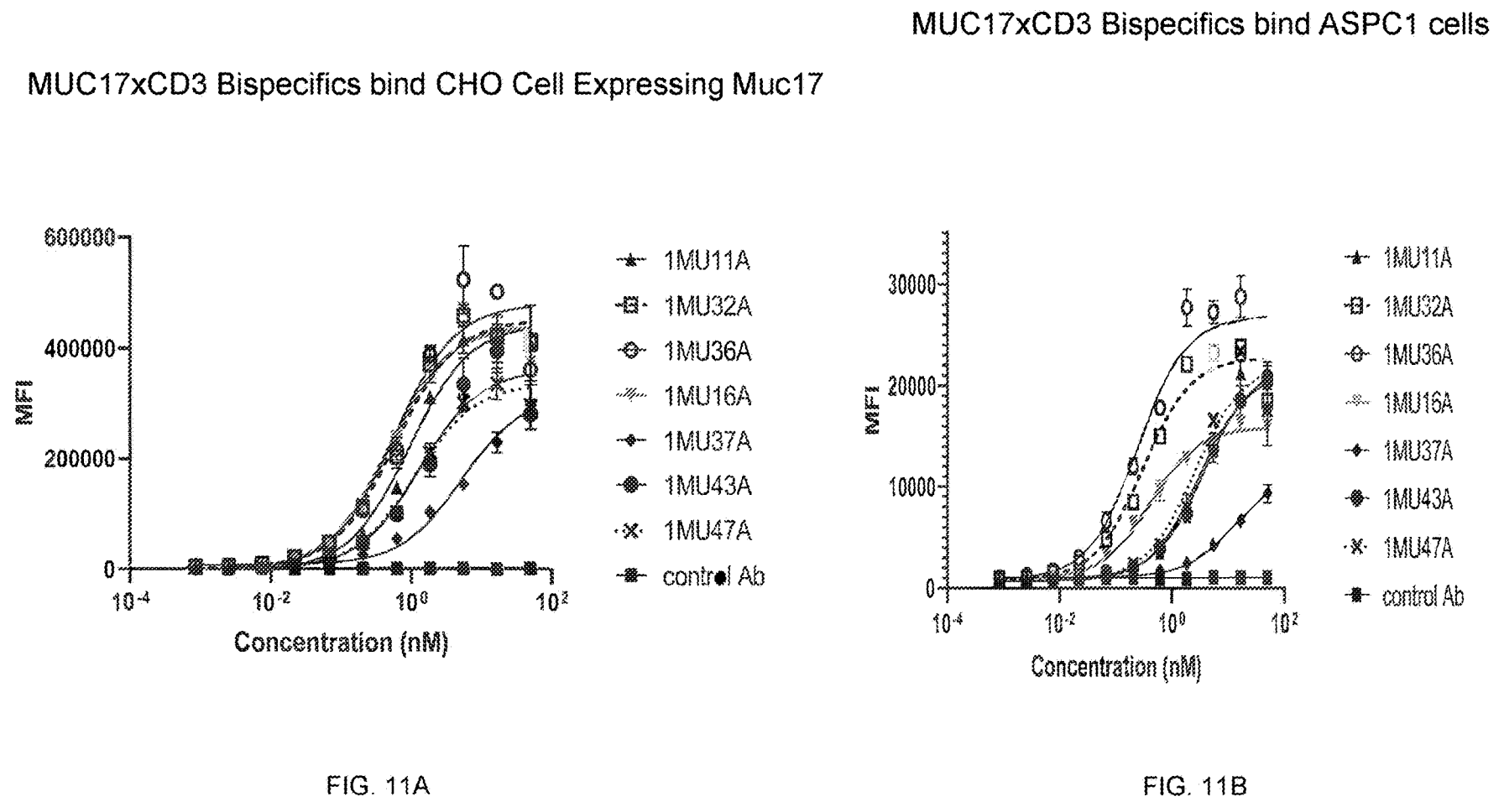

To evaluate the ability of anti-MUC17 antibodies to bind cell expressed MUC17, serial dilutions of the anti-MUC17 antibodies were added to the MUC17 expressing CHO-K1 cells at a concentration of 20,000 cells/well. The antibody:cell mixtures were incubated at 4° C. for 20 minutes, washed 3 times, and stained with the secondary antibody, PE labeled F(ab')2-Goat anti-human IgG Fc (Thermo H10104) at 4° C. for 20 minutes. Cells were washed and resuspended in 7-Amino-Actinomycin D (7-AAD) solution and fixed in 10% neutral buffered formalin solution for 15 minutes before analysis with the iQue Intellicyt system. FIG. 11A is a graph of the concentration (nM) versus the mean fluorescence intensity (MFI) of binding to MUC17-CHO cells.

The experiment was repeated with APSC1 cells, which endogenously express full length human MUC17. FIG. 11B shows a graph of the concentration (nM) versus the mean fluorescence intensity (MFI) for the antibodies binding to the ASPC1 cells.

Example 8

Hu1MU11A and Hu1MU32A Retain Muc17 Binding Activity in the Scfv Format

Figure 12:
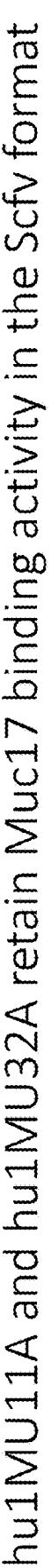
FIG. 12 graph showing hu1MU11A and hu1MU32A retain Muc17 binding activity in the Scfv format.

FIG. 12 is a graph of concentration (nM) of the Fab-Fc and Scfv-Fc versions of the molecules versus absorbance at 650 nm for binding to MUC17.

Example 9

Figure 13:
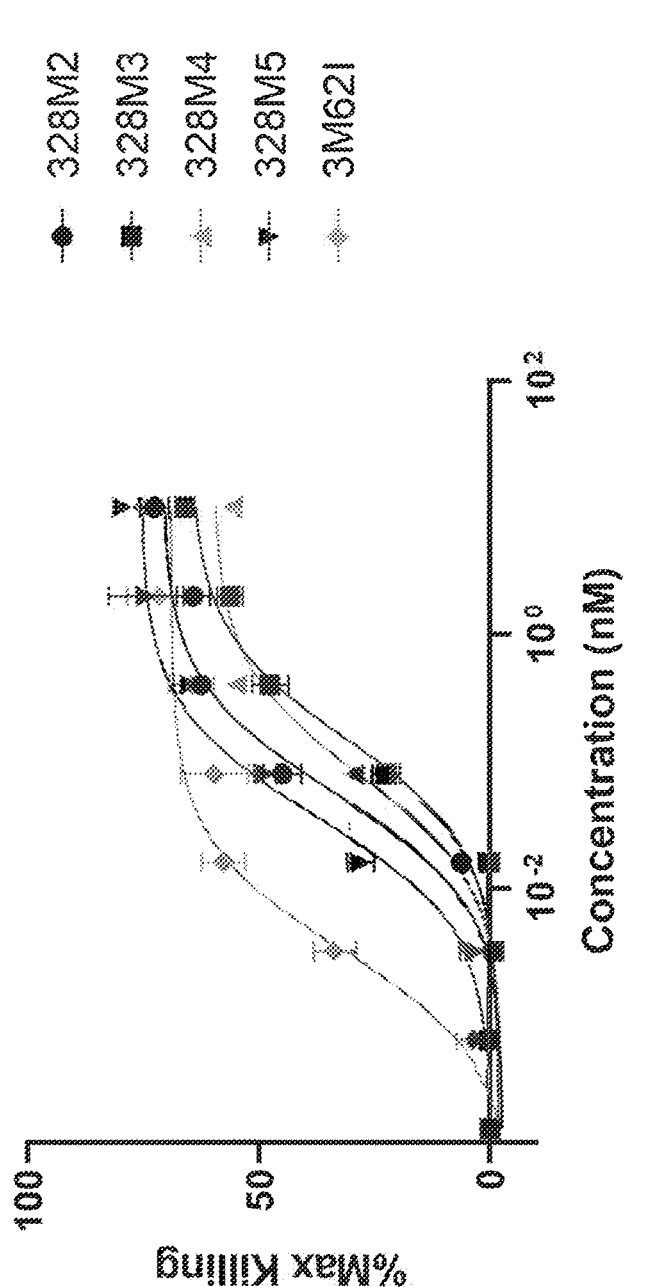
FIG. 13 is a graph that demonstrates CD3xCD28xMuc17 trispecific molecules have similar maximum killing of ASPC1 cells by PBMCs as the CD3 bispecific 3M62I.

CD3×CD28×Muc17 Trispecific Molecules have Similar Maximum Killing of ASPC1 Cells by PBMCs as the CD3 Bispecific 3M62I The experiment was conducted to evaluate the ability of human peripheral mononuclear (PBMCs) effector cells to kill Muc17 expressing CHO target cells when stimulated by MUC17×CD3×CD28 trispecific molecules. Cell cytotoxicity was determined as the amount of lactate dehydrogenase (LDH) released from damaged cells as a percent of the total LDH release with 1% Triton-X (Max Killing) added to the cell mixtures at time 0. For the cytotoxicity assays, target (MUC17-CHO or ASPC1) and effector cells (human PBMCs) were suspended in 200 ul of medium containing 10% serum at an effector to target ratio of 10:1, in a 96-well plate. Dilutions of the bispecific molecules were added to the cultures in triplicate. The 96-well plates were cultured at 37° C. for 48 hours. The cells were then centrifuged at 250×g for 10 min, and 100 μl of the supernatant plus were transferred into corresponding wells of an optically clear 96-well plate containing 100 μl LDH assay reagent per well. The plates were then incubated for up to 30 min at room temperature. The absorbance of all samples was measured at 490-500 nm using a microtiter plate reader. FIG. 13 is a graph of the concentration (nM) of the molecules versus % of maximum killing.

Example 10

Figure 14:
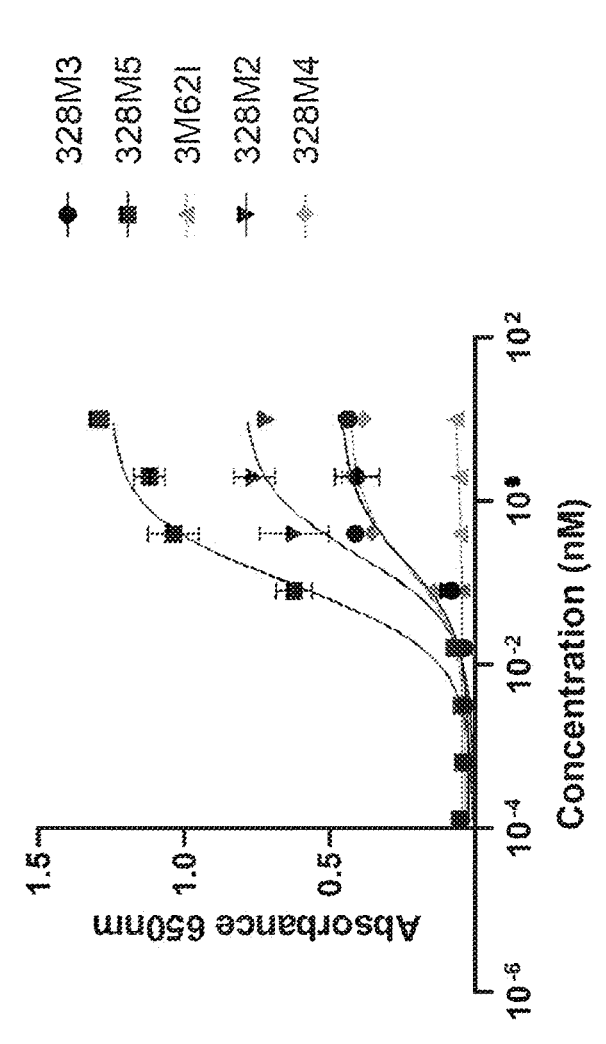
FIG. 14 is a graph that demonstrates Muc17xCD3xcD28 Trispecific molecules 328M2,328M 3, 328M4, and 328M5 activate PBMCs in the presence of ASPC1 cells to secrete IL-2 at levels higher than that of the CD3 bispecific, 3M62I.

Muc17×CD3×cD28 Trispecific Molecules 328M2, 328M 3, 328M 4, and 328M 5 Activate PBMCs in the Presence of ASPC1 Cells to Secrete IL-2 at Levels Higher than that of the CD3 Bispecific, 3M62I FIG. 14 is a graph of concentration (nM) of the molecules versus absorbance at 650 nm from the ELISA to detect secreted IL-2 in the media as described in Example 6.

Example 11

Figure 15:
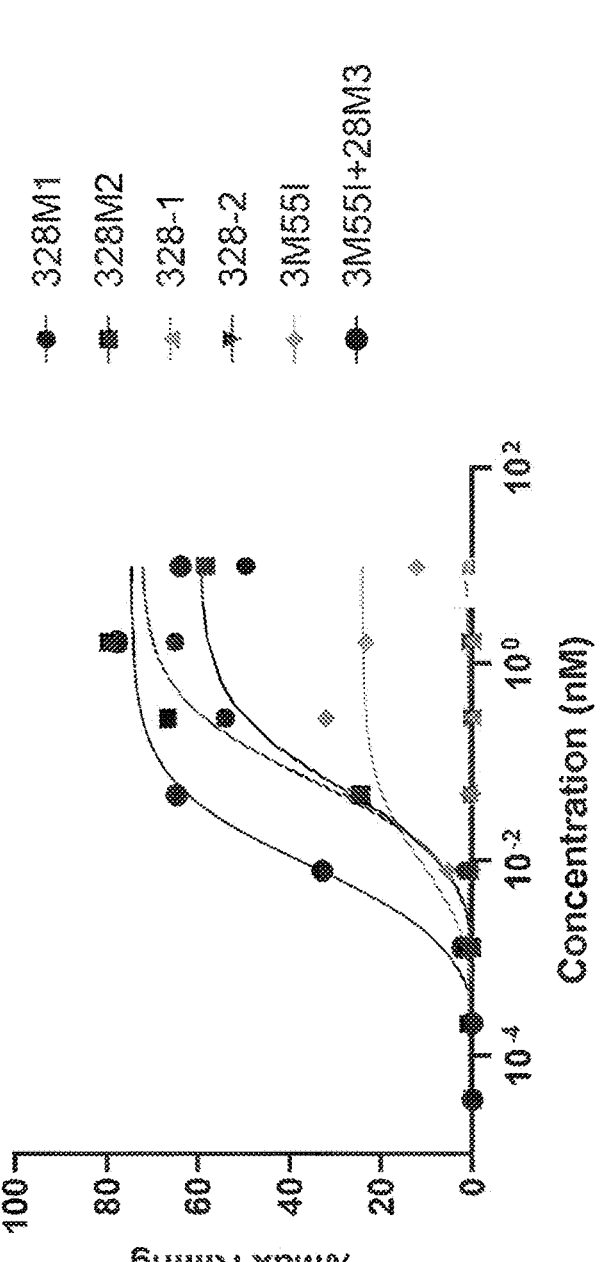
FIG. 15 is a graph that demonstrates CD3ScfvxCD28-scFvxMuc17Fab trispecific molecules 328M1 and 328M2 activate T-cells to kill MUC17-CHO cells better than the CD3 bispecific 3M55I, and similar to the combination of CD3 and CD28 bispecifics, 3M55I+28M3.

CD3Scfv×CD28SScfv×MUC17-Fab trispecific molecules 328MI and 328M2 activate T-cells to kill MUC17-CHO cells better than the CD3 bispecific 3M55I, and similar to the combination of CD3 and CD28 bispecifics, 3M55I+28M3. FIG. 15 is a graph of the concentration (nM) of the molecules versus % of maximum killing.

Example 12

CD28Scfv×CD3Scfv×Muc17Fab Trispecific 328M2 Activates PBMCs to Express CD25 Only when in the Presence of Muc17 Expressing CHO Cells and Cannot Activate without Muc17 Target Cells. In Contrast the CD3scFv×CD28scFv×Muc17-Fab Trispecific 328M1 is Able to Non-Specifically Activate Cells in the Absence of Muc17, Similarly to the Bispecific Lacking Muc17 Binding, 328-1

FIG. 16A shows the expression of CD25(MFI) stimulated by increasing concentrations of the bispecific and trispecific molecules T cells when PBMCs are in the presence of MUC17 expressing CHO cells, showing both 328M1 and 328M2 active T cells to express CD25 similarly.

FIG. 16B shows the expression of CD25(MFI) stimulated by increasing concentrations of the bispecific and trispecific molecules T cells when PBMCs are in the presence of parental CHO cells, showing 328M1 stimulates T cells whereas 328M2 can not stimulate without MUC17 expressing cells. Similarly, 328-1, which lacks the anti-MUC17 Fab, also activates T cells in the absence of MUC17 target cells, whereas 328-2 cannot.

Versions-1 have the configuration CD3Scfv-CD28Scfv-Fc×MUC17Fab-Fc or Fc and versions-2 have the configuration CD28scfv-CD3Scfv-Fc×MUC17Fab-Fc or Fc. This indicates the version-2 configuration, CD28scfv-CD3Scfv-Fc, has improved properties over the version-1 configuration, CD3Scfv-CD28Scfv-Fc, because version-2 configuration requires the presence of target cells to activate T cells and thus is less likely to cause non-specific activation of T cells and potential toxicity.

Example 13

CD137×CD3×Muc17 Trispecific Molecules 34M1 and 34M4 Increase CD4 and CD8 T Cell Numbers when PBMCs are Cultured with Muc17 Expressing CHO Cells to a Greater Level than the Benchmark CD3 Bispecific 3M8B7

Figures 17A, 17B:
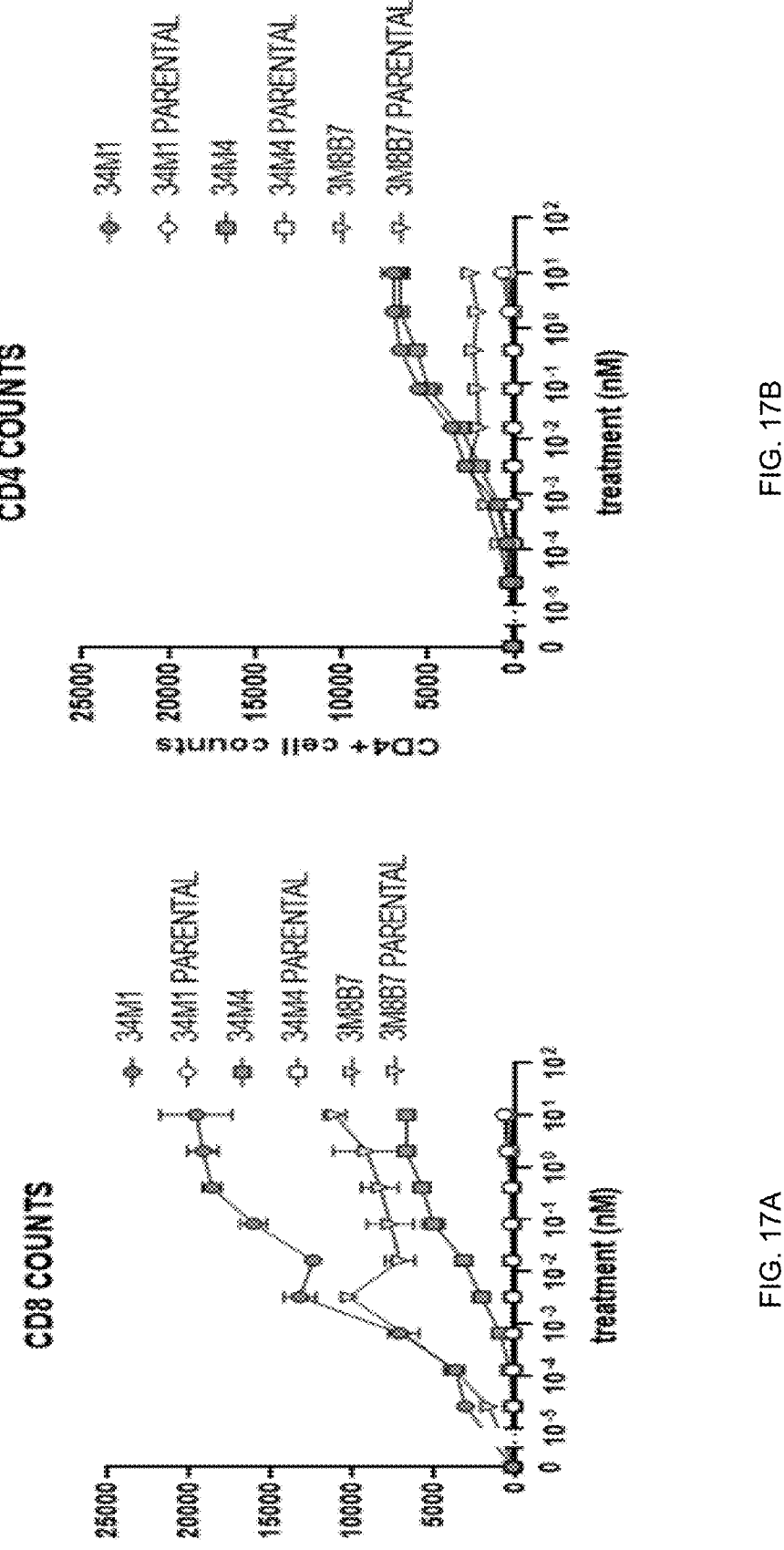
FIGS. 17A and 17B are graphs that demonstrates CD137x CD3xMuc17 trispecific molecules 34M1 and 34M4 increase CD4 and CD8 T cell numbers when PBMCs are cultured with Muc17 expressing CHO cells to a greater level than the benchmark CD3 bispecific 3M8B7.

FIG. 17A is a graph of concentration of the molecules in nM (treatment (nM)) versus CD8+ cell counts as determined by staining the cells with fluorescently labeled antibodies against CD3 and CD4 or CD8 and assessment by flow cytometry.

FIG. 17B is a graph of concentration of the molecules in nM (treatment (nM)) versus CD4+ cell counts as determined by staining the cells with fluorescently labeled antibodies against CD3 and CD4 or CD8 and assessment by flow cytometry.

Example 14

Trispecific Molecules 328C1, 328C 2, 328C3, 328C4 Activate T-Cells to Secrete IL-2 Better to a Greater Level than the 3C27I CD3×CIdn18.2 Bite Alone.

Figure 21:
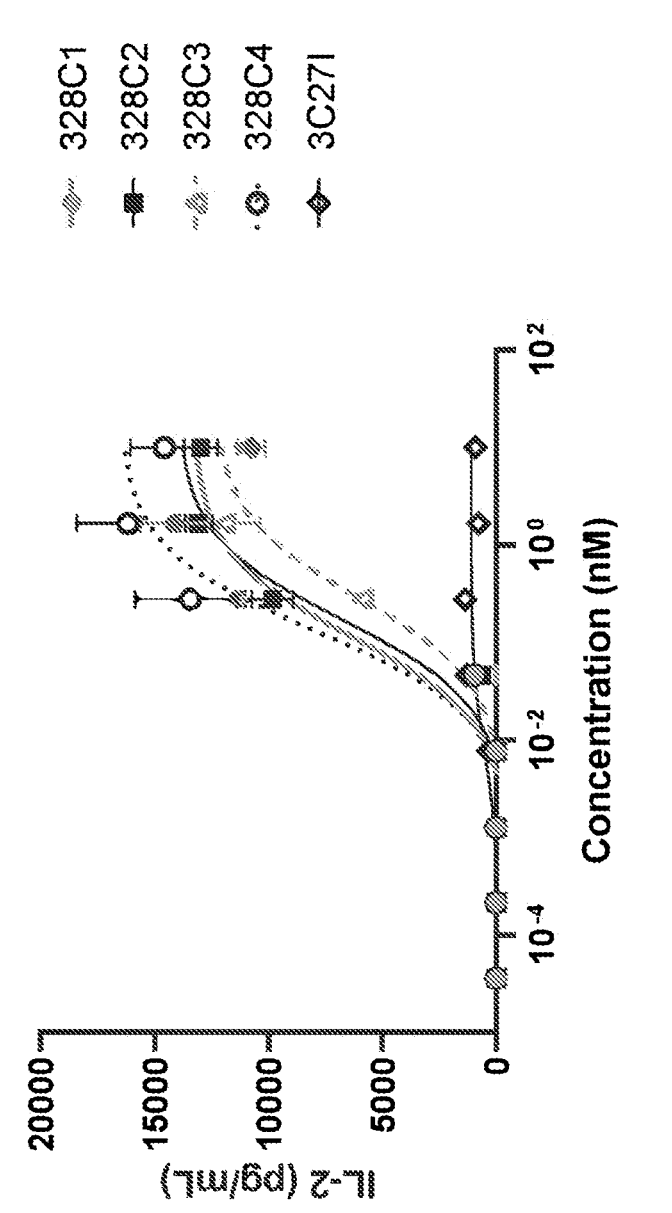
FIG. 21 is a graph that demonstrates trispecific molecules 328C1, 328C 2, 328C3, 328C4 activate T-cells to secrete IL-2 better to a greater level than the 3C27I CD3x CLDN18.2 bispecific alone.

FIG. 21 is a graph of concentration (nM) of the molecules versus concentration of secreted IL-2 (pg/mL) as determined by ELISA.

Example 15

Figure 22:
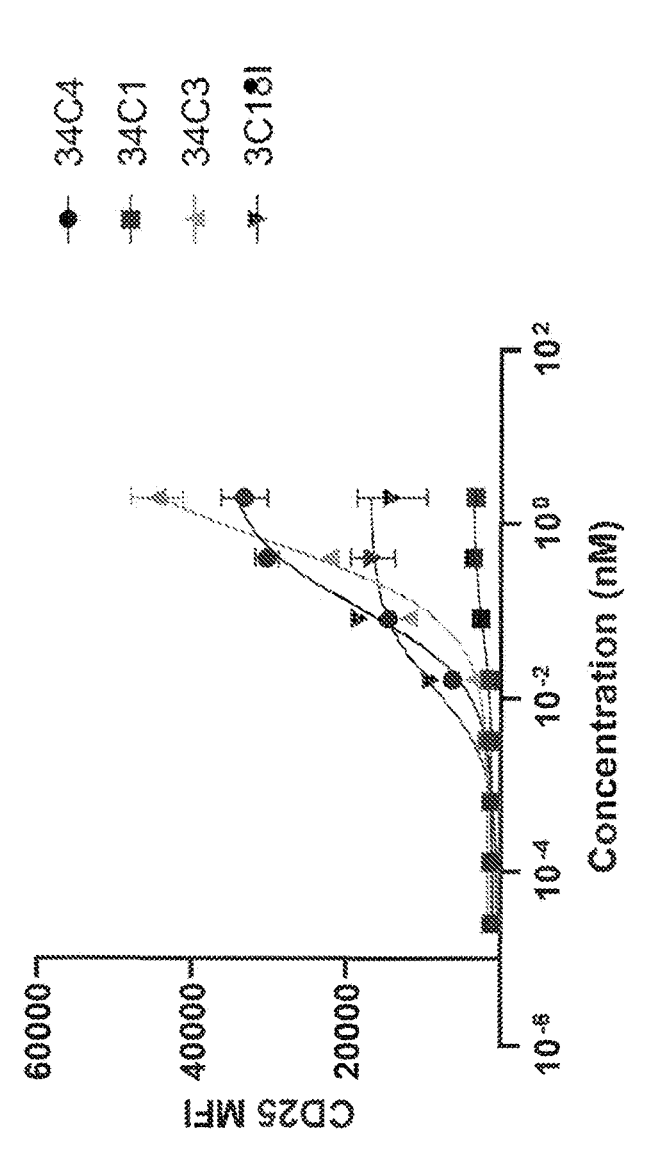
FIG. 22 is a graph that demonstrates CD3xCD137x CLDN18.2 trispecific molecules 34C4 and 34C3 activate PBMCs in the presence of SNU-601 cells to express more CD25 than bispecific 3C18I.

CD3×CD137×CLDN18.2 Trispecific Molecules 34C4 and 34C3 Activate PBMCs in the Presence of SNU-601 Cells to Express More CD25 than 3C18I FIG. 22 is a graph of the concentration (nM) of the molecules versus CD25 mean fluorescence intensity (MFI) on CD3+ T cells from the cultures.

Example 16

Figure 23:
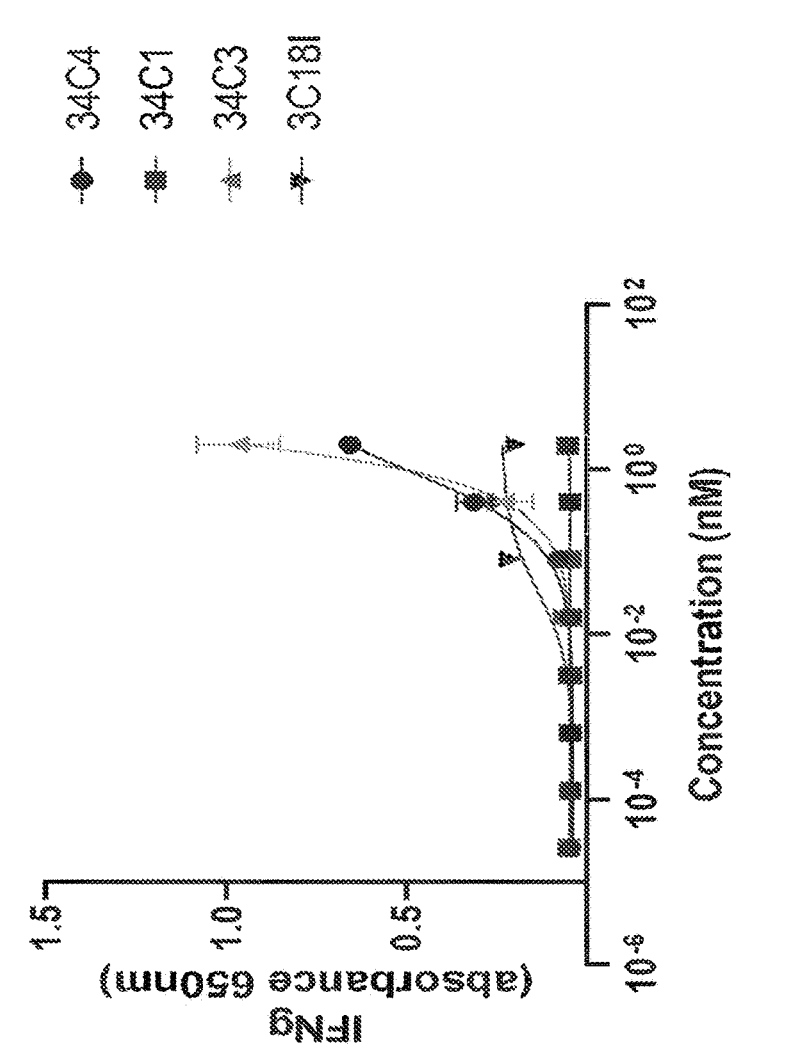
FIG. 23 is a graph that demonstrates CD3xCD137x CLDN18.2 trispecific molecules 34C4 and 34C3 activate PBMCs in the presence of SNU-601 cells to secrete more IFNgamma than bispecific 3C18I alone.

CD3×CD137×CLDN18.2 Trispecific Molecules 34C4 and 34C3 Activate PBMCs in the Presence of SNU-601 Cells to Secrete More IFNgamma than 3C18I Alone FIG. 23 is a graph of the concentration (nM) of the molecules versus IFNg (absorbance at 650 nm) as determined by ELISA.

Example 17

CD3×CD137×CLDN18.2 Trispecific 34C3 Increases CD8 T Cell Numbers Beyond What is Stimulated by the CD3 T Cell Engager 3C27I in the Presence of CHO Cells Expressing CLDN18.2

Figure 24:
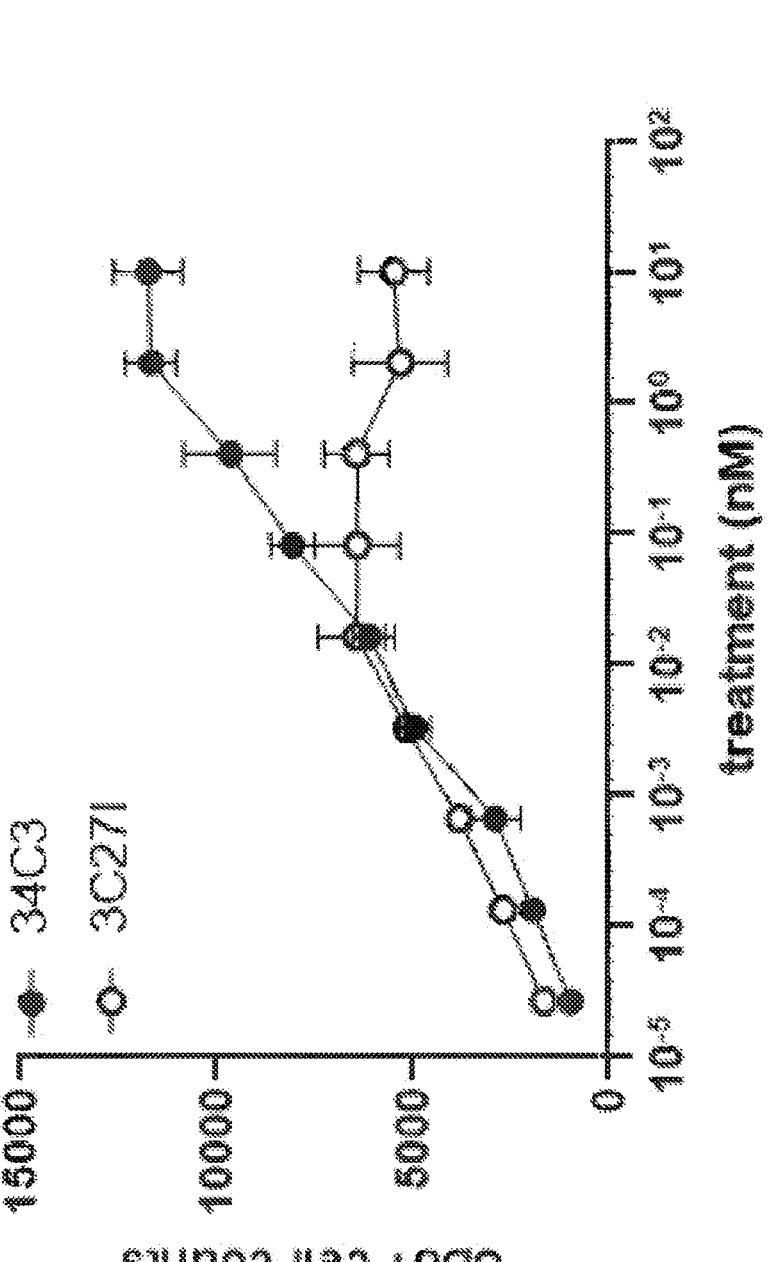
FIG. 24 is a graph that demonstrates CD3xCD137x CLDN18.2 trispecific 34C3 increases CD8 T cell numbers beyond what is stimulated by the CD3 T cell engager 3C27I in the presence of CHO cells expressing CLDN18.2.

FIG. 24 is a graph of the concentration of the molecules in nM (treatment (nM)) versus CD8+ cell counts as determined by flow cytometry from the cultures.

The therapeutic method of the present specification may include the step of administering the composition including the antibody at a pharmaceutically effective amount. The total daily dose should be determined through appropriate medical judgment by a physician, and administered once or several times. The specific therapeutically effective dose level for any particular patient may vary depending on various factors well known in the medical art, including the kind and degree of the response to be achieved, concrete compositions according to whether other agents are used therewith or not, the patient's age, body weight, health condition, gender, and diet, the time and route of administration, the secretion rate of the composition, the time period of therapy, other drugs used in combination or coincident with the composition disclosed herein, and like factors well known in the medical arts.

In still another aspect, the present specification provides a use of the therapeutic protein or the pharmaceutical composition including the same in the preparation of drugs for the prevention or treatment of cancer, a neurodegenerative or an infectious disease.

In one embodiment, the dose of the composition may be administered daily, semi-weekly, weekly, bi-weekly, or monthly. The period of treatment may be for a week, two weeks, a month, two months, four months, six months, eight months, a year, or longer. The initial dose may be larger than a sustaining dose. In one embodiment, the dose ranges from a weekly dose of at least 0.01 mg/kg, at least 0.25 mg/kg, at least 0.3 mg/kg, at least 0.5 mg/kg, at least 0.75 mg/kg, at least 1 mg/kg, at least 2 mg/kg, at least 3 mg/kg, at least 4 mg/kg, at least 5 mg/kg, at least 6 mg/kg, at least 7 mg/kg, at least 8 mg/kg, at least 9 mg/kg, at least 10 mg/kg, at least 15 mg/kg, at least 20 mg/kg, at least 25 mg/kg, or at least 30 mg/kg In one embodiment, a weekly dose may be at most 1.5 mg/kg, at most 2 mg/kg, at most 2.5 mg/kg, at most 3 mg/kg, at most 4 mg/kg, at most 5 mg/kg, at most 6 mg/kg, at most 7 mg/kg, at most 8 mg/kg, at most 9 mg/kg, at most 10 mg/kg, at most 15 mg/kg, at most 20 mg/kg, at most 25 mg/kg, or at most 30 mg/kg. In a particular aspect, the weekly dose may range from 5 mg/kg to 20 mg/kg. In an alternative aspect, the weekly dose may range from 10 mg/kg to 15 mg/kg.

The present specification also provides a pharmaceutical composition for the administration to a subject. The pharmaceutical composition disclosed herein may further include a pharmaceutically acceptable carrier, excipient, or diluent. As used herein, the term "pharmaceutically acceptable" means that the composition is sufficient to achieve the therapeutic effects without deleterious side effects, and may be readily determined depending on the type of the diseases, the patient's age, body weight, health conditions, gender, and drug sensitivity, administration route, administration mode, administration frequency, duration of treatment, drugs used in combination or coincident with the composition disclosed herein, and other factors known in medicine.

The pharmaceutical composition including the antibody disclosed herein may further include a pharmaceutically acceptable carrier. For oral administration, the carrier may include, but is not limited to, a binder, a lubricant, a disintegrant, an excipient, a solubilizer, a dispersing agent, a stabilizer, a suspending agent, a colorant, and a flavorant. For injectable preparations, the carrier may include a buffering agent, a preserving agent, an analgesic, a solubilizer, an isotonic agent, and a stabilizer. For preparations for topical administration, the carrier may include a base, an excipient, a lubricant, and a preserving agent.

The disclosed compositions may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into an ampule as a single dosage form or a multidose container. The pharmaceutical composition may also be formulated into solutions, suspensions, tablets, pills, capsules and long-acting preparations.

On the other hand, examples of the carrier, the excipient, and the diluent suitable for the pharmaceutical formulations include, without limitation, lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, flavorants, and antiseptics.

Further, the pharmaceutical composition disclosed herein may have any formulation selected from the group consisting of tablets, pills, powders, granules, capsules, suspensions, liquids for internal use, emulsions, syrups, sterile aqueous solutions, non-aqueous solvents, lyophilized formulations and suppositories.

The composition may be formulated into a single dosage form suitable for the patient's body, and preferably is formulated into a preparation useful for peptide drugs according to the typical method in the pharmaceutical field so as to be administered by an oral or parenteral route such as through skin, intravenous, intramuscular, intra-arterial, intramedullary, intramedullary, intraventricular, pulmonary, transdermal, subcutaneous, intraperitoneal, intranasal, intracolonic, topical, sublingual, vaginal, or rectal administration, but is not limited thereto.

The composition may be used by blending with a variety of pharmaceutically acceptable carriers such as physiological saline or organic solvents. In order to increase the stability or absorptivity, carbohydrates such as glucose, sucrose or dextrans, antioxidants such as ascorbic acid or glutathione, chelating agents, low molecular weight proteins or other stabilizers may be used.

The administration dose and frequency of the pharmaceutical composition disclosed herein are determined by the type of active ingredient, together with various factors such as the disease to be treated, administration route, patient's age, gender, and body weight, and disease severity.

The total effective dose of the compositions disclosed herein may be administered to a patient in a single dose, or may be administered for a long period of time in multiple doses according to a fractionated treatment protocol. In the pharmaceutical composition disclosed herein, the content of active ingredient may vary depending on the disease severity. Preferably, the total daily dose of the peptide disclosed herein may be approximately 0.0001 μg to 500 mg per 1 kg of body weight of a patient. However, the effective dose of the peptide is determined considering various factors including patient's age, body weight, health conditions, gender, disease severity, diet, and secretion rate, in addition to administration route and treatment frequency of the pharmaceutical composition. In view of this, those skilled in the art may easily determine an effective dose suitable for the particular use of the pharmaceutical composition disclosed herein. The pharmaceutical composition disclosed herein is not particularly limited to the formulation, and administration route and mode, as long as it shows suitable effects.

Moreover, the pharmaceutical composition may be administered alone or in combination or coincident with other pharmaceutical formulations showing prophylactic or therapeutic efficacy.

In still another aspect, the present specification provides a method for preventing or treating of cancer, infectious diseases or neurodegenerative diseases comprising the step of administering to a subject the chimeric protein or the pharmaceutical composition including the same.

Given the teachings and guidance provided herein, those skilled in the art will understand that a formulation described herein can be equally applicable to many types of biopharmaceuticals, including those exemplified, as well as others known in the art. Given the teachings and guidance provided herein, those skilled in the art also will understand that the selection of, for example, type(s) or and/or amount(s) of one or more excipients, surfactants and/or optional components can be made based on the chemical and functional compatibility with the biopharmaceutical to be formulated and/or the mode of administration as well as other chemical, functional, physiological and/or medical factors well known in the art. For example, non-reducing sugars exhibit favorable excipient properties when used with polypeptide biopharmaceuticals compared to reducing sugars. Accordingly, exemplary formulations are exemplified further herein with reference to polypeptide biopharmaceuticals. However, the range of applicability, chemical and physical properties, considerations and methodology applied to polypeptide biopharmaceutical can be similarly applicable to biopharmaceuticals other than polypeptide biopharmaceuticals.

In various embodiments, a formulation can include, without limitation, combinations of bioactive agents (such as viruses, proteins, antibodies, peptides and the like as described herein) in the formulation. For example, a formulation as described herein can include a single bioactive agent for treatment of one or more conditions, including without limitation, disease. A formulation as described herein also can include, in an embodiment, without limitation, two or more different bioactive agents for a single or multiple conditions. Use of multiple bioactive agents in a formulation can be directed to, for example, the same or different indications. Similarly, in another embodiment, multiple bioactive agents can be used in a formulation to treat, for example, both a pathological condition and one or more side effects caused by the primary treatment. In a further embodiment, multiple bioactive agents also can be included, without limitation, in a formulation as described herein to accomplish different medical purposes including, for example, simultaneous treatment and monitoring of the progression of the pathological condition. In an additional embodiment, multiple, concurrent therapies such as those exemplified herein as well as other combinations well known in the art are particularly useful for patient compliance because a single formulation can be sufficient for some or all suggested treatments and/or diagnosis. Those skilled in the art will know those bioactive agents that can be admixed for a wide range of combination therapies. Similarly, in various embodiments, a formulation can be used with a small molecule drug and combinations of one or more bioactive agents together with one or more small molecule pharmaceuticals. Therefore, in various embodiments a formulation is provided containing 1, 2, 3, 4, 5 or 6 or more different bioactive agents, as well as, for one or more bioactive agents combined with one or more small molecule pharmaceuticals.

In various embodiments, a formulation can include, one or more preservatives and/or additives known in the art. Similarly, a formulation can further be formulated, without limitation, into any of various known delivery formulations. For example, in an embodiment, a formulation can include, surfactants, adjuvant, biodegradable polymers, hydrogels, etc., such optional components, their chemical and functional characteristics are known in the art. Similarly known in the art are formulations that facilitate rapid, sustained or delayed release of the bioactive agents after administration. A formulation as described can be produced to include these or other formulation components known in the art.

The composition can therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data. In various embodiments, the bioactive agents in formulations described herein can, without limitation, be administered to patients throughout an extended time period, such as chronic administration for a chronic condition. The composition can be a solid, a semi-solid or an aerosol and a pharmaceutical compositions is formulated as a tablet, geltab, lozenge, orally dissolved strip, capsule, syrup, oral suspension, emulsion, granule, sprinkle or pellet.

In an embodiment, for oral, rectal, vaginal, parenteral, pulmonary, sublingual and/or intranasal delivery formulations, tablets can be made by compression or molding, optionally with one or more accessory ingredients or additives. In an embodiment, compressed tablets are prepared, for example, by compressing in a suitable tabletting machine, the active ingredients in a free-flowing form such as a powder or granules, optionally mixed with a binder (for example, without limitation, povidone, gelatin, hydroxypropylmethyl cellulose), lubricant, inert diluent, preservative, disintegrant (for example, without limitation, sodium starch glycolate, cross-linked povidone, cross-linked sodium carboxymethyl cellulose) and/or surface-active or dispersing agent.

In an embodiment, molded tablets are made, for example, without limitation, by molding in a suitable tabletting machine, a mixture of powdered compounds moistened with an inert liquid diluent. In an embodiment, the tablets may optionally be coated or scored, and may be formulated so as to provide slow or controlled release of the active ingredients, using, for example, without limitation, hydroxypropylmethyl cellulose in varying proportions to provide the desired release profile. In an embodiment, tablets may optionally be provided with a coating, without limitation, such as a thin film, sugar coating, or an enteric coating to provide release in parts of the gut other than the stomach. In an embodiment, processes, equipment, and toll manufacturers for tablet and capsule making are well-known in the art.

In an embodiment, capsule formulations can utilize either hard or soft capsules, including, without limitation, gelatin capsules or vegetarian capsules such as those made out of hydroxymethylpropylcellulose (HMPC). In an embodiment, a type of capsule is a gelatin capsule. In an embodiment, capsules may be filled using a capsule filling machine such as, without limitation, those available from commercial suppliers such as Miranda International or employing capsule manufacturing techniques well-known in the industry, as described in detail in Pharmaceutical Capsules, 2.sup.nd Ed., F. Podczeck and B. Jones, 2004. In an embodiment, capsule formulations may be prepared, without limitation, using a toll manufacturing center such as the Chao Center for Industrial Pharmacy & Contract Manufacturing, located at Purdue Research Park.

Packaging and instruments for administration may be determined by a variety of considerations, such as, without limitation, the volume of material to be administered, the conditions for storage, whether skilled healthcare practitioners will administer or patient self-compliance, the dosage regime, the geopolitical environment (e.g., exposure to extreme conditions of temperature for developing nations), and other practical considerations.

Injection devices include pen injectors, auto injectors, safety syringes, injection pumps, infusion pumps, glass prefilled syringes, plastic prefilled syringes and needle free injectors syringes may be prefilled with liquid, or may be dual chambered, for example, for use with lyophilized material. An example of a syringe for such use is the Lyo-Ject™, a dual-chamber pre-filled lyosyringe available from Vetter GmbH, Ravensburg, Germany. Another example is the LyoTip which is a prefilled syringe designed to conveniently deliver lyophilized formulations available from LyoTip, Inc., Camarillo, California, U.S.A. Administration by injection may be, without limitation intravenous, intramuscular, intraperitoneal, or subcutaneous, as appropriate. Administrations by non-injection route may be, without limitation, nasal, oral, cocular, dermal, or pulmonary, as appropriate.

In certain embodiments, kits can comprise, without limitation, one or more single or multi-chambered syringes (e.g., liquid syringes and lyosyringes) for administering one or more formulations described herein. In various embodiments, the kit can comprise formulation components for parenteral, subcutaneous, intramuscular or IV administration, sealed in a vial under partial vacuum in a form ready for loading into a syringe and administration to a subject. In this regard, the composition can be disposed therein under partial vacuum. In all of these embodiments and others, the kits can contain one or more vials in accordance with any of the foregoing, wherein each vial contains a single unit dose for administration to a subject.

The kits can comprise lyophilates, disposed as herein, that upon reconstitution provide compositions in accordance therewith. In various embodiment the kits can contain a lyophilate and a sterile diluent for reconstituting the lyophilate.

Also described herein, are methods for treating a subject in need of therapy, comprising administering to the subject an effective amount of a formulation as described herein. The therapeutically effective amount or dose of a formulation will depend on the disease or condition of the subject and actual clinical setting.

In an embodiment, a formulation as described herein can be administered by any suitable route, specifically by parental (including subcutaneous, intramuscular, intravenous and intradermal) administration. It will also be appreciated that the preferred route will vary with the condition and age of the recipient, and the disease being treated. Methods of determining the most effective means and dosage of administration are known to those of skill in the art and will vary, without limitation, with the composition used for therapy, the purpose of the therapy, and the subject being treated. Single or multiple administrations can be carried out, without limitation, the dose level and pattern being selected by the treating physician. Suitable dosage formulations and methods of administering the agents are known in the art.

The formulations as described herein can be used in the manufacture of medicaments and for the treatment of humans and other animals by administration in accordance with conventional procedures.

Also provided herein are combinatorial methods for developing suitable virus formulations using combinations of amino acids. These methods are effective for developing stable liquid or lyophilized formulations, and particularly pharmaceutical virus formulations.

Compositions in accordance with embodiments described herein have desirable properties, such as desirable solubility, viscosity, syringeability and stability. Lyophilates in accordance with embodiments described herein have desirable properties, as well, such as desirable recovery, stability and reconstitution.

In an embodiment, the pH of the pharmaceutical formulation is at least about 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, or 9.

In an embodiment, the pH of the pharmaceutical formulation is from about 3 to about 9, about 4 to about 19, about 5 to about 9, about 6 to about 8, about 6 to about 7, about 6 to about 9, about 5 to about 6, about 5 to about 7, about 5 to about 8, about 4 to about 9, about 4 to about 8, about 4 to about 7, about 4 to about 6, about 4 to about 5, about 3 to about 8, about 3 to about 7, about 3 to about 6, about 3 to about 5, about 3 to about 4, about 7 to about 8, about 7 to about 9, about 7 to about 10.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

TABLE 20

| Seq ID | sequence | name |
| --- | --- | --- |
| 1 | DYIFSNYYIE | HCDR1;<br>DLL3.2,<br>DLL3.4 |
| 2 | DYTFSNYYIE | HCDR1;<br>DLL3.1 |
| 3 | DYYMN | HCDR1,<br>DLL3.9 |
| 4 | DYYVN | HCDR1;<br>DLL3.8 |
| 5 | GFTFSNYGMH | HCDR1:<br>DLL3.10,<br>DLL3.27,<br>DLL3.29,<br>DLL3.30,<br>DLL3.31, |

TABLE 20-continued

| Seq ID | sequence | name |
|---|---|---|
| | | DLL3.32, DLL3.33, DLL3.38 |
| 6 | GFTFSSYGMH | HCDR1: DLL3.5, DLL3.12 DLL3.13, DLL3.14, DLL3.15, DLL3.16, DLL3.17 DLL3.18, DLL3.19. DLL3.20, DLL3.21, DLL3.22, DLL3.23, DLL3.24, DLL3.25, DLL3.26 |
| 7 | GFTFSSYGMH | HCDR1: DLL3.3, DLL3.11 |
| 8 | SAYYWN | HCDR1: DLL23.34, DLL3.35 |
| 9 | SYYWS | HCDR1: DDL3.28 |
| 10 | EILPGNGNTVYNEKFKD | HCDR2; DLL3.1 |
| 11 | EILPGTGNTVYNEKFKD | HCDR2: DLL3.2, DLL3.4 |
| 12 | IISPNDGGTNYNQKFKG | HCDR2; DLL3.8 |
| 13 | VINPDNGITTYNQKFKG | HCDR2; DLL3.9 |
| 14 | VINPYNDITIYNQKFQG | HCDR2: DLL3.3 |
| 15 | VISGSGSSKYYADSVKG | HCDR2; DLL3.11, DLL3.15, DLL3.18, DLL3.22 |
| 16 | VISHHGSSKYYADSVKG | HCDR2: DLL3.5, DLL3.10, DLL3.12, DLL3.14, DLL3.17, DLL3.19, DLL3.21, DLL3.23, DLL3.25, DLL3.26, DLL3.27, DLL3.31, DLL3.32, DLL3.33 |
| 17 | VISHHGSSKYYARSVKG | HCDR2: DLL3.29, DLL3.30, DLL3.36 |

TABLE 20-continued

| SEQUENCES | | |
|---|---|---|
| Seq ID | sequence | name |
| 18 | VISYDGSSKYYADSVKG | HCDR2; DLL3.13, DLL3.16, DLL3.20, DLL3.24 |
| 19 | YISDVGHNYYNPSLKN | HCDR2; DLL3.34 |
| 20 | YISDVGSNNYNPSLKN | HCDR2; DLL3.35 |
| 21 | YVYYSGTTNYNPSLKS | HCDR2; DLL3.28 |
| 22 | WGDYALFAN | HCDR3: DLL3.1, DLL3.2, DLL3.4 |
| 23 | DQVFAY | HCDR3; DLL3.8, DLL3.34, DLL3.35 |
| 24 | DWFFYLFDY | HCDR3; DLL3.5, DLL3.10, DLL3.11, DLL3.12, DLL3.13, DLL3.14, DLL3.15, DLL3.16, DLL3.17, DLL3.26, DLL3.27, DLL3.31 |
| 25 | DWFYFIFDY | HCDR3; DLL3.18, DLL3.19, DLL3.20, DLL3.21, DLL3.22, DLL3.23, DLL3.24, DLL3.25, DLL3.32, DLL3.33 |
| 26 | DWWELVFDY | HCDR3; DLL3.29, DLL3.20, DLL3.36 |
| 27 | EGVLYDGYYEGAY | HCDR3; DLL3.3 |
| 28 | GVWNYERSFDY | HCDR3; DLL3.9 |
| 29 | SIAVTGFYFDY | HCDR3; DLL3.28 |
| 30 | SASSSVSYMH | LCDR1; DLL3.35 |
| 31 | KASQNVGIAVA | LCDR1; DLL3.3 |

TABLE 20-continued

| SEQUENCES | | |
| --- | --- |
| Seq ID sequence | name |

| 32 | KASQNVGTNVA | LCDR1;<br>DLL3.1,<br>DLL3.2,<br>DLL3.4,<br>DLL3.9,<br>DLL3.28 |
| 33 | KSSQSLLHSDAKTFLY | LCDR1;<br>DLL3.22,<br>DLL3.23,<br>DLL3.24,<br>DLL3.25,<br>DLL3.26,<br>DLL3.27,<br>DLL3.32,<br>DLL3.33 |
| 34 | KSSQSLLHSDGKTFLY | LDCR1:<br>DLL3.5,<br>DLL3.10,<br>DLL3.15,<br>DLL3.16,<br>DLL3.17,<br>DLL3.29,<br>DLL3.30,<br>DLL3.32,<br>DLL3.36 |
| 35 | RASESVHSYGNSLIH | LDCR1;<br>DLL3.34 |
| 36 | RSSKSLLHSNGITYLY | LCDR1;<br>DLL3.8 |
| 37 | RSSOSLLHSDAKTFLD | LCDR1;<br>DLL3.18,<br>DLL3.19,<br>DLL3.20,<br>DLL3.21, |
| 38 | RSSQSLLHSDGKTFLD | LCDR1:<br>DLL3.11,<br>DLL3.12,<br>DLL3.13,<br>DLL3.14 |
| 39 | SASYRYS | LCDR2:<br>DLL3.4,<br>DLL3.28 |
| 40 | AASNRYT | LCDR2:<br>DLL3.3 |
| 41 | DTSKLAS | LCDR2;<br>DLL3.35 |
| 42 | EVSNRAS | LCDR2;<br>DLL3.11,<br>DLL3.12,<br>DLL3.13,<br>DLL3.14,<br>DLL3.18,<br>DLL3.19,<br>DLL3.20,<br>DLL3.21 |
| 43 | EVSNRFS | LCDR2:<br>DLL3.5,<br>DLL3.10,<br>DLL3.15,<br>DLL3.16,<br>DLL3.17,<br>DLL3.22,<br>DLL3.23,<br>DLL3.14, |

TABLE 20-continued

| | SEQUENCES | |
|---|---|---|
| Seq ID | sequence | name |
| | | DLL3.25, |
| | | DLL3.26, |
| | | DLL3.27, |
| | | DLL3.29, |
| | | DLL3.30, |
| | | DLL3.31, |
| | | DLL3.32, |
| | | DLL3.33, |
| | | DLL3.36 |
| 44 | QMSNLAS | LCDR2; DLL3.8 |
| 45 | RASNLES | LCDR2; DLL3.34 |
| 46 | SASYRYS | LCDR2; DLL3.1, DLL3.2, DLL3.9 |
| 47 | QQYSTYPYT | LCDR3: DLL3.3 |
| 48 | AQNLELP | LCDR3: DLL3.8 |
| 49 | LQGERLPFT | LCDR3; DLL3.5, DLL3.10, DLL3.11, DLL3.12, DLL3.13, DLL3.14, DLL3.15, DLL3.16, DLL3.17, DLL3.26, DLL3.27, DLL3.31 |
| 50 | LQGIHLPFT | LCDR3; DLL3.29, DLL3.30, DLL3.36 |
| 51 | LQGRELPFT | LCDR3; DLL3.18, DLL3.19, DLL3.20, DLL3.21, DLL3.22, DLL3.23, DLL3.24, DLL3.25, DLL3.32, DLL3.33 |
| 52 | QQTNEDP | LCDR3; DLL3.34 |
| 53 | QQWSSNPLT | LCDR3; DLL3.35 |
| 54 | QQYNNYPLT | LCDR3; DLL3.4, DLL3.9, DLL3.28 |
| 55 | QQYNSYPFT | LCDR3; DLL3.1, DLL3.2 |
| 56 | EVQLLESGGGLVQPGGSLRLSCAASGFTFSSYGMHWVRQAPGK GLEWVAVISGSGSSKYYADSVKGRFTISRDNSKNTLYLQMNSLRA EDTAVYYCARDWFFYLFDYWGQGTLVTVSS | VH; DLL3.11, DLL3.15 |

TABLE 20-continued

| | SEQUENCES | |
|---|---|---|
| Seq ID sequence | | name |

| | | |
|---|---|---|
| 57 | EVQLLESGGGLVQPGGSLRLSCAASGFTFSSYGMHWVRQAPGK GLEWVAVISGSGSSKYYADSVKGRFTISRDNSKNTLYLQMNSLRA EDTAVYYCARDWFYFIFDYWGQGTLVTVSS | VH: DLL3.18, DLL3.22 |
| 58 | EVQLLESGGGLVQPGGSLRLSCAASGFTFSSYGMHWVRQAPGK GLEWVAVISHHGSSKYYADSVKGRFTISRDNSKNTLYLQMNSLRA EDTAVYYCARDWFFYLFDYWGQGTLVTVSS | VH; DLL3.5, DLL3.12, DLL3.26 |
| 59 | EVQLLESGGGLVQPGGSLRLSCAASGFTFSSYGMHWVRQAPGK GLEWVAVISHHGSSKYYADSVKGRFTISRDNSKNTLYLQMNSLRA EDTAVYYCARDWFYFIFDYWGQGTLVTVSS | VH; DLL3.19, DLL3.23 |
| 60 | EVQLLESGGGLVQPGGSLRLSCAASGFTFSSYGMHWVRQAPGK GLEWVAVISYDGSSKYYADSVKGRFTISRDNSKNTLYLQMNSLRA EDTAVYYCARDWFFYLFDYWGQGTLVTVSS | VH; DLL3.13, DLL3.16, |
| 61 | EVQLLESGGGLVQPGGSLRLSCAASGFTFSSYGMHWVRQAPGK GLEWVAVISYDGSSKYYADSVKGRFTISRDNSKNTLYLQMNSLRA EDTAVYYCARDWFFYLFDYWGQGTLVTVSS | VH; DLL3.20, DLL3.24 |
| 62 | EVQLLESGGGLVQPGGSLRLSCAASGFTFSSYGMHWVRQAPGK GLEWVSVISHHGSSKYYADSVKGRFTISRDNSKNTLYLQMNSLRA EDTAVYYCAKDWFFYLFDYWGQGTLVTVSS | VH; DLL3.14, DLL3.17 |
| 63 | EVQLLESGGGLVQPGGSLRLSCAASGFTFSSYGMHWVRQAPGK GLEWVSVISHHGSSKYYADSVKGRFTISRDNSKNTLYLQMNSLRA EDTAVYYCAKDWFFYFIFDYWGQGTLVTVSS | VH; DLL3.21, DLL3.25 |
| 64 | EVQLQQSGPVLVKPGASVKMSCKASGFTFTDYYMNWVKQSHGK SLEWIGVINPDNGITTYNQKFKGKATLTVDKSSSTAYMELNGLTSE DSAVYYCARGVWNYERSFDYWGQGTTLTVSS | VH; DLL3.9 |
| 65 | EVQLVESGGGLVQPGGSLRLSCAASGFTFSNYGMHWVRQAPGK GLEWVAVISHHGSSKYYADSVKGRYTISRDNSKNTLYLQMNSLRA EDTAVYYCARDWFFYLFDYWGQGTLVTVSS | VH DLL3.27 |
| 66 | QVQLQESGPGLVKPSETLSLTCTVSGGSISSYYWSWIRQPPGKGL EWIGYVYYSGTTNYNPSLKSRVTISVDTSKNQFSLKLSSVTAADTA VYYCASIAVTGFYFDYWGQGTLVTVSS | VH; DLL3.28 |
| 67 | QVQLQQSGPVLVKPGASVKMSCKASGYSFTDYYVNWVKQSHGK SLEWIGIISPNDGGTNYNQKFKGKATLTVDKSSSTAYMEVNSLTSE DSAVYYCARDDDLGWYFDVWGTGTTVTVSS | VH; DLL3.8 |
| 68 | QVQLVESGGGAVQPGRSLRLSCAASGFTFSNYGMHWVRQAPGK GLEWVAVISHHGSSKYYARSVKGRFTISRDNSKNTLYLEMNSLRA EDTAVYYCARDWWELVFDYWGQGTLVTVSS | VH DLL3.29, DLL3.30, DLL3.36 |
| 69 | QVQLVESGGGVVQPGRSLRLSCAASGFTFSNYGMHWVRQAPGK GLEWVAVISHHGSSKYYADSVKGRFTISRDNSKNTLYLQMNSLRA EDTAVYYCARDWFFYLFDYWGQGTLVTVSS | VH DLL3.10, DLL3.31 |
| 70 | QVQLVESGGGVVQPGRSLRLSCAASGFTFSNYGMHWVRQAPGK GLEWVAVISHHGSSKYYADSVKGRFTISRDNSKNTLYLQMNSLRA EDTAVYYCARDWFYFIFDYWGQGTLVTVSS | VH; DLL3.32, DLL3.33 |
| 71 | QVQLVQSGAEVKKPGASVKVSCKASDYTFSNYYIEWVRQAPGQG LEWMGEILPGNGNTVYNEKFKDRVTMTVDTSTSTAYMELRSLRSD DTAVYYCARWGDYALFANWGQGTLVTVSS | VH; DLL3.1 |
| 72 | QVQLVQSGAEVKKPGASVKVSCKASGYTFTDYFMNWVRQAPGQ GLEWMGVINPYNDITIYNQKFQGRVTMTVDRSTSTVYMELSSLRS EDTAVYYCAREGVLYDGYYEGAYWGQGTLVTVSS | VH; DLL3.3 |
| 73 | QVQLVQSGAEVKKPGASVKVSCKATDYIFSNYYIEWVRQAPGQGL EWMGEILPGTGNTVYNEKFKDRVTMTVDTSTSTVYMELSSLRSED TAVYYCARWGDYALFANWGQGTLVTVSS | VH; DLL3.2, DLL3.4 |
| 74 | SDVQLQESGPGLVKPSQSLSLTCSVTGYSITSAYYWNWIRQFPGN KLEWMGYISDVGHNYYNPSLKNRISITRDTSKNQFFLKLNSVTPED TATYYCARDQVFAYWGQGTLVTVSA | VH DLL3.34 |

TABLE 20-continued

| | SEQUENCES | |
|---|---|---|
| Seq ID | sequence | name |
| 75 | SDVQLQESGPGLVKPSQSLSLTCSVTGYSITSAYYWNWIRQFPGN KLEWMGYISDVGSNNYNPSLKNRISITRDTFKNQFFLKLNSVTTED TATYFCTRDQVFAYWGQGTLVTVS | VH DLL3.35 |
| 76 | DIQLTQSPSFLSASVGDRVTITCKASQNVGIAVAWYQQKPGKAPKL LIYAASNRYTGVPSRFSGSGSGTEFTLTISSLQPEDFATYYCQQYS TYPYTFGQGTKLEIK | VL; DLL3.3 |
| 77 | DIQMTQSPSFLSASVGDRVTITCKASQNVGTNVAWYQQKPGKAPK PLIYSTSYRYSGVPSRFSGSGSGTEFTLTISSLQPEDFATYYCQQY NNYPLTFGGGTKVEIK | VL; DLL3.4 |
| 78 | DIQMTQSPSSLSASVGDRVTITCKSSQSLLHSDAKTFLYWYQQKP GKAPKLLIYEVSNRFSGVPSRFSGSGSGTDFTLTISSLQPEDFATY YCLQGERLPFTFGQGTKVEIK | VL; DLL3.26 |
| 78 | DIQMTQSPSSLSASVGDRVTITCKSSQSLLHSDAKTFLYWYQQKP GKAPKLLIYEVSNRFSGVPSRFSGSGSGTDFTLTISSLQPEDFATY YCLQGERLPFTFGQGTKVEIK | VL; DLL3.27 |
| 79 | DIQMTQSPSTLSASVGDRVTITCKASQNVGTNVAWYQQKPGKAPK ALIYSASYRYSGVPSRFSGSGSGTEFTLTISSLQPDDFATYYCQQY NSYPFTFGQGTKLEIK | VL; DLL3.1 |
| 79 | DIQMTQSPSTLSASVGDRVTITCKASQNVGTNVAWYQQKPGKAPK ALIYSASYRYSGVPSRFSGSGSGTEFTLTISSLQPDDFATYYCQQY NSYPFTFGQGTKLEIK | VL; DLL3.2 |
| 80 | DIVMTQAAFSNPVTVGTSASISCRSSKSLLHSNGITYLYWYLQKPG QSPQLLIYQMSNLASGVPDRFSSSGSGTDFTLRISRVEAEDVGVY YCAQNLELPWTFGGGTKLEIK | VL; DLL3.8 |
| 81 | DIVMTQSPKFMSTSVGDRVSVTCKASQNVGTNVAWYQQKPGQSP KALIYSASYRYSGVPDRFTGSGSGTDFTLTFSSVQSEDLAEYFCQ QYNNYPLTFGGGTKLEIK | VL; DLL3.9 |
| 82 | DIVMTQSPLSLPVTPGEPASISCKSSQSLLHSDAKTFLYWYLQKPG QSPQLLIYEVSNRFSGVPDRFSGSGSGTDFTLKISRVEAEDVGVYY CLQGRELPFTFGQGTKVEIK | VL; DLL3.22, DLL3.23, DLL3.24, DLL3.25 |
| 83 | DIVMTQSPLSLPVTPGEPASISCKSSQSLLHSDGKTFLYWYLQKPG QSPQLLIYEVSNRFSGVPDRFSGSGSGTDFTLKISRVEAEDVGVYY CLQGERLPFTFGQGTKVEIK | VL; DLL3.5, DLL3.15, DLL3.16, DLL3.17 |
| 84 | DIVMTQSPLSLPVTPGEPASISCRSSQSLLHSDAKTFLDWYLQKPG QSPQLLIYEVSNRASGVPDRFSGSGSGTDFTLKISRVEAEDVGVYY CLQGRELPFTFGQGTKVEIK | VL DLL3.18, DLL3.19, DLL3.20, DLL3.21 |
| 85 | DIVMTQSPLSLPVTPGEPASISCRSSQSLLHSDGKTFLDWYLQKPG QSPQLLIYEVSNRASGVPDRFSGSGSGTDFTLKISRVEAEDVGVYY CLQGERLPFTFGQGTKVEIK | VL; DLL3.11, DLL3.12, DLL3.13, DLL3.14 |
| 86 | DIVMTQTPLSLSVTPGQPASISCKSSQSLLHSDAKTFLYWYLQKPG QPPQLLIYEVSNRFSGVPDRFSGSGSGTDFTLKISRVEAEDVGVYY CLQGRELPFTFGPGTKVEIK | VL DLL3.32, DLL3.33 |
| 87 | DIVMTQTPLSLSVTPGQPASISCKSSQSLLHSDGKTFLYWYLQKPG QPPQLLIYEVSNRFSGVPDRFSGSGSGTDFTLKISRVEAEDVGVYY CLQGERLPFTFGPGTKVEIK | VL; DLL3.10, DLL3.31 |
| 88 | DIVMTQTPLSLSVTPGQPASISCKSSQSLLHSDGKTFLYWYLQKPG QPPQLLIYEVSNRFSGVPDRFSGSGSGTDFTLKISRVEAEDVGVYY CLQGIHLPFTFGPGTKVEIK | VL; DLL3.29, DLL3.30, DLL3.36 |
| 89 | DTVLTQSPASLAVSLGQRATISCRASESVHSYGNSLIHWYQQKPG QPPRLLIYRASNLESGIPARFSGSGSRTDFTLTINPVEADDVATYYC QQTNEDPLTFGAGTKLELK | VL; DLL3.34 |

TABLE 20-continued

| Seq ID sequence | | name |
|---|---|---|
| 90 | EIVLTQSPGTLSLSPGERVTLSCRASQRVNNNYLAWYQQRPGQAP<br>RLLIYGASSRATGIPDRFSGSGSGTDFTLTISRLEPEDFAVYYCQQ<br>YDRSPLTFGGGTKLEIK | VL; DLL3.28 |
| 91 | QIVLTQSPAIMSASPGEKVTMTCSASSSVSYMHWYQQKSGTSPKR<br>WIYDTSKLASGVPARFSGSGSGTSYSLTISSMEAEDAATYYCQQW<br>SSNPLTFGAGTKLELK | VL; DLL3.35 |
| 92 | GFTFSSFGMH | HCDR1;<br>Muc17.7,<br>Muc17.21,<br>Muc17.22,<br>Muc17.23,<br>Muc17.24 |
| 93 | GYAFSDYWIN | HCDR1:<br>Muc17.2 |
| 94 | GYEFSSHWMN | HCDR1;<br>Muc17.1,<br>Muc17.8,<br>Muc17.9,<br>muc17.10,<br>Muc17.11,<br>Muc17.12,<br>Muc17.13,<br>Muc17.14,<br>Muc17.25,<br>Muc71.26,<br>Muc17.27,<br>Muc17.28,<br>Muc17.29,<br>Muc17.30,<br>Muc17.31 |
| 95 | GYIFSNHWMN | HCDR1:<br>Mcu17.3 |
| 96 | GYTFTSYWLN | HCDR1;<br>Muc17.17,<br>Muc17.42,<br>Muc17.43,<br>Muc17.44,<br>Muc17.46,<br>Muc17.47 |
| 97 | GYTFTSYWMN | HCDR1;<br>Muc17.4,<br>Muc17.5,<br>Muc17.6,<br>Muc17.15,<br>Muc17.16,<br>Muc17.18,<br>Muc17.19,<br>Muc17.20,<br>Muc17.32,<br>Muc17.33,<br>Muc17.34,<br>Muc17.35,<br>Muc17.36,<br>Muc17.37,<br>Muc17.38,<br>Muc17.39,<br>Muc17.40,<br>Muc17.41,<br>Muc17.45,<br>Muc17.48,<br>Muc17.49 |
| 98 | GYTFTSYWMN | HCDR1;<br>Mcu17.31 |

TABLE 20-continued

| Seq ID | sequence | name |
|---|---|---|
| 99 | MIHPSDSESRLNQKFKD | HCDR2; Muc17.17. Muc17.39, Muc17.40, Muc17.41, Muc17.46, Muc17.47 |
| 100 | MIHPSDSETRLNQEFKD | HCDR2; Muc17.5, Muc17.20 |
| 101 | MIHPSDSETRLNQKFKD | HCDR2; Muc17.4, Muc17.15, Muc17.16, Muc17.18, Muc17.19, Muc17.31, Muc17.33, Muc17.34, Muc17.35, Muc17.36, Muc17.37, Muc17.38, Muc17.42, Muc17.43, Muc17.44, Muc17.45, Muc17.48, Muc17.49 |
| 102 | MIHPSDSETRLNQKFTD | HCDR2; Muc17.6 |
| 103 | QIYPGDGDINYNEKFRG | HCDR2; Muc17.1, Muc17.9, Muc17.10, Muc17.11, Muc17.12, Muc17.13, Muc17.14, Muc17.25, Muc17.26, Muc17.27, Muc17.28, Muc17.29, Muc17.30, Muc17.31 |
| 104 | QIYPGDGDINYNGKFRG | HCDR2; Muc17.3 |
| 105 | QVYPGDDDINYNGKFRG | HCDR2; Muc17.2 |
| 106 | YISSGSSTIYYADTVKG | HCDR2; Muc17.7, Muc17.21, Muc17.22, Muc17.23, Muc17.24 |
| 107 | HGNYVMDY | HCDR2; Muc17.8 |
| 108 | HGNYVMDY | HCDR3; Muc17.1, Muc17.2, Muc17.8, Muc17.9, Muc17.10, Muc17.11, Muc17.12, |

TABLE 20-continued

| | SEQUENCES | |
| --- | --- | --- |
| Seq ID | sequence | name |
| | | Muc17.13,<br>Muc17.14,<br>Muc17.25,<br>Muc17.26,<br>Muc17.27,<br>Muc17.28,<br>Muc17.29,<br>Muc17.30,<br>Muc17.31 |
| 109 | QGIITSVQEFAY | HCDR3;<br>Muc17.4,<br>Muc17.6,<br>Muc17.15,<br>Muc17.16,<br>Muc17.17,<br>Muc17.18,<br>Muc17.19,<br>Muc17.31,<br>Muc17.32,<br>Muc17.33,<br>Muc17.34,<br>Muc17.35,<br>Muc17.36,<br>Muc17.37,<br>Muc17.38,<br>Muc17.39,<br>Muc17.40,<br>Muc17.41,<br>Muc17.42,<br>Muc17.43,<br>Muc17.44,<br>Muc17.45,<br>Muc17.46,<br>Muc17.48,<br>Muc17.49 |
| 110 | QGVITSVQEFAY | HCDR3;<br>Muc17.5,<br>Muc17.20 |
| 111 | WGYYGSSYFAY | HCDR3;<br>Muc17.7,<br>Muc17.21,<br>Muc17.22,<br>Muc17.23,<br>Muc17.24 |
| 112 | HGNYLMDY | HCDR3;<br>Muc17.3 |
| 113 | SASSSLNYIY | LCDR1;<br>Muc17.6 |
| 114 | SASSSVNYIF | LCDR1;<br>Muc17.18,<br>Muc17.19,<br>Muc17.41,<br>Muc17.44,<br>Muc17.46 |
| 115 | SASSSVNYIY | LCDR1;<br>Muc17.4,<br>Muc17.5,<br>Muc17.15,<br>Muc17.16,<br>Muc17.17,<br>Muc17.31,<br>Muc17.32,<br>Muc17.33,<br>Muc17.34,<br>Muc17.35,<br>Muc17.36,<br>Muc17.37,<br>Muc17.38,<br>Muc17.39, |

88

TABLE 20-continued

| Seq ID sequence | name |
|---|---|
| | Muc17.40, Muc17.41, Muc17.43, Muc17.45, Muc17.47, Muc17.48, Muc17.49 |
| 116  SASSSVSYMF | LCDR1; Muc17.1, Muc17.2, Muc17.8, Muc17.9, Muc17.10, Muc17.11, Muc17.12, Muc17.13, Muc17.14, Muc17.25, Muc17.26, Muc17.27, Muc17.28, Muc17.29, Muc17.30, Muc17.31 |
| 117  SVSSNVDYVF | LCDR1; Muc17.3 |
| 118  KASEDIYNRLA | LCDR1; Muc17.7, Muc17.21, Muc17.22, Muc17.23, Muc17.24 |
| 119  RTSNLAS | LCDR2; Muc17.1, Muc17.2, Muc17.4, Muc17.5, Muc17.6, Muc17.8, Muc17.9, Muc17.10, Muc17.11, Muc17.12, Muc17.13, Muc17.14, Muc17.15, Muc17.16, Muc17.17, Muc17.18, Muc17.19, Muc17.20, Muc17.25, Muc17.26, Muc17.27, Muc17.28, Muc17.29, Muc17.30, Muc17.31, Muc17.32, Muc17.33, Muc17.34, Muc17.36, Muc17.37, Muc17.38, Muc17.39, Muc17.40, Muc17.41, Muc17.42, Muc17.43, Muc17.44, Muc17.45, Muc17.46, |

TABLE 20-continued

| | | |
|---|---|---|
| | SEQUENCES | |
| Seq ID sequence | | name |
| | | Muc17.48, Muc17.49 |
| 121 | GATNLET | LCDR2; Muc17.7, Muc17.21, Muc17.22, Muc17.23, Muc17.24 |
| 122 | QQFHDYPRT | LCDR3; Muc17.1, Muc17.8, Muc17.9, Muc17.10, Muc17.11, Muc17.12, Muc17.13, Muc17.14, Muc17.25, Muc17.26, Muc17.27, Muc17.28, Muc17.29, Muc17.30, Muc17.31 |
| 123 | QQFHSYPRT | LCDR3; Muc17.2, Muc17.3 |
| 124 | QQFWRTPPT | LCDR3; Muc17.7, Muc17.21, Muc17.22, Muc17.23 |
| 125 | QQYHSYPLT | LCDR3; Muc17.4, Muc17.5, Muc17.6, Muc17.15, Muc17.16, Muc17.17, Muc17.18, Muc17.19, Muc17.20 Muc17.31, Muc17.32, Muc17.33, Muc17.34, Muc17.35, Muc17.36, Muc17.37, Muc17.38, Muc17.39, Muc17.40, Muc17.41, Muc17.42, Muc17.43, Muc17.44, Muc17.45, Muc17.47, Muc17.48, Muc17.49 |
| 126 | CQQFWRTPPT | LCDR3; Muc17.24 |
| 127 | EVQLVQSGAEVKKPGESLKISCKGSGYEFSSHWMNWVRQMPGK GLEWMGQIYPGDGDINYNEKFRGQVTISADKSISTAYLQWSSLKA SDTAMYYCARHGNYVMDYWGQGTLVTVSS | VH; Muc17.1, Muc17.8, Muc17.9, Muc17.10, Muc17.11, Muc17.12, |

TABLE 20-continued

| | SEQUENCES | |
|---|---|---|
| Seq ID | sequence | name |
| | | Muc17.13, Muc17.14 |
| 128 | QVQLVQSGAEVKKP+E60:J60GSSVKVSCKASGYTFTSYWLNWV RQAPGQGLEWMGMIHPSDSESRLNQKFKDRVTITADKSTSTAYM ELSSLRSEDTAVYYCARQGIITSVQEFAYWGQGTLVTVSS | VH; Muc17.17 |
| 129 | QVQLVQSGAEVKKPGASVKVSCKASGYEFSSHWMNWVRQAPGQ GLEWMGQIYPGDGDINYNEKFRGRVTMTRDTSTSTVYMELSSLRS EDTAVYYCARHGNYVMDYWGQGTLVTVSS | VH; Muc17.29, Muc17.30, Muc17.31 |
| 130 | QVQLVQSGAEVKKPGASVKVSCKASGYTFTSYWMNWVRQAPGQ GLEWIGMIHPSDSETRLNQKFKDRVTLTVDKSSSTAYMELSSLRSE DTAVYYCARQGIITSVQEFAYWGQGTLVTVSS | VH Muc17.45 |
| 131 | QVQLVQSGAEVKKPGASVKVSCKASGYTFTSYWMNWVRQAPGQ GLEWMGMIHPSDSETRLNQEFKDRVTMTRDTSTSTVYMELSSLR SEDTAVYYCARQGVITSVQEFAYWGQGTLVTVSS | VH; Muc17.5, Muc17.20 |
| 132 | QVQLVQSGAEVKKPGASVKVSCKASGYTFTSYWMNWVRQAPGQ GLEWMGMIHPSDSETRLNQKFKDRVTLTRDKSISTAYMELSRLRS DDTAVYYCARQGIITSVQEFAYWGQGTLVTVSS | VH Muc17.37 |
| 133 | QVQLVQSGAEVKKPGASVKVSCKASGYTFTSYWMNWVRQAPGQ GLEWMGMIHPSDSETRLNQKFKDRVTL TVDKSISTAYMELSRLRS DDTAVYYCARQGIITSVQEFAYWGQGTLVTVSS | VH Muc17.35 |
| 134 | QVQLVQSGAEVKKPGASVKVSCKASGYTFTSYWMNWVRQAPGQ GLEWMGMIHPSDSETRLNQKFKDRVTLTVDTSISTAYMELSRLRS DDTAVYYCARQGIITSVQEFAYWGQGTLVTVSS | VH; Muc17.36 |
| 135 | QVQLVQSGAEVKKPGASVKVSCKASGYTFTSYWMNWVRQAPGQ GLEWMGMIHPSDSETRLNQKFKDRVTMTRDTSISTAYMELSRLRS DDTAVYYCARQGIITSVQEFAYWGQGTLVTVSS | VH; Muc17.23, Muc17.33, Muc17.34 |
| 136 | QVQLVQSGAEVKKPGASVKVSCKASGYTFTSYWMNWVRQAPGQ GLEWMGMIHPSDSETRLNQKFKDRVTMTRDTSTSTVYMELSSLR SEDTAVYYCARQGIITSVQEFAYWGQGTLVTVSS | VH; Muc17.31, Muc17.48, Muc17.49 |
| 137 | QVQLVQSGAEVKKPGASVKVSCKASGYTFTSYWMNWVRQAPGQ GLEWMGMIHPSDSETRLNQKFKDRVTMTVDKSISTAYMELSRLRS DDTAVYYCARQGIITSVQEFAYWGQGTLVTVSS | VH; Muc17.38 |
| 138 | QVQLVQSGAEVKKPGASVKVSCKASGYTFTSYWMNWVRQAPGQ GLEWMGMIHPSDSETRLNQKFTDRVTMTRDTSTSTVYMELSSLRS EDTAVYYCARQGIITSVQEFAYWGQGTLVTVSS | VH Muc17.6 |
| 139 | QVQLVQSGAEVKKPGSSVKVSCKASGYAFSDYWINWVRQAPGQ GLEWMGQVYPGDDDINYNGKFRGRVTITADKSTSTAYMELSSLRS EDTAVYYCARHGNYVMDYWGQGTTVTVSS | VH Muc17.2 |
| 140 | QVQLVQSGAEVKKPGSSVKVSCKASGYEFSSHWMNWVRQAPGQ GLEWMGQIYPGDGDINYNEKFRGRVTITADKSTSTA YMELSSLRS EDTAVYYCARHGNYVMDYWGQGTTVTVSS | Vh Muc17.25, Muc17.26, Muc17.27, Muc17.28 |
| 141 | QVQLVQSGAEVKKPGSSVKVSCKASGYIFSNHWMNWVRQAPGQ GLEWMGQIYPGDGDINYNGKFRGRVTITADKSTSTAYMELSSLRS EDTAVYYCARHGNYLMDYWGQGTTVTVSS | VH; Muc17.3 |
| 142 | QVQLVQSGAEVKKPGSSVKVSCKASGYTFTSYWLNWVRQAPGQ GLEWMGMIHPSDSESRLNQKFKDRVTITADKSTSTAYMELSSLRS EDTAVYYCARQGIITSVQEFAYWGQGTLVTVSS | VH; Mucc. 17.46, Muc17.47 |
| 143 | QVQLVQSGAEVKKPGSSVKVSCKASGYTFTSYWLNWVRQAPGQ GLEWMGMIHPSDSETRLNQKFKDRVTITADKSTSTAYMELSSLRS EDTAVYYCARQGIITSVQEFAYWGQGTLVTVSS | VH; Muc17.42, Muc17.43, Muc17.44 |

TABLE 20-continued

| | SEQUENCES | |
|---|---|---|
| Seq ID | sequence | name |

| 144 | QVQLVQSGAEVKKPGSSVKVSCKASGYTFTSYWMNWVRQAPGQ GLEWMGMIHPSDSESRLNQKFKDRVTITADKSTSTAYMELSSLRS EDTAVYYCARQGIITSVQEFAYWGQGTLVTVSS | VH; Muc17.39, Muc17.40, Muc17.41 |
| 145 | QVQLVQSGAEVKKPGSSVKVSCKASGYTFTSYWMNWVRQAPGQ GLEWMGMIHPSDSETRLNQKFKDRVTITADKSTSTAYMELSSLRS EDTAVYYCARQGIITSVQEFAYWGQGTLVTVSS | VH; Muc17.4, Muc17.15, Muc17.16, Muc17.18, Muc17.19 |
| 146 | EVQLVESGGGLVQPGGSLRLSCAASGFTFSSFGMHWVRQAPGK GLEWVSYISSGSSTIYYADTVKGRFTISRDNAKNSLYLQMNSLRAE DTAVYYCARWGYYGSSYFAYWGQGTLVTVSS | VH; Muc17.7, Muc17.21, Muc17.22, Muc17.23, Muc17.24 |
| 147 | DIQMTQSPSSLSASVGDRVTITCKASEDIYNRLAWYQQKPGKAPKL LIYGATNLETGVPSRFSGSGSGTDFTFTISSLQPEDIATYYCQQFW RTPPTFGGGTKVEIK | VL; Muc17.24 |
| 148 | DIQMTQSPSSLSASVGDRVTITCKASEDIYNRLAWYQQKPGKAPK PLISGATNLETGVPSRFSGSGSGKDYTLTISSLQPEDIATYYCQQF WRTPPTFGGGTKVEIK | VL; Muc17.21 |
| 149 | DIQMTQSPSSLSASVGDRVTITCKASEDIYNRLAWYQQKPGKAPK PLISGATNLETGVPSRFSGSGSGTDFTFTISSLQPEDIATYYCQQF WRTPPTFGGGTKVEIK | VL; Muc17.7 |
| 150 | DIQMTQSPSSLSASVGDRVTITCKASEDIYNRLAWYQQKPGKAPK PLIYGATNLETGVPSRFSGSGSGTDFTFTISSLQPEDIATYYCQQF WRTPPTFGGGTKVEIK | VL; Muc17.22 |
| 151 | EIVLTQSPATLSLSPGERATLSCSASSSVNYIFWYQQKPGQAPRLLI YRTSNLASGIPARFSGSGSGTDFTLTISSLEPEDFAVYYCQQYHSY PLTFGGGTKVEIK | VL; Muc17.18 |
| 152 | EIVLTQSPATLSLSPGERATLSCSASSSVNYIYWYQQKPGQAPRLLI YRTSNLASGIPARFSGSGSGTDFTLTISSLEPEDFAVYYCQQYHSY PLTFGGGTKVEIK | VL; Muc17.16, Muc17.17, Muc17.34, Muc17.39, Muc17.42, Muc17.49 |
| 153 | EIVLTQSPATLSLSPGERATLSCSASSSVSYMFWYQQKPGQAPRL LIYRTSNLASGIPARFSGSGSGTDFTLTISSLEPEDFAVYYCQQFHD YPRTFGGGTKVEIK | VL; Muc17.8, Muc17.27, Muc17.31 |
| 154 | EIVLTQSPATLSLSPGERATLSCSASSSVSYMFWYQQKPGQAPRL LIYRTSNLASGIPARFSGSGSGTDFTLTISSLEPEDFAVYYCQQFHS YPRTFGGGTKVEIK | VL; Muc17.2 |
| 155 | EIVLTQSPATLSLSPGERATLSCSASSSVSYMFWYQQKPGQAPRP WIYRTSNLASGIPPRFSGSGSGTDYTLTISSLEPEDFAVYYCQQFH DYPRTFGGGTKVEIK | VL; Muc17.28 |
| 156 | EIVLTQSPATLSLSPGERATLSCSVSSNVDYVFWYQQKPGQAPRL LIYRTSNLATGIPARFSGSGSGTDFTLTISSLEPEDFAVYYCQQFHS YPRTFGGGTKVEIK | VL; Muc17.3 |
| 157 | EIVLTQSPATLSVSPGERATLSCSASSSVNYIYWYQQKPGQAPRP WIYRTSNLASGIPARFSGSGSGTEYTLTISSLQSEDFAVYYCQQYH SYPLTFGGGTKVEIK | VL; Muc17.20 |
| 158 | EIVMTQSPATLSVSPGERATLSCSASSSLNYIYWYQQKPGQAPRLL IYRTSNLASGIPARFSGSGSGTEFTLTISSLQSEDFAVYYCQQYHS YPLTFGGGTKVEIK | VL; Muc17.6 |

TABLE 20-continued

| | SEQUENCES | |
|---|---|---|
| Seq ID | sequence | name |

| 159 | EIVMTQSPATLSVSPGERATLSCSASSSVNYIYWYQQKPGQAPRL LIYRTSNLASGIPARFSGSGSGTEFTLTISSLQSEDFAVYYCQQYHS YPLTFGGGTKVEIK | VL; Muc17.5, Muc17.15, Muc17.33, Muc17.45, Muc17.48 |
| 160 | EIVMTQSPATLSVSPGERATLSCSASSSVSYMFWYQQKPGQAPRL LIYRTSNLASGIPARFSGSGSGTEFTLTISSLQSEDFAVYYCQQFHD YPRTFGGGTKVEIK | VL; Muc17.14, Muc17.26, Muc17.30 |
| 161 | IQLTQSPSFLSASVGDRVTITCSASSSVSYMFWYQQKPGKAPKLLI YRTSNLASGVPPRFSGSGSGTEFTLTISSLQPEDFATYYCQQFHD YPRTFGGGTKVEIK | VL; Muc17.13 |
| 162 | IQLTQSPSFLSASVGDRVTITCSASSSVSYMFWYQQKPGKAPKLLI YRTSNLASGVPPRFSGSGSGTEYTLTISSLQPEDFATYYCQQFHD YPRTFGGGTKVEIKR | VL; Muc17.11 |
| 163 | IQLTQSPSFLSASVGDRVTITCSASSSVSYMFWYQQKPGKAPKLLI YRTSNLASGVPSRFSGSGSGTEFTLTISSLQPEDFATYYCQQFHD YPRTFGGGTKVEIK | VL; Muc17.9, Muc17.25, Muc17.29 |
| 164 | IQLTQSPSFLSASVGDRVTITCSASSSVSYMFWYQQKPGKAPKLLI YRTSNLASGVPSRFSGSGSGTEYTLTISSLQPEDFATYYCQQFHD YPRTFGGGTKVEIK | VL; Muc17.10 |
| 165 | IQLTQSPSFLSASVGDRVTITCSASSSVSYMFWYQQKPGKAPKPW IYRTSNLASGVPPRFSGSGSGTEYTLTISSLQPEDFATYYCQQFHD YPRTFGGGTKVEIK | VL; Muc17.12 |
| 166 | IQLTQSPSFLSASVGDRVTITCSASSSVSYMFWYQQKPGKAPKPW IYRTSNLASGVPSRFSGSGSGTEFTLTISSLQPEDFATYYCQQFHD YPRTFGGGTKVEIK | VL; Muc17.1 |
| 167 | IQMTQSPSSLSASVGDRVTITCSASSSVNYIFWYQQKPGKAPKLLI YRTSNLASGVPSRFSGSGSGTDFTLTISSLQPEDFATYYCQQYHS YPLTFGGGTKVEIK | VL; Muc17.19, Muc17.41, Muc17.44, Muc17.46 |
| 168 | IQMTQSPSSLSASVGDRVTITCSASSSVNYIYWYQQKPGKAPKLLI YRTSNLASGVPSRFSGSGSGTDFTLTISSLQPEDFATYYCQQYHS YPLTFGGGTKVEIK | VL; Muc17.4, Muc17.31, Muc17.32, Muc17.35, Muc17.36, Muc17.387, Muc17.38, Muc17.40, Muc17.43, Muc17.47 |
| 169 | DIQMTQSPSSLSASVGDRVTITCKASEDIYNRLAWYQQKPGKAPKL LIYGATNLETGVPSRFSGSGSGKDYTLTISSLQPEDIATYYCQQFW RTPPTFGGGTKVEIK | VL; Muc17.23 |
| 170 | GFTFSSFGMH | HCDR1; CLDN182.3, CLDN182.&, CLDN182.12, CLDN182.13 |
| 171 | GYAFNNYWMN | HCDR1; CLDN182.5 |
| 172 | GYAFSSYWMN | HCDR1; CLDN182.6, CLDN182.9, CLDN182.15, CLDN182.16 |

TABLE 20-continued

| | SEQUENCES | |
|---|---|---|
| Seq ID | sequence | name |
| 173 | GYTFTNFGIT | HCDR1; CLDN182.4, CLDN182.8, CLDN182.10, CLDN18.11 |
| 174 | GYTFTNSGMN | HCDR1; CLDN182.2, CLDN182.14, CLDN182.17 |
| 175 | GYTFTNYGMN | HCDR1; CLDN182.1 |
| 176 | EIYPSSGNTFYNEKFKG | HCDR2; CLDN182.4, CLDN182.8, CLDN182.10, CLDN182.11 |
| 177 | QISPGNGNSNFNGKFKG | HCDR2; CLDN182.5 |
| 178 | QIYPGNGNSNFNGKFKA | HCDR2; CLDN182.6, CLDN182.9, CLDN182.15, CLDN182.16 |
| 179 | WINTNTGEPTFAEEFRG | HCDR2; CLDN182.2, CLDN182.14, CLDN182.17 |
| 180 | WINTNTGEPTYAEEFKG | HCDR2; CLDN182.1 |
| 181 | YISSGNSAIYYADTVNG | HCDR2; CLDN182.3, CLDN182.7, CLDN182.12, CLDN182.13 |
| 182 | GGGPLRSRYFDY | HCDR3; CLDN182.4, CDLN182.8, CLDN182.10, CLDN182.11 |
| 183 | GGRFGNAMDY | HCDR3; CLDN182.6, CLDN182.9, CLDN182.15, CLDN182.16 |
| 184 | GGRYGNAMDY | HCDR3; CLDN182.5 |
| 185 | LRYGNSFDY | HCDR3; CLDN182.3, CLDN182.7, CLDN182.12, CLDN182.13 |
| 186 | YFYGNSFVY | HCDR3; CLDN182.1 |
| 187 | YYYGNSFAY | HCDR3; CLDN182.2, CLDN182.14, CLDN182.17 |
| 188 | KSSQSLLNSGNQKAJYLT | LCDR1; CLDN182.1, CLDN182.2, |

TABLE 20-continued

| Seq ID | sequence | name |
|---|---|---|
| | | CLDN182.3, CLDN182.6, CLDN182.7, CLDN182.9, CLDN182.12, CLDN182.13, CLDN182.14, CLDN182.15, CLDN182.16, CLDN182.17 |
| 189 | KSSQSLLNSGNQRNYLT | LCDR1; CLDN182.5 |
| 190 | RSSQSLFSSGNQKNYLT | LCDR1; CLDN182.4, CLDN182.8, CLDN182.10, CLDN182.11 |
| 191 | WVASTRES | LCDR2; CLDN182.1, CLDN182.2, CLDN182.3, CLDN182.4, CLND182.5, CLDN182.6, CLDN182.7, CLDN182.8, CLDN182.9, CLND182.10, CLDN182.11, CLDN182.12, CLDN182.13, CLDN182.14, CLDN182.15, CLDN182.16, CLDN182.17 |
| 192 | QNAYFYPYT | LCDR3; CLDN182.5, CLDN182.6, CLND182.9, CLDN182.15, CLDN182.16 |
| 193 | QNDYYYPLT | LCDR3; CLDN182.4, CLDN182.8, CLND182.10, CLDN182.11 |
| 194 | QNNYFYPLT | LCDR3; CLDN182.2, CLND182.14, CLND182.17 |
| 195 | QNNYNFPLT | LCDR3; CLDN182.1 |
| 196 | QNNYYYPLT | LCDR3; CLDN182.3, CLND182.7, CLND182.12, CLND182.13 |
| 197 | EVQLVESGGGLVQPGGSLRLSCAASGFTFSSFGMHVWRQAPGK GLEVWAYISSGNSAIYYADTVNGRFTISRDNPKNTLYLQMNSLRAE DTAVYYCARLRYGNSFDYWGQGTLVTVSS | VH; CLDN182.12, CLND182.13 |
| 198 | EVQLVESGGGLVQPGGSLRLSCAASGFTFSSFGMHVWRQAPGK GLEVWSYISSGNSAIYYADTVNGRFTISRDNAKNSLYLQMNSLRAE DTAVYYCARLRYGNSFDYWGQGTLVTVSS | VH; CLDN182.3, CLDN182.7 |

101 102

TABLE 20-continued

| SEQUENCES | | |
| --- | --- | --- |
| Seq ID | sequence | name |

| 199 | QIQLVQSGAEVKKPGASVKVSCKASGYTFTNSGMNVWRQAPGQ GLEWMGWINTNTGEPTFAEEFRGRVTFTLDTSASTAYMELSRLRS DDTAVYYCARYYYGNSFAYWGQGTLVTVSS | VH; CLDN182.14 |
| 200 | QVQLVQSGAEVKKPGASVKVSCKASGYTFTNFGITVWRQAPGQG LEWIGEIYPSSGNTFYNEKFKGRVTLTADKSSSAAYMELRSLRSD DTAVYYCARGGGPLRSRYFDYWGQGTLVTVSS | VH; CLDN182.10, CLND182.11 |
| 201 | QVQLVQSGAEVKKPGASVKVSCKASGYTFTNFGITVWRQAPGQG LEWMGEIYPSSGNTFYNEKFKGRVTMTTDTSTSTAYMELRSLRSD DTAVYYCARGGGPLRSRYFDYWGQGTLVTVSS | VH; CLDN182.4, CLND182.8 |
| 202 | QVQLVQSGAEVKKPGASVKVSCKASGYTFTNSGMNVWRQAPGQ GLEWMGWINTNTGEPTFAEEFRGRVTMTRDTSISTAYMELSRLRS DDTAVYYCARYYYGNSFAYWGQGTLVTVSS | VH CLND182.2, CLND182.17 |
| 203 | QVQLVQSGAEVKKPGASVKVSCKASGYTFTNYGMNVWRQAPGQ GLEWMGWINTNTGEPTYAEEFKGRVTMTRDTSISTAYMELSRLRS DDTAVYYCARYFGNSFVYWGQGTLVTVSS | VH; CLDN182.1 |
| 204 | QVQLVQSGAEVKKPGSSVKVSCKASGYAFNNYWMNVWRQAPGQ GLEWMGQISPGNGNSNFNGKFKGRVTITADKSTSTAYMELSSLRS EDTAVYYCARGGRYGNAMDYWGQGTTVTVSS | VH; CLND182.5 |
| 205 | QVQLVQSGAEVKKPGSSVKVSCKASGYAFSSYWMNVWRQAPGQ GLEWIGQIYPGNGNSNFNGKFKARVTLTADKSSSTAYMELSSLRS EDTAVYYCARGGRFGNAMDYWGQGTTVTVSS | VH; CLND182.15, CLND182.16 |
| 206 | QVQLVQSGAEVKKPGSSVKVSCKASGYAFSSYWMNVWRQAPGQ GLEWMGQIYPGNGNSNFNGKFKARVTITADKSTSTAYMELSSLRS EDTAVYYCARGGRFGNAMDYWGQGTTVTVSS | VH; CLDN182.6, CLDN182.9 |
| 207 | DIVMTQSPDSLAVSLGERATINCKSSQSLLNSGNQKNYLTWYQQK PGQPPKLLIFWASTRESGVPDRFSGSGSGTDFTLTISSLQAEDVAV YYCQNNYYYPLTFGGGTKVEIK | VL; CLND182.7, CLND182.13 |
| 206 | DIVMTQSPDSLAVSLGERATINCKSSQSLLNSGNQKNYLTWYQQK PGQPPKLLIYWASTRESGVPDRFSGSGSGTDFTLTISSLQAEDVA VYYCQNAYFYPYTFGGGTKVEIK | VL; CLDN182.6, CLDN182.15 |
| 207 | DIVMTQSPDSLAVSLGERATINCKSSQSLLNSGNQKNYLTWYQQK PGQPPKLLIYWASTRESGVPDRFSGSGSGTDFTLTISSLQAEDVA VYYCQNNYFYPLTFGGGTKVEIK | VL; CLND182.2, CLND182.14 CLND182.17 |
| 208 | DIVMTQSPDSLAVSLGERATINCKSSQSLLNSGNQKNYLTWYQQK PGQPPKLLIYWASTRESGVPDRFSGSGSGTDFTLTISSLQAEDVAV YYCQNNYNFPLTFGGGTKVEIK | VL; CLND182.1 |
| 209 | DIVMTQSPDSLAVSLGERATINCKSSQSLLNSGNQKNYLTWYQQK PGQPPKLLIYWASTRESGVPDRFSGSGSGTDFTLTISSLQAEDVA VYYCQNNYYYPLTFGGGTKVEIK | VL; CLDN182.3, CLDN182.12 |
| 210 | DIVMTQSPDSLAVSLGERATINCKSSQSLLNSGNQRNYLTWYQQK PGQPPKLLIYWASTRESGVPDRFSGSGSGTDFTLTISSLQAEDVA VYYCQNAYFYPYTFGGGTKVEIK | VL; CLDN182.5 |
| 211 | DIVMTQSPDSLAVSLGERATINCRSSQSLFSSGNQKNYLTWYQQK PGQPPKLLIYWASTRESGVPDRFSGSGSGADFTLTISSLQAEDVAV YYCQNDYYYPLTFGGGTKVEIK | VL; CLDN182.8, CLND182.11 |
| 212 | DIVMTQSPDSLAVSLGERATINCRSSQSLFSSGNQKNYLTWYQQK PGQPPKLLIYWASTRESGVPDRFSGSGSGTDFTLTISSLQAEDVA VYYCQNDYYYPLTFGGGTKVEIK | VL; CLND812.4, CLND182.10 |
| 213 | DIVMTQSPDSLAVSLGERATMNCKSSQSLLNSGNQKNYLTWYQQ KPGQPPKLLIYWASTRESGVPDRFSGSGSGTDFTLTISSLQAEDVA VYYCQNAYFYPYTFGGGTKVEIK | VL; CLND182.9, CLND182.16 |
| 214 | SGGGGS | 1xG4S |
| 215 | GGGGSGGGGSGGGGS | 3xG4S |
| 216 | GKPGSGKPGSGKPGSGKPGS | CL |

TABLE 20-continued

SEQUENCES

| Seq ID | sequence | name |
|---|---|---|
| 217 | ASTKGPSVFPLAPSSKSTSGGTAALGCLVKDYFPEPVTVSWNSGA<br>LTSGVHTFPAVLQSSGLYSLSSVVTVPSSSLGTQTYICNVNHKPSN<br>TKVDKRVEPKSCDKTHTCPPCPAPELLGGPSVFLFPPKPKDTLMIS<br>RTPEVTCVVVDVSHEDPEVKFNWYVDGVEVHNAKTKPREEQYNS<br>TYRVVSVLTVLHQDWLNGKEYKCKVSNKALPAPIEKTISKAKGQPR<br>EPQVYTLPPSRDELTKNQVSLTCLVKGFYPSDIAVEWESNGQPEN<br>NYKTTPPVLDSDGSFFLYSKLTVDKSRWQQGNVFSCSVMHEALH<br>NHYTQKSLSLSPGK | CH1-3 IgG1 |
| 218 | ASTKGPSVFPLAPSSKSTSGGTAALGCLVKDYFPEPVTVSWNSGA<br>LTSGVHTFPAVLQSSGLYSLSSVVTVPSSSLGTQTYICNVNHKPSN<br>TKVDKRVEPKSCDKTHTCPPCPAPELLGGPSVFLFPPKPKDTLMIS<br>RTPEVTCVVVDVSHEDPEVKFNWYVDGVEVHNAKTKPREEQYAS<br>TYRVVSVLTVLHQDWLNGKEYKCKVSNKALPAPIEKTISKAKGQPR<br>EPQVYTLPPSRDELTKNQVSLTCLVKGFYPSDIAVEWESNGQPEN<br>NYKTTPPVLDSDGSFFLYSKLTVDKSRWQQGNVFSCSVMHEALH<br>NHYTQKSLSLSPGK | CH1-3 IgG1<br>(N297A) |
| 219 | ASTKGPSVFPLAPSSKSTSGGTAALGCLVKDYFPEPVTVSWNSGA<br>LTSGVHTFPAVLQSSGLYSLSSVVTVPSSSLGTQTYICNVNHKPSN<br>TKVDKRVEPKSCDKTHTCPPCPAPEFEGGPSVFLFPPKPKDTLMIS<br>RTPEVTCVVVDVSHEDPEVKFNWYVDGVEVHNAKTKPREEQYNS<br>TYRVVSVLTVLHQDWLNGKEYKCKVSNKALPASIEKTISKAKGQPR<br>EPQVYTLPPSRDELTKNQVSLTCLVKGFYPSDIAVEWESNGQPEN<br>NYKTTPPVLDSDGSFFLYSKLTVDKSRWQQGNVFSCSVMHEALH<br>NHYTQKSLSLSPGK | CH1-3 IgG1<br>(L234F/L23<br>5E/P331S) |
| 220 | ASTKGPSVFPLAPSSKSTSGGTAALGCLVKDYFPEPVTVSWNSGA<br>LTSGVHTFPAVLQSSGLYSLSSVVTVPSSSLGTQTYICNVNHKPSN<br>TKVDKRVEPKSCDKTHTCPPCPAPELLGGPSVFLFPPKPKDTLMIS<br>RTPEVTCVVVDVSHEDPEVKFNWYVDGVEVHNAKTKPREEQYNS<br>TYRVVSVLTVLHQDWLNGKEYKCKVSNKALPAPIEKTISKAKGQPR<br>EPQVCTLPPSRDELTKNQVSLTCLVEGFYPSDIAVEWESNGQPEN<br>NYKTTPPVLDSDGSFFLYSDLTVDKSRWQQGNVFSCSVMHEALH<br>NHYTQESLSLSPGK | CH1-3 IgG1<br>(Y349C/K370E/<br>K409D/K439E) |
| 221 | ASTKGPSVFPLAPSSKSTSGGTAALGCLVKDYFPEPVTVSWNSGA<br>LTSGVHTFPAVLQSSGLYSLSSVVTVPSSSLGTQTYICNVNHKPSN<br>TKVDKRVEPKSCDKTHTCPPCPAPELLGGPSVFLFPPKPKDTLMIS<br>RTPEVTCVVVDVSHEDPEVKFNWYVDGVEVHNAKTKPREEQYNS<br>TYRVVSVLTVLHQDWLNGKEYKCKVSNKALPAPIEKTISKAKGQPR<br>EPQVYTLPPCRKKLTKNQVSLTCLVKGFYPSDIAVEWESNGQPEN<br>NYKTTPPVLKSDGSFFLYSKLTVDKSRWQQGNVFSCSVMHEALH<br>NHYTQKSLSLSPGK | CH1-3 IgG1<br>(S354C/<br>D356K/<br>E357K/<br>D399K) |
| 222 | ASTKGPSVFPLAPSSKSTSGGTAALGCLVKDYFPEPVTVSWNSGA<br>LTSGVHTFPAVLQSSGLYSLSSVVTVPSSSLGTQTYICNVNHKPSN<br>TKVDKRVEPKSCDKTHTCPPCPAPELLGGPSVFLFPPKPKDTLMIS<br>RTPEVTCVVVDVSHEDPEVKFNWYVDGVEVHNAKTKPREEQYNS<br>TYRVVSVLTVLHQDWLNGKEYKCKVSNKALPAPIEKTISKAKGQPR<br>EPQVYTLPPSRDELTKNQVSLWCLVKGFYPSDIAVEWESNGQPEN<br>NYKTTPPVLDSDGSFFLYSKLTVDKSRWQQGNVFSCSVMHEALH<br>NHYTQKSLSLSPGK | CH1-3 IgG1<br>(S354C/T366W) |
| 223 | ASTKGPSVFPLAPSSKSTSGGTAALGCLVKDYFPEPVTVSWNSGA<br>LTSGVHTFPAVLQSSGLYSLSSVVTVPSSSLGTQTYICNVNHKPSN<br>TKVDKRVEPKSCDKTHTCPPCPAPELLGGPSVFLFPPKPKDTLMIS<br>RTPEVTCVVVDVSHEDPEVKFNWYVDGVEVHNAKTKPREEQYNS<br>TYRVVSVLTVLHQDWLNGKEYKCKVSNKALPAPIEKTISKAKGQPR<br>EPQVYTLPPSRDELTKNQVSLSCAVKGFYPSDIAVEWESNGQPEN<br>NYKTTPPVLDSDGSFFLVSKLTVDKSRWQQGNVFSCSVMHEALH<br>NHYTQKSLSLSPGK | CH1-3 IgG1<br>(Y349C/<br>T366S/<br>L368A/<br>Y407V) |
| 224 | ASTKGPSVFPLAPSSKSTSGGTAALGCLVKDYFPEPVTVSWNSGA<br>LTSGVHTFPAVLQSSGLYSLSSVVTVPSSSLGTQTYICNVNHKPSN<br>TKVDKRVEPKSCDKTHTCPPCPAPEFEGGPSVFLFPPKPKDTLMIS<br>RTPEVTCVVVDVSHEDPEVKFNWYVDGVEVHNAKTKPREEQYNS<br>TYRVVSVLTVLHQDWLNGKEYKCKVSNKALPASIEKTISKAKGQPR<br>EPQVCTLPPSRDELTKNQVSLTCLVEGFYPSDIAVEWESNGQPEN<br>NYKTTPPVLDSDGSFFLYSDLTVDKSRWQQGNVFSCSVMHEALH<br>NHYTQESLSLSPGK | CH1-3 IgG1<br>(L234F/L23<br>5E/P331S/<br>Y349C/K37<br>0E/K409D/K<br>439E) |
| 225 | ASTKGPSVFPLAPSSKSTSGGTAALGCLVKDYFPEPVTVSWNSGA<br>LTSGVHTFPAVLQSSGLYSLSSVVTVPSSSLGTQTYICNVNHKPSN<br>TKVDKRVEPKSCDKTHTCPPCPAPEFEGGPSVFLFPPKPKDTLMIS<br>RTPEVTCVVVDVSHEDPEVKFNWYVDGVEVHNAKTKPREEQYNS | CH1-3 IgG1<br>(L234F/L23<br>5E/P331S/<br>S354C/ |

TABLE 20-continued

SEQUENCES

| Seq ID | sequence | name |
|---|---|---|
| | TYRVVSVLTVLHQDWLNGKEYKCKVSNKALPASIEKTISKAKGQPR EPQVYTLPPCRKKLTKNQVSLTCLVKGFYPSDIAVEWESNGQPEN NYKTTPPVLKSDGSFFLYSKLTVDKSRWQQGNVFSCSVMHEALH NHYTQKSLSLSPGK | D356K/ E357K/ O399K) |
| 226 | ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKRVEPKSCDKTHTCPPCPAPEFEGGPSVFLFPPKPKDTLMIS RTPEVTCVVVDVSHEDPEVKFNWYVDGVEVHNAKTKPREEQYNS TYRVVSVLTVLHQDWLNGKEYKCKVSNKALPASIEKTISKAKGQPR EPQVYTLPPSRDELTKNQVSLWCLVKGFYPSDIAVEWESNGQPEN NYKTTPPVLDSDGSFFLYSKLTVDKSRWQQGNVFSCSVMHEALH NHYTQKSLSLSPGK | CH1-3 IgG1 (L234F/L23 5E/P331S/ S354C/T36 6W) |
| 227 | ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKRVEPKSCDKTHTCPPCPAPEFEGGPSVFLFPPKPKDTLMIS RTPEVTCVVVDVSHEDPEVKFNWYVDGVEVHNAKTKPREEQYNS TYRVVSVLTVLHQDWLNGKEYKCKVSNKALPASIEKTISKAKGQPR EPQVYTLPPSRDELTKNQVSLSCAVKGFYPSDIAVEWESNGQPEN NYKTTPPVLDSDGSFFLYSKLTVDKSRWQQGNVFSCSVMHEALH NHYTQKSLSLSPGK | CH1-3 IgG1 (L234F/L23 5E/P331S/ Y349C/ T366S/ L368A/ Y407V) |
| 228 | ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKRVEPKSCDKTHTCPPCPAPELLGGPSVFLFPPKPKDTLMIS RTPEVTCVVVDVSHEDPEVKFNWYVDGVEVHNAKTKPREEQYAS TYRVVSVLTVLHQDWLNGKEYKCKVSNKALPAPIEKTISKAKGQPR EPQVCTLPPSRDELTKNQVSLTCLVEGFYPSDIAVEWESNGQPEN NYKTTPPVLDSDGSFFLYSDLTVDKSRWQQGNVFSCSVMHEALH NHYTQESLSLSPGK | CH1-3 IgG1 (N297A/ Y349C/K37 0E/K409D/K 439E) |
| 229 | ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKRVEPKSCDKTHTCPPCPAPELLGGPSVFLFPPKPKDTLMIS RTPEVTCVVVDVSHEDPEVKFNWYVDGVEVHNAKTKPREEQYAS TYRVVSVLTVLHQDWLNGKEYKCKVSNKALPAPIEKTISKAKGQPR EPQVYTLPPCRKKLTKNQVSLTCLVKGFYPSDIAVEWESNGQPEN NYKTTPPVLKSDGSFFLYSKLTVDKSRWQQGNVFSCSVMHEALH NHYTQKSLSLSPGK | CH1-3 IgG1 (N297A/ S354C/ D356K/ E357K/ O399K) |
| 230 | ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKRVEPKSCDKTHTCPPCPAPELLGGPSVFLFPPKPKDTLMIS RTPEVTCVVVDVSHEDPEVKFNWYVDGVEVHNAKTKPREEQYAS TYRVVSVLTVLHQDWLNGKEYKCKVSNKALPAPIEKTISKAKGQPR EPQVYTLPPSRDELTKNQVSLWCLVKGFYPSDIAVEWESNGQPEN NYKTTPPVLDSDGSFFLYSKLTVDKSRWQQGNVFSCSVMHEALH NHYTQKSLSLSPGK | CH1-3 IgG1 (N297A/ S354C/T36 6W) |
| 231 | ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKRVEPKSCDKTHTCPPCPAPELLGGPSVFLFPPKPKDTLMIS RTPEVTCVVVDVSHEDPEVKFNWYVDGVEVHNAKTKPREEQYAS TYRVVSVLTVLHQDWLNGKEYKCKVSNKALPAPIEKTISKAKGQPR EPQVYTLPPSRDELTKNQVSLSCAVKGFYPSDIAVEWESNGQPEN NYKTTPPVLDSDGSFFLYSKLTVDKSRWQQGNVFSCSVMHEALH NHYTQKSLSLSPGK | CH1-3 IgG1 (N297A/ Y349C/ T366S/ L368A/ Y407V) |
| 232 | EPKSSDKTHTCPPCPAPELLGGPSVFLFPPKPKDTLMISRTPEVTC VVVDVSHEDPEVKFNWYVDGVEVHNAKTKPREEQYNSTYRVVSV LTVLHQDWLNGKEYKCKVSNKALPAPIEKTISKAKGQPREPQVYTL PPSRDELTKNQVSLTCLVKGFYPSDIAVEWESNGQPENNYKTTPP VLDSDGSFFLYSKLTVDKSRWQQGNVFSCSVMHEALHNHYTQKS LSLSPGK | Fc IgG1 |
| 233 | EPKSSDKTHTCPPCPAPELLGGPSVFLFPPKPKDTLMISRTPEVTC VVVDVSHEDPEVKFNWYVDGVEVHNAKTKPREEQYASTYRVVSV LTVLHQDWLNGKEYKCKVSNKALPAPIEKTISKAKGQPREPQVYTL PPSRDELTKNQVSLTCLVKGFYPSDIAVEWESNGQPENNYKTTPP VLDSDGSFFLYSKLTVDKSRWQQGNVFSCSVMHEALHNHYTQKS LSLSPGK | Fc IgG1 (N297A) |

TABLE 20-continued

| Seq ID | sequence | name |
|---|---|---|
| 234 | EPKSSDKTHTCPPCPAPEFEGGPSVFLFPPKPKDTLMISRTPEVTC<br>VVVDVSHEDPEVKFNWYVDGVEVHNAKTKPREEQYNSTYRVVSV<br>LTVLHQDWLNGKEYKCKVSNKALPASIEKTISKAKGQPREPQVTL<br>PPSRDELTKNQVSLTCLVKGFYPSDIAVEWESNGQPENNYKTTPP<br>VLDSDGSFFLYSKLTVDKSRWQQGNVFSCSVMHEALHNHYTQKS<br>LSLSPGK | Fc IgG1<br>(L234F/L23<br>5E/P331S) |
| 235 | EPKSSDKTHTCPPCPAPELLGGPSVFLFPPKPKDTLMISRTPEVTC<br>VVVDVSHEDPEVKFNWYVDGVEVHNAKTKPREEQYNSTYRVVSV<br>LTVLHQDWLNGKEYKCKVSNKALPAPIEKTISKAKGQPREPQVCTL<br>PPSRDELTKNQVSLTCLVEGFYPSDIAVEWESNGQPENNYKTTPP<br>VLDSDGSFFLYSDLTVDKSRWQQGNVFSCSVMHEALHNHYTQES<br>LSLSPGK | Fc IgG1<br>(Y349C/K37<br>0E/K409D/K<br>439E) |
| 236 | EPKSSDKTHTCPPCPAPELLGGPSVFLFPPKPKDTLMISRTPEVTC<br>VVVDVSHEDPEVKFNWYVDGVEVHNAKTKPREEQYNSTYRVVSV<br>LTVLHQDWLNGKEYKCKVSNKALPAPIEKTISKAKGQPREPQVYTL<br>PPCRKKLTKNQVSLTCLVKGFYPSDIAVEWESNGQPENNYKTTPP<br>VLKSDGSFFLYSKLTVDKSRWQQGNVFSCSVMHEALHNHYTQKS<br>LSLSPGK | Fc IgG1<br>(S354C/<br>D356K/<br>E357K/<br>D399K) |
| 237 | EPKSSDKTHTCPPCPAPELLGGPSVFLFPPKPKDTLMISRTPEVTC<br>VVVDVSHEDPEVKFNWYVDGVEVHNAKTKPREEQYNSTYRVVSV<br>LTVLHQDWLNGKEYKCKVSNKALPAPIEKTISKAKGQPREPQVYTL<br>PPSRDELTKNQVSLWCLVKGFYPSDIAVEWESNGQPENNYKTTPP<br>VLDSDGSFFLYSKLTVDKSRWQQGNVFSCSVMHEALHNHYTQKS<br>LSLSPGK | Fc IgG1<br>(S354C/T36<br>6W |
| 238 | EPKSSDKTHTCPPCPAPELLGGPSVFLFPPKPKDTLMISRTPEVTC<br>VVVDVSHEDPEVKFNWYVDGVEVHNAKTKPREEQYNSTYRVVSV<br>LTVLHQDWLNGKEYKCKVSNKALPAPIEKTISKAKGQPREPQVYTL<br>PPSRDELTKNQVSLSCAVKGFYPSDIAVEWESNGQPENNYKTTPP<br>VLDSDGSFFLVSKLTVDKSRWQQGNVFSCSVMHEALHNHYTQKS<br>LSLSPGK | Fc IgG1<br>(Y349C/<br>T366S/<br>L368A/<br>Y407V) |
| 239 | EPKSSDKTHTCPPCPAPEFEGGPSVFLFPPKPKDTLMISRTPEVTC<br>VVVDVSHEDPEVKFNWYVDGVEVHNAKTKPREEQYNSTYRVVSV<br>LTVLHQDWLNGKEYKCKVSNKALPASIEKTISKAKGQPREPQVCTL<br>PPSRDELTKNQVSLTCLVEGFYPSDIAVEWESNGQPENNYKTTPP<br>VLDSDGSFFLYSDLTVDKSRWQQGNVFSCSVMHEALHNHYTQES<br>LSLSPGK | Fc IgG1<br>(L234F/L23<br>5E/P331S/<br>Y349C/K37<br>0E/K409D/K<br>439E) |
| 240 | EPKSSDKTHTCPPCPAPEFEGGPSVFLFPPKPKDTLMISRTPEVTC<br>VVVDVSHEDPEVKFNWYVDGVEVHNAKTKPREEQYNSTYRVVSV<br>LTVLHQDWLNGKEYKCKVSNKALPASIEKTISKAKGQPREPQVYTL<br>PPCRKKLTKNQVSLTCLVKGFYPSDIAVEWESNGQPENNYKTTPP<br>VLKSDGSFFLYSKLTVDKSRWQQGNVFSCSVMHEALHNHYTQKS<br>LSLSPGK | Fc IgG1<br>(L234F/L23<br>5E/P331S/<br>S354C/<br>D356K/<br>E357K/<br>D399K) |
| 241 | EPKSSDKTHTCPPCPAPEFEGGPSVFLFPPKPKDTLMISRTPEVTC<br>VVVDVSHEDPEVKFNWYVDGVEVHNAKTKPREEQYNSTYRVVSV<br>LTVLHQDWLNGKEYKCKVSNKALPASIEKTISKAKGQPREPQVYTL<br>PPSRDELTKNQVSLWCLVKGFYPSDIAVEWESNGQPENNYKTTPP<br>VLDSDGSFFLYSKLTVDKSRWQQGNVFSCSVMHEALHNHYTQKS<br>LSLSPGK | Fc IgG1<br>(L234F/L23<br>5E/P331S/<br>S354C/T36<br>6W) |
| 242 | EPKSSDKTHTCPPCPAPEFEGGPSVFLFPPKPKDTLMISRTPEVTC<br>VVVDVSHEDPEVKFNWYVDGVEVHNAKTKPREEQYNSTYRVVSV<br>LTVLHQDWLNGKEYKCKVSNKALPASIEKTISKAKGQPREPQVYTL<br>PPSRDELTKNQVSLSCAVKGFYPSDIAVEWESNGQPENNYKTTPP<br>VLDSDGSFFLVSKLTVDKSRWQQGNVFSCSVMHEALHNHYTQKS<br>LSLSPGK | Fc IgG1<br>(L234F/L23<br>5E/P331S/<br>Y349C/<br>T366S/<br>L368A/<br>Y407V) |
| 243 | EPKSSDKTHTCPPCPAPELLGGPSVFLFPPKPKDTLMISRTPEVTC<br>VVVDVSHEDPEVKFNWYVDGVEVHNAKTKPREEQYASTYRVVSV<br>LTVLHQDWLNGKEYKCKVSNKALPAPIEKTISKAKGQPREPQVCTL<br>PPSRDELTKNQVSLTCLVEGFYPSDIAVEWESNGQPENNYKTTPP<br>VLDSDGSFFLYSDLTVDKSRWQQGNVFSCSVMHEALHNHYTQES<br>LSLSPGK | Fc IgG1<br>(N297A/<br>Y349C/K37<br>0E/K409D/K<br>439E) |
| 244 | EPKSSDKTHTCPPCPAPELLGGPSVFLFPPKPKDTLMISRTPEVTC<br>VVVDVSHEDPEVKFNWYVDGVEVHNAKTKPREEQYASTYRVVSV<br>LTVLHQDWLNGKEYKCKVSNKALPAPIEKTISKAKGQPREPQVYTL | Fc IgG1<br>(N297A/<br>S354C/ |

TABLE 20-continued

| | SEQUENCES | |
|---|---|---|
| Seq ID | sequence | name |

| | PPCRKKLTKNQVSLTCLVKGFYPSDIAVEWESNGQPENNYKTTPP VLKSDGSFFLYSKLTVDKSRWQQGNVFSCSVMHEALHNHYTQKS LSLSPGK | D356K/ E357K/ D399K) |
| 245 | EPKSSDKTHTCPPCPAPELLGGPSVFLFPPKPKDTLMISRTPEVTC VVVDVSHEDPEVKFNWYVDGVEVHNAKTKPREEQYASTYRVVSV LTVLHQDWLNGKEYKCKVSNKALPAPIEKTISKAKGQPREPQVYTL PPSRDELTKNQVSLWCLVKGFYPSDIAVEWESNGQPENNYKTTPP VLDSDGSFFLYSKLTVDKSRWQQGNVFSCSVMHEALHNHYTQKS LSLSPGK | Fc IgG1 (N297A/ S354C/T36 6W) |
| 246 | EPKSSDKTHTCPPCPAPELLGGPSVFLFPPKPKDTLMISRTPEVTC VVVDVSHEDPEVKFNWYVDGVEVHNAKTKPREEQYASTYRVVSV LTVLHQDWLNGKEYKCKVSNKALPAPIEKTISKAKGQPREPQVYTL PPSRDELTKNQVSLSCAVKGFYPSDIAVEWESNGQPENNYKTTPP VLDSDGSFFLVSKLTVDKSRWQQGNVFSCSVMHEALHNHYTQKS LSLSPGK | Fc IgG1 (N297A/ Y349C/ T366S/ L368A/ Y407V) |
| 247 | RTVAAPSVFIFPPSDEQLKSGTASVVCLLNNFYPREAKVQWKVDN ALQSGNSQESVTEQDSKDSTYSLSSTLTLSKADYEKHKVYACEVT HQGLSSPVTKSFNRGEC | CL1 |
| 248 | EVQLVESGGGLVQPKGSLKLSCAASGFTFNTYAMNWVRQAPGKG LEWVARIRSKYNNYATYYADSVKDRFTISRDDSQSILYLQMNNLKT EDTAMYYCVRHGNFGNSYVSWFAYWGQGTLVTVSS | VH; CD3vA |
| 249 | EVQLVESGGGLVQPGGSLRLSCAASGFTFSTYAMNWVRQAPGK GLEWVGRIRSKANNYATYYADSVKGRFTISRDDSKNTLYLQMNSL RAEDTAVYYCVRHGNFGDSYVSWFAYWGQGTLVTVSS | VH; CD3vB |
| 250 | EVQLVESGGGLVQPGGSLRLSCAASGFTFSTYAMNWVRQAPGK GLEWVGRIRSKYNNYATYYADSVKGRFTISRDDSKNTLYLQMNSL RAEDTAVYYCVRHGNFGDSYVSWFAYWGQGTLVTVSS | VH; CD3vC |
| 251 | EVQLVESGGGLVQPGGSLRLSCAASGFTFSTYAMNWVRQAPGK GLEWVGRIRSKINNYATYYADSVKGRFTISRDDSKNTLYLQMNSLR AEDTAVYYCVRHGNFGDSYVSWFAYWGQGTLVTVSS | VH; CD3vD |
| 252 | EVQLVESGGGLVQPGGSLRLSCAASGFTFSTYAMNWVRQAPGK GLEWVGRIRSKLNNYATYYADSVKGRFTISRDDSKNTLYLQMNSL RAEDTAVYYCVRHGNFGDSYVSWFAYWGQGTLVTVSS | VH; CD3vE |
| 253 | EVQLVESGGGLVQPGGSLRLSCAASGFTFSTYAMNWVRQAPGK GLEWVGRIRSKVNNYATYYADSVKGRFTISRDDSKNTLYLQMNSL RAEDTAVYYCVRHGNFGDSYVSWFAYWGQGTLVTVSS | VH; CD3vF |
| 254 | EVQLVESGGGLVQPGGSLRLSCAASGFTFSTYAMNWVRQAPGK GLEWVGRIRSKSNNYATYYADSVKGRFTISRDDSKNTLYLQMNSL RAEDTAVYYCVRHGNFGDSYVSWFAYWGQGTLVTVSS | VH; CD3vG |
| 255 | EVQLVESGGGLVQPGGSLRLSCAASGFTFSTYAMDWVRQAPGK GLEWVGRIRSKYNNYATYYADSVKGRFTISRDDSKNTLYLQMNSL RAEDTAVYYCVRHGNFGDSYVSWFAYWGQGTLVTVSS | VH; CD3vH |
| 256 | EVQLVESGGGLVQPGGSLRLSCAASGFTFSTYAMNWVRQAPGK GLEWVGRIRSKYNNYATYYADSVKGRFTISRDDSKNTLYLQMNSL RAEDTAVYYCVRHGNFGDSYVSWFEYWGQGTLVTVSS | VH; CD3vI |
| 257 | EVQLVESGGGLVQPGGSLRLSCAASGFTFSTYAMNWVRQAPGK GLEWVGRIRSKYNNYATYYADSVKGRFTISRDDSKNTLYLQMNSL RAEDTAVYYCVRHGNFGDSYVSWFDYWGQGTLVTVSS | VH; CD3vJ |
| 258 | EVQLVESGGGLVQPGGSLRLSCAASGFTFSTYAMNWVRQAPGK GLEWVGRIRSKYNNYATYYADSVKGRFTISRDDSKNTLYLQMNSL RAEDTAVYYCVRHGNFGDSYVSWFNYWGQGTLVTVSS | VH; CD3vK |
| 259 | EVQLVESGGGLVQPGGSLRLSCAASGFTFSTYAMNWVRQAPGK GLEWVGRIRSKYNNYATYYADSVKGRFTISRDDSKNTLYLQMNSL RAEDTAVYYCVRHGNFGDSYVSYFAYWGQGTLVTVSS | VH; CD3vL |
| 260 | QLVESGGGLVQPGGSLRLSCAASGFTFSTYAMNWVRQAPGKGLE WVGRIRSKANNYATYYADSVKGRFTISRDDSKNTLYLQMNSLRAE DTAVYYCVRHGNFGDSYVSWFAYWGQGTLVTVSS | VH; CD3vB2 |

TABLE 20-continued

| | SEQUENCES | |
|---|---|---|
| Seq ID | sequence | name |

261 QAVVTQEPSLTVSPGGTVTLTCGSSTGAVTTSNYANWVQQKPGK
SPRGLIGGTNKRAPGVPARFSGSLLGGKAALTISGAQPEDEADYY
CALWYSNHWVFGGGTKLTVL
VL; CD3

262 EVQLVESGGGLVQPGGSLRLSCAASGFTFSTYAMNWVRQAPGK
GLEWVGRIRSKANNYATYYADSVKGRFTISRDDSKNTLYLQMNSL
RAEDTAVYYCVRHGNFGDSYVSWFAYWGQGTLVTVSSGKPGSG
KPGSGKPGSGKPGSQAVVTQEPSLTVSPGGTVTLTCGSSTGAVT
TSNYANWVQQKPGKSPRGLIGGTNKRAPGVPARFSGSLLGGKAA
LTISGAQPEDEADYYCALWYSNHWVFGGGTKLTVLEPKSSDKTHT
CPPCPAPEFEGGPSVFLFPPKPKDTLMISRTPEVTCVVVDVSHED
PEVKFNWYVDGVEVHNAKTKPREEQYNSTYRVVSVLTVLHQDWL
NGKEYKCKVSNKALPASIEKTISKAKGQPREPQVYTLPPCRKKLTK
NQVSLTCLVKGFYPSDIAVEWESNGQPENNYKTTPPVLKSDGSFF
LYSKLTVDKSRWQQGNVFSCSVMHEALHNHYTQKSLSLSPGK
CD3vB
scfv-Fc 263 EVQLVESGGGLVQPGGSLRLSCAASGFTFSTYAMNWVRQAPGK
GLEWVGRIRSKYNNYATYYADSVKGRFTISRDDSKNTLYLQMNSL
RAEDTAVYYCVRHGNFGDSYVSWFAYWGQGTLVTVSSGKPGSG
KPGSGKPGSGKPGSQAVVTQEPSLTVSPGGTVTLTCGSSTGAVT
TSNYANWVQQKPGKSPRGLIGGTNKRAPGVPARFSGSLLGGKAA
LTISGAQPEDEADYYCALWYSNHWVFGGGTKLTVLEPKSSDKTHT
CPPCPAPEFEGGPSVFLFPPKPKDTLMISRTPEVTCVVVDVSHED
PEVKFNWYVDGVEVHNAKTKPREEQYNSTYRVVSVLTVLHQDWL
NGKEYKCKVSNKALPASIEKTISKAKGQPREPQVYTLPPCRKKLTK
NQVSLTCLVKGFYPSDIAVEWESNGQPENNYKTTPPVLKSDGSFF
LYSKLTVDKSRWQQGNVFSCSVMHEALHNHYTQKSLSLSPGK
CD3vC
scfv-Fc 264 EVQLVESGGGLVQPGGSLRLSCAASGFTFSTYAMNWVRQAPGK
GLEWVGRIRSKINNYATYYADSVKGRFTISRDDSKNTLYLQMNSLR
AEDTAVYYCVRHGNFGDSYVSWFAYWGQGTLVTVSSGKPGSGK
PGSGKPGSGKPGSQAVVTQEPSLTVSPGGTVTLTCGSSTGAVTT
SNYANWVQQKPGKSPRGLIGGTNKRAPGVPARFSGSLLGGKAAL
TISGAQPEDEADYYCALWYSNHWVFGGGTKLTVLEPKSSDKTHTC
PPCPAPEFEGGPSVFLFPPKPKDTLMISRTPEVTCVVVDVSHEDPE
VKFNWYVDGVEVHNAKTKPREEQYNSTYRVVSVLTVLHQDWLNG
KEYKCKVSNKALPASIEKTISKAKGQPREPQVYTLPPCRKKLTKNQ
VSLTCLVKGFYPSDIAVEWESNGQPENNYKTTPPVLKSDGSFFLY
SKLTVDKSRWQQGNVFSCSVMHEALHNHYTQKSLSLSPGK
CD3vD
scfv-Fc 265 EVQLVESGGGLVQPGGSLRLSCAASGFTFSTYAMNWVRQAPGK
GLEWVGRIRSKLNNYATYYADSVKGRFTISRDDSKNTLYLQMNSL
RAEDTAVYYCVRHGNFGDSYVSWFAYWGQGTLVTVSSGKPGSG
KPGSGKPGSGKPGSQAVVTQEPSLTVSPGGTVTLTCGSSTGAVT
TSNYANWVQQKPGKSPRGLIGGTNKRAPGVPARFSGSLLGGKAA
LTISGAQPEDEADYYCALWYSNHWVFGGGTKLTVLEPKSSDKTHT
CPPCPAPEFEGGPSVFLFPPKPKDTLMISRTPEVTCVVVDVSHED
PEVKFNWYVDGVEVHNAKTKPREEQYNSTYRVVSVLTVLHQDWL
NGKEYKCKVSNKALPASIEKTISKAKGQPREPQVYTLPPCRKKLTK
NQVSLTCLVKGFYPSDIAVEWESNGQPENNYKTTPPVLKSDGSFF
LYSKLTVDKSRWQQGNVFSCSVMHEALHNHYTQKSLSLSPGK
CD3vE
scfv-Fc 266 EVQLVESGGGLVQPGGSLRLSCAASGFTFSTYAMNWVRQAPGK
GLEWVGRIRSKVNNYATYYADSVKGRFTISRDDSKNTLYLQMNSL
RAEDTAVYYCVRHGNFGDSYVSWFAYWGQGTLVTVSSGKPGSG
KPGSGKPGSGKPGSQAVVTQEPSLTVSPGGTVTLTCGSSTGAVT
TSNYANWVQQKPGKSPRGLIGGTNKRAPGVPARFSGSLLGGKAA
LTISGAQPEDEADYYCALWYSNHWVFGGGTKLTVLEPKSSDKTHT
CPPCPAPEFEGGPSVFLFPPKPKDTLMISRTPEVTCVVVDVSHED
PEVKFNWYVDGVEVHNAKTKPREEQYNSTYRVVSVLTVLHQDWL
NGKEYKCKVSNKALPASIEKTISKAKGQPREPQVYTLPPCRKKLTK
NQVSLTCLVKGFYPSDIAVEWESNGQPENNYKTTPPVLKSDGSFF
LYSKLTVDKSRWQQGNVFSCSVMHEALHNHYTQKSLSLSPGK
CD3vF scfv-
fc 267 EVQLVESGGGLVQPGGSLRLSCAASGFTFSTYAMNWVRQAPGK
GLEWVGRIRSKSNNYATYYADSVKGRFTISRDDSKNTLYLQMNSL
RAEDTAVYYCVRHGNFGDSYVSWFAYWGQGTLVTVSSGKPGSG
KPGSGKPGSGKPGSQAVVTQEPSLTVSPGGTVTLTCGSSTGAVT
TSNYANWVQQKPGKSPRGLIGGTNKRAPGVPARFSGSLLGGKAA
LTISGAQPEDEADYYCALWYSNHWVFGGGTKLTVLEPKSSDKTHT
CPPCPAPEFEGGPSVFLFPPKPKDTLMISRTPEVTCVVVDVSHED
PEVKFNWYVDGVEVHNAKTKPREEQYNSTYRVVSVLTVLHQDWL
NGKEYKCKVSNKALPASIEKTISKAKGQPREPQVYTLPPCRKKLTK
NQVSLTCLVKGFYPSDIAVEWESNGQPENNYKTTPPVLKSDGSFF
LYSKLTVDKSRWQQGNVFSCSVMHEALHNHYTQKSLSLSPGK
CD3vG
scfv-Fc TABLE 20-continued

| | SEQUENCES | |
|---|---|---|
| Seq ID | sequence | name |

| 268 | EVQLVESGGGLVQPGGSLRLSCAASGFTFSTYAMDWVRQAPGK GLEWVGRIRSKYNNYATYYADSVKGRFTISRDDSKNTLYLQMNSL RAEDTAVYYCVRHGNFGDSYVSWFAYWGQGTLVTVSSGKPGSG KPGSGKPGSGKPGSQAVVTQEPSLTVSPGGTVTLTCGSSTGAVT TSNYANWVQQKPGKSPRGLIGGTNKRAPGVPARFSGSLLGGKAA LTISGAQPEDEADYYCALWYSNHWVFGGGTKLTVLEPKSSDKTHT CPPCPAPEFEGGPSVFLFPPKPKDTLMISRTPEVTCVVVDVSHED PEVKFNWYVDGVEVHNAKTKPREEQYNSTYRVVSVLTVLHQDWL NGKEYKCKVSNKALPASIEKTISKAKGQPREPQVYTLPPCRKKLTK NQVSLTCLVKGFYPSDIAVEWESNGQPENNYKTTPPVLKSDGSFF LYSKLTVDKSRWQQGNVFSCSVMHEALHNHYTQKSLSLSPGK | CD3vH scfv-Fc |
| 269 | EVQLVESGGGLVQPGGSLRLSCAASGFTFSTYAMNWVRQAPGK GLEWVGRIRSKYNNYATYYADSVKGRFTISRDDSKNTLYLQMNSL RAEDTAVYYCVRHGNFGDSYVSWFEYWGQGTLVTVSSGKPGSG KPGSGKPGSGKPGSQAVVTQEPSLTVSPGGTVTLTCGSSTGAVT TSNYANWVQQKPGKSPRGLIGGTNKRAPGVPARFSGSLLGGKAA LTISGAQPEDEADYYCALWYSNHWVFGGGTKLTVLEPKSSDKTHT CPPCPAPEFEGGPSVFLFPPKPKDTLMISRTPEVTCVVVDVSHED PEVKFNWYVDGVEVHNAKTKPREEQYNSTYRVVSVLTVLHQDWL NGKEYKCKVSNKALPASIEKTISKAKGQPREPQVYTLPPCRKKLTK NQVSLTCLVKGFYPSDIAVEWESNGQPENNYKTTPPVLKSDGSFF LYSKLTVDKSRWQQGNVFSCSVMHEALHNHYTQKSLSLSPGK | CD3vI scfv-Fc |
| 270 | EVQLVESGGGLVQPGGSLRLSCAASGFTFSTYAMNWVRQAPGK GLEWVGRIRSKYNNYATYYADSVKGRFTISRDDSKNTLYLQMNSL RAEDTAVYYCVRHGNFGDSYVSWFDYWGQGTLVTVSSGKPGSG KPGSGKPGSGKPGSQAVVTQEPSLTVSPGGTVTLTCGSSTGAVT TSNYANWVQQKPGKSPRGLIGGTNKRAPGVPARFSGSLLGGKAA LTISGAQPEDEADYYCALWYSNHWVFGGGTKLTVLEPKSSDKTHT CPPCPAPEFEGGPSVFLFPPKPKDTLMISRTPEVTCVVVDVSHED PEVKFNWYVDGVEVHNAKTKPREEQYNSTYRVVSVLTVLHQDWL NGKEYKCKVSNKALPASIEKTISKAKGQPREPQVYTLPPCRKKLTK NQVSLTCLVKGFYPSDIAVEWESNGQPENNYKTTPPVLKSDGSFF LYSKLTVDKSRWQQGNVFSCSVMHEALHNHYTQKSLSLSPGK | CD3vJ scfv-Fc |
| 271 | EVQLVESGGGLVQPGGSLRLSCAASGFTFSTYAMNWVRQAPGK GLEWVGRIRSKYNNYATYYADSVKGRFTISRDDSKNTLYLQMNSL RAEDTAVYYCVRHGNFGDSYVSWFNYWGQGTLVTVSSGKPGSG KPGSGKPGSGKPGSQAVVTQEPSLTVSPGGTVTLTCGSSTGAVT TSNYANWVQQKPGKSPRGLIGGTNKRAPGVPARFSGSLLGGKAA LTISGAQPEDEADYYCALWYSNHWVFGGGTKLTVLEPKSSDKTHT CPPCPAPEFEGGPSVFLFPPKPKDTLMISRTPEVTCVVVDVSHED PEVKFNWYVDGVEVHNAKTKPREEQYNSTYRVVSVLTVLHQDWL NGKEYKCKVSNKALPASIEKTISKAKGQPREPQVYTLPPCRKKLTK NQVSLTCLVKGFYPSDIAVEWESNGQPENNYKTTPPVLKSDGSFF LYSKLTVDKSRWQQGNVFSCSVMHEALHNHYTQKSLSLSPGK | CD3vK scfv-Fc |
| 272 | EVQLVESGGGLVQPGGSLRLSCAASGFTFSTYAMNWVRQAPGK GLEWVGRIRSKYNNYATYYADSVKGRFTISRDDSKNTLYLQMNSL RAEDTAVYYCVRHGNFGDSYVSYFAYWGQGTLVTVSSGKPGSGK PGSGKPGSGKPGSQAVVTQEPSLTVSPGGTVTLTCGSSTGAVTT SNYANWVQQKPGKSPRGLIGGTNKRAPGVPARFSGSLLGGKAAL TISGAQPEDEADYYCALWYSNHWVFGGGTKLTVLEPKSSDKTHTC PPCPAPEFEGGPSVFLFPPKPKDTLMISRTPEVTCVVVDVSHEDPE VKFNWYVDGVEVHNAKTKPREEQYNSTYRVVSVLTVLHQDWLNG KEYKCKVSNKALPASIEKTISKAKGQPREPQVYTLPPCRKKLTKNQ VSLTCLVKGFYPSDIAVEWESNGQPENNYKTTPPVLKSDGSFFLY SKLTVDKSRWQQGNVFSCSVMHEALHNHYTQKSLSLSPGK | CD3vI scfv-Fc |
| 273 | QLVESGGGLVQPGGSLRLSCAASGFTFSTYAMNWVRQAPGKGLE WVGRIRSKANNYATYYADSVKGRFTISRDDSKNTLYLQMNSLRAE DTAVYYCVRHGNFGDSYVSWFAYWGQGTLVTVSSGKPGSGKPG SGKPGSGKPGSQAVVTQEPSLTVSPGGTVTLTCGSSTGAVTTSN YANWVQQKPGKSPRGLIGGTNKRAPGVPARFSGSLLGGKAALTIS GAQPEDEADYYCALWYSNHWVFGGGTKLTVLEPKSSDKTHTCPP CPAPEFEGGPSVFLFPPKPKDTLMISRTPEVTCVVVDVSHEDPEVK FNWYVDGVEVHNAKTKPREEQYNSTYRVVSVLTVLHQDWLNGKE YKCKVSNKALPASIEKTISKAKGQPREPQVYTLPPCRKKLTKNQVS LTCLVKGFYPSDIAVEWESNGQPENNYKTTPPVLKSDGSFFLYSKL TVDKSRWQQGNVFSCSVMHEALHNHYTQKSLSLSPGK | CD3vB2 |
| 274 | EVQLLESGGGLVQPGGSLRLSCAASGFTFSSYGMHWVRQAPGK GLEWVAVISGSGSSKYYADSVKGRFTISRDNSKNTLYLQMNSLRA EDTAVYYCARDWFFYLFDYWGQGTLVTVSSASTKGPSVFPLAPSS | HC; DLL3 |

TABLE 20-continued

SEQUENCES

| Seq ID | sequence | name |
|--------|----------|------|
| | KSTSGGTAALGCLVKDYFPEPVTVSWNSGALTSGVHTFPAVLQSS<br>GLYSLSSVVTVPSSSLGTQTYICNVNHKPSNTKVDKRVEPKSCDKT<br>HTCPPCPAPEFEGGPSVFLFPPKPKDTLMISRTPEVTCVVVDVSHE<br>DPEVKFNWYVDGVEVHNAKTKPREEQYNSTYRVVSVLTVLHQDW<br>LNGKEYKCKVSNKALPASIEKTISKAKGQPREPQVCTLPPSRDELT<br>KNQVSLTCLVEGFYPSDIAVEWESNGQPENNYKTTPPVLDSDGSF<br>FLYSDLTVDKSRWQQGNVFSCSVMHEALHNHYTQESLSLSPGK | |
| 275 | EVQLLESGGGLVQPGGSLRLSCAASGFTFSSYGMHWVRQAPGK<br>GLEWVAVISGSGSSKYYADSVKGRFTISRDNSKNTLYLQMNSLRA<br>EDTAVYYCARDWFYFIFDYWGQGTLVTVSSASTKGPSVFPLAPSS<br>KSTSGGTAALGCLVKDYFPEPVTVSWNSGALTSGVHTFPAVLQSS<br>GLYSLSSVVTVPSSSLGTQTYICNVNHKPSNTKVDKRVEPKSCDKT<br>HTCPPCPAPEFEGGPSVFLFPPKPKDTLMISRTPEVTCVVVDVSHE<br>DPEVKFNWYVDGVEVHNAKTKPREEQYNSTYRVVSVLTVLHQDW<br>LNGKEYKCKVSNKALPASIEKTISKAKGQPREPQVCTLPPSRDELT<br>KNQVSLTCLVEGFYPSDIAVEWESNGQPENNYKTTPPVLDSDGSF<br>FLYSDLTVDKSRWQQGNVFSCSVMHEALHNHYTQESLSLSPGK | HC;<br>DLL3.11,<br>DLL3.15 |
| 276 | EVQLLESGGGLVQPGGSLRLSCAASGFTFSSYGMHWVRQAPGK<br>GLEWVAVISHHGSSKYYADSVKGRFTISRDNSKNTLYLQMNSLRA<br>EDTAVYYCARDWFFYLFDYWGQGTLVTVSSASTKGPSVFPLAPSS<br>KSTSGGTAALGCLVKDYFPEPVTVSWNSGALTSGVHTFPAVLQSS<br>GLYSLSSVVTVPSSSLGTQTYICNVNHKPSNTKVDKRVEPKSCDKT<br>HTCPPCPAPEFEGGPSVFLFPPKPKDTLMISRTPEVTCVVVDVSHE<br>DPEVKFNWYVDGVEVHNAKTKPREEQYNSTYRVVSVLTVLHQDW<br>LNGKEYKCKVSNKALPASIEKTISKAKGQPREPQVCTLPPSRDELT<br>KNQVSLTCLVEGFYPSDIAVEWESNGQPENNYKTTPPVLDSDGSF<br>FLYSDLTVDKSRWQQGNVFSCSVMHEALHNHYTQESLSLSPGK | HC:<br>DLL3.18,<br>DLL3.22 |
| 277 | EVQLLESGGGLVQPGGSLRLSCAASGFTFSSYGMHWVRQAPGK<br>GLEWVAVISHHGSSKYYADSVKGRFTISRDNSKNTLYLQMNSLRA<br>EDTAVYYCARDWFYFIFDYWGQGTLVTVSSASTKGPSVFPLAPSS<br>KSTSGGTAALGCLVKDYFPEPVTVSWNSGALTSGVHTFPAVLQSS<br>GLYSLSSVVTVPSSSLGTQTYICNVNHKPSNTKVDKRVEPKSCDKT<br>HTCPPCPAPEFEGGPSVFLFPPKPKDTLMISRTPEVTCVVVDVSHE<br>DPEVKFNWYVDGVEVHNAKTKPREEQYNSTYRVVSVLTVLHQDW<br>LNGKEYKCKVSNKALPASIEKTISKAKGQPREPQVCTLPPSRDELT<br>KNQVSLTCLVEGFYPSDIAVEWESNGQPENNYKTTPPVLDSDGSF<br>FLYSDLTVDKSRWQQGNVFSCSVMHEALHNHYTQESLSLSPGK | HC; DLL3.5,<br>DLL3.12,<br>DLL3.26 |
| 278 | EVQLLESGGGLVQPGGSLRLSCAASGFTFSSYGMHWVRQAPGK<br>GLEWVAVISYDGSSKYYADSVKGRFTISRDNSKNTLYLQMNSLRA<br>EDTAVYYCARDWFFYLFDYWGQGTLVTVSSASTKGPSVFPLAPSS<br>KSTSGGTAALGCLVKDYFPEPVTVSWNSGALTSGVHTFPAVLQSS<br>GLYSLSSVVTVPSSSLGTQTYICNVNHKPSNTKVDKRVEPKSCDKT<br>HTCPPCPAPEFEGGPSVFLFPPKPKDTLMISRTPEVTCVVVDVSHE<br>DPEVKFNWYVDGVEVHNAKTKPREEQYNSTYRVVSVLTVLHQDW<br>LNGKEYKCKVSNKALPASIEKTISKAKGQPREPQVCTLPPSRDELT<br>KNQVSLTCLVEGFYPSDIAVEWESNGQPENNYKTTPPVLDSDGSF<br>FLYSDLTVDKSRWQQGNVFSCSVMHEALHNHYTQESLSLSPGK | HC;<br>DLL3.19,<br>DLL3.23 |
| 279 | EVQLLESGGGLVQPGGSLRLSCAASGFTFSSYGMHWVRQAPGK<br>GLEWVAVISYDGSSKYYADSVKGRFTISRDNSKNTLYLQMNSLRA<br>EDTAVYYCARDWFYFIFDYWGQGTLVTVSSASTKGPSVFPLAPSS<br>KSTSGGTAALGCLVKDYFPEPVTVSWNSGALTSGVHTFPAVLQSS<br>GLYSLSSVVTVPSSSLGTQTYICNVNHKPSNTKVDKRVEPKSCDKT<br>HTCPPCPAPEFEGGPSVFLFPPKPKDTLMISRTPEVTCVVVDVSHE<br>DPEVKFNWYVDGVEVHNAKTKPREEQYNSTYRVVSVLTVLHQDW<br>LNGKEYKCKVSNKALPASIEKTISKAKGQPREPQVCTLPPSRDELT<br>KNQVSLTCLVEGFYPSDIAVEWESNGQPENNYKTTPPVLDSDGSF<br>FLYSDLTVDKSRWQQGNVFSCSVMHEALHNHYTQESLSLSPGK | HC;<br>DLL3.13,<br>DLL3.16, |
| 280 | EVQLLESGGGLVQPGGSLRLSCAASGFTFSSYGMHWVRQAPGK<br>GLEWVSVISHHGSSKYYADSVKGRFTISRDNSKNTLYLQMNSLRA<br>EDTAVYYCAKDWFFYLFDYWGQGTLVTVSSASTKGPSVFPLAPSS<br>KSTSGGTAALGCLVKDYFPEPVTVSWNSGALTSGVHTFPAVLQSS<br>GLYSLSSVVTVPSSSLGTQTYICNVNHKPSNTKVDKRVEPKSCDKT<br>HTCPPCPAPEFEGGPSVFLFPPKPKDTLMISRTPEVTCVVVDVSHE<br>DPEVKFNWYVDGVEVHNAKTKPREEQYNSTYRVVSVLTVLHQDW<br>LNGKEYKCKVSNKALPASIEKTISKAKGQPREPQVCTLPPSRDELT<br>KNQVSLTCLVEGFYPSDIAVEWESNGQPENNYKTTPPVLDSDGSF<br>FLYSDLTVDKSRWQQGNVFSCSVMHEALHNHYTQESLSLSPGK | HC;<br>DLL3.20,<br>DLL3.24 |

TABLE 20-continued

SEQUENCES

| Seq ID | sequence | name |
|---|---|---|
| 281 | EVQLLESGGGLVQPGGSLRLSCAASGFTFSSYGMHWVRQAPGK<br>GLEWVSVISHHGSSKYYADSVKGRFTISRDNSKNTLYLQMNSLRA<br>EDTAVYYCAKDWFYFIFDYWGQGTLVTVSSASTKGPSVFPLAPSS<br>KSTSGGTAALGCLVKDYFPEPVTVSWNSGALTSGVHTFPAVLQSS<br>GLYSLSSVVTVPSSSLGTQTYICNVNHKPSNTKVDKRVEPKSCDKT<br>HTCPPCPAPEFEGGPSVFLFPPKPKDTLMISRTPEVTCVVVDVSHE<br>DPEVKFNWYVDGVEVHNAKTKPREEQYNSTYRVVSVLTVLHQDW<br>LNGKEYKCKVSNKALPASIEKTISKAKGQPREPQVCTLPPSRDELT<br>KNQVSLTCLVEGFYPSDIAVEWESNGQPENNYKTTPPVLDSDGSF<br>FLYSDLTVDKSRWQQGNVFSCSVMHEALHNHYTQESLSLSPGK | HC;<br>DLL3.14,<br>DLL3.17 |
| 282 | EVQLQQSGPVLVKPGASVKMSCKASGFTFTDYYMNWVKQSHGK<br>SLEWIGVINPDNGITTYNQKFKGKATLTVDKSSSTAYMELNGLTSE<br>DSAVYYCARGVWNYERSFDYWGQGTTLTVSSASTKGPSVFPLAP<br>SSKSTSGGTAALGCLVKDYFPEPVTVSWNSGALTSGVHTFPAVLQ<br>SSGLYSLSSVVTVPSSSLGTQTYICNVNHKPSNTKVDKRVEPKSC<br>DKTHTCPPCPAPEFEGGPSVFLFPPKPKDTLMISRTPEVTCVVVDV<br>SHEDPEVKFNWYVDGVEVHNAKTKPREEQYNSTYRVVSVLTVLH<br>QDWLNGKEYKCKVSNKALPASIEKTISKAKGQPREPQVCTLPPSR<br>DELTKNQVSLTCLVEGFYPSDIAVEWESNGQPENNYKTTPPVLDS<br>DGSFFLYSDLTVDKSRWQQGNVFSCSVMHEALHNHYTQESLSLS<br>PGK | HC;<br>DLL3.21,<br>DLL3.25 |
| 283 | EVQLVESGGGLVQPGGSLRLSCAASGFTFSNYGMHWVRQAPGK<br>GLEWVAVISHHGSSKYYADSVKGRYTISRDNSKNTLYLQMNSLRA<br>EDTAVYYCARDWFFYLFDYWGQGTLVTVSSASTKGPSVFPLAPSS<br>KSTSGGTAALGCLVKDYFPEPVTVSWNSGALTSGVHTFPAVLQSS<br>GLYSLSSVVTVPSSSLGTQTYICNVNHKPSNTKVDKRVEPKSCDKT<br>HTCPPCPAPEFEGGPSVFLFPPKPKDTLMISRTPEVTCVVVDVSHE<br>DPEVKFNWYVDGVEVHNAKTKPREEQYNSTYRVVSVLTVLHQDW<br>LNGKEYKCKVSNKALPASIEKTISKAKGQPREPQVCTLPPSRDELT<br>KNQVSLTCLVEGFYPSDIAVEWESNGQPENNYKTTPPVLDSDGSF<br>FLYSDLTVDKSRWQQGNVFSCSVMHEALHNHYTQESLSLSPGK | HC; DLL3.9 |
| 284 | QVQLQESGPGLVKPSETLSLTCTVSGGSISSYYWSWIRQPPGKGL<br>EWIGYVYYSGTTNYNPSLKSRVTISVDTSKNQFSLKLSSVTAADTA<br>VYYCASIAVTGFYFDYWGQGTLVTVSSASTKGPSVFPLAPSSKST<br>SGGTAALGCLVKDYFPEPVTVSWNSGALTSGVHTFPAVLQSSGLY<br>SLSSVVTVPSSSLGTQTYICNVNHKPSNTKVDKRVEPKSCDKTHT<br>CPPCPAPEFEGGPSVFLFPPKPKDTLMISRTPEVTCVVVDVSHED<br>PEVKFNWYVDGVEVHNAKTKPREEQYNSTYRVVSVLTVLHQDWL<br>NGKEYKCKVSNKALPASIEKTISKAKGQPREPQVCTLPPSRDELTK<br>NQVSLTCLVEGFYPSDIAVEWESNGQPENNYKTTPPVLDSDGSFF<br>LYSDLTVDKSRWQQGNVFSCSVMHEALHNHYTQESLSLSPGK | HC;<br>DLL3.27 |
| 285 | QVQLQQSGPVLVKPGASVKMSCKASGYSFTDYYVNWVKQSHGK<br>SLEWIGIISPNDGGTNYNQKFKGKATLTVDKSSSTAYMEVNSLTSE<br>DSAVYYCARDDDLGWYFDVWGTGTTVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD<br>KTHTCPPCPAPEFEGGPSVFLFPPKPKDTLMISRTPEVTCVVVDVS<br>HEDPEVKFNWYVDGVEVHNAKTKPREEQYNSTYRVVSVLTVLHQ<br>DWLNGKEYKCKVSNKALPASIEKTISKAKGQPREPQVCTLPPSRD<br>ELTKNQVSLTCLVEGFYPSDIAVEWESNGQPENNYKTTPPVLDSD<br>GSFFLYSDLTVDKSRWQQGNVFSCSVMHEALHNHYTQESLSLSP<br>GK | HC;<br>DLL3.28 |
| 286 | QVQLVESGGGAVQPGRSLRLSCAASGFTFSNYGMHWVRQAPGK<br>GLEWVAVISHHGSSKYYARSVKGRFTISRDNSKNTLYLEMNSLRA<br>EDTAVYYCARDWWELVFDYWGQGTLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD<br>KTHTCPPCPAPEFEGGPSVFLFPPKPKDTLMISRTPEVTCVVVDVS<br>HEDPEVKFNWYVDGVEVHNAKTKPREEQYNSTYRVVSVLTVLHQ<br>DWLNGKEYKCKVSNKALPASIEKTISKAKGQPREPQVCTLPPSRD<br>ELTKNQVSLTCLVEGFYPSDIAVEWESNGQPENNYKTTPPVLDSD<br>GSFFLYSDLTVDKSRWQQGNVFSCSVMHEALHNHYTQESLSLSP<br>GK | HC;<br>DLL3.8 |
| 287 | QVQLVESGGGAVQPGRSLRLSCAASGFTFSNYGMHWVRQAPGK<br>GLEWVAVISHHGSSKYYARSVKGRFTISRDNSKNTLYLEMNSLRA<br>EDTAVYYCARDWWELVFDYWGQGTLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD<br>KTHTCPPCPAPEFEGGPSVFLFPPKPKDTLMISRTPEVTCVVVDVS | HC;<br>DLL3.29,<br>DLL3.30,<br>DLL3.36 |

TABLE 20-continued

| | SEQUENCES | |
|---|---|---|
| Seq ID | sequence | name |

| | | |
|---|---|---|
| | HEDPEVKFNWYVDGVEVHNAKTKPREEQYNSTYRVVSVLTVLHQ DWLNGKEYKCKVSNKALPASIEKTISKAKGQPREPQVCTLPPSRD ELTKNQVSLTCLVEGFYPSDIAVEWESNGQPENNYKTTPPVLDSD GSFFLYSDLTVDKSRWQQGNVFSCSVMHEALHNHYTQESLSLSP GK | |
| 288 | QVQLVESGGGVVQPGRSLRLSCAASGFTFSNYGMHWVRQAPGK GLEWVAVISHHGSSKYYADSVKGRFTISRDNSKNTLYLQMNSLRA EDTAVYYCARDWFFYLFDYWGQGTLVTVSSASTKGPSVFPLAPSS KSTSGGTAALGCLVKDYFPEPVTVSWNSGALTSGVHTFPAVLQSS GLYSLSSVVTVPSSSLGTQTYICNVNHKPSNTKVDKRVEPKSCDKT HTCPPCPAPEFEGGPSVFLFPPKPKDTLMISRTPEVTCVVVDVSHE DPEVKFNWYVDGVEVHNAKTKPREEQYNSTYRVVSVLTVLHQDW LNGKEYKCKVSNKALPASIEKTISKAKGQPREPQVCTLPPSRDELT KNQVSLTCLVEGFYPSDIAVEWESNGQPENNYKTTPPVLDSDGSF FLYSDLTVDKSRWQQGNVFSCSVMHEALHNHYTQESLSLSPGK | HC DLL3.10, DLL3.31 |
| 289 | QVQLVESGGGVVQPGRSLRLSCAASGFTFSNYGMHWVRQAPGK GLEWVAVISHHGSSKYYADSVKGRFTISRDNSKNTLYLQMNSLRA EDTAVYYCARDWFYFIFDYWGQGTLVTVSSASTKGPSVFPLAPSS KSTSGGTAALGCLVKDYFPEPVTVSWNSGALTSGVHTFPAVLQSS GLYSLSSVVTVPSSSLGTQTYICNVNHKPSNTKVDKRVEPKSCDKT HTCPPCPAPEFEGGPSVFLFPPKPKDTLMISRTPEVTCVVVDVSHE DPEVKFNWYVDGVEVHNAKTKPREEQYNSTYRVVSVLTVLHQDW LNGKEYKCKVSNKALPASIEKTISKAKGQPREPQVCTLPPSRDELT KNQVSLTCLVEGFYPSDIAVEWESNGQPENNYKTTPPVLDSDGSF FLYSDLTVDKSRWQQGNVFSCSVMHEALHNHYTQESLSLSPGK | HC; DLL3.32, DLL3.33 |
| 290 | QVQLVQSGAEVKKPGASVKVSCKASDYTFSNYYIEWVRQAPGQG LEWMGEILPGNGNTVYNEKFKDRVTMTVDTSTSTAYMELRSLRSD DTAVYYCARWGDYALFANWGQGTLVTVSSASTKGPSVFPLAPSS KSTSGGTAALGCLVKDYFPEPVTVSWNSGALTSGVHTFPAVLQSS GLYSLSSVVTVPSSSLGTQTYICNVNHKPSNTKVDKRVEPKSCDKT HTCPPCPAPEFEGGPSVFLFPPKPKDTLMISRTPEVTCVVVDVSHE DPEVKFNWYVDGVEVHNAKTKPREEQYNSTYRVVSVLTVLHQDW LNGKEYKCKVSNKALPASIEKTISKAKGQPREPQVCTLPPSRDELK NQVSLTCLVEGFYPSDIAVEWESNGQPENNYKTTPPVLDSDGSFF LYSDLTVDKSRWQQGNVFSCSVMHEALHNHYTQESLSLSPGK | HC; DLL3.1 |
| 291 | QVQLVQSGAEVKKPGASVKVSCKASGYTFTDYFMNWVRQAPGQ GLEWMGVINPYNDITIYNQKFQGRVTMTVDRSTSTVYMELSSLRS EDTAVYYCAREGVLYDGYYEGAYWGQGTLVTVSSASTKGPSVFP LAPSSKSTSGGTAALGCLVKDYFPEPVTVSWNSGALTSGVHTFPA VLQSSGLYSLSSVVTVPSSSLGTQTYICNVNHKPSNTKVDKRVEPK SCDKTHTCPPCPAPEFEGGPSVFLFPPKPKDTLMISRTPEVTCVVV DVSHEDPEVKFNWYVDGVEVHNAKTKPREEQYNSTYRVVSVLTV LHQDWLNGKEYKCKVSNKALPASIEKTISKAKGQPREPQVCTLPP SRDELTKNQVSLTCLVEGFYPSDIAVEWESNGQPENNYKTTPPVL DSDGSFFLYSDLTVDKSRWQQGNVFSCSVMHEALHNHYTQESLS LSPGK | HC; DLL3.3 |
| 292 | QVQLVQSGAEVKKPGASVKVSCKATDYIFSNYYIEWVRQAPGQGL EWMGEILPGTGNTVYNEKFKDRVTMTVDTSTSTVYMELSSLRSED TAVYYCARWGDYALFANWGQGTLVTVSSASTKGPSVFPLAPSSK STSGGTAALGCLVKDYFPEPVTVSWNSGALTSGVHTFPAVLQSSG LYSLSSVVTVPSSSLGTQTYICNVNHKPSNTKVDKRVEPKSCDKTH TCPPCPAPEFEGGPSVFLFPPKPKDTLMISRTPEVTCVVVDVSHED PEVKFNWYVDGVEVHNAKTKPREEQYNSTYRVVSVLTVLHQDWL NGKEYKCKVSNKALPASIEKTISKAKGQPREPQVCTLPPSRDELTK NQVSLTCLVEGFYPSDIAVEWESNGQPENNYKTTPPVLDSDGSFF LYSDLTVDKSRWQQGNVFSCSVMHEALHNHYTQESLSLSPGK | HC; DLL3.2, DLL3.4 |
| 293 | SDVQLQESGPGLVKPSQSLSLTCSVTGYSITSAYYWNWIRQFPGN KLEWMGYISDVGHNYYNPSLKNRISITRDTSKNQFFLKLNSVTPED TATYYCARDQVFAYWGQGTLVTVSAASTKGPSVFPLAPSSKSTSG GTAALGCLVKDYFPEPVTVSWNSGALTSGVHTFPAVLQSSGLYSL SSVVTVPSSSLGTQTYICNVNHKPSNTKVDKRVEPKSCDKTHTCP PCPAPEFEGGPSVFLFPPKPKDTLMISRTPEVTCVVVDVSHEDPEV KFNWYVDGVEVHNAKTKPREEQYNSTYRVVSVLTVLHQDWLNGK EYKCKVSNKALPASIEKTISKAKGQPREPQVCTLPPSRDELTKNQV SLTCLVEGFYPSDIAVEWESNGQPENNYKTTPPVLDSDGSFFLYS DLTVDKSRWQQGNVFSCSVMHEALHNHYTQESLSLSPGK | HC; DLL3.34 |
| 294 | SDVQLQESGPGLVKPSQSLSLTCSVTGYSITSAYYWNWIRQFPGN KLEWMGYISDVGSNNYNPSLKNRISITRDTFKNQFFLKLNSVTTED TATYFCTRDQVFAYWGQGTLVTVSAASTKGPSVFPLAPSSKSTSG | HC; DLL3.35 |

TABLE 20-continued

| | SEQUENCES | |
|---|---|---|
| Seq ID | sequence | name |

| | GTAALGCLVKDYFPEPVTVSWNSGALTSGVHTFPAVLQSSGLYSL SSVVTVPSSSLGTQTYICNVNHKPSNTKVDKRVEPKSCDKTHTCP PCPAPEFEGGPSVFLFPPKPKDTLMISRTPEVTCVVVDVSHEDPEV KFNWYVDGVEVHNAKTKPREEQYNSTYRVVSVLTVLHQDWLNGK EYKCKVSNKALPASIEKTISKAKGQPREPQVCTLPPSRDELTKNQV SLTCLVEGFYPSDIAVEWESNGQPENNYKTTPPVLDSDGSFFLYS DLTVDKSRWQQGNVFSCSVMHEALHNHYTQESLSLSPGK | |
| 295 | DIQLTQSPSFLSASVGDRVTITCKASQNVGIAVAWYQQKPGKAPKL LIYAASNRYTGVPSRFSGSGSGTEFTLTISSLQPEDFATYYCQQYS TYPYTFGQGTKLEIKRTVAAPSVFIFPPSDEQLKSGTASVVCLLNNF YPREAKVQWKVDNALQSGNSQESVTEQDSKDSTYSLSSTLTLSKA DYEKHKVYACEVTHQGLSSPVTKSFNRGEC | LC; DLL3.3 |
| 296 | DIQMTQSPSFLSASVGDRVTITCKASQNVGTNVAWYQQKPGKAPK PLIYSTSYRYSGVPSRFSGSGSGTEFTLTISSLQPEDFATYYCQQY NNYPLTFGGGTKVEIKRTVAAPSVFIFPPSDEQLKSGTASVVCLLN NFYPREAKVQWKVDNALQSGNSQESVTEQDSKDSTYSLSSTLTLS KADYEKHKVYACEVTHQGLSSPVTKSFNRGEC | LC; DLL3.4 |
| 297 | DIQMTQSPSSLSASVGDRVTITCKSSQSLLHSDAKTFLYWYQQKP GKAPKLLIYEVSNRFSGVPSRFSGSGSGTDFTLTISSLQPEDFATY YCLQGERLPFTFGQGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC | LC; DLL3.26 |
| 298 | DIQMTQSPSTLSASVGDRVTITCKASQNVGTNVAWYQQKPGKAPK ALIYSASYRYSGVPSRFSGSGSGTEFTLTISSLQPDDFATYYCQQY NSYPFTFGQGTKLEIKRTVAAPSVFIFPPSDEQLKSGTASVVCLLN NFYPREAKVQWKVDNALQSGNSQESVTEQDSKDSTYSLSSTLTLS KADYEKHKVYACEVTHQGLSSPVTKSFNRGEC | LC; DLL3.27 |
| 299 | DIVMTQAAFSNPVTVGTSASISCRSSKSLLHSNGITYLYWYLQKPG QSPQLLIYQMSNLASGVPDRFSSSGSGTDFTLRISRVEAEDVGVY YCAQNLELPWTFGGGTKLEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC | LC; DLL3.1 |
| 300 | DIVMTQSPKFMSTSVGDRVSVTCKASQNVGTNVAWYQQKPGQSP KALIYSASYRYSGVPDRFTGSGSGTDFTLTFSSVQSEDLAEYFCQ QYNNYPLTFGGGTKLEIKRRTVAAPSVFIFPPSDEQLKSGTASVVC LLNNFYPREAKVQWKVDNALQSGNSQESVTEQDSKDSTYSLSSTL TLSKADYEKHKVYACEVTHQGLSSPVTKSFNRGEC | LC; DLL3.2 |
| 301 | DIVMTQSPLSLPVTPGEPASISCKSSQSLLHSDAKTFLYWYLQKPG QSPQLLIYEVSNRFSGVPDRFSGSGSGTDFTLKISRVEAEDVGVYY CLQGRELPFTFGQGTKVEIKRTVAAPSVFIFPPSDEQLKSGTASVV CLLNNFYPREAKVQWKVDNALQSGNSQESVTEQDSKDSTYSLSS TLTLSKADYEKHKVYACEVTHQGLSSPVTKSFNRGEC | LC; DLL3.8 |
| 302 | DIVMTQSPLSLPVTPGEPASISCKSSQSLLHSDGKTFLYWYLQKPG QSPQLLIYEVSNRFSGVPDRFSGSGSGTDFTLKISRVEAEDVGVYY CLQGERLPFTFGQGTKVEIKRTVAAPSVFIFPPSDEQLKSGTASVV CLLNNFYPREAKVQWKVDNALQSGNSQESVTEQDSKDSTYSLSS TLTLSKADYEKHKVYACEVTHQGLSSPVTKSFNRGEC | LC; DLL3.9 |
| 303 | DIVMTQSPLSLPVTPGEPASISCRSSQSLLHSDAKTFLDWYLQKPG QSPQLLIYEVSNRASGVPDRFSGSGSGTDFTLKISRVEAEDVGVYY CLQGRELPFTFGQGTKVEIKRTVAAPSVFIFPPSDEQLKSGTASVV CLLNNFYPREAKVQWKVDNALQSGNSQESVTEQDSKDSTYSLSS TLTLSKADYEKHKVYACEVTHQGLSSPVTKSFNRGEC | LC; DLL3.22, DLL3.23, DLL3.24, DLL3.25 |
| 304 | DIVMTQSPLSLPVTPGEPASISCRSSQSLLHSDGKTFLDWYLQKPG QSPQLLIYEVSNRASGVPDRFSGSGSGTDFTLKISRVEAEDVGVYY CLQGERLPFTFGQGTKVEIKRTVAAPSVFIFPPSDEQLKSGTASVV CLLNNFYPREAKVQWKVDNALQSGNSQESVTEQDSKDSTYSLSS TLTLSKADYEKHKVYACEVTHQGLSSPVTKSFNRGEC | LC; DLL3.5, DLL3.15, DLL3.16, DLL3.17 |
| 305 | DIVMTQTPLSLSVTPGQPASISCKSSQSLLHSDAKTFLYWYLQKPG QPPQLLIYEVSNRFSGVPDRFSGSGSGTDFTLKISRVEAEDVGVYY CLQGRELPFTFGPGTKVEIKRTVAAPSVFIFPPSDEQLKSGTASVV CLLNNFYPREAKVQWKVDNALQSGNSQESVTEQDSKDSTYSLSS TLTLSKADYEKHKVYACEVTHQGLSSPVTKSFNRGEC | LC DLL3.18, DLL3.19, DLL3.20, DLL3.21 |

TABLE 20-continued

| | SEQUENCES | |
|---|---|---|
| Seq ID | sequence | name |

| 306 | DIVMTQTPLSLSVTPGQPASISCKSSQSLLHSDAKTFLYWYLQKPG<br>QPPQLLIYEVSNRFSGVPDRFSGSGSGTDFTLKISRVEAEDVGVYY<br>CLQGRELPFTFGPGTKVEIKSTFGQGTKVEIKRTVAAPSVFIFPPSD<br>EQLKSGTASVVCLLNNFYPREAKVQWKVDNALQSGNSQESVTEQ<br>DSKDSTYSLSSTLTLSKADYEKHKVYACEVTHQGLSSPVTKSFNR<br>GEC | LC;<br>DLL3.11,<br>DLL3.12,<br>DLL3.13,<br>DLL3.14 |
| 307 | DIVMTQTPLSLSVTPGQPASISCKSSQSLLHSDGKTFLYWYLQKPG<br>QPPQLLIYEVSNRFSGVPDRFSGSGSGTDFTLKISRVEAEDVGVYY<br>CLQGERLPFTFGPGTKVEIKRTVAAPSVFIFPPSDEQLKSGTASVV<br>CLLNNFYPREAKVQWKVDNALQSGNSQESVTEQDSKDSTYSLSS<br>TLTLSKADYEKHKVYACEVTHQGLSSPVTKSFNRGEC | LC<br>DLL3.32,<br>DLL3.33 |
| 308 | DIVMTQTPLSLSVTPGQPASISCKSSQSLLHSDGKTFLYWYLQKPG<br>QPPQLLIYEVSNRFSGVPDRFSGSGSGTDFTLKISRVEAEDVGVYY<br>CLQGERLPFTFGPGTKVEIKSTFGQGTKVEIKRTVAAPSVFIFPPSD<br>EQLKSGTASVVCLLNNFYPREAKVQWKVDNALQSGNSQESVTEQ<br>DSKDSTYSLSSTLTLSKADYEKHKVYACEVTHQGLSSPVTKSFNR<br>GEC | LC;<br>DLL3.10,<br>DLL3.31 |
| 309 | DIVMTQTPLSLSVTPGQPASISCKSSQSLLHSDGKTFLYWYLQKPG<br>QPPQLLIYEVSNRFSGVPDRFSGSGSGTDFTLKISRVEAEDVGVYY<br>CLQGIHLPFTFGPGTKVEIKRTVAAPSVFIFPPSDEQLKSGTASVVC<br>LLNNFYPREAKVQWKVDNALQSGNSQESVTEQDSKDSTYSLSSTL<br>TLSKADYEKHKVYACEVTHQGLSSPVTKSFNRGEC | LC;<br>DLL3.29,<br>DLL3.30,<br>DLL3.36 |
| 310 | DIVMTQTPLSLSVTPGQPASISCKSSQSLLHSDGKTFLYWYLQKPG<br>QPPQLLIYEVSNRFSGVPDRFSGSGSGTDFTLKISRVEAEDVGVYY<br>CLQGIHLPFTFGPGTKVEIKSTFGQGTKVEIKRTVAAPSVFIFPPSD<br>EQLKSGTASVVCLLNNFYPREAKVQWKVDNALQSGNSQESVTEQ<br>DSKDSTYSLSSTLTLSKADYEKHKVYACEVTHQGLSSPVTKSFNR<br>GEC | LC;<br>DLL3.29.1 |
| 311 | DTVLTQSPASLAVSLGQRATISCRASESVHSYGNSLIHWYQQKPG<br>QPPRLLIYRASNLESGIPARFSGSGSRTDFTLTINPVEADDVATYYC<br>QQTNEDPLTFGAGTKLELKRTVAAPSVFIFPPSDEQLKSGTASVVC<br>LLNNFYPREAKVQWKVDNALQSGNSQESVTEQDSKDSTYSLSSTL<br>TLSKADYEKHKVYACEVTHQGLSSPVTKSFNRGEC | LC;<br>DLL3.34 |
| 312 | EIVLTQSPGTLSLSPGERVTLSCRASQRVNNNYLAWYQQRPGQAP<br>RLLIYGASSRATGIPDRFSGSGSGTDFTLTISRLEPEDFAVYYCQQ<br>YDRSPLTFGGGTKLEIKRTVAAPSVFIFPPSDEQLKSGTASVVCLLN<br>NFYPREAKVQWKVDNALQSGNSQESVTEQDSKDSTYSLSSTLTLS<br>KADYEKHKVYACEVTHQGLSSPVTKSFNRGEC | LC;<br>DLL3.28 |
| 313 | QIVLTQSPAIMSASPGEKVTMTCSASSSVSYMHWYQQKSGTSPKR<br>WIYDTSKLASGVPARFSGSGSGTSYSLTISSMEAEDAATYYCQQW<br>SSNPLTFGAGTKLELKRTVAAPSVFIFPPSDEQLKSGTASVVCLLN<br>NFYPREAKVQWKVDNALQSGNSQESVTEQDSKDSTYSLSSTLTLS<br>KADYEKHKVYACEVTHQGLSSPVTKSFNRGEC | LC;<br>DLL3.35 |
| 341 | QVQLVQSGAEVKKPGASVKVSCKASDYTFSNYYIEWVRQAPGQG<br>LEWMGEILPGNGNTVYNEKFKDRVTMTVDTSTSTAYMELRSLRSD<br>DTAVYYCARWGDYALFANWGQGTLVTVSSGGGGSGGGGSGGGG<br>GSDIQMTQSPSTLSASVGDRVTITCKASQNVGTNVAWYQQKPGK<br>APKALIYSASYRYSGVPSRFSGSGSGTEFTLTISSLQPDDFATYYC<br>QQYNSYPFTFGQGTKLEIKSGGGSEVQLVESGGGLVQPGGSLRL<br>SCAASGFTFSTYAMNWVRQAPGKGLEWVGRIRSKYNNYATYYAD<br>SVKGRFTISRDDSKNTLYLQMNSLRAEDTAVYYCVRHGNFGDSYV<br>SWFAYWGQGTLVTVSSGKPGSGKPGSGKPGSGKPGSQAVVTQE<br>PSLTVSPGGTVTLTCGSSTGAVTTSNYANWVQQKPGKSPRGLIGG<br>TNKRAPGVPARFSGSLLGGKAALTISGAQPEDEADYYCALWYSNH<br>WVFGGGTKLTVLEPKSSDKTHTCPPCPAPEFEGGPSVFLFPPKPK<br>DTLMISRTPEVTCVVVDVSHEDPEVKFNWYVDGVEVHNAKTKPRE<br>EQYNSTYRVVSVLTVLHQDWLNGKEYKCKVSNKALPASIEKTISKA<br>KGQPREPQVYTLPPCRKKLTKNQVSLTCLVKGFYPSDIAVEWESN<br>GQPENNYKTTPPVLKSDGSFFLYSKLTVDKSRWQQGNVFSCSVM<br>HEALHNHYTQKSLSLSPGK | DLL3Scfv-<br>CD3Scfv-Fv |
| 342 | QVQLVQSGAEVKKPGASVKVSCKATDYIFSNYYIEWVRQAPGQGL<br>EWMGEILPGTGNTVYNEKFKDRVTMTVDTSTSTVYMELSSLRSED<br>TAVYYCARWGDYALFANWGQGTLVTVSSGGGGSGGGGSGGGG<br>SDIQMTQSPSTLSASVGDRVTITCKASQNVGTNVAWYQQKPGKAP<br>KALIYSASYRYSGVPSRFSGSGSGTEFTLTISSLQPDDFATYYCQQ<br>YNSYPFTFGQGTKLEIKSGGGSEVQLVESGGGLVQPGGSLRLSCA | DLL3Scfv-<br>CD3Scfv-Fv |

TABLE 20-continued

SEQUENCES

| Seq ID | sequence | name |
|---|---|---|
| | ASGFTFSTYAMNWVRQAPGKGLEWVGRIRSKYNNYATYYADSVK<br>GRFTISRDDSKNTLYLQMNSLRAEDTAVYYCVRHGNFGDSYVSW<br>FAYWGQGTLVTVSSGKPGSGKPGSGKPGSGKPGSQAVVTQEPS<br>LTVSPGGTVTLTCGSSTGAVTTSNYANWVQQPGKSPRGLIGGTN<br>KRAPGVPARFSGSLLGGKAALTISGAQPEDEADYYCALWYSNHW<br>VFGGGTKLTVLEPKSSDKTHTCPPCPAPEFEGGPSVFLFPPKPKD<br>TLMISRTPEVTCVVVDVSHEDPEVKFNWYVDGVEVHNAKTKPREE<br>QYNSTYRVVSVLTVLHQDWLNGKEYKCKVSNKALPASIEKTISKAK<br>GQPREPQVYTLPPCRKKLTKNQVSLTCLVKGFYPSDIAVEWESNG<br>QPENNYKTTPPVLKSDGSFFLYSKLTVDKSRWQQGNVFSCSVMH<br>EALHNHYTQKSLSLSPGK | |
| 343 | QVQLVQSGAEVKKPGASVKVSCKASGYTFTDYFMNWVRQAPGQ<br>GLEWMGVINPYNDITIYNQKFQGRVTMTVDRSTSTVYMELSSLRS<br>EDTAVYYCAREGVLYDGYYEGAYWGQGTLVTVSSGGGGSGGGG<br>SGGGGSDIQLTQSPSFLSASVGDRVTITCKASQNVGIAVAWYQQK<br>PGKAPKLLIYAASNRYTGVPSRFSGSGSGTEFTLTISSLQPEDFAT<br>YYCQQYSTYPYTFGQGTKLEIKSGGGSEVQLVESGGGLVQPGGS<br>LRLSCAASGFTFSTYAMNWVRQAPGKGLEWVGRIRSKYNNYATY<br>YADSVKGRFTISRDDSKNTLYLQMNSLRAEDTAVYYCVRHGNFGD<br>SYVSWFAYWGQGTLVTVSSGKPGSGKPGSGKPGSGKPGSQAVV<br>TQEPSLTVSPGGTVTLTCGSSTGAVTTSNYANWVQQPGKSPRG<br>LIGGTNKRAPGVPARFSGSLLGGKAALTISGAQPEDEADYYCALW<br>YSNHWVFGGGTKLTVLEPKSSDKTHTCPPCPAPEFEGGPSVFLFP<br>PKPKDTLMISRTPEVTCVVVDVSHEDPEVKFNWYVDGVEVHNAKT<br>KPREEQYNSTYRVVSVLTVLHQDWLNGKEYKCKVSNKALPASIEK<br>TISKAKGQPREPQVYTLPPCRKKLTKNQVSLTCLVKGFYPSDIAVE<br>WESNGQPENNYKTTPPVLKSDGSFFLYSKLTVDKSRWQQGNVFS<br>CSVMHEALHNHYTQKSLSLSPGK | DLL3Scfv-<br>CD3Scfv-Fv |
| 344 | QVQLVQSGAEVKKPGASVKVSCKASGYTFTDYFMNWVRQAPGQ<br>CLEWMGVINPYNDITIYNQKFQGRVTMTVDRSTSTVYMELSSLRS<br>EDTAVYYCAREGVLYDGYYEGAYWGQGTLVTVSSGGGGSGGGG<br>SGGGGSDIQLTQSPSFLSASVGDRVTITCKASQNVGIAVAWYQQK<br>PGKAPKLLIYAASNRYTGVPSRFSGSGSGTEFTLTISSLQPEDFAT<br>YYCQQYSTYPYTFGCGTKLEIKSGGGSEVQLVESGGGLVQPGGS<br>LRLSCAASGFTFSTYAMNWVRQAPGKGLEWVGRIRSKYNNYATY<br>YADSVKGRFTISRDDSKNTLYLQMNSLRAEDTAVYYCVRHGNFGD<br>SYVSWFEYWGQGTLVTVSSGKPGSGKPGSGKPGSGKPGSQAVV<br>TQEPSLTVSPGGTVTLTCGSSTGAVTTSNYANWVQQPGKSPRG<br>LIGGTNKRAPGVPARFSGSLLGGKAALTISGAQPEDEADYYCALW<br>YSNHWVFGGGTKLTVLEPKSSDKTHTCPPCPAPEFEGGPSVFLFP<br>PKPKDTLMISRTPEVTCVVVDVSHEDPEVKFNWYVDGVEVHNAKT<br>KPREEQYNSTYRVVSVLTVLHQDWLNGKEYKCKVSNKALPASIEK<br>TISKAKGQPREPQVYTLPPCRKKLTKNQVSLTCLVKGFYPSDIAVE<br>WESNGQPENNYKTTPPVLKSDGSFFLYSKLTVDKSRWQQGNVFS<br>CSVMHEALHNHYTQKSLSLSPGK | DLL3Scfv-<br>CD3Scfv-Fv |
| 345 | QVQLVQSGAEVKKPGASVKVSCKATDYIFSNYYIEWVRQAPGQGL<br>EWMGEILPGTGNTVNEKFKDRVTMTVDTSTSTVYMELSSLRSED<br>TAVYYCARWGDYALFANWGQGTLVTVSSGGGGGGGGSGGGG<br>SDIQMTQSPSFLSASVGDRVTITCKASQNVGTNVAWYQQKPGKAP<br>KPLIYSTSYRYSGVPSRFSGSGSGTEFTLTISSLQPEDFATYYCQQ<br>YNNYPLTFGGGTKVEIKSGGGSEVQLVESGGGLVQPGGSLRLSC<br>AASGFTFSTYAMNWVRQAPGKGLEWVGRIRSKYNNYATYYADSV<br>KGRFTISRDDSKNTLYLQMNSLRAEDTAVYYCVRHGNFGDSYVS<br>WFAYWGQGTLVTVSSGKPGSGKPGSGKPGSGKPGSQAVVTQEP<br>SLTVSPGGTVTLTCGSSTGAVTTSNYANWVQQPGKSPRGLIGGT<br>NKRAPGVPARFSGSLLGGKAALTISGAQPEDEADYYCALWYSNH<br>WVFGGGTKLTVLEPKSSDKTHTCPPCPAPEFEGGPSVFLFPPKPK<br>DTLMISRTPEVTCVVVDVSHEDPEVKFNWYVDGVEVHNAKTKPRE<br>EQYNSTYRVVSVLTVLHQDWLNGKEYKCKVSNKALPASIEKTISKA<br>KGQPREPQVYTLPPCRKKLTKNQVSLTCLVKGFYPSDIAVEWESN<br>GQPENNYKTTPPVLKSDGSFFLYSKLTVDKSRWQQGNVFSCSVM<br>HEALHNHYTQKSLSLSPGK | DLL3Scfv-<br>CD3Scfv-Fv |
| 346 | QVQLVQSGAEVKKPGASVKVSCKASGYTFTDYFMNWVRQAPGQ<br>GLEWMGVINPYNDITIYNQKFQGRVTMTVDRSTSTVYMELSSLRS<br>EDTAVYYCAREGVLYDGYYEGAYWGQGTLVTVSSGGGGSGGGG<br>SGGGGSDIQLTQSPSFLSASVGDRVTITCKASQNVGIAVAWYQQK<br>PGKAPKLLIYAASNRYTGVPSRFSGSGSGTEFTLTISSLQPEDFAT<br>YYCQQYSTYPYTFGQGTKLEIKSGGGSEVQLVESGGGLVQPGGS<br>LRLSCAASGFTFSTYAMNWVRQAPGKGLEWVGRIRSKYNNYATY<br>YADSVKGRFTISRDDSKNTLYLQMNSLRAEDTAVYYCVRHGNFGD<br>SYVSWFAYWGQGTLVTVSSGKPGSGKPGSGKPGSGKPGSQAVV<br>TQEPSLTVSPGGTVTLTCGSSTGAVTTSNYANWVQQPGKSPRG | DLL3Scfv-<br>CD3Scfv-Fv |

TABLE 20-continued

SEQUENCES

| Seq ID | sequence | name |
|---|---|---|
| | LIGGTNKRAPGVPARFSGSLLGGKAALTISGAQPEDEADYYCALW<br>YSNHWVFGGGTKLTVLEPKSSDKTHTCPPCPAPEFEGGPSVFLFP<br>PKPKDTLMISRTPEVTCVVVDVSHEDPEVKFNWYVDGVEVHNAKT<br>KPREEQYNSTYRVVSVLTVLHQDWLNGKEYKCKVSNKALPASIEK<br>TISKAKGQPREPQVYTLPPCRKKLTKNQVSLTCLVKGFYPSDIAVE<br>WESNGQPENNYKTTPPVLKSDGSFFLYSKLTVDKSRWQQGNVFS<br>CSVMHEALHNHYTQKSLSLSPGK | |
| 347 | QVQLVQSGAEVKKPGASVKVSCKASGYTFTDYFMNWVRQAPGQ<br>GLEWMGVINPYNDITIYNQKFQGRVTMTVDRSTSTVYMELSSLRS<br>EDTAVYYCAREGVLYDGYYEGAYWGQGTLVTVSSGGGGSGGGG<br>SGGGGSDIQLTQSPSFLSASVGDRVTITCKASQNVGIAVAWYQQK<br>PGKAPKLLIYAASNRYTGVPSRFSGSGSGTEFTLTISSLQPEDFAT<br>YYCQQYSTYPYTFGQGTKLEIKSGGGSEVQLVESGGGLVQPGGS<br>LRLSCAASGFTFSTYAMNWVRQAPGKGLEWVGRIRSKYNNYATY<br>YADSVKGRFTISRDDSKNTLYLQMNSLRAEDTAVYYCVRHGNFGD<br>SYVSWFEYWGQGTLVTVSSGKPGSGKPGSGKPGSGKPGSQAVV<br>TQEPSLTVSPGGTVTLTCGSSTGAVTTSNYANWVQQKPGKSPRG<br>LIGGTNKRAPGVPARFSGSLLGGKAALTISGAQPEDEADYYCALW<br>YSNHWVFGGGTKLTVLEPKSSDKTHTCPPCPAPEFEGGPSVFLFP<br>PKPKDTLMISRTPEVTCVVVDVSHEDPEVKFNWYVDGVEVHNAKT<br>KPREEQYNSTYRVVSVLTVLHQDWLNGKEYKCKVSNKALPASIEK<br>TISKAKGQPREPQVYTLPPCRKKLTKNQVSLTCLVKGFYPSDIAVE<br>WESNGQPENNYKTTPPVLKSDGSFFLYSKLTVDKSRWQQGNVFS<br>CSVMHEALHNHYTQKSLSLSPGK | DLL3Scfv-<br>CD3Scfv-Fv |
| 348 | QVQLVQSGAEVKKPGASVKVSCKASGYTFTDYFMNWVRQAPGQ<br>GLEWMGVINPYNDITIYNQKFQGRVTMTVDRSTSTVYMELSSLRS<br>EDTAVYYCAREGVLYDGYYEGAYWGQGTLVTVSSGGGGSGGGG<br>SGGGGSDIQLTQSPSFLSASVGDRVTITCKASQNVGIAVAWYQQK<br>PGKAPKLLIYAASNRYTGVPSRFSGSGSGTEFTLTISSLQPEDFAT<br>YYCQQYSTYPYTFGQGTKLEIKSGGGSEVQLVESGGGLVQPGGS<br>LRLSCAASGFTFSTYAMNWVRQAPGKGLEWVGRIRSKYNNYATY<br>YADSVKGRFTISRDDSKNTLYLQMNSLRAEDTAVYYCVRHGNFGD<br>SYVSWFNYWGQGTLVTVSSGKPGSGKPGSGKPGSGKPGSQAVV<br>TQEPSLTVSPGGTVTLTCGSSTGAVTTSNYANWVQQKPGKSPRG<br>LIGGTNKRAPGVPARFSGSLLGGKAALTISGAQPEDEADYYCALW<br>YSNHWVFGGGTKLTVLEPKSSDKTHTCPPCPAPEFEGGPSVFLFP<br>PKPKDTLMISRTPEVTCVVVDVSHEDPEVKFNWYVDGVEVHNAKT<br>KPREEQYNSTYRVVSVLTVLHQDWLNGKEYKCKVSNKALPASIEK<br>TISKAKGQPREPQVYTLPPCRKKLTKNQVSLTCLVKGFYPSDIAVE<br>WESNGQPENNYKTTPPVLKSDGSFFLYSKLTVDKSRWQQGNVFS<br>CSVMHEALHNHYTQKSLSLSPGK | DLL3Scfv-<br>CD3Scfv-Fv |
| 349 | EVQLVQSGAEVKKPGESLKISCKGSGYEFSSHWMNWVRQMPGK<br>CLEWMGQIYPGDGDINYNEKFRGQVTISADKSISTAYLQWSSLKAS<br>DTAMYYCARHGNYVMDYWGQGTLVTVSSGGGGSGGGGSGGGG<br>SGGGGSIQLTQSPSFLSASVGDRVTITCSASSSVSYMFWYQQKPG<br>KAPKPWIYRTSNLASGVPSRFSGSGSGTEFTLTISSLQPEDFATYY<br>CQQFHDYPRTFGCGTKVEIKSGGGSEVQLVESGGGLVQPGGSLR<br>LSCAASGFTFSTYAMNWVRQAPGKGLEWVGRIRSKYNNYATYYA<br>DSVKGRFTISRDDSKNTLYLQMNSLRAEDTAVYYCVRHGNFGDSY<br>VSWFEYWGQGTLVTVSSGKPGSGKPGSGKPGSGKPGSQAVVTQ<br>EPSLTVSPGGTVTLTCGSSTGAVTTSNYANWVQQKPGKSPRGLIG<br>GTNKRAPGVPARFSGSLLGGKAALTISGAQPEDEADYYCALWYSN<br>HWVFGGGTKLTVLEPKSSDKTHTCPPCPAPEFEGGPSVFLFPPKP<br>KDTLMISRTPEVTCVVVDVSHEDPEVKFNWYVDGVEVHNAKTKPR<br>EEQYNSTYRVVSVLTVLHQDWLNGKEYKCKVSNKALPASIEKTISK<br>AKGQPREPQVYTLPPCRKKLTKNQVSLTCLVKGFYPSDIAVEWES<br>NGQPENNYKTTPPVLKSDGSFFLYSKLTVDKSRWQQGNVFSCSV<br>MHEALHNHYTQKSLSLSPGK | Muc17scfv-<br>CD3scfv |
| 350 | EVQLVQSGAEVKKPGESLKISCKGSGYEFSSHWMNWVRQMPGK<br>GLEWMGQIYPGDGDINYNEKFRGQVTISADKSISTAYLQWSSLKA<br>SDTAMYYCARHGNYVMDYWGQGTLVTVSSGGGGSGGGGSGGGG<br>GSGGGGSIQLTQSPSFLSASVGDRVTITCSASSSVSYMFWYQQKP<br>GKAPKPWIYRTSNLASGVPSRFSGSGSGTEFTLTISSLQPEDFATY<br>YCQQFHDYPRTFGGGTKVEIKSGGGSEVQLVESGGGLVQPGGSL<br>RLSCAASGFTFSTYAMNWVRQAPGKGLEWVGRIRSKYNNYATYY<br>ADSVKGRFTISRDDSKNTLYLQMNSLRAEDTAVYYCVRHGNFGDS<br>YVSWFAYWGQGTLVTVSSGKPGSGKPGSGKPGSGKPGSQAVVT<br>QEPSLTVSPGGTVTLTCGSSTGAVTTSNYANWVQQKPGKSPRGLI<br>GGTNKRAPGVPARFSGSLLGGKAALTISGAQPEDEADYYCALWYS<br>NHWVFGGGTKLTVLEPKSSDKTHTCPPCPAPEFEGGPSVFLFPPK<br>PKDTLMISRTPEVTCVVVDVSHEDPEVKFNWYVDGVEVHNAKTKP<br>REEQYNSTYRVVSVLTVLHQDWLNGKEYKCKVSNKALPASIEKTIS | Muc17scfv-<br>CD3scfv |

TABLE 20-continued

| | SEQUENCES | |
|---|---|---|
| Seq ID | sequence | name |

KAKGQPREPQVYTLPPCRKKLTKNQVSLTCLVKGFYPSDIAVEWE
SNGQPENNYKTTPPVLKSDGSFFLYSKLTVDKSRWQQGNVFSCS
VMHEALHNHYTQKSLSLSPGK

351   QVQLQQWGAGLLKPSETLSLTCAVYGGSFSGYYWSWIRQPPGKC   Muc17scfv-
LEWIGDIDASGSTKYNPSLKSRVTISLDTSKNQFSLKLNSVTAADTA  CD3scfv
VYFCARKKYSTVWSYFDNWGQGTLVTVSSGGGGSGGGGSGGGG
GSSYELTQPSSVSVPPGQTASITCSGDKLGDKYASWYQQKPGQS
PVLVIYQDRKRPSGVPERFSGSNSGNTATLTISGTQAMDEADYYC
QAWGSSTAVFGCGTKLTVLSGGGGSEVQLVESGGGLVQPGGSL
KLSCAASGFTFNKYAMNWVRQAPGKGLEWVARIRSKYNNYATYY
ADSVKDRFTISRDDSKNTAYLQMNNLKTEDTAVYYCVRHGNFGNS
YISYWAYWGQGTLVTVSSGGGGSGGGGSGGGGSQTVVTQEPSL
TVSPGGTVTLTCGSSTGAVTSGNYPNWVQQKPGQAPRGLIGGTK
FLAPGTPARFSGSLLGGKAALTLSGVQPEDEAEYYCVLWYSNRW
VFGGGTKLTVLGGGGDKTHTCPPCPAPELLGGPSVFLFPPKPKDT
LMISRTPEVTCVVVDVSHEDPEVKFNWYVDGVEVHNAKTKPCEEQ
YGSTYRCVSVLTVLHQDWLNGKEYKCKVSNKALPAPIEKTISKAKG
QPREPQVYTLPPSREEMTKNQVSLTCLVKGFYPSDIAVEWESNGQ
PENNYKTTPPVLDSDGSFFLYSKLTVDKSRWQQGNVFSCSVMHE
ALHNHYTQKSLSLSPGKGGGGSGGGGSGGGGSGGGGSGGGGS
GGGGSDKTHTCPPCPAPELLGGPSVFLFPPKPKDTLMISRTPEVT
CVVVDVSHEDPEVKFNWYVDGVEVHNAKTKPCEEQYGSTYRCVS
VLTVLHQDWLNGKEYKCKVSNKALPAPIEKTISKAKGQPREPQVYT
LPPSREEMTKNQVSLTCLVKGFYPSDIAVEWESNGQPENNYKTTP
PVLDSDGSFFLYSKLTVDKSRWQQGNVF
SCSVMHEALHNHYTQKSLSLSPGK 352   QVQLVESGGGVVQPGRSLRLSCAASGFTFSNHGMHWVRQAPGK   Muc17scfv-
CLEWVAGIWSEGSNKYYADAVKGRFTISRDNSKNTLYLQMNSLRA  CD3scfv
EDTAVYYCARATYTTGWSYFDYWGQGTLVTVSSGGGGSGGGGS
GGGGSSYELTQPPSVSVSPGQTASITCSGDKLGDKYASWYQQKS
GQSPV
LVIYQDAKRPSGIPERFSGSNSGNTATLTISGTQAMDEADYYCQAF
HQSTWVFGCGTQLT
VLSGGGGSEVQLVESGGGLVQPGGSLKLSCAASGFTFNKYAMN
WVRQAPGKGLEWVARIR
SKYNNYATYYADSVKDRFTISRDDSKNTAYLQMNNLKTEDTAVYY
CVRHGNFGNSYISYW
AYWGQGTLVTVSSGGGGSGGGGSGGGGSQTVVTQEPSLTVSPG
GTVTLTCGSSTGAVTSG
NYPNWVQQKPGQAPRGLIGGTKFLAPGTPARFSGSLLGGKAALTL
SGVQPEDEAEYYCVL
WYSNRWVFGGGTKLTVLGGGGDKTHTCPPCPAPELLGGPSVFLF
PPKPKDTLMISRTPEV
TCVVVDVSHEDPEVKFNWYVDGVEVHNAKTKPCEEQYGSTYRCV
SVLTVLHQDWLNGKEY
KCKVSNKALPAPIEKTISKAKGQPREPQVYTLPPSREEMTKNQVSL
TCLVKGFYPSDIAVEWESNGQPENNYKTTPPVLDSDGSFFLYSKL
TVDKSRWQQGNVFSCSVMHEALHNHYTQKSLSLSPGKGGGGSG
GGGSGGGGSGGGGSGGGGSGGGGSDKTHTCPPCPAPELLGGP
SVFLFPPKPKDTLMISRTPEVTCVVVDVSHEDPEVKFNWYVDGVE
VHNAKTKPCEEQYGSTYRCVSVLTVLHQDWLNGKEYKCKVSNKA
LPAPIEKTISKAKGQPREPQVYTLPPSREEMTKNQVSLTCLVKGFY
PSDIAVEWESNGQPENNYKTTPPVLDSDGSFFLYSKLTVDKSRWQ
QGNVFSCSVMHEALHNHYTQKSLSLSPGK 353   QVQLVQSGAEVKKPGSSVKVSCKASGYTFTSYWLNWVRQAPGQ   Muc17scfv-
GLEWMGMIHPSDSESRLNQKFKDRVTITADKSTSTAYMELSSLRS  CD3scfv
EDTAVYYCARQGIITSVQEFAYWGQGTLVTVSSGGGGSGGGGSG
GGGSGGGGSIQMTQSPSSLSASVGDRVTITCSASSSVNYIFWYQQ
KPGKAPKLLIYRTSNLASGVPSRFSGSGSGTDFTLTISSLQPEDFAT
YYCQQYHSYPLTFGGGTKVEIKSGGGGSEVQLVESGGGLVQPGG
SLRLSCAASGFTFSTYAMNWVRQAPGKGLEWVGRIRSKYNNYAT
YYADSVKGRFTISRDDSKNTLYLQMNSLRAEDTAVYYCVRHGNFG
DSYVSWFEYWGQGTLVTVSSGKPGSGKPGSGKPGSGKPGSQAV
VTQEPSLTVSPGGTVTLTCGSSTGAVTTSNYANWVQQKPGKSPR
GLIGGTNKRAPGVPARFSGSLLGGKAALTISGAQPEDEADYYCAL
WYSNHWVFGGGTKLTVLEPKSSDKTHTCPPCPAPEFEGGPSVFL
FPPKPKDTLMISRTPEVTCVVVDVSHEDPEVKFNWYVDGVEVHNA
KTKPREEQYNSTYRVVSVLTVLHQDWLNGKEYKCKVSNKALPASI
EKTISKAKGQPREPQVYTLPPCRKKLTKNQVSLTCLVKGFYPSDIA
VEWESNGQPENNYKTTPPVLKSDGSFFLYSKLTVDKSRWQQGNV
FSCSVMHEALHNHYTQKSLSLSPGK TABLE 20-continued

SEQUENCES

| Seq ID | sequence | name |
|---|---|---|
| 354 | QVQLVQSGAEVKKPGSSVKVSCKASGYTFTSYWLNWVRQAPGQ GLEWMGMIHPSDSESRLNQKFKDRVTITADKSTSTAYMELSSLRS EDTAVYYCARQGIITSVQEFAYWGQGTLVTVSSGGGGSGGGGSG GGGSGGGGSIQMTQSPSSLSASVGDRVTITCSASSSVNYIFWYQQ KPGKAPKLLIYRTSNLASGVPSRFSGSGSGTDFTLTISSLQPEDFAT YYCQQYHSYPLTFGGGTKVEIKSGGGSEVQLVESGGGLVQPGGS LRLSCAASGFTFSTYAMNWVRQAPGKGLEWVGRIRSKYNNYATY YADSVKGRFTISRDDSKNTLYLQMNSLRAEDTAVYYCVRHGNFGD SYVSWFEYWGQGTLVTVSSGKPGSGKPGSGKPGSGKPGSQAVV TQEPSLTVSPGGTVTLTCGSSTGAVTTSNYANWVQQKPGKSPRG LIGGTNKRAPGVPARFSGSLLGGKAALTISGAQPEDEADYYCALW YSNHWVFGGGTKLTVLEPKSSDKTHTCPPCPAPEFEGGPSVFLFP PKPKDTLMISRTPEVTCVVVDVSHEDPEVKFNWYVDGVEVHNAKT KPREEQYNSTYRVVSVLTVLHQDWLNGKEYKCKVSNKALPASIEK TISKAKGQPREPQVYTLPPCRKKLTKNQVSLTCLVKGFYPSDIAVE WESNGQPENNYKTTPPVLKSDGSFFLYSKLTVDKSRWQQGNVFS CSVMHEALHNHYTQKSLSLSPGK | Muc17scfv-CD3scfv |
| 355 | QVQLVQSGAEVKKPGSSVKVSCKASGYTFTSYWLNWVRQAPGQ GLEWMGMIHPSDSE<u>S</u>RLNQKFKDRVTITADKSTSTAYMELSSLRS EDTAVYYCARQGII<u>T</u>SVQEFAYWGQGTLVTVSSGGGGSGGGGSG GGGSGGGGSIQMTQSPSSLSASVGDRVTITCSASSSVNYIYWYQ QKPGKAPKLLIYRTSNLASGVPSRFSGSGSGTDFTLTISSLQPEDF ATYYCQQYHSYPLTFGGGTKVEIKSGGGGSEVQLVESGGGLVQP GGSLRLSCAASGFTFSTYAMNWVRQAPGKGLEWVGRIRSKYNNY ATYYADSVKGRFTISRDDSKNTLYLQMNSLRAEDTAVYYCVRHGN FGDSYVSWFEYWGQGTLVTVSSGKPGSGKPGSGKPGSGKPGSQ AVVTQEPSLTVSPGGTVTLTCGSSTGAVTTSNYANWVQQKPGKS PRGLIGGTNKRAPGVPARFSGSLLGGKAALTISGAQPEDEADYYC ALWYSNHWVFGGGTKLTVLEPKSSDKTHTCPPCPAPEFEGGPSV FLFPPKPKDTLMISRTPEVTCVVVDVSHEDPEVKFNWYVDGVEVH NAKTKPREEQYNSTYRVVSVLTVLHQDWLNGKEYKCKVSNKALPA SIEKTISKAKGQPREPQVYTLPPCRKKLTKNQVSLTCLVKGFYPSDI AVEWESNGQPENNYKTTPPVLKSDGSFFLYSKLTVDKSRWQQGN VFSCSVMHEALHNHYTQKSLSLSPGK | Muc17scfv-CD3scfv |
| 356 | QVQLVQSGAEVKKPGSSVKVSCKASGYTFTSYWbNWVRQAPGQ GLEWMGMIHPSDSETRLNQKFKDRVTITADKSTSTAYMELSSLRS EDTAVYYCARQGIITSVQEFAYWGQGTLVTVSSGGGGSGGGGSG GGGSGGGGSIQMTQSPSSLSASVGDRVTITCSASSSVNYIfWYQQ KPGKAPKLLIYRTSNLASGVPSRFSGSGSGTDFTLTISSLQPEDFAT YYCQQYHSYPLTFGGGTKVEIKSGGGGSEVQLVESGGGLVQPGG SLRLSCAASGFTFSTYAMNWVRQAPGKGLEWVGRIRSKYNNYAT YYADSVKGRFTISRDDSKNTLYLQMNSLRAEDTAVYYCVRHGNFG DSYVSWFEYWGQGTLVTVSSGKPGSGKPGSGKPGSGKPGSQAV VTQEPSLTVSPGGTVTLTCGSSTGAVTTSNYANWVQQKPGKSPR GLIGGTNKRAPGVPARFSGSLLGGKAALTISGAQPEDEADYYCAL WYSNHWVFGGGTKLTVLEPKSSDKTHTCPPCPAPEFEGGPSVFL FPPKPKDTLMISRTPEVTCVVVDVSHEDPEVKFNWYVDGVEVHNA KTKPREEQYNSTYRVVSVLTVLHQDWLNGKEYKCKVSNKALPASI EKTISKAKGQPREPQVYTLPPCRKKLTKNQVSLTCLVKGFYPSDIA VEWESNGQPENNYKTTPPVLKSDGSFFLYSKLTVDKSRWQQGNV FSCSVMHEALHNHYTQKSLSLSPGK | Muc17scfv-CD3scfv |
| 357 | QVQLVQSGAEVKKPGSSVKVSCKASGYTFTSYWbNWVRQAPGQ GLEWMGMIHPSDSETRLNQKFKDRVTITADKSTSTAYMELSSLRS EDTAVYYCARQGIITSVQEFAYWGQGTLVTVSSGGGGSGGGGSG GGGSGGGGSIQMTQSPSSLSASVGDRVTITCSASSSVNYIYWYQ QKPGKAPKLLIYRTSNLASGVPSRFSGSGSGTDFTLTISSLQPEDF ATYYCQQYHSYPLTFGGGTKVEIKSGGGGSEVQLVESGGGLVQP GGSLRLSCAASGFTFSTYAMNWVRQAPGKGLEWVGRIRSKYNNY ATYYADSVKGRFTISRDDSKNTLYLQMNSLRAEDTAVYYCVRHGN FGDSYVSWFEYWGQGTLVTVSSGKPGSGKPGSGKPGSGKPGSQ AVVTQEPSLTVSPGGTVTLTCGSSTGAVTTSNYANWVQQKPGKS PRGLIGGTNKRAPGVPARFSGSLLGGKAALTISGAQPEDEADYYC ALWYSNHWVFGGGTKLTVLEPKSSDKTHTCPPCPAPEFEGGPSV FLFPPKPKDTLMISRTPEVTCVVVDVSHEDPEVKFNWYVDGVEVH NAKTKPREEQYNSTYRVVSVLTVLHQDWLNGKEYKCKVSNKALPA SIEKTISKAKGQPREPQVYTLPPCRKKLTKNQVSLTCLVKGFYPSDI AVEWESNGQPENNYKTTPPVLKSDGSFFLYSKLTVDKSRWQQGN VFSCSVMHEALHNHYTQKSLSLSPGK | Muc17scfv-CD3scfv |
| 358 | QVQLVQSGAEVKKPGSSVKVSCKASGYTFTSYWMNWVRQAPGQ GLEWMGMIHPSDSE<u>S</u>RLNQKFKDRVTITADKSTSTAYMELSSLRS EDTAVYYCARQGII<u>T</u>SVQEFAYWGQGTLVTVSSGGGGSGGGGSG | Muc17scfv-CD3scfv |

TABLE 20-continued

| | SEQUENCES | |
| --- | --- | --- |
| Seq ID | sequence | name |

| | | |
| --- | --- | --- |
| | GGGSGGGGSIQMTQSPSSLSASVGDRVTITCSASSSVNYIfWYQQ<br>KPGKAPKLLIYRTSNLASGVPSRFSGSGSGTDFTLTISSLQPEDFAT<br>YYCQQYHSYPLTFGGGTKVEIKSGGGGSEVQLVESGGGLVQPGG<br>SLRLSCAASGFTFSTYAMNWVRQAPGKGLEWVGRIRSKYNNYAT<br>YYADSVKGRFTISRDDSKNTLYLQMNSLRAEDTAVYYCVRHGNFG<br>DSYVSWFEYWGQGTLVTVSSGKPGSGKPGSGKPGSGKPGSQAV<br>VTQEPSLTVSPGGTVTLTCGSSTGAVTTSNYANWVQQKPGKSPR<br>GLIGGTNKRAPGVPARFSGSLLGGKAALTISGAQPEDEADYYCAL<br>WYSNHWVFGGGTKLTVLEPKSSDKTHTCPPCPAPEFEGGPSVFL<br>FPPKPKDTLMISRTPEVTCVVVDVSHEDPEVKFNWYVDGVEVHNA<br>KTKPREEQYNSTYRVVSVLTVLHQDWLNGKEYKCKVSNKALPASI<br>EKTISKAKGQPREPQVYTLPPCRKKLTKNQVSLTCLVKGFYPSDIA<br>VEWESNGQPENNYKTTPPVLKSDGSFFLYSKLTVDKSRWQQGNV<br>FSCSVMHEALHNHYTQKSLSLSPG | |
| 359 | QVQLVQSGAEVKKPGSSVKVSCKASGYTFTSYWMNWVRQAPGQ<br>GLEWMGMIHPSDSESRLNQKFKDRVTITADKSTSTAYMELSSLRS<br>EDTAVYYCARQGIITSVQEFAYWGQGTLVTVSSGGGGSGGGGSG<br>GGGSGGGGSIQMTQSPSSLSASVGDRVTITCSASSSVNYIYWYQ<br>QKPGKAPKLLIYRTSNLASGVPSRFSGSGSGTDFTLTISSLQPEDF<br>ATYYCQQYHSYPLTFGGGTKVEIKSGGGGSEVQLVESGGGLVQP<br>GGSLRLSCAASGFTFSTYAMNWVRQAPGKGLEWVGRIRSKYNNY<br>ATYYADSVKGRFTISRDDSKNTLYLQMNSLRAEDTAVYYCVRHGN<br>FGDSYVSWFEYWGQGTLVTVSSGKPGSGKPGSGKPGSGKPGSQ<br>AVVTQEPSLTVSPGGTVTLTCGSSTGAVTTSNYANWVQQKPGKS<br>PRGLIGGTNKRAPGVPARFSGSLLGGKAALTISGAQPEDEADYYC<br>ALWYSNHWVFGGGTKLTVLEPKSSDKTHTCPPCPAPEFEGGPSV<br>FLFPPKPKDTLMISRTPEVTCVVVDVSHEDPEVKFNWYVDGVEVH<br>NAKTKPREEQYNSTYRVVSVLTVLHQDWLNGKEYKCKVSNKALPA<br>SIEKTISKAKGQPREPQVYTLPPCRKKLTKNQVSLTCLVKGFYPSDI<br>AVEWESNGQPENNYKTTPPVLKSDGSFFLYSKLTVDKSRWQQGN<br>VFSCSVMHEALHNHYTQKSLSLSPGK | Muc17scfv-<br>CD3scfv |
| 360 | QVQLVQSGAEVKKPGSSVKVSCKASGYTFTSYWMNWVRQAPGQ<br>GLEWMGMIHPSDSETRLNQKFKDRVTITADKSTSTAYMELSSLRS<br>EDTAVYYCARQGIITSVQEFAYWGQGTLVTVSSGGGGSGGGGSG<br>GGGSGGGGSIQMTQSPSSLSASVGDRVTITCSASSSVNYIfWYQQ<br>KPGKAPKLLIYRTSNLASGVPSRFSGSGSGTDFTLTISSLQPEDFAT<br>YYCQQYHSYPLTFGGGTKVEIKSGGGGSEVQLVESGGGLVQPGG<br>SLRLSCAASGFTFSTYAMNWVRQAPGKGLEWVGRIRSKYNNYAT<br>YYADSVKGRFTISRDDSKNTLYLQMNSLRAEDTAVYYCVRHGNFG<br>DSYVSWFEYWGQGTLVTVSSGKPGSGKPGSGKPGSGKPGSQAV<br>VTQEPSLTVSPGGTVTLTCGSSTGAVTTSNYANWVQQKPGKSPR<br>GLIGGTNKRAPGVPARFSGSLLGGKAALTISGAQPEDEADYYCAL<br>WYSNHWVFGGGTKLTVLEPKSSDKTHTCPPCPAPEFEGGPSVFL<br>FPPKPKDTLMISRTPEVTCVVVDVSHEDPEVKFNWYVDGVEVHNA<br>KTKPREEQYNSTYRVVSVLTVLHQDWLNGKEYKCKVSNKALPASI<br>EKTISKAKGQPREPQVYTLPPCRKKLTKNQVSLTCLVKGFYPSDIA<br>VEWESNGQPENNYKTTPPVLKSDGSFFLYSKLTVDKSRWQQGNV<br>FSCSVMHEALHNHYTQKSLSLSPGK | Muc17scfv-<br>CD3scfv |
| 361 | QVQLVQSGAEVKKPGSSVKVSCKASGYTFTSYWMNWVRQAPGQ<br>GLEWMGMIHPSDSETRLNQKFKDRVTITADKSTSTAYMELSSLRS<br>EDTAVYYCARQGIITSVQEFAYWGQGTLVTVSSGGGGSGGGGSG<br>GGGSGGGGSIQMTQSPSSLSASVGDRVTITCSASSSVNYIYWYQ<br>QKPGKAPKLLIYRTSNLASGVPSRFSGSGSGTDFTLTISSLQPEDF<br>ATYYCQQYHSYPLTFGGGTKVEIKSGGGGSEVQLVESGGGLVQP<br>GGSLRLSCAASGFTFSTYAMNWVRQAFGKGLEWVGRIRSKYNNY<br>ATYYADSVKGRFTISRDDSKNTLYLQMNSLRAEDTAVYYCVRHGN<br>FGDSYVSWFEYWGQGTLVTVSSGKPGSGKPGSGKPGSGKPGSQ<br>AVVTQERSLTVSPGGTVTLTCGSSTGAVTTSNYANWVQQKPGKS<br>PRGLIGGTNKRAPGVPARFSGSLLGGKAALTISGAQPEDEADYYC<br>ALWYSNHWVFGGGTKLTVLEPKSSDKTHTCPPCPAPEFEGGPSV<br>FLFPPKPKDTLMISRTPEVTCVVVQVSHEDPEVKFNWYVDGVEVH<br>NAKTKPREEQYNSTYRVVSVLTVLHQDWLNGKEYKCKVSNKALPA<br>SIEKTISKAKGQPREPQVYTLPPCRKKLTKNQVSLTCLVKGFYPSDI<br>AVEWESNGQPENNYKTTPPVLKSDGSFFLYSKLTVDKSRWQQGN<br>VFSCSVMHEALHNHYTQKSLSLSPG | Muc17scfV-<br>CD3scfv |
| 362 | QVQLVQSGAEVKKPGSSVKVSCKASGYTFTSYWMNWVRQAPGQ<br>GLEWMGMIHPSDSETRLNQKFKDRVTITADKSTSTAYMELSSLRS<br>EDTAVYYCARQGIITSVQEFAYWGQGTLVTVSSGGGGSGGGGSG<br>GGGSGGGGSIQMTQSPSSLSASVGDRVTITCSASSSVNYIYWYQ<br>QKPGKAPKLLIYRTSNLASGVPSRFSGSGSGTDFTITISSLQPEDF<br>ATYYCQQYHSYPLTFGGGTKVEIKSGGGGSEVQLVESGGGLVQPG<br>GSLRLSCAASGFTFSTYAMNWVRQAPGKGLEWWGRIRSKINNYAT | Muc17scfv-<br>CD3scfv |

TABLE 20-continued

SEQUENCES

| Seq ID | sequence | name |
|--------|----------|------|
| | YYADSVKGRFTISRDDSKNTLYLQMNSLRAEDTAVYYCVRHGNFG DSYVSWFAYWGQGTLVTVSSGKPGSGKPGSGKPGSGKPGSQAV VTQEPSLTVSPGGTVTLTCGSSTGAVTTSNYANWVQQKPGKSPR GLIGGTNKRAPGVPARFSGSLLGGKAALTISGAQPEDEADYYCAL WYSNHWVFGGGTKLTVLEPKSSDKTHTCPPCPAPEFEGGPSVFL FPPKPKDTLMISRTPEVTCVVVDVSHEDPEVKFNWYVDGVEVHNA KTKPREEQYNSTYRVVSVLIVLHQDWLNGKEYKCKVSNKALPASI EKTISKAKGQPREPQVYTLPPCRKKLTKNQVSLTCLVKGFYPSDIA VEWESNGQPENNYKTTPPVLKSDGSFFLYSKLTVDKSRWQQGNV FSCSVMHEALHNHYTQKSLSLSPGK | |
| 363 | QVQLVQSGAEVKKPGSSVKVSCKASGYTFTSYWMNWVRQAPGQ GLEWMGMIHPSDSETRLNQKFKDRVTITADKSTSTAYMELSSLRS EDTAVYYCARQGIITSVQEFAYWGQGTLVTVSSGGGGSGGGGSG GGGSGGGGSIQMTQSPSSLSASVGDRVTITCSASSSVNYIYWYQ QKPGKAPKLLIYRTSNLASGVPSRFSGSGSGTDFTLTISSLQPEDF ATYYCQQYHSYPLTFGGGTKVEIKSGGGSEVQLVESGGGLVQPG GSLRLSCAASGFTFSTYAMNWVRQAPGKGLEWVGRIRSKYNNYA TYYADSVKGRFTISRDDSKNTLYLQMNSLRAEDTAVYYCVRHGNF GDSYVSWFAYWGQGTLVTVSSGKPGSGKPGSGKPGSGKPGSQA VVTQEPSLTVSPGGTVTLTCGSSTGAVTTSNYANWVQQKPGKSP RGLIGGTNKRAPGVPARFSGSLLGGKAALTISGAQPEDEADYYCA LWYSNHWVFGGGTKLTVLEPKSSDKTHTCPPCPAPEFEGGPSVF LFPPKPKDTLMISRTPEVTCVVVDVSHEDPEVKFNWYVDGVEVHN AKTKPREEQYNSTYRVVSVLTVLHQDWLNGKEYKCKVSNKALPAS IEKTISKAKGQPREPQVYTLPPCRKKLTKNQVSLTCLVKGFYPSDIA VEWESNGQPENNYKTTPPVLKSDGSFFLYSKLTVDKSRWQQGNV FSCSVMHEALHNHYTQKSLSLSPGK | Muc17scfv-CD3scfv |
| 364 | QVQLVQSGAEVKKPGSSVKVSCKASGYTFTSYWMNWVRQAPGQ GLEWMGMIHPSDSETRLNQKFKDRVTITADKSTSTAYMELSSLRS EDTAVYYCARQGIITSVQEFAYWGQGTLVTVSSGGGGSGGGGSG GGGSGGGGSIQMTQSPSSLSASVGDRVTITCSASSSVNYIYWYQ QKPGKAPKLLIYRTSNLASGVPSRFSGSGSGTDFTLTISSLQPEDF ATYYCQQYHSYPLTFGGGTKVEIKSGGGSEVQLVESGGGLVQPG GSLRLSCAASGFTFSTYAMNWVRQARGKGLEWVGRIRSKYNNYA TYYADSVKGRFTISRDDSKNTLYLQMNSLRAEDTAVYYCVRHGNF GDSYVSWFEYWGQGTLVTVSSGKPGSGKPGSGKPGSGKPGSQA VVTQERSLTVSPGGTVTLTCGSSTGAVTTSNYANWVQQKPGKSP RGLIGGTNKRAPGVPARFSGSLLGGKAALTISGAQPEDEADYYCA LWYSNHWVFGGGTKLTVLEPKSSDKTHTCPPCPAPEFEGGPSVF LFPPKPKDTLMISRTPEVTCVVVDVSHEDPEVKFNWYVDGVEVAN AKTKPREEQYNSTYRVVSVLTVLHQDWLNGKEYKCKVSNKALPAS IEKTISKAKGQPREPQVYTLPPCRKKLTKNQVSLTCLVKGFYPSDIA VEWESNGQPENNYKTTPPVLKSDGSFFLYSKLTVDKSRWQQGNV FSCSVMHEALMNNYTQKSLSLSPGK | Muc17scfv-CD3scfv |
| 365 | QVQLVQSGAEVKKPGSSVKVSCKASGYTFTSYWMNWVRQAPGQ GLEWMGMIHPSDSETRLNQKFKDRVTITADKSTSTAYMELSSLRS EDTAVYYCARQGIITSVQEFNYWGQGTLVTVSSGGGGSGGGGSG GGGGGGGGSIQMTQSPSSLSASVGDRVTITCSASSSVNYIYWYQ QKPGKAPKLLIYRTSNLASGVPSRFSGSGSGTDFTLTISSLQPEDF ATYYCQQYHSYPLTFGGGTKVEIKSGGGSEVQLVESGGGLVQPG GSLRISCAASGFTFSTYAMNWVRQAPGKGLEWVGRIRSKYNNYA TYYADSVKGRFTISRDDSKNTLYLQMNSLRAEDTAVYYCVRHGNF GDSYVSWFAYWGQGTLVTVSSGKPGSGKPGSGKPGSGKPGSQA VVTQEPSLTVSPGGTVTLTCGSSTGAVTTSNYANWVQQKPGKSP RGLIGGTNKRAPGVPARFSGSLLGGKAALTISGAQPEDEADYYCA LWYSNHWVFGGGTKLTVLEPKSSDKTHTCPPCPAPEFEGGPSVF LFPPKPKDTLMISRTPEVTCVVVDVSHEDPEVKFNWYVDGVEVHN AKTKPREEQYNSTYRVVSVLTVLHQDWLNGKEYKCKVSNKALPAS IEKTISKAKGQPREPQVYTLPPCRKKLTKNQVSLTCLVKGFYPSDIA VEWESNGQPENNYKTTPPVLKSDGSFFLYSKLTVDKSRWQQGNV FSCSVMHEALHNHYTQKSLSLSPGK | Muc17scfv-CD3scfv |
| 366 | EVQLVQSGAEVKKPGESLKISCKGSGYEFSSHWMNWVRQMPGK GLEWMGQIYPGQGDINYNEKFRGQVTISADKSISTAYLQWSSLKA SDTAMYYCARHGNYVMDYWGQGTLVTVSSGKPGSGKPGSGKPG SGKPGSIQLTQSPSFLSASVGDRVTITCSASSSVSYMFWYQQKPG KAPKPWIYRTSNLASGVPSRFSGSGSGTEFTLTISSLQPEDFATYY CQQFHDYPRTFGGGTKVEIKEPKSSDKTHTCPPCPAPEFEGGPSV FLFPPKPKDTLMISRTPEVTCVVVDVSHEDPEVKFNWYVDGVEVH NAKTKPREEQYNSTYRVVSVLTVLHQDWLNGKEYKCKVSNKALPA SIEKTISKAKGQPREPQVYTLPPCRKKLTKNQVSLTCLVKGFYPSDI AVEWESNGQPENNYKTTPPVLKSDGSFFLYSKLTVDKSRWQQGN VFSCSVMHEALHNHYTQKSLSLSPGK | Muc17scfv-Fc |

TABLE 20-continued

| Seq ID sequence | name |
|---|---|
| 367 QVQLVQSGAEVKKPGSSVKVSCKASGYTFTSYWMNWVRQAPGQ<br>GLEWMGMIHPSDSETRLNQKFKDRVTITADKSTSTAYMELSSLRS<br>EDTAVYYCARQGIITSVQEFAYWGQGTLVTVSSSGKPGSGKPGSGK<br>PGSGKPGSIQMTQSPSSLSASVGDRVTITCSASSSVNYIYWYQQK<br>PGKAPKLLIYRTSNLASGVPSRFSGSGSGTDFTLTISSLQPEDFATY<br>YCQQYHSYPLTFGGGTKVEIKEPKSSDKTHTCPPCPAPEFEGGPS<br>VFLFPPPKPKDTLMISRTPEVTCVVVDVSHEDPEVKFNWYVDGVEV<br>HNAKTKPREEQYNSTYRVVSVLTVLHQDWLNGKEYKCKVSNKAL<br>PASIEKTISKAKGQPREPQVYTLPPCRKKLTKNQVSLTCLVKGFYP<br>SDIAVEWESNGQPENNYKTTPPVLKSDGSFFLYSKLTVDKSRWQQ<br>GNVFSCSVMHEALHNHYTQKSLSLSPGK | Muc17scfv-<br>Fc |
| 368 EVQLVESGGGLVQPGGSLRLSCAASGFTFSSFGMHWWRQARGK<br>GLEWVSYISSGSSTIYYADTVKGRFTISRDNAKNSLYLQMNSLRAE<br>DTAVYYCARWGYYGSSYFAYWGQGTLVTVSSASTKGPSVFPLAP<br>SSKSTSGGTAALGCLVKDYFPEPVTVSWNSGALTSGVHTFPAVLQ<br>SSGLYSLSSVVTVPSSSLGTQTYICNVNHKPSNTKVDKRVEPKSG<br>DKTHTCPPCPAPEFEGGPSVFLFPPPKPKDTLMISRTPEVTCVVVDV<br>SHEDPEVKFNWYVDGVEVHNAKTKPREEQYNSTYRVVSVLTVLH<br>QDWLNGKEYKCKVSNKALPASIEKTISKAKGQPREPQVCTLPPSR<br>DELTKNQVSLTCLVEGFYPSDIAVEWESNGQPENNYKTTPPVLDS<br>DGSFFLYSDLTVDKSRWQQGNVFSCSVMHEALHNHYTQESLSLS<br>PGK | HC;<br>Muc17.7,<br>Muc17.21,<br>Muc17.22,<br>Muc17.23,<br>Muc17.24 |
| 369 EVQLVQSGAEVKKPGESLKISCKGSGYEFSSHWMNWVRQMPGK<br>GLEWMGQIYPGDGDINYNEKFRGQVTISADKSISTAYLQWSSLKA<br>SDTAMYYCARHGNYVMDYWGQGTLVTVSSASTKGPSVFPLAPSS<br>KSTSGGTAALGCLVKDYFPEPVTVSWNSGALTSGVHTFPAVLQSS<br>GLYSLSSVVTVPSSSLGTQTYICNVNHKPSNTKVDKRVEPKSCDKT<br>HTCPPCPAPEFEGGPSVFLFPPPKPKDTLMISRTPEVTCVVVDVSHE<br>DPEVKFNWYVDGVEVHNAKTKPREEQYNSTYRVVSVLTVLHQDW<br>LNGKEYKCKVSNKALPASIEKTISKAKGQPREPQVCTLPPSRDELT<br>KNQVSLTCLVEGFYPSDIAVEWESNGQPENNYKTTPPVLQSDGSF<br>FLYSDLTVDKSRWQQGNVFSCSVMHEALHNHYTQESLSLSPGK | HC;<br>Muc17.1,<br>Muc17.8,<br>Muc17.9,<br>Muc17.10,<br>Muc17.11,<br>Muc17.12,<br>Muc17.13,<br>Muc17.14 |
| 370 QVQLVQSGAEVKKPGASVKVSCKASGYEFSSHWMNWWVRQAPGQ<br>GLEWMGQIYPGDGDINYNEKFRGRVTMTRDTSTSTVYMELSSLRS<br>EDTAVYYCARHGNYVMDYWGQGTLVTVSSASTKGPSVFPLAPSS<br>KSTSGGTAALGCLVKDYFPEPVTVSWNSGALTSGVHTFPAVLQSS<br>GLYSLSSVVTVPSSSLGTQTYICNVNHKPSNTKVDKRVEPKSCDKT<br>HTCPPCPAPEFEGGPSVFLFPPPKPKDTLMISRTPEVTCVVVDVSHE<br>DREVKFNWYVDGVEVHNAKTKPREEQYNSTYRVVSVLTVLHQDW<br>LNGKEYKCKVSNKALPASIEKTISKAKGQPREPQVCTLPPSRDELT<br>KNQVSLTCLVEGFYPSDIAVEWESNGQPENNYKTTPPVLDSDGSF<br>FLYSDLTVDKSRWQQGNVFSCSVMHEALHNHYTQESLSLSPGK | HC;<br>Muc17.29,<br>Muc17.30,<br>Muc17.31 |
| 371 QVQLVQSGAEVKKPGASVKVSCKASGYTFTSYWMNWVRQAPGQ<br>GLEWIGMIHPSDSETRLNQKFKDRVILTVQKSSSTAYMELSSLRSE<br>DTAVYYCARQGIITSVQEFAYWGQGTLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVQKRVEPKSCD<br>KTHTCPPCPAPEFEGGPSVFLFPPPKPKDTLMISRTPEVTCVVVDVS<br>HEDPEVKFNWYVDGVEVHNAKTKPREEQYNSTYRVVSVLTVLHQ<br>DWLNGKEYKCKVSNKALPASIEKTISKAKGQPREPQVCTLPPSRD<br>ELTKNQVSLTCLVEGFYPSDIAVEWESNGQPENNYKTTPPVLDSD<br>GSFFLYSDLTVDKSRWQQGNVFSCSVMHEALHNHYTQESLSLSP<br>GK | HC;<br>Muc17.45 |
| 372 QVQLVQSGAEVKKPGASVKVSCKASGYTFTSYWMNWVRQAPGQ<br>GLEWMGMIHPSDSETRLNQEFKDRVTMTRDTSTSTVYMELSSLR<br>SEDTAVYYCARQGVITSVQEFAYWGQGTLVTVSSASTKGPSVFPL<br>APSSKSTSGGTAALGCLVKDYFPEPVTVSWNSGALTSGVHTFPAV<br>LQSSGLYSLSSVVTVPSSSLGTQTYICNVNHKPSNTKVDKRVEPKS<br>CDKTHTCPPCPAPEFEGGPSVFLFPPPKPKDTLMISRTPEVTCVVVD<br>VSHEDPEVKPNWYVDGVEVHNAKTKPREEQYNSTYRVVSVLTVL<br>HQDWLNGKEYKCKVSNKALPASIEKTISKAKGQPREPQVCTLPPS<br>RDELTKNQVSLTCLVEGFYPSDIAVEWESNGQPENNYKTTPPVLD<br>SDGSFFLYSDLTVDKSRWQQGNVFSCSVMHEALHNHYTQESLSL<br>SPGK | HC;<br>Muc17.5,<br>Muc17.20 |
| 373 QVQLVQSGAEVKKPGASVKVSCKASGYTFTSYWMNWVRQAPGQ<br>GLEWMGMIHPSDSETRLNQKFKDRVTLTRDKSISTAYMELSRLRS<br>DDTAVYYCARQGIITSVQEFAYWGQGTLVTVSSASTKGPSVFPLA<br>PSSKSTSGGTAALGCLVKDYFPEPVTVSWNSGALTSGVHTFPAVL<br>QSSGLYSLSSVVTVPSSSLGTQTYICNVNHKPSNTKVDKRVEPKS | HC;<br>Muc17.37 |

TABLE 20-continued

| SEQUENCES | | |
|---|---|---|
| Seq ID | sequence | name |

| | | |
|---|---|---|
| | CDKTHTCPPCPAPEREGGPSVFLAPPKPKDTLMISRTPEVTCVVVD<br>VSHEDPEVKFNWYVDGVEVHNAKTKPREEQYNSTYRVVSVLTVL<br>HQDWLNGKEYKCKVSNKALPASIEKTISKAKGQPREPQVCTLPPS<br>RDELTKNQVSLTCLVEGFYPSDIAVEWESNGQPENNYKTTPPVLD<br>SDGSFFLYSDLTVDKSRWQQGNVFSCSVMHEALHNHYTQESLSL<br>SPGK | |
| 374 | QVQLVQSGAEVKKPGASVKVSCKASGYTFTSYWMNWVRQAPGQ<br>GLEWMGMIHPSDSETRLNQKFKDRVTLTVDKSISTAYMELSRLRS<br>DDTAVYYCARQGIITSVQEFAYWGQGTLVTVSSASTKGPSVFPLA<br>PSSKSTSGGTAALGCLVKDYFPEPVTVSWNSGALTSGVHTFPAVL<br>QSSGLYSLSSVVTVPSSSLGTQTYICNVNHKPSNTKVDKRVEPKS<br>CDKTHTCPPCPAPEFEGGPSVFLFPPKPKDTLMISRTPEVTCVVVD<br>VSHEDPEVKFNWYVDGVEVHNAKTKPREEQYNSTYRVVSVLTVL<br>HQDWLNGKEYKCKVSNKALPASIEKTISKAKGQPREPQVCTLPPS<br>RDELTKNQVSLTCLVEGFYPSDIAVEWESNGQPENNYKTTPPVLD<br>SDGSFFLYSDLTVDKSRWQQGNVFSCSVMMEALMNHYTQESLSL<br>SPGK | HC;<br>Muc17.35 |
| 375 | QVQLVQSGAEVKKPGASVKVSCKASGYTFTSYWMNWVRQAPGQ<br>GLEWMGMIHPSDSETRLNGKPKDRVTLTVDTSISTAYMELSRLRS<br>DDTAVYYCARQGIITSVQEFAYWGQGTLVTVSSASTKGPSVFPLA<br>PSSKSTSGGTAALGCLVKDYFPEPVTVSWNSGALTSGVHTFPAVL<br>QSSGLYSLSSVVTVPSSSLGTQTYICNVNHKPSNTKVDKRVEPKS<br>CDKTHTCPPCPAPEFEGGPSVFLFPPKPKDTLMISRTPEVTCVVVD<br>VSHEDPEVKFNWYVDGVEVHNAKTKPREEQYNSTYRVVSVLTVL<br>HQDWLNGKEYKCKVSNKALPASIEKTISKAKGQPREPQVCTLPPS<br>RDELTKNQVSLTCLVEGFYPSDIAVEWESNGQPENNYKTTPPVLD<br>SDGSFFLYSDLTVDKSRWQQGNVFSCSVMHEALHNHYTQESLSL<br>SPGK | HC;<br>Muc17.36 |
| 376 | QVQLVQSGAEVKKPGASVKVSCKASGYTFTSYWMNWVRQAPGQ<br>GLEWMGMIHPSDSETRLNQKFKDRVTMTRDTSISTAYMELSRLRS<br>DDTAVYYCARQGIITSVQEFAYWGQGTLVTVSSASTKGPSVFPLA<br>PSSKSTSGGTAALGCLVKDYFPEPVTVSWNSGALTSGVHTFPAVL<br>QSSGLYSLSSVVTVPSSSLGTQTYICNVNHKPSNTKVDKRVEPKS<br>CDKTHTCPPCPAPEFEGGPSVFLFPPKPKDTLMISRTPEVTCVVVD<br>VSHEDPEVKFNWYVDGVEVHNAKTKPREEQYNSTYRVVSVLTVL<br>HQDWLNGKEYKCKVSNKALPASIEKTISKAKGQPREPQVCTLPPS<br>RDELTKNQVSLTCLVEGFYPSDIAVEWESNGQPENNYKTTPPVLD<br>SDGSFFLYSDLTVDKSRWQQGNVFSCSVMHEALHNHYTQESLSL<br>SPGK | HC;<br>Muc17.232,<br>Muc17.33,<br>Muc17.34 |
| 377 | QVQLVQSGAEVKKPGASVKVSCKASGYTFTSYWMNWVRQAPGQ<br>GLEWMGMIHPSDSETRLNQKFKDRVTMTRDTSTSTVYMELSSLR<br>SEDTAVYYCARQGIITSVQEFAYWGQGTLVTVSSASTKGPSVFPLA<br>PSSKSTSGGTAALGCLVKDYFREPVTVSWNSGALTSGVHTFPAVL<br>QSSGLYSLSSVVTVPSSSLGTQTYICNVNHKPSNTKVDKRVEPKS<br>CDKTHTCPPCPAPEPEGGPSVFLFPPKPKDTLMISRTPEVTCVVVD<br>VSHEDPEVKFNWYVDGVEVHNAKTKPREEQYNSTYRVVSVLTVL<br>HQDWLNGKEYKCKVSNKALPASIEKTISKAKGQPREPQVCTLPPS<br>RDELTKNQVSLTCLVEGFYPSDIAVEWESNGQPENNYKTTPPVLD<br>SDGSFFLYSDLTVDKSRWQQGNVFSCSVMHEALHNHYTQESLSL<br>SPGK | HC:<br>Muc17.31,<br>Muc17.48,<br>Muc17.49 |
| 378 | QVQLVQSGAEVKKPGASVKVSCKASGYTFTSYWMNWVRQAPGQ<br>GLEWMGMIHPSDSETRLNQKFKDRVTMTVDKSISTAYMELSRLRS<br>DDTAVYYCARQGIITSVQEFAYWGQGTLVTVSSASTKGPSVFPLA<br>PSSKSTSGGTAALGCLVKDYFPEPVTVSWNSGALTSGVHTFPAVL<br>QSSGLYSLSSVVTVPSSSLGTQTYICNVNHKPSNTKVDKRVEPKS<br>CDKTHTCPPCPAPEFEGGPSVFLFPPKPKDTLMISRTPEVTCVVVD<br>VSHEDPEVKFNWYVDGVEVNNAKTKPREEQYNSTYRVVSVLTVL<br>HQDWLNGKEYKCKVSNKALPASIEKTISKAKGQPREPQVCTLPPS<br>RDELTKNQVSLTCLVEGFYPSDIAVEWESNGQPENNYKTTPPVLD<br>SDGSFFLYSDLTVDKSRWQQGNVFSCSVMHEALHNHYTQESLSL<br>SPGK | HC;<br>Muc17.38 |
| 379 | QVQLVQSGAEVKKPGSSVKVSCKASGYEFSSHWMNWVRQAPGQ<br>GLEWMGQIYPGDGDINYNEKFRGRVTITADKSTSTAYMELSSLRS<br>EDTAVYYCARHGNYVMDYWGQGTTVTVSSASTKGPSVFPLAPSS<br>KSTSGGTAALGCLVKDYFPEPVTVSWNSGALTSGVHTFPAVLQSS<br>GLYSLSSVVTVPSSSLGTQTYICNVNHKPSNTKVDKRVEPKSCDKT<br>HTCPPCPAPEFEGGPSVFLFPPKPKDTLMISRTPEVTCVVVDVSHE<br>DPEVKENWYVDGVEVHNAKTKPREEQYNSTYRVVSVLTVLNQDW | HC<br>Muc17.25,<br>Muc17.26,<br>Muc17.27,<br>Muc17,28 |

TABLE 20-continued

| SEQUENCES | |
|---|---|

| Seq ID | sequence | name |
|---|---|---|
| | LNGKEYKCKVSNKALPASIEKTISKAKGQPREPQVCTLPPSRDELT<br>KNQVSLTCLVEGFYPSDIAVEWESNGQPENNYKTTPPVLDSDGSF<br>FLYSDLTVDKSRWQQGNVFSCSVMHEALHNHYTQESLSLSPGK | |
| 380 | QVQLVQSGAEVKKPGSSVKVSCKASGYTFTSYWMNWVRQAPGQ<br>GLEWMGMIHPSDSETRLNQKFKDRVTITADKSTSTAYMELSSLRS<br>EDTAVYYCARQGIITSVQEFAYWGQGTLVTVSSASTKGPSVFPLAP<br>SSKSTSGGTAALGCLVKDYFPEPVTVSWNSGALTSGVHTFPAVLQ<br>SSGLYSLSSVVTVPSSSLGTQTYICNVNHKPSNTKVDKRVEPKSC<br>DKTHTCPPCPAPEFEGGPSVFLAPPKPKDTLMISRTPEVTCVVVDV<br>SHEDPEVKFNWYVDGVEVHNAKTKPREEQYNSTYRVVSVLTVLH<br>QDWLNGKEYKCKVSNKALPASIEKTISKAKGQPREPQVCTLPPSR<br>DELTKNQVSLTCLVEGFYPSDIAVEWESNGQPENNYKTTPPVLDS<br>DGSFFLYSDLTVDKSRWQQGNVFSCSVMHEALHNHYTQESLSLS<br>PGK | HC;<br>Muc17.4,<br>Muc17.15,<br>Muc17.16,<br>Muc17.18,<br>Muc17.19 |
| 381 | DIQMTQSPSSLSASVGDRVTITCKASEDIYNRLAWYQQKPGKAPKL<br>LIYGATNLETGVPSRFSGSGSGKDYTLTISSLQPEDIATYYCQQFW<br>RTPPTFGGGTKVEIKRTVAAPSVFIFPPSDEQLKSGTASVVCLLNN<br>FYPREAKVQWKVDNALQSGNSQESVTEQDSKDSTYSLSSTLTLSK<br>ADYEKHKVYACEVTHQGLSSPVTKSFNRGEC | LC;<br>Muc17,23 |
| 382 | DIQMTQSPSSLSASVGDRVTITCKASEDIYNRLAWYQQKPGKAPKL<br>LIYGATNLETGVPSRFSGSGSGTDFTFTISSLQPEDIATYYCQQFW<br>RTPPTFGGGTKVEIKRTVAAPSVFIFPPSDEQLKSGTASVVCLLNN<br>FYPREAKVQWKVDNALQSGNSQESVTEQDSKDSTYSLSSTLTLSK<br>ADYEKHKVYACEVTHQGLSSPVTKSFNRGEC | LC;<br>Muc17.24 |
| 383 | DIQMTQSPSSLSASVGDRVTITCKASEDIYNRLAWYQQKPGKAPK<br>PLISGATNLETGVPSRFSGSGSGKDYTLTISSLQPEDIATYYCQQF<br>WRTPPTFGGGTKVEIKRTVAAPSVFIFPPSDEQLKSGTASVVCLLN<br>NFYPREAKVQWKVDNALQSGNSQESVTEQDSKDSTYSLSSTLTLS<br>KADYEKHKVYACEVTHQGLSSPVTKSENRGEC | LC;<br>Muc17.21 |
| 384 | DIQMTQSPSSLSASVGDRVTITCKASEDIYNRLAWYQQKPGKAPK<br>PLISGATNLETGVPSRFSGSGSGTDFTFTISSLQPEDIATYYCQQF<br>WRTPPTFGGGTKVEIKRTVAAPSVFIFPPSDEQLKSGTASVVCLLN<br>NFYPREAKVQWKVDNALQSGNSQESVTEQDSKDSTYSLSSTLTLS<br>KADYEKHKVYACEVTHQGLSSPVTKSENRGEC | LC;<br>Muc17.7 |
| 385 | DIQMTQSPSSLSASVGDRVTITCKASEDIYNRLAWYQQKPGKAPK<br>PLIYGATNLETGVPSRFSGSGSGTDFTFTISSLQPEDIATYYCQQF<br>WRTPPTFGGGTKVEIKRTVAARSVFIFRPSDEQLKSGTASVVCLLN<br>NFYPREAKVQWKVDNALQSGNSQESVTEQDSKDSTYSLSSTLTLS<br>KADYEKHKVYACEVTHQGLSSPVTKSFNRGEC | LC;<br>Muc17.22 |
| 386 | EIVLTQSPATLSLSPGERATLSCSASSSVNYIYWYQQKPGQAPRLLI<br>YRTSNLASGIPARFSGSGSGTDFTLTISSLEPEDFAVYYCQQYHSY<br>PLTFGGGTKVEIKRTVAAPSVFIFPPSDEQLKSGTASVVCLLNNFYP<br>REAKVQWKVDNALQSGNSQESVTEQDSKDSTYSLSSTLTLSKAD<br>YEKHKVYACEVTHQGLSSPVTKSFNRGEC | LC;<br>Muc17.16,<br>Muc17.17,<br>Muc17.34,<br>Muc17.39,<br>Muc17.42,<br>Muc17.49 |
| 387 | EIVLTQSPATLSLSPGERATLSCSASSSVSYMFWYQQKPGQAPRL<br>LIYRTSNLASGIRARFSGSGSGTDFTLTISSLEPEDFAVYYCQQFHD<br>YPRTFGGGTKVEIKRTVAAPSVFIFPPSDEQLKSGTASVVCLLNNF<br>YPREAKVQWKVDNALQSGNSQESVTEQDSKDSTYSLSSTLTLSKA<br>DYEKHKVYACEVTHQGLSSPVTKSFNRGEG | LC;<br>Muc17.8.<br>Muc17.27,<br>Muc17.31 |
| 388 | EIVLTQSPATLSLSPGERATLSCSASSSVSYMFWYQQKPGQAPRP<br>WIYRTSNLASGIPPRFSGSGSGTDYTLTISSLEPEDFAVYYCQQFH<br>DYPRTFGGGTKVEIKRTVAAPSVFIFPPSDEQLKSGTASVVCLLNN<br>FYPREAKVQWKVQNALQSGNSQESVTEQDSKDSTYSLSSTLILSK<br>ADYEKHKVYACEVTHQGLSSPVIKSFNRGEC | LC;<br>Muc17.28 |
| 389 | EIVLTQSPATLSVSPGERATLSCSASSSVNYIYWYQQKPGQAPRP<br>WYRTSNLASGIPARFSGSGSGTEYTLTISSLQSEDFAVYYCQQYH<br>SYPLTFGGGTKVEIKRTVAAPSVFIFPPSDEQLKSGTASVVGLLNNF<br>YPREAKVQWKVDNALQSGNSQESVTEQDSKDSTYSLSSTLTLSKA<br>DYEKHKVYACEVTHQGLSSPVTKSFNRGEC | LC;<br>Muc17.20 |

TABLE 20-continued

| | SEQUENCES | |
| --- | --- | --- |
| Seq ID | sequence | name |

| | | |
| --- | --- | --- |
| 390 | EIVMTQSPATLSVSPGERATLSCSASSSVNYIYWYQQKPGQAPRL<br>LIYRTSNLASGIPARFSGSGSGTEFTLTISSLQSEDFAVYYCQQYHS<br>YPLTFGGGTKVEIKRTVAAPSVFIFPPSDEQLKSGTASVVCLLNNFY<br>PREAKVQWKVQNALQSGNSQESVTEQDSKDSTYSLSSTLTLSKA<br>DYEKHKVYACEVTHQGLSSVTKSFNRGEC | LC;<br>Muc17.5,<br>Muc17.15,<br>Muc17.33,<br>Muc17.45,<br>Muc17.48 |
| 391 | EIVMTQSPATLSVSPGERATLSCSASSSVSYMFWYQQKPGQAPRL<br>LIYRTSNLASGIPARFSGSGSGTEFTLTISSLQSEDFAVYYCQQFHD<br>YPRTFGGGTKVEIKRTVAAPSVFIFPPSDEQLKSGTASVVCLLNNF<br>YPREAKVQWKVDNALQSGNSQESVTEQDSKDSTYSLSSTLTLSKA<br>DYEKNKVYACEVTHQGLSSPVTKSENRGEC | LC;<br>Muc17.14,<br>Muc17.26,<br>Muc17.30 |
| 392 | IQLTQSPSFLSASVGDRVTITCSASSSVSYMFWYQQKPGKAPKLLI<br>YRTSNLASGVPPRFSGSGSGTEFTLTISSLQPEDFATYYCQQFHD<br>YPRTFGGGTKVEIKRTVAAPSVFIFPPSDEQLKSGTASVVQLLNNF<br>YPREAKVQWKVDNALQSGNSQESVTEQDSKDSTYSLSSTLTLSKA<br>DYEKHKVYACEVTHQGLSSPVTKSFNRGEC | LC;<br>Muc17.13 |
| 393 | IQLTQSPSFLSASVGDRVTITCSASSSVSYMFWYQQKPGKAPKLLI<br>YRTSNLASGVPPRFSGSGSGTEYTLTISSLQPEDFATYYCQQFHD<br>YPRTFGGGTKVEIKRTVAAPSVFIFPPSDEQLKSGTASVVCLLNNA<br>YPREAKVQWKVDNALQSGNSQESVTEQDSKDSTYSLSSTLTLSKA<br>DYEKHKVYACEVTHQGLSSPVTKSFNRGEC | LC;<br>Muc17.11 |
| 394 | IQLTQSPSFLSASVGDRVTITCSASSSVSYMFWYQQKPGKAPKLLI<br>YRTSNLASGVPSRFSGSGSGTEFTLTISSLQPEDFATYYCQQFHD<br>YPRTFGGGTKVEIKRTVAARSVFIFPPSDEQLKSGTASVVQLLNNF<br>YPREAKVQWKVDNALQSGNSQESVTEQDSKDSTYSLSSTLTLSKA<br>DYEKHKVYACEVTHQGLSSPVTKSFNRGEC | LC:<br>Muc17.9,<br>Muc17.25.<br>Muc17.29 |
| 396 | IQLTQSPSFLSASVGDRVTITCSASSSVSYMFWYQQKPGKAPKLLI<br>YRTSNLASGVPSRFSGSGSGTEYTLTISSLQPEDFATYYCQQFHD<br>YPRTFGGGTKVEIKRTVAAPSVFIFPPSDEQLKSGTASVVQLLNNF<br>YPREAKVQWKVDNALQSGNSQESVTEQDSKDSTYSLSSTLTLSKA<br>DYEKHKVYACEVTHQGLSSPVTKSFNRGEC | LC:<br>Muc17.10 |
| 397 | IQLTQSPSFLSASVGDRVTITCSASSSVSYMFWYQQKPGKAPKPW<br>IYRTSNLASGVPPRFSGSGSGTEYTLTISSLQPEDFATYYCQQPHD<br>YPRTFGGGTKVEIKRTVAAPSVFIFPPSDEQLKSGTASVVCLLNNF<br>YPREAKVQWKVDNALQSGNSQESVTEQDSKDSTYSLSSTLTLSKA<br>DYEKHKVYACEVTHQGLSSPVTKSFNRGEC | LC;<br>Muc17.12 |
| 398 | IQLTQSPSFLSASVGDRVTITCSASSSVSYMFWYQQKPGKAPKPWV<br>IYRTSNLASGVPSRFSGSGSGTEFTLTISSLQPEDFATYYCQQFHD<br>YPRTFGGGTKVEIKRTVAAPSVFIFPPSDEQLKSGTASVVQLLNNF<br>YPREAKVQWKVQNALQSGNSQESVTEQDSKDSTYSLSSTLTLSKÅ<br>DYEKHKVYACEVTHQGLSSPVTKSFNRGEC | LC:<br>Muc17.1 |
| 399 | IQMTQSPSSLSASVGDRVTITCSASSSVNYIYWYQQKPGKAPKLLI<br>YRTSNLASGVPSRFSGSGSGTDATLTISSLQPEDFATYYCQQYHS<br>YPLTFGGGTKVEIKRTVAAPSVFIFPPSDEQLKSGTÅSVVQLLNNFY<br>PREAKVQWKVDNALQSGNSQESVTEQDSKDSTYSLSSTLTLSKA<br>DYEKHKVYACEVTHQGLSSPVTKSFNRGEC | LC;<br>Muc17.4,<br>Muc17.31,<br>Muc17.32,<br>Muc17.35,<br>Muc17.36,<br>Muc17,387,<br>Muc17.38,<br>Muc17.40,<br>Muc17.43,<br>Muc17.47 |
| 400 | QAVVTQEPSLTVSPGGTVTLTCGSSTGAVTTSNYANWWVQQKPGK<br>SPRGLIGGTNKRAPGVPARFSGSLLGGKAALTISGAQPEDEADYY<br>CALWYSNHWVFGGGTKLTVLRTVAAPSVFIFPPSDEQLKSGTASV<br>VCLLNNFYPREAKVQWKVDNALQSGNSQESVTEQDSKDSTYSLS<br>STLTLSKADYEKHKVYACEVTHQGLSSPVTKSENRGEC | LC; CD3 |
| 401 | EVQLVESGGGLVQPGGSLRLSCAASGFTFSSFGMHWVRQAPGK<br>GLEWVAYISSGNSAIYYADTVNGRFTISRDNPKNTLYLQMNSLRAE<br>DTAVYYCARLRYGNSFDYWGQGTLVTVSSASTKGPSVFPLAPSSK<br>STSGGTAALGCLVKDYFPEPVTVSWNSGALTSGVHTFPAVLQSSG<br>LYSLSSVVTVPSSSLGTQTYICNVNHKPSNTKVDKRVEPKSCDKTH<br>TCPPCPAPEFEGGPSVELFPPKPKDTLMISRTPEVTCVVVDVSHED<br>PEVKPNWYVDGVEVHNAKTKPREEQYNSTYRVVSVLTVLHQDWL<br>NGKEYKCKVSNKALPASIEKTISKAKGQPREPQVCTLPPSRDELTK | HC;<br>CLDN182.12<br>CLND182.13 |

TABLE 20-continued

| | SEQUENCES | |
|---|---|---|
| Seq ID | sequence | name |

| | NQVSLTCLVEGFYPSDIAVEWESNGQPENNYKTTPPVLQSDGSFF<br>LYSDLTVDKSRWQQGNVFSCSVMHEALHNHYTQESLSLSPGK | |
| 402 | EVQLVESGGGLVQPGGSLRLSCAASGFTFSSFGMHWRQAPGK<br>GLEWVSYISSGNSAIYYADTVNGRFTISRDNAKNSLYLQMNSLRAE<br>DTAVYYCARLRYGNSFDYWGQGTLVTVSSASTKGPSVFPLAPSSK<br>STSGGTAALGCLVKDYFPEPVTVSWNSGALTSGVHTFPAVLQSSG<br>LYSLSSVVTVPSSSLGTQTYICNVNHKPSNTKVDKRVEPKSCDKTH<br>TCPPCPAPEFEGGPSVFLFPPKPKDTLMISRTPEVTCVVVDVSHED<br>PEVKFNWYVDGVEVHNAKTKPREEQYNSTYRVVSVLTVLHQDWL<br>NGKEYKCKVSNKALPASIEKTISKAKGQPREPQVCTLPPSRDELTK<br>NQVSLTCLVEGFYPSDIAVEWESNGQPENNYKTTPPVLDSDGSFF<br>LYSDLTVDKSRWQQGNVFSCSVMHEALHNHYTQESLSLSPGK | HC<br>CLDN182.3,<br>CLDN182.7 |
| 403 | QIQLVQSGAEVKKPGASVKVSCKASGYTFTNSGMNWVRQAPGQ<br>GLEWMGWINTNTGEPTFAEEFRGRVTFTLQTSASTAYMELSRLRS<br>DDTAVYYCARYYYGNSFAYWGQGTLVTVSSASTKGPSVFPLAPS<br>SKSTSGGTAALGCLVKDYPPEPVTVSWNSGALTSGVHTFPAVLQS<br>SGLYSLSSVVTVPSSSLGTQTYIGNVNHKPSNTKVDKRVEPKSCD<br>KTHTCPPCPAPEFEGGPSVFLFPPKPKDTLMISRTPEVTCVVVDVS<br>HEDPEVKFNWYVDGVEVHNAKTKPREEQYNSTYRVVSVLTVLHQ<br>DWLNGKEYKCKVSNKALPASIEKTISKAKGQPREPQVCTLPPSRD<br>ELTKNQVSLTCLVEGFYPSDIAVEWESNGQPENNYKTTPPVLDSD<br>GSFFLYSDLTVDKSRWQQGNVFSCSVMHEALHNHYTQESLSLSP<br>GK | HC;<br>CLDN182.14 |
| 404 | QVQLVQSGAEVKKPGASVKVSCKASGYTFTNFGITWVRQAPGQG<br>LEWIGETYPSSGNTFYNEKFKGRVTLTADKSSSAAYMELRSLRSCD<br>TAVYYCARGGGPLRSRYFDYWGQGTLVTVSSASTKGRSVFPLAP<br>SSKSTSGGTAALGCLVKDYPPEPVTVSWNSGALTSGVHTFPAVLQ<br>SSGLYSLSSVVTVPSSSLGTQTYICNVNHKPSNTKVDKRVEPKSC<br>DKTHTCPPCPAPEFEGGPSVFLFPPKPKDTLMISRTPEVTCVVVDV<br>SHEDPEVKFNWYVDGVEVHNAKTKPREEQYNSTYRVVSVLTVLH<br>QDWLNGKEYKCKVSNKALPASIEKTISKAKGQPREPQVCTLPPSR<br>DELTKNQVSLTCLVEGFYPSDIAVEWESNGQPENNYKTTPPVLDS<br>DGSFFLYSDLTVDKSRWQQGNVFSCSVMHEALHNHYTQESLSLS<br>PGK | HC;<br>CLDN182.10,<br>CLND182.11 |
| 405 | QVQLVQSGAEVKKPGASVKVSCKASGYTFTNFGITWVRQAPGQG<br>LEWMGEIYPSSQNTFYNEKFKGRVTMTTDTSTSTAYMELRSLRSD<br>DTAVYYCARGGGPLRSRYFDYWGQGTLVTVSSASTKGPSVEPLA<br>PSSKSTSGGTAALGCLVKDYPPEPVTVSWNSGALTSGVHTFPAVL<br>QSSGLYSLSSVVTVPSSSLGTQTYICNVNHKPSNTKVDKRVEPKS<br>CDKTHTCPPCPAPEFEGGPSVFLFPPKPKDTLMISRTPEVTCVVVD<br>VSHEDPEVKPNWYVDGVEVHNAKTKPREFQYNSTYRVVSVLTVL<br>HQDWLNGKEYKCKVSNKALPASIEKTISKAKGQPREPQVCTLPPS<br>RDELTKNQVSLTCLVEGFYPSDIAVEWESNGQPENNYKTTPPVLD<br>SDGSFFLYSDLTVDKSRWQQGNVFSCSVMHEALHNHYTQESLSL<br>SPGK | HC;<br>CLDN182.4,<br>CLND182.8 |
| 406 | QVQLVQSGAFVKKPGASVKVSCKASGYTFTNSGMNWVRQAPGQ<br>GLEWMGWINTNTGERTFAEEFRGRVTMTRDTSISTAYMELSRLRS<br>DDTAVYYCARYYYGNSFAYWGQGTLVTVSSASTKGPSVFPLAPS<br>SKSTSGGTAALGCLVKDYFPERVTVSWNSGALTSGVHTFPAVLQS<br>SGLYSLSSVVTVPSSSLGTQTYICNVNHKPSNTKVDKRVEPKSCD<br>KTHTCPPCPAPEFEGGPSVFLFPPKPKDTLMISRTPEVTCVVVDVS<br>HEDPEVKFNWYVDGVEVHNAKTKPREEQYNSTYRVVSVLTVLHQ<br>DWLNGKEYKCKVSNKALPASIEKTISKAKGQPREPQVCTLPPSRD<br>ELTKNQVSLTCLVEGFYPSDIAVEWESNGQPENNYKTTPPVLDSD<br>CSFFLYSDLTVDKSRWQQGNVFSCSVMHEALHNHYTQESLSLSP<br>GK | HC;<br>CLND182.2,<br>CLND182.17 |
| 407 | QVQLVQSGAFVKKPGASVKVSCKASGYTFTNYGMNWVRQAPGQ<br>GLEWMGWINTNTGEPTYAEEFKGRVTMTRDTSISTAYMELSRLRS<br>DDTAVYYCARYFYGNSFVYWGQGTLVTVSSASTKGPSVFPLAPSS<br>KSTSGGTAALGCLVKDYFPEPVTVSWNSGALTSGVHTFPAVLQSS<br>GLYSLSSVVTVPSSSIGTQTYICNVNHKPSNTKVDKRVEPKSCDKT<br>HTCPPCPAPEFEGGPSVFLFPPKPKDTLMISRTPEVTCVVVDVSHE<br>DPEVKFNWYVDGVEVHNAKTKPREEQYNSTYRVVSVLTVLHQDW<br>LNGKEYKCKVSNKALPASIEKTISKAKGQPREPQVCTLPPSRDELT<br>KNQVSLTCLVEGFYPSDIAVEWESNGQPENNYKTTPPVLDSDGSF<br>FLYSDLIVQKSRWQQGNVFSCSVMHEALHNHYTQESLSLSPGK | HC;<br>CLDN182.1 |
| 408 | QVQLVQSGAEVKKPGSSVKVSCKASGYAFNNYWMNWVRQAPGQ<br>GLEWMGQISPGNGNSNFNGKFKGRVTITADKSTSTAYMELSSLRS<br>EDTAVYYCARGGRYGNAMDYWGQGTTVTVSSASTKGPSVFPLAP | HC;<br>CLND182.5 |

TABLE 20-continued

| | SEQUENCES | |
| --- | --- | --- |
| Seq ID | sequence | name |

| | | |
| --- | --- | --- |
| | SSKSTSGGTAALGCLVKDYFPEPVTVSWNSGALTSGVHTFPAVLQ<br>SSGLYSLSSVVTVPSSSLGTQTYICNVNHKPSNTKVDKRVEPKSC<br>DKTHTCPPCPAPEFEGGPSVFLFPPKPKDTLMISRTPEVTCVVVDV<br>SHEDPEVKFNWYVDGVEVHNAKTKPREEQYNSTYRVVSVLTVLH<br>QDWLNGKEYKCKVSNKALPASIEKTISKAKGQPREPQVCTLPPSR<br>DELTKNQVSLTCLVEGFYPSDIAVEWESNGQPENNYKTTPPVLDS<br>DGSFFLYSDLTVDKSRWQQGNVFSCSVMHEALHNHYTQESLSLS<br>PGK | |
| 409 | QVQLVQSGAEVKKPGSSVKVSCKASGYAFSSYWMNWVRQAPGQ<br>GLEWIGQIYPGNGNSNFNGKFKARVTLTADKSSSTAYMELSSLRS<br>EDTAVYYCARGGRFGNAMDYWGQGTTVTVSSASTKGPSVFPLAP<br>SSKSTSGGTAALGCLVKDYFPEPVTVSWNSGALTSGVHTFPAVLQ<br>SSGLYSLSSVVTVPSSSLGTQTYICNVNHKPSNTKVQKRVEPKSG<br>DKTHTCPPCPAPEREGGPSVFLFPPKPKDTLMISRTPEVTCVVVDV<br>SHEDPEVKFNWYVDGVEVHNAKTKPREEQYNSTYRVVSVLTVLH<br>QDWLNGKEYKCKVSNKALPASIEKTISKAKGQPREPQVCTLPPSR<br>DELTKNQVSLTCLVEGFYPSDIAVEWESNGQPENNYKTTPPVLDS<br>DGSFFLYSDLTVDKSRWQQGNVFSCSVMHEALHNHYTQESLSLS<br>PGK | HC;<br>CLND182.15,<br>CLND182.16 |
| 410 | QVQLVQSGAEVKKPGSSVKVSCKASGYAFSSYWMNWWRQAPGQ<br>GLEWMGQIYPGNGNSNFNGKFKARVTITADKSTSTAYMELSSLRS<br>EDTAVYYCARGGRFGNAMDYWGQGTTVTVSSASTKGPSVFPLAP<br>SSKSTSGGTAALGCLVKDYFPEPVTVSWNSGALTSGVHTFPAVLQ<br>SSGLYSLSSVVTVPSSSLGTQTYICNVNHKPSNTKVDKRVEPKSC<br>DKTHTCPPCPAPEFEGGPSVFLFPPKPKDTLMISRTPEVTCVVVDV<br>SHEDPEVKFNWYVDGVEVHNAKTKPREEQYNSTYRVVSVLTVLH<br>QDWLNGKEYKCKVSNKALPASIEKTISKAKGQPREPQVCTLPPSR<br>DELTKNQVSLTCLVEGFYPSDIAVEWESNGQPENNYKTTPPVLDS<br>DGSFFLYSDLTVDKSRWQQGNVFSCSVMHEALHNHYTQESLSLS<br>PGK | HC;<br>CLDN182.6,<br>CLDN182.9 |
| 411 | DIVMTQSPDSLAVSLGERATINCKSSQSLLNSGNQKNYLTWYQQK<br>PGQPPKLLIFWASTRESGVPDRFSGSGSGTDFTLTISSLQAEDVAV<br>YYCQNNYYYPLTFGGGTKVEIKRTVAAPSVFIFPPSDEQLKSGTAS<br>VVCLLNNFYPREAKVQWKVDNALQSGNSQESVTEQDSKDSTYSL<br>SSTLTLSKADYEKHKVYACEVTHQGLSSPVTKSFNRGEC | LC;<br>CLND182.7,<br>CLND182.13 |
| 412 | DIVMTQSPDSLAVSLGERATINCKSSQSLLNSGNQKNYLTWYQQK<br>PGQPPKLLIYWASTRESGVPDRFSGSGSGTDFTLTISSLQAEDVAV<br>YYCQNAYFYPYTFGGGTKVEIKRTVAAPSVFIFPPSDEQLKSGTAS<br>VVCLLNNFYPREAKVQWKVDNALQSGNSQESVTEQDSKDSTYSL<br>SSTLTLSKADYEKHKVYACEVTHQGLSSPVTKSFNRGEC | LC;<br>CLDN182.6,<br>CLND182.15 |
| 413 | DIVMTQSPDSLAVSLGERATINCKSSQSLLNSGNQKNYLTWYQQK<br>PGQPPKLLIYWASTRESGVPDRFSGSGSGTDFTLTISSLQAEDVAV<br>YYCQNNYFYPLTFGGGTKVEIKRTVAAPSVFIFPPSDEQLKSGTAS<br>VVCLLNNFYPREAKVQWKVDNALQSGNSQESVTEQDSKDSTYSL<br>SSTLTLSKADYEKHKVYACEVTHQGLSSPVTKSFNRGEC | LC;<br>CLDN182.2,<br>CLDN182.14,<br>GUND182.17 |
| 414 | DIVMTQSPDSLAVSLGERATINCKSSQSLLNSGNQKNYLTWYQQK<br>PGQPPKLLIYWASTRESGVPDRFSGSGSGTDFTLTISSLQAEDVAV<br>YYCQNNYNFPLTFGGGTKVEIKRTVAAPSVFIFPPSDEQLKSGTAS<br>VVCLLNNFYPREAKVQWKVDNALQSGNSQESVTEQDSKDSTYSL<br>SSTLTLSKADYEKHKVYAGEVTHQGLSSPVTKSFNRGEC | LC;<br>CLND182.1 |
| 415 | DIVMTQSPDSLAVSLGERATINCKSSQSLLNSGNQKNYLTWYQQK<br>PGQPPKLLIYWASTRESGVPDRFSGSGSGTDFTLTISSLQAEDVAV<br>YYCQNNYYYPLTFGGGTKVEIKRTVAAPSVFIFPPSDEQLKSGTAS<br>VVCLLNNFYPREAKVQWKVQNALQSGNSQESVTEQDSKDSTYSL<br>SSTLTLSKADYEKHKVYACEVTHQGLSSPVTKSFNRGEC | LC;<br>CLDN182.3,<br>CLDN182.12 |
| 416 | DIVMTQSPDSLAVSLGERATINCKSSQSLLNSGNQRNYLTWYQQK<br>PGQPPKLLIYWASTRESGVPDRFSGSGSGTDFTLTISSLQAEDVAV<br>YYCQNAYFYPYTFGGGTKVEIKRTVAAPSVFIFPPSDEQLKSGTAS<br>VVCLLNNFYPREAKVQWKVDNALQSGNSQESVTEQDSKDSTYSL<br>SSTLTLSKADYEKHKVYACEVTHQGLSSPVTKSFNRGEC | LC;<br>CLND182.5 |
| 417 | DIVMTQSPDSLAVSLGERATINGRSSQSLFSSGNQKNYLTWYQQK<br>PGQPPKLLIYWASTRESGVPDRFSGSGSGADFTLTISSLQAEDVAV<br>YYCQNDYYYPLTFGGGTKVEIKRTVAAPSVFIFPPSDEQLKSGTAS<br>VVCLLNNFYPREAKVQWKVDNALQSGNSQESVTEQDSKDSTYSL<br>SSTLTLSKADYEKHKVYACEVTHQGLSSPVTKSENRGEC | LC;<br>CLDN182.8,<br>CLND182.11 |

TABLE 20-continued

| Seq ID | sequence | name |
|--------|----------|------|
| 418 | DIVMTQSPDSLAVSLGERATINGRSSQSLFSSGNQKNYLTWYQQK PGQPPKLLIYWASTRESGVPDRFSGSGSGTDFTLTISSLQAEDVAV YYCQNDYYYPLTFGGGTKVEIKRTVAAPSVFIFPPSDEQLKSGTAS VVCLLNNFYPREAKVQWKVQNALQSGNSQESVTEQDSKDSTYSL SSTLTLSKADYEKHKVYACEVTHQGLSSPVTKSFNRGEC | LC; CLND812.4, CLND182.10 |
| 419 | DIVMTQSPDSLAVSLGERATMNCKSSQSLLNSGNQKNYLTWYQQ KPGQPPKLLIYWASTRESGVPDRFSGSGSGTDFTLTISSLQAEDVA VYYCQNAYFYPYTFGGGTKVEIKRTVAAPSVFIFPPSDEQLKSGTA SVVCLLNNFYPREAKVQWKVDNALQSGNSQESVTEQDSKDSTYS LSSTLTLSKADYEKHKVYACEVTHQGLSSPVTKSFNRGEC | LC; CLND182.9, CLND182.16 |
| 420 | QVQLVQSGAEVKKPGASVKVSCKASGYTFTSYYIHWVRQAPGQG LEWIGCIYPGNVNTNYNEKFKDRATLTVDTSISTAYMELSRLRSDD TAVYFCTRSHYGLQWNFDVWGQGTTVTVSS | VH; CD28 |
| 421 | QVQLVQSGAEVKKPGASVKVSCKASGYTFTSYYIHWVRQAPGQG LEWIGSIYPGNVNTNYNEKFKDRATLTVDTSISTAYMELSRLRSDD TAVYFCTRSHYGLDWNFDVWGQGTTVTVSS | VH; CD28 (C50S) |
| 422 | QVQLVQSGAEVKKRGASVKVSCKASGYTFTSYYIHWVRQAPGQG LEWIGAIYPGNVNTNYNEKFKDRATLTVQTSISTAYMELSRLRSDD TAVYFCTRSHYGLDWNFDVWGQGTTVTVSS | VH; CD28 (C50A) |
| 423 | QVQLVQSGAEVKKPGASVKVSCKASGYTFTSYYIHWVRQAPGQG LEWIGGIYPGNVNTNYNEKFKDRATLTVDTSISTAYMELSRLRSDD TAVYFCTRSHYGLQWNFDVWGQGTTVTVSS | VH; CD28 (C50G) |
| 424 | DIQMTQSPSSLSASVGDRVTITCHASQNIYVWLNWYQQKPGKAPK LLIYKASNLHTGVPSRFSGSGSGTDFTLTISSLQPEDFATYYCQQG QTYPYTFGGGTKVEIK | VL CD28 |
| 425 | QVQLVQSGAEVKKPGASVKVSCKASGYTFTSYYIHWVRQAPGQG LEWIGCIYPGNVNTNYNEKFKDRATLTVDTSISTAYMELSRLRSDD TAVYFCTRSHYGLQWNFDVWGQGTTVTVSSASTKGPSVFPLARS SKSTSGGTAALGCLVKDYFPEPVTVSWNSGALTSGVHTFPAVLQS SGLYSLSSVVTVPSSSLGTQTYICNVNHKPSNTKVDKRVERKSCD KTHTCPPCPAPEFEGGPSVFLFPPKPKDTLMISRTPEVTCVVVDVS HEDPEVKFNWYVDGVEVHNAKTKPREFQYNSTYRVVSVLTVLHQ DWLNGKEYKCKVSNKALPASIEKTISKAKGQPREPQVCTLPPSRD ELTKNQVSLTCLVEGFYPSDIAVEWESNGQPENNYKITPPVLQSD GSFFLYSDLTVDKSRWQQGNVFSCSVMHEALHNHYTQESLSLSP GK | HC; CD28 |
| 426 | DIQMTQSPSSLSASVGDRVTITCHASQNIYVWLNWYQQKRGKAPK LUYKASNIHTGVPSRFSGSGSGTDFTLTISSLQPEDFATYYCQQG QTYPYTFGGGTKVEIKRTVAAPSVFIFPPSDEQLKSGTASVVCLLN NFYPREAKVQWKVDNALQSGNSQESVTEQDSKDSTYSLSSTLTLS KADYEKHKVYACEVTHQGLSSPVTKSFNRGEC | LC; CD28 |
| 427 | QVQLVQSGAEVKKPGASVKVSCKASGYTFTSYYIHWVRQAPGQG LEWIGCIYPGNVNTNYNEKFKDRATLTVDTSISTAYMELSRLRSDD TAVYFCTRSHYGLQWNFDVWGQGTTVTVSSGKPGSGKPGSGKP GSGKPGSDIQMTQSPSSLSASVGDRVTITCHASQNIYVWLNWYQ QKPGKAPKLLIYKASNLHTGVPSRFSGSGSGTDFTLTISSLQPEDF ATYYCQQGQTYPYTFGGGTKVEIKEPKSSDKTHTCPPCPAPEFEG GPSVFLFPPKPKDTLMISRTPEVTCVVVDVSHEDPEVKFNWYVDG VEVHNAKTKPREEQYNSTYRVVSVLTVLHQDWLNGKEYKCKVSN KALPASIEKTISKAKGQPREPQVYTLPPCRKKLTKNQVSLTCLVKG FYPSDIAVEWESNGQPENNYKTTPPVLKSDGSFFLYSKLTVDKSR WQQGNVFSCSVMHEALHNHYTQKSLSLSPGK | CD28 Scfv-Fc |
| 428 | QVQLVQSGAFVKKPGASVKVSCKASGYTFTSYYIHWRQAPGQG LEWIGGIYPGNVNTNYNEKFKDRATLTVDTSISTAYMELSRLRSDD TAVYFCTRSHYGLQWNFDVWGQGTTVTVSSGKPGSGKPGSGKP GSGKPCSDIQMTQSPSSLSASVGDRVTITCHASQNIYVWLNWYQ QKPGKAPKLLIYKASNLHTGVPSRFSGSGSGTDFTLTISSLQPEDF ATYYCQQGQTYPYTFGGGTKVEIKERKSSDKTHTCPPCPAPEFEG GPSVFLFPPKPKDTLMISRTPEVTCVVVDVSHEDPEVKFNWYVDG VEVHNAKTKPREEQYNSTYRVVSVLTVLHQDWLNGKEYKCKVSN KALPASIEKTISKAKGQPREPQVYTLPPCRKKLTKNQVSLTCLVKG FYPSDIAVEWESNGQPENNYKTTPPVLKSDGSFFLYSKLTVDKSR WQQGNVFSCSVMHEALHNHYTQKSLSLSPGK | CD28 (C50G) Scfv-Fc |

TABLE 20-continued

SEQUENCES

| Seq ID | sequence | name |
|---|---|---|
| 429 | QVQLVQSGAEVKKPGASVKVSCKASGYTFTSYYIHWVRQAPGQG<br>LEWIGAIYPGNVNTNYNEKFKDRATLTVDTSISTAYMELSRLSDD<br>TAVYFCTRSHYGLQWNFDVWGQGTTVTVSSGKPGSGKPGSGKP<br>GSGKPGSDIQMTQSPSSLSASVGDRVTITCHASQNIYVWLNWYQ<br>QKPGKAPKLLIYKASNLHTGVPSRFSGSGSGTDFTLTISSLQPEDA<br>ATYYCQQGQTYPYTFGGGTKVEIKEPKSSDKTHTCPPCPAPEFEG<br>GPSVFLFPPKPKDTLMISRTPEVTCVWVDVSHEDPEVKFNWYVDG<br>VEVHNAKTKPREEQYNSTYRVVSVLTVLHQDWLNGKEYKCKVSN<br>KALPASIEKTISKAKGQPREPQVYTLPPCRKKLTKNQVSLTCLVKG<br>FYPSDIAVEWESNGQPENNYKTTPPVLKSDGSFFLYSKLTVDKSR<br>WQQGNVFSCSVMHEALHNHYTQKSLSLSPGK | CD28<br>(C50A) scfv-<br>Fc |
| 430 | QVQLVQSGAEVKKPGASVKVSCKASGYTFTSYYIHWVRQAPGQG<br>LEWIGSIYPGNVNTNYNEKFKDRATLTVDTSISTAYMELSRLSDD<br>TAVYFCTRSHYGLDWNFDVWGQGTTVTVSSGKPGSGKPGSGKP<br>GSGKPGSDIQMTQSPSSLSASVGDRVTITCHASQNIYVWLNWYQ<br>QKPGKAPKLLIYKASNLHTGVPSRFSGSGSGTDFTITISSLQPEDF<br>ATYYCQQGQTYPYTFGGGTKVEIKERKSSDKTHTCPPCPAPEFEG<br>GPSVFLFPPKPKDTLMISRTPEVTCVVVDVSHEDPEVKENWYVDG<br>VEVHNAKTKPREEQYNSTYRVVSVILTVLHQDWLNGKEYKCKVSN<br>KALPASIEKTISKAKGQPREPQVYTLPPCRKKLTKNQVSLTCLVKG<br>FYPSDIAVEWESNGQPENNYKTTPPVLKSDGSFFLYSKLTVDKSR<br>WQQGNVFSCSVMHEALHNHYTQKSLSLSPGK | CD28<br>(C50S)<br>scfv-Fc |
| 431 | QVQLVQSGAEVKKPGASVKVSCKASDYTFSNYYIEWVRQAPGQG<br>LEWMGEILPGNGNTVYNEKFKDRVTMTVDTSTSTAYMELRSLRSD<br>DTAVYYCARWGDYALFANWGQGTLVTVSSGGGGGGGGSGGG<br>GSDIQMTQSPSTLSASVGDRVTITCKASQNVGTNVAWYQQKPGK<br>APKALIYSASYRYSGVPSRFSGSGSGTEFTLTISSLQPDDFATYYC<br>QQYNSYPFTFGQGTKLEIKERKSSDKTHTCPPCPAPEFEGGPSVF<br>LFPPKPKDTLMISRTPEVTCVVVDVSHEDPEVKFNWYVDGVEVHN<br>AKTKPREEQYNSTYRVVSVLTVLHQDWLNGKEYKCKVSNKALPAS<br>IEKTISKAKGQPREPQVYTLPPCRKKLTKNQVSLTCLVKGFYPSDIA<br>VEWESNGQPENNYKTTPPVLKSDGSFFLYSKLTVDKSRWQQGNV<br>FSCSVMHEALNNHYTQKSLSLSPGK | DLL3scfv-<br>Fc |
| 432 | QVQLVQSGAEVKKPGASVKVSCKASGYTFTDYFMNWVRQAPGQ<br>GLEWMGVINPYNDITIYNQKFQGRVTMTVQRSTSTVYMELSSLRS<br>EDTAVYYCAREGVLYDGYYEGAYWGQGTLVTVSSGGGGSGGGG<br>SGGGGSDIQLTQSPSFLSASVGDRVTITCKASQNVGIAVAWYQQK<br>PGKAPKLLIYAASNRYTGVPSRFSGSGSGTEFTLTISSLQPEDFAT<br>YYCQQYSTYPYTFGQGTKLEIKERKSSDKTHTCPPCPAPEFEGGP<br>SVFLAPPKPKDTLMISRTPEVTCVVVDVSHEDPEVKFNWYVDGVE<br>VHNAKTKPREEQYNSTYRVVSVLTVLHQDWLNGKEYKCKVSNKA<br>LPASIEKTISKAKGQPREPQVYTLPPCRKKLTKNQVSLTCLVKGFY<br>PSDIAVEWESNGQPENNYKTTPPVLKSDGSFFLYSKLTVQKSRWQ<br>QGNVFSCSVMHEALHNHYTQKSLSLSPGK | DLL3scfv-<br>Fc |
| 433 | QVQLVQSGAEVKKPGASVKVSCKATDYIFSNYYIEWVRQAPGQGL<br>EWMGEILPGTGNTVYNEKFKDRVTMTVDTSTSTVYMELSSLRSED<br>TAVYYCARWGDYALFANWGQGTLVTVSSGGGGGGGGSGGGG<br>SDIQMTQSPSFLSASVGDRVTITCKASQNVGTNVAWYQQKGKAP<br>KPLYSTSYRYSGVPSRFSGSGSGTEFTLTISSLQPEDFATYYCQQ<br>YNNYPLTFGGGTKVEIKERKSSDKTHTCPPCPAPEFEGGPSVFLFR<br>PKPKDTLMISRTPEVTCVVVDVSHEDPEVKFNWYVDGVEVHNAKT<br>KPREEQYNSTYRVVSVLTVLHQDWLNGKEYKCKVSNKALPASIEK<br>TISKAKGQPREPQVYTLPPCRKKLTKNQVSLTCLVKGFYPSDIAVE<br>WESNGQPENNYKTTPPVLKSDGSFFLYSKLTVDKSRWQQGNVFS<br>CSVMMEALMNMYTQKSLSLSPGK | DLL3scfv-<br>Fc |
| 434 | QVQLVQSGAEVKKPGASVKVSCKATDYIFSNYYIEWWVRQAPGQGL<br>EWMGEILPGTGNTVYNEKFKDRVTMTVDTSTSTVYMELSSLRSED<br>TAVYYCARWGDYALFANWGQGTLVTVSSGGGGGGGGGSGGGG<br>SDIQMTQSPSTLSASVGDRVTITCKASQNVGTNVAWYQQKPGKAP<br>KALIYSASYRYSGVPSRFSGSGSGTEFTLTISSLQPDDFATYYCQQ<br>YNSYPFTFGQGTKLEIKEPKSSDKTHTCFPCPAPEFEGGPSVFLFP<br>PKPKDTLMISRTPEVTCVVVDVSHEDPEVKFNWYVDGVEVHNAKT<br>KPREEQYNSTYRVVSVLTVLHQDWLNGKEYKCKVSNKALPASIEK<br>TISKAKGQPREPQVYTLPPCRKKLTKNQVSLTCLVKGFYPSDIAVE<br>WESNGQPENNYKTTPPVLKSDGSFFLYSKLTVDKSRWQQGNVFS<br>CSVMHEALHNMYTQKSLSLSPGK | DLL3scfV-<br>Fc |
| 435 | QVQLVQSGAEVKKPGASVKVSCKASGYTFTSYYIHWVRQAPGQC<br>LEWIGSIYPGNVNTNYNEKFKDRATLTVDTSISTAYMELSRLSDD<br>TAVYFCTRSHYGLQWNFDVWGQGTTVTVSSGKPGSGKPGSGKP | CD28<br>(C50S)<br>Scfv(CC)-Fc |

TABLE 20-continued

| | SEQUENCES | |
| --- | --- | --- |
| Seq ID | sequence | name |

| | | |
| --- | --- | --- |
| | GSGKPGSDIQMTQSPSSLSASVGDRVTITCHASQNIYVWLNWYQ<br>QKPGKAPKLLIYKASNLHTGVPSRFSGSGSGTDFTLTISSLQPEDF<br>ATYYCQQGQTYPYTFGCGTKVEIKERKSSDKTHTCPPCPAPEFEG<br>GPSVFLFPPKPKDTLMISRTPEVTCVVVDVSHEDPEVKFNWYVDG<br>VEVHNAKTKPREEQYNSTYRVVSVLTVLHQDWLNGKEYKCKVSN<br>KALPASIEKTISKAKGQPREPQVYTLPPCRKKLTKNQVSLTCLVKG<br>FYPSDIAVEWESNGQPENNYKTTPPVLKSDGSFFLYSKLTVDKSR<br>WQQGNVFSCSVMHEALHNHYTQKSLSLSPGK | |
| 436 | QVQLVQSGAEVKKPGASVKVSCKASGYTFTSYYIHWVRQAPGQG<br>LEWIGSIYPGNVNTNYNEKFKDRATLTVDTSISTAYMELSRLRSDD<br>TAVYFCTRSHYGLQWNFDVWGQGTTVTVSSGGGGGGGGGSGG<br>GGSGGGGSDIQMTQSPSSLSASVGDRVTITCHASQNIYVWLNWY<br>QQKPGKAPKLLIYKASNLHTGVPSRFSGSGSGTDFTLTISSLQPED<br>FATYYCQQGQTYPYTFGGGTKVEIKERKSSDKTHTCPPCPAREFE<br>GGPSVFLPPPKPKDTLMISRTPEVTGVVVDVSHEDPEVKPNWYVD<br>GVEVHNAKTKPREEQYNSTYRVVSVLTVLNQDWINGKEYKCKVS<br>NKALPASIEKTISKAKGQPREPQVYTLPPCRKKLTKNQVSLTCLVK<br>GFYPSDIAVEWESNGQPENNYKTTPPVLKSDGSFFLYSKLTVDKS<br>RWQQGNVFSCSVMHEALHNHYTQKSLSLSPGK | CD28<br>(C50S)<br>Scfv(G4S)-<br>Fc |
| 437 | QVQLQQWGAGLLKPSETLSLTCAVYGGSFSGYYWSWIRQSPEKG<br>LEWIGEINHGGYVTYNPSLESRVTISVDTSKNQFSLKLSSVTAADTA<br>VYYCARDYGPGNYDWYFDLWGRGTLVTVSSASTKGPSVFPLAPS<br>SKSTSGGTAALGCLVKDYFPEPVTVSWNSGALTSGVHTFPAVLQS<br>SGLYSLSSVVTVPSSSIGTQTYICNVNHKPSNTKVDKRVEPKSCD<br>KTHTCPPCPAPEFEGGPSVFLFPPKPKDTLMISRTPEVTCVVVDVS<br>HEDPEVKFNWYVDGVEVHNAKTKPREEQYNSTYRVVSVLTVLHQ<br>DWLNGKEYKCKVSNKALPASIEKTISKAKGQPREPQVCTLPPSRD<br>ELTKNQVSLTCLVEGFYPSDIAVEWESNGQPENNYKTTPPVLDSD<br>GSFFLYSDLTVDKSRWQQGNVFSCSVMHEALHNHYTQESLSLSP<br>GK | HC;<br>CD137.U |
| 438 | EIVLTQSPATLSLSPGERATLSCRASQSVSSYLAWYQQKPGQAPR<br>LUIYDASNRATGIPARFSGSGSGTDFTLTISSLEPEDFAVYYCQQRS<br>NWPPALTFGGGTKVEIKRTVAAPSVFIFPPSDEQLKSGTASVVCLL<br>NNFYPREAKVQWKVDNALQSGNSQESVTEQDSKDSTYSLSSTLT<br>LSKADYEKHKVYACEVTHQGLSSPVTKSFNRGEC | LC;<br>CD137.U |
| 439 | QVQLVQSGAEVKKPGASVKVSCKASGYTESSYWMHWVRQAPGQ<br>RLEWMGEINPGNGHTNYSQKFQGRVTITVDKSASTAYMELSSLRS<br>EDTAVYYCARSFTTARAFAYWGQGTLVTVSSASTKGPSVFPLAPS<br>SKSTSGGTAALGCLVKDYFPEPVTVSWNSGALTSGVHTFPAVLQS<br>SGLYSLSSVVTVPSSSIGTQTYICNVNHKPSNTKVQKRVEPKSCD<br>KTHTCPPCPAPEFEGGPSVFLFPPKPKDTLMISRTPEVTGVVVDVS<br>HEDPEVKFNWYVDGVEVHNAKTKPREEQYNSTYRVVSVLTVLHQ<br>DWLNGKEYKCKVSNKALPASIEKTISKAKGQPREPQVCTLPPSRD<br>ELTKNQVSLTGLVEGFYPSDIAVEWESNGQPENNYKTTPPVLDSD<br>GSFFLYSDLTVDKSRWQQGNVFSCSVMHEALHNHYTQESLSLSP | HC;<br>CD137.B |
| 440 | DIVMTQSPPTLSLSPGERVTLSCRASQSISDYLHWYQQKPGQSPR<br>LUKYASQSISGIPARFSGSGSGTDFTLTISSLEPEDFAVYYCQDGH<br>SFPPPTFGGGTKVEIKRTVAAPSVFIFPPSDEQLKSGTASVVQLLNN<br>FYPREAKVQWKVDNALQSGNSQESVTEQDSKDSTYSLSSTLTLSK<br>ADYEKHKVYACEVTHQGLSSPVTKSFNRGEC | LC;<br>CD137.B |
| 441 | QVQLQQWGAGLLKPSETLSLTCAVYGGSFSGYYWSWIRQSPEKG<br>LEWIGEINHGGYVTYNPSLESRVTISVDTSKNQFSLKLSSVTAADTA<br>VYYCARDYGPGNYDWYFDLWGRGTLVTVSSGGKPGSGKPGSGKP<br>SGKPGSEIVLTQSPATLSLSPGERATLSCRASQSVSSYLAWYQQ<br>KPGQAPRLLIYDASNRATGIPARFSGSGSGTDFTLTISSLEPEDFAV<br>YYCQQRSNWPPALTFGGGTKVEIKEPKSSDKTHTCPPCPAPEFEG<br>GPSVFLFPPKPKDTLMISRTPEVTCVVVDVSHEDPEVKFNWYVDG<br>VEVHNAKTKPREEQYNSTYRVVSVLTVLHQDWLNGKEYKCKVSN<br>KALPASIEKTISKAKGQPREPQVYTLPPCRKKLTKNQVSLTCLVKG<br>FYPSDIAVEWESNGQPENNYKTTPPVLKSDGSFFLYSKLTVDKSR<br>WQQGNVFSCSVMHEALHNHYTQKSLSLSPGK | CD137.U<br>scfv(CL)-Fc |
| 442 | QVQLQQWGAGLLKPSETLSLTCAVYGGSFSGYYWSWIRQSPEKG<br>LEWIGEINHGGYVTYNPSLESRVTISVDTSKNQFSLKLSSVTAADTA<br>VYYCARDYGPGNYDWYFDLWGRGTLVTVSSGGGGGGGGGGGGG<br>GGSEIVLTQSPATLSLSPGERATLSCRASQSVSSYLAWYQQKPGQ<br>APRLLIYDASNRATGIPARFSGSGSGTDFTLTISSLEPEDFAVYYCQ<br>QRSNWPPALTFGGGTKVEIKREPKSSDKTHTCPPCPAPEFEGGPS<br>VFLFPPKPKDTLMISRTPEVTCVVVDVSHEDPEVKFNWYVDGVEV<br>HNAKTKPREEQYNSTYRVVSVLTVLHQDWINGKEYKCKVSNKAL | CD137.U<br>scfv(G4S)-<br>Fc |

TABLE 20-continued

| SEQUENCES | | |
|---|---|---|
| Seq ID sequence | | name |

PASIEKTISKAKGQPREPQVYTLPPCRKKLTKNQVSLTCLVKGFYP
SDIAVEWESNGQPENNYKITPPVLKSDGSFFLYSKLTVQK
GNVFSCSVMHEALHNHYTQKSLSLSPGK

443 QVQLQQWGAGLLKPSETLSLTCAVYGGSFSGYYWSWIRQSPEKG        CD137.U
LEWIGEINHGGYVTYNPSLESRVTISVQTSKNQFSLKLSSVTAADTA       scfv (6x)-Fc
VYYCARDYGPGNYDWYFDLWGRGTLVTVSSGGGGGGGGGGGG
GGSGGGGGGGGSGGGGSEIVLTQSPATLSLSFGERATLSCRAS
QSVSSYLAWYQQKPGQAPRLLIYDASNRATGIPARFSGSGSGTDF
TLTISSLEPEDFAVYYCQQRSNWPPALTFGGGTKVEIKEPKSSDKT
HTCPPCPAPEFEGGPSVFLFPPKPKDTLMISRTPEVTCVVVDVSHE
DPEVKFNWYVDGVEVHNAKTKPREEQYNSTYRVVSVLTVLHQDW
LNGKEYKCKVSNKALPASIEKTISKAKGQPREPQVYTLPPCRKKLT
KNQVSLTCLVKGFYPSDIAVEWESNGQPENNYKTTPPVLKSDGSF
FLYSKLTVDKSRWQQGNVFSCSVMHEALHNHYTQKSLSLSPGK 444 EIVLTQSPATLSLSPGERATLSCRASQSVSSYLAWYQQKPGQAPR        CD137.U
LUIYDASNRATGIPARFSGSGSGTDFTLTISSLEPEDFAVYYCQQRS     scfv(VLVH)
NWPPALTFGGGTKVEIKGKPGSGKPGSGKPGSGKPGSQVQLQQ          Fc
WGAGLLKPSETLSLTCAVYGGSFSGYYWSWIRQSPEKGLEWIGEI
NHGGYVTYNPSLESRVTISVDTSKNQFSLKLSSVTAADTAVYYCAR
DYGPGNYDWYFDLWGRGTLVTVSSEPKSSDKTHTCPPCPAPEFE
GGPSVFLFPPKPKDTLMISRTPEVTCVVVDVSHEDPEVKFNWYVD
GVEVHNAKTKPREEQYNSTYRVVSVLTVLHQDWLNGKEYKCKVS
NKALPASIEKTISKAKGQPREPQVYTLPPCRKKLIKNQVSLTCLVK
GFYPSDIAVEWESNGQPENNYKTTPPVLKSDGSFFLYSKLTVDKS
RWQQGNVFSCSVMHEALHNHYTQKSLSLSPGK 445 QVQLQQWGAGLLKPSETLSLTCAVYGGSFSGYYWSWIRQSPEKG        CD137.U(G
LEWIGEINHGGYVTYNPSLESRVTISVDTSKNQFSLKLSSVTAADTA      99S) scfv-
VYYCARDYGPGNYDWYFDLWGRGTLVTVSSGGGGSGGGGSGG         Fc
GGSEIVLTQSPATLSLSPGERATLSCRASQSVSSYLAWYQQKPGQ
APRLLIYDASNRATGIPARFSGSGSGTDFTLTISSLEPEDFAVYYCQ
QRSNWPPALTFSGGTKVEIKREPKSSDKTHTCPFCPAPEFEGGPS
VFLFPPKPKDTLMISRTPEVTCVVVDVSHEDPEVKFNWYVDGVEV
HNAKTKPREEQYNSTYRVVSVLTVLHQDWLNGKEYKCKVSNKAL
PASIEKTISKAKGQPREPQVYTLPPCRKKLTKNQVSLTCLVKGFYP
SDIAVEWESNGQPENNYKTTPPVLKSDGSFFLYSKLTVDKSRWQQ
GNVFSCSVMHEALHNHYTQKSLSLSPGK 446 QVQLQESGPGLVKPSETLSLTCTVSGGSFSGYYWSWIRQPPGKG        CD137.Uv1
LEWIGEINHGGYVTYNPSLESRVTISVDTSKNQFSLKLSSVTAADTA      scfv-Fc
VYYCARDYGPGNYDWYFDLWGRGTLVTVSSGKPGSGKPGSGKP
GSGKPGSEIVLTQSPGTLSLSPGERATLSCRASQSVSSSYLAWYQ
QKPGQAPRLLIYDASNRATGIFDRFSGSGSGTDFTLTISRLEPEDF
AVYYCQQRSNWPPALTFGGGTKVEIKEPKSSDKTHTCPPCPAPEF
EGGPSVFLFPPKPKDTLMISRTPEVTCVVVDVSHEDPEVKFNWYV
DGVEVHNAKTKPREEQYNSTYRVVSVLTVLHQDWLNGKEYKCKV
SNKALPASIEKTISKAKGQPREPQVYTLPPCRKKLTKNQVSLTCLV
KGFYPSDIAVEWESNGQPENNYKTTPPVLKSDGSFFLYSKLTVDK
SRWQQGNVFSCSVMHEALHNHYTQKSLSLSPGK 447 EVQLLESGGGLVQPGGSLRLSCAASGGSFSGYYWSWVRQAPGK        CD137.Uv2
GLEWWVSEINHGGYVTYNPSLESRFTISRDNSKNTLYLQMNSLRAE      scfv-Fc
DTAVYYCAKDYGPGNYDWYFDLWGRGTLVTVSSGKPGSGKPGS
GKPGSGKPGSEIVLTQSPGTLSLSPGERATLSCRASQSVSSSYLA
WYQQKPGQAPRLLIYDASNRATGIPDRESGSGSGTDFTLTISRLER
EDFAVYYCQQRSNWPPALTFGGGTKVEIKEPKSSDKTHTCPPCPA
PEFEGGPSVFLFPPKPKDTLMISRTPEVTCVVVDVSHEDPEVKEN
WYVDGVEVHNAKTKPREEQYNSTYRVVSVLTVLHQDWLNGKEYK
CKVSNKALPASIEKTISKAKGQPREPQVYTLPPCRKKLTKNQVSLT
CLVKGFYPSDIAVEWESNGQPENNYKTTPRVLKSDGSFFLYSKLT
VDKSRWQQGNVFSCSVMHEALHNHYTQKSLSLSPGK 448 QVQLVQSGAEVKKPGSSVKVSCKASGGSFSGYYWSWVRQAPGQ        CD137.Uv3
GLEWMGEINHGGYVTYNPSLESRVTITADESTSTAYMELSSLRSE       scfv-Fc
DTAVYYCARDYGPGNYDWYFDLWGRGTLVTVSSGKPGSGKPGS
GKPGSGKPGSEIVLTQSPGTLSLSPGERATLSGRASQSVSSSYLA
WYQQKPGQAPRLLIYDASNRATGIPDRFSGSGSGTDFTLTISRLEP
EDFAVYYCQQRSNWPPALTFGGGTKVEIKEPKSSDKTHTCPPCPÅ
PEFEGGPSVFLFPPKPKDTLMISRTPEVTCVVVDVSHEDPEVKEN
WYVDGVEVHNAKTKPREEQYNSTYRVVSVLTVLHQDWLNGKEYK
CKVSNKALPASIEKTISKAKGQPREPQVYTLPPCRKKLTKNQVSLT
CLVKGFYPSDIAVEWESNGQPENNYKTTPPVLKSDGSFFLYSKLT
VDKSRWQQGNVFSCSVMHEALHNHYTQKSLSLSPGK TABLE 20-continued

SEQUENCES

| Seq ID | sequence | name |
|---|---|---|
| 449 | QVQLQQWGAGLLKPSETLSLTCAVYGGSFSGYYWSWIRQSPEKC LEWIGEINHGGYVTYNPSLESRVTISVDTSKNQFSLKLSSVTAADTA VYYCARDYGPGNYDWYFDLWGRGTLVTVSSGKPGSGKPGSGKP GSGGKPGSEIVLTQSPATLSLSPGERATLSCRASQSVSSYLAWYQQ KPGQAPRLLIYDASNRATGIPARFSGSGSGTDFTLTISSLEPEDFAV YYCQQRSNWPPALTFGCGTKVEIKEPKSSDKTHTCPPCPAPEFEG GPSVFLFPPKPKDTLMISRTPEVTCVVVDVSHEDPEVKFNWYVDG VEVHNAKTKPREEQYNSTYRVVSVLTVLHQDWLNGKEYKCKVSN KALPASIEKTISKAKGQPREPQVYTLPPCRKKLTKNQVSLTCLVKG FYPSDIAVEWESNGQPENNYKTTPPVLKSDGSFFLYSKLTVDKSR WQQGNVFSCSVMHEALHNHYTQKSLSLSPGK | CD137 |
| 450 | QVQLGQWGAGLLKPSETLSLTCAVYGGSFSGYYWSWIRQSPEKC LEWIGEINHGGYVTYNPSLESRVTISVDTSKNQFSLKLSSVTAADTA VYYCARDYGPGNYDWYFDLWGRGTLVTVSSGKPGSGKPGSGKP GSGGKPGSEIVLTQSPATLSLSPGERATLSCRASQSVSSYLAWYQQ KPGQAPRLLIYDASNRATGIPARFSGSGSGTDFTLTISSLEPEDFAV YYCQQRSNWPPALTFGCGTKVEIKEPKSSDKTHTCPPCPAPEFEG GPSVFLFPPKPKDTLMISRTPEVTCVVDVSHEDPEVKFNWYVDG VEVHNAKTKPREEQYNSTYRVVSVLTVLHQDWLNGKEYKCKVSN KALPASIEKTISKAKGQPREPQVYTLPPCRKKLTKNQVSLTCLVKG FYPSDIAVEWESNGQPENNYKTTPPVLKSDGSFFLYSKLTVDKSR WQQGNVFSCSVMHEALHNHYTQKSLSLSPGK | CD137.U scfv(CC)-Fc |
| 451 | QVQLVQSGAEVKKPGASVKVSCKASGYTFSSYWMHWRQAPGQ RLEWMGEINPGNGHTNYSQKFQGRVTITVDKSASTAYMELSSLRS EDTAVYYCARSFTTARAFAYWGQGTLVTVSSGKPGSGKPGSGKP GSGGKPGSDIVMTQSPPTLSLSPGERVTLSCRASQSISDYLHWYQQ KPGQSPRLLIKYASQSISGIPARFSGSGSGTDFTLTISSLEPEDFAV YYCQDGHSFPPTFGGGTKVEIKEPKSSDKTHTCPPCPAPEFEGGP SVFLFPPKPKDTLMISRTPEVTCVVVDVSHEDPEVKFNWYVDGVE VHNAKTKPREEQYNSTYRVVSVLTVLHQDWLNGKEYKCKVSNKA LPASIEKTISKAKGQPREPQVYTLPPCRKKLTKNQVSLTCLVKGFY PSDIAVEWESNGQPENNYKTTPPVLKSDGSFFLYSKLTVDKSRWQ QGNVFSCSVMHEALMNHYTQKSLSLSPGK | CD137.B scfv-Fc |
| 452 | QVQLVQSGAEVKKPGASVKVSCKASGYTFSSYWMHWRQAPGQ RLEWMGEINPGNGHTNYAQKFQGRVTITVDKSASTAYMELSSLRS EDTAVYYCARSFTTARAFAYWGQGTLVTVSSGKPGSGKPGSGKP GSGGKPGSDIVMTQSPPTLSLSPGERVTLSCRASQSISDYLHWYQQ KPGQSPRLLIKYASQSISGIPARFSGSGSGTDFTLTISSLEPEDFAV YYCQDGHSFPPTFGGGTKVEIKEPKSSDKTHTCPPCPÁPEFEGGP SVFLFPPKPKDTLMISRTPEVTCVVVDVSHEDPEVKFNWYVDGVE VHNAKTKPREEQYNSTYRVVSVLTVLHQDWLNGKEYKCKVSNKA LPASIEKTISKAKGQPREPQVYTLPPCRKKLTKNQVSLTCLVKGFY PSDIAVEWESNGQPENNYKTTPPVLKSDGSFFLYSKLTVDKSRWQ QGNVFSCSVMHEALMNHYTQKSLSLSPGK | CD137.b(S60A) scfv-fc |
| 453 | QVQLVQSGAEVKKPGASVKVSCKASGYTFSSYWMHWVRQAPGQ RLEWMGEINPGNGHTNYNQKFQGRVTITVDKSASTAYMELSSLRS EDTAVYYCARSFTTARAFAYWGQGTLVTVSSGKPGSGKPGSGKP GSGGKPGSDIVMTQSPPTLSLSPGERVTLSCRASQSISDYLHWYQQ KPGQSPRLLIKYASQSISGIPARFSGSGSGTDFTLTISSLEPEDFAV YYCQDGHSFPPTFGGGTKVEIKEPKSSDKTHTCPPCPAPEFEGGP SVFLFPPKPKDTLMISRTPEVTCVVVDVSHEDPEVKPNWYVDGVE VHNAKTKPREEQYNSTYRVVSVLTVLHQDWLNGKEYKCKVSNKA LPASIEKTISKAKGQPREPQVYTLPPCRKKLTKNQVSLTCLVKGFY PSDIAVEWESNGQPENNYKTTPPVLKSDGSFFLYSKLTVDKSRWQ QGNVFSCSVMHEALHNHYTQKSLSLSPGK | CD137.B (S50N) scfv-fc |
| 454 | EVQLVESGGGLVQPGGSLRLSCAASGFTFSDYWMSWVRQAPGK GLEWVADIKNDGSYTNYAPSLTNRFTISRDNAKNSLYLQMNSLRA EDTAVYYCARELTGTWGQGTMVTVSSGKPGSGKPGSGKPGSGK PGSDIVMTQSPDSLAVSLGERATINCKSSQSLLSSGNQKNYLAWY QQKPGQPPKLLIYYASTRQSGVPDRFSGSGSGTDFTLTISSLQAED VAVYYCLQYDRYPFTFGQGTKLEIKEPKSSDKTHTCPPCPAPEFE GGPSVFLFPPKPKDTLMISRTPEVTCVVVDVSHEDPEVKFNWYVD GVEVHNAKTKPREEQYNSTYRVVSVLTVLHQDWLNGKEYKCKVS NKALPASIEKTISKAKGQPREPQVYTLPPCRKKLTKNQVSLTCLVK GFYPSDIAVEWESNGQPENNYKTTPPVLKSDGSFFLYSKLTVDKS RWQQGNVFSCSVMHEALHNHYTQKSLSLSPGK | CD137.39 scfv-Fc |
| 455 | EVQLVESGGGLVQPGGSLRLSCAASGFTFSDYWMSWVRQAPGK GLEWVADIKNDGSYTNYVDSVKGRFTISRDNAKNSLYLQMNSLRA EDTAVYYCARELTGTWGQGTLVTVSSGKPGSGKPGSGKPGSGKP GSDIIMTQSPDSLAVSLGERATINCKSSQSLLSSGNQKNYLAWYQ | CD137.39v 1 scfv-Fc |

TABLE 20-continued

| | SEQUENCES | |
|---|---|---|
| Seq ID | sequence | name |

```
        QKPGQPPELLIYYASTRQSGVPDRFSGSGSGTDFTLTISSLQAEDV
        AVYYCLQYDRYPFTEGQGTKLEIKERKSSDKTHTCPPCPAPEFEG
        GPSVFLFPPKPKDTLMISRTPEVTCVVVDVSHEDPEVKENWYVDG
        VEVHNAKTKPREEQYNSTYRVVSVLTVLHQDWLNGKEYKCKVSN
        KALPASIEKTISKAKGQPREPQVYTLPPCRKKLTKNQVSLTCLVKG
        FYPSDIAVEWESNGQPENNYKTTPPVLKSDGSFFLYSKLTVDKSR
        WQQGNVFSCSVMHEALHNHYTQKSLSLSPGK

456     EVQLVESGGGLVQPGGSLRLSCAASGFTFSDYWMSWWVRQAPGK      CD137.39v
        GLEWVADIKNDGSYTNYVDSVKGRFTISRDNAKNSLYLQMNSLRA    2 scfv-Fc
        EDTAVYYCARELTGTWGQGTLVTVSSGKPGSGKPGSGKPGSGKP
        GSDIVMTQSPDSLAVSLGERATINCKSSQSLLSSGNQKNYLAWYQ
        QKPGQPPKLUIYYASTRQSGVPDRFSGSGSGTDFTLTISSLQAEDV
        AVYYCLQYDRYPFTEGQGTKLEIKERKSSDKTHTCPPCPAPEFEG
        GPSVFLFPPKPKDTLMISRTPEVTCVVVDVSHEDPEVKENWYVDG
        VEVHNAKTKPREEQYNSTYRVVSVLTVLHQDWLNGKEYKCKVSN
        KALPASIEKTISKAKGQPREPQVYTLPPCRKKLTKNQVSLTCLVKG
        FYPSDIAVEWESNGQPENNYKTTPPVLKSDGSFFLYSKLTVDKSR
        WQQGNVFSCSVMHEALHNHYTQKSLSLSPGK 457     EVQLVESGGGLVQPGGSLRLSCAASGFTFSDYWMSWVRQAPGK      CD137.39v
        GMEWVGDIKNDGSYTNYAPSLTNRFTISRDNARNSLYLQMNSLRA   3 scfv-Fc
        EDTAVYYCTRELTGTWGQGTLVTVSSGKPGSGKPGSGKPGSGKP
        GSDIIMTQSPDSLAVSLGERATINCKSSQSLLSSGNQKNYLAWYQ
        QKPGQPPELLIYYASTRQSGVPDRFSGSGSGTDFTLTISSLQAEDV
        AVYYCLQYDRYPFTFGQGTKLEIKERKSSDKTHTCPPCPAPEFEG
        GPSVFLFPPKPKDTLMISRTPEVTCVVVDVSHEDPEVKENWYVQG
        VEVHNAKTKPREEQYNSTYRVVSVLTVLHQDWLNGKEYKCKVSN
        KALPASIEKTISKAKGQPREPQVYTLPPCRKKLTKNQVSLTCLVKG
        FYPSDIAVEWESNGQPENNYKTTPPVLKSDGSFFLYSKLTVDKSR
        WQQGNVFSCSVMHEALHNHYTQKSLSLSPGK 458     EVQLVESGGGLVQPGGSLRLSCAASGFTFSDYWMSWVRQAPGK      CD137.39V
        GMEWVGDIKNDGSYTNYAPSLTNRFTISRDNARNSLYLQMNSLRA   4 scfv-Fc
        EDTAVYYCTRELTGTWGQGTLVTVSSGKPGSGKPGSGKPGSGKP
        GSDIVMTQSPDSLAVSLGERATINCKSSQSLLSSGNQKNYLAWYQ
        QKPGQPPKLUYYASTRQSGVPDRFSGSGSGTDFTLTISSLQAEDV
        AVYYCLQYDRYPFTFGQGTKLEIKEPKSSDKTHTCPPCPAPEFEG
        GPSVFLFPPKPKDTLMISRTPEVTCVVVDVSHEDPEVKFNWYVDG
        VEVHNAKTKPREEQYNSTYRVVSVLTVLHQDWLNGKEYKCKVSN
        KALPASIEKTISKAKGQPREPQVYTLPPCRKKLTKNQVSLTCLVKG
        FYPSDIAVEWESNGQPENNYKTTPPVLKSDGSFFLYSKLTVDKSR
        WQQGNVFSCSVMHEALHNHYTQKSLSLSPGK 459     QVKLVESGAEVKKPGASVKVSCKASGYTFTSYWMHWVRQAPGQ      CD137.Bv1
        VLEWMGEINPGNGHTSYAQKFQGRVTLTVDKSTSTAYMELSSLRS    scfv-Fc
        EDTAVYYCARSFTTARAFAYWGQGTTVTVSSGKPGSGKPGSGKP
        GSCKPGSDIQMTQSPSSLSASVGDRVTITCRASQSISDYLHWYQQ
        KPGKAPKLLIKYASQSISGVPSRFSGSGSGTDFTLTISSLQPEDFAT
        YYCQDSHSFPPTFGGGTKVEIKERKSSDKTHTCPPCPAPEFEGGP
        SVFLFPPKPKDTLMISRTPEVTCVVVDVSHEDPEVKENWYVDGVE
        VHNAKTKPREEQYNSTYRVVSVLTVLHQDWLNGKEYKCKVSNKA
        LPASIEKTISKAKGQPREPQVYTLPPCRKKLTKNQVSLTCLVKGFY
        PSDIAVEWESNGQPENNYKTTPPVLKSDGSFFLYSKLTVDKSRWQ
        QGNVFSCSVMHEALHNHYTQKSLSLSPGK 460     QVKLVESGAEVKKPGASVKVSCKASGYTFTSYWMHWVRQAPGQ      CD137.Bv2
        VLEWMGEINPGNGHTSYAQKFQGRVTLTVDKSTSTAYMELSSLRS    scfv-fc
        EDTAVYYCARSFTTARAFAYWGQGTTVTVSSGKPGSGKPGSGKP
        GSGKPGSDIVMTQSPPTLSLSPGERVTLSCRASQSISDYLHWYQQ
        KPGQSPRLLIKYASQSISGIPARFSGSGSGTDFTLTISSLEPEDFAV
        YYCQDGHSFPPTFGGGTKVEIKEPKSSDKTHTCPPCPAPEFEGGP
        SVFLFPPKPKDTLMISRTPEVTCVVVDVSHEDPEVKFNWYVDGVE
        VHNAKTKPREEQYNSTYRVVSVLTVLHQDWLNGKEYKCKVSNKA
        LPASIEKTISKAKGQPREPQVYTLPPCRKKLTKNQVSLTCLVKGFY
        PSDIAVEWESNGQPENNYKTTPPVLKSDGSFFLYSKLTVDKSRWQ
        QGNVFSCSVMHEALHNHYTQKSLSLSPGK 461     QVQLVQSGAEVKKPGASVKLSCKASGYTFSSYWMEIWVRQAPGQ     CD137.Bv3
        GLEMGEINPGNGHTNYNEKFKSRVTMTRDTSTSTAYMELSSLRS     scfv-fc
        EDTAVYYCARSFKTARAFAYWGQGTLVTVSSGKPGSGKPGSGKP
        GSGKPGSDIVMTQSPAFLSVTRGEKVTITCRASQTISDYLHWYQQ
        KPDQAPKLUKYASQSISGIPSRFSGSGSGTDFTFTISSLEAEDAAT
        YYCQDGHSWPPTFGQGTKLEIKEPKSSDKTHTCPPCPAPEFEGG
        PSVFLFPPKPKDTLMISRTPEVTCVVVDVSHEDPEVKFNWYVDGV
        EVHNAKTKPREEQYNSTYRVVSVLTVLHQDWLNGKEYKCKVSNK
```

TABLE 20-continued

| SEQUENCES |
| --- |

| Seq ID | sequence | name |
| --- | --- | --- |
|  | ALPASIEKTISKAKGGPREPQVYTLPPCRKKLTKNQVSLTCLVKGF<br>YPSDIAVEWESNGQPENNYKTTPPVLKSDGSFFLYSKLTVDKSRW<br>QQGNVFSCSVMHEALHNHYTQKSLSLSPGK |  |
| 462 | QVQLVQSGAEVKKPGASVKVSCKASGYTFTSYWMHWVRQAPGQ<br>GLEWMGIINPGNGHTSYAQKFQGRVTMTRDTSTSTVYMELSSLRS<br>EDTAVYYCARSFTTARAFAYWGQGTTVTVSSGKPGSGKPGSGKP<br>GSGKPGSDIQMTQSPSSLSASVGDRVTITGRASQSISDYLHWYQQ<br>KPGKAPKLLIKYASQSISGVPSRFSGSGSGTDFTLTISSLQPEDFAT<br>YYCQDSHSFPPTFGGGTKVEIKEPKSSDKTHTCPPCPAPEFEGGP<br>SVFLFPPKPKDTLMISRTPEVTCVVVDVSHEDPEVKFNWYVDGVE<br>VHNAKTKPREEQYNSTYRVVSVLTVLHQDWLNGKEYKCKVSNKA<br>LPASIEKTISKAKGQPREPQVYTLPPCRKKLTKNQVSLTCLVKGFY<br>PSDIAVEWESNGQPENNYKTTPPVLKSDGSFFLYSKLTVDKSRWQ<br>QGNVFSCSVMHEALHNHYTQKSLSLSPGK | CD137.Bv4<br>scfv-fc |
| 463 | QVQLVQSGAEVKKPGASVKVSCKASGYTFTSYWMHWVRQAPGQ<br>GLEWMGIINPGNGHTSYAQKFQGRVTMTRDTSTSTVYMELSSLRS<br>EDTAVYYCARSFTTARAFAYWGQGTTVTVSSGKPGSGKPGSGKP<br>GSGKPGSDIVMTQSPPTLSLSPGERVTLSCRASQSISDYLHWYQQ<br>KPGQSPRLLIKYASQSISGIPARFSGSGSGTDFTLTISSLEPEDFAV<br>YYCQDGHSFPPTFGGGTKVEIKEPKSSDKTHTCPPCPÅPEFEGGP<br>SVFLFPPKPKDTLMISRTPEVTCVVVDVSHEDPEVKFNWYVDGVE<br>VHNAKTKPREEQYNSTYRVVSVLTVLHQDWLNGKEYKCKVSNKA<br>LPASIEKTISKAKGQPREPQVYTLPPCRKKLTKNQVSLTCLVKGFY<br>PSDIAVEWESNGQPENNYKTTPPVLKSDGSFFLYSKLTVDKSRWQ<br>QGNVFSCSVMHEALHNHYTQKSLSLSPGK | CD137.Bv5<br>scfv-fc |
| 464 | QVQLVQSGAEVKKPGASVKVSCKASGYTFTSYWMHWVRQAPGQ<br>RLEWMGEINPSNGHTKYSQKFQGRVTITVDKSASTAYMELSSLRS<br>EDTAVYYCARSFTTARAFAYWGQGTLVTVSSGKPGSGKPGSGKP<br>GSGKPGSDIQMTQSPSSLSASVGDRVTITCRASQSISDYLHWYQQ<br>KPGKAPKLLIKYASQSISGVPSRFSGSGSGTDFTLTISSLQPEDFAT<br>YYCQDSHSFPPTFGGGTKVEIKEPKSSDKTHTCPPCPAPEFEGGP<br>SVFLFPPKPKDTLMISRTPEVTCVVVDVSHEDPEVKFNWYVDGVE<br>VHNAKTKPREEQYNSTYRVVSVLTVLHQDWLNGKEYKCKVSNKA<br>LPASIEKTISKAKGQPREPQVYTLPPCRKKLTKNQVSLTCLVKGFY<br>PSDIAVEWESNGQPENNYKTTPPVLKSDGSFFLYSKLTVDKSRWQ<br>QGNVFSCSVMHEALHNHYTQKSLSLSPGK | CD137.Bv6 |
| 465 | QVQLVQSGAEVKKPGASVKVSCKASGYTFTSYWMHWVRQAPGQ<br>RLEWMGEINPSNGHTKYSQKFQGRVTITVDKSASTAYMELSSLRS<br>EDTAVYYCARSFTTARAFAYWGQGTLVTVSSGKPGSGKPGSGKP<br>GSGKPGSDIVMTQSPPTLSLSPGERVTLSCRASQSISDYLHWYQQ<br>KPGQSPRLLIKYASQSISGIPARFSGSGSGTDFTLTISSLEPEDFAV<br>YYCQDGHSFPPTFGGGTKVEIKEPKSSDKTHTCPPCPAPEFEGGP<br>SVFLFPPKPKDTLMISRTPEVTCVVVDVSHEDPEVKFNWYVDGVE<br>VHNAKTKPREEQYNSTYRVVSVLTVLHQDWLNGKEYKCKVSNKA<br>LPASIEKTISKAKGQPREPQVYTLPPCRKKLTKNQVSLTCLVKGFY<br>PSDIAVEWESNGQPENNYKTTPPVLKSDGSFFLYSKLTVDKSRWQ<br>QGNVFSCSVMHEALHNHYTQKSLSLSPGK | CD137.Bv7<br>scfv-fc |
| 466 | QVQLVQSGAEVKKPGASVKVSCKASGYTFTDYFMNWVRQAPGQ<br>CLEWMGVINPYNDITIYNQKFQGRVTMTVDRSTSTVYMELSSLRS<br>EDTAVYYCAREGVLYDGYYEGAYWGQGTLVTVSSGKPGSGKPG<br>SGKPGSGKPGSDIQLTQSPSFLSASVGDRVTITCKASQNVGIAVA<br>WYQQKPGKAPKLLIYAASNRYTGVPSRFSGSGSGTEFTLTISSLQP<br>EDFATYYCQQYSTYPYTFGCGTKLEIKEPKSSGKTHTCPPCPAPER<br>EGGPSVFLFPPKPKDTLMISRTPEVTCVVVDVSHEDPEVKENWYV<br>DGVEVHNAKTKPREEQYNSTYRVVSVLTVLHQDWLNGKEYKCKV<br>SNKALPASIEKTISKAKGQPREPQVYTLPPCRKKLTKNQVSLTCLV<br>KGFYPSDIAVEWESNGQPENNYKTTPPVLKSDGSFFLYSKLTVDK<br>SRWQQGNVFSCSVMHEALHNHYTQKSLSLSPGK | DLL3 scfv-<br>Fc |
| 467 | EVQLLESGGGLVQPGGSLRLSCAASGFTFSSYGMHWVRQAPGK<br>GLEWVAVISHHGSSKYYADSVKGRFTISRDNSKNTLYLQMNSLRA<br>EDTAVYYCARDWFFYLFDYWGQGTLVTVSSGKPGSGKPGSGKP<br>GSGKPGSDIVMTQSPLSLPVTPGEPASISCKSSQSLLHSDGKTFLY<br>WYLQKPGQSPQLLIYEVSNRFSGVPDRFSGSGSGTDFTLKISRVE<br>AEDVGVYYCLQGERLPFTFGQGTKVEIKEPKSSDKTHTCPPCPAP<br>EFEGGRSVFLFPPKPKDTLMISRTPEVTCVVVDVSHEDPEVKFNW<br>YVDGVEVHNAKTKPREEQYNSTYRVVSVLTVLHQDWLNGKEYKC<br>KVSNKALPASIEKTISKAKGQPREPQVYTLPPCRKKLTKNQVSLTC<br>LVKGFYPSDIAVEWESNGQPENNYKTTPPVLKSDGSFFLYSKLTV<br>DKSRWQQGNVFSCSVMHEALHNHYTQKSLSLSPGK | DLL3 scfv-<br>Fc |

TABLE 20-continued

| | SEQUENCES | |
|---|---|---|
| Seq ID | sequence | name |
| 468 | QVQLVQSGAEVKKPGASVKVSCKASGYTFTDYFMNWVRQAPGQ GLEWMGVINPYNDITIYNQKFQGRVTMTVDRSTSTVYMELSSLRS EDTAVYYCAREGVLYDGYYEGAYWGQGTLVTVSSGGGGSGGGG SGGGGSDIQLTQSPSFLSASVGDRVTITCKASQNVGIAVAWYQQK PCKAPKLLIYAASNRYTGVPSRFSGSGSGTEFTLTISSLQPEDFAT YYCQQYSTYPYTFGQGTKLEIKSGGGGSQVQLVQSGAEVKKPGA SVKVSCKASGYTFSSYWMHWRQAPGQRLEWMGEINPGNGHTN YSQKFQGRVTITVDKSASTAYMELSSLRSEDTAVYYCARSFTTARA FAYWGQGTLVTVSSGKPGSGKPGSGKPGSGKPGSDIVMTQSPPT LSLSPGERVTLSCRASQSISDYLHWYQQKPGQSPRLLIKYASQSIS GIPARFSGSGSGTDFTLTISSLEPEDFAVYYCQDGHSFPPTFGGGT KVEIKEPKSSDKTHTCPPCPAPEFEGGPSVFLFPPKPKDTLMISRT PEVTCVVVDVSHEDPEVKFNWYVDGVEVHNAKTKPREEQYNSTY RVVSVLTVLHQDWLNGKEYKCKVSNKALPASIEKTISKAKGQPREP QVYTLPPCRKKLTKNQVSLTCLVKGFYPSDIAVEWESNGQPENNY KTTPPVLKSDGSFFLYSKLTVDKSRWQQGNVFSCSVMHEALHNH YTQKSLSLSPGK | DLL3scFv- 41BBscFv-fc x 41BBFab-fc |
| 469 | QVQLVQSGAEVKKPGASVKVSCKASGYTFSSYWMHWVRQARGQ RLEWMGEINPGNGHTNYSQKFQGRVTITVDKSASTAYMELSSLRS EDTAVYYCARSFTTARAFAYWGQGTLVTVSSGGGGGGGGGGGG GGSGGGGSDIVMTQSPPTLSLSPGERVTLSCRASQSISDYLHWYQ QKPGQSPRLLIKYASQSISGIPARFSGSGSGTDFTLTISSLEPEDFA VYYCQDGHSFPPTFGGGTKVEIKSGGGGSQVQLVQSGAEVKKPG ASVKVSCKASGYTFSSYWMHWVRQAPGQRLFWMGFINPGNGHT NYSQKFQGRVTITVDKSASTAYMELSSLRSEDTAVYYCARSFTTA RAFAYWGQGTLVTVSSGKPGSGKPGSGKPGSGKPGSDIVMTQSP PTLSLSPGERVTLSCRASQSISDYLHWYQQKPGQSPRLLIKYASQS ISGIPARFSGSGSGTDFTLTISSLEPEDFAVYYCQDGHSFPPTFGG GTKVEIKEPKSSDKTHTCPPCPAPEFEGGPSVFLFPPKPKDTLMIS RTPEVTCVVVDVSHEDPEVKFNWYVDGVEVHNAKTKPREEQYNS TYRVVSVLTVLHQDWLNGKEYKCKVSNKALPASIEKTISKAKGQPR EPQVYTLPPCRKKLTKNQVSLTCLVKGFYPSDIAVEWESNGQPEN NYKTTPPVLKSDGSFFLYSKLTVDKSRWQQGNVFSCSVMHEALH NHYTQKSLSLSPGK | 4-1BBscFv- 41BBscFv-Fc X DLL3Fab-Fc |
| 470 | QVQLVQSGAEVKKPGASVKVSCKASGYTFSSYWMHWVRQAPGQ RLEWMGEINPGNGHTNYSQKFQGRVTITVDKSASTAYMELSSLRS EDTAVYYCARSFTTARAFAYWGQGTLVTVSSASTKGPSVFPLAPS SKSTSGGTAALGCLVKDYFPEPVTVSWNSGALTSGVHTFPAVLQS SGLYSLSSVVTVPSSSLGTQTYICNVNHKPSNTKVDKRVEPKSCD KTHTCPPCPAPEFEGGPSVFLFPPKPKDTLMISRTPEVTCVVVDVS HEDPEVKFNWYVDGVEVHNAKTKPREEQYNSTYRVVSVLTVLHQ DWLNGKEYKCKVSNKALPASIEKTISKAKGQPREPQVCTLPPSRD ELTKNQVSLTCLVEGFYPSDIAVEWESNGQPENNYKTTPPVLDSD GSFFLYSDLTVDKSRWQQGNVFSCSVMHEALHNHYTQESLSLSP GKSGGGGSQVQLVQSGAEVKKPGASVKVSCKASGYTFTDYFMN WVRQAPGQGLEWMGVINPYNDITIYNQKFQGRVTMTVQRSTSTV YMELSSLRSEDTAVYYCAREGVLYDGYYEGAYWGQGTLVTVSSG GGGSGGGGSGGGGSDIQLTQSPSFLSASVGDRVTITCKASQNVGI AVAWYQQKPGKAPKLLIYAASNRYTGVPSRFSGSGSGTEFTLTISS LQPEDFATYYCQQYSTYPYTFGQGTKLEIK | 41BBFab- Fc- DLL3scFv |
| 471 | QVQLQQWGAGLLKPSETLSLTCAVYGGSESGYYWSWIRQSPEKG LEWIGEINHGGYVTYNPSLESRVTISVQTSKNQFSLKLSSVTAADTA VYYCARDYGPGNYDWYFDLWGRGTLVTVSSASTKGPSVFPLAPS SKSTSGGTAALGCLVKDYFREPVTVSWNSGALTSGVHTFPAVLQS SGLYSLSSVVTVPSSSLGTQTYICNVNHKPSNTKVDKRVEPKSCD KTHTCPPCPAPEFEGGPSVFLFPPKPKDTLMISRTPEVTCVVVDVS HEDPEVKFNWYVDGVEVHNAKTKPREEQYNSTYRVVSVLTVLHQ DWLNGKEYKCKVSNKALPASIEKTISKAKGQPREPQVYTLPPCRK KLTKNQVSLTCLVKGFYPSDIAVEWESNGQPENNYKTTPPVLKSD GSFFLYSKLTVDKSRWQQGNVFSCSVMHEALHNHYTQKSLSLSP GKSGGGGSQVQLVQSGAEVKKPGASVKVSCKASGYTFTDYFMN WRQAPGQGLEWMGVINPYNDITIYNQKFQGRVTMTVDRSTSTV YMELSSLRSEDTAVYYCAREGVLYDGYYEGAYWGQGTLVTVSSG GGGSGGGGSGGGGSDIQITQSPSFLSASVGDRVTITCKASQNVGI AVAWYQQKPGKAPKLLIYAASNRYTGVPSRFSGSGSGTEFTLTISS LQPEDFATYYCQQYSTYPYTFGQGTKLEIK | 41BBFab- Fc- DLL3scFv |
| 472 | QVQLVQSGAEVKKPGASVKVSCKASGYTFSSYWMHWVRQAPGQ RLEWMGEINPGNGHTNYSQKFQGRVTITVDKSASTAYMELSSLRS EDTAVYYCARSFTTARAFAYWGQGTLVTVSSASTKGPSVFPLAPS SKSTSGGTAALGCLVKDYFPEPVTVSWNSGALTSGVHTFPAVLQS SGLYSLSSVVTVPSSSLGTQTYICNVNHKPSNTKVDKRVERKSCD KTHTCPPCPAPEFEGGPSVFLFPPKPKDTLMISRTPEVTCVVVDVS | 41BBFab- DLL3scFv |

TABLE 20-continued

SEQUENCES

| Seq ID | sequence | name |
|---|---|---|
| | HEDPEVKPNWYVDGVEVHNAKTKPREEQYNSTYRVVSVLTVLHQ<br>DWLNGKEYKCKVSNKALPASIEKTISKAKGQPREPQVYTLPPCRK<br>KLTKNQVSLTCLVKGFYPSDIAVEWESNGQPENNYKTTPPVLKSD<br>GSFFLYSKLTVDKSRWQQGNVFSCSVMHEALHNHYTQKSLSLSP<br>GKSGGGGSQVQLVQSGAEVKKPGASVKVSCKASGYTFTDYFMN<br>WVRQAPGQGLEWMGVINPYNDITIYNQKFQGRVTMTVDRSTSTV<br>YMELSSLRSEDTAVYYCAREGVLYDGYYEGAYWGQGTLVTVSSG<br>GGGGGGGGGGGGGSDIQLTQSPSFLSASVGDRVTITCKASQNVGI<br>AVAWYQQKPCKAPKLLIYAASNRYTGVPSRFSGSGSGTEFTLTISS<br>LQPEDFATYYCQQYSTYPYTFGQGTKLEIK | |
| 473 | QVQLQQWGAGLLKPSETLSLTCAVYGGSFSGYYWSWIRQSPEKG<br>LEWIGEINHGGYVTYNPSLESRVTISVDTSKNQFSLKLSSVTAADTA<br>VYYCARDYGPGNYDWYFDLWGRGTLVTVSSASTKGPSVFPLAPS<br>SKSTSGGTAALGCLVKDYFPEFVTVSWNSGALTSGVHTFPAVLQS<br>SGLYSLSSVVTVPSSSLGTQTYICNVNHKPSNTKVDKRVEPKSCD<br>KTHTCPPCPAPEFEGGPSVFLFPPKPKDTLMISRTPEVTCVVVDVS<br>HEDPEVKFNWYVDGVEVHNAKTKPREEQYNSTYRVVSVLTVLHQ<br>DWLNGKEYKCKVSNKALPASIEKTISKAKGQPREPQVCTLPPSRD<br>ELTKNQVSLTCLVEGFYPSDIAVEWESNGQPENNYKTTPPVLDSD<br>GSFFLYSDLTVDKSRWQQGNVFSCSVMHEALHNHYTQESLSLSP<br>GKSGGGGSQVQLVQSGAEVKKPGASVKVSCKASGYTFTDYFMN<br>WVRQAPGQGLEWMGVINPYNDITTYNQKFQGRVTMTVQRSTSTV<br>YMELSSLRSEDTAVYYCAREGVLYDGYYEGAYWGQGTLVTVSSG<br>GGGGGGGSGGGGSDIQLTQSPSFLSASVGDRVTITCKASQNVGI<br>AVAWYQQKPGKAPKLLIYAASNRYTGVPSRFSGSGSGTEFTLTISS<br>LQPEDFATYYCQQYSTYPYTFGQGTKLEIK | 41BBFab-<br>Fc-<br>DLL3scFv |
| 474 | EVQLVQSGAEVKKPGESLKISCKGSGYEFSSHWMNWVRQMPGK<br>CLEWMGQIYPGDGDINYNEKFRGQVTISADKSISTAYLQWSSLKAS<br>DTAMYYCARHGNYVMDYWGQGTLVTVSSGKPGSGKPGSGKPGS<br>GKPGSIQLTQSPSFLSASVGDRVTITCSASSSVSYMFWYQQKPGK<br>APKPWYRTSNLASGVPSRFSGSGSGTEFTLTISSLQPEDFATYYC<br>QQFHDYPRTFGCGTKVEIKEPKSSDKTHTCPPCPAPEFEGGPSVF<br>LFPPKPKDTLMISRTPEVTCVVVDVSHEDPEVKFNWYVDGVEVHN<br>AKTKPREEQYNSTYRVVSVLTVLHQDWLNGKEYKCKVSNKALPAS<br>IEKTISKAKGQPREPQVYTLPPCRKKLTKNQVSLTCLVKGFYPSDIA<br>VEWESNGQPENNYKTTPPVLKSDGSFFLYSKLTVDKSRWQQGNV<br>FSCSVMHEALHNHYTQKSLSLSPGK | Muc17scfv-<br>fc |
| 475 | QVQLVQSGAEVKKPGASVKVSCKASGYTFTNFGITWVRQAPGQG<br>LEWMGETYPSSQNTFYNEKFKGRVTMTTDTSTSTAYMELRSLRSD<br>DTAVYYCARGGGPLRSRYFDYWGQGTLVTVSSGKPGSGKPGSG<br>KPGSGKPGSDIVMTQSPDSLAVSLGERATINGRSSQSLFSSGNQK<br>NYLTWYQQKPGQPPKLLIYWASTRESGVPDRFSGSGSGTDFTLTI<br>SSLQAEDVAVYYCQNDYYYPLTFGGGTKVEIKEPKSSDKTHTCFP<br>CPAPEFEGGPSVFLFPPKPKDTLMISRTPEVTCVVVDVSHEDPEVK<br>FNWYVDGVEVHNAKTKPREEQYNSTYRVVSVLTVLHQDWLNGKE<br>YKCKVSNKALPASIEKTISKAKGQPREPQVYTLPPCRKKLTKNQVS<br>LTCLVKGFYPSDIAVEWESNGQPENNYKTTPPVLKSDGSFFLYSKL<br>TVDKSRWQQGNVFSCSVMHEALHNHYTQKSLSLSPGK | CLDN182.<br>scfv-Fc |
| 476 | EVQLVESGGGLVQPGGSLRLSCAASGFTFSSFGMHWWRQAPGK<br>GLEWWSYISSGNSAIYYADTVNGRFTISRDNAKNSLYLQMNSLRAE<br>DTAVYYCARLRYGNSFDYWGQGTLVTVSSGKPGSGKPGSGKPG<br>SGKPGSDIVMTQSPDSLAVSLGERATINCKSSQSLLNSGNQKNYL<br>TWYQQKPGQPPKLLIYWASTRESGVPDRFSGSGSGTDFTLTISSL<br>QAEDVAVYYCQNNYYYPLTFGGGTKVEIKEPKSSDKTHTCPPGRA<br>PEFEGGPSVFLFPPKPKDTLMISRTPEVTCVVVDVSHEDPEVKEN<br>WYVDGVEVHNAKTKPREFQYNSTYRVVSVLTVLHQDWLNGKEYK<br>CKVSNKALPASIEKTISKAKGQPREPQVYTLPPCRKKLTKNQVSLT<br>CLVKGFYPSDIAVEWESNGQPENNYKTTPPVLKSDGSFFLYSKLT<br>VDKSRWQQGNVFSCSVMHEALHNHYTQKSLSLSPGK | CLDN182.<br>scfv-Fc |
| 477 | QVQLVQSGAEVKKPGSSVKVSCKASGYAFNNYWMNWVRQAPGQ<br>GLEWMGQISPGNGNSNFNGKFKGRVTITADKSTSTAYMELSSLRS<br>EDTAVYYCARGGRYGNAMDYWGQGTTVTVSSGKPGSGKPGSGK<br>PGSGKPGSDIVMTQSPDSLAVSLGERATINCKSSQSLLNSGNQRN<br>YLTWYQQKPGQPPKLLIYWASTRESGVPDRFSGSGSGTDFTLTIS<br>SLQAEDVAVYYCQNAYFYPYTFGGGTKVEIKEPKSSDKTHTCPPC<br>PAPEFEGGPSVFLFPPKPKDTLMISRTPEVTCVVVDVSHEDPEVKF<br>NWYVDGVEVHNAKTKPREEQYNSTYRVVSVLTVLHQDWLNGKEY<br>KCKVSNKALPASIEKTISKAKGQPREPQVYTLPPCRKKLTKNQVSL<br>TCLVKGFYPSDIAVEWESNGQPENNYKTTPPVLKSDGSFFLYSKLT<br>VDKSRWQQGNVFSCSVMHEALHNHYTQKSLSLSPGK | CLDN182.<br>scfv-Fc |

TABLE 20-continued

SEQUENCES

| Seq ID | sequence | name |
|---|---|---|
| 478 | QVQLVQSGAEVKKPGASVKVSCKASGYTFTNSGMNWVRQAPGQ GLEWMGWINTNTGEPTFAEEFRGRVTMTRDTSISTAYMELSRLRS DDTAVYYCARYYYGNSFAYWGQGTLVTVSSGKPGSGKPGSGKP GSGKPGSDIVMTQSPDSLAVSLGERATINCKSSQSLLNSGNQKNY LTWYGQKPGQPPKLUYWASTRESGVPDRFSGSGSGTDFTLTISS LQAEDVAVYYCQNNYFYPLTFGGGTKVEIKEPKSSDKTHTCPPCP APEFEGGPSVFLPPPKPKDTLMISRTPEVTCVVVDVSHEDPEVKFN WYVDGVEVHNAKTKPREEQYNSTYRVVSVLTVLHQDWLNGKEYK CKVSNKALPASIEKTISKAKGQPREPQVYTLPPCRKKLTKNQVSLT CLVKGFYPSDIAVEWESNGQPENNYKITPPVLKSDGSFFLYSKLT VDKSRWQQGNVFSCSVMHEALHNHYTQKSLSLSPGK | CLDN182. scfv-Fc |
| 479 | QVQLVQSGAEVKKPGASVKVSCKASGYTFTSYWMHWVRQAPGQ GLEWMGIINPNGNGHTSYAQKFQGRVTMTRDTSTSTVYMELSSLRS EDTAVYYCARSFTTARAFAYWGQGTTVTVSSGKPGSGKPGSGKP GSGKPGSDIQMTQSPSSLSASVGDRVTITCRASQSISDYLHWYQQ KPGKAPKLLIKYASQSISGVPSRFSGSGSGTDFTLTISSLQPEDFAT YYCQDSHSFPPTFGGGTKVEIKEPKSSDKTHTCPPCPAPEFEGGR SVFLFPPPKPKDTLMISRTPEVTCVVVDVSHEDPEVKFNWYVDGVE VHNAKTKPREEQYNSTYRVVSVLTVLHQDWLNGKEYKCKVSNKA LPASIEKTISKAKGQPREPQVYTLPPCRKKLTKNQVSLTCLVKGFY PSDIAVEWESNGQPENNYKTTPPVLKSDGSFFLYSKLTVDKSRWQ QGNVFSCSVMHEALHNHYTQKSLSLSPGK | CD137.bV8 scfv-Fc |
| 480 | EVQLVESGGGLVQPGGSLRLSCAASGFTFSTYAMNWVRQAPGK GLEWVGRIRSKYNNYATYYADSVKGRFTISRDDSKNTLYLQMNSL RAEDTAVYYCVRHGNFGDSYVSWFEYWGQGTLVTVSSGGGGSG GGGSGGGGSGGGGSQAVVTQERSLTVSPGGTVTLTCGSSTGAV TTSNYANWVQQKPGKSPRGLIGGTNKRAPGVPARFSGSLLGGKA ALTISGAQPEDEADYYCALWYSNHWVFGGGTKLTVLSGGGGSQV QLVQSGAEVKKPGASVKVSCKASGYTFTSYYIHWRQAPGQGLE WIGSIYPGNVNTNYNEKFKDRATLTVDTSISTAYMELSRLRSDDTA VYFCTRSHYGLDWNFDVWGQGTTVTVSSGKPGSGKPGSGKPGS GKPGSDIQMTQSPSSLSASVGDRVTITCHASQNIYVWLNWYQQKP GKAPKLLIYKASNLHTGVPSRFSGSGSGTDFTLTISSLQPEDFATYY CQQGQTYPYTFGGGTKVEIKEPKSSDKTHTCPPCPAPEFEGGPSV FLFPPPKPKDTLMISRTPEVTCVVVDVSHEDPEVKFNWYVDGVEVH NAKTKPREEQYNSTYRVVSVLTVLHQDWLNGKEYKCKVSNKALPA SIEKTISKAKGQPREPQVYTLPPCRKKLTKNQVSLTCLVKGFYPSDI AVEWESNGQPENNYKTTPPVLKSDGSFFLYSKLTVDKSRWQQGN VFSCSVMHEALHNHYTQKSLSLSPGK | CD3scfv-CD28scfv-Fc |
| 481 | QVQLVQSGAEVKKPGASVKVSCKASGYTFTSYYIHWRQAPGQG LEWIGSIYPGNVNTNYNEKFKDRATLTVDTSISTAYMELSRLRSDD TAVYFCTRSHYGLQWNFDVWGQGTTVTVSSGKPGSGKPGSGKP GSGKPGSDIQMTQSPSSLSASVGDRVTITCHASQNIYVWLNWYQ QKPGKAPKLLIYKASNLHTGVPSRFSGSGSGTDFTLTISSLQPEDF ATYYCQQGQTYPYTFGGGTKVEIKSGGGGSEVQLVESGGGLVQR GGSLRLSCAASGFTFSTYAMNWVRQAPGKGLEWVGRIRSKYNNY ATYYADSVKGRFTISRDDSKNTLYLQMNSLRAEDTAVYYCVRHGN FGDSYVSWFEYWGQGTLVTVSSGGGGSGGGGGGGGGGGS QAVVTQFPSLTVSPGGTVTLTCGSSTGAVTTSNYANWWVQQKPGK SPRGLIGGTNKRAPGVPARFSGSLLGGKAALTISGAQPEDEADYY CALWYSNHWVFGGGTKLTVLEPKSSDKTHTCPPCPAPEFEGGPS VFLFPPPKPKDTLMISRTPEVTCVVVDVSHEDPEVKFNWYVDGVEV HNAKTKPREEQYNSTYRVVSVLTVLHQDWLNGKEYKCKVSNKAL PASIEKTISKAKGQPREPQVYTLPPCRKKLTKNQVSLTCLVKGFYP SDIAVEWESNGQPENNYKTTPPVLKSDGSFFLYSKLTVDKSRWQQ GNVFSCSVMHEALHNHYTQKSLSLSPGK | CD28scfv-CD3scfv-Fc |
| 482 | DVQLQESGPGLVKPSQSLSLTCTVTGYSITSDYAWNWIRQFPGNK LEWMGYIRYSGSTSYNPSLKSRISITRDTSKNQFFLQLNSVTTEDT ATYYCARDWPRPSYWYFDVWGAGTTVTVSSASTKGPSVFPLAPS SKSTSGGTAALGCLVKDYFPEPVTVSWNSGALTSGVHTFPAVLQS SGLYSLSSVVTVPSSSLGTQTYICNVNHKPSNTKVDKRVEPKSCD KTHTCPPCPAPEFEGGPSVFLFPPPKPKDTLMISRTPEVTGVVVDVS HEDREVKFNWYVDGVEVHNAKTKPREEQYNSTYRVVSVLTVLHQ DWLNGKEYKCKVSNKALPASIEKTISKAKGQPREPQVCTLPPSRD ELTKNQVSLTCLVEGFYPSDIAVEWESNGQPENNYKTTPPVLDSD GSFFLYSDLTVDKSRWQQGNVFSCSVMHEALHNHYTQESLSLSP GK | HC; CD28 |

TABLE 20-continued

SEQUENCES

| Seq ID | sequence | name |
|---|---|---|
| 483 | DIQTTQTTSSLSASLGDRVTISCRAGQDISNYLNWYQQKPDGTVKL<br>LIYYTSRLHSGVPSRFSGSGSGTDYSLTISNLEQEDIATYFCQQGH<br>TLPWTFGGGTKLEIKRTVAAPSVFIFPPSDEQLKSGTASVVCLLNN<br>FYPREAKVQWKVDNALQSGNSQESVTEQDSKDSTYSLSSTLTLSK<br>ADYEKHKVYACEVTHQGLSSPVTKSFNRGEC | LC-CD28 |
| 484 | EVQLVESGGGLVQPGGSLRLSCAASGFTFSDYWMSWVRQAPGK<br>GLEWVADIKNDGSYTNYAPSLINRFTISRDNAKNSLYLQMNSLRA<br>EDTAVYYCARELTGTWGQGTMVTVSBGGGGSGGGGGGGGSG<br>GGGSDIVMTQSPDSLAVSLGERATINCKSSQSLLSSGNQKNYLAW<br>YQQKPGQPPKLLIYYASTRQSGVPDRFSGSGSGTDFTLTISSLQAE<br>DVAVYYCLQYDRYPFTFGQGTKLEIKSGGGGSEVQLVESGGGLV<br>QPGGSLRLSCAASGFTFSTYAMNWVRQAPGKGLEWVGRIRSKYN<br>NYATYYADSVKGRFTISRDDSKNTLYLQMNSLRAEDTAVYYCVRH<br>GNFGDSYVSWFEYWGQGTLVTVSSGKPGSGKPGSGKPGSGKPG<br>SQAVVTQEPSLTVSPGGTVTLTCGSSTGAVTTSNYANWVQQKPG<br>KSPRGLIGGTNKRAPGVPARFSGSLLGGKAALTISGAQPEDEADY<br>YCALWYSNHWVFGGGTKLTVLEPKSSDKTHTCPPCPAPEFEGGP<br>SVFLFPPKPKDTLMISRTPEVTCVVVDVSHEDPEVKENWYVDGVE<br>VHNAKTKPREEQYNSTYRVVSVLTVLHQDWLNGKEYKCKVSNKA<br>LPASIEKTISKAKGQPREPQVYTLPPCRKKLTKNQVSLTCLVKGFY<br>PSDIAVEWESNGQPENNYKTTPPVLKSDGSFFLYSKLTVDKSRWQ<br>QGNVFSCSVMHEALHNHYTQKSLSLSPGK | CD137.39scfv-<br>CD3scfv-<br>Fc |
| 486 | QVQLVQSGAEVKKPGASVKVSCKASGYTFSSYWMHWVRQAPGQ<br>RLEWMGEINPNGNGHTNYSQKFQGRVTITVDKSASTAYMELSSLRS<br>EDTAVYYCARSFTTARAFAYWGQGTLVTVSSGGGGGGGGGGGG<br>GGSGGGGSDIVMTQSPPTLSLSPGERVTLSCRASQSISDYLHWYQ<br>QKPGQSPRLLIKYASQSISGIPARFSGSGSGTDFTLTISSLEPEDFA<br>VYYCQDGHSFPPTFGGGTKVEIKSGGGGSEVQLVESGGGLVQPG<br>GSLRLSCAASGFTFSTYAMNWVRQAPGKGLEWYGRIRSKYNNYA<br>TYYADSVKGRFTISRDDSKNTLYLQMNSLRAEDTAVYYCVRHGNF<br>GDSYVSWFEYWGQGTLVTVSSGKPGSGKPGSGKPGSGKPGSQA<br>VVTQFPSLTVSPGGTVTLTCGSSTGAVTTSNYANWVQQKPGKSP<br>RGLIGGTNKRAPGVPARFSGSLLGGKAALTISGAQPEDEADYYCA<br>LWYSNHWVFGGGTKLTVLEPKSSDKTHTCPPCPAPEFEGGPSVF<br>LFPPKPKDTLMISRTPEVTCVVVDVSHEDPEVKFNWYVDGVEVHN<br>AKTKPREEQYNSTYRVVSVLTVLHQDWLNGKEYKCKVSNKALPAS<br>IEKTISKAKGQPREPQVYTLPPCRKKLTKNQVSLTCLVKGFYPSDIA<br>VEWESNGQPENNYKTTPPVLKSDGSFFLYSKLTVDKSRWQQGNV<br>FSCSVMHEALHNHYTQKSLSLSPGK | CD137.b<br>scfv-<br>CD3scfv-Fc |
| 487 | QVQLQQWGAGLLKPSETLSLTCAVYGGSFSGYYWSWIRQSPEKG<br>LEWIGEINHGGYVTYNPSLESRVTISVDTSKNQFSLKLSSVTAADTA<br>VYYCARDYGPGNYDWYFDLWGRGTLVTVSSASTKGPSVFPLARS<br>SKSTSGGTAALGCLVKDYFPEPVTVSWNSGALTSGVHTFPAVLQS<br>SGLYSLSSVVTVPSSSLGTQTYICNVNHKPSNTKVDKRVERKSCD<br>KTHTCPPCPAPEFEGGPSVFLFPPKPKDTLMISRTPEVTCVVVDVS<br>HEDPEVKFNWYVDGVEVHNAKTKPREEQYNSTYRVVSVLTVLHQ<br>DWLNGKEYKCKVSNKALPASIEKTISKAKGQPREPQVYTLPPCRK<br>KLTKNQVSLTCLVKGFYPSDIAVEWESNGQPENNYKTTPPVLKSD<br>GSFFLYSKLTVDKSRWQQGNVFSCSVMHEALHNHYTQKSLSLSP<br>GKSGGGGSEVQLVESGGGLVQPGGSLRLSCAASGFTFSTYAMN<br>VWRQAPGKGLEWVGRIRSKYNNYATYYADSVKGRFTISRDDSKN<br>TLYLQMNSLRAEDTAVYYCVRHGNFGDSYVSWFEYWGQGTLVTV<br>SSGGGGGGGGSGGGSGGGGSQAVVTQERSLTVSPGGTVTLT<br>CGSSTGAVTTSNYANWVQQKPGKSPRGLIGGTNKRAPGVPARFS<br>GSLLGGKAALTISGAQPEDEADYYCALWYSNHWWFGGGTKLTVL | Fc-U-<br>Fc-CD3scfv |
| 488 | EPKSSDKTHTCPPCPAPEFEGGPSVFLFPPKPKDTUMISRTPEVTC<br>VVVDVSHEDPEVKFNWYVDGVEVHNAKTKPREEQYNSTYRVVSV<br>LTVLHQDWLNGKEYKCKVSNKALPASIEKTISKAKGQPREPQVCTL<br>PPSRDELTKNQVSLTCLVEGFYPSDIAVEWESNGQPENNYKTTPP<br>VLDSDGSFFLYSDLTVDKSRWQQGNVFSCSVMHEALHNHYTQES<br>LSLSPGKSGGGSQVQLVQSGAEVKKPGASVKVSCKASGYTFSSY<br>WMHWWVRQAPGQRLEWMGEINPNGNGHTNYSQKFQGRVTITVDKS<br>ASTAYMELSSLRSEDTAVYYCARSFTTARAFAYWGQGTLVTVSSG<br>KPGSGKPGSGKPGSGKPGSDIVMTQSPPTLSLSPGERVTLSCRAS<br>QSISDYLHWYQQKPGQSPRLLIKYASQSISGIPARFSGSGSGTDFT<br>LTISSLEPEDFAVYYCQDGHSFPPTFGGGTKVEIK | Fc-<br>CD137.Bscfv |
| 489 | EPKSSDKTHTCPPCPAPEFEGGPSVFLFPPKPKDTLMISRTPEVTG<br>VVVDVSHEDPEVKFNWYVDGVEVHNAKTKPREEQYNSTYRVVSV<br>LTVLHQDWLNGKEYKCKVSNKALPASIEKTISKAKGQPREPQVCTL<br>PPSRDELTKNQVSLTCLVEGFYPSDIAVEWESNGQPENNYKTTPP | Fc-<br>CD137.Bscfv-<br>CD137.Bscfv |

TABLE 20-continued

| SEQUENCES | | |
|---|---|---|
| Seq ID | sequence | name |

VLDSDGSFFLYSDLTVDKSRWQQGNVFSCSVMHEALHNHYTQES
LSLSPGKSGGGSQVQLVQSGAEVKKPGASVKVSCKASGYTFSSY
WMHWVRQAPGQRLEWMGEINPGNGHTNYSQKFQGRVTITVDKS
ASTAYMELSSLRSEDTAVYYCARSFTTARAFAYWGQGTLVTVSSG
KPGSGKPGSGKPGSGKPGSDIVMTQSPPTLSLSPGERVTLSCRAS
QSISDYLHWYQQKPGQSPRLLIKYASQSISGIPARFSGSGSGTDFT
LTISSLEREDFAVYYCQDGHSFPPTFGGGTKVEIKSGGGSQVQLV
QSGAEVKKPGASVKVSCKASGYTFSSYWMHWVRQAPGQRLEW
MGEINPGNGHTNYSQKFQGRVTITVDKSASTAYMELSSLRSEDTA
VYYCARSFTTARAFAYWGQGTLVTVSSGKPGSGKPGSGKPGSGK
PGSDIVMTQSPPTLSLSPGERVTLSCRASQSISDYLHWYQQKPGQ
SPRLLIKYASQSISGIPARFSGSGSGTDFTLTISSLEPEDFAVYYCQ
DGHSFPPTFGGGTKVEIK

490    EVQLVESGGGLVQPGGSLRLSCAASGFTESTYAMNWVRQAPGK      CD3scfv-
GLEWVGRIRSKYNNYATYYADSVKGRFTISRDDSKNTLYLQMNSL     CD137.39scfv-Fc
RAEDTAVYYCVRHGNFGDSYVSWFEYWGQGTLVTVSSGGGGSG
GGGSGGGGGGGGSQAVVTQEPSLTVSPGGTVTLTCGSSTGAV
TTSNYANWVQQKPGKSPRGLIGGTNKRAPGVPARFSGSLLQGKA
ALTISGAQPEDEADYYCALWYSNHWVFGGGTKLTVLSGGGGSEV
QLVESGGGLVQPGGSLRLSCAASGFTFSDYWMSWVRQARGKGL
EWVADIKNDGSYTNYAPSLINRFTISRDNAKNSLYLQMNSLRAED
TAVYYCARELTGTWGQGTMVTVSSGKPGSGKPGSGKPGSGKPG
SDIVMTQSPDSLAVSLGERATINCKSSQSLLSSGNQKNYLAWYQQ
KPGQPPKLLIYYASTRQSGVPDRFSGSGSGTDFTLTISSLQAEDVA
VYYCLQYDRYPFTFGQGTKLEIKEPKSSDKTHTCPPCPAPEFEGG
PSVFLFPPKPKDTLMISRTPEVTCVVVDVSHEDPEVKFNWYVDGV
EVHNAKTKPREEQYNSTYRVVSVLTVLHQDWLNGKEYKCKVSNK
ALPASIEKTISKAKGQPREPQVYTLPPCRKKLTKNQVSLTCLVKGF
YPSDIAVEWESNGQPENNYKTTPPVLKSDGSFFLYSKLTVDKSRW
QQGNVFSCSVMHEALHNHYTQKSLSLSPGK 491    EVQLVESGGGLVQRGGSLRLSCAASGFTFSTYAMNWVRQAPGK      CD3scfv-
GLEWVGRIRSKYNNYATYYADSVKGRFTISRDDSKNTLYLQMNSL     CD137.Bscfv-Fc
RAEDTAVYYCVRHGNFGDSYVSWFEYWGQGTLVTVSSGGGGSG
GGGSGGGGSGGGGSQAVVTQEPSLTVSPGGTVTLTCGSSTGAV
TTSNYANWVQQKPGKSPRGLIGGTNKRAPGVPARFSGSLLGGKA
ALTISGAQREDEADYYCALWYSNHWVFGGGTKLTVLSGGGGSQV
QLVQSGAEVKKPGASVKVSCKASGYTFSSYWMHWVRQAPGQRL
EWMGEINPGNGHTNYSQKFQGRVTITVDKSASTAYMELSSLRSED
TAVYYCARSFTTARAFAYWGQGTLVTVSSGKPGSGKPGSGKPGS
GKPGSDIVMTQSPPTLSLSPGERVTLSCRASQSISDYLHWYQQKR
GQSPRLLIKYASQSISGIPARFSGSGSGTDFTLTISSLEPEDFAVYY
CQDGHSFPPTFGGGTKVEIKEPKSSDKTHTCPPCPAPEFEGGPSV
FLFPPKPKDTLMISRTPEVTCVVVDVSHEDPEVKENWYVDGVEVH
NAKTKPREEQYNSTYRVVSVLTVLHQDWLNGKEYKCKVSNKALPA
SIEKTISKAKGQPREPQVYTLPPCRKKLTKNQVSLTCLVKGFYPSDI
AVEWESNGQPENNYKTTPPVLKSDGSFFLYSKLTVDKSRWQQGN
VFSCSVMHEALHNHYTQKSLSLSPGK 492    QVQLVQSGAEVKKPGASVKVSCKASGYTFTNFGITWVRQAPGQG     CLDN182scfv-
LEWMGBYPSSGNTFYNEKFKGRVTMTTDTSTSTAYMELRSLRSD      CD3scfv-Fc
DTAVYYCARGGGPLRSRYFDYWGQGTLVTVSSGGGGSGGGGSG
GGGSGGGGSDIVMTQSPDSLAVSLGERATINCRSSQSLFSSGNQ
KNYLTWYQQKPGQPPKLLIYWASTRESGVPDRFSGSGSGTDFTLT
ISSLQAEDVAVYYCQNDYYYPLTFGGGTKVEIKSGGGGSEVQLVE
SGGGLVQPGGSLRLSCAASGFTFSTYAMNWVRQAPGKGLEWVG
RIRSKYNNYATYYADSVKGRFTISRDDSKNTLYLQMNSLRAEDTAV
YYCVRHGNFGDSYVSWFEYWGQGTLVTVSSGKPGSGKPGSGKP
GSGKPGSQAVVTQEPSLTVSPGGTVTLTCGSSTGAVTTSNYANW
VQQKPGKSPRGLIGGTNKRAPGVPARFSGSLLGGKAALTISGAQR
EDEADYYCALWYSNHWVFGGGTKLTVLEPKSSDKTHTCPPCPAP
EFEGGPSVFLFPPKPKDTLMISRTPEVTCVVVDVSHEDPEVKFNW
YVDGVEVHNAKTKPREEQYNSTYRVVSVLTVLHQDWLNGKEYKC
KVSNKALPASIEKTISKAKGQPREPQVYTLPPCRKKLTKNQVSLTC
LVKGFYPSDIAVEWESNGQPENNYKTTPPVLKSDGSFFLYSKLTV
DKSRWQQGNVFSCSVMHEALHNHYTQKSLSLSPGK 493    QVQLVQSGAEVKKPGASVKVSCKASGYTFTNSGMNWVRQAPGQ     CLDN182scfv-
GLEWMGWINTNTGEPTFAEEFRGRVTMTRDTSISTAYMELSRLRS     CD3scfv-Fc
DDTAVYYCARYYYGNSFAYWGQGTLVTVSSGGGGGGGGGGGG
GGGSGGGGSDIVMTQSPDSLAVSLGERATINCKSSQSLLNSGNQKN
YLTWYQQKPGQPPKLLIYWASTRESGVPDRFSGSGSGTDFTLTIS
SLQAEDVAVYYCQNNYFYPLTFGGGTKVEIKSGGGGSEVQLVESG
GGLVQPGGSLRLSCAASGFTFSTYAMNWVRQAPGKGLEWVGRIR
SKYNNYATYYADSVKGRFTISRDDSKNTLYLQMNSLRAEDTAVYY TABLE 20-continued

| SEQUENCES | | |
| --- | --- | --- |
| Seq ID | sequence | name |

CVRHGNFGDSYVSWFEYWGQGTLVTVSSGKPGSGKPGSGKPGS
GKPGSQAVVTQEPSLTVSPGGTVTLTCGSSTGAVTTSNYANWVQ
QKPGKSPRGLIGGTNKRAPGVPARFSGSLLGGKAALTISGAQPED
EADYYCALWYSNHWVFGGGTKLTVLERKSSDKTHTCPPCPAPEF
EGGPSVFLFPPKPKDTLMISRTPEVTCVVVDVSHEDPEVKFNWYV
DGVEVHNAKTKPREEQYNSTYRVVSVLTVLHQDWLNGKEYKCKV
SNKALPASIEKTISKAKGQPREPQVYTLPPCRKKLTKNQVSLTCLV
KGFYPSDIAVEWESNGQPENNYKTTPPVLKSDGSFFLYSKLTVDK
SRWQQGNVFSCSVMHEALHNHYTQKSLSLSPGK

494    QVQLQQWGAGLLKPSETLSLTCAVYGGSFSGYYWSWIRQSPEKG    CD137.Ufab-
       LEWIGEINHGGYVTYNPSLESRVTISVQTSKNQFSLKLSSVTAADTA    Fc--
       VYYCARDYGPGNYDWYFDLWGRGTLVTVSSSASTKGPSVFPLARS    CD3scfv-
       SKSTSGGTAALGCLVKDYFPEPVTVSWNSGALTSGVHTFPAVLQS    DLL3scfv
       SGLYSLSSVVTVPSSSLGTQTYICNVNHKPSNTKVDKRVEPKSCD
       KTHTCPPCPAPEFEGGPSVFLFPPKPKDTLMISRTPEVTGVVVDVS
       HEDPEVKFNWYVDGVEVHNAKTKPREEQYNSTYRVVSVLTVLHQ
       DWLNGKEYKCKVSNKALPASIEKTISKAKGQPREPQVYTLPPCRK
       KLTKNQVSLTCLVKGFYPSDIAVEWESNGQPENNYKTTPPVLKSD
       GSFFLYSKLTVDKSRWQQGNVFSCSVMHEALHNHYTQKSLSLSP
       GKSGGGGSEVQLVESGGGLVQPGGSLRLSCAASGFTFSTYAMN
       WVRQAPGKGLEWVGRIRSKYNNYATYYADSVKGRATISRDDSKN
       TLYLQMNSLRAEDTAVYYCVRHGNFGDSYVSWFEYWGQGTLVTV
       SSGGGGSGGGGSGGGGGGGGGSQAVVTQEPSLTVSPGGTVTLT
       CGSSTGAVTTSNYANWWQQKPGKSPRGLIGGTNKRAPGVPARFS
       GSLLGGKAALTISGAQPEDEADYYCALWYSNHWVFGGGTKLTVLS
       GGGGSQVQLVQSGAEVKKPGASVKVSCKASGYTFTDYFMNWVR
       QAPGQGLEWMGVINPYNDITIYNQKFQGRVTMTVDRSTSTVYMEL
       SSLRSEDTAVYYCAREGVLYDGYYEGAYWGQGTLVTVSSGGGGS
       GGGGSGGGGSDIQLTQSPSFLSASVGDRVTITCKASQNVGIAVAW
       YQQKPGKAPKLLIYAASNRYTGVPSRFSGSGSGTEFTLTISSLQPE
       DFATYYCQQYSTYPYTFGQGTKLEIK 495    QVQLVQSGAEVKKPGASVKVSCKASGYTFSSYWMHWVRQAPGQ    CD137.Bfab-
       RLEWMGEINPGNGHTNYSQKFQGRVTITVDKSASTAYMELSSLRS    Fc-
       EDTAVYYCARSFTTARAFAYWGQGTLVTVSSSASTKGPSVFPLAPS    CDSscfv
       SKSTSGGTAALGCLVKDYFPEPVTVSWNSGALTSGVHTFPAVLQS
       SGLYSLSSVVTVPSSSIGTQTYICNVNHKPSNTKVQKRVEPKSCD
       KTHTCPPCPAPEFEGGPSVFLFPPKPKDTLMISRTPEVTCVVVDVS
       HEDPEVKENWYVDGVEVHNAKTKPREEQYNSTYRVVSVLTVLHQ
       DWLNGKEYKCKVSNKALPASIEKTISKAKGQPREPQVCTLPPSRD
       ELTKNQVSLTCLVEGFYPSDIAVEWESNGQPENNYKTTPPVLDSD
       GSFFLYSDLTVDKSRWQQGNVFSCSVMHEALHNHYTQESLSLSP
       GKSGGGGSEVQLVESGGGLVQPGGSLRLSCAASGFTESTYAMN
       WWRQAPGKGLEWVGRIRSKYNNYATYYADSVKGRFTISRDDSKN
       TLYLQMNSLRAEDTAVYYCVRHGNFGDSYVSWFEYWGQGTLVTV
       SSGGGGSGGGGSGGGGSGGGGSQAVVTQEPSLTVSPGGTVTLT
       CGSSTGAVTTSNYANWVQQKRGKSPRGLIGGTNKRAPGVPARFS
       GSLLGGKAALTISGAQPEDEADYYCALWYSNHWVFGGGTKLTVL 496    QVQLVQSGAEVKKPGASVKVSCKASGYTESSYWMHWVRQAPGQ    CD137.Bfab-
       RLEWMGEINPGNGHTNYSQKFQGRVTITVDKSASTAYMELSSLRS    Fc--
       EDTAVYYCARSFTTARAFAYWGQGTLVTVSSSASTKGPSVFPLAPS    CD3scfv-
       SKSTSGGTAALGCLVKDYFPEPVTVSWNSGALTSGVHTFPAVLQS    DLL3scfv
       SGLYSLSSVVTVPSSSLGTQTYICNVNHKPSNTKVDKRVEPKSCD
       KTHTCPPCPAPEFEGGPSVFLAPPKPKDTLMISRTPEVTCVVVDVS
       HEDPEVKFNWYVDGVEVHNAKTKPREEQYNSTYRVVSVLTVLHQ
       DWINGKEYKCKVSNKALPASIEKTISKAKGQPREPQVCTLPPSRD
       ELTKNQVSLTCLVEGFYPSDIAVEWESNGQPENNYKTTPPVLQSD
       GSFFLYSDLTVDKSRWQQGNVFSCSVMHEALHNHYTQESLSLSP
       GKSGGGGSEVQLVESGGGLVQPGGSLRLSCAASGFTFSTYAMN
       WRQAPGKGLEWVGRIRSKYNNYATYYADSVKGRATISRDDSKN
       TLYLQMNSLRAEDTAVYYCVRHGNFGDSYVSWFEYWGQGTLVTV
       SSGGGGSGGGGSGGSGGGGSQAVVTQEPSLTVSPGGTVTLT
       CGSSTGAVTTSNYANWVQQKFGKSPRGLIGGTNKRAPGVPARFS
       GSLLGGKAALTISGAQPEDEADYYCALWYSNHWVFGGGTKLTVLS
       GGGGSQVQLVQSGAEVKKPGASVKVSCKASGYTFTDYFMNWVR
       QAPGQGLEWMGVINPYNDITIYNQKFQGRVTMTVDRSTSTVYMEL
       SSLRSEDTAVYYCAREGVLYDGYYEGAYWGQGTLVTVSSGGGGS
       GGGGSGGGGSDIQLTQSPSFLSASVGDRVTITCKASQNVGIAVAW
       YQQKPGKAPKLLIYAASNRYTGVPSRFSGSGSGTEFTLTISSLQPE
       DFATYYCQQYSTYPYTFGQGTKLEIK 497    QVQLVQSGAEVKKPGASVKVSCKASGYTFTDYFMNWVRQAPGQ    DLL3scfv-
       GLEWMGVINPYNDITIYNQKFQGRVTMTVQRSTSTVYMELSSLRS    CD3scfv-
       EDTAVYYCAREGVLYDGYYEGAYWGQGTLVTVSSGGGGGGGG    Fc- TABLE 20-continued

SEQUENCES

| Seq ID | sequence | name |
|---|---|---|
| | SGGGGSDIQLTQSPSFLSASVGDRVTITCKASQNVGIAVAWYQQK<br>PGKAPKLUYAASNRYTGVPSRFSGSGSGTEFTLTISSLQPEDFAT<br>YYCQQYSTYPYTFGQGTKLEIKSGGGSEVQLVESGGGLVQPGGS<br>LRLSCAASGFTFSTYAMNWVRQAPGKGLEWVGRIRSKYNNYATY<br>YADSVKGRFTISRDDSKNTLYLQMNSLRAEDTAVYYCVRHGNFGD<br>SYVSWFEYWGQGTLVTVSSGKPGSGKPGSGKPGSGKPGSQAVV<br>TQEPSLTVSPGGTVTLTCGSSTGAVTTSNYANWVQQKPGKSPRG<br>LIGGTNKRAPGVPARFSGSLLGGKAALTISGAQPEDEADYYCALW<br>YSNHWVFGGGTKLTVLEPKSSDKTHTCPPCPAPEFEGGPSVFLAP<br>PKPKDTLMISRTPEVTCVVVDVSHEDPEVKFNWYVDGVEVHNAKT<br>KPREEQYNSTYRVVSVLIVLHQDWLNGKEYKCKVSNKALPASIEK<br>TISKAKGQPREPQVYTLPPCRKKLTKNQVSLTCLVKGFYPSDIAVE<br>WESNGQPENNYKTTPPVLKSDGSFFLYSKLTVDKSRWQQGNVFS<br>CSVMNEALNNHYTQKSLSLSPGKSGGGSQVQLVQSGAEVKKPGA<br>SVKVSCKASGYTFSSYWMHWVRQAPGQRLEWMGEINPGNGHTN<br>YSQKFQGRVTITVDKSASTAYMELSSLRSEDTAVYYCARSFTTARA<br>FAYWGQGTLVTVSSGKPGSGKPGSGKPGSGKPGSDIVMTQSPPT<br>LSLSPGERVTLSCRASQSISDYLHWYQQKPGQSPRLLIKYASQSIS<br>GIPARFSGSGSGTDFTLTISSLEPEDFAVYYCQDGHSFPPTFGGGT<br>KVEIK | CD137.Bscfv |
| 498 | QVQLVQSGAEVKKPGASVKVSCKASGYTFTDYFMNWVRQAPGQ<br>GLEWMGVINPYNDITIYNQKFQGRVTMTVDRSTSTVYMELSSLRS<br>EDTAVYYCAREGVLYDGYYEGAYWGQGTLVTVSSASTKGPSVFP<br>LAPSSKSTSGGTAALGCLVKDYFPEPVTVSWNSGALTSGVHTFPA<br>VLQSSGLYSLSSVVTVPSSSLGTQTYICNVNHKPSNTKVDKRVEPK<br>SCDKTHTCPPCPAPEFEGGPSVFLFPPKPKDTLMISRTPEVTCVVV<br>DVSHEDPEVKFNWYVDGVEVHNAKTKPREEQYNSTYRVVSVLTV<br>LHQDWLNGKEYKCKVSNKALPASIEKTISKAKGQPREPQVCTLPP<br>SRDELTKNQVSLTCLVEGFYPSDIAVEWESNGQPENNYKTTPPVL<br>DSDGSFFLYSDLTVDKSRWQQGNVFSCSVMHEALHNHYTQESLS<br>LSPGKSGGGSQVQLVQSGAEVKKPGASVKVSCKASGYTFSSYW<br>MHWWRQAPGQRLEWMIGEINPGNGHTNYSQKFQGRVTITVDKSÁ<br>STAYMELSSLRSEDTAVYYCARSFTTARAFAYWGQGTLVTVSSGK<br>PGSGKPGSGKFGSGKPGSDIVMTQSPPTLSLSPGERVTLSCRAS<br>QSISDYLHWYQQKPGQSPRLLIKYASQSISGIPARFSGSGSGTDFT<br>LTISSLEPEDFAVYYCQDGHSFPPTFGGGTKVEIK | DLL3Fab-<br>Fc-<br>CD137.Bscfv |
| 499 | QVQLVQSGAEVKKPGASVKVSCKASGYTFTDYFMNWRQAPGQ<br>GLEWMGVINPYNDITIYNQKFQGRVTMTVDRSTSTVYMELSSLRS<br>EDTAVYYCAREGVLYDGYYEGAYWGQGTLVTVSSASTKGPSVFP<br>LARSSKSTSGGTAALGCLVKDYFREPVTVSWNSGALTSGVHTFRA<br>VLQSSGLYSLSSVVTVPSSSLGTQTYICNVNHKPSNTKVDKRVEPK<br>SCDKTHTCPPCPAPEFEGGPSVFLFPPKPKDTLMISRTPEVTCVVV<br>DVSHEDPEVKFNWYVDGVEVHNAKTKPREEQYNSTYRVVSVLTV<br>LHQDWLNGKEYKCKVSNKALPASIEKTISKAKGQPREPQVCTLPP<br>SRDELTKNQVSLTCLVEGFYPSDIAVEWESNGQPENNYKTTPPVL<br>DSDGSFFLYSDLTVDKSRWQQGNVFSCSVMHEALHNHYTQESLS<br>LSPGKSGGGSQVQLVQSGAEVKKPGASVKVSCKASGYTFSSYW<br>MHWVRQAPGQRLEWMGEINPGNGHTNYSQKFQGRVTITVDKSA<br>STAYMELSSLRSEDTAVYYCARSFTTARAFAYWGQGTLVTVSSGK<br>PGSGKPGSGKPGSGKPGSDIVMTQSPPTLSLSPGERVTLSCRAS<br>QSISDYLHWYQQKPGQSPRLLIKYASQSISGIPARFSGSGSGTDFT<br>LTISSLEPEDFAVYYCQDGHSFPPTFGGGTKVEIKSGGGSQVQLV<br>QSGAEVKKPGASVKVSCKASGYTFSSYWMHWRQAPGQRLEW<br>MGEINPGNGHTNYSQKFQGRVTITVDKSASTAYMELSSLRSEDTA<br>VYYCARSFTTARAFAYWGQGTLVTVSSGKPGSGKPGSGKPGSGK<br>PGSDIVMTQSPPTLSLSPGERVTLSCRASQSISDYLHWYQQKPGQ<br>SPRLLIKYASQSISGIPARFSGSGSGTDFTLTISSLEPEDFAVYYCQ<br>DGHSFPPTFGGGTKVEIK | DLL3Fab-<br>Fc-<br>CD137.Bscfv-<br>CD137.Bscfv |
| 500 | QVQLVQSGAEVKKPGASVKVSCKASGYTFTSYYINWVRQAPGQG<br>LEWIGSIYPGNVNTNYNEKFKDRATLTVDTSISTAYMELSRLRSDD<br>TAVFYCTRSHYGLDWNFDVWGQGTTVTVSSGGGGSGGGGSGG<br>GGSGGGGSDIQMTQSPSSLSASVGDRVTITCHASQNIYVWLNWY<br>QQKPGKAPKLLIYKASNLHTGVPSRFSGSGSGTDFTLTISSLQPED<br>FATYYCQQGQTYPYTFGGGTKVEIKSGGGGSQVQLVQSGAEVKK<br>PGASVKVSCKASGYTFSSYWMHWVRQAPGQRLEWMGEINPGNG<br>HTNYSQKFQGRVTITVQKSASTAYMELSSLRSEDTAVYYCARSFTT<br>ARAFAYWGQGTLVTVSSGKPGSGKPGSGKPGSGKPGSDIVMTQS<br>PPTLSLSPGERVTLSCRASQSISDYLHWYQQKPGQSPRLLIKYASQ<br>SISGIPARFSGSGSGTDFTLTISSLEPEDFAVYYCQDGHSFPPTFG<br>GGTKVEIKEPKSSDKTHTCPPCPAPEFEGGPSVFLFPPKPKDTLMI<br>SRTPEVTCVVVDVSHEDPEVKFNWYVDGVEVHNAKTKPREEQYN<br>STYRVVSVLTVLHQDWLNGKEYKCKVSNKALPASIEKTISKAKGQP<br>REPQVYTLPPCRKKLTKNQVSLTCLVKGFYPSDIAVEWESNGQPE | CD28(C50S)<br>scfv-<br>CD137.Bscfv-<br>Fc |

TABLE 20-continued

SEQUENCES

| Seq ID | sequence | name |
|---|---|---|
| | NNYKTTPPVLKSDGSFFLYSKLTVDKSRWQQGNVFSCSVMHEAL HNHYTQKSLSLSPGK | |
| 501 | QVQLVQSGAEVKKPGASVKVSCKASGYTFTSYYINWVRQAPGQG LEWIGSIYPGNVNTNYNEKFKDRATLTVDTSISTAYMELSRLRSDD TAVYFCTRSHYGLDWNFDVWGQGTTVTVSSGGGGSGGGGSGG GGSGGGGSDIQMTQSPSSLSASVGDRVTITCHASQNIYVWLNWY QQKPGKAPKLLIYKASNLHTGVPSRFSGSGSGTDFTLTISSLQPED FATYYCQQGQTYPYTFGGGTKVEIKSGGGGSEVQLVESGGGLVQ PGGSLRLSCAASGFTFSDYWMSWVRQAPGKGLEWVADIKNDGS YTNYAPSLTNRFTISRDNAKNSLYLQMNSLRAEDTAVYYCARELTG TWGQGTMVTVSSGKPGSGKPGSGKPGSGKPGSDIVMTQSPDSL AVSLGERATINCKSSQSLLSSGNQKNYLAWYQQKRGQPPKLLIYY ASTRQSGVPDRFSGSGSGTDFTLTISSLQAEDVAVYYCLQYDRYP FTFGQGTKLEIKEPKSSDKTHTCPPCPAPEFEGGPSVFLFPPKPKD TLMISRTPEVTCVVVDVSHEDPEVKFNWYVDGVEVHNAKTKPREE QYNSTYRVVSVLTVLHQDWLNGKEYKCKVSNKALPASIEKTISKAK GQPREPQVYTLPPCRKKLTKNQVSLTCLVKGFYPSDIAVEWESNG QPENNYKTTPPVLKSDGSFFLYSKLTVDKSRWQQGNVFSCSVMH EALHNHYTQKSLSLSPGK | CD28(C50S) scfv- CD137.39scfv- Fc |
| 502 | QVQLVQSGAEVKKPGASVKVSCKASGYTFSSYWMHWVRQAPGQ RLEWMGEINPGNGHTNYSQKFQGRVTITVDKSASTAYMELSSLRS EDTAVYYCARSFTTARAFAYWGQGTLVTVSSGGGGSGGGGSGG GGSGGGGSDIVMTQSPPTLSLSPGERVTLSCRASQSISDYLHWYQ QKPGQSPRLLIKYASQSISGIPARFSGSGSGTDFTLTISSLEPEDFA VYYCQDGHSFPPTFGGGTKVEIKSGGGGSQVQLVQSGAEVKKPG ASVKVSCKASGYTFTSYYIHWVRQAPGQGLEWIGSIYPGNVNTNY NEKFKDRATLTVDTSISTAYMELSRLRSDDTAVYFCTRSHYGLDW NFDVWGQGTTVTVSSGKPGSGKPGSGKPGSGKPGSDIQMTQSP SSLSASVGDRVTITCHASQNIYVWLNWYQQKPGKAPKLUYKASNL HTGVPSRFSGSGSGTDFTLTISSLQPEDFATYYCQQGQTYPYTFG GGTKVEIKEPKSSDKTHTCPPCPAPEFEGGPSVFLFPPKPKDTLMI SRTPEVTCVVVDVSHEDPEVKFNWYVDGVEVHNAKTKPREEQYN STYRVVSVLTVLHQDWLNGKEYKCKVSNKALPASIEKTISKAKGQP REPQVYTLPPCRKKLTKNQVSLTCLVKGFYPSDIAVEWESNGQPE NNYKTTPPVLKSDGSFFLYSKLTVDKSRWQQGNVFSCSVMHEAL HNHYTQKSLSLSPGK | CD137.Bscfv- CD28(C50S) scfv-Fc |
| 503 | EVQLVESGGGLVQPGGSLRLSCAASGFTFSDYWMSWVRQAPGK GLEWVADIKNDGSYTNYAPSLTNRFTISRDNAKNSLYLQMNSLRA EDTAVYYCARELTGTWGQGTMVTVSSGGGGSGGGGSGGGGSG GGGSDIVMTQSPDSLAVSLGERATINCKSSQSLUSSGNQKNYLAW YQQKPGQPPKLLIYYASTRQSGVPDRFSGSGSGTDFTLTISSLQAE DVAVYYCLQYDRYPFTFGQGTKLEIKSGGGGSQVQLVQSGAEVK KPGASVKVSCKASGYTFTSYYINWVRQAPGQGLEWIGSIYPGNVN TNYNEKFKDRATLTVDTSISTAYMELSRLRSDDTAVYFCTRSHYGL DWNFDVWGQGTTVTVSSGKPGSGKPGSGKPGSGKFGSDIQMTQ SPSSLSASVGDRVTITCHASQNIYVWLNWYQQKPGKAPKLLIYKAS NLHTGVPSRFSGSGSGTDFTLTISSLQPEDFATYYCQQGQTYPYT FGGGTKVEIKEPKSSDKTHTCPPCPAPEFEGGPSVFLFPPKPKDTL MISRTPEVTGVVVDVSHEDPEVKFNWYVDGVEVHNAKTKPREEQ YNSTYRVVSVLTVLHQDWLNGKEYKCKVSNKALPASIEKTISKAKG QPREPQVYTLPPCRKKLTKNQVSLTCLVKGFYPSDIAVEWESNGQ PENNYKTTPPVLKSDGSFFLYSKLTVDKSRWQQGNVFSCSVMHE ALHNHYTQKSLSLSPGK | CD137.39scfv- CD28(C50S) scfv-Fc |
| 504 | GGGGS | linker |
| 505 | GKPGS | linker |
| 506 | GEPGS | linker |
| 507 | GGPGS | linker |

The invention claimed is:

1. An anti-CD28, anti-CD3, and anti-DLL3 trispecific antibody, comprising:

a first peptide chain comprising (1) an anti-CD28 single chain fragment variable region (scFv), (2) an anti-CD3 scFv and (3) one peptide chain of a fragment crystallizable region (Fc region);

a second peptide chain comprising (1) one peptide chain of an anti-DLL3 Fab fragment and (2) another peptide chain of the Fc region; and a third peptide chain comprising another peptide chain of the anti-DLL3 Fab fragment, and wherein the first peptide chain comprises SEQ ID NO: 481, the second peptide chain comprises SEQ ID NO: 276 and the third peptide chain comprises SEQ ID NO: 302; or wherein the first peptide chain comprises SEQ ID NO: 481, the second peptide chain comprises SEQ ID NO: 291 and the third peptide chain comprises SEQ ID NO: 295; or wherein the first peptide chain comprises SEQ ID NO: 481, the second peptide chain comprises SEQ ID NO: 290 and the third peptide chain comprises SEQ ID NO: 298; or wherein the first peptide chain comprises SEQ ID NO: 481, the second peptide chain comprises SEQ ID NO: 276 and the third peptide chain comprises SEQ ID NO: 297.

2. The trispecific antibody of claim 1, wherein the first peptide chain comprises SEQ ID NO: 481, the second peptide chain comprises SEQ ID NO: 276 and the third peptide chain comprises SEQ ID NO: 302.

3. The trispecific antibody of claim 1, wherein the first peptide chain comprises SEQ ID NO: 481, the second peptide chain comprises SEQ ID NO: 291 and the third peptide chain comprises SEQ ID NO: 295.

4. The trispecific antibody of claim 1, wherein the first peptide chain comprises SEQ ID NO: 481, the second peptide chain comprises SEQ ID NO: 290 and the third peptide chain comprises SEQ ID NO: 298.

5. The trispecific antibody of claim 1, wherein the first peptide chain comprises SEQ ID NO: 481, the second peptide chain comprises SEQ ID NO: 276 and the third peptide chain comprises SEQ ID NO: 297.

* * * * *